> United States Patent [19]
> Shiraishi et al.

[11] Patent Number: 6,166,006
[45] Date of Patent: Dec. 26, 2000

[54] ANILIDE DERIVATIVE, PRODUCTION AND USE THEREOF

[75] Inventors: Mitsuru Shiraishi, Hyogo; Takahito Kitayoshi, Osaka; Yoshio Aramaki; Susumu Honda, both of Hyogo; Tsuneo Oda, Osaka, all of Japan

[73] Assignee: Takeda Chemical Industries, Ltd., Osaka, Japan

[21] Appl. No.: 09/213,379

[22] Filed: Dec. 17, 1998

[30] Foreign Application Priority Data

Dec. 19, 1997 [JP] Japan .................................. 9-351481

[51] Int. Cl.[7] ...................... A61K 31/165; A61K 31/351; A61K 31/4453; A61K 31/55; C07C 233/62; C07D 211/06; C07D 233/16; C07D 309/04; C07D 405/10

[52] U.S. Cl. .................... 514/213.01; 514/311; 514/314; 514/319; 514/320; 514/357; 514/422; 514/431; 514/432; 514/450; 514/451; 514/617; 540/593; 544/145; 544/147; 544/331; 546/173; 546/202; 546/205; 546/333; 546/196; 548/517; 549/9; 549/28; 549/424; 549/355; 564/16; 564/180

[58] Field of Search .............................. 540/593; 544/145, 544/147, 331; 546/202, 173, 205, 333, 196; 549/9, 355, 424, 28; 514/213, 311, 314, 319, 320, 357, 422, 431, 432, 450, 451, 617; 548/517; 564/16, 180

[56] References Cited

FOREIGN PATENT DOCUMENTS

96/01267  1/1996  WIPO .

OTHER PUBLICATIONS

Derwent Abstract of JP 07025756–A, Jan. 27, 1995.
Derwent Abstract of JP 07025757–A, Jan. 27, 1995.

*Primary Examiner*—Fiona T. Powers
*Attorney, Agent, or Firm*—Wenderoth, Lind & Ponack, L.L.P.

[57] ABSTRACT

This invention is to provide a compound of the formula:

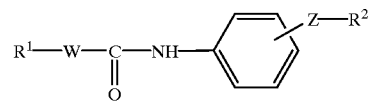

wherein $R^1$ is an optionally substituted 5- to 6-membered ring: C is a divalent group of the formula:

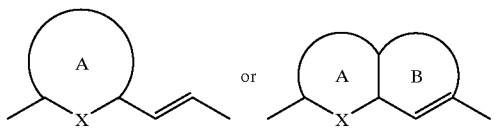

wherein the ring A is an optionally substituted 5- to 6-membered aromatic ring, X is an optionally substituted C, N or O atom, and the ring B is an optionally substituted 5- to 7-membered ring; Z is a chemical bond or a divalent group; $R^2$ is (1) an optionally substituted amino group in which a nitrogen atom may form a quaternary ammonium, etc., or a salt thereof, which is useful for antagonizing MCP-1 receptor.

26 Claims, No Drawings

ANILIDE DERIVATIVE, PRODUCTION AND USE THEREOF

TECHNICAL FIELD

The present invention relates to an anilide derivative or a salt thereof having antagonistic activity on MCP-1 (monocyte chemoattractant protein-1) receptor, production method and use thereof.

BACKGROUND ART

MCP-1 is known to be a monocyte chemotactic factor relating to inflammatory diseases, and belongs to CC chemokine sub-family. MCP-1 is found to express not only from monocyte but also from cardiac muscle cell, blood vessel endothelial cell, fibroblast, chondrocyte, smooth muscle cell, mesangial cell, aveolar cell, T lymphocyte, macrophage, etc. in various pathosis (specifically, angiostenosis, arteriosclerosis, rheumatic arthritis, diabetic microangiopathy, granulomatous inflammation (tuberculosis, sarcoidosis, etc.), solid cancer, diastolic cardiomyopathy (chronic heart failure, etc.), glomerulonephritis, etc.), and MCP-1 deeply relate to crisis and progression these pathosis. Therefore, MCP-1 receptor antagonists are used as a medicament for the treatment and prophylaxis of these pathosis.

So far, there have been only a little reports on low molecule compounds having antagonistic activity on MCP-1 receptor. For example, it is disclosed that aryloxy-propanolamine derivatives being active as β-blocker show weak inhibitory activity on MCP-1 binding to its receptor in JP-A-25756/1995 and that phenylethanolamine derivatives having sympathetic activity and sympatholytic activity show weak inhibitory activity on MCP-1 binding to its receptor in JP-A-25757/1995.

On the other hand, phosphonic acid derivatives having osteogenesis activity is disclosed in JP-A-73476/1996 but there is no description on MCP-1 receptor antagonistic activity.

The present invention is to provide a new anilide derivative or a salt thereof having antagonistic activity on MCP-1 receptor and therapeutic and prophylactic effect on cardiac infarction, myocarditis, cardiomyopathy, chronic heart failure, restenosis after angioplasty, disorder after reperfusion in lung and heart, inflammatory diseases (e.g. arteriosclerosis, arteriosclerosis after heart transplantation, (chronic) rheumatic arthritis, nephritis, etc.), rejection after organ transplantation, fibroid lung, renal insufficiency, diabetic diseases (e.g. diabetes, diabetic nephropathy, diabetic complication, diabetic retinopathy, diabetic retinitis, diabetic microangiopathy, etc.), tumor (e.g. bladder cancer, breast carcinoma, cervical carcinoma, chronic lymphocytic leukemia, chronic myelocytic leukemia, colon carcinoma, multiple myeloma, malignant myeloma, prostatic cancer, lung cancer, stomach cancer, Hodgkin's disease, etc.) infectious diseases (e.g. tuberculosis, invasive staphylococcia, etc.), etc.; production method and use thereof.

DISCLOSURE OF INVENTION

The present inventors diligently made extensive studies on compounds having MCP-1 receptor antagonistic activity and, as a result, they found that an anilide derivative of the following formula (I) or a salt thereof [hereinafter, referred to as Compound (I)] unexpectedly possesses potent MCP-1 receptor antagonistic activity and clinically desirable pharmaceutical effect. Based on the finding, the present invention was accomplished.

More specifically, the present invention relates to (1) a compound of the formula:

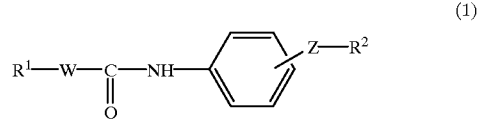

wherein $R^1$ is an optionally substituted 5- to 6-membered ring, W is a divalent group of the formula:

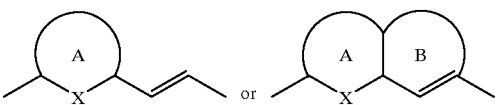

wherein the ring A is an optionally substituted 5- to 6-membered aromatic ring, X is an optionally substituted carbon atom, an optionally substituted nitrogen atom, sulfur atom or oxygen atom, the ring B is an optionally substituted 5- to 7-membered ring, Z is a chemical bond or a divalent group, $R^2$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group binding through a sulfur atom or (4) a group of the formula:

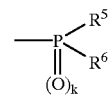

wherein k is 0 or 1, and when k is 0, a phosphorus atom may form a phosphonium; and $R^5$ and $R^6$ are independently an optionally substituted hydrocarbon group or an optionally substituted amino group, and $R^5$ and $R^6$ may bind to each other to form a cyclic group together with the adjacent phosphorus atom, or a salt thereof;

(2) a compound of the above (1), wherein $R^1$ is benzene, furan, thiophene, pyridine, cyclopentane, cyclohexane, pyrrolidine, piperidine, piperazine, morpholine, thiomorpholine or tetrahydropyran, each of which may be substituted;

(3) a compound of the above (1), wherein $R^1$ is an optionally substituted benzene;

(4) a compound of the above (1), wherein the ring A is furan, thiophene, pyrrole, pyridine or benzene, each of which may be substituted;

(5) a compound of the above (1), wherein the ring A is an optionally substituted benzene;

(6) a compound of the above (1), wherein W is a group of the formula:

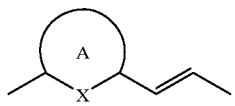

wherein each symbol is as defined in the above (1);
(7) a compound of the above (1), wherein W is a group of the formula:

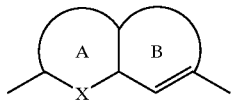

wherein each symbol is as defined in the above (1);
(8) a compound of the above (7), wherein the ring B is a 5- to 7-membered ring group of the formula:

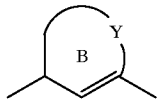

wherein Y is —Y'—(CH$_2$)$_m$— (Y' is —S—, —O—, —NH— or —CH$_2$—, and m is an integer of 0–2), —CH=CH— or —N=CH—), which may have a substituent at any possible position;
(9) a compound of the above (8), wherein Y is —Y'—(CH$_2$)$_2$— (Y' is —S—, —O—, —NH— or —CH$_2$—);
(10) a compound of the above (8), wherein Y is —(CH$_2$)$_2$—, —(CH$_2$)$_3$— or —O—(CH$_2$)$_2$—;
(11) a compound of the above (10), wherein the ring A is an optionally substituted benzene;
(12) a compound of the above (1), wherein Z is an optionally substituted C$_{1-3}$ alkylene;
(13) a compound of the above (1), wherein Z is a divalent group of the formula: —Z'—(CH$_2$)$_n$— (Z' is —CH(OH)—, —C(O)— or —CH$_2$—, and n is an integer of 0–2) in which an optional methylene group may be substituted;
(14) a compound of the above (1), wherein Z is methylene;
(15) a compound of the above (1), wherein Z is substituted at para position of the benzene ring;
(16) a compound of the above (1), wherein R$^2$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, or (3) a group of the formula:

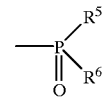

wherein R$^5$ and R$^6$ are independently an optionally substituted hydrocarbon group, and R$^5$ and R$^6$ may bind to each other to form a cyclic group together with the adjacent phosphorus atom;
(17) a compound of the formula:

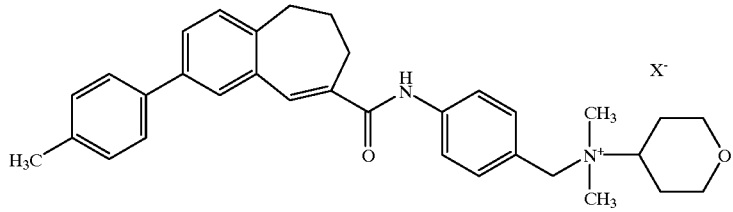

wherein X$^-$ is an anion;
(18) a compound of the above (17), wherein X is a halogen atom;
(19) a compound selected from the class consisting of
N-methyl-N-[4-[[[2-(4-methylphenyl)-6,7-dihydro-5H-benzocyclohepten-8-yl]carbonyl]amino]benzyl]-piperidinium iodide,
N-methyl-N-[4-[[[7-(4-methylphenyl)-2,3-dihydro-1-benzoxepin-4-yl]carbonyl]amino]benzyl]piperidinium iodide,
N-[4-[N-methyl-N-(tetrahydropyran-4-yl)aminomethyl]-phenyl]-7-(4-methylphenyl)-2,3-dihydro-1-benzoxepine-4-carboxmide,
N-[4-[N-methyl-N-(tetrahydropyran-4-yl)aminomethyl]-phenyl]-7-(4-morpholinophenyl)-2,3-dihydro-1-benzoxepine-4-carboxmide,
7-(4-ethoxyphenyl)-N-[4-[N-methyl-N-(tetrahydropyran-4-yl)aminomethyl]phenyl]-2,3-dihydro-1-benzoxepine-4-carboxmide,
N,N-dimethyl-N-[4-[[[2-(4-methylphenyl)-6,7-dihydro-5H-benzocyclohepten-8-yl]carbonyl]amino]benzyl]-N-(tetrahydropyran-4-yl)ammonium iodide and
N-methyl-N-[4-[[[7-(4-methylphenyl)-3,4-dihydro-naphthalen-2-yl]carbonyl]amino]benzyl]piperidinium iodide,
or a salt thereof;
(20) a method for producing a compound of the formula:

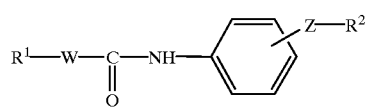

wherein each symbol is as defined above (1) or a salt thereof, which comprises subjecting a compound of the formula:

R$^1$—W—COOH (II)

wherein each symbol is as defined above (1), a salt or a reactive derivative thereof to condensation reaction with a compound of the formula:

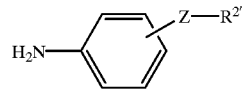
(III)

wherein Z is as defined above (1) and $R^{2'}$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group binding through a sulfur atom or (4) a group of the formula:

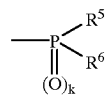

wherein k is 0 or 1, and when k is 0, a phosphorus atom may form a phosphonium; and $R^5$ and $R^6$ are independently an optionally substituted hydrocarbon group or an optionally substituted amino group, and $R^5$ and $R^6$ may bind to each other to form a cyclic group together with the adjacent phosphorus atom, the above groups (1)–(4) being optionally protected, or a salt thereof, and, if desired, subjecting the obtained product to deprotection, oxidation, reduction and/or ammoniumation;

(21) 3-(4-methylphenyl)-8,9-dihydro-7H-benzocycloheptene-6-carboxylic acid or a salt thereof;

(22) a pharmaceutical composition comprising a compound of the above (1) or a salt thereof;

(23) a composition of the above (22), which is for antagonizing MCP-1 receptor;

(24) a composition of the above (22), which is for the treatment or prophylaxis of cardiac infarction or myocarditis;

(25) a pharmaceutical composition for antagonizing MCP-1 receptor (or a pharmaceutical composition for inhibiting binding of MCP-1 (a ligand) to MCP-1 receptor or a pharmaceutical composition for antagonizing binding of MCP-1 to its receptor), which comprises a compound of the formula:

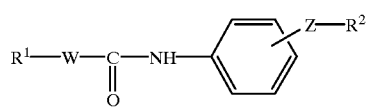
(I')

wherein $R^1$ is an optionally substituted 5- to 6-membered ring, W is a divalent group of the formula:

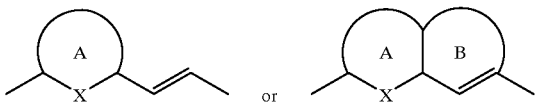

wherein the ring A is an optionally substituted 5- to 6-membered aromatic ring, X is an optionally substituted carbon atom, an optionally substituted nitrogen atom, sulfur atom or oxygen atom, the ring B is an optionally substituted 5- to 7-membered ring, Z is a chemical bond or a divalent group, $R^2$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group binding through a sulfur atom or (4) a group of the formula:

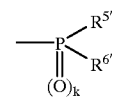

wherein k is 0 or 1, and when k is 0, a phosphorus atom may form a phosphonium; and $R^{5'}$ and $R^{6'}$ are independently an optionally substituted hydrocarbon group, an optionally substituted hydroxy group or an optionally substituted amino group, and $R^{5'}$ and $R^{6'}$ may bind to each other to form a cyclic group together with the adjacent phosphorus atom, or a salt thereof;

(26) a method for antagonizing MCP-1 receptor which comprises administering to a mammal in need thereof an effective amount of a compound of the formula:

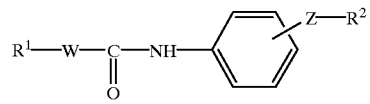

wherein $R^1$ is an optionally substituted 5- to 6-membered ring;

W is a divalent group of the formula:

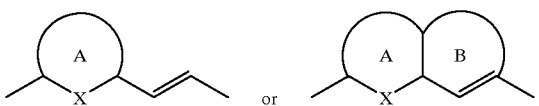

wherein the ring A is an optionally substituted 5- to 6-membered aromatic ring, X is an optionally substituted carbon atom, an optionally substituted nitrogen atom, sulfur atom or oxygen atom, and the ring B is an optionally substituted 5- to 7-membered ring; Z is a chemical bond or a divalent group; $R^2$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group binding through a sulfur atom or (4) a group of the formula:

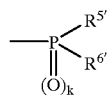

wherein k is 0 or 1, and when k is 0, a phosphorus atom may form a phosphonium; and $R^{5'}$ and $R6'$ are independently an optionally substituted hydrocarbon group, an optionally substituted hydroxy group or an optionally substituted amino group, and $R^{5'}$ and $R^{6'}$ may bind to each other to form a cyclic group together with the adjacent phosphorus atom, or a salt thereof;

(27) a method for antagonizing MCP-1 receptor which comprises administering to a mammal in need thereof an effective amount of a compound of the above (1) or a salt thereof;

(28) use of a compound of the formula:

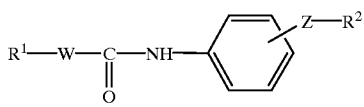

wherein R is an optionally substituted 5- to 6-membered ring;
W is a divalent group of the formula:

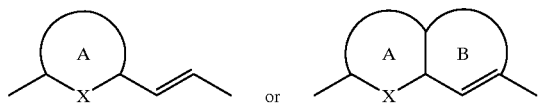

wherein the ring A is an optionally substituted 5- to 6-membered aromatic ring, X is an optionally substituted carbon atom, an optionally substituted nitrogen atom, sulfur atom or oxygen atom, and the ring B is an optionally substituted 5- to 7-membered ring; Z is a chemical bond or a divalent group; $R^2$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group binding through a sulfur atom or (4) a group of the formula:

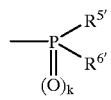

wherein k is 0 or 1, and when k is 0, a phosphorus atom may form a phosphonium; and $R^{5'}$ and $R^{6'}$ are independently an optionally substituted hydrocarbon group, an optionally substituted hydroxy group or an optionally substituted amino group, and $R^{5'}$ and $R^{6'}$ may bind to each other to form a cyclic group together with the adjacent phosphorus atom, or a salt thereof, for the manufacture of a medicament for antagonizing MCP-1 receptor;

(29) use of a compound of the above (1) or a salt thereof for the manufacture of a medicament for antagonizing MCP-1 receptor; etc.

In the above formula (I), examples of the "5- to 6-membered ring" of the "optionally substituted 5- to 6-membered ring" represented by $R^1$ include a 6-membered aromatic hydrocarbon such as benzene, etc.; a 5- to 6-membered aliphatic hydrocarbon such as cyclopentane, cyclohexane, cyclopentene, cyclohexene, cyclopentanediene, cyclohexanediene, etc.; 5- to 6-membered aromatic heterocyclic ring containing 1 to 4 hetero-atoms consisting of 1 to 2 kinds of hetero-atoms selected from oxygen atom, sulfur atom and nitrogen atom such as furan, thiophene, pyrrole, imidazole, pyrazole, thiazole, oxazole, isothiazole, isoxazole, tetrazole, pyridine, pyrazine, pyrimidine, pyridazine, triazole, etc.; 5- to 6-membered non-aromatic heterocyclic ring containing 1 to 4 hetero-atoms consisting of 1 to 2 kinds of hetero-atoms selected from oxygen atom, sulfur atom and nitrogen atom such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, tetrahydrothiopyran, etc.; etc. Among others, benzene, furan, thiophene, pyridine, cyclopentane, cyclohexane, pyrrolidine, piperidine, piperazine, morpholine, thiomorpholine, tetrahydropyran (preferably, 6-membered ring), etc. are preferable, and in particular, benzene is preferable.

Example of the "substituents" which the "5- to 6-membered ring" in the "optionally substituted 5- to 6-membered ring" represented by $R^1$ may have include halogen atom, nitro, cyano, an optionally substituted alkyl, an optionally substituted cycloalkyl, an optionally substituted hydroxy group, an optionally substituted thiol group wherein a sulfur atom may be optionally oxidized to form a sulfinyl group or a sulfonyl group, an optionally substituted amino group, an optionally substituted acyl, an optionally esterified carboxyl group, an optionally substituted aromatic group, etc.

Examples of the halogen as the substituents for $R^1$ include fluorine, chlorine, bromine, iodine, etc. Among others, fluorine and chlorine are preferable.

Examples of the alkyl in the optionally substituted alkyl as the substituents for $R^1$ include a straight or branched $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., and preferably lower ($C_{1-6}$) alkyl.

Examples of the substituents in the optionally substituted alkyl include halogen (e.g. fluorine, chlorine, bromine, iodine, etc.), nitro, cyano, hydroxy group, thiol group, amino group, carboxyl group, an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the cycloalkyl in the optionally substituted cycloalkyl as the substituents for $R^1$ include $C_{3-7}$ cycloalkyl, etc. such as cyclopropyl, cyclobutyl, cyclopentyl, cyclohexyl, cycloheptyl, etc.

Examples of the substituents in the optionally substituted cycloalkyl include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g.

acetyl, propionyl, etc.), $C_{1-4}$ alkylsulfonyl (e.g. methanesulfonyl, ethanesulfonyl, etc.), etc., and the number of the substituents are preferably 1 to 3.

Examples of the substituents in the optionally substituted hydroxy group as the substituents for $R^1$ include (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted alkenyl (e.g. $C_{2-10}$ alkenyl such as allyl, crotyl, 2-pentenyl, 3-hexenyl, etc., preferably lower ($C_{2-6}$)alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.):

(5) an optionally substituted aralkyl (e.g. phenyl-$C_{1-4}$ alkyl (e.g. benzyl, phenethyl, etc.), etc.);

(6) an optionally substituted acyl (e.g. $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.), etc.);

(7) an optionally substituted aryl (e.g. phenyl, naphthyl, etc.); etc.

Examples of the substituents which the above-mentioned (1) optionally substituted alkyl, (2) optionally substituted cycloalkyl, (3) optionally substituted alkenyl, (4) optionally substituted cycloalkenyl, (5) optionally substituted aralkyl, (6) optionally substituted acyl and (7) optionally substituted aryl may have include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the substituents in the optionally substituted thiol group as the substituents for $R^1$ are similar to the above-described substituents in the optionally substituted hydroxy group as the substituents for $R^1$, and among others, (1) an optionally substituted alkyl (e.g. $C_{10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted aralkyl (e.g. phenyl-$C_{1-4}$ alkyl (e.g. benzyl, phenethyl, etc.), etc.);

(4) an optionally substituted aryl (e.g. phenyl, naphthyl, etc.); etc. are preferable.

Examples of the substituents which the above-mentioned (1) optionally substituted alkyl, (2) optionally substituted cycloalkyl, (3) optionally substituted aralkyl and (4) optionally substituted aryl may have include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the substituents in the optionally substituted amino group as the substituents for $R^1$ are similar to the above-described substituents in the optionally substituted hydroxy group as the substituents for $R^1$, and examples of the optionally substituted amino group as the substituents for $R^1$ include an amino group which may have one to two substituents selected from the above-described substituents in the optionally substituted hydroxy group as the substituents for $R^1$, etc. Among others, as the substituents in the optionally substituted amino group as the substituents for $R^1$, (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted alkenyl (e.g. $C_{2-10}$ alkenyl such as allyl, crotyl, 2-pentenyl, 3-hexenyl, etc., preferably lower ($C_{2-6}$) alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(5) an optionally substituted acyl (e.g. $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.), etc.);

(6) an optionally substituted aryl (e.g. phenyl, naphthyl, etc.); etc. are preferable.

Examples of the substituents, which each of the above-described (1) optionally substituted alkyl, (2) optionally substituted cycloalkyl, (3) optionally substituted alkenyl, (4) optionally substituted cycloalkenyl, (5) optionally substituted acyl and (6) optionally substituted aryl may have, include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

The substituents in the optionally substituted amino group as the substituents for $R^1$ may bind to each other to form a cyclic amino group (e.g. 5- to 6-membered cyclic amino, etc. such as tetrahydropyrrole, piperazine, piperidine, morpholine, thiomorpholine, pyrrole, imidazole, etc.). Said cyclic amino group may have a substituent, and examples of the substituents include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the optionally substituted acyl as the substituents for $R^1$ include a carbonyl group or a sulfonyl group binding to (1) hydrogen;
(2) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);
(3) an optionally substituted cycloalkyl (e.g. $C_{3-7}$ cycloalkyl, etc. such as cyclopropyl, cyclobutyl, cyclopentyl, cyclohexyl, cycloheptyl, etc.);
(4) an optionally substituted alkenyl (e.g. $C_{2-10}$ alkenyl such as allyl, crotyl, 2-pentenyl,3-hexenyl, etc., preferably lower ($C_{2-6}$) alkenyl, etc.);
(5) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);
(6) an optionally substituted 5- to 6-membered monocyclic aromatic group (e.g. phenyl, pyridyl, etc.); etc.

Examples of the acyl include acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, methanesulfonyl, ethanesulfonyl, etc.

Examples of the substituents, which the above-mentioned (2) optionally substituted alkyl, (3) optionally substituted cycloalkyl, (4) optionally substituted alkenyl, (5) optionally substituted cycloalkenyl and (6) optionally substituted 5- to 6-membered monocyclic aromatic group may have, include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the optionally esterified carboxyl group as the substituents for $R^1$ include a carbonyloxy group binding to (1) hydrogen;
(2) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);
(3) an optionally substituted cycloalkyl (e.g. $C_{3-7}$ cycloalkyl, etc. such as cyclopropyl, cyclobutyl, cyclopentyl, cyclohexyl, cycloheptyl, etc.);
(4) an optionally substituted alkenyl (e.g. $C_{2-10}$ alkenyl such as allyl, crotyl, 2-pentenyl, 3-hexenyl, etc., preferably lower ($C_{2-6}$) alkenyl, etc.);
(5) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);
(6) an optionally substituted aryl (e.g. phenyl, naphthyl, etc.); etc., and preferably carboxyl, lower ($C_{1-6}$) alkoxycarbonyl, aryloxycarbonyl (e.g. methoxycarbonyl, ethoxycarbonyl, propoxycarbonyl, phenoxycarbonyl, naphthoxycarbonyl, etc.), etc.

Examples of the substituents, which the above-mentioned (2) optionally substituted alkyl, (3) optionally substituted cycloalkyl, (4) optionally substituted alkenyl, (5) optionally substituted cycloalkenyl and (6) optionally substituted aryl may have, include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the aromatic group in the optionally substituted aromatic group as the substituents for $R^1$ include 5- to 6-membered homocyclic or heterocyclic ring aromatic ring, etc. suchasphenyl, pyridyl, furyl, thienyl, pyrrolyl, imidazolyl, pyrazolyl, thiazolyl, oxazolyl, isothiazolyl, isoxazolyl, tetrazolyl, pyrazinyl, pyrimidinyl, pyridazinyl, triazolyl, etc.

Examples of the substituents for these aromatic group include halogen (e.g. fluorine, chlorine, bromine, iodine, etc.), nitro, cyano, hydroxygroup, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

The number of the above-mentioned substituents for $R^1$ is 1–4 (preferably 1–2) and they may be same or different and present at any possible position on the ring represented by $R^1$. When two or more substituents are present on the 5- to 6-membered ring in the "an optionally substituted 5- to 6-membered ring" represented by $R^1$, two substituents among them may bind to each other to form a lower ($C_{1-6}$) alkylene (e.g. trimethylene, tetramethylene, etc.), a lower ($C_{1-6}$) alkyleneoxy (e.g. —$CH_2$—O—$CH_2$—, —O—$CH_2$—$CH_2$—, etc.), a lower ($C_{1-6}$) alkylenedioxy (e.g. —O—$CH_2$—O—, —O—$CH_2$—$CH_2$—O—, etc.), a lower ($C_{2-6}$) alkenylene (e.g. —$CH_2$—CH=CH—, —$CH_2$—$CH_2$—CH=CH—, —$CH_2$—CH=CH—$CH_2$—, etc.), a lower ($C_{4-6}$) alkadienylene (e.g. —CH=CH—CH=CH—, etc.), etc.

Preferred examples of the "substituents", which the "5- to 6-membered ring" in the "an optionally substituted 5- to 6-membered ring" represented by $R^1$ may have, include an optionally halogenated lower ($C_{1-4}$) alkyl (e.g. methyl, ethyl, t-butyl, trifluoromethyl, etc.), an optionally halogenated lower ($C_{1-4}$) alkoxy (e.g. methoxy, ethoxy, t-butoxy, trifluoromethoxy, etc.), halogen (e.g. fluorine, chlorine, etc.), nitro, cyano, an amino group optionally substituted with 1–2 lower ($C_{1-4}$) alkyl groups (e.g. amino, methylamino, dimethylamino, etc.), 5- to 6-membered cyclic amino (e.g. 1-pyrrolidinyl, 1-piperazinyl, 1-piperidinyl, 4-morpholino, 4-thiomorpholin, 1-imidazolyl, 4-tetrahydropyranyl, etc.), etc., and when $R^1$ is a benzene, the "substituent" is preferably present at para position.

In the above formula (I), examples of the "5- to 6-membered aromatic ring" in the "optionally substituted 5- to 6-membered aromatic ring" represented by A include 6-membered aromatic hydrocarbon such as benzene, etc.; 5- to 6-membered aromatic heterocyclic ring containing 1 to 3 hetero-atoms consisting of 1 to 2 kinds of hetero-atoms selected from oxygen atom, sulfur atom and nitrogen atom such as furan, thiophene, pyrrole, imidazole, pyrazole, thiazole, oxazole, isothiazole, isoxazole, pyridine, pyrazine, pyrimidine, pyridazine, triazole, etc.; etc. Among others, benzene, furan, thiophene, pyridine (preferably, 6-membered ring) etc. are preferable, and in particular benzene is preferable.

Examples of the "substituents", which the "5- to 6-membered aromatic ring" in the "optionally substituted 5- to 6-membered aromatic ring" represented by A may have, are similar to the "substituents" which the "5- to 6-membered ring" in the "optionally substituted 5- to 6-membered ring" represented by $R^1$ may have. The number of said substituents for the ring A is 1–4 (preferably 1–2), and they may be same or different and present at any possible position (e.g. the position of the group X and the other positions) on the ring represented by A.

In the above formula (I), a group of the formula:

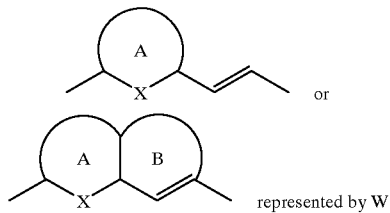 or

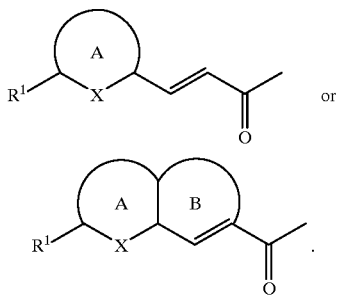 represented by W binds to adjacent groups in the following manner:

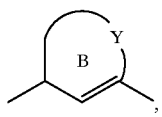

In the above formula (I), examples of the "5- to 7-membered ring" in the "optionally substituted 5- to 7-membered ring" represented by B include a 5- to 7-membered ring group of the formula:

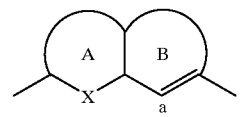

which may have a substituent at any possible position, etc.

In the above formula, the divalent group represented by Y may be any divalent group as far as the ring B forms an optionally substituted 5- to 7-membered ring, and preferred examples of the divalent groups include (1) —$(CH_2)_{a1}$—O—$(CH_2)_{a2}$— ($a_1$ and $a_2$ are same or different and 0, 1 or 2, provided that the sum of $a_1$ and $a_2$ is 2 or less), —O—(CH=CH)—, —(CH=CH)—O—;

(2) —$(CH_2)_{b1}$—S—$(CH_2)_{b2}$— ($b_1$ and $b_2$ are same or different and 0, 1 or 2, provided that the sum of $b_1$ and $b_2$ is 2 or less), —S—(CH=CH)—, —(CH=CH)—S—;

(3) —$(CH_2)_{d1}$— ($d_1$ is 1, 2 or 3), —$CH_2$—(CH=CH)—, —(CH=CH)—$CH_2$—, —CH=CH—;

(4) —$(CH_2)_{e1}$—NH—$(CH_2)_{e2}$— ($e_1$ and $e_2$ are same or different and 0, 1 or 2, provided that the sum of $e_1$ and $e_2$ is 2 or less), —NH—(CH=CH)—, —(CH=CH)—NH—, —$(CH_2)_{e6}$—(N=CH)—$(CH_2)_{e7}$—, —$(CH_2)_{e7}$—(CH=N)—$(CH_2)_{e6}$— (one of $e_6$ and $e_7$ is 0, and the other is 1), —$(CH_2)_{e8}$—(N=N)—$(CH_2)_{e9}$—(one of $e_8$ and $e_9$ is 0, and the other is 1); etc. More preferred examples of the divalent groups include —O—, —O—$CH_2$—, —O—$CH_2$—$CH_2$—, —O—CH=CH—, —S—, —S—$CH_2$—, —S—$CH_2$—$CH_2$—, —S—CH=CH—, —$CH_2$—, —$(CH_2)_2$—, —$(CH_2)_3$—, —CH=CH—, —CH=CH—$CH_2$—, —$CH_2$—CH=CH—, —NH—, —N=CH—, —CH=N—, —N=N— (in which each of the above formulas represent that it binds to the ring A through its left chemical bond), etc.

The divalent group may have a substituent. Examples of the substituent include those for the "5- to 6-membered ring" in the "optionally substituted 5- to 6-membered ring" represented by $R^1$ and an oxo group, etc. Among others, a lower ($C_{1-3}$) alkyl (e.g. methyl, ethyl, propyl, etc.), a phenyl group, an oxo group, a hydroxy group, etc. are preferable. In addition, the divalent group may be —O—C(0)—(in which each of the above formulas represent that it binds to the ring A through its left chemical bond), etc. The number of the substituents are preferably 1 to 4 (preferably, 1–2), and they may be same or different and bind to the divalent group at any possible position.

As the divalent group represented by Y, a group of the formula: —Y'—$(CH_2)_m$—(Y' is —S—, —O—, —NH— or —$CH_2$—, and m is an integer of 0–2), —CH=CH—, —N=CH—, —$(CH_2)_m$—Y'— (Y' is —S—, —O—, —NH— or —$CH_2$—, and m is an integer of 0–2), —CH=N— (in which each of the above formulas represent that it binds to the ring A through its left chemical bond), etc. is preferable. Among others, a group of the formula: —Y'—$(CH_2)_m$— (Y' is —S—, —O—, —NH— or —$CH_2$—, and m is an integer of 0–2), —CH=CH—, —N=CH— (in which each of the above formulas represent that it binds to the ring A through its left chemical bond), etc. is preferable. In particular, Y is preferably a group of the formula: —Y'—$(CH_2)_2$— (Y' is —S——O—, —NH— or —$CH_2$— (preferably —S—, —O— or —$CH_2$—, more preferably —O— or —$CH_2$—)) in which the formula binds to the ring A through its left chemical bond, etc.; and the ring B is preferably a 7-membered ring. As the divalent group represented by Y, a group of the formula: —$(CH_2)_2$—, —$(CH_2)_3$— or —O—$(CH_2)_2$— is preferable.

Examples of the "substituents", which the "5- to 7-membered ring" in the "optionally substituted 5- to 7-membered ring" represented by B may have, include those for the "5- to 6-membered ring" in the "optionally substituted 5- to 6-membered ring" represented by $R^1$ and an oxo group, etc. The number of the substituents are preferably 1 to 4 (preferably, 1–2), and they may be same or different and bind to the divalent group at any possible position.

In a group of the formula:

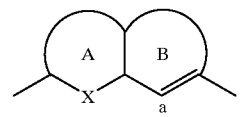

represented by W, a carbon atom at the position a is preferably unsubstituted.

In the above formula (I), examples of the divalent group represented by Z include an optionally substituted divalent group whose straight chain is constituted by 1 to 4 carbon atoms (e.g. $C_{1-4}$ alkylene, $C_{2-4}$ alkenylene, etc., preferably $C_{1-3}$ alkylene, more preferably methylene), etc. The group Z may be bound to any possible position of the benzene ring, and preferably to para position of the benzene ring.

The divalent group represented by Z may be any divalent group whose straight chain is constituted by 1 to 4 atoms and exemplified by an alkylene chain of the formula: —$(CH_2)_{k1}$— ($k_1$ is an integer of 1–4), an alkenylene chain of the formula: —$(CH_2)_{k2}$—(CH=CH)—$(CH_2)_{k3}$— ($k_2$ and $k_3$ are same or different and 0, 1 or 2, provided that the sum of $k_2$ and $k_3$ is 2 or less), etc.

Examples of the substituent for the divalent group represented by Z include any one which is capable of binding to the straight chain of the divalent group, and preferably $C_{1-6}$ lower alkyl (e.g. methyl, ethyl, propyl, isopropyl, butyl, isobutyl, sec-butyl, tert-butyl, pentyl, isopentyl, neopentyl, hexyl, etc.), lower ($C_{3-7}$) cycloalkyl (e.g. cyclopropyl, cyclobutyl, cyclopentyl, cyclohexyl, cycloheptyl, etc.), an optionally esterified phosphono group, an optionally esterified carboxyl group, hydroxy group, oxo, etc., and more preferably $C_{1-6}$ lower alkyl (preferably $C_{1-3}$ alkyl), hydroxy group, oxo, etc.

Examples of the optionally esterified phosphono group include a group of the formula: P(O) (O$R^7$) (O$R^8$) wherein $R^7$ and $R^8$ are independently hydrogen, a $C_{1-6}$ alkyl group or a $C_{3-7}$ cycloalkyl group, and $R^7$ and $R^8$ may bind to each other to form a 5- to 7-membered ring.

In the above formula, examples of the $C_{1-6}$ alkyl group represented by $R^7$ and $R^8$ include methyl, ethyl, propyl, isopropyl, butyl, isobutyl, sec-butyl, tert-butyl, pentyl, isopentyl, neopentyl, hexyl, etc., and examples of the $C_{3-7}$ cycloalkyl include cyclopropyl, cyclobutyl, cyclopentyl, cyclohexyl, cycloheptyl, etc. Among other, a straight $C_{1-6}$ lower alkyl is preferable and $C_{1-3}$ lower alkyl is more preferable. The groups $R^7$ and $R^8$ may be same or different, and preferably the groups $R^7$ and $R^8$ are same. When $R^7$ and $R^8$ may bind to each other to form a 5- to 7-membered ring, the groups $R^7$ and $R^8$ bind to each other to represent a straight $C_{2-4}$ alkylene chain of the formula: —$(CH_2)_2$—, —$(CH_2)_3$—, —$(CH_2)_4$—, etc. Said chain may have a substituent, and examples of the substituent include hydroxy group, halogen, etc.

Examples of the optionally esterified carboxyl group include a carboxyl group and an ester group formed by binding a carboxyl group to a $C_{1-6}$ alkyl group or a $C_{3-7}$ cycloalkyl group (e.g. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, etc.).

As the divalent group represented by Z, an optionally substituted $C_{1-3}$ alkylene is preferable, and $C_{1-3}$ alkylene which may be substituted by $C_{1-3}$ alkyl, hydroxy group or oxo is more preferable.

Among others, as the divalent group represented by Z, a group of the formula: —Z'—$(CH_2)_n$— or —$(CH_2)_n$—Z'— (Z' is —CH(OH)—, —C(O)— or —$CH_2$—, and n is an integer of 0–2) in which each of the above formulas represent that it binds to the benzene ring through its left chemical bond and each of the methylene groups may be substituted by 1–2 same or different substituents is preferable, a group of the formula: —Z'—$(CH_2)_n$— (Z' is —CH(OH)—, —C(O)— or —$CH_2$—, and n is an integer of 0–2 (preferably, n is 0)) in which the formula binds to the benzene ring through its left chemical bond and each of the methylene groups may be substituted by 1–2 same or different substituents is more preferable, and methylene is particularly preferable.

In the above-mentioned formula (I), examples of the "amino group" in the "optionally substituted amino group in which a nitrogen atom may form a quaternary ammonium" represented by $R^2$ include an amino group which may have 1–2 substituents, an amino group having 3 substituents wherein the nitrogen atom forms a quaternary ammonium, etc. When the number of the substituents on the nitrogen atom is 2 or more, these substituents may be same or different. When the total number of the substituents and hydrogen atoms on the nitrogen atom is 3, the "amino group" represented by $R^2$ may be any type of an amino group represented by the formula: —$N^+R_3$, —$N^+R_2R'$ or —$N^+RR'R''$ (R, R' and R'' are independently a hydrogen atom or a substituent). Examples of the counter anion of the amino group wherein the nitrogen atom forms a quaternary ammonium include an anion of a halogen atom (e.g. Cl$^-$, Br$^-$, I$^-$, etc.), etc., and also an anion derived from an inorganic acid such as hydrochloric acid, hydrobromic acid, nitric acid, sulfuric acid, phosphoric acid, etc.; an anion derived from an organic acid such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.; an anion derived from an acidic amino acid such as aspartic acid, glutamic acid, etc.; etc. Among others, Cl$^-$, Br$^-$, I$^-$, etc. are preferable.

Examples of the substituents for said amino group include (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-8}$ cycloalkyl, etc. such as cyclopropyl, cyclobutyl, cyclopentyl, cyclohexyl, cycloheptyl, cyclooctyl, etc.), provided that (2-1) said cycloalkyl may contain one hetero-atom selected from a sulfur atom, an oxygen atom and a nitrogen atom to form oxirane, thiorane, aziridine, tetrahydrofuran, tetrahydrothiophene, pyrrolidine, tetrahydropyran, tetrahydrothiopyran, tetrahydrothiopyran 1-oxide, piperidine, etc. (preferably, 6-membered ring such as tetrahydropyran, tetrahydrothiopyran, piperidine, etc.) and these groups preferably bind to the amino group at their 3- or 4-position (preferably, 4-position), that (2-2) said cycloalkyl may be fused with a benzene ring to form indane, tetrahydronaphthalene, etc. (preferably, indane, etc.), and that (2-3) said cycloalkyl may have a bridging comprising a straight chain constituted by 1–2 carbon atoms to form a bridged hydrocarbon residue such as bicyclo [2.2.1]heptyl, bicyclo[2.2.2]octyl, bicyclo[3.2.1] octyl, bicyclo[3.2.2]nonyl, etc., preferably, a cyclohexyl group, etc. having a bridging comprising a straight chain constituted by 1–2 carbon atoms, and more preferably bicyclo[2.2.1]heptyl, etc.;

(3) an optionally substituted alkenyl (e.g. $C_{2-10}$ alkenyl such as allyl, crotyl, 2-pentenyl,3-hexenyl, etc., preferably lower ($C_{2-6}$)alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(5) an optionally substituted aralkyl (e.g. phenyl-$C_{1-4}$ alkyl (e.g. benzyl, phenethyl, etc.), etc.);

(6) an optionally substituted acyl (e.g. $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.), etc.);

(7) an optionally substituted aryl (e.g. phenyl, naphthyl, etc.);

(8) an optionally substituted heterocyclic ring group (e.g. 5- to 6-membered aromatic heterocyclic ring containing 1 to 4 hetero-atoms consisting of 1 to 2 kinds of hetero-atoms selected from oxygen atom, sulfur atom and nitrogen atom such as furan, thiophene, pyrrole, imidazole, pyrazole, thiazole, oxazole, isothiazole, isoxazole, tetrazole, pyridine, pyrazine, pyrimidine, pyridazine, triazole, etc.; 5- to 6-membered non-aromatic heterocyclic ring containing 1 to 4 hetero-atoms consisting of 1 to 2 kinds of hetero-atoms selected from oxygen atom, sulfur atom and nitrogen atom such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, etc.; etc.; preferably 5- to 6-membered non-aromatic heterocyclic ring, etc.; more preferably 5- to 6-membered non-aromatic heterocyclic ring containing one hetero-atom, etc. such as tetrahydrofuran, piperidine, tetrahydropyran, tetrahydrothiopyran, etc.); etc.

Examples of the substituents, which the above-mentioned (1) optionally substituted alkyl, (2) optionally substituted cycloalkyl, (3) optionally substituted alkenyl, (4) optionally substituted cycloalkenyl, (5) optionally substituted aralkyl, (6) optionally substituted acyl, (7) optionally substituted aryl and (8) optionally substituted heterocyclic ring group may have, include halogen (e.g. fluorine, chlorine, bromine, iodine, etc.), an optionally halogenated lower ($C_{1-4}$) alkyl, an optionally halogenated $C_{1-4}$ alkoxy (e.g. methoxy, ethoxy, trifluoromethoxy, trifluoroethoxy, etc.), $C_{1-4}$ alkylenedioxy (e.g. —O—$CH_2$—O—, —O—$CH_2$—$CH_2$—O—, etc.), $C_{2-4}$ alkanoyl (e.g. acetyl, propionyl, etc.), $C_{1-4}$ alkylsulfonyl (e.g. methanesulfonyl, ethanesulfonyl, etc.), phenyl-lower ($C_{1-4}$) alkyl, $C_{3-7}$ cycloalkyl, cyano, nitro, hydroxy group, thiol group, amino group, carboxyl group, lower ($C_{1-4}$) alkoxy-carbonyl (preferably, halogen, an optionally halogenated lower ($C_{1-4}$) alkyl, an optionally halogenated lower ($C_{1-4}$) alkoxy, phenyl-lower ($C_{1-4}$) alkyl, $C_{3-7}$ cycloalkyl, cyano, hydroxy group, etc.), etc., and the number of the substituents are preferably 1 to 3.

In the above formula (I), preferred examples of the "optionally substituted amino group in which a nitrogen atom may form a quaternary ammonium" represented by $R^2$ include an amino group which may have 1–3 substituents selected from (1) a straight or branched lower ($C_{1-6}$) alkyl which may have 1 to 3 substituents selected from halogen, cyano, hydroxy group or $C_{3-7}$ cycloalkyl;

(2) a $C_{5-8}$ cycloalkyl which may have 1 to 3 substituents selected from halogen, an optionally halogenated lower ($C_{1-4}$) alkyl or phenyl-lower ($C_{1-4}$) alkyl, which may contain one hetero-atom selected from a sulfur atom, an oxygen atom and a nitrogen atom, which may be fused with a benzene ring, and which may have a bridging comprising a straight chain constituted by 1–2 carbon atoms (e.g. cyclopentyl, cyclohexyl, cycloheptyl, cyclooctyl, tetrahydropyranyl, tetrahydrothiapyranyl, piperidinyl, indanyl, tetrahydronaphthalenyl, bicyclo [2.2.1]heptyl, etc., each of which may be substituted);

(3) a phenyl-lower ($C_{1-4}$) alkyl which may have 1 to 3 substituents selected from halogen, an optionally halogenated lower ($C_{1-4}$) alkyl or an optionally halogenated lower ($C_{1-4}$) alkoxy;

(4) a phenyl which may have 1 to 3 substituents selected from halogen, an optionally halogenated lower ($C_{1-4}$) alkyl or an optionally halogenated lower ($C_{1-4}$) alkoxy; and (5) a 5- to 6-membered aromatic heterocyclic ring (e.g. furan, thiophene, pyrrole, pyridine, etc.) which may have 1 to 3 substituents selected from halogen, an optionally halogenated lower ($C_{1-4}$) alkyl, an optionally halogenated lower ($C_{1-4}$) alkoxy, an optionally halogenated lower ($C_{1-4}$) alkoxy-lower ($C_{1-4}$) alkoxy, phenyl-lower ($C_{1-4}$) alkyl, cyano or hydroxy group.

In the above formula (I), examples of the "nitrogen-containing heterocyclic ring" in the "optionally substituted nitrogen-containing heterocyclic ring group which may contain a sulfur atom or an oxygen atom as ring constituting atoms and wherein a nitrogen atom may form a quaternary ammonium" include a 5- to 6-membered aromatic heterocyclic ring which may contain 1 to 3 hetero-atoms consisting of 1 to 2 kinds of hetero-atoms selected from an oxygen atom, a sulfur atom and a nitrogen atom other than one nitrogen atom such as pyrrole, imidazole, pyrazole, thiazole, oxazole, isothiazole, isoxazole, tetrazole, pyridine, pyrazine, pyrimidine, pyridazine, triazole, etc.; 5–8 membered non-aromatic heterocyclic ring which may contain 1 to 3 hetero-atoms consisting of 1 to 2 kinds of hetero-atoms selected from an oxygen atom, a sulfur atom and a nitrogen atom other than one nitrogen atom such as pyrrolidine, pyrroline, imidazolidine, imidazoline, pyrazolidine, pyrazoline, piperidine, piperazine, oxazine, oxadiazine, thiazine, thiadiazine, morpholine, thiomorpholine, azacycloheptane, azacyclooctane (azocane), etc.; etc. These nitrogen-containing heterocyclic rings may have a bridging comprising a straight chain constituted by 1–2 carbon atoms to form a bridged nitrogen-containing heterocyclic ring azabicyclo [2.2.1]heptane, azabicyclo[2.2.2]octane (quinuclidine), etc. (preferably, piperidine having a bridging comprising a straight chain constituted by 1–2 carbon atoms, etc.).

Among the above-exemplified nitrogen-containing heterocyclic rings, pyridine, imidazole, pyrrolidine, piperidine, piperazine, morpholine, thiomorpholine, azabicyclo[2.2.2] octane (preferably, a 6-membered ring) are preferable.

The nitrogen atom of said "nitrogen-containing heterocyclic ring" may form a quaternary ammonium or may be oxidized. When the nitrogen atom of said "nitrogen-containing heterocyclic ring" forms a quaternary ammonium, examples of the counter anion of the "nitrogen-containing heterocyclic ring wherein the nitrogen atom forms a quaternary ammonium" include an anion of a halogen atom (e.g. $Cl^-$, $Br^-$, $I^-$, etc.), etc., and also an anion derived from an inorganic acid such as hydrochloric acid, hydrobromic acid, nitric acid, sulfuric acid, phosphoric acid, etc.; an anion derived from an organic acid such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.; an anion derived from an acidic amino acid such as aspartic acid, glutamic acid, etc.; etc. Among others, $Cl^-$, $Br^-$, $I^-$, etc. are preferable.

Said "nitrogen-containing heterocyclic ring" may bind to the divalent group represented by Z through either a carbon atom or a nitrogen atom, and may be 2-pyridyl, 3-pyridyl, 2-piperidinyl, etc. which binds to the divalent group represented by Z through a carbon atoms. Preferably, the "nitrogen-containing heterocyclic ring" binds to the divalent group represented by Z through a nitrogen atom, as exemplified by the following formulas:

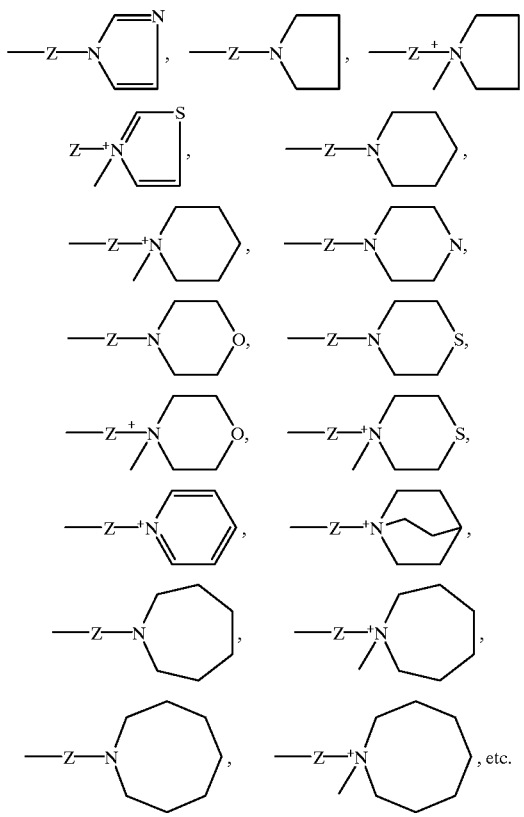

Examples of the substituents, which said "nitrogen containing heterocyclic ring" may have, include halogen (e.g. fluorine, chlorine, bromine, iodine, etc.), an optionally substituted lower ($C_{1-4}$) alkyl, an optionally substituted lower ($C_{1-4}$) alkoxy, an optionally substituted phenyl, an optionally substituted mono- or di-phenyl-lower ($C_{1-4}$) alkyl, an optionally substituted $C_{3-7}$ cycloalkyl, cyano, nitro, hydroxy group, thiol group, amino group, carboxyl group, lower ($C_{1-4}$) alkoxy-carbonyl, lower ($C_{2-4}$) alkanoyl, lower ($C_{1-4}$) alkylsulfonyl, an optionally substituted heterocyclic ring group (e. g. 5- to 6-membered aromatic heterocyclic ring containing 1 to 4 hetero-atoms consisting of 1 to 2 kinds of hetero-atoms selected from an oxygen atom, a sulfur atom and a nitrogen atom such as furan, thiophene, pyrrole, imidazole, pyrazole, thiazole, oxazole, isothiazole, isoxazole, tetrazole, pyridine, pyrazine, pyrimidine, pyridazine, triazole, etc.; 5- to 6-membered non-aromatic heterocyclic ring containing 1 to 4 hetero-atoms consisting of 1 to 2 kinds of hetero-atoms selected from an oxygen atom, a sulfur atom and a nitrogen atom such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, tetrahydrothiopyran, etc.; etc.), etc., and the number of the substituents is preferably 1–3.

Examples of the substituent, which the "optionally substituted lower ($C_{1-4}$,) alkyl", the "optionally substituted lower ($C_{1-4}$) alkoxy", the "optionally substituted phenyl", the "optionally substituted mono- or di-phenyl-lower ($C_{1-4}$) alkyl", the "optionally substituted $C_{3-7}$ cycloalkyl" and the "optionally substituted heterocyclic ring group" as a substituent for said "nitrogen-containing heterocyclic ring" may have, include halogen (e.g. fluorine, chlorine, bromine, iodine, etc.), an optionally halogenated lower ($C_{1-4}$) alkyl, an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), $C_{1-3}$ alkylenedioxy (e.g. methylenedioxy, ethylenedioxy, etc.), cyano, nitro, hydroxy group, thiol group, amino group, carboxyl group, lower ($C_{1-4}$) alkoxy-carbonyl, etc., and the number of the substituents are preferably 1 to 3.

In the above formula (I), preferred example of the substituents for the "nitrogen-containing heterocyclic ring" in the "optionally substituted nitrogen-containing heterocyclic ring group which may contain a sulfur atom or an oxygen atom as ring constituting atoms and wherein a nitrogen atom may form a quaternary ammonium" include (1) halogen, (2) cyano, (3) hydroxy group, (4) carboxyl group, (5) lower ($C_{1-4}$) alkoxy-carbonyl, (6) lower ($C_{1-4}$) alkyl which may be substituted with halogen, hydroxy group or lower ($C_{1-4}$) alkoxy, (7) lower ($C_{1-4}$,) alkoxy which may be substituted with halogen, hydroxy group or lower ($C_{1-4}$) alkoxy, (8) phenyl which may be substituted with halogen, lower ($C_{1-4}$) alkyl, hydroxy group, lower ($C_{1-4}$) alkoxy or $C_{1-3}$ alkylenedioxy, (9) mono- or di-phenyl-lower ($C_{1-4}$) alkyl whose benzene ring may be substituted with halogen, lower ($C_{1-4}$) alkyl, hydroxy group, lower ($C_{1-4}$) alkoxy or $C_{1-3}$ alkylenedioxy, (10) 5- to 6-membered aromatic heterocyclic ring such as furan, thiophene, pyrrole, pyridine, etc., etc.

In the above formula (I), examples of the "group binding through a sulfur atom" represented by $R^2$ include a group of the formula: —$S(O)_m$—$R^s$ wherein m is an integer of 0–2, and $R^s$ is a substituent.

In the above formula, preferred examples of the "substituent" represented by $R^s$ include (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted aralkyl (e.g. phenyl-$C_{1-4}$ alkyl (e.g. benzyl, phenethyl, etc.), etc.);

(4) an optionally substituted aryl (e.g. phenyl, naphthyl, etc.) etc.

Examples of the substituent, which the above-mentioned (1) optionally substituted alkyl, (2) optionally substituted cycloalkyl, (3) optionally substituted aralkyl and (4) an optionally substituted aryl may have, include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

In the above formula (I), examples of the "hydrocarbon group" in the "optionally substituted hydrocarbon group" represented by $R^5$ and $R^6$ of the "group of the formula:

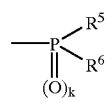

wherein k is 0 or 1, and when k is 0, a phosphorus atom may form a phosphonium; and $R^5$ and $R^6$ are independently an optionally substituted hydrocarbon group or an optionally substituted amino group, and $R^5$ and $R^6$ may bind to each other to form a cyclic group together with the adjacent phosphorus atom" represented by $R^2$ include (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted alkenyl (e.g. $C_{2-10}$ alkenyl such as allyl, crotyl, 2-pentenyl, 3-hexenyl, etc., preferably lower ($C_{2-6}$) alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(5) an optionally substituted alkynyl (e.g. $C_{2-10}$ alkynyl such as ethynyl, 1-propynyl, 2-propynyl, 1-butynyl, 2-pentynyl, 3-hexynyl, etc., preferably lower ($C_{2-6}$) alkynyl, etc.);

(6) an optionally substituted aralkyl (e.g. phenyl-$C_{1-4}$ alkyl (e.g. benzyl, phenethyl, etc.), etc.);

(7) an optionally substituted aryl (e.g. phenyl, naphthyl, etc.); etc.

Examples of the substituents, which the above-mentioned (1) optionally substituted alkyl, (2) optionally substituted cycloalkyl, (3) optionally substituted alkenyl, (4) optionally substituted cycloalkenyl, (5) optionally substituted alkynyl, (6) optionally substituted aralkyl and (7) optionally substituted aryl may have, include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

Examples of the optionally substituted amino group represented by $R^5$ and $R^6$ include an amino group which may have 1–2 substituents selected from (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted alkenyl (e.g. $C_{2-10}$ alkenyl such as allyl, crotyl, 2-pentenyl, 3-hexenyl, etc., preferably lower ($C_{2-6}$)alkenyl, etc.);

(4) an optionally substituted cycloalkenyl (e.g. $C_{3-7}$ cycloalkenyl such as 2-cyclopentenyl, 2-cyclohexenyl, 2-cyclopentenylmethyl, 2-cyclohexenylmethyl, etc., etc.);

(5) an optionally substituted acyl (e.g. $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.), etc.);

(6) an amino group which may have 1–2 optionally substituted aryl groups (e.g. phenyl, naphthyl, etc.); etc.

Examples of the substituent, which the above mentioned (1) optionally substituted alkyl, (2) optionally substituted cycloalkyl, (3) optionally substituted alkenyl, (4) optionally substituted cycloalkenyl, (5) optionally substituted acyl and (6) optionally substituted aryl may have, include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

In the above formula, the groups $R^5$ and $R^6$ may bind to each other to form a cyclic group (preferably, 5- to 7-membered ring) together with the adjacent phosphorus atom. Said cyclic group may have a substituent. Examples of the substituent include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

In the above formula (I), examples of the counter anion, when the phosphorus atom forms a phosphonium, include an anion of a halogen atom (e.g. $Cl^-$, $Br^-$, $I^-$, etc.), etc., and also an anion derived from an inorganic acid such as hydrochloric acid, hydrobromic acid, nitric acid, sulfuric acid, phosphoric acid, etc.; an anion derived from an organic acid such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.; an anion derived from an acidic amino acid such as aspartic acid, glutamic acid, etc.; etc. Among others, $Cl^-$, $Br^-$, $I^-$, etc. are preferable.

As the group $R^2$, (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group of the formula:

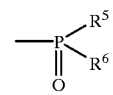

wherein $R^5$ and $R^6$ are independently an optionally substituted hydrocarbon group, and $R^5$ and $R^6$ may bind to each other to form a cyclic group together with the adjacent phosphorus atom, etc. are preferable.

In the above formula (I'), examples of the "optionally substituted hydrocarbon group" and the "optionally substituted amino group" represented by $R^{5'}$ and $R^{6'}$ in the "group of the formula:

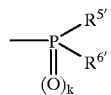

wherein k is 0 or 1, and when k is 0, a phosphorus atom may form a phosphonium; and $R^{5'}$ and $R^{6'}$ are independently an optionally substituted hydrocarbon group, an optionally substituted hydroxy group or an optionally substituted amino group, and $R^{5'}$ and $R^{6'}$ may bind to each other to form a cyclic group together with the adjacent phosphorus atom" represented by $R^2$ include those exemplified as the "optionally substituted hydrocarbon group" and the "optionally substituted amino group" represented by $R^5$ and $R^6$, respectively.

In the above formula (I'), examples of the "optionally substituted hydroxy group" represented by $R^{5'}$ and $R^{6'}$ include a hydroxy group which may-have (1) an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.);

(2) an optionally substituted cycloalkyl (e.g. $C_{3-7}$ cycloalkyl, etc. such as cyclopropyl, cyclobutyl, cyclopentyl, cyclohexyl, cycloheptyl, etc.);

(3) an optionally substituted alkenyl (e.g. $C_{2-10}$ alkenyl such as allyl, crotyl, 2-pentenyl,3-hexenyl, etc., preferably lower ( $C_{2-6}$)alkenyl, etc.);

(4) an optionally substituted cycloalkenyl (e.g. $C_{3-7}$ cycloalkenyl, etc. such as 2-cyclopentenyl, 2-cyclohexenyl, 2-cyclopentenylmethyl, 2-cyclohexenylmethyl, etc.);

(5) an optionally substituted aralkyl (e.g. phenyl-$C_{1-4}$ alkyl (e.g. benzyl, phenethyl, etc.), etc.);

(6) an optionally substituted acyl (e.g. $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.), etc.);

(7) an optionally substituted aryl (e.g. phenyl, naphthyl, etc.); etc.

Examples of the substituents, which the above-mentioned (1) optionally substituted alkyl, (2) optionally substituted cycloalkyl, (3) optionally substituted alkenyl, (4) optionally substituted cycloalkenyl, (5) optionally substituted aralkyl, (6) optionally substituted acyl and (7) optionally substituted aryl may have, include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

In the above formula, the groups $R^{5'}$ and $R^{6'}$ may bind to each other to form a cyclic group (preferably, 5- to 7-membered ring) together with the adjacent phosphorus atom. Said cyclic group may have a substituent. Examples of the substituent include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.), etc., and the number of the substituents are preferably 1 to 3.

In the above formula (I'), examples of the counter anion, when the phosphorus atom forms a phosphonium, include an anion of a halogen atom (e.g. $Cl^-$, $Br^-$, $I^-$, etc.), etc., and also an anion derived from an inorganic acid such as hydrochloric acid, hydrobromic acid, nitric acid, sulfuric acid, phosphoric acid, etc.; an anion derived from an organic acid such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.; an anion derived from an acidic amino acid such as aspartic acid, glutamic acid, etc.; etc. Among others, $Cl^-$, $Br^-$, $I^-$, etc. are preferable.

As the group $R^2$, (1) an optionally substituted amino group in which a nitrogen atom may form a quaternary ammonium is preferable, and a group of the formula:

—$N^+RR'R''$ wherein R, R' and R" are independently an optionally substituted aliphatic hydrocarbon group or an optionally substituted alicyclic heterocyclic ring group is more preferable.

Among the Compound (I), a compound of the formula:

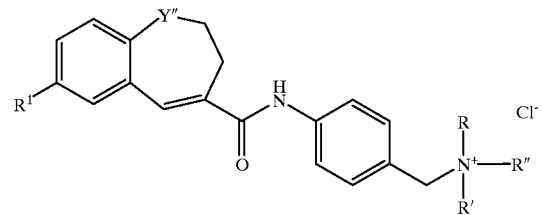

wherein $R^1$ is an optionally substituted benzene or an optionally substituted thiophene; Y" is —$CH_2$—, —S— or —O—; and R, R' and R" are independently an optionally substituted aliphatic hydrocarbon group or an optionally substituted alicyclic heterocyclic ring group is preferable.

Examples of the "optionally substituted aliphatic hydrocarbon group" and the "optionally substituted alicyclic heterocyclic ring group" represented by R, R' or R" include those exemplified by the substituents for the "optionally substituted amino" represented by $R^2$. Among them, as the group R or R', an optionally substituted acyclic hydrocarbon group is preferable, an optionally substituted $C_{1-6}$ alkyl group is more preferable, and methyl is most preferable; and as the group R", an optionally substituted alicyclic hydrocarbon group (more preferably, an optionally substituted $C_{3-8}$ cycloalkyl group; further more preferably, an optionally substituted cyclohexyl) or an optionally substituted alicyclic heterocyclic ring group (more preferably, an optionally substituted saturated alicyclic heterocyclic ring group (preferably 6-membered ring group); further more preferably, an optionally substituted tetrahydropyranyl, an optionally substituted tetrahydrothiopyranyl or an optionally substituted piperidyl; most preferably, an optionally substituted tetrahydropyranyl) is preferable.

Among the Compound (I), a compound of the formula:

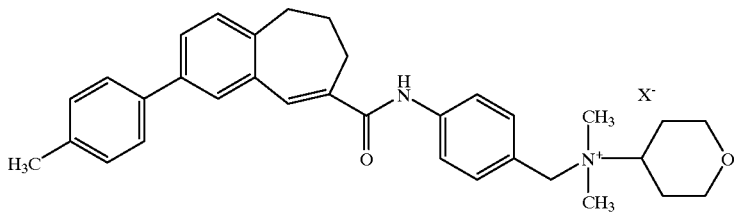

wherein X⁻ is an anion is preferable.

Examples of the anion include that of a halogen atom; that derived from an inorganic acid such as hydrochloric acid, hydrobromic acid, nitric acid, sulfuric acid, phosphoric acid, etc.; that derived from an organic acid such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.; that derived from an acidic amino acid such as aspartic acid, glutamic acid, etc.; etc. Among others, an anion of a halogen atom is preferable.

Among the Compound (I), the following compounds and their salts are preferable:

N-methyl-N-[4-[[[2-(4-methylphenyl)-6,7-dihydro-5H-benzocyclohepten-8-yl]carbonyl]amino]benzyl]-piperidinium iodide;

N-methyl-N-[4-[[[7-(4-methylphenyl)-2,3-dihydro-1-benzoxepin-4-y]carbonyl]amino]benzyl]piperidinium iodide;

N-[4-[N-methyl-N-(tetrahydropyran-4-yl)aminomethyl]-phenyl]-7-(4-methylphenyl)-2,3-dihydro-1-benzoxepine-4-carboxmide;

N-[4-[N-methyl-N-(tetrahydropyran-4-yl)aminomethyl]-phenyl]-7-(4-morpholinophenyl)-2,3-dihydro-1-benzoxepine-4-carboxmide;

7-(4-ethoxyphenyl)-N-[4-[N-methyl-N-(tetrahydropyran-4-yl)aminomethyl]phenyl]-2,3-dihydro-1-benzoxepine-4-carboxmide;

N,N-dimethyl-N-[4-[[[2-(4-methylphenyl)-6,7-dihydro-5H-benzocyclohepten-8-yl]carbonyl]amino]benzyl]-N-(tetrahydropyran-4-yl)ammonium iodide;

N,N-dimethyl-N-[4-[[[7-(4-methylphenyl)-2,3-dihydro-1-benzoxepin-4-yl]carbonyl]amino]benzyl]-N-(4-oxocyclohexyl)ammonium chloride;

N,N-dimethyl-N-[4-[[[7-(4-ethoxyphenyl)-2,3-dihydro-1-benzoxepin-4-yl]carbonyl]amino]benzyl]-N-(tetrahydropyran-4-yl)ammonium chloride;

N-methyl-N-[4-[[[7-(4-methylphenyl)-3,4-dihydro-naphthalen-2-yl]carbonyl]amino]benzyl]piperidinium iodide; etc.

Examples of the salts of the compound represented by the formula (I) [including the formula (I')] include a pharmaceutically acceptable salt such as a salt with inorganic base, a salt with organic base, a salt with inorganic acid, a salt with organic acid, a salt with basic or acidic amino acid, etc. Examples of the salt with the inorganic base include a salt with alkali metal (e.g. sodium, potassium, etc.), alkaline earth metal (e.g. calcium, magnesium, etc.), aluminum, ammonium, etc. Examples of the salt with the organic base include a salt with trimethylamine, triethylamine, pyridine, picoline, ethanolamine, diethanolamine, triethanolamine, dicyclohexylamine, N,N'-dibenzylethylenediamine, etc. Examples of the salt with the inorganic acid include a salt with hydrochloric acid, hydrobromic acid, nitric acid, sulfuric acid, phosphoric acid, etc. Examples of the salt with the organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Examples of the salt with the basic amino acid include a salt with arginine, lysine, ornithine, etc. Examples of the salt with the acidic amino acid include a salt with aspartic acid, glutamic acid, etc.

The compound of the formula (I) [including the formula (I')] of the present invention may be hydrated or solvated. When the compound of the formula (I) [including the formula (I')] of the present invention exists as configuration isomer, diastereomer, conformer, etc., it is possible to isolate individual isomers with per se known separation and purification method, if desired. When the compound of the formula (I) [including the formula (I')] of the present invention is racemate, it can be separated into (S)-compound and (R)-compound with usual optical resolution and individual optical isomers and a mixture thereof are included in the scope of the present invention.

The present compound of the formula (I) or a salt thereof (hereinafter, "Compound (I)" include the compound of the formula (I) and its salt; and also a compound of the formula (I') and its salt) alone or as an admixture with a pharmaceutically acceptable carrier (e.g. solid formulations such as tablets, capsules, granules, powders, etc.; liquid formulations such as syrups, injections, etc.) may be orally or non-orally administered.

Examples of non-oral formulations include injections, drops, suppositories, pessaryies, etc.

Examples of the carriers include various organic or inorganic carriers which are generally used in this field. For example, an excipient, a lubricant, a binder, an disintegrating agent, etc. are used in the solid formulations, and a solvent, a solubilizer, a suspending agent, a isotonizing agent, a buffer, a soothing agent, etc. are used in the liquid formulations. In addition, if desired, an appropriate additive such as a preservative, an antioxidant, a colorant, a sweetener, etc. may be used in the above formulations.

Examples of the excipient include lactose, sucrose, D-mannitol, starch, crystalline cellulose, light silic acid anhydride, etc. Examples of the lubricant include magnesium stearate, calcium stearate, talc, colloidal silica, etc. Examples of the binder include crystalline cellulose, sucrose, D-mannitol, dextrin, hydroxypropyl cellulose, hydroxypropylmethyl cellulose, polyvinylpyrrolidone, etc. Examples of the disintegrating agent include starch, carboxymethyl cellulose, carboxymethyl cellulose calcium, croscarmellose sodium, sodium carboxymethyl starch, etc. Examples of the solvent include water for injection, alcohol, propyleneglycol, macrogol, sesame oil, corn oil, etc. Examples of the solubilizer include polyethyleneglycol, propyleneglycol, D-mannitol, benzyl benzoate, ethanol, trisaminomethane, cholesterol, triethanolamine, sodium carbonate, sodium citrate, etc. Examples of the suspending agent include surfactants such as stearyl triethanolamine, sodium laurylsulfate, laurylaminopropionic acid, lecithin, benzalkonium chloride, benzetonium chloride, glycerin monostearate, etc.; hydrophilic polymers such as polyvinylalcohol, polyvinylpyrrolidone, sodium carboxymethyl cellulose, methyl cellulose, hydroxymethyl cellulose, hydroxyethyl cellulose, hydroxypropyl cellulose, etc.; etc. Examples of the isotonizing agent include sodium chloride, glycerin, D-mannitol, etc. Examples of the buffer include a buffer solution of phosphate, acetate, carbonate, citrate, etc. Examples of the soothing agent include benzylalcohol, etc. Examples of the preservative include paraoxybenzoic acid esters, chlorobutanol, benzylalcohol, phenethylalcohol, dehydroacetic acid, sorbic acid, etc. Examples of the antioxidant include sulfites, ascorbic acid, etc.

The present invention is further to provide a production method of a compound of the formula (I) or a salt thereof.

The compound of the formula (I) or a salt thereof can be produced in accordance with per se known methods, for example, the methods described below, the methods described in JP-A-73476/1996, or analogous methods thereto.

A salt of the compound of the formulas (I), (II), (III), (IV), (V), (I-1), (I-2) and (I-3) may be similar to that of the compound the formula (I).

In the following reaction steps, when the starting compounds have, as substituents, an amino group, a carboxyl group and/or hydroxy group, these groups may be protected by ordinary protective groups such as those generally employed in peptide chemistry, etc. After the reaction, if necessary, the protective groups may be removed to obtain the desired compound.

Examples of the amino-protective group include an optionally substituted $C_{1-6}$alkylcarbonyl (e.g. formyl, methylcarbonyl, ethylcarbonyl, etc.), phenylcarbonyl, $C_{1-6}$ alkyloxycarbonyl (e.g. methoxycarbonyl, ethoxycarbonyl, t-butoxycarbonyl, etc.), aryloxycarbonyl (e.g. phenoxycarbonyl, etc.), $C_{7-10}$ aralkyloxycarbonyl (e.g. benzyloxycarbonyl, etc.), trityl, phthaloyl, etc. These protective groups may be substituted by 1 to 3 substituents such as halogen atom (e.g. fluorine, chlorine, bromine, iodine, etc.), $C_{1-6}$ alkylcarbonyl (e.g. acetyl, propionyl, butyryl, etc.), nitro group, etc.

Examples of the carboxyl-protective group include an optionally substituted $C_{1-6}$ alkyl (e.g. methyl, ethyl, propyl, isopropyl, butyl, tert-butyl, etc.), phenyl, trityl, silyl, etc. These protective groups may be substituted by 1 to 3 substituents such as halogen atom (e.g. fluorine, chlorine, bromine, iodine, etc.), $C_{1-6}$ alkylcarbonyl (e.g. formyl, acetyl, propionyl, butyryl, etc.), nitro group, etc.

Examples of the hydroxy-protective group include an optionally substituted $C_{1-6}$ alkyl (e.g. methyl, ethyl, propyl, isopropyl, butyl, tert-butyl, etc.), phenyl, $C_{7-10}$ aralkyl (e.g. benzyl, etc.), $C_{1-6}$ alkylcarbonyl (e.g. formyl, acetyl, propionyl, etc.), phenyloxycarbonyl, $C_{7-10}$ aralkyloxycarbonyl (e.g. benzyloxycarbonyl, etc.), pyranyl, furanyl, silyl, etc. These protective groups may be substituted by 1 to 4 substituents such as halogen atom (e.g. fluorine, chlorine, bromine, iodine, etc.), $C_{1-6}$ alkyl, phenyl, $C_{7-10}$ aralkyl, nitro group, etc.

These protective group may be introduced or removed by per se known methods (e.g. a method described in Protective Groups in Organic Chemistry (J. F. W. McOmie et al.; Plenum Press Inc.) or the methods analogous thereto. For example, employable method for removing the protective groups is a method using an acid, a base, reduction, ultraviolet ray, hydrazine, phenylhydrazine, sodium N-methyldithiocarbamate, tetrabutylammonium fluoride, palladium acetate, etc.

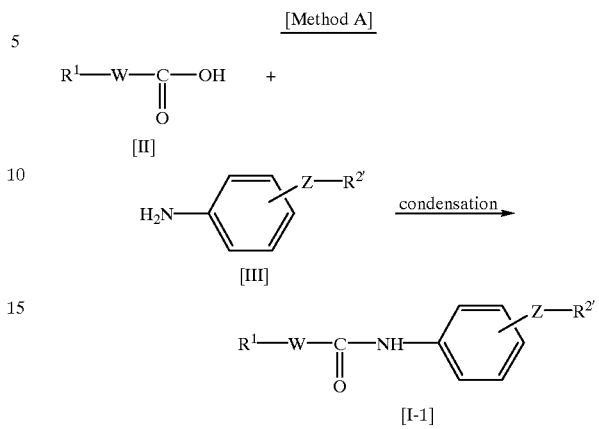

[Method A]

herein each symbol is as defined above.

This production method is carried out by reacting the compound [II] with the aniline derivative [III] to obtain the anilide Compound [I-1].

The condensation reaction of the compounds [II] and [III] is carried out by usual methods for peptide synthesis. Said methods for peptide synthesis are employed according to optional known methods, for example, methods described in "Peptide Synthesis" written by M. Bodansky and M. A. Ondetti, Interscience, New York, 1966; "The Proteins", volume 2, written by F. M. Finn and K. Hofmann, H. Nenrath and R. L. Hill edition, Academic Press Inc., New York, 1976; "peputido-gosei no kiso to jikken (Basis and Experiment of Peptide Synthesis)" written by Nobuo Izumiya et al., Maruzen K. K.,1985; etc., as well as azide method, chloride method, acid anhydride method, mixed acid anhydride method, DCC method, active ester method, method using Woodward reagent K, carbonyldiimidazole method, oxidation-reduction method, DCC/HONB method, etc. and in addition WSC method, method using diethyl cyanophosphate (DEPC), etc.

The condensation reaction can be carried out in a solvent. Examples of the solvents to be employed in the reaction include anhydrous or hydrous N,N-dimethylformamide (DMF), dimethylsulfoxide, pyridine, chloroform, dichloromethane, tetrahydrofuran, dioxane, acetonitrile, or a suitable mixture of these solvents. The reaction temperature is generally about −20° C. to about 50° C., preferably about −10° C. to about 30° C. and the reaction time is generally about 1 to about 100 hours, preferably about 2 to about 40 hours.

The thus obtained anilide derivative [I-1] can be isolated and purified by known separation and purification methods such as concentration, concentration under reduced pressure, extraction, crystallization, recrystallization, solvent convert, chromatography, etc.

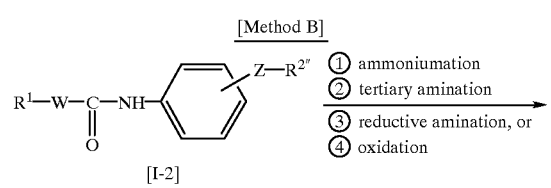

[Method B]

-continued

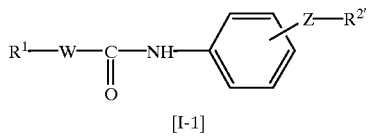

[I-1]

①̂ When the group $R^{2''}$ in Compound [I-2] is, for example, a tertiary amine residue, Compound [I-1] wherein the group $R^{2'}$ is an quaternary ammonium can be produced by reacting Compound [I-2] with halogenated alkyl or halogenated aralkyl. Examples of a halogen atom include chlorine, bromine, iodine, etc. and usually about 1 to 5 moles of the halogenated alkyl (e.g. halogenated lower ($C_{1-6}$) alkyl, etc.) or halogenated aralkyl (e.g. halogenated lower ($C_{1-4}$) alkyl-phenyl, etc.) is used per mole of Compound [I-2]. The reaction is carried out in an inert solvent such as toluene, benzene, xylene, dichloromethane, chloroform, 1,2-dichloroethane, dimethylformamide, dimethylacetamide, etc., or a suitable mixture of these solvents. The reaction temperature is generally about 10° C. to about 160° C., preferably about 20° C. to about 120° C. and the reaction time is generally about 1 hour to about 100 hours, preferably about 2 hours to about 40 hours. This reaction is preferably carried out under inert gas (e.g. nitrogen, argon, etc.) atmosphere.

②̂ When the group $R^{2''}$ in Compound [I-2] is, for example, a secondary amine residue, Compound [I-1] wherein the group $R^{2''}$ is a tertiary amino can be produced by reacting Compound [I-2] with halogenated alkyl or halogenated aralkyl. Examples of a halogen atom include chlorine, bromine iodine, etc. and usually about 1 to 2 moles of the halogenated alkyl or halogenated aralkyl is used per mole of Compound [I-2]. If necessary, the reaction smoothly proceeds by addition of about once to thrice moles of a base such as triethylamine, diisopropylethylamine, pyridine, lithium hydride, sodium hydride, sodium methoxide, sodium ethoxide, sodium carbonate, potassium carbonate, sodium hydrogen carbonate and further sodium iodide, potassium iodide, etc.

This tertiary amination reaction is carried out in an inert solvent such as methanol, ethanol, propanol, isopropanol, n-butanol, tetrahydrofuran, diethylether, dimethoxyethane, 1,4-dioxane, toluene, benzene, xylene, dichloromethane, chloroform, 1,2-dichloroethane, dimethylformamide (DMF), dimethylsulfoxide (DMSO), pyridine, etc., or a suitable mixture of these solvents. The reaction temperature is generally about 0° C. to 180° C., and the reaction time is generally about 1 hour to about 40 hours. This reaction is preferably carried out under inert gas (e.g. nitrogen, argon, etc.) atmosphere.

③̂ When the group $R^{2''}$ in Compound [I-2] is, for example, a secondary amine residue, Compound [I-1] wherein the group $R^{2'}$ is a tertiary amino can be produced by reacting Compound [I-2] with aldehyde compound in the presence of a reductive amination reagent such as triacetoxysodium boron hydride, cyanosodium boron hydride, sodium boron hydride, etc.

The conditions of this reductive amination reaction varies depending on the reagent to be used. For example, when triacetoxysodium boron hydride is used ,reaction is carried out in an inert solvent such as dichloromethane, chloroform, 1,2-dichloroethane, tetrahydrofuran, diethylether, dioxane, acetonitrile, dimethylformamide (DMF), etc., or a suitable mixture of these solvents. In this case, about 1 to 2 moles of the reagent is used per mole of Compound [I-2]. The reaction temperature is generally about 0° C. to about 80° C., and the reaction time is generally about 1 hour to about 40 hours. This reaction is preferably carried out under inert gas (e.g. nitrogen, argon, etc.) atmosphere.

④ When the group $R^{2''}$ in Compound [I-2] is, for example, a sulfide residue or a tertiary amine residue, Compound [I-1] wherein the group $R^{2'}$ is a sulfinyl group, a sulfonyl group or an amine oxide group can be produced by reacting Compound [I-2] with an oxidizing agent such as m-chloroperbenzoic acid, perbenzoic acid, p-nitroperbenzoic acid, magnesium monoperoxyphthalate, peracetic acid, hydrogen peroxide, sodium periodate, potassium periodate, etc. The conditions of this oxidation reaction varies depending on the oxidizing agent to be used. For example, when m-chloroperbenzoic acid is used, reaction is carried out in an inert solvent such as dichloromethane, chloroform, 1,2-dichloroethane, diethylether, tetrahydrofuran, acetone, ethyl acetate, etc., or a suitable mixture of these solvents. Usually, about 1–3 moles of oxidizing agent is used per mole of Compound [I-2]. The reaction temperature is generally about −25° C. to about 80° C. (preferably −25° C. to 25° C.), and the reaction time is generally about 1 hour to about 40 hours.

[Method C]

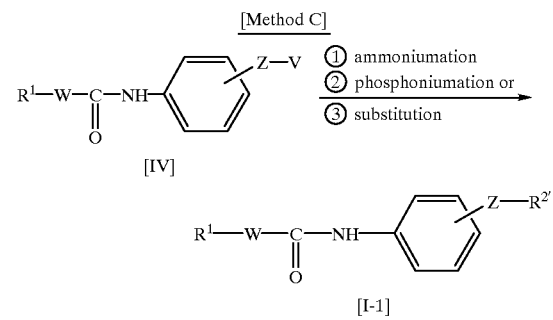

wherein V in the Compound [IV] is a halogen atom (chlorine, bromine, iodine, etc.), or a sulfonyloxy group (methanesulfonyloxy group, trifluoromethanesulfonyloxy group, benzenesulfonyloxy group, toluenesulfonyloxy group, etc.), and the other symbols are as defined above.

①̂ Compound [I-1] wherein the group $R^{2'}$ is a quaternary ammonium can be produced by reacting Compound [IV] and a tertiary amine. The reaction is carried out in an inert solvent such as toluene, benzene, xylene, dichloromethane, chloroform, 1,2-dichloroethane, dimethylformamide (DMF), dimethylacetamide, etc., or a suitable mixture of these solvents. Usually, about 1–3 moles of the tertiary amine is used per mole of Compound [IV]. The reaction temperature is generally about 10° C. to about 120° C., and the reaction time is generally about 1 hour to about 40 hours. This reaction is preferably carried out under inert gas (e.g. nitrogen, argon, etc.) atmosphere.

②̂ Compound [I-1] wherein the group $R^{2'}$ is a quaternary phosphonium can be produced by reacting Compound [IV] and a tertiary phosphine. The reaction is carried out in an inert solvent such as toluene, benzene, xylene, dichloromethane, chloroform, 1,2-dichloroethane, acetonitrile, dimethylformamide (DMF), or a suitable mixture of these solvents. Usually, about 1–2 moles of the tertiary phosphine is used per mole of Compound [IV]. The reaction temperature is generally about 20° C. to about 150° C., and the reaction time is generally about 1 hour to about 50 hours. This reaction is preferably carried out under inert gas (e.g. nitrogen, argon, etc.) atmosphere.

③̂ Compound [I-1] wherein the group $R^{2'}$ is a secondary or tertiary amino group or a thio group can be produced by reacting Compound [IV] and primary or secondary amine compound or thiol compound. Usually, about 1° C. to 3 moles of the primary or secondary amine compound or the thiol compound is used per mole of Compound [IV]. If necessary, the reaction smoothly proceeds by addition of about once to thrice moles of a base such as triethylamine, diisopropylethylamine, pyridine, lithium hydride, sodium hydride, sodium methoxide, sodium ethoxide, sodium carbonate, potassium carbonate, sodium hydrogen carbonate and further sodium iodide, potassium iodide, etc. This substitution reaction is carried out in an inert solvent such as methanol, ethanol, propanol, isopropanol, n-butanol, tetrahydrofuran, diethylether, dimethoxyethane, 1,4-dioxane, toluene, benzene, xylene, dichloromethane, chloroform, 1,2-dichloroethane, dimethylformamide (DMF),dimethylsulfoxide (DMSO), pyridine, etc., or a suitable mixture of these solvents. The reaction temperature is generally about −10° C. to about 180° C., and the reaction time is generally about 1 hour to about 40 hours. The reaction is carried out preferably under inert gas (e.g. nitrogen, argon, etc.) atmosphere.

[Method D]

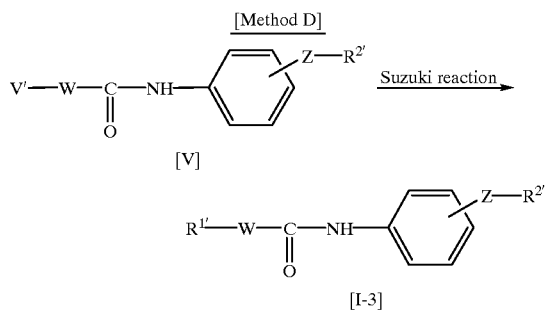

wherein V' is a halogen atom (bromine, iodine, etc.) or a sulfonyloxy group (trifluoromethanesulfonyloxy group, etc.), and the other symbols are as defined above.

Compound [I-3] wherein the group $R^{1'}$ is a 5- to 6-membered aromatic ring group can be produced by subjecting Compound [V] to, for example, Suzuki reaction [cross condensation reaction of aryl borate with e.g. aryl halide or aryloxy trifluoromethanesulfonate in the presence of palladium catalyst; A. Suzuki et al., Synth. Commun. 1981, 11, 513]. Usually, about 1–1.5 times moles of aryl borate is used per mole of Compound [V].

Compound [II] used as a starting material can be produced by a known method (e.g. method described in JP-A-73476/1996, etc.) or the methods analogous thereto. For example, Compound [II] can be produced by a method described in the following Reaction Scheme I, a method described in the following Reference Examples or the methods analogous thereto.

Reaction Scheme I

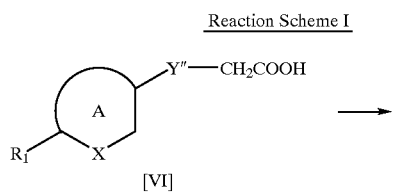

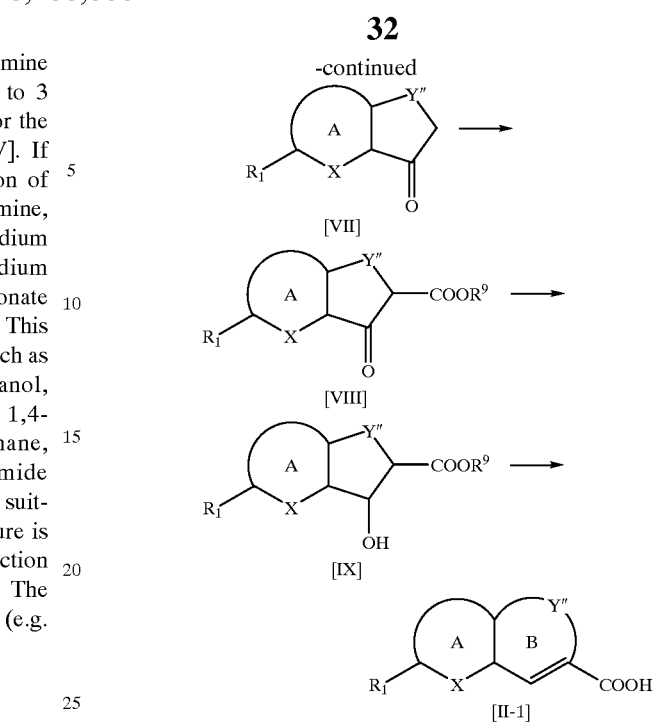

wherein $R^9$ is a $C_{1-4}$ alkyl group, Y″ is a divalent group, which does not contain a unsaturated bond and by which the ring B forms a 5- to 7-membered ring, and the other symbols are as defined above.

In this reaction, the compound of the formula [VI] is heated with a polyphosphoric acid, or Compound [VI] is converted to acid chloride with thionyl chloride, oxalyl chloride, phosphorous oxychloride, phosphorous pentachloride, etc., followed by subjecting the resulting acid chloride to usual Friedel-Crafts reaction and cyclizing the same to produce Compound [VII]. Compound [VII] is reacted with carbonate ester in the presence of a base to produce ketoester [VIII]. Compound [VIII] is subjected to reduction with catalytic hydrogenation or sodium boron hydride, etc. to produce Compound [IX]. Compound [IX] is subjected to dehydration and ester hydrolysis by per se known method to produce unsaturated carboxylic acid [II-1].

Compound [III] can be produced by a known method (e.g. method described in JP-A-73476/1996, etc.) or the methods analogous thereto. For example, Compound [III] can be produced by a method described in the following Reaction Scheme II, a method described in the following Reference Examples or the methods analogous thereto.

Reaction Scheme II

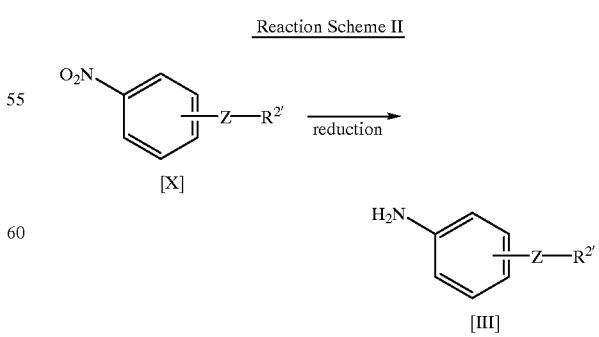

The reduction of Compound [X] can be carried out per se known methods, for example, reduction with metal, reduction with metal hydride, reduction with metal hydride complex compound, reduction with diborane or substituted borane, catalytic hydrogenation, etc. That is, this reaction is carried out by treating Compound [X] with reduction agent. Examples of the reduction agent include metal such as reduced iron, zinc powder, etc.; alkali metal boron hydride (e.g. sodium boron hydride, lithium boron hydride, etc.); metal hydride complex compound such as aluminum lithium hydride, etc.; metal hydride such as sodium hydride etc.; organic tin compound (triphenyltin hydride, etc.), metal complex compound and metal salt such as nickel compound, zinc compound etc.; catalytic reduction agent using hydrogen and transit metal catalyst such as palladium, plutinum, rhodium, etc.; diborane; etc. Among others, as the reduction agent, catalytic reduction agent using hydrogen and transit metal catalyst such as palladium, plutinum, rhodium, etc.; reduced iron, etc. are preferable. The reaction is carried out in a solvent which does not affect the reaction. Examples of the solvent include benzene, toluene, xylene, chloroform, carbon tetrachloride, dichloromethane, 1,2-dichloroethane, 1,1,2,2-tetrachloroethane, diethylether, tetrahydrofuran, dioxane, methanol, ethanol, propanol, isopropanol, 2-methoxyethanol, N,N-dimethylformamide, acetic acid, or a suitable mixture of these solvents, etc. The solvent is appropriately selected depending on kind of the reduction agent. The reaction temperature is generally about $-20°$ C. to about $150°$ C., preferably about $0°$ C. to about $100°$ C., and the reaction time is generally about 1 to about 24 hours.

The resulting Compound [III] can be separated and purified with know separation and purification methods such as concentration, concentration under reduced pressure, extraction, crystallization, was recrystallized with, solvent conversion, chromatography, etc.

The compound of the formula (I) or a salt thereof of the present invention has potent antagonistic activity on MCP-1 receptor and therefore can be used for the treatment or prophylaxis of various inflammatory diseases, cardiac infarction, myocarditis, etc. in human and animals (e.g. mouse, rat, cat, dog, rabbit, bovine, swine, etc.). The compound of the formula (I) or a salt thereof of the present invention is low toxic and safely used as MCP-1 receptor antagonist (e.g. a medicament for the treatment or prophylaxis of cardiac infarction, myocarditis, etc.).

The dose per day of the compound of the formula (I) or a salt thereof varies depending on the condition and body weight of a patient, administration route, etc. Typical daily dose per adult patient (body weight: 50 Kg) for oral administration is about 5–100 mg, preferably about 10–600 mg, and in particular about 15–150 mg, as active ingredient [the compound of the formula (I) or a salt thereof] and the compound of the formula (I) or a salt thereof is administered once or 2–3 times par day.

BEST MODE FOR CARRYING OUT THE INVENTION

The present invention is hereinafter described in more detail by means of the following Test Example, Reference Example and Working Example, which are mere examples of the present invention and are not construed as limitative to the present invention.

TEST EXAMPLE 1
Determination of Inhibitory Activity on MCP-1 Receptor

According to a method described in Working Example 1 of JP-A-238688/1997, human MCP-1 receptor gene was prepared. Said gene was inserted to plasmid pMCR, which was introduced into CHO cell. The resultant transformant [CHO(MCR); FERM BP-5446; IFO 50461] was used for the following experiment.

On 96 well culture plate (Packard Instrument Company), $7\times10^4$ cell/well of CHO cells expressing human MCP-1 receptor were inoculated, and the cells were cultivated at $37°$ C. overnight. The medium was removed by means of suction. To the residue were added a buffer solution (D-MEM containing 0.5% BSA and 20 mM HEPES; pH7.4), Test Compound (1 $\mu$M) and $^{125}$I-human recombinant MCP-1 (Amersham; final concentration: 100 pM), and the mixture was allowed to react at room temperature for 40 minutes. The buffer solution was removed by means of suction and washed twice with PBS. To the residue was added MICROSCINT-20 (Packard Instrument Company), radioactivity of $^{125}$I (cpm) was determined with Topcount (Packard).

The count number (cpm) (non-specific binding) of $^{125}$I which binds to CHO cells (mock) having a vector was taken from the count number (cpm) of $^{125}$I which binds to CHO cells expressing human MCP-1 receptor to obtain the amended count number, which was converted into 100%, and inhibition rate of Test Compound (whose number is referred to in the following Examples) against MCP-1 binding to its receptor was calculated. The results are shown in Table 1.

TABLE 1

| Compound Number | Inhibition Rate (%) |
| --- | --- |
| 16 | 89 |
| 72 | 77 |
| 94 | 92 |
| 97 | 96 |
| 128 | 80 |
| 151 | 80 |
| 178 | 64 |
| 220 | 98 |

TEST EXAMPLE 2
Chemotaxis Inhibition Assay

To a lower chamber of 96 well chemotaxis chamber (Neuro Probe, AB96) was added a solution of 20 nM MCP-1 (chemotaxis inducer) in buffer (D-MEM containing 0.5% BSA and 20 mM HEPES; pH7. 4), and the chamber was covered by a filter coated with bovine fibronectin. To its upper chamber were added CHO cells expressing human MCP-1 receptor ($2\times10^5$ cell/well) and Test Compound (1 $\mu$M), followed by incubation at $37°$ C. in 5% $CO_2$ for 4 hours. The cells migrated under the filter was stained with Diff Quick, and absorbance at 600 nm of wave length (O.D at 600 nm) was determined by microplate reader. The absorbance in the absence of MCP-1 in the lower chamber was taken from the absorbance in the presence of MCP-1 in the lower chamber to obtain the amended absorbance ($\Delta$O.D, chemotaxis induced by MCP-1), which was converted into 100%, and chemotaxis inhibition rate of Test Compound was calculated.

The results are shown in Table 2.
2 A drug containing about 10–300 mg of the compound of the formula (I') or a salt thereof and a drug containing about 300–1200 mg of saquinavir to one adult patient (body weight: 50 Kg) are administered. Each of the drugs may be administered to the one and the same subject simultaneously or with time intervals of 12 hours or less.

BEST MODE FOR CARRYING OUT THE INVENTION

The present invention is hereinafter described in more detail by means of the following Test Example, Reference Example and Working Example, which are mere examples of the present invention and are not construed as limitative to the present invention.

The following gene manipulation is carried out in accordance with methods described in textbook (Maniatis et al., Molecular Cloning, Cold Spring Harbor Laboratory, 1989) or protocol attached to reagents.

TEST EXAMPLE (1) Cloning of Human CCR5 Chemokine Receptor

Cloning of CCR5 gene was carried out by PCR (polymerase chain reaction) from human spleen cDNA. With using 0.5 ng of spleen cDNA (Toyobo, QUICK-Clone cDNA) as template, PCR was performed in DNA Thermal Cycler 480 (Perkin-Elmer) (reaction conditions: 30 cycles of 95° C. for 1 minute, 60° C. for 1 minute, and 75° C. for 5 minutes) by adding primer set, 5'-CAGGATCCGATG GATTATCAAGTGTCAAGTCCAA-3' (25 pmol) and 5'-TCTAGATCACAAGCC CACAGATATTTCCTGCTCC-3' (25 pmol), which were designed referring to nucleotide sequence of CCR5 gene reported by Samson et al. (Biochemistry, 35(11), 3362–3367 (1996)) and by using TaKaRa EX Taq (Takara Shuzo). The resultant PCR product was subjected to agarose gel electrophoresis to collect about 1.0 kb DNA fragment, which was subjected to Original TA Cloning Kit (Funakoshi) to carry out cloning of CCR5 gene.

(2) Preparation of Plasmid for Expression of Human CCR5

The plasmid obtained in the above (1) was digested with restriction enzymes XbaI (Takara Shuzo) and BamHI (Takara Shuzo) and subjected to agarose gel electrophoresis to collect about 1.0 kb DNA fragment. The DNA fragment was mixed with plasmid pcDNA3.1 (Funakoshi) for expression in animal cells, said plasmid being digested with XbaI and BamHI, and they were ligated with DNA Ligation Kit Ver.2 (Takara Shuzo). The resulting plasmid was subjected to transformation of competent cell of E. coli JM109 (Takara Shuzo) to obtain plasmid pCKR5.

(3) Introduction of Dlasmid for Expression of Human CCR5 into CHO-K1 Cell and Expression of said Plasmid in CHO-K1 Cell CHO-K1 cells were grown in 750 ml of tissue culture flask (Becton Dickinson) using Ham's F12 medium (Nihon Pharmaceutical) containing 10% fetal calf serum (Life Tech Oriental) and took off with 0.5 g/L trypsin-0.2 g/L EDTA (Life Tech Oriental). The cells were washed with PBS (Life Tech Oriental), centrifuged (1000 rpm, 5 minutes), and suspended in PBS. With using Gene Pulser (Bio-Rad Laboratories), DNA was introduced into the cells under the conditions shown below. That is, to the cuvette of 0.4 cm gap were added $8 \times 10^6$ cells and 10 μg of plasmid pCKR5 for expression of human CCR5, and electroporation was carried out under 0.25 kV of voltage and 960 μF of capacitance. The cells were transferred into Ham's F12 medium (Nihon Pharmaceutical) containing 10% fetal calf serum, and cultivated for 24 hours. The cells were again took off and centrifuged, and suspended in Ham's F12 medium (Nihon Pharmaceutical) containing 10% fetal calf serum and 500 μg/ml of geneticin (Life Tech Oriental). The suspension was diluted to give $10^4$ cells/ml of the suspension, which was inoculated on 96 well plate (Becton Dickinson) to give geneticin resistant cells. The resulting geneticin resistant cells were cultivated in 96 well plate (Becton Dickinson), and cells expressing CCR5 were selected from the geneticin resistant cells. That is, in assay buffer (Ham's F12 medium containing 0.5% BSA and 20 mM HEPES (Wako Pure Chemical, pH7.2) to which was added 200 pM of [$^{125}$I]-RANTES (Amersham) as ligand, binding reaction was carried out at room temperature for 40 minutes, and the buffer was washed with cooled PBS. To the buffer was added 50 μl/well of 1M NaOH, and the mixture was stirred. Radioactivity was determined with γ-counter to select CHO/CCR5 cells which specifically bind to the ligand.

(4) Evaluation of Test Compounds based on CCR5 Antagonistic Activity

The CHO/CCR5 were inoculated on 96 well microplate ($5 \times 10^4$ cells/well) and cultivated for 24 hours. The medium was removed by means of suction, and to each well was added assay buffer containing Test Compound (1 μM) and then 100 pM of [$^{125}$I]-RANTES (Amersham) as ligand. Binding assay was carried out at room temperature for 30 minutes, and assay buffer was removed by means of suction. Each well was washed twice with cooled PBS, and 200 μl of Microscint-20 (Packard Instrument, Inc.) was added to each well. Radio-activity was determined with Top-Count Micro Scintillation Counter (Packard Instrument, Inc.).

According to the method described above, inhibition rate of Test Compound (whose number is referred to in the following Examples) to CCR5 binding.

The results are shown in Table 1.

TABLE 1

| Compound Number | Inhibition Rate (%) |
|---|---|
| 16 | 88 |
| 92 | 100 |
| 96 | 93 |
| 97 | 94 |
| 100 | 100 |
| 128 | 87 |
| 180 | 99 |
| 209 | 80 |
| 248 | 99 |
| 249 | 96 |
| 250 | 96 |
| Ref Ex 51 | 73 |

(5) Inhibitory Effect on HIV-1 Infection to MAGI-CCR5 Cell

The plasmid where β-galactosidase gene was ligated downstream of HIV-1 LTR was introduced into CD4 positive HeLa cell, to which human CCR5 was further introduced to obtain transformant MAGI-CCR5. By using said transformant MAGI-CCR5, degree of HIV-1 infection was calculated from β-galactosidase activity (blue color due to decomposition of 5-bromo-4-chloro-3-indolyl-β-D-galactopyranoside). Specifically, MAGI-CCR5 cells were suspended in DMEM medium containing 10% serum to prepare $5 \times 10^4$ cells/ml suspension. To each well of 96 well plate was inoculated 200 μl of the suspension, and the cells were cultivated at 37° C. overnight. The medium was removed by means of suction, and to the residue was added 100 μl of the above medium containing 1.6 μM of Test Compound 96 or 0.064 μM of Test Compound 248 and 100 μl of the above medium containing 300PFU of HIV-1 BA-L cells. The cells were cultivated at 37° C. for 2 days. The medium was removed by means of suction. To the residue was added 200 μl of cell fixative (PBS containing 1% formaldehyde and 0.2% glutaraldehyde), and the mixture was allowed to stand at room temperature for 5 minutes and washed twice with PBS. To the mixture was added 100 μl of staining solution (PBS containing 4 μM potassium ferrocyanide, 4 μM potassium ferricyanade, 2 μM $MgCl_2$ and 0.4 mg/ml X-gal), and the mixture was allowed to stand at 37° C. for 50 minutes and washed twice with PBS. The number of blue cells was counted by microscope and defined as the number of cells infected with HIV-1. According to this method, inhibition rate on HIV-1 infection was determined and found that Compounds 96 and 248 respectively show 92% and 100% inhibition on HIV-1 infection.

(6) Inhibitory Effect on HIV-1 Infection to Human PBMC

From normal person human peripheral blood mononuclear cells (PBMC) were separated, and the cells were stimulated with 10 μg/ml of PHA (Phytohemaglutinin) and 20U/ml of interleukin-2 (IL-2) for 3 days. The cells were suspended in RPMI-1640 medium containing 20% serum to prepare $1 \times 10^6$/ml suspension. To the suspension were infected HIV-1 BA-L cells (20 ng as an amount of p24 antigen), and viruses were absorbed at 37° C. for 2 hours. The cells were washed and suspended in RPMI-1640 medium containing 20% serum and IL-2 20U/ml to prepare $1 \times 10^5$/ml suspension. To the PBMC suspension was added the same amount of a solution which contains 2.0 μM of Test Compound 96 or 0.32 μM of Test Compound 248, and the cells were cultivated at 37° C. for 7 days in carbon dioxide gas incubator. The amount of p24 antigen in supernatant of the cultivated medium was determined by enzyme-linked immunosorbent assay (ELISA) and defined as degree of HIV-1 infection. According to this method, inhibition rate on HIV-1 infection was determined and found that Compounds 96 and 248 respectively show 96% and 74% inhibition on HIV-1 infection.

The pharmaceutical composition for antagonizing CCR5 (e.g. a medicament for the treatment or prophylaxis of infectious disease of HIV, a medicament for the treatment or prophylaxis of AIDS, etc.) comprising the compound of the formula (I') or a salt thereof of the present invention, as an active ingredient, can be prepared, for example, by the following prescriptions:

1. Capsule

| | |
|---|---|
| (1) Compound obtained in Working Example 128 | 40 mg |
| (2) lactose | 70 mg |
| (3) fine crystalline cellulose | 9 mg |
| (4) magnesium stearate | 1 mg |
| 1 capsule | 120 mg |

(1), (2), (3) and ½ of (4) are mixed and then granulated. To the granules is added the remainder of (4), and the whole is filled into a gelatin capsule.

2. Tablet

| | |
|---|---|
| (1) Compound obtained in Working Example 128 | 40 mg |
| (2) lactose | 58 mg |
| (3) corn starch | 18 mg |
| (4) fine crystalline cellulose | 3.5 mg |
| (5) magnesium stearate | 0.5 mg |
| 1 tablet | 120 mg |

(1), (2), (3), ⅔ of (4) and ½ of (5) are mixed and then granulated. To the granules are added the remainders of (4) and (5), followed by subjecting the mixture to compression molding.

3. Injection

A mixture of Compound obtained in Working Example 248 (500 mg), mannitol (1000 mg) and polysorbate 80 (100 mg) is dissolved in distilled water (10 ml), and to the solution is added distilled water to make the whole volume 20 ml. The solution is filtered under sterile conditions. Each 2 ml of the solution is filled into a vial for injection under sterile conditions.

WORKING EXAMPLE

REFERENCE EXAMPLE 1

In THF (50 ml) was dissolved 4-nitrobenzylchloride (5.00 g), and piperidine (6.20 g) was added to the mixture. The reaction mixture was stirred at room temperature for 20 hours. To the mixture was added water (500 ml), and the mixture was extracted with ethyl acetate. The organic layer was washed with saturated sodium chloride solution, dried with anhydrous sodium sulfate and concentrated under reduced pressure. The residue was separated and purified with column chromatography (ethyl acetate/hexane=1/2) to give 1-(4-nitrobenzyl)piperidine (6.41 g) as pale yellow oil. $^1$H NMR (200 MHz, CDCl$_3$) δ: 1.38–1.70 (6H, m), 2.30–2.45 (4H, m), 3.55 (2H, s), 7.51 (2H, d, J=8.8 Hz), 8.17 (2H, d, J=8.8 Hz).

REFERENCE EXAMPLE 2

In ethanol(50 ml) was dissolved 1-(4-nitrobenzyl)-hydrochloric acid to the aqueous layer and extracted with ethyl acetate. The organic layer was washed with saturated sodium chloride solution, dried with anhydrous sodium sulfate and concentrated under reduced pressure. The residue was recrystallized from ethanol-water to give 7-phenyl-3,4-dihydronaphthalene-2-carboxylic acid (7.47 g) as brown crystals.

mp 204–208° C.; $^1$H NMR (200 MHz, CDCl$_3$) δ: 2.61–2.73 (2H, m), 2.88–3.00 (2H, m), 7.23–7.60 (8H, m), 7.74 (1H, s).

REFERENCE EXAMPLE 10

In THF (250 ml) was dissolved 4-nitrobenzylbromide (25.0 g), and to the mixture was added morpholine (25.2 ml) at 0° C. The reaction mixture was stirred for 15 hours at room temperature. To the mixture was added water (500 ml), and the mixture was extracted with ethyl acetate. The organic layer was washed with saturated sodium chloride solution, dried with anhydrous sodium sulfate and concentrated under reduced pressure. The residue was separated and purified with column chromatography (ethyl acetate) to give 4-(4-nitrobenzyl)morpholine (25.5 g) as pale yellow crystals. A portion of the crystals was recrystallized from diisopropylether to give pale yellow crystals which were used for various analyses. mp 79–80° C.

Elemental Analysis for $C_{11}H_{14}N_2O_3$; Calcd: C, 59.45; H, 6.35; N, 12.60. Found: C, 59.68; H, 6.25; N, 12.75. IR (KBr) cm$^{-1}$: 3350, 1518, 1344, 1111, 1009, 864, 744; $^1$H NMR (200 MHz, CDCl$_3$) δ: 2.37–2.55 (4H, m), 3.59 (2H, s), 3.65–3.80 (4H, m), 7.53 (2H, d, J=8.4 Hz), 8.18 (2H, d, J=8.4 Hz).

REFERENCE EXAMPLE 11

In ethanol (300 ml) was dissolved 4-(4-nitrobenzyl)-morpholine (25.8 g), and to the mixture was added dried 10% palladium on carbon (Pd—C) (1.00 g). Under hydrogen atmosphere, the mixture was stirred at room temperature under atmospheric pressure for 20 hours. The palladium was filtered off, and the filtrate was concentrated. The residue was separated and purified with column chromatography (ethyl acetate) to give 4-(4-aminobenzyl)-morpholine (430 mg) as pale yellow crystals.

mp 98–99° C.; Elemental Analysis for $C_{11}H_{16}N_2O$; Calcd: C, 68.72; H, 8.39; N, 14.57. Found: C, 68.57; H, 8.25; N, 14.59. IR (KBr) cm$^{-1}$: 3350, 2804, 1635, 1516, 1282, 1111, 1005, 860; $^1$H NMR (200 MHz, CDCl$_3$) δ: 2.32–2.52 (4H, m), 3.39 (2H, s), 3.45–3.80 (6H, m), 6.64 (2H, d, J=8.2 Hz), 7.09 (2H, d, J=8.2 Hz).

REFERENCE EXAMPLE 12

In THF (250 ml) was dissolved 4-nitrobenzyl bromide (25.0 g), and to the mixture was added pyrrolidine (24.1 ml)

at 0° C. The reaction mixture was stirred at room temperature for 60 hours. To the mixture was added water (500 ml), and the mixture was extracted with ethyl acetate. The organic layer was washed with saturated sodium chloride solution, dried with anhydrous sodium sulfate, and concentrated under reduced pressure. The residue was separated and purified with column chromatography (ethyl acetate) to give 1-(4-nitrobenzyl)pyrrolidine (23.5 g) as orange oil.

$^1$H NMR (200 MHz, CDCl$_3$) δ: 1.75–1.85 (4H, m), 2.43–2.58 (4H, m), 3.71 (2H, s), 7.51 (2H, d, J=8.6 Hz), 8.18 (2H, d, J=8.6 Hz).

REFERENCE EXAMPLE 13

In ethanol (100 ml) was dissolved 1-(4-nitrobenzyl)-pyrrolidine (23.5 g), and to the mixture was added dried 10% palladium on carbon (1.00 g). Under hydrogen atmosphere, the mixture was stirred at room temperature under atmospheric pressure for 20 hours. The palladium was filtered off, and the filtrate was concentrated. The residue was separated and purified with column chromatography (ethyl acetate/triethylamine=10/1) to give 1-(4-aminobenzyl)pyrrolidine (8.54 g) as orange oil.

$^1$H NMR (200 MHz, CDCl$_3$) δ: 1.60–1.90 (4H, m), 2.35–2.55 (4H, m), 3.45–3.70 (4H, m), 6.64 (2H, d, J=8.4 Hz), 7.11 (2H, d, J=8.4 Hz).

REFERENCE EXAMPLE 14

In THF (250 ml) was dissolved 4-nitrobenzyl bromide (25.0 g), and to the mixture was added 50% dimethylamine solution (29 ml) at 0° C. The reaction mixture was stirred at room temperature for 60 hours. To the mixture was added water (500 ml), and the mixture was extracted with ethyl acetate. The organic layer was washed with saturated sodium chloride solution, dried with anhydrous sodium sulfate, and concentrated under reduced pressure. The residue was separated and purified with column chromatography (ethyl acetate) to give dimethyl-4-nitrobenzylamine (20.7 g) as orange oil.

$^1$H NMR (200 MHz, CDCl$_3$) δ: 2.26 (6H, s), 3.52 (2H, s), 7.50 (2H, d, J=8.8 Hz), 8.19 (2H, d, J=8.8 Hz).

REFERENCE EXAMPLE 15

In ethanol (100 ml) was dissolved dimethyl-4-nitrobenzylamine (20.7 g), and to the mixture was added dried 10% palladium on carbon (1.00 g). Under hydrogen atmosphere, the mixture was stirred at room temperature under atmospheric pressure for 20 hours. The palladium was filtered off, and the filtrate was concentrated. The residue was separated and purified with column chromatography (ethyl acetate) to give 4-aminobenzyl-dimethylamine (8.75 g) as pale yellow oil.

$^1$H NMR (200 MHz, CDCl$_3$) δ: 2.21 (6H, s), 3.31 (2H, s), 3.53–3.70 (2H, br), 6.65 (2H, d, J=8.4 Hz), 7.08 (2H, d, J=8.4 Hz).

REFERENCE EXAMPLE 16

In THF (250 ml) was dissolved 3-nitrobenzyl chloride (25.0 g), and to the mixture was added piperidine (36 ml). The reaction mixture was stirred at room temperature for 20 hours. To the mixture was added water (500 ml), and the mixture was extracted with ethyl acetate. The organic layer was washed with saturated sodium chloride solution, dried with anhydrous sodium sulfate, and concentrated under reduced pressure. The residue was separated and purified with column chromatography (ethyl acetate) to give 1-(3-nitrobenzyl)piperidine (32.2 g) as pale yellow oil.

$^1$H NMR (200 MHz, CDCl$_3$) δ: 1.40–1.66 (6H, m), 2.33–2.44 (4H, m), 3.54 (2H, s), 7.47 (1H, t, J=8.0 Hz), 7.67 (1H, d, J=8.0 Hz), 8.10 (1H, d, J=8.0 Hz), 8.20 (1H, s).

REFERENCE EXAMPLE 17

In ethanol (100 ml) was dissolved 1-(3-nitrobenzyl)-piperidine (32.2 g), and to the mixture was added dried 10% palladium on carbon (1.61 g). Under hydrogen atmosphere, the mixture was stirred at room temperature under atmospheric pressure for 24 hours. The palladium was filtered off, and the filtrate was concentrated. The residue was recrystallized from diisopropylether-hexane to give 1-(3-aminobenzyl)piperidine (15.8 g) as colorless crystals.

mp 109–110° C.; Elemental Analysis for C$_{12}$H$_{18}$N$_2$; Calcd: C, 75.74; H, 9.53; N, 14.72. Found: C, 75.81; H, 9.13; N, 14.87. IR (KBr) cm$^{-1}$: 3398, 3184, 2948, 1643, 1606, 1454, 1302, 1101, 995, 795, 775, 698; $^1$H NMR (200 MHz, CDCl$_3$) δ: 1.35–1.65 (6H, m), 2.25–2.45 (4H, m), 3.38 (2H, s), 3.50–3.75 (2H, br), 6.57 (1H, brd, J=7.9 Hz), 6.65–6.75 (2H, m), 7.08 (1H, t, J=7.9 Hz).

REFERENCE EXAMPLE 18

In DMF (100 ml) was dissolved 4-(2-bromoethyl) nitrobenzene (25.0 g), and to the solution were added piperidine (12.9 ml) and potassium carbonate (18.0 g). The mixture was stirred at 70° C. for 15 hours, and to the mixture was added water (900 ml), and then the mixture was extracted with ethyl acetate. The organic layer was washed with saturated sodium chloride solution, dried with anhydrous sodium sulfate, and concentrated under reduced pressure. The residue was separated and purified with column chromatography (ethyl acetate) to give 1-[2-(4-nitro-phenyl) ethyl]piperidine (24.8 g) as orange oil.

$^1$H NMR (200 MHz, CDCl$_3$) δ: 1.39–1.75 (6H, m), 2.35–2.65 (6H, m), 2.85–3.00 (2H, m), 7.36 (2H, d, J=8.8 Hz), 8.14 (2H, d, J=8.8 Hz).

REFERENCE EXAMPLE 19

In ethanol (100 ml) was dissolved 1-[2-(4-nitrophenyl) ethyl]piperidine (24.8 g), and to the mixture was added dried 10% palladium on carbon(1.24 g). Under hydrogen atmosphere, the mixture was stirred at room temperature under atmospheric pressure for 86 hours. The palladium was filtered off, and the filtrate was concentrated to give 1-[2-(4-aminophenyl)ethyl]-piperidine (21.7 g) as pale brown oil.

$^1$H NMR (200 MHz, CDCl$_3$) δ: 1.40–1.80 (6H, m), 2.35–2.60 (6H, m), 2.60–2.80 (2H, m), 3.40–3.70 (2H, br), 6.62 (2H, d, J=8.4 Hz), 7.00 (2H, d, J=8.4 Hz).

REFERENCE EXAMPLE 20

In methanol (35 ml) was dissolved 7-phenyl-3,4-dihydro-naphthalene-2-carboxylic acid (1.50 g), and to the mixture was added concentrated sulfuric acid (0.1 ml), and then the mixture was refluxed for 9 hours. The reaction mixture was cooled to room temperature, and to the mixture was added 5% sodium hydrogen carbonate solution, and then the mixture was extracted with ethyl acetate. The organic layer was washed with saturated sodium chloride solution, dried with anhydrous sodium sulfate, and concentrated under reduced pressure. The residue was dissolved in ethyl acetate (100 ml), and to the mixture was added activated manganese dioxide (9 g). The mixture was refluxed for 48 hours and then cooled to room temperature. The manganese dioxide was filtered off, and the filtrate was concentrated. The residue was dissolved in methanol (15 ml), and to the mixture was added 1N sodium hydroxide (10 ml). The mixture was refluxed for 4 hours and then cooled to room temperature. The mixture was acidified with dilute hydrochloric acid, and extracted with ethyl acetate. The organic layer was washed with saturated sodium chloride solution, dried with anhydrous sodium sulfate, and concentrated under reduced pressure. The residue was recrystallized from ethyl acetate-diisopropylether to give 7-phenylnaphthalene-2-carboxylic acid (783 mg) as colorless crystals.

mp 244–245° C.; Elemental Analysis for $C_{17}H_{12}O_2$; Calcd: C, 82.24; H, 4.87. Found: C, 82.10; H, 4.85. IR (KBr) cm$^{-1}$: 3053, 1701, 1684, 1429, 1302, 860, 756, 696; $^1$H NMR (200 MHz, CDCl$_3$) δ: 7.37–7.57 (3H, m), 7.70–7.77 (2H, m), 7.86–8.02 (3H, m), 8.10–8.20 (2H, m), 8.77 (1H, s).

REFERENCE EXAMPLE 21

To a solution of 4-nitrobenzylalcohol (4.59 g) in methanol (300 ml) was added copper chloride (I) (17.8 g) at room temperature, and then was gradually added potassium boron hydride (11.3 g) for 40 minutes. The reaction mixture was stirred at room temperature for 2 hours and concentrated under reduced pressure. To the residue was added water, and the mixture was extracted with ethyl acetate. The organic layer was dried with anhydrous sodium sulfate, and concentrated under reduced pressure. The residue was separated and purified with column chromatography (ethyl acetate/hexane=3/1) to give 4-aminobenzylalcohol (1.31 g) as pale yellow crystals.

mp 53–55° C.; Elemental Analysis for $C_7H_9NO$; Calcd: C, 68.27; H, 7.37; N, 11.37. Found: C, 68.43; H, 7.43; N, 11.49. IR (KBr) cm$^{-1}$: 3375, 3219, 1614, 1514, 1470, 1259, 1041, 854, 827, 748, 509; $^1$H NMR (200 MHz, CDCl$_3$) δ: 3.50–3.85 (2H, br), 4.56 (2H, s), 6.68 (2H, d, J=8.4 Hz), 7.17 (2H, d, J=8.4 Hz).

REFERENCE EXAMPLE 22

In THF (10ml) was dissolved 7-phenyl-3,4-dihydronaphthalene-2-carboxylic acid (500 mg), and to the solution were added oxalyl chloride (262 μl) and a drop of DMF. The mixture was stirred at room temperature for 1 hour and concentrated under reduced pressure. The residue was dissolved in DMF (5 ml), and to the mixture was dropwise added a solution of 4-aminobenzylalcohol (246 mg) in pyridine (10 ml) at 0° C. The reaction mixture was stirred at 0° C. for 3 hours. To the mixture was added water (500 ml), and then the mixture was extracted with ethyl acetate. The organic layer was washed with saturated sodium chloride solution, dried with anhydrous sodium sulfate, and concentrated under reduced pressure. The residue was recrystallized from ethyl acetate-acetone to given-[4-(hydroxymethyl)phenyl]-7-phenyl-3,4-dihydronaphthalene-2-carboxamide (486 mg) as pale brown crystals.

mp 207–210° C.; Elemental Analysis for $C_{24}H_{21}NO_2 \cdot 0.5H_2O$; Calcd: C, 79.10; H, 6.08; N, 3.84. Found: C, 79.35; H, 5.97; N, 3.86. IR (KBr) cm$^{-1}$: 3332, 1651, 1618, 1597, 1527, 1412, 1317, 831, 764, 700; $^1$HNMR (200 MHz, DMSO-d$_6$) δ: 2.50–2.66 (2H, m), 2.80–2.95 (2H, m), 4.46 (2H, s), 7.23–7.72 (13H, m), 9.91 (1H, s).

REFERENCE EXAMPLE 23

Under argon atmosphere, a mixture of 7-(trifluoromethanesulfoxy)-1-tetralone (9.02 g), 4-methylphenyl borate (5.00 g), potassium carbonate (8.46 g), toluene (300 ml), ethanol (30 ml) and water (30 ml) was stirred at room temperature for 30 minutes, and to the mixture was added tetrakis(triphenylphosphine)palladium (1.06 g). The mixture was refluxed for 14 hours. The reaction mixture was cooled to room temperature. The organic layer was separated, dried with anhydrous sodium sulfate, and concentrated under reduced pressure. The residue was separated and purified with column chromatography (ethyl acetate/toluene=1/10) to give 7-(4-methylphenyl)-1-tetralone (5.23 g) as colorless crystals.

mp 86–87° C.; Elemental Analysis for $C_{17}H_{16}O$; Calcd: C, 86.41; H, 6.82. Found: C, 86.30; H, 6.69. IR (KBr) cm$^{-1}$: 2947, 1682, 1606, 1489, 1435, 1323, 1223, 1178, 810; $^1$H NMR (200 MHz, CDCl$_3$) δ: 2.10–2.24 (2H, m), 2.39 (3H, s), 2.69 (2H, t, J=6.6 Hz), 3.00 (2H, t, J=6.0 Hz), 7.21–7.35 (3H, m), 7.52 (2H, d, J=8.4 Hz), 7.71 (1H, dd, J=2.2, 8.2 Hz), 8.27 (1H, d, J=2.2 Hz).

REFERENCE EXAMPLE 24

Under argon atmosphere, a mixture of 7-(trifluoromethanesulfoxy)-1-tetralone (17.5 g), 4-fluorophenyl borate (10.0 g), potassium carbonate (16.6 g), toluene (500 ml), ethanol (50 ml) and water (50 ml) was stirred at room temperature for 30 minutes, and to the mixture was added tetrakis(triphenylphosphine)palladium (2.08 g). The mixture was refluxed for 14 hours. The reaction mixture was cooled to room temperature. The organic layer was separated, dried with anhydrous sodium sulfate, and concentrated under reduced pressure. The residue was separated and purified with column chromatography (ethyl acetate/toluene=1/10) to give 7-(4-fluorophenyl)-1-tetralone (13.8 g) as brown oil.

$^1$H NMR (200 MHz, CDCl$_3$) δ: 2.10–2.24 (2H, m), 2.70 (2H, t, J=6.6 Hz), 3.01 (2H, t, J=6.0 Hz), 7.07–7.19 (2H, m), 7.30 (1H, d, J=7.6 Hz), 7.53–7.62 (2H, m), 7.67 (1H, dd, J=2.2, 8.2 Hz), 8.23 (1H, d, J=2.2 Hz).

REFERENCE EXAMPLE 25

A mixture of sodium methoxide (5.63 g), dimethyl carbonate (33 ml) and 7-(4-methylphenyl)-1-tetralone (4.93 g) was refluxed for 30 minutes. The reaction mixture was cooled to 0° C., and to the mixture was gradually added 3Nhydrochloricacid(80 ml). The mixture was extracted with ethyl acetate. The organic layer was washed with saturated sodium chloride solution, dried with anhydrous sodium sulfate, and concentrated under reduced pressure. The residue was dissolved in THF (30 ml), and to the mixture was added sodium boron hydride (494 mg) at 0° C. and then was dropwise added methanol (3 ml) for 30 minutes. The reaction mixture was stirred at 0° C. for 4 hours, and to the mixture was added water (500 ml). The mixture was extracted with ethyl acetate. The organic layer was washed with saturated sodium chloride solution, dried with anhydrous sodium sulfate, and concentrated under reduced pressure. The residue was dissolved in methanol (20 ml), and to the mixture was added 1N sodium hydroxide (20 ml). The mixture was refluxed for 4 hours, cooled, acidified with concentrated hydrochloric acid, and extracted with ethyl acetate. The organic layer was washed with saturated sodium chloride solution, dried with anhydrous sodium sulfate, and concentrated under reduced pressure. The residue was dissolved in Diglyme (20 ml), and to the mixture was added concentrated hydrochloric acid (4 ml). The mixture was stirred at 100° C. for 2 hours, and to the mixture was added water (500 ml). The mixture was extracted with ethyl acetate. The organic layer was washed with saturated sodium chloride solution, and concentrated under reduced pressure. The residue was dissolved in 0.5N sodium hydroxide (400 ml), and the mixture was washed with diethylether. The aqueous layer was separated and acidified with concentrated hydrochloric acid. The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give 7-(4-methyl-phenyl)-3,4-dihydronaphthalene-2-carboxylic acid (1.96 g) as pale brown crystals.

mp 230–231° C.; Elemental Analysis for $C_{18}H_{16}O_2$; Calcd: C, 81.79; H, 6.10. Found: C, 81.62; H, 6.11. IR (KBr) $cm^{-1}$: 3023, 2908, 1697, 1682, 1626, 1431, 1300, 928, 810; $^1$H NMR (200 MHz, $CDCl_3$) δ: 2.40 (3H, s), 2.61–2.71 (2H, m), 2.89–2.98 (2H, m), 7.22–7.28 (3H, m), 7.45–7.51 (4H, m), 7.73 (1H, s).

REFERENCE EXAMPLE 26

A mixture of sodium methoxide (15.5 g), dimethyl carbonate (91 ml) and 7-(4-fluorophenyl)-1-tetralone (13.8 g) was refluxed for 30 minutes. The reaction mixture was cooled to 0° C., and to the mixture was gradually added 3N hydrochloric acid (200 ml). The mixture was extracted with ethyl acetate. The organic layer was washed with saturated sodium chloride solution, dried with anhydrous sodium sulfate, and concentrated under reduced pressure. The residue was dissolved in THF (90 ml), and to the mixture was added sodium boron hydride (1.36 g) at 0° C. and then was dropwise added methanol (9 ml) for 30 minutes. The reaction mixture was stirred at 0° C. for 4 hours, and to the mixture was added water (500 ml). The mixture was extracted with ethyl acetate. The organic layer was washed with saturated sodium chloride solution, and concentrated under reduced pressure. The residue was dissolved in methanol (80 ml), and to the mixture was added 1N sodium hydroxide (100 ml). The mixture was refluxed for 4 hours and cooled to room temperature. The mixture was acidified with concentrated hydrochloric acid and extracted with ethyl acetate. The organic layer was washed with saturated sodium chloride solution, dried with anhydrous sodium sulfate, and concentrated under reduced pressure. The residue was dissolved in Diglyme (50 ml), and to the mixture was added concentrated hydrochloric acid (10 ml). The mixture was stirred at 100° C. for 2 hours, and to the mixture was added water (500 ml). The mixture was extracted with ethyl acetate. The organic layer was washed with saturated sodium chloride solution, and concentrated under reduced pressure. The residue was dissolved in 0.5N sodium hydroxide (400 ml), and the mixture was washed with diethylether. The aqueous layer was separated, acidified with concentrated hydrochloric acid and extracted with ethyl acetate. The organic layer was washed with saturated sodium chloride solution, dried with anhydrous sodium sulfate, and concentrated under reduced pressure. The residue was recrystallized from ethyl acetate-diisopropylether to give 7-(4-fluorophenyl)-3,4-dihydronaphthalene-2-carboxylic acid (6.0 g) as pale brown crystals.

mp 213–214° C.; Elemental Analysis for $C_{17}H_{13}O_2F$; Calcd: C, 76.11; H, 4.88. Found: C, 76.02; H, 4.97. IR (KBr) $cm^{-1}$: 2953, 1695, 1518, 1431, 1300, 1281, 1246, 930, 824; $^1$H NMR (200 MHz, $CDCl_3$) δ: 2.61–2.72 (2H, m), 2.90–2.99 (2H, m), 7.08–7.19 (2H, m), 7.23–7.29 (1H, m), 7.41–7.58 (4H, m), 7.72 (1H, s).

REFERENCE EXAMPLE 27

To a mixture of N-[4-(hydroxymethyl)phenyl]-7-phenyl-3,4-dihydronaphthalene-2-carboxamide (566 mg), lithium chloride (135 mg), triethylamine (446 μl) and dichloromethane (50 ml) was added methanesulfonyl chloride (172 μl), and the mixture was stirred at room temperature for 2 hours. To the reaction mixture was added dilute hydrochloric acid. The organic layer was separated, washed with saturated sodium chloride solution, dried with anhydrous sodium sulfate, and concentrated under reduced pressure. The residue was recrystallized from ethyl acetate-hexane to give N-[4-(chloromethyl)phenyl]-7-phenyl-3,4-dihydronaphthalene-2-carboxamide (494 mg) as colorless crystals.

mp 176–177° C.; Elemental Analysis for $C_{24}H_{20}NOCl$; Calcd: C, 77.10; H, 5.39; N, 3.75. Found: C, 76.95; H, 5.47; N, 3.82. IR (KBr) $cm^{-1}$: 3327, 1649, 1618, 1527, 1412, 1317, 831, 764, 700; $^1$H NMR (200 MHz, DMSO-$d_6$) δ: 2.55–2.68 (2H, m), 2.85–2.95 (2H, m), 4.74 (2H, s), 7.30–7.80 (13H, m), 10.05 (1H, s).

REFERENCE EXAMPLE 28

A mixture of 4-nitrobenzylalcohol(10.0 g), tertbutyldimethylsilyl chloride (11.8 g), imidazole (11.2 g) and DMF (50 ml) was stirred at room temperature for 1.5 hours. To the mixture was added water (500 ml), and the mixture was extracted with ethyl acetate. The organic layer was washed with saturated sodium chloride solution, dried with anhydrous sodium sulfate, and concentrated under reduced pressure. The residue was separated and purified with column chromatography (ethyl acetate/hexane=1/7) to give tertbutyldimethyl-4-nitrobenzyloxysilane (17.5 g) as pale yellow oil.

$^1$H NMR (200 MHz, $CDCl_3$) δ: 0.13 (6H, s), 0.96 (9H, s), 4.83 (2H, s), 7.48 (2H, d, J=8.6 Hz), 8.20 (2H, d, J=8.6 Hz).

REFERENCE EXAMPLE 29

In ethanol (80 ml) was dissolved tert-butyldimethyl-4-nitrobenzyloxysilane (16.5 g), and to the mixture was added dried 5% palladium on carbon (0.83 g). Under hydrogen atmosphere, the mixture was stirred at room temperature under atmospheric pressure for 7.5hours. The palladium was filtered off, and the filtrate was concentrated. The residue was separated and purified with column chromatography (ethyl acetate/hexane=1/4) to give 4-aminobenzyloxy-tert-butyldimethylsilane (13.8 g) as colorless oil.

IR (neat) $cm^{-1}$: 3359, 2954, 2856, 1626, 1518, 1471, 1375, 1257, 1072, 837, 777; $^1$H NMR (200 MHz, $CDCl_3$) δ: 0.07 (6H, s), 0.92 (9H, s), 3.50–3.70 (2H, br), 4.62 (2H, s), 6.65 (2H, d, J=8.4 Hz), 7.11 (2H, d, J=8.4 Hz).

REFERENCE EXAMPLE 30

In THF (60 ml) was dissolved 7-(4-methylphenyl)-3,4-dihydro-naphthalene-2-carboxylic acid (4.02 g). To the solution were added oxalyl chloride (1.99 ml) and a drop of DMF, and the mixture was stirred at room temperature for 1 hour and concentrated under reduced pressure. The residue was dissolved in THF (30 ml), and to the mixture was dropwise added a solution of 4-amino-benzyloxy-tert-butyldimethylsilane (3.97 g) and triethylamine (2.56 ml) in THF (30 ml) at room temperature. The reaction mixture was stirred at room temperature for 19 hours. To the mixture was added water (300 ml), and the mixture was extracted with ethyl acetate. The organic layer was washed with saturated sodium chloride solution, dried with anhydrous sodium sulfate, and concentrated under reduced pressure. The residue was separated and purified with column chromatography (ethyl acetate/toluene/hexane=1/5/5). The resulting oil was dissolved in acetone (60 ml), and to the mixture was added 6N hydrochloric acid(2 ml). The mixture was stirred at room temperature for 30 minutes. To the reaction mixture were added 0.5% sodium hydroxide (500 ml) and diisopropylether (200 ml), and the mixture was stirred at room temperature for 5 minutes. The resulting precipitate s was filtered and recrystallized from acetone-diisopropylether to give N-[4-(hydroxy-methyl)phenyl]-7-(4-methylphenyl)-3,4-dihydro-naphthalene-2-carboxamide (4.54 g) as pale brown crystals.

mp 219–220° C.; Elemental Analysis for $C_{25}H_{23}NO_2$; Calcd: C, 81.27; H, 6.27; N, 3.79. Found: C, 81.23; H,5.99; N, 3.80. IR (KBr) cm$^{-1}$: 3315, 1647, 1618, 1597, 1531, 1414, 1321, 810; $^1$H NMR (200 MHz, DMSO-d$_6$) δ: 2.35 (3H, s), 2.55–2.65 (2H, m), 2.83–2.93 (2H, m), 4.46 (2H, d, J=5.6 Hz), 5.13 (1H, t, J=5.6 Hz), 7.23–7.33 (5H, m), 7.44–7.58 (5H, m), 7.69 (2H, d, J=8.4 Hz), 9.93 (1H, s).

REFERENCE EXAMPLE 31

To a mixture of N-[4-(hydroxymethyl)phenyl]-7-(4-methylphenyl)-3,4-dihydronaphthalene-2-carboxamide (2.20 g), lithium chloride (505 mg), triethylamine (1.67 ml), DMAP [4-dimethylaminopyridine] (catalytic amount) and dichloromethane (200 ml) was added methanesulfonyl chloride (645 μl), and the mixture was stirred at room temperature for 42 hours and concentrated under reduced pressure. To the residue was added 0.5N hydrochloric acid (200 ml), and the mixture was extracted with ethyl acetate. The organic layer was dried with anhydrous sodium sulfate and concentrated under reduced pressure. The residue was recrystallized from ethyl acetate-hexane to give N-[4-(chloromethyl)-phenyl]-7-(4-methylphenyl)-3,4-dihydronaphthalene-2-carboxamide (973 mg) as colorless crystals.

mp 178–179° C.; Elemental Analysis for $C_{25}H_{22}NOCl$; Calcd: C, 77.41; H, 5.72; N, 3.61. Found: C, 77.34; H, 5.89; N, 3.65. IR (KBr) cm$^{-1}$: 3332, 1651, 1620, 1529, 1412, 1319, 812; $^1$H NMR (200 MHz, DMSO-d$_6$) δ: 2.35 (3H, s), 2.55–2.68 (2H, m), 2.83–2.93 (2H, m), 4.74 (2H, s), 7.24–7.60 (10H, m), 7.76 (2H, d, J=8.6 Hz), 10.04 (1H, s).

REFERENCE EXAMPLE 32

Under argon atmosphere, 6-methoxy-1-indanone (10.0 g) was dissolved in xylene (10 ml), and to the mixture was added aluminum chloride (16.4 g). The mixture was refluxed for 2 hours and then cooled to room temperature. To the mixture was added 3N hydrochloric acid (100 ml), and the mixture was extracted with ethyl acetate. The organic layer was washed with saturated sodium chloride solution, dried with anhydrous sodium sulfate, and concentrated under reduced pressure. The residue was separated and purified with column chromatography (ethyl acetate) to give 6-hydroxy-1-indanone (7.36 g) as pale brown crystals.

$^1$H NMR (200 MHz, CDCl$_3$) δ: 2.67–2.76 (2H, m), 3.02–3.11 (2H, m), 5.61 (1H, s), 7.10–7.21 (2H, m), 7.36 (1H, d, J=8.0 Hz).

REFERENCE EXAMPLE 33

Under argon atmosphere, 6-hydroxy-1-indanone (7.36 g) and triethylamine (20.9 ml) were dissolved in dichloromethane (120 ml), and to the mixture was dropwise added trifluoromethanesulfonic acid anhydride (8.78 ml) at 0° C. The reaction mixture was stirred at 0° C. for 1 hour, and to the mixture was added water (200 ml). The organic layer was separated, washed with water, dried with anhydrous sodium sulfate and concentrated under reduced pressure. The residue was separated and purified with column chromatography (ethyl acetate/hexane=1/4) to give 6-(trifluoromethanesulfoxy)-1-indanone (11.5 g) as brown oil.

$^1$H NMR (200 MHz, CDCl$_3$) δ: 2.75–2.83 (2H, m), 3.17–3.24 (2H, m), 7.50 (1H, dd, J=2.4, 8.4 Hz), 7.60 (1H, d, J=8.4 Hz), 7.64 (1H, d, J=2.4 Hz).

REFERENCE EXAMPLE 34

Under argon atmosphere, a mixture of 6-(trifluoromethanesulfoxy)-1-indanone (11.5 g), 4-methylphenyl borate (6.69 g), potassium carbonate (11.3 g), toluene (400 ml), ethanol (40 ml) and water (40 ml) was stirred at room temperature for 30 minutes, and to the mixture was added tetrakis(triphenylphosphine)palladium (1.42 g). The mixture was refluxed for 17 hours and cooled to room temperature. The organic layer was separated, dried with anhydrous sodium sulfate, and concentrated under reduced pressure. The residue was separated and purified with column chromatography (ethyl acetate/toluene=1/10) and recrystallized from ethyl acetate-hexane to give 6-(4-methylphenyl)-1-indanone (5.20 g) as pale brown crystals.

mp 121–122° C.; Elemental Analysis for $C_{16}H_{14}O$; Calcd: C, 86.45; H, 6.35. Found: C, 86.46; H,6.23. IR (KBr) cm$^{-1}$: 1703, 1614, 1483, 1448, 1404, 1304, 814; $^1$H NMR (200 MHz, CDCl$_3$) δ: 2.40 (3H, s), 2.70–2.79 (2H, m), 3.13–3.22 (2H, m), 7.23–7.29 (2H, m), 7.48–7.57 (3H, m), 7.83 (1H, dd, J=1.8, 8.0 Hz), 7.96 (1H, s).

REFERENCE EXAMPLE 35

A solution of 6-(4-methylphenyl)-1-indanone (4.97 g) in THF (33 ml) was dropwise added to a refluxed mixture of 60% sodium hydride (3.26 g), potassium hydride (catalytic amount), dimethyl carbonate (6.65 ml) and THF (100 ml), and the mixture was ref luxed for 6 hours. The reaction mixture was cooled to 0° C., and to the mixture was gradually added 2N hydrochloric acid (150 ml). The mixture was extracted with ethyl acetate, and the organic layer was washed with saturated sodium chloride solution, dried with anhydrous sodium sulfate, and concentrated under reduced pressure. The residue was separated and purified with column chromatography (ethyl acetate/toluene=1/3) to give a brown solid. The solid was dissolved in dichloromethane (100 ml), and to the mixture was added sodium boron hydride (391 mg) at 0° C. and then was dropwise added methanol (10 ml). The reaction mixture was stirred at 0° C. for 1.5 hours, and to the mixture was added water (500 ml). The mixture was extracted with ethyl acetate, and the organic layer was washed with saturated sodium chloride solution, dried with anhydrous sodium sulfate, and concentrated under reduced pressure. The residue was dissolved in methanol (30 ml), and to the mixture was added 1N sodium hydroxide (40 ml). The mixture was refluxed for 2 hours and cooled to room temperature. To the mixture was added water, and the mixture was washed with diethylether. The aqueous layer was acidified with concentrated hydrochloric acid and extracted with ethyl acetate. The organic layer was washed with saturated sodium chloride solution, dried with anhydrous sodium sulfate, and concentrated under reduced pressure. The residue was dissolved in Diglyme (30 ml), and to the mixture was added concentrated hydrochloric acid (6 ml). The mixture was stirred at 100° C. for 2 hours, and to the solution were added 0.5% sodium hydrogen carbonate solution (500 ml) and hexane(500 ml). The resulting precipitate was filtered to give 5-(4-methylphenyl)-indene-2-carboxylic acid (2.72 g) as brown crystals.

mp 226–229° C. (decomp.); Elemental Analysis for $C_{17}H_{14}O_2 \cdot 0.1H_2O$; Calcd: C, 80.99; H, 5.68. Found: C, 80.92; H, 5.55. IR (KBr) cm$^{-1}$: 2999, 1670, 1572, 1259, 808; $^1$H NMR (200 MHz, DMSO-d$_6$) δ: 2.35 (3H, s), 3.63–3.70 (2H, m), 7.28 (2H, d, J=8.0 Hz), 7.53–7.73 (5H, m), 7.83 (1H, d, J=6.0 Hz).

REFERENCE EXAMPLE 36

A mixture of hexamethyleneimine (15.0 g), ethyl iodide (14.5 ml), potassium carbonate (31.3 g) and ethanol (300 ml) was refluxed for 6 hours and concentrated under reduced pressure. To the residue was added diethylether, and insoluble material was filtered off. The filtrate was under reduced pressure to give 1-ethylperhydroazepine (4.56 g) as colorless oil.

bp 73–76° C./70 mmHg; IR (neat) cm$^{-1}$: 2927, 1452, 1352, 1190, 1140, 1093; $^1$H NMR (200 MHz, CDCl$_3$) δ: 1.05 (3H, t, J=7.2 Hz), 1.55–1.72 (8H, m), 2.47–2.65 (6H, m).

REFERENCE EXAMPLE 37

A mixture of hexamethyleneimine (15.0 g), 1-propyl iodide (29.5 ml), potassium carbonate (31.3 g) and ethanol (300 ml) was refluxed for 42 hours and concentrated under reduced pressure. To the residue was added diethylether, and insoluble material was filtered off. The filtrate was under reduced pressure to give 1-propylperhydroazepine (2.50 g) as colorless oil.

bp 70–74° C./50 mmHg IR (neat) cm$^{-1}$: 2926, 1749, 1458, 1375, 1259, 1184, 1138, 1082; $^1$H NMR (200 MHz, CDCl$_3$) δ: 0.87 (3H, t, J=7.5 Hz), 1.40–1.80 (10H, m), 2.36–2.46 (2H, m), 2.55–2.67 (4H, m).

REFERENCE EXAMPLE 38

A mixture of heptamethyleneimine (10.0 g), ethyl iodide (8.48 ml), potassium carbonate (18.3 g) and ethanol (200 ml) was refluxed for 13 hours and concentrated under reduced pressure. To the residue was added diethylether, and insoluble material was filtered off. The filtrate was under reduced pressure to give 1-ethylperhydroazocine (2.29 g) as colorless oil.

bp 76–78° C./40 mmHg IR (neat) cm$^{-1}$: 2920, 1475, 1446, 1371, 1252, 1225, 1161, 1093; $^1$H NMR (200 MHz, CDCl$_3$) δ: 1.03 (3H, t, J=6.9 Hz), 1.48–1.72 (10H, m), 2.42–2.60 (6H, m).

REFERENCE EXAMPLE 39

Under argon atmosphere, a mixture of methyl (E)-3-(trifluoromethanesulfoxy)cinnamate (9.00 g), 4-methylphenyl borate (4.73 g), potassium carbonate (8.02 g), toluene (300 ml), ethanol (30 ml) and water (30 ml) was stirred at room temperature for 30 minutes. To the mixture was added tetrakis(triphenylphosphine)palladium (1.01 g), and the mixture was refluxed for 24 hours. The reaction mixture was cooled to room temperature, and the organic layer was separated, dried with anhydrous sodium sulfate, and concentrated under reduced pressure. The residue was separated and purified with column chromatography (ethyl acetate/toluene/hexane=1/5/5) to give colorless oil, which was dissolved in methanol (50 ml). To the mixture was added 1N sodium hydroxide (50 ml), and the mixture was refluxed for 1 hour. The reaction mixture was cooled to room temperature, acidified with concentrated hydro-chloric acid and extracted with ethyl acetate. The organic layer was washed with saturated sodium chloride solution, dried with anhydrous sodium sulfate, and concentrated under reduced pressure. The residue was recrystallized from ethyl acetate-diisopropylether to give (E)-3-(4-methyl-phenyl)cinnamic acid (5.15 g) as colorless crystals.

mp 192–194° C.; Elemental Analysis for $C_{16}H_{14}O_2 \cdot 0.1H_2O$; Calcd: C, 80.04; H, 5.96. Found: C, 80.13; H, 5.94. IR (KBr) cm$^{-1}$: 2922, 1687, 1628, 1435, 1321, 1282, 1225, 798; $^1$H NMR (200 MHz, CDCl$_3$) δ: 2.41 (3H, s), 6.52 (1H, d, J=16.0 Hz), 7.23–7.30 (2H, m), 7.40–7.53 (4H, m), 7.56–7.65 (1H, m), 7.73 (1H, s), 7.85 (1H, d, J=16.0 Hz).

REFERENCE EXAMPLE 40

In THF (50 ml) was dissolved (E)-3-(4-methylphenyl)-cinnamic acid (5.00 g), and to the solution were added oxalyl chloride (2.38 ml) and a drop of DMF. The mixture was stirred at room temperature for 1 hour and concentrated under reduced pressure. The residue was dissolved in THF (50 ml), and to the mixture were added 4-aminobenzyloxy-tert-butyl-dimethylsilane (5.48 g) and triethylamine (3.53 ml) at room temperature. The reaction mixture was stirred at room temperature for 3 hours, and to the mixture was added water (200 ml). The mixture was extracted with ethyl acetate, and the organic layer was washed with saturated sodium chloride solution, dried with anhydrous sodium sulfate, and concentrated under reduced pressure. The residue was separated and purified with column chromatography (ethyl acetate/toluene/hexane=1/5/5) to give oil, which was dissolved in acetone (50 ml). To the mixture was added 6N hydrochloric acid (1 ml), and the mixture was stirred at room temperature for 30 minutes. To the reaction mixture were added 0.5% sodium hydroxide (500 ml) and diisopropylether (200 ml), and the mixture was stirred at room temperature for 5 minutes. The resulting precipitate was filtered and recrystallized from acetone-diisopropylether to give (E)-N-[4-(hydroxymethyl)-phenyl]-3-(4-methylphenyl)-cinnamamide (6.18 g) as pale yellow crystals.

mp 220–223° C.; Elemental Analysis for $C_{23}H_{21}NO_2$; Calcd: C, 80.44; H, 6.16; N, 4.08. Found: C, 80.12; H, 6.15; N, 4.00. IR (KBr) cm$^{-1}$: 3294, 1662, 1624, 1603, 1541, 1516, 1414, 1346, 1250, 1184, 999, 787; $^1$H NMR (200 MHz, DMSO-d$_6$) δ: 2.36 (3H, s), 4.46 (2H, s), 6.93 (1H, d, J=15.4 Hz), 7.22–7.33 (4H, m), 7.46–7.71 (8H, m), 7.89 (1H, s), 10.18 (1H, s).

REFERENCE EXAMPLE 41

To a mixture of (E)-N-[4-(hydroxymethyl)phenyl]-3-(4-methylphenyl)cinnamamide (3.00 g), lithium chloride (741 mg), triethylamine (3.06 ml), DMAP(catalytic amount) and dichloro-methane (300 ml) was added methanesulfonyl chloride (1.15 ml), and the mixture was stirred at room temperature for 13 hours. To the reaction mixture was added 4N hydrochloric acid ethyl acetate solution (3.3 ml), and the mixture was purified with column chromatography (ethyl acetate) and recrystallized from ethyl acetatediisopropylether to give (E)-N-[4-(chloromethyl)phenyl]-3-(4-methylphenyl)cinnamamide (2.00 g) as colorless crystals.

mp 178–180° C.; Elemental Analysis for $C_{23}H_{20}NOCl \cdot 0.1H_2O$; Calcd: C, 75.96; H, 5.60; N, 3.85. Found: C, 75.93; H, 5.50; N, 3.88. IR (KBr) cm$^{-1}$: 3344, 3045, 1664, 1628, 1531, 1412, 1338, 1248, 1176, 968, 793, 658; $^1$H NMR (200 MHz, CDCl$_3$) δ: 2.41 (3H, s), 4.58 (2H, s), 6.61 (1H, d, J=15.6 Hz), 7.25–7.31 (2H, m), 7.33–7.53 (7H, m), 7.55–7.67 (3H, m), 7.74 (1H, s), 7.83 (1H, d, J=15.6 Hz).

REFERENCE EXAMPLE 42

To a solution cooled at −78° C. of 2-bromopyridine (10.0 g) in diethylether (200 ml) was dropwise added 1.6M butyllithium hexane solution (39.6 ml) for 10 minutes. The mixture was stirred at −78° C. for 1 hour, and to the mixture was dropwise added a solution of 4-nitrobenzaldehyde in THF (50 ml). The reaction mixture was stirred at −78° C. for 3 hours, and to the mixture was added water (100 ml). The mixture was extracted with ethyl acetate, and the organic layer was washed with saturated sodium chloride solution, dried with anhydrous sodium sulfate, and concentrated under reduced pressure. The residue was separated and purified with column chromatography (ethyl acetate/toluene=1/2) and re-crystallized from duisopropylether to give (4-nitrophenyl)-(2-pyridyl)methanol (4.50 g) as orange crystals.

mp 114–1150° C.; Elemental Analysis for $C_{12}H_{10}N_2O_3$; Calcd: C, 62.61; H, 4.38; N, 12.17. Found: C, 62.61; H, 4.27; N, 12.16. IR (KBr) cm$^{-1}$: 3113, 2852, 1595, 1506, 1437, 1336, 1267, 1068, 1047, 1007, 847, 814, 777, 756, 743, 706; $^1$H NMR (20° C. MHz, CDCl$_3$) δ:5.44 (1H, br s), 5.86 (1H, s), 7.14–7.29 (2H, m), 7.55–7.73 (3H, m), 8.20 (2H, d, J=8.8 Hz), 8.59 (1H. d, J=5.0 Hz).

REFERENCE EXAMPLE 43

In ethanol (50 ml) was dissolved (4-nitrophenyl)-(2-pyridyl)methanol (2.30 g), and to the mixture was added dried 10% palladium on carbon (0.12 g). Under hydrogen atmosphere, the mixture was stirred at room temperature under atmospheric pressure for 19 hours. The palladium was filtered off, and the filtrate was concentrated. The residue was recrystallized f rom ethyl acetate-hexane to give (4-aminophenyl) (2-pyridyl)methanol (1.90 g) as pale yellow crystals.

mp 139–140° C.; Elemental Analysis for $C_{12}H_{12}N_2O$; Calcd: C. 71.98; H, 6.04; N, 13.99. Found: C, 71.76; H. 6.01; N, 13.82. IR (KBr) cm$^{-1}$: 3292, 1612, 1589, 1512, 1473, 1439, 1263, 1055, 816, 752, 569; $^1$H NMR (200 MHz, CDCl$_3$) δ: 3.65 (2H, br s), 5.14 (1H, br s), 5.65 (1H, s), 6.65 (2H, d, J=8.8 Hz)., 7.10–7.22 (4H, m), 7.61 (1H, dt, J=1.8, 7.6 Hz) 8.55 (1H, d, J=4.8 Hz).

REFERENCE EXAMPLE 44

Under argon atmosphere, ethyl 3-hydroxycinnamate (mp 88–89° C.; 20.0 g) and triethylamine (34.5 ml) were dissolved in dichloromethane (200 ml), and to the mixture was dropwise added trifluoromethanesulfonic acid anhydride (31.6 g) at −5° C. for 40 minutes. The reaction mixture was stirred at −5° C. to 0° C. for 20 minutes, and to the mixture was added water (200 ml). The organic layer was separated, washed with saturated sodium chloride solution, dried with anhydrous magnesium sulfate and concentrated under reduced pressure. The residue was separated and purified with column chromatography (ethylacetate/hexane=1/4) and crystallized from hexane to give ethyl 3-(trifluoromethanesulfoxy)cinnamate (33.5 g).

mp 52–53° C.; $^1$H NMR (200 MHz, CDCl$_3$) δ: 3.83 (3H, s), 6.48 (1H, d, J=16.0 Hz), 7.30 (1H, m), 7.41 (1H, t, J=1.6 Hz), 7.51 (2H, m), 7.67 (1H, d, J=16.0 Hz).

REFERENCE EXAMPLE 45

Under argon atmosphere, a mixture of ethyl 3-(trifluoromethanesulfoxy)cinnamate (3.10 g), 4-methylphenyl borate (1.63 g), potassium carbonate (2.76 g), toluene (100 ml), ethanol (10 ml) and water (10 ml) was stirred at room temperature for 30 minutes. To the mixture was added tetrakis(triphenylphosphine)palladium (0.46 g), and the mixture was refluxed for 18 hours. The reaction mixture was cooled to room temperature. The organic layer was separated, washed with saturated sodium chloride solution, dried with anhydrous magnesium sulfate and concentrated under reduced pressure. The residue was separated and purified with column chromatography (ethyl acetate/hexane=1/6) to give ethyl 3-(4-methylphenyl)-cinnamate (2.21 g) as colorless oil. The oil (2.20 g) was dissolved in tetrahydrofuran (20 ml). To the mixture was added 2N sodium hydroxide (8.7 ml), and the mixture was stirred at 50° C. for 2 hours. The reaction mixture was cooled, acidified with potassium hydrogen sulfate and extracted with ethyl acetate. The organic layer was washed with saturated sodium chloride solution, dried with anhydrous magnesium sulfate and concentrated under reduced pressure. The residue was washed with isopropylether to give 3-(4-methylphenyl)cinnamic acid (1.54 g) as colorless crystals.

mp 186–187° C.; $^1$H NMR (200 MHz, CDCl$_3$) δ:2.41 (3H, s), 6.53 (1H, d, J=16.0 Hz), 7.28 (2H, d, J=7.4 Hz), 7.46–7.52 (4H, m), 7.50 (1H, s), 7.63 (1H, m), 7.86 (1H, d, J=16.0 Hz).

REFERENCE EXAMPLE 46

Under argon atmosphere, a mixture of ethyl 3-(trifluoromethanesulfoxy)cinnamate (3.10 g), 2-methylphenyl borate (mp 165–166° C. ; 1.63 g), potassium carbonate (2.76 g), toluene (100 ml), ethanol (10 ml) and water (10 ml) was stirred at room temperature for 30 minutes. To the mixture was added tetrakis(triphenylphosphine)palladium (0.46 g), and the mixture was refluxed for 18 hours. The reaction mixture was cooled to room temperature, and the organic layer was separated, washed with saturated sodium chloride solution, dried with anhydrous magnesium sulfate and concentrated under reduced pressure. The residue was separated and purified with column chromatography (ethyl acetate/hexane=1/6) to give ethyl 3-(4-methylphenyl)cinnamate (2.51 g) as pale yellow oil. The oil (2.50 g) was dissolved in tetrahydrofuran (20 ml). To the mixture was added 2N sodium hydroxide (10.0ml), and the mixture was stirred at 50° C. for 2 hours. The reaction mixture was cooled, acidified with potassium hydrogen sulfate and extracted with ethyl acetate. The organic layer was washed with saturated sodium chloride solution, dried with anhydrous magnesium sulfate and concentrated under reduced pressure. The residue was washed with isopropylether to give 3-(2-methylphenyl)cinnamic acid (1.96 g) as colorless crystals.

mp 124–125° C.; $^1$H NMR (200 MHz, CDCl$_3$) δ: 2.27 (3H, s), 6.49 (1H, d, J=16.0 Hz), 7.23–7.30 (4H, m), 7.36–7.57 (4H, m), d, J=7.4 Hz), 7.84 (1H, d, J=16.0 Hz).

REFERENCE EXAMPLE 47

Under argon atmosphere, a mixture of ethyl 3-(trifluoromethanesulfoxy)cinnamate (3.10 g), 2,5-dimethylphenyl borate (mp 184–186° C. ; 1.80 g), potassium carbonate (2.76 g), toluene (100 ml), ethanol (10 ml) and water (10 ml) was stirred at room temperature for 30 minutes. To the mixture was added tetrakis(triphenylphosphine)palladium (0.46 g), and the mixture was refluxed for 27 hours. The reaction mixture was cooled to room temperature, and the organic layer was separated, washed with saturated sodium chloride solution, dried with anhydrous magnesium sulfate and concentrated under reduced pressure. The residue was separated and purified with column chromatography (ethyl acetate/hexane=1/6) to give ethyl 3-(2,5-dimethylphenyl)cinnamate (2.66 g) as pale yellow oil. The oil (2.50 g) was dissolved in tetrahydrofuran (20 ml), and to the mixture was added 2N sodium hydroxide (10.0 ml). The mixture was stirred at 50° C. for 2 hours, cooled, acidified with potassium hydrogen sulfate and extracted with ethyl acetate. The organic layer was washed with saturated sodium chloride solution, dried with anhydrous magnesium sulfate and concentrated under reduced pressure. The residue was washed with isopropylether to give 3-(2,5-dimethylphenyl)cinnamic acid (1.96 g) as colorless crystals.

mp 156–157° C.; $^1$H NMR (200 MHz, CDCl$_3$) δ: 2.23 (3H, s), 2.60 (3H, s), 6.49 (1H, d, J=16.0 Hz), 7.06 (1H, s), 7.14 (2H, ABq, J=7.8 Hz), 7.35–7.55 (4H, m), 7.36–7.57 (4H, m), 7.84 (1H, d, J=16.0 Hz).

REFERENCE EXAMPLE 48

Under argon atmosphere, a mixture of ethyl 3-(trifluoromethanesulfoxy)cinnamate (3.10 g), 3-nitrophenyl borate (2.00 g), potassium carbonate (2.76 g), toluene (100 ml), ethanol (10 ml) and water (10 ml) was stirred at room temperature for 30 minutes. To the mixture was added tetrakis(triphenylphosphine)palladium (0.46 g), and the mixture was refluxed for 24 hours. The reaction mixture was cooled to room temperature. The organic layer was separated, washed with saturated sodium chloride solution, dried with anhydrous magnesium sulfate and concentrated under reduced pressure. The residue was separated and purified with column chromatography (ethyl acetate/hexane=1/6) to give ethyl 3-(3-nitrophenyl)-cinnamate (2.40 g) as pale yellow crystals. The crystals (2.40 g) were dissolved in tetrahydrofuran (20 ml), and to the mixture was added 2N sodium hydroxide (8.5 ml). The mixture was stirred at 50° C. for 2 hours, cooled, acidified with potassium hydrogen sulfate and extracted with ethyl acetate. The organic layer was washed with saturated sodium chloride solution, dried with anhydrous magnesium sulfate and concentrated under reduced pressure. The residue was washed with isopropylether to give 3-(3-nitrophenyl)cinnamic acid (1.88 g) as pale yellow crystals.

mp247–248° C.; $^1$H NMR (200 MHz, DMSO-d$_6$) δ: 6.59 (1H, d, J=16.0 Hz), 7.51–7.76 (4H, m), 7.70 (1H, d, J=16.0 Hz), 7.96 (1H, d, J=9.0 Hz), 8.09 (1H, m), 8.22 (1H, m), 8.49 (1H, d, J=1.8 Hz).

WORKING EXAMPLE 1 (PRODUCTION OF COMPOUND 1)

In THF (5 ml) was dissolved 7-cyclohexyl-3,4-dihydronaphthalene-2-carboxylic acid (200 mg), and to the solution were added oxalyl chloride (82 µl) and a drop of DMF. The mixture was stirred at room temperature for 1 hour and concentrated under reduced pressure. The residue was dissolved in THF (5 ml), and to the solution were added 1-(4-aminobenzyl)piperidine (164 mg) and triethylamine (484 µl) at room temperature. The reaction mixture was stirred at room temperature for 3 hours, and to the mixture was added water (100 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give 7-cyclohexyl-N-[4-(piperidinomethyl)-phenyl]-3,4-dihydronaphthalene-2-carboxamide (Compound 1) (223 mg) as colorless crystals.

mp 180–181° C,; Elemental Analysis for $C_{29}H_{36}N_2O_2$; Calcd: C, 81.27; H, 8.47; N, 6.54. Found: C, 81.03; H, 8.42; N, 6.53. IR (KBr) cm$^{-1}$: 3430, 2931, 1645, 1597, 1514, 1412, 1317, 824; $^1$H NMR (200 MHz, CDCl$_3$) δ: 1.20–1.90 (16H, m), 2.30–2.57 (5H, m), 2.60–2.72 (2H, m), 2.85–2.97 (2H, m), 3.46 (2H, s), 7.05–7.15 (3H, m), 7.25–7.34 (3H, m), 7.50–7.60 (3H, m).

WORKING EXAMPLE 2 (PRODUCTION OF COMPOUND 2)

In DMF (2 ml) was dissolved 7-cyclohexyl-N-[4-(piperidinomethyl)phenyl]-3,4-dihydronaphthalene-2-carboxamide (120 mg), and to the mixture was added methyl iodide (45 µl). The mixture was stirred at room temperature for 24 hours and concentrated under reduced pressure. The residue was recrystallized from ethyl acetate to give 1-[4-(7-cyclohexyl-3,4-dihydro-naphthalene-2-carboxamido) benzyl]-1-methylpiperidinium iodide (Compound 2) (148 mg) as colorless crystals.

mp 188–191° C.; Elemental Analysis for $C_{30}H_{39}N_2OI$; Calcd: C, 63.15; H, 6.89; N, 4.91; I, 22.24. Found: C, 63.03; H, 6.93; N, 5.03; I, 22.22. IR (KBr) cm$^{-1}$: 3430, 2929, 1649, 1599, 1520, 1417, 1321, 1248; $^1$H NMR (200 MHz, DMSO-d$_6$) δ: 1.20–1.90 (16H, m), 2.40–2.65 (3H, m), 2.75–2.95 (5H, m), 3.20–3.45 (4H, m), 4.53 (2H, s), 7.14 (3H, s), 7.38 (1H, s), 7.49 (2H, d, J=8.6 Hz), 7.88 (2H, d, J=8.6 Hz), 10.12 (1H, s).

WORKING EXAMPLE 3 (PRODUCTION OF COMPOUND 3)

In THF (3 ml) was dissolved 7-cyclohexyl-3,4-dihydronaphthalene-2-carboxylic acid (100 mg), and to the solution were added oxalyl chloride (41 µl) and a drop of DMF. The mixture was stirred at room temperature for 1 hour and concentrated under reduced pressure. The residue was dissolved in THF (3 ml), and to the solution were added p-(4-aminobenzyl)-N,N'-diethyl-phosphondiamide (104 mg) andtriethylamine(60 µl )at room temperature. The reaction mixture was stirred at room temperature for 72 hours, and to the mixture was added water (100 ml). The mixture was extracted with ethyl acetate. The organic layer was washed with saturated sodium chloride solution, dried with anhydrous sodium sulfate, and concentrated under reduced pressure. The residue was separated and purified with column chromatography (ethyl acetate/methanol=10/1) and was recrystallized from diisopropylether to give 7-cyclohexyl-N-[4-[bis(ethylamino)phosphorylmethyl]-phenyl]-3,4-dihydronaphthalene-2-carboxamide (Compound 3) (140 mg) as colorless crystals.

mp 163–165° C.; Elemental Analysis for $C_{28}H_{38}N_3O_2P$; Calcd: C, 70.12; H, 7.99; N, 8.76. Found: C, 70.01; H, 7.99; N, 8.93. IR (KBr) cm$^{-1}$: 3250, 2926, 1645, 1599, 1514, 1414, 1321, 1250, 1182, 1126; $^1$H NMR (200 MHz, CDCl$_3$) δ: 1.10 (6H, t, J=7.1 Hz), 1.20–1.90 (10H, m), 1.95–2.20 (2H, m), 2.40–2.57 (1H, m), 2.60–2.72 (2H, m), 2.80–3.05 (7H, m), 3.12 (1H, s), 7.05–7.15 (3H, m), 7.22–7.32 (3H, m), 7.59 (2H, d, J=8.2 Hz), 7.83 (1H, s).

WORKING EXAMPLE 4 (PRODUCTION OF COMPOUND 4)

In THF (20 ml) was dissolved 7-phenyl-3,4-dihydronaphthalene-2-carboxylic acid (1.00 g), and to the solution were added oxalyl chloride (523 µl) and a drop of DMF. The mixture was added at room temperature for 1 hour and concentrated under reduced pressure. The residue was dissolved in THF (20 ml), and to the solution were added 1- (4-aminobenzyl)piperidine (837 mg) and triethylamine (673 µl) at room temperature. The reaction mixture was stirred at room temperature for 2 hours, and to the mixture was added water (150 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give 7-phenyl-N-[4-(piperidinomethyl)phenyl]-3,4-dihydronaphthalene-2-carboxamide (Compound 4) (1.15 g) as pale brown crystals.

mp 163–164° C.; Elemental Analysis for $C_{29}H_{30}N_2O \cdot 0.1H_2O$; Calcd: C, 82.08; H, 7.17; N, 6.60. Found: C, 81.94; H, 7.22; N, 6.49. IR (KBr) cm$^{-1}$: 3336, 2935, 1651, 1527, 1412, 1317, 762, 698; $^1$H NMR (200 MHz, CDCl$_3$) δ: 1.35–1.70 (6H, m), 2.30–2.45 (4H, m), 2.65–2.80 (2H, m), 2.92–3.04 (2H, m), 3.46 (2H, s), 7.23–7.62 (14H, m).

WORKING EXAMPLE 5 (PRODUCTION OF COMPOUND 5)

In DMF (3 ml) was dissolved 7-phenyl-N-[4-(piperidinomethyl)phenyl]-3,4-dihydronaphthalene-2-carboxamide (240 mg), and to the mixture was added methyl iodide (106 μl). The mixture was stirred at room temperature for 60 hours and concentrated under reduced pressure. The residue was recrystallized from ethyl acetate to give 1-methyl-1-[4-(7-phenyl-3,4-dihydro-naphthalene-2-carboxamido)benzyl]piperidinium iodide (Compound 5) (247 mg) as colorless crystals.

mp 183–186° C.; Elemental Analysis for $C_{30}H_{33}N_2OI$; Calcd: C, 63.83; H, 5.89; N, 4.96. Found: C, 63.54; H, 5.82; N, 5.05. IR (KBr) cm$^{-1}$: 3450, 1649, 1599, 1520, 1417, 1319; $^1$H NMR (200 MHz, DMSO-d$_6$) δ: 1.40–2.00 (6H, m), 2.55–2.70 (2H, m), 2.80–3.00 (5H, m), 3.20–3.45 (4H, m), 4.53 (2H, s), 7.30–7.70 (11H, m), 7.89 (2H, d, J=8.6 Hz), 10.18 (1H, s).

WORKING EXAMPLE 6 (PRODUCTION OF COMPOUND 6)

In THF (10 ml) was dissolved 7-phenyl-3,4-dihydronaphthalene- 2-carboxylic acid (500 mg), and to the solution were added oxalyl chloride (262 μl) and a drop of DMF. The mixture was stirred at room temperature for 1 hour and concentrated under reduced pressure. The residue was dissolved in THF (10 ml), and to the solution were added 4-aminobenzyldimethylamine (330 mg) and triethylamine (337 μl) at room temperature. The reaction mixture was stirred at room temperature for 3 hours, and to the mixture was added water(100 ml). The mixture was extracted with ethyl acetate. The organic layer was washed with saturated sodium chloride solution, dried with anhydrous sodium sulfate, and concentrated under reduced pressure. The residue was separated and purified with column chromatography (ethyl acetate/triethylamine=20/1) and recrystallized from ethyl acetate-hexane to give N-[4-(dimethylaminomethyl)phenyl]-7-phenyl-3,4-dihydronaphthalene-2-carboxamide (Compound 6) (131 mg) as colorless crystals.

mp 182–184° C.; Elemental Analysis for $C_{26}H_{26}N_2O \cdot 0.2H_2O$; Calcd: C, 80.88; H, 6.89; N, 7.26. Found: C, 81.00; H. 6.90; N, 7.19. IR (KBr) cm$^{-1}$: 3328, 1649, 1529, 1410, 1317, 762, 698; $^1$H NMR (200 MHz, CDCl$_3$) δ: 2.24 (6H, s), 2.65–2.80 (2H, m), 2.94–3.03 (2H, m), 3.41 (2H, s), 7.25–7.63 (14H, m).

WORKING EXAMPLE 7 (PRODUCTION OF COMPOUND 7)

In THF (10 ml) was dissolved 7-phenyl-3,4-dihydronaphthalene-2-carboxylic acid (500 mg), and to the solution were added oxalyl chloride (262 μl) and a drop of DMF. The mixture was stirred at room temperature for 1 hour and concentrated under reduced pressure. The residue was dissolved in THF (10 ml), and to the solution were added 1-(4-aminobenzyl)pyrrolidine (388 mg) and triethylamine (337 μl) at room temperature. The reaction mixture was stirred at room temperature for 3 hours, and to the mixture was added water (100 ml). The mixture was extracted with ethyl acetate. The organic layer was washed with saturated sodium chloride solution, dried with anhydrous sodium sulfate, and concentrated under reduced pressure. The residue was separated and purified with column chromatography (ethyl acetate/triethylamine=20/1) and recrystallized from ethyl acetate-diisopropylether to give 7-phenyl-N-[4-(1-pyrrolidinylmethyl)phenyl]-3,4-dihydronaphthalene-2-carboxamide (Compound 7) (107 mg) as colorless crystals.

mp 186–187° C.; Elemental Analysis for $C_{28}H_{28}N_2O \cdot 0.1H_2O$; Calcd: C, 81.96; H, 6.93; N, 6.83. Found: C, 81.78; H, 6.84; N, 6.89. IR (KBr) cm$^{-1}$: 3329, 2962, 1649, 1529, 1410, 1319, 762, 698; $^1$H NMR (200 MHz, CDCl$_3$) δ: 1.75–1.85 (4H, m), 2.45–2.55 (4H, m), 2.65–2.80 (2H, m), 2.90–3.05 (2H, m), 3.60 (2H, s), 7.25–7.60 (14H, m).

WORKING EXAMPLE 8 (PRODUCTION OF COMPOUND 8)

In THF (10 ml) was dissolved 7-phenyl-3,4-dihydronaphthalene-2-carboxylic acid (500 mg), and to the solution were added oxalyl chloride (262 μl) and a drop of DMF. The mixture was stirred at room temperature for 1 hour and concentrated under reduced pressure. The residue was dissolved in THF (10 ml), and to the solution were added 1- (4-aminobenzyl)morpholine (423 mg) and triethylamine (337 μl) at room temperature. The reaction mixture was stirred at room temperature for 2 hours, and to the mixture was added water (100 ml). The mixture was extracted with ethyl acetate. The organic layer was washed with saturated sodium chloride solution, dried with anhydrous sodium sulfate, and concentrated under reduced pressure. The residue was separated and purified with column chromatography (ethyl acetate) and recrystallized from ethyl acetate-hexane to give N-[4-(morpholinomethyl)-phenyl]-7-phenyl-3,4-dihydronaphthalene-2-carboxamide (659 mg) as colorless crystals.

mp 186–187° C.; Elemental Analysis for $C_{28}H_{28}N_2O_2$; Calcd: C, 79.22; H, 6.65; N, 6.60. Found: C, 78.89; H, 6.50; N, 6.66. IR (KBr) cm$^{-1}$: 3450, 1651, 1620, 1597, 1527, 1412, 1319, 1113, 764, 700; $^1$H NMR (200 MHz, CDCl$_3$) δ: 2.38–2.47 (4H, m), 2.66–2.78 (2H, m), 2.92–3.03 (2H, m), 3.48 (2H, s), 3.67–3.75 (4H, m), 7.25–7.60 (14H, m).

WORKING EXAMPLE 9 (PRODUCTION OF COMPOUND 9)

In THF (10 ml) was dissolved 7-phenyl-3,4-dihydronaphthalene-2-carboxylic acid (500 mg), and to the solution were added oxalyl chloride (262 μl) and a drop of DMF. The mixture was stirred at room temperature for 1 hour and concentrated under reduced pressure. The residue was dissolved in THF (10 ml), and to the solution were added 1-[2-(4-aminophenyl)ethyl]piperidine (450 mg) and triethylamine (337 μl) at room temperature. The reaction mixture was stirred at room temperature for 1 hour, and to the mixture was added water (100 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give 7-phenyl-N-[4-(2-piperidinoethyl)phenyl]-3,4-dihydro-naphthalene-2-carboxamide (Compound 9) (576 mg) as pale brown crystals.

mp 157–159° C.; Elemental Analysis for $C_{30}H_{32}N_2O$; Calcd: C, 82.53; H, 7.39; N, 6.42. Found: C, 82.29; H, 7.24; N, 6.32. IR (KBr) cm$^{-1}$: 3332, 2933, 1651, 1524, 1412, 1317, 1257, 1117, 762, 698; $^1$HNMR (200 MHz, CDCl$_3$) δ: 1.40–1.80 (6H, m), 2.40–2.60 (6H, m), 2.65–2.85 (4H, m), 2.90–3.00 (2H, m), 7.15–7.60 (14H, m).

WORKING EXAMPLE 10 (PRODUCTION OF COMPOUND 10)

In DMF (2 ml) was dissolved N-[4-(dimethylaminomethyl)phenyl]-7-phenyl-3,4-dihydronaphthalene-2-carboxamide (80 mg), and to the mixture was added methyl iodide (39 µl). The mixture was stirred at room temperature for 17 hours and concentrated under reduced pressure. The residue was recrystallized from methanolethyl acetate to give trimethyl[4-(7-phenyl-3,4-dihydronaphthalene-2-carboxamido)benzyl]ammonium iodide (Compound 10) (92 mg) as colorless crystals.

mp 190–192° C.; Elemental Analysis for $C_{27}H_{29}N_2OI.0.5H_2O$; Calcd: C, 60.79; H, 5.67; N, 5.25. Found: C, 60.81; H, 5.59; N, 5.30. IR (KBr) cm$^{-1}$: 3450, 1662, 1595, 1520, 1483, 1416, 1319, 1250, 764, 700; $^1$H NMR (200 MHz, CDCl$_3$) δ: 2.65–2.80 (2H, m), 2.80–2.95 (2H, m), 3.23 (9H, s), 4.98 (2H, s), 7.18 (1H, d, J=8.0 Hz), 7.30–7.60 (9H, m), 7.69 (1H, s), 7.82–7.90 (2H, m), 8.71 (1H, s).

WORKING EXAMPLE 11 (PRODUCTION OF COMPOUND 11)

In DMF (2 ml) was dissolved 7-phenyl-N-[4-(1-pyrrolidinylmethyl)phenyl]-3,4-dihydronaphthalene-2-carboxamide (70 mg), and to the mixture was added methyl iodide (32 µl). The mixture was stirred at room temperature for 17 hours and concentrated under reduced pressure. The residue was recrystallized from methanol-ethyl acetate to give 1-methyl-i-[4-(7-phenyl-3,4-dihydronaphthalene-2-carboxamido)benzyl]pyrrolidinium iodide (Compound 11) (78 mg) as pale yellow crystals.

mp 156–160° C.; Elemental Analysis for $C_{29}H_{31}N_2OI.1.0H_2O$; Calcd: C, 61.27; H, 5.85; N, 4.93. Found: C, 61.23; H, 5.89; N, 5.04. IR (KBr) cm$^{-1}$: 3442, 1655, 1593, 1520, 1416, 1317, 1248, 766, 700; $^1$H NMR (200 MHz, CDCl$_3$) δ: 2.05–2.40 (4H, m), 2.65–2.76 (2H, m), 2.82–2.95 (2H, m), 3.05 (3H, s), 3.43–3.57 (2H, m), 3.80–4.00 (2H, m), 4.98 (2H, s), 7.18 (1H, d, J=8.0 Hz), 7.30–7.56 (9H, m), 7.70 (1H, s), 7.80–7.90 (2H, m), 8.74 (1H, s).

WORKING EXAMPLE 12 (PRODUCTION OF COMPOUND 12)

In DMF (4 ml) was dissolved N-[4-(morpholinomethyl)phenyl]-7-phenyl-3,4-dihydronaphthalene-2-carboxamide (450 mg), and to the mixture was added methyl iodide (198 µl). The mixture was stirred at room temperature for 18 hours and concentrated under reduced pressure. The residue was recrystallized from ethyl acetate to give 4-methyl-4-[4-(7-phenyl-3,4-dihydro-naphthalene-2-carboxamido)benzyl]morpholinium iodide (Compound 12) (575 mg) as pale yellow crystals.

mp 166–170° C.; Elemental Analysis for $C_{29}H_{31}N_2O_2I.0.5H_2O$; Calcd: C, 60.53; H, 5.60; N, 4.87. Found: C, 60.41; H, 5.61; N, 4.74. IR (KBr) cm$^{-1}$: 3450, 1653, 1593, 1520, 1481, 1416, 1317, 1246, 1122, 887, 764, 698; $^1$H NMR (200 MHz, CDCl$_3$) δ: 2.60–2.75 (2H, m), 2.75–2.90 (2H, m), 3.22 (3H, s), 3.35–3.50 (2H, m), 3.55–3.75 (2H, m), 3.80–4.05 (4H, m), 5.13 (2H, s), 7.12 (1H, d, J=7.6 Hz), 7.25–7.55 (9H, m), 7.71 (1H, s), 7.80–7.87 (2H, m), 8.95 (1H, s).

WORKING EXAMPLE 13 (PRODUCTION OF COMPOUND 13)

In DMF (4 ml) was dissolved 7-phenyl-N-[4-(2-piperidinoethyl)phenyl]-3,4-dihydronaphthalene-2-carboxamide (350 mg), and to the mixture was added methyl iodide (150 µl). The mixture was stirred at room temperature for 14 hours and concentrated under reduced pressure. The residue was recrystallized from methanolethyl acetate to give 1-methyl-1-[2-[4-(7-phenyl-3,4-dihydronaphthalene-2-carboxamide)phenyl]ethyl]piperidinium iodide (Compound 13) (410 mg) as pale brown crystals.

mp 219–220° C.; Elemental Analysis for $C_{31}H_{35}N_2OI.0.2H_2O$; Calcd: C, 63.96; H, 6.13; N, 4.81. Found: C, 63.91; H, 6.06; N, 4.89. IR (KBr) cm$^{-1}$: 2941, 1666, 1595, 1520, 1313, 1240, 1205, 837, 768, 702; $^1$H NMR (200 MHz, DMSO-d$_6$) δ: 1.45–1.90 (6H, m), 2.55–2.70 (2H, m), 2.80–3.17 (7H, m), 3.25–3.60 (6H, m), 7.25–7.80 (13H, m), 9.95 (1H, s).

WORKING EXAMPLE 14 (PRODUCTION OF COMPOUND 14)

In THF (10 ml) was dissolved 7-(4-methylphenyl)-3,4-dihydronaphthalene-2-carboxylic acid (500 mg), and to the solution were added oxalyl chloride (248 µl) and a drop of DMF. The mixture was stirred at room temperature for 1 hour and concentrated under reduced pressure. The residue was dissolved in THF (10 ml), and to the solution were added 1- (4-aminobenzyl)piperidine (396 mg) and triethylamine (318 µl) at room temperature. The reaction mixture was stirred at room temperature for 14 hours, and to the mixture was added water (100 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give 7-(4-methylphenyl)-N-[4-(piperidinomethyl)phenyl]-3,4-dihydronaphthalene-2-carboxamide (Compound 14) (616 mg) as pale brown crystals.

mp 187–189° C.; Elemental Analysis for $C_{30}H_{32}N_2O$; Calcd: C, 82.53; H, 7.39; N, 6.42. Found: C, 82.26; H, 7.36; N, 6.37. IR (KBr) cm$^{-1}$: 3310, 2931, 1643, 1599, 1527, 1412, 1315, 1255, 806; $^1$H NMR (200 MHz, CDCl$_3$) δ: 1.38–1.65 (6H, m), 2.32–2.42 (7H, m), 2.65–2.77 (2H, m), 2.92–3.02 (2H, m), 3.46 (2H, s), 7.20–7.34 (6H, m), 7.40–7.58 (7H, m).

WORKING EXAMPLE 15 (Production of Compound 15)

In THF (10 ml) was dissolved 7-(4-fluorophenyl)-3,4-dihydronaphthalene-2-carboxylic acid (500 mg), and to the solution were added oxalyl chloride (243 µl) and a drop of DMF. The mixture was stirred at room temperature for 1 hour and concentrated under reduced pressure. The residue was dissolved in THF (10 ml), and to the solution were added 1-(4-aminobenzyl)piperidine (389 mg) and triethylamine (313 µl) at room temperature. The reaction mixture was stirred at room temperature for 14 hours, and to the mixture was added water (100 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give 7-(4-fluorophenyl)-N-[4-(piperidinomethyl)phenyl]-3,4-dihydronaphthalene-2-carboxamide (Compound 15) (736 mg) as pale yellow crystals.

mp 175–176° C.; Elemental Analysis for $C_{29}H_{29}N_2OF.0.2H_2O$; Calcd: C, 78.42; H, 6.67; N, 6.31. Found: C, 78.36; H, 6.68; N, 6.23. IR (KBr) $cm^{-1}$: 3329, 2935, 1649, 1595, 1518, 1319, 1244, 824; $^1H$ NMR (200 MHz, $CDCl_3$) δ: 1.35–1.65 (6H, m), 2.34–2.41 (4H, m), 2.67–2.77 (2H, m), 2.92–3.02 (2H, m), 3.46 (2H, s), 7.07–7.58 (13H, m).

WORKING EXAMPLE 16 (Production of Compound 16)

In DMF (3 ml) was dissolved 7-(4-methylphenyl)-N-[4-(piperidinomethyl)phenyl]-3,4-dihydronaphthalene-2-carboxamide (400 mg), and to the mixture was added methyl iodide (171 μl). The mixture was stirred at room temperature for 18 hours and concentrated under reduced pressure. The residue was recrystallized from ethyl acetate to give 1-methyl-1-[4-[7-(4-methylphenyl)-3,4-dihydronaphthalene-2-carboxamido]benzyl]piperidinium iodide (Compound 16) (490 mg) as colorless crystals.

mp 202–204° C.; Elemental Analysis for $C_{31}H_{35}N_2OI.0.5H_2O$; Calcd: C, 63.37; H, 6.18; N, 4.77. Found: C, 63.69; H, 5.98; N, 4.87. IR (KBr) $cm^{-1}$: 3450, 3294, 2941, 1649, 1622, 1599, 1520, 1417, 1319, 1248, 812; $^1H$ NMR (200 MHz, DMSO-$d_6$) δ: 1.40–2.00 (6H, m), 2.35 (3H, s), 2.55–2.67 (2H, m), 2.82–2.95 (5H, m), 3.22–3.35 (4H, m), 4.53 (2H, s), 7.24–7.35 (3H, m), 7.46–7.60 (7H, m), 7.89 (2H, d, J=8.8 Hz), 10.15 (1H, s).

WORKING EXAMPLE 17 (Production of Compound 17)

In DMF (3 ml) was dissolved 7-(4-fluorophenyl)-N-[4-(piperidinomethyl)phenyl]-3,4-dihydronaphthalene-2-carboxamide (500 mg), and to the mixture was added methyl iodide (212 μl). The mixture was stirred at room temperature for 18 hours and concentrated under reduced pressure. The residue was recrystallized from ethyl acetate to give 1-[4-[7-(4-fluoro-phenyl)-3,4-dihydronaphthalene-2-carboxamido]benzyl]-1-methylpiperidinium iodide (Compound 17) (610 mg) as colorless crystals.

mp 177–180° C.; Elemental Analysis for $C_{30}H_{32}N_2OFI.0.2H_2O$; Calcd: C, 61.48; H, 5.57; N, 4.78. Found: C, 61.38; H, 5.50; N, 4.81. IR (KBr) $cm^{-1}$: 3450, 3310, 2947, 1651, 1597, 1518, 1416, 1319, 1246, 1225, 824; $^1H$ NMR (200 MHz, DMSO-$d_6$) δ: 1.40–2.00 (6H, m), 2.55–2.67 (2H, m), 2.85–2.96 (5H, m), 3.20–3.38 (4H, m), 4.53 (2H, s), 7.25–7.38 (3H, m), 7.46–7.60 (5H, m), 7.67–7.76 (2H, m), 7.89 (2H, d, J=8.6 Hz), 10.17 (1H, s).

WORKING EXAMPLE 18 (Production of Compound 18)

To a mixture of N-[4-(hydroxymethyl)phenyl]-7-phenyl-3,4-dihydronaphthalene-2-carboxamide (200 mg), triethylamine (158 μl) and THF (10 ml) was added methanesulfonic acid anhydride (118 mg) at 0° C., and the mixture was stirred at room temperature for 3 hours. To the reaction mixture was added dilute hydrochloric acid, and the mixture was extracted with ethyl acetate. The organic layer was washed with saturated sodium chloride solution, dried with anhydrous sodium sulfate, and concentrated under reduced pressure. The residue was dissolved in DMF (3 ml), and to the mixture was added pyridine (137tt1). The mixture was stirred at room temperature for 96 hours and concentrated under reduced pressure. The residue was recrystallized from ethyl acetate-methanol to give 1-[4-(7-phenyl-3,4-dihydronaphthalene-2-carboxamido)-benzyl]pyridinium chloride (Compound 18) (95 mg) as colorless crystals.

mp 162–164° C.; Elemental Analysis for $C_{29}H_{25}N_2OCl.1.0H_2O$; Calcd: C, 73.95; H, 5.78; N, 5.95; Cl, 7.53. Found: C, 74.25; H, 5.94; N, 5.92; Cl, 7.12. IR (KBr) $cm^{-1}$: 3450, 3030, 1653, 1595, 1520, 1416, 1323, 1254, 1213, 762; $^1H$ NMR (200 MHz, $CDCl_3$) δ: 2.50–2.75 (4H, m), 5.92 (2H, br s), 7.00 (1H, d, J=8.0 Hz), 7.15–7.40 (9H, m), 7.60–7.85 (5H, m), 8.08–8.25 (1H, br), 9.21 (2H, br s), 9.73 (1H, br s).

WORKING EXAMPLE 19 (Production of Compound 19)

To a mixture of N-[4-(hydroxymethyl)phenyl]-7-phenyl-3,4-dihydronaphthalene-2-carboxamide (200 mg), lithium chloride (95 mg), triethylamine (182/111) and dichloromethane (20 ml) was added methanesulfonyl chloride (174/111), and the mixture was stirred at room temperature for 2 hours. To the reaction mixture was added dilute hydrochloric acid. The organic layer was separated, washed with saturated sodium chloride solution, dried with anhydrous sodium sulfate, and concentrated under reduced pressure. The residue was dissolved in DMF (3 ml), and to the mixture was added 3-lutidine (167/111). The reaction mixture was stirred at room temperature for 17 hours and concentrated under reduced pressure. The residue was recrystallized from ethyl acetate-methanol to give 3-methyl-1-[4-(7-phenyl-3,4-dihydro-naphthalene- 2-carboxamido)benzyl]pyridinium chloride (90 mg) as colorless crystals.

mp 136–140° C.; Elemental Analysis for $C_{30}H_{27}N_2OCl.1.5H_2O$; Calcd: C, 72.94; H, 6.12; N, 5.67. Found: C, 73.19; H, 6.37; N, 5.61. IR (KBr) $cm^{-1}$: 3450, 3030, 1653, 1597, 1520, 1416, 1319, 1250, 1213, 764; $^1H$ NMR (200 MHz, $CDCl_3$) δ: 2.48 (3H, s), 2.65–2.90 (4H, m), 6.03 (2H, br s), 7.12–7.20 (1H, m), 7.25–7.55 (9H, m), 7.70–7.82 (4H, m), 7.95–8.07 (1H, m), 9.29 (2H, br s), 9.35–9.50 (1H, br).

WORKING EXAMPLE 20 (Production of Compound 20)

To a mixture of N-[4-(hydroxymethyl)phenyl]-7-phenyl-3,4-dihydronaphthalene-2-carboxamide (200 mg), lithium chloride (48 mg), triethylamine (158 μl) and dichloromethane (30 ml) was added methanesulfonyl chloride (61 μl), and the mixture was stirred at room temperature for 2 hours. To the reaction mixture was added dilute hydrochloric acid. The organic layer was separated, washed with saturated sodium chloride solution, dried with anhydrous sodium sulfate, and concentrated under reduced pressure. The residue was dissolved in DMF (3 ml), and to the mixture was added 3,5-lutidine (193 μl). The reaction mixture was stirred at room temperature for 65 hours and concentrated under reduced pressure. The residue was recrystallized from ethyl acetate-methanol to give 3,5-dimethyl-1-[4-(7-phenyl-3,4-dihydronaphthalene-2-carboxamido)benzyl]pyridinium chloride (Compound 20) (186 mg) as colorless crystals.

mp 163–165° C.; Elemental Analysis for $C_{31}H_{29}N_2OCl.1.3H_2O$; Calcd: C, 73.81; H, 6.31; N, 5.55.

Found: C, 73.85; H. 6.29; N, 5.49. IR (KBr) cm$^{-1}$: 3450, 3030, 1655, 1597, 1520, 1483, 1416, 1319, 1252, 766; $^1$H NMR (200 MHz, CDCl$_3$) δ: 2.44 (6H, s), 2.67–2.92 (4H, m), 5.99 (2H, s), 7.16 (1H, d, J=7.6 Hz), 7.25–7.55 (9H, m), 7.77–7.90 (4H, m), 9.20 (1H, s), 9.72 (1H, br s).

WORKING EXAMPLE 21 (Production of Compound 21)

In DMF (3 ml) was dissolved N-[4-(chloromethyl)-phenyl]-7-phenyl-3,4-dihydronaphthalene-2-carboxamide (140 mg), and to the mixture was added 4-cyanopyridine (117 mg). The mixture was stirred at 70° for 24 hours and concentrated under reduced pressure. The residue was recrystallized from ethyl acetate-methanol to give 4-cyano-1-[4-(7-phenyl-3,4-dihydro-naphthalene-2-carboxamido) benzyl]pyridinium chloride (Compound 21) (141 mg) as pale brown crystals.

mp 163–165° C.; Elemental Analysis for C$_{30}$H$_{24}$N$_3$OCl.0.5H$_2$O; Calcd: C, 73.99; H, 5.17; N, 8.63. Found: C, 73.71; H, 5.29; N, 8.47. IR (KBr) cm$^{-1}$: 3430, 3024, 1653, 1597, 1524, 1416, 1319, 1252, 829, 764 $^1$H NMR (200 MHz, DMSO-d$_6$) δ: 2.50–2.65 (2H, m), 2.82–2.93 (2H, m), 5.92 (2H, s), 7.29–7.67 (11H, m), 7.85 (2H, d, J=8.6 Hz), 8.73 (2H, d, J=6.8 Hz), 9.54 (2H, d, J=6.8 Hz), 10.19 (1H, s).

WORKING EXAMPLE 22 (Production of Compound 22)

In DMF (3 ml) was dissolved N-[4-(chloromethyl)-phenyl]-7-phenyl-3,4-dihydronaphthalene-2-carboxamide (160 mg), and to the mixture was added 3-cyanopyridine (133 mg). The mixture was stirred at 70° C. for 24 hours and concentrated under reduced pressure. The residue was recrystallized from ethyl acetate-methanol to give 3-cyano-1-[4-(7-phenyl-3,4-dihydro-naphthalene-2-carboxamido) benzyl]pyridinium chloride (Compound 22) (58 mg) as pale orange crystals.

mp 158–161° C.; Elemental Analysis for C$_{30}$H$_{24}$N$_3$OCl.1.5H$_2$O; Calcd: C, 71.35; H, 5.39; N, 8.32. Found: C, 71.28; H, 5.49; N, 8.40. IR (KBr) cm$^{-1}$: 3450, 3028, 1653, 1597, 1520, 1416, 1319, 1252, 766; $^1$H NMR (200 MHz, DMSO-d$_6$) δ:2.55–2.68 (2H, m), 2.82–2.95 (2H, m), 5.88 (2H, s), 7.30–7.90 (13H, m), 8.32–8.42 (1H, m), 9.13 (1H, d, J=8.0 Hz), 9.47 (1H, d, J=5.8 Hz), 10.05 (1H, s), 10.21 (1H, s).

WORKING EXAMPLE 23 (Production of Compound 23)

In DMF (3 ml) was dissolved N-[4-(chloromethyl) phenyl]-7-phenyl-3,4-dihydronaphthalene-2-carboxamide (160 mg), and to the mixture was added 3-chloropyridine (122 μl). The mixture was stirred at 70° C. for 24 hours and concentrated under reduced pressure. The residue was recrystallized from ethyl acetate-methanol to give 3-chloro-1-[4-(7-phenyl-3,4-dihydro-naphthalene-2-carboxamido) benzyl]pyridinium chloride (Compound 23) (110 mg) as pale yellow crystals.

mp 136–139° C.; Elemental Analysis for C$_{29}$H$_{24}$N$_2$OCl$_2$.0.5H$_2$O; Calcd: C, 70.16; H, 5.08; N, 5.64. Found: C, 70.13; H, 5.03; N, 5.68. IR (KBr) cm$^{-1}$: 3450, 3028, 1653, 1597, 1520, 1483, 1416, 1317, 1252, 1213, 1165, 766, 700; $^1$H NMR (200 MHz, DMSO-d$_6$) δ: 2.55–2.68 (2H, m), 2.82–2.95 (2H, m), 5.85 (2H, s), 7.30–7.70 (11H, m), 7.86 (2H, d, J=8.4 Hz), 8.16–8.26 (1H, m), 8.81 (1H, d, J=7.6 Hz), 9.24 (1H, d, J=6.0 Hz), 9.72 (1H, s), 10.21 (1H, s).

WORKING EXAMPLE 24 (Production of Compound 24)

In DMF (3 ml) was dissolved N-[4-(chloromethyl) phenyl]-7-phenyl-3,4-dihydronaphthalene-2-carboxamide (140 mg), and to the mixture was added 1-ethylpiperidine (154 μl). The mixture was stirred at room temperature for 14 hours and concentrated under reduced pressure. The residue was recrystallized from ethyl acetate-methanol to give 1-ethyl-1-[4-(7-phenyl-3,4-dihydro-naphthalene-2-carboxamido)benzyl]piperidinium chloride (Compound 24) (125 mg) as colorless crystals.

mp 153–156° C.; Elemental Analysis for C$_{31}$H$_{35}$N$_2$OCl.1.5H$_2$O; Calcd: C, 72.42; H, 7.45; N, 5.45. Found: C, 72.14; H, 7.41; N, 5.32. IR (KBr) cm$^{-1}$: 3450, 2943, 1655, 1595, 1520, 1483, 1416, 1319, 1255, 1217, 766, 700; $^1$H NMR (200 MHz, CDCl$_3$) δ: 1.30–1.42 (3H, m), 1.60–1.90 (6H, m), 2.68–2.95 (4H, m), 3.27–3.45 (4H, m), 3.55–3.70 (2H, m), 4.75 (2H, s), 7.17 (1H, d, J=7.8 Hz), 7.25–7.60(9H, m), 7.90 (1H, s), 8.03 (2H, d, J=8.6 Hz), 10.00 (1H, s).

WORKING EXAMPLE 25 (Production of Compound 25)

In DMF (3 ml) was dissolved N-[4-(chloromethyl) phenyl]-7-phenyl-3,4-dihydronaphthalene-2-carboxamide (160 mg), and to the mixture was added triethylamine (180 μl). The mixture was stirred at room temperature for 14 hours and concentrated under reduced pressure. The residue was recrystallized from ethyl acetate to give triethyl[4-(7-phenyl-3,4-dihydronaphthalene-2-carboxamido)benzyl] ammonium chloride (Compound 25) (176 mg) as colorless crystals.

mp 205–206° C.; Elemental Analysis for C$_{30}$H$_{35}$N$_2$OCl.0.2H$_2$O; Calcd: C, 75.28; H, 7.45; N, 5.85. Found: C, 75.10; H, 7.38; N, 5.91. IR (KBr) cm$^{-1}$: 3450, 3007, 1655, 1599, 1519, 1483, 1416, 1319, 1252, 1215, 768, 704; $^1$H NMR (200 MHz, CDCl$_3$) δ: 1.37 (9H, t, J=6.9 Hz), 2.72–2.96 (4H, m), 3.22 (6H, q, J=6.9 Hz), 4.62 (2H, s), 7.15–7.45 (7H, m), 7.50–7.60 (3H, m), 7.99 (1H, s), 8.12 (2H, d, J=8.6 Hz), 10.19 (1H, s).

WORKING EXAMPLE 26 (Production of Compound 26)

In DMF (3 ml) was dissolved N-[4-(chloromethyl)-phenyl]-7-phenyl-3,4-dihydronaphthalene-2-carboxamide (160 mg), and to the mixture was added tripropylamine (244 μl). The mixture was stirred at room temperature for 14 hours and concentrated under reduced pressure. The residue was recrystallized from ethyl acetate to give [4-(7-phenyl-3,4-dihydronaphthalene-2-carboxamido)benzyl] tripropylammonium chloride (Compound 26) (205 mg) as colorless crystals.

mp 206–207° C.; Elemental Analysis for C$_{33}$H$_{41}$N$_2$OCl.0.5H$_2$O; Calcd: C, 75.33; H, 8.05; N, 5.32. Found: C, 75.59; H, 7.88; N, 5.63. IR (KBr) cm$^{-1}$: 3450, 2970, 1649, 1595, 1524, 1481, 1417, 1317, 1252, 1217, 770, 708; $^1$H NMR (200 MHz, CDCl$_3$) δ: 0.94 (9H, t, J=7.2 Hz), 1.60–1.90 (6H, m), 2.79–3.10 (10H, m), 4.64 (2H, s), 7.07 (2H, d, J=8.4 Hz), 7.20 (1H, d, J=7.8 Hz), 7.31–7.45 (4H, m), 7.54–7.60 (3H,m), 8.10 (1H, s), 8.19 (2H, d, J=8.6 Hz), 10.43 (1H, s).

WORKING EXAMPLE 27 (Production of Compound 27)

In DMF (3 ml) was dissolved N-[4-(chloromethyl)-phenyl]-7-phenyl-3,4-dihydronaphthalene-2-carboxamide (160 mg), and to the mixture was added 3-ethylpyridine (146 μl). The mixture was stirred at 70° C. for 72 hours and concentrated under reduced pressure. The residue was recrystallized from ethyl acetate-methanol to give 3-ethyl-1-[4-(7-phenyl-3,4-dihydro-naphthalene-2-carboxamido) benzyl]pyridinium chloride (Compound 27) (185 mg) as colorless crystals.

mp 142–145° C.; Elemental Analysis for $C_{31}H_{29}N_2OCl.0.5H_2O$; Calcd: C, 75.98; H, 6.17; N, 5.72. Found: C, 75.96; H, 6.13; N, 5.99. IR (KBr) cm$^{-1}$: 3381, 1657, 1597, 1520, 1416, 1317, 1252, 762; $^1$H NMR (200 MHz, CDCl$_3$) δ: 1.25 (3H, t, J=7.6 Hz), 2.64–2.88 (6H, m), 6.09 (2H, s), 7.14 (1H, d, J=7.8 Hz), 7.25–7.52 (9H, m), 7.71–7.88 (4H, m), 8.04 (1H, d, J=8.0 Hz), 9.37 (1H, d, J=6.0 Hz), 9.43 (1H, s), 9.81 (1H, s).

WORKING EXAMPLE 28 (Production of Compound 28)

In DMF (3 ml) was dissolved N-[4-(chloromethyl)-phenyl]-7-phenyl-3,4-dihydronaphthalene-2-carboxamide (160 mg), and to the mixture was added 2-picoline (126 μl). The mixture was stirred at 70° C. for 63 hours and concentrated under reduced pressure. The residue was recrystallized from ethyl acetate-methanol to give 2-methyl-1-[4-(7-phenyl-3,4-dihydronaphthalene-2-carboxamido)benzyl] pyridinium chloride (Compound 28) (140 mg) as pale brown crystals.

mp 152–155° C.; Elemental Analysis for $C_{30}H_{27}N_2OCl.1.0H_2O$; Calcd: C, 74.29; H, 6.03; N, 5.78. Found: C, 74.56; H, 5.93; N, 5.80. IR (KBr) cm$^{-1}$: 3402, 1630, 1597, 1520, 1414, 1319, 1250, 764, 700; $^1$H NMR (200 MHz, CDCl$_3$) δ: 2.60–2.90 (7H, m), 6.07 (2H, s), 7.04–7.15 (3H, m), 7.25–7.50 (7H, m), 7.65 (1H, d, J=7.8 Hz), 7.72–7.92 (4H, m), 8.12–8.22 (1H, m), 9.63 (1H, d, J=6.2 Hz), 9.86 (1H, s).

WORKING EXAMPLE 29 (Production of Compound 29)

In DMF (3 ml) was dissolved N-[4-(chloromethyl)-phenyl]-7-phenyl-3,4-dihydronaphthalene-2-carboxamide (160 mg), and to the mixture was added thiazole (91 μl). The mixture was stirred at 100° C. for 48 hours and concentrated under reduced pressure. The residue was recrystallized from ethyl acetate-methanol to give 3-[4-(7-phenyl-3,4-dihydronaphthalene-2-carboxamido)benzyl]thiazolium chloride (Compound 29) (133 mg) as pale brown crystals.

mp 149–152° C.; Elemental Analysis for $C_{27}H_{23}N_2OSCl.0.5H_2O$; Calcd: C, 69.29; H, 5.17; N, 5.99. Found: C, 69.43; H, 4.88; N, 6.12. IR (KBr) cm$^{-1}$: 3419, 3026, 1649, 1597, 1520, 1414, 1317, 1252, 764, 698; $^1$H NMR (200 MHz, DMSO-d$_6$) δ: 2.55–2.67 (2H, m), 2.82–2.96 (2H, m), 5.78 (2H, s), 7.29–7.71 (11H, m), 7.84 (2H, d, J=8.2 Hz), 8.33–8.40 (1H, m), 8.58–8.66 (1H, m), 10.18 (1H, s), 10.42 (1H, s).

WORKING EXAMPLE 30 (Production of Compound 30)

In DMF (3 ml) was dissolved N-[4-(chloromethyl)phenyl]-7-phenyl-3,4-dihydronaphthalene-2-carboxamide (160 mg), and to the mixture was added quinuclidine (285 mg). The mixture was stirred at 100° C. for 24 hours and concentrated under reduced pressure. The residue was recrystallized from ethyl acetate-methanol to give 1-[4-(7-phenyl-3,4-dihydronaphthalene-2-carboxamide)benzyl] quinuclidium chloride (Compound 30) (62 mg) as colorless crystals.

mp 250–252° C.; Elemental Analysis for $C_{31}H_{33}N_2OCl.0.9H_2O$; Calcd: C, 74.28; H, 7.00; N, 5.59. Found: C, 74.48; H, 7.01; N, 5.56. IR (KBr) cm$^{-1}$: 3425, 2945, 1655, 1595, 1520, 1416, 1319, 1255, 833, 766, 700; $^1$H NMR (200 MHz, CDCl$_3$) δ: 1.75–2.15 (7H, m), 2.68–2.90 (4H, m), 3.40–3.70 (6H, m), 4.73 (2H, s), 7.15 (1H, d, J=7.8 Hz), 7.25–7.56 (9H, m), 7.88 (1H, s), 7.96 (2H, d, J=8.0 Hz), 9.93 (1H, s).

WORKING EXAMPLE 31 (Production of Compound 31)

In DMF (3 ml) was dissolved N-[4-(chloromethyl) phenyl]-7-phenyl-3,4-dihydronaphthalene-2-carboxamide (150 mg), and to the mixture was added ethyl 1-methylpiperidine-4-carboxylate (206 mg). The mixture was stirred at room temperature for 15 hours and concentrated under reduced pressure. The residue was recrystallized from ethyl acetate-methanol to give 4-ethoxycarbonyl-1-methyl-1-[4-(7-phenyl-3,4-dihydronaphthalene-2-carboxamido)benzyl]piperidinium chloride (Compound 31) (185 mg, ratio of isomers=37:63) as colorless crystals.

mp 153–156° C.; Elemental Analysis for $C_{33}H_{37}N_2O_3Cl.0.5H_2O$; Calcd: C, 71.53; H, 6.91; N, 5.06. Found: C, 71.69; H, 6.76; N, 5.11. IR (KBr) cm$^{-1}$: 3388, 1726, 1655, 1595, 1520, 1483, 1416, 1319, 1254, 1214, 766, 700; $^1$H NMR (200 MHz, CDCl$_3$) δ: 1.15–1.30 (3H, m), 2.05–2.22 (3H, m), 2.65–2.92 (6H, m), 3.02 (1.11H, s), 3.13 (1.89H, s), 3.38–3.75 (3.26H, m), 3.88–4.22 (2.74H, m), 4.76 (1.26H, s), 5.09 (0.74H, s), 7.15 (1H, dd, J=4.4, 7.6 Hz), 7.25–7.55 (9H, m), 7.83 (1H, s), 7.94 (1H, d, J=8.4 Hz), 8.00 (1H, d, J=8.4 Hz), 9.74 (0.63H, s), 9.84 (0.37H, s).

WORKING EXAMPLE 32 (Production of Compound 32)

In THF (10 ml) was dissolved N-[4-(chloromethyl) phenyl]-7-phenyl-3,4-dihydronaphthalene-2-carboxamide (300 mg), and to the mixture was added hexamethylene-imine (270 μl). The mixture was refluxed for 3.5 hours. The reaction mixture was cooled to room temperature, and to the mixture was added water (30 ml). The mixture was extracted with ethyl acetate. The organic layer was washed with saturated sodium chloride solution, dried with anhydrous sodium sulfate, and concentrated under reduced pressure. The residue was separated and purified with column chromatography (ethyl acetate/triethylamine=20/1) and recrystallized from ethyl acetate-hexane to give N-[4-(1-perhydroazepinylmethyl)-phenyl]-7-phenyl-3,4-dihydronaphthalene-2-carboxamide (Compound 32) (257 mg) as colorless crystals.

mp 168–170° C.; Elemental Analysis for $C_{30}H_{32}N_2O$; Calcd: C, 82.53; H, 7.39; N, 6.42. Found: C, 82.28; H, 7.26; N, 6.37. IR (KBr) cm$^{-1}$: 3304, 2924, 1645, 1601, 1520, 1410, 1317, 1254, 831, 762, 698; $^1$H NMR (200 MHz, CDCl$_3$) δ: 1.61 (8H, s), 2.56–2.76 (6H, m), 2.92–3.03 (2H, m), 3.61 (2H, s), 7.23–7.61 (14H, m).

WORKING EXAMPLE 33 (Production of Compound 33)

In DMF (3 ml) was dissolved N-[4-(1-perhydro-azepinylmethyl)phenyl]-7-phenyl-3,4-dihydronaphthalene-2-carboxamide (150 mg), and to the mixture was added methyl iodide (64 μl). The mixture was stirred at room temperature for 12 hours and concentrated under reduced pressure. The residue was recrystallized from ethyl acetate-methanol to give 1-methyl-1-[4-(7-phenyl-3,4-dihydronaphthalene-2-carboxamido)benzyl]perhydro-azepinium iodide (180 mg) as colorless crystals.

mp 197–199° C.; Elemental Analysis for C$_{31}$H$_{35}$N$_2$OI.0.5H$_2$O; Calcd: C, 63.37; H, 6.18; N, 4.77. Found: C, 63.39; H, 6.31; N, 4.71. IR (KBr) cm$^{-1}$: 3427, 3267, 2937, 1660, 1593, 1520, 1481, 1417, 1313, 1250, 694; $^1$H NMR (200 MHz, DMSO-d$_6$) δ: 1.50–1.70 (4H, m), 1.80–1.96 (4H, m), 2.55–2.68 (2H, m), 2.83–2.97 (5H, m), 3.22–3.36 (2H, m), 3.40–3.60 (2H, m), 4.50 (2H, s), 7.30–7.70 (11H, m), 7.89 (2H, d, J=8.4 Hz), 10.19 (1H, s).

WORKING EXAMPLE 34 (Production of Compound 34)

In DMF (3 ml) was dissolved N-[4-(chloromethyl)-phenyl]-7-(4-methylphenyl)-3,4-dihydronaphthalene-2-carboxamide (150 mg), and to the mixture was added 1-ethylpiperidine (159 μl). The mixture was stirred at room temperature for 20 hours. To the reaction mixture was added ethyl acetate (100 ml), and the resulting precipitate was filtered to give 1-ethyl-1-[4-[7-(4-methylphenyl)-3,4-dihydronaphthalene-2-carboxamido]benzyl]piperidinium chloride (Compound 34) (156 mg) as colorless crystals.

mp 207–209° C.; Elemental Analysis for C$_{32}$H$_{37}$N$_2$OCl; Calcd: C, 76.70; H, 7.44; N, 5.59. Found: C, 76.33; H, 7.22; N, 5.67. IR (KBr) cm$^{-1}$: 3440, 2945, 1651, 1595, 1520, 1416, 1321, 1248, 808; $^1$H NMR (200 MHz, CDCl$_3$) δ: 1.36 (3H, t, J=6.0 Hz), 1.60–1.90 (6H, m), 2.37 (3H, s), 2.68–2.92 (4H, m), 3.26–3.42 (4H, m), 3.52–3.70 (2H, m), 4.76 (2H, s), 7.11–7.23 (3H, m), 7.31–7.52 (6H, m), 7.90 (1H, s), 8.04 (2H, d, J=8.4 Hz), 10.07 (1H, s).

WORKING EXAMPLE 35 (Production of Compound 35)

In THF (15 ml) was dissolved N-[4-(chloromethyl)phenyl]-7-(4-methylphenyl)-3,4-dihydronaphthalene-2-carboxamide (300 mg), and to the mixture was added 4-benzylpiperidine (408 μl). The mixture was ref luxed for 19 hours. The reaction mixture was cooled to room temperature, and to the mixture was added water (100 ml). The mixture was extracted with ethyl acetate. The organic layer was washed with saturated sodium chloride solution, dried with anhydrous sodium sulfate, and concentrated under reduced pressure. The residue was separated and purified with column chromatography (ethyl acetate) and recrystallized from ethyl acetate-hexane to give N-[4-(4-benzylpiperidinomethyl)phenyl]-7-(4-methylphenyl)-3,4-dihydronaphthalene-2-carboxamide (Compound 35) (259 mg) as colorless crystals.

mp 199–201° C.; Elemental Analysis for C$_{37}$H$_{38}$N$_2$O; Calcd: C, 84.37; H, 7.27; N, 5.32. Found: C, 84.34; H, 7.18; N, 5.39. IR (KBr) cm$^{-1}$: 3439, 2920, 1647, 1520, 1412, 1315, 808, 700; $^1$H NMR (200 MHz, CDCl$_3$) δ: 1.20–1.70 (5H, m), 1.80–1.97 (2H, m), 2.40 (3H, s), 2.53 (2H, d, J=6.2 Hz), 2.65–2.78 (2H, m), 2.80–3.02 (4H, m), 3.45 (2H, s), 7.09–7.36 (11H, m), 7.40–7.63 (7H, m).

WORKING EXAMPLE 36 (Production of Compound 36)

In DMF (3 ml) was dissolved N-[4-(4-benzyl-piperidinomethyl)phenyl]-7-(4-methylphenyl)-3,4-dihydronaphthalene-2-carboxamide (150 mg), and to the mixture was added methyl iodide(53 μl). The mixture was stirred at room temperature for 23 hours. To the reaction mixture was added ethyl acetate(100 ml), and the resulting precipitate was filtered to give 4-benzyl-1-methyl-1-[4-[7-(4-methylphenyl)-3,4-dihydronaphthalene-2-carboxamido]benzyl]piperidinium iodide (Compound 36) (141 mg, ratio of isomers=19:81) as colorless crystals.

mp 209–212° C.; Elemental Analysis for C$_{38}$H$_{41}$N$_2$OI.0.5H$_2$O; Calcd: C, 67.35; H, 6.25; N, 4.13. Found: C, 67.28; H, 6.33; N, 4.08. IR (KBr) cm$^{-1}$: 3439, 1659, 1593, 1520, 1416, 1317, 1250, 812; $^1$H NMR (200 MHz, DMSO-d$_6$) δ: 1.55–2.00 (5H, m), 2.35 (3H, s), 2.52–2.75 (4H, m), 2.80–3.00 (5H, m), 3.20–3.40 (4H, m), 4.49 (1.62H, s), 4.60 (0.38H, s), 7.13–7.60 (15H, m), 7.80–7.90 (2H, m), 10.15 (1H, s).

WORKING EXAMPLE 37 (Production of Compound 37)

In DMF (3 ml) was dissolved N-[4-(chloromethyl)phenyl]-7-(4-methylphenyl)-3,4-dihydronaphthalene-2-carboxamide (150 mg), and to the mixture was added 1-ethylperhydroazepine (98 mg). The mixture was stirred at room temperature for 15 hours. To the reaction mixture was added ethyl acetate (100 ml), and the resulting precipitate was filtered and recrystallized from ethyl acetate-methanol to give 1-ethyl-1-[4-[7-(4-methyl-phenyl)-3,4-dihydronaphthalene-2-carboxamido]benzyl] perhydroazepinium chloride (Compound 37) (137 mg) as colorless crystals.

mp 207–210° C.; Elemental Analysis for C$_{33}$H$_{39}$N$_2$OCl.0.5H$_2$O; Calcd: C, 75.62; H, 7.69; N, 5.34. Found: C, 75.82; H, 7.69; N, 5.42. IR (KBr) cm$^{-1}$: 3431, 2931, 1653, 1597, 1520, 1325, 1255, 808; $^1$H NMR (200 MHz, DMSO-d$_6$) δ: 1.40 (3H, t, J=7.1Hz), 1.50–1.65 (4H, m), 1.70–1.90 (4H, m), 2.35 (3H, s), 2.55–2.67 (2H, m), 2.80–2.93 (2H, m), 3.12–3.35 (4H, m), 3.40–3.57 (2H, m), 4.47 (2H, s), 7.23–7.35 (3H, m), 7.50–7.60 (7H, m), 7.91 (2H, d, J=8.4 Hz), 10.26 (1H, s).

WORKING EXAMPLE 38 (Production of Compound 38)

In DMF (3 ml) was dissolved N-[4-(chloromethyl)phenyl]-7-(4-methylphenyl)-3,4-dihydronaphthalene-2-carboxamide (150 mg), and to the mixture was added 1-propylperhydroazepine (109 mg). The mixture was stirred at room temperature for 15 hours. To the reaction mixture was added ethyl acetate (100 ml), and the resulting precipitate was filtered to give 1-[4-[7-(4-methylphenyl)-3,4-dihydronaphthalene-2-carboxamido]benzyl]-1-propylperhydroazepinium chloride (Compound 38) (163 mg) as colorless crystals.

mp 195–199° C.; Elemental Analysis for C$_{34}$H$_{41}$N$_2$OCl.0.5H$_2$O; Calcd: C, 75.88; H, 7.87; N, 5.21. Found: C, 76.07; H, 7.83; N, 5.21. IR (KBr) cm$^{-1}$: 3423, 2937, 1651, 1595, 1520, 1317, 1250, 814; $^1$H NMR (200 MHz, DMSO-d$_6$) δ: 0.93 (3H, t, J=7.2 Hz), 1.52–1.65 (4H, m), 1.75–1.93 (6H, m), 2.35 (3H, s), 2.55–2.68 (2H, m), 2.80–2.95 (2H, m), 3.00–3.13 (2H, m), 3.22–3.40 (2H, m), 3.40–3.58 (2H, m), 4.49 (2H, s), 7.23–7.35 (3H, m), 7.46–7.60 (7H, m), 7.90 (2H, d, J=8.0 Hz), 10.22 (1H, s).

WORKING EXAMPLE 39 (Production of Compound 39)

In DMF (3 ml) was dissolved N-[4-(chloromethyl)phenyl]-7-(4-methylphenyl)-3,4-dihydronaphthalene-2-carboxamide (150 mg), and to the mixture was added 1-ethylperhydroazocine (109 mg). The mixture was stirred at room temperature for 14 hours. To the reaction mixture was added ethyl acetate (100 ml), and the resulting precipitate was filtered and recrystallized from ethyl acetate-methanol to give 1-ethyl-1-[4-[7-(4-methyl-phenyl)-3,4-dihydronaphthalene-2-carboxamido]benzyl] perhydroazocinium chloride (Compound 39) (142 mg) as colorless crystals.

mp 197–199° C.; Elemental Analysis for $C_{34}H_{41}N_2OCl\cdot0.5H_2O$; Calcd: C, 75,88; H, 7.87; N, 5.21. Found: C, 75.67; H, 7.88; N, 5.30. IR (KBr) cm$^{-1}$: 3437, 2926, 1655, 1595, 1520, 1489, 1416, 1321, 1252, 812; $^1$H NMR (200 MHz, DMSO-d$_6$) δ: 1.30–2.00 (13H, m), 2.35 (3H, s), 2.55–2.70 (2H, m), 2.85–3.00 (2H, m), 3.05–3.50 (6H, m), 4.44 (2H, s), 7.20–7.37 (3H, m), 7.40–7.60 (7H, m), 7.92 (2H, d, J=8.6 Hz), 10.28 (1H, s).

WORKING EXAMPLE 40 (Production of Compound 40)

In THF (7 ml) was dissolved N-[4-(chloromethyl)phenyl]-7-(4-methylphenyl)-3,4-dihydro-naphthalene-2-carboxamide (150 mg), and to the mixture was added 1-methylpiperazine (129 μl). The mixture was refluxed for 24 hours. The reaction mixture was cooled to room temperature, and to the mixture was added 5% sodium hydrogen carbonate solution (50 ml). The mixture was extracted with ethyl acetate. The organic layer was washed with saturated sodium chloride solution, dried with anhydrous sodium sulfate, and concentrated under reduced pressure. The residue was separated and purified with column chromatography (ethyl acetate/triethylamine=20/1) and recrystallized from ethyl acetate-hexane to give 7-(4-methylphenyl)-N-[4-(4-methyl-1-piperazinylmethyl)phenyl]-3,4-dihydronaphthalene-2-carboxamide (Compound 40) (105 mg) as colorless crystals.

mp 174–175° C.; Elemental Analysis for $C_{30}H_{33}N_3O$; Calcd: C, 79.79; H, 7.37; N, 9.30. Found: C, 79.43; H, 7.41; N, 9.28. IR (KBr) cm$^{-1}$: 3327, 2941, 2794, 1643, 1524, 1315, 1163, 1011, 808; $^1$H NMR (200 MHz, CDCl$_3$) δ: 2.29 (3H, s), 2.35–2.60 (8H, m), 2.40 (3H, s), 2.65–2.78 (2H, m), 2.90–3.02 (2H, m), 3.48 (2H, s), 7.20–7.35 (6H, m), 7.39–7.63 (7H, m).

WORKING EXAMPLE 41 (Production of Compound 41)

In DMF (3 ml) was dissolved N-[4-(chloromethyl)phenyl]-7-(4-methylphenyl)-3,4-dihydronaphthalene-2-carboxamide (150 mg), and to the solution were added 1-(2-methoxyphenyl)piperazine (97 mg) and potassium carbonate (268 mg). The mixture was stirred at room temperature for 13 hours, and to the mixture was added water (50 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give N-[4-[1-(2-methoxyphenyl)-4-piperazinylmethyl]phenyl]-7-(4-methylphenyl)-3,4-dihydronaphthalene-2-carboxamide (Compound 41) (142 mg) as colorless crystals.

mp 202–205° C.; Elemental Analysis for $C_{36}H_{37}N_3O_2$; Calcd: C, 79.53; H, 6.86; N, 7.73. Found: C, 79.28; H, 6.68; N, 7.66. IR (KBr) cm$^{-1}$: 3350, 2933, 2812, 1649, 1595, 1520, 1500, 1313, 1240, 812, 746; $^1$H NMR (200 MHz, CDCl$_3$) δ: 2.40 (3H, s), 2.60–2.75 (6H, m), 2.90–3.12 (6H, m), 3.57 (2H, s), 3.86 (3H, s), 6.80–7.03 (4H, m), 7.20–7.28 (3H, m), 7.30–7.38 (3H, m), 7.40–7.51 (4H, m), 7.53–7.63 (3H, m).

WORKING EXAMPLE 42 (Production of Compound 42)

In THF (7 ml) was dissolved N-[4-(chloromethyl)phenyl]-7-(4-methylphenyl)-3,4-dihydronaphthalene-2-carboxamide (150 mg), and to the mixture was added 1-(2-pyrimidyl) piperazine (190 mg). The mixture was refluxed for 24 hours. The reaction mixture was cooled to room temperature, and to the mixture was added 5% sodium hydrogen carbonate solution (50 ml). The mixture was extracted with ethyl acetate. The organic layer was washed with saturated sodium chloride solution, dried with anhydrous sodium sulfate, and concentrated under reduced pressure. The residue was separated and purified with column chromatography (ethyl acetate) and recrystallized from ethyl acetate-hexane to give 7-(4-methylphenyl)-N-[4-[1-(2-pyrimidyl)-4-piperazinylmethyl]-phenyl]-3,4-dihydronaphthalene-2-carboxamide (Compound 42) (166 mg) as colorless crystals.

mp 203–204° C.; Elemental Analysis for $C_{33}H_{33}N_5O$; Calcd: C, 76.87; H, 6.45; N, 13.58. Found: C, 76.77; H, 6.40; N, 13.60. IR (KBr) cm$^{-1}$: 3367, 2935, 1649, 1585, 1516, 1448, 1358, 1313, 1255, 984, 808; $^1$H NMR (200 MHz, CDCl$_3$) δ: 2.40 (3H, s), 2.47–2.54 (4H, m), 2.65–2.78 (2H, m), 2.93–3.03 (2H, m), 3.53 (2H, s), 3.79–3.87 (4H, m), 6.47 (1H, t, J=4.8 Hz), 7.23–7.28 (3H, m), 7.30–7.38 (3H, m), 7.42–7.52 (4H, m), 7.54–7.62 (3H, m), 8.30 (2H, d J=4.8 Hz).

WORKING EXAMPLE 43 (Production of Compound 43)

In DMF (3 ml) was dissolved N-[4-(chloromethyl)phenyl]-7-(4-methylphenyl)-3,4-dihydronaphthalene-2-carboxamide (150 mg), and to the solution were added 1-benzhydrylpiperazine (127 mg) and potassium carbonate (268 mg). The mixture was stirred at room temperature for 24 hours, and to the mixture was added water (50 ml). The mixture was extracted with ethyl acetate. The organic layer was washed with saturated sodium chloride solution, dried with anhydrous sodium sulfate, and concentrated under reduced pressure. The residue was recrystallized from acetone-diisopropylether to give N-[4-(4-benzhydryl-1-piperazinyl-methyl)phenyl]-7-(4-methylphenyl)-3,4-dihydronaphthalene-2-carboxamide (Compound 43) (140 mg) as colorless crystals.

mp 217–218° C.; Elemental Analysis for $C_{42}H_{41}N_3O$; Calcd: C, 83.55; H, 6.84; N, 6.96. Found: C, 83.25; H, 6.86; N, 7.06. IR (KBr) cm$^{-1}$: 3417, 2954, 2812, 1659, 1618, 1520, 1410, 1313, 1007, 810, 706; $^1$H NMR (200 MHz, DMSO-d$_6$) δ: 2.20–2.65 (13H, m), 2.80–2.93 (2H, m), 3.42 (s, 2H), 4.26 (1H, s), 7.10–7.70 (22H, m), 9.90 (1H, s).

WORKING EXAMPLE 44 (Production of Compound 44)

In DMF (3 ml) was dissolved N-[4-(chloromethyl)phenyl]-7-(4-methylphenyl)-3,4-dihydronaphthalene-2-carboxamide (150 mg), and to the solution were added 1-(2-furoyl)piperazine hydrochloride (109 mg) and potassium carbonate (268 mg). The mixture was stirred at room temperature for 18 hours, and to the mixture was added water (50 ml). The mixture was extracted with ethyl acetate. The organic layer was washed with saturated sodium chloride solution, dried with anhydrous sodium sulfate, and concentrated under reduced pressure. The residue was purified with ethyl acetate-diisopropylether to give N-[4-[1-(2-furoyl)-4-piperazinylmethyl]phenyl]-7-(4-methylphenyl)-3,4-dihydronaphthalene-2-carboxamide (Compound 44) (112 mg) as colorless amorphous.

IR (KBr) cm$^{-1}$: 3309, 2920, 1618, 1518, 1489, 1437, 1313, 1184, 1001, 812, 754; Elemental Analysis for $C_{34}H_{33}N_3O_3$; Calcd: C, 76.81; H, 6.26; N, 7.90. Found: C, 76.60; H, 6.02; N, 7.61. $^1$H NMR (200 MHz, CDCl$_3$) δ: 2.40 (3H, s), 2.43–2.55 (4H, m), 2.65–2.78 (2H, m), 2.90–3.03

(2H, m), 3.52 (2H, s), 3.73–3.87 (4H, m), 6.44–6.49 (1H, m), 6.98 (1H, d, J=3.2 Hz), 7.20–7.68 (14H, m).

WORKING EXAMPLE 45 (Production of Compound 45)

In DMF (3 ml) was dissolved N-[4-(chloromethyl) phenyl]-7-(4-methylphenyl)-3,4-dihydronaphthalene-2-carboxamide (150 mg), and to the solution were added 1-(3,4,5-trimethoxybenzyl)piperazine (138 mg) and potassium carbonate (268 mg). The mixture was stirred at room temperature for 48 hours, and to the mixture was added water (50 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give N-[4-[1-(3,4,5-trimethoxybenzyl)-4-piperazinylmethyl]phenyl]- 7-(4-methylphenyl)-3,4-dihydronaphthalene-2-carboxamide (Compound 45) (155 mg) as pale yellow crystals.

mp 143–144° C.; Elemental Analysis for $C_{39}H_{43}N_3O_4$; Calcd: C, 75.82; H, 7.02; N, 6.80. Found: C, 75.74; H, 6.85; N, 6.75. IR (KBr) cm$^{-1}$: 3425, 2935, 2806, 1649, 1593, 1520, 1458, 1421, 1313, 1236, 1128, 1009, 810; $^1$H NMR (200 MHz, CDCl$_3$) δ: 2.40 (3H, s), 2.40–2.55 (8H, m), 2.65–2.77 (2H, m), 2.90–3.03 (2H, m), 3.45 (2H, s), 3.51 (2H, s), 3.84 (3H, s), 3.86 (6H, s), 6.56 (2H, s), 7.20–7.36 (6H, m), 7.40–7.62 (7H, m).

WORKING EXAMPLE 46 (Production of Compound 46)

In THF (7 ml) was dissolved N-[4-(chloromethyl) phenyl]-7-(4-methylphenyl)-3,4-dihydronaphthalene-2-carboxamide (150 mg), and to the mixture was added 1-(2-hydroxyethyl)piperazine (142 μl). The mixture was refluxed for 22 hours. The reaction mixture was cooled to room temperature, and to the mixture was added 5% sodium hydrogen carbonate solution (50 ml). The mixture was extracted with ethyl acetate. The organic layer was washed with saturated sodium chloride solution, dried with anhydrous sodium sulfate, and concentrated under reduced pressure. The residue was recrystallized from ethyl acetate-hexane to give N-[4-[1-(2-hydroxyethyl)-4-piperazinylmethyl]phenyl]-7-(4-methylphenyl)-3,4-dihydronaphthalene-2-carboxamide (Compound 46) (158 mg) as colorless crystals.

mp 185–187° C.; Elemental Analysis for $C_{31}H_{35}N_3O_2 \cdot 0.3H_2O$; Calcd: C, 76.45; H, 7.37; N, 8.63. Found: C, 76.64; H, 7.13; N, 8.35. IR (KBr) cm$^{-1}$: 3319, 2937, 2816, 1649, 1597, 1520, 1412, 1317, 812; $^1$H NMR (200 MHz, CDCl$_3$) δ: 2.40 (3H, s), 2.43–2.61 (10H, m), 2.65–2.78 (2H, m), 2.92–3.03 (2H, m), 3.50 (2H, s), 3.61 (2H, t, J=5.5 Hz), 7.21–7.36 (6H, m), 7.40–7.63 (7H, m).

WORKING EXAMPLE 47 (Production of Compound 47)

In THF (7 ml) was dissolved N-[4-(chloromethyl) phenyl]-7-(4-methylphenyl)-3,4-dihydronaphthalene-2-carboxamide (150 mg), and to the mixture was added 3-aminopyridine (109 mg). The mixture was refluxed for 45 hours. The reaction mixture was cooled to room temperature, and to the mixture was added 5% sodium hydrogen carbonate solution (50 ml). The mixture was extracted with ethyl acetate. The organic layer was washed with saturated sodium chloride solution, dried with anhydrous sodium sulfate, and concentrated under reduced pressure. The residue was separated and purified with column chromatography (ethyl acetate/hexane=3/1) and recrystallized from ethyl acetate-hexane to give 7-(4-methylphenyl)-N-[4-[N-(3-pyridyl)aminomethyl]phenyl]-3,4-dihydronaphthalene-2-carboxamide (Compound 47) (14 mg) as colorless crystals.

mp 212–214° C.; IR (KBr) cm$^{-1}$: 3383, 3022, 1655, 1591, 1516, 1412, 1315, 1254, 808, 708; $^1$H NMR (200 MHz, CDCl$_3$) δ: 2.40 (3H, s), 2.66–2.78 (2H, m), 2.92–3.03 (2H, m), 4.05–4.18 (1H, br), 4.30–4.37 (2H, m), 6.88 (1H, ddd, J=1.4, 2.8, 8.0 Hz), 7.08 (1H, dd, J=4.8, 8.0 Hz), 7.23–7.30 (3H, m), 7.32–7.39 (3H, m), 7.41–7.51 (4H, m), 7.58–7.65 (3H, m), 7.98 (1H, dd, J=1.4, 4.8 Hz), 8.09 (1H, d, J=2.8 Hz).

WORKING EXAMPLE 48 (Production of Compound 48)

In DMF (3 ml) was dissolved N-[4-(chloromethyl) phenyl]-7-(4-methylphenyl)-3,4-dihydronaphthalene-2-carboxamide (150 mg), and to the mixture was added 2-amino-1,3-propanediol (106 mg). The mixture was stirred at room temperature for 72 hours, and to the mixture was added water(50 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give N-[4-[(1,3-dihydroxy-2-propyl)aminomethyl]phenyl]-7-(4-methyl-phenyl)-3,4-dihydronaphthalene-2-carboxamide (Compound 48) (60 mg) as colorless crystals.

mp 189–193° C.; Elemental Analysis for $C_{28}H_{30}N_2O_3$; Calcd: C, 75.99; H, 6.83; N, 6.33. Found: C, 75.64; H, 6.86; N, 6.11. IR (KBr) cm$^{-1}$: 3332, 2931, 1649, 1620, 1597, 1520, 1412, 1319, 1255, 1045, 812; $^1$H NMR (200 MHz, DMSO-d$_6$) δ: 2.35 (3H, s), 2.53–2.65 (2H, m), 2.80–2.93 (2H, m), 3.28–3.45 (5H, m), 3.73 (2H, s), 4.43 (2H, s), 7.20–7.35 (5H, m), 7.43–7.59 (5H, m), 7.67 (2H, d, J=8.4 Hz), 9.90 (1H, s).

WORKING EXAMPLE 49 (Production of Compound 49)

In THF (10 ml) was dissolved N-[4-(chloromethyl) phenyl]-7-(4-methylphenyl)-3,4-dihydronaphthalene-2-carboxamide (300 mg), and to the mixture was added 4-hydroxypiperidine (235 mg). The mixture was refluxed for 24 hours. The reaction mixture was cooled to room temperature, and to the mixture was added 5% sodium hydrogen carbonate solution (50 ml). The mixture was extracted with ethyl acetate. The organic layer was washed with saturated sodium chloride solution, dried with anhydrous sodium sulfate, and concentrated under reduced pressure. The residue was recrystallized from ethyl acetate-hexane to give N-[4-(4-hydroxypiperidinomethyl)phenyl]-7-(4-methylphenyl)-3,4-dihydronaphthalene-2-carboxamide (Compound 49) (271 mg) as colorless crystals.

mp 223–224° C.; Elemental Analysis for $C_{30}H_{32}N_2O_2$; Calcd: C, 79.61; H, 7.13; N, 6.19. Found: C, 79.54; H, 7.00; N, 6.15. IR (KBr) cm$^{-1}$: 3321, 2937, 1651, 1622, 1597, 1520, 1412, 1319, 1070, 812; $^1$H NMR (200 MHz, DMSO-d$_6$) δ: 1.28–1.47 (2H, m), 1.63–1.78 (2H, m), 1.88–2.08 (2H, m), 2.25–2.70 (7H, m), 2.80–2.92 (2H, m), 3.23–3.50 (2H, m), 4.50–4.58 (1H, m), 7.17–7.33 (5H, m), 7.45 (1H, s), 7.48–7.60 (4H, m), 7.67 (2H, d, J=8.0 Hz), 9.92 (1H, s).

WORKING EXAMPLE 50 (Production of Compound 50)

In THF (10 ml) was dissolved N-[4-(chloromethyl) phenyl]-7-(4-methylphenyl)-3,4-dihydro-naphthalene-2- carboxamide (300 mg), and to the mixture was added thiomorpholine (233 μl). The mixture was refluxed for 20 hours. The reaction mixture was cooled to room temperature, and to the mixture was added 5% sodium hydrogen carbonate solution (50 ml). The mixture was extracted with ethyl acetate. The organic layer was washed with saturated sodium chloride solution, dried with anhydrous sodium sulfate, and concentrated under reduced pressure. The residue was recrystallized from ethyl acetate-hexane to give 7-(4-methylphenyl)-N-[4-(thiomorpholinomethyl)phenyl]-3,4-dihydro-naphthalene-2-carboxamide (Compound 50) (309 mg) as colorless crystals.

mp 178–180° C.; Elemental Analysis for $C_{29}H_{30}N_2OS$; Calcd: C, 76.61; H, 6.65; N, 6.16. Found: C, 76.39; H, 6.71; N, 5.94. IR (KBr) $cm^{-1}$: 3307, 2910, 2810, 1648, 1599, 1520, 1412, 1315, 1257, 806; $^1H$ NMR (200 MHz, $CDCl_3$) δ: 2.40 (3H, s), 2.57–2.75 (10H, m), 2.90–3.03 (2H, m), 3.50 (2H, s), 7.22–7.62 (13H, m).

WORKING EXAMPLE 51 (Production of Compound 51)

In THF (10 ml) was dissolved N-[4-(chloromethyl)-phenyl]-7-(4-methylphenyl)-3,4-dihydronaphthalene-2-carboxamide (300 mg), and to the mixture was added diethanolamine (222 μl). The mixture was refluxed for 34 hours. The reaction mixture was cooled to room temperature, and to the mixture was added 5% sodium hydrogen carbonate solution (50 ml). The mixture was extracted with ethyl acetate. The organic layer was washed with saturated sodium chloride solution, dried with anhydrous sodium sulfate, and concentrated under reduced pressure. The residue was separated and purified with column chromatography (ethyl acetate/triethylamine=10/1) and recrystallized from ethyl acetate-hexane to give N-[4-[N,N-bis(2-hydroxyethyl)aminomethyl]phenyl]-7-(4-methylphenyl)-3,4-dihydronaphthalene-2-carboxamide (Compound 51) (148 mg) as colorless crystals.

mp 150–151° C.; Elemental Analysis for $C_{29}H_{32}N_2O_3$; Calcd: C, 76.29; H, 7.06; N, 6.14. Found: C, 75.90; H, 7.10; N, 6.18. IR (KBr) $cm^{-1}$: 3307, 2943, 1645, 1599, 1524, 1412, 1321, 1255, 1036, 804; $^1H$ NMR (200 MHz, $CDCl_3$) δ: 2.40 (3H, s), 2.64–2.75 (6H, m), 2.90–3.00 (2H, m), 3.58–3.70 (6H, m), 7.20–7.37 (6H, m), 7.40–7.51 (4H, m), 7.58 (2H, d, J=8.4 Hz), 7.67–7.77 (1H,

WORKING EXAMPLE 52 (Production of Compound 52)

In DMF (5 ml) was dissolved N-[4-(chloromethyl) phenyl]-7-(4-methylphenyl)-3,4-dihydronaphthalene-2-carboxamide (150 mg), and to the mixture was added pyridine (94 μl). The mixture was stirred at 70° C. for 24 hours, and to the mixture was added water (50 ml). The mixture was washed with ethyl acetate. The aqueous layer was allowed to stand at room temperature for 3 hours. The resulting precipitate was filtered and purified with ethyl acetate-methanol to give 1-[7-(4-methylphenyl)-3,4-dihydronaphthalene-2-carboxamido)benzyl]pyridinium chloride (Compound 52) (74 mg) as colorless amorphous.

Elemental Analysis for $C_{30}H_{27}N_2OCl.0.5H_2O$; Calcd: C, 75.70; H, 5.93; N, 5.88. Found: C, 75.83; H, 6.02; N, 5.63. IR (KBr) $cm^{-1}$: 3413, 1655, 1595, 1518, 1414, 1317, 1248, 810; $^1H$ NMR (200 MHz, DMSO-$d_6$) δ: 2.35 (3H, s), 2.55–2.67 (2H, m), 2.80–2.93 (2H, m), 5.85 (2H, s), 7.24–7.34 (3H, m), 7.50–7.60 (7H, m), 7.85 (2H, d, J=8.6 Hz), 8.14–8.25 (2H, m), 8.64 (1H, t, J=7.7 Hz), 9.20–9.30 (2H, m), 10.18 (1H, s).

WORKING EXAMPLE 53 (Production of Compound 53)

A solution of N-(4-chloromethylphenyl)-7-(4-methylphenyl)-2,3-dihydro-1-benzoxepine-4-carboxamide (0.2 g) and sodium cyclohexylsulfide (0.08 g) in dimethylformamide (10 ml) was stirred at room temperature for 2.5 hours. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-(cyclohexylthiomethyl)phenyl)-7-(4-methylphenyl)-2,3-dihydro-1-benzoxepine-4-carboxamide (Compound 53) (0.19 g) as colorless crystals.

mp 161–162° C.; $^1H$-NMR (δ ppm, $CDCl_3$): 1.23–1.42 (6H, m), 1.63–1.75 (2H, m), 1.92–2.05 (2H, m), 2.39 (3H, s), 2.49–2.59 (1H, m), 3.07 (2H, t, J=4.5 Hz), 3.73 (2H, s), 4.36 (2H, t, J=4.5 Hz), 7.06 (1H, d, J=8.2 Hz), 7.22–7.34 (5H, m), 7.44–7.59 (7H, m). IR(KBr) ν: 2928, 2851, 1651 $cm^{-1}$. Anal. for $C_{31}H_{33}NO_2S$: Calcd. C, 76.98; H, 6.88; N, 2.90. Found C, 76.65; H, 6.59; N, 3.09.

WORKING EXAMPLE 54 (Production of Compound 54)

In DMF (3 ml) was dissolved 3,4-dihydro-N-[4-(4-hydroxypiperidinomethyl)phenyl]-7-(4-methylphenyl)-naphthalene-2-carboxamide (130 mg), and to the mixture was added methyl iodide(54 μl). The mixture was stirred at room temperature for 17 hours, and to the mixture was added ethyl acetate (100 ml). The resulting precipitate was filtered and recrystallized from ethyl acetate-methanol to give 4-hydroxy-1-methyl-1-[4-[7-(4-methylphenyl)-3,4-dihydronaphthalene-2-carboxamido]benzyl]-piperidinium iodide (Compound 54) (138 mg, ratio of isomers=58:42) as colorless crystals.

mp 157–161° C.; Elemental Analysis for $C_{31}H_{35}N_2O_2I.0.5H_2O$; Calcd: C, 61.69; H, 6.01; N, 4.64. Found: C, 61.75; H, 5.84; N, 4.64. IR (KBr) $cm^{-1}$: 3396, 1655, 1595, 1520, 1416, 1319, 1250, 812; $^1H$ NMR (200 MHz, DMSO-$d_6$) δ: 1.65–1.90 (2H, m), 1.96–2.20 (2H, m), 2.35 (3H, s), 2.55–2.68 (2H, m), 2.82–3.00 (5H, m), 3.10–3.57 (4H, m), 3.70–3.90 (1H, m), 4.50–4.60 (2H, m), 5.05 (0.42H, d, J=2.8 Hz), 5.12 (0.58H, d, J=3.6 Hz), 7.22–7.35 (3H, m), 7.42–7.60 (7H, m), 7.83–7.93 (2H, m), 10.18 (1H, s).

WORKING EXAMPLE 55 (Production of Compound 55)

In DMF (3 ml) was dissolved 7-(4-methylphenyl)-N-[4-(thiomorpholinomethyl)phenyl]-3,4-dihydro-naphthalene-2-carboxamide (160 mg), and to the mixture was added methyl iodide(66 μl). The mixture was stirred at room temperature for 17 hours, and to the mixture was added ethyl acetate (100 ml). The resulting precipitate was filtered and recrystallized from ethyl acetate-methanol to give 4-methyl-4-[4-[7-(4-methyl-phenyl)-3,4-dihydronaphthalene-2-carboxamido]benzyl]-thiomorpholinium iodide (Compound 55) (165 mg) as colorless crystals.

mp 183–185° C.; Elemental Analysis for $C_{30}H_{33}N_2OSI.0.2H_2O$; Calcd: C, 60.04; H, 5.61; N, 4.67. Found: C, 59.91; H, 5.52; N, 4.66. IR (KBr) $cm^{-1}$: 3423, 1651, 1597, 1520, 1416, 1319, 1250, 812; $^1H$ NMR (200 MHz, DMSO-$d_6$) δ: 2.35 (3H, s), 2.55–2.68 (2H, m), 2.83–3.30 (9H, m), 3.40–3.65 (4H, m), 4.62 (2H, s), 7.25–7.35 (3H, m), 7.45–7.61 (7H, m), 7.90 (2H, d, J=8.6 Hz), 10.19 (1H, s).

WORKING EXAMPLE 56 (Production of Compound 56)

In DMF (3 ml) was dissolved N-[4-[N,N-bis(2-hydroxyethyl)aminomethyl]phenyl]-7-(4-methylphenyl)-3,4-dihydronaphthalene-2-carboxamide (100 m g), and to the mixture was added methyl iodide (41 μl). The mixture was stirred at room temperature for 22 hours. The solvent was evaporated and the residue was purified with ethyl acetate-methanol to give bis(2-hydroxyethyl)methyl[4-[7-(4-methylphenyl)-3,4-naphthalene-2-carboxamido]-benzyl] ammonium iodide (Compound 56) (101 mg) as colorless amorphous.

Elemental Analysis for $C_{30}H_{35}N_2O_3I.0.5H_2O$; Calcd: C, 59.31; H, 5.97; N, 4.61. Found: C, 59.19; H, 5.74; N, 4.68. IR (KBr) cm$^{-1}$: 3365, 1651, 1593, 1520, 1416, 1319, 1250, 810; $^1$H NMR (200 MHz, DMSO-d$_6$) δ: 2.35 (3H, s), 2.55–2.67 (2H, m), 2.84–3.01 (5H, m), 3.27–3.55 (4H, m), 3.88–3.98 (4H, m), 4.62 (2H, s), 5.33 (2H, t, J=4.8 Hz), 7.25–7.35 (3H, m), 7.47–7.60 (7H, m), 7.88 (2H, d, J=8.4 Hz), 10.18 (1H, s).

WORKING EXAMPLE 57 (Production of Compound 57)

In DMF (3 ml) was dissolved (E)-N-[4-(chloromethyl)phenyl]-3-(4-methylphenyl)cinnamamide (200 mg), and to the solution were added 1-(3,4-methylenedioxybenzyl)piperazine (158 mg) and potassium carbonate (382 mg). The mixture was stirred at room temperature for 16 hours, and to the mixture was added water (50 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give (E)-N-[4-[1-(3,4-methylenedioxybenzyl)-4-piperazinylmethyl]phenyl]-3-(4-methylphenyl)cinnamamide (Compound 57) (266 mg) as colorless crystals.

mp 204–207° C.; Elemental Analysis for $C_{35}H_{35}N_3O_3.0.5H_2O$; Calcd: C, 75.79; H, 6.54; N, 7.58. Found: C, 76.19; H, 6.48; N, 7.83. IR (KBr) cm$^{-1}$: 2939, 2806, 1664, 1626, 1524, 1491, 1246, 1041, 1007, 970, 824, 795; $^1$H NMR (200 MHz, CDCl$_3$) δ: 2.30–2.60 (8H, m), 2.41 (3H, s), 3.41 (2H, s), 3.48 (2H, s), 5.93 (2H, s), 6.61 (1H, d, J=15.6 Hz), 6.73 (2H, s), 6.84 (1H, s), 7.23–7.32 (4H, m), 7.35–7.60 (8H, m), 7.72 (1H, s), 7.81 (1H, d, J=15.6 Hz).

WORKING EXAMPLE 58 (Production of Compound 58)

In THF (10 ml) was dissolved 7-phenylnaphthalene-2-carboxylic acid (350 mg), and to the solution were added oxalyl chloride (184 μl) and a drop of DMF. The mixture was stirred at room temperature for 1 hour and concentrated under reduced pressure. The residue was dissolved in THF (10 ml), and to the solution were added 1-(4-aminobenzyl)piperidine (295 mg) and triethylamine (237 μl) at room temperature. The reaction mixture was stirred at room temperature for 2 hours, and to the mixture was added water (100 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give N-[4-(piperidinomethyl)phenyl]-7-phenylnaphthalene-2-carboxamide (Compound 58) (491 mg) as pale yellow crystals.

mp 177–178° C.; Elemental Analysis for $C_{29}H_{28}N_2O.0.2H_2O$; Calcd: C, 82.12; H, 6.75; N, 6.60. Found: C, 82.26; H, 6.80; N, 6.62. IR (KBr) cm$^{-1}$: 3313, 2933, 1649, 1527, 1317, 849, 754, 692; $^1$H NMR (200 MHz, CDCl$_3$) δ: 1.37–1.65 (6H, m), 2.35–2.45 (4H, m), 3.48 (2H, s), 7.33–7.57 (5H, m), 7.62–7.77 (4H, m), 7.83–8.01 (5H, m), 8.15 (1H, s), 8.44 (1H, s).

WORKING EXAMPLE 59 (Production of Compound 59)

In DMF (3 ml) was dissolved N-[4-(piperidinomethyl)phenyl]-7-phenylnaphthalene-2-carboxamide (300 mg), and to the mixture was added methyl iodide (133 μl). The mixture was stirred at room temperature for 16 hours and concentrated under reduced pressure. The residue was recrystallized from ethyl acetate to give 1-[4-(7-phenylnaphthalene- 2-carboxamido)benzyl]-1-methylpiperidinium iodide (Compound 59) (374 mg) as pale yellow crystals.

mp 203–207° C.; Elemental Analysis for $C_{30}H_{31}N_2OI.1.0H_2O$; Calcd: C, 62.07; H, 5.73; N, 4.83. Found: C, 61.82; H, 5.43; N, 4.87. IR (KBr) cm$^{-1}$: 3450, 1655, 1597, 1520, 1417, 1317, 1250, 700; $^1$H NMR (200 MHz, DMSO-d$_6$) δ: 1.40–2.00 (6H, m), 2.94 (3H, s), 3.25–3.40 (4H, m), 4.56 (2H, s), 7.40–7.60 (5H, m), 7.84–7.89 (2H, m), 7.95–8.17 (6H, m), 8.40 (1H, s), 8.66 (1H, s), 10.68 (1H, s).

WORKING EXAMPLE 60 (Production of Compound 60)

In THF (15 ml) was dissolved 5-(4-methylphenyl)-indene-2-carboxylic acid (500 mg), and to the solution were added oxalyl chloride (262 μl) and a drop of DMF. The mixture was stirred at room temperature for 1 hour and concentrated under reduced pressure. The residue was dissolved in THF (15 ml), and to the solution were added 1-(4-aminobenzyl)piperidine (419 mg) and triethylamine (336 μl) at room temperature. The reaction mixture was stirred at room temperature for 16 hours, and to the mixture was added water (100 ml). The mixture was extracted with ethyl acetate. The organic layer was washed with saturated sodium chloride solution, dried with anhydrous sodium sulfate, and concentrated under reduced pressure. The residue was recrystallized from ethyl acetate-hexane to give N-[4-(piperidinomethyl)phenyl]-5-(4-methylphenyl)-indene-2-carboxamide (Compound 60) (549 mg) as colorless crystals.

mp 219–220° C.; Elemental Analysis for $C_{29}H_{30}N_2O$; Calcd: C, 82.43; H, 7.16; N, 6.63. Found: C, 82.17; H, 7.13; N, 6.56. IR (KBr) cm$^{-1}$: 3346, 2935, 1645, 1597, 1516, 1408, 1315, 1250, 808; $^1$H NMR (200 MHz, DMSO-d$_6$) δ: 1.34–1.57 (6H, m), 2.25–2.40 (7H, m), 3.30–3.43 (2H, m), 3.80–3.90 (2H, m), 7.20–7.32 (4H, m), 7.56–7.68 (4H, m), 7.72 (2H, d, J=8.4 Hz), 7.83 (2H, s), 9.96 (1H, s).

WORKING EXAMPLE 61 (Production of Compound 61)

In DMF (10 ml) was dissolved N-[4-(piperidinomethyl)phenyl]-5-(4-methylphenyl)indene-2-carboxamide (400 mg), and to the mixture was added methyl iodide (177 μl). The mixture was stirred at room temperature for 86 hours and concentrated under reduced pressure. The residue was recrystallized from ethyl acetate to give 1-[4-[5-(4-methylphenyl)indene-2-carboxamido]-benzyl]-1-methylpiperidinium iodide (Compound 61) (516 mg) as pale yellow crystals.

mp 199–201° C.; Elemental Analysis for $C_{30}H_{33}N_2OI.0.5H_2O$; Calcd: C, 62.83; H, 5.98; N, 4.88. Found: C, 62.56; H, 5.87; N, 4.97. IR (KBr) cm$^{-1}$: 3450, 2947, 1651, 1595, 1520, 1416,1322, 1246, 808; $^1$H NMR (200 MHz, DMSO-d$_6$) δ: 1.40–2.00 (6H, m), 2.36 (3H, s), 2.92 (3H, s), 3.20–3.40 (4H, m), 3.80–3.90 (2H, m), 4.54 (2H, s), 7.30 (2H, d, J=8.0 Hz), 7.52 (2H, d, J=8.0 Hz), 7.55–7.70 (4H, m), 7.85–7.97 (4H, m), 10.20–10.25 (1H, m).

WORKING EXAMPLE 62 (Production of Compound 62)

In DMF (3 ml) was dissolved (E)-N-[4-(chloromethyl)phenyl]-3-(4-methylphenyl)cinnamamide (200 mg), and to the solution were added 1-(4-methoxyphenyl)piperazine dihydrochloride (190 mg) and potassium carbonate (382 mg). The mixture was stirred at room temperature for 14 hours, and to the mixture was added water (50 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give (E)-N-[4-[1-(4-methoxyphenyl)-4-piperazinylmethyl]phenyl]-3-(4-methylphenyl)cinnamamide (Compound 62) (224 mg) as colorless crystals.

mp 207–208° C.; Elemental Analysis for $C_{34}H_{35}N_3O_2$; Calcd: C, 78.89; H, 6.81; N, 8.12. Found: C, 78.59; H, 6.65; N, 8.13. IR (KBr) cm$^{-1}$: 2937, 2812, 1662, 1626, 1512, 1248, 820, 795; $^1$H NMR (200 MHz, CDCl$_3$) δ: 2.41 (3H, s), 2.56–2.65 (4H, m), 3.04–3.13 (4H, m), 3.54 (2H, s), 3.76 (3H, s), 6.61 (1H, d, J=15.6 Hz), 6.78–6.94 (4H, m), 7.23–7.63 (12H, m), 7.73 (1H, s), 7.82 (1H, d, J=15.6 Hz).

WORKING EXAMPLE 63 (Production of Compound 63)

In DMF (3 ml) was dissolved (E)-N-[4-(chloromethyl)phenyl]-3- (4-methylphenyl)cinnamamide (200 mg), and to the solution were added 2-(3,4-dimethoxyphenyl)ethylmethylamine (132 μl) and potassium carbonate (382 mg). The mixture was stirred at room temperature for 12 hours, and to the mixture was added water (50 ml). The mixture was extracted with ethyl acetate. The organic layer was washed with saturated sodium chloride solution, dried with anhydrous sodium sulfate, and concentrated under reduced pressure. The residue was separated and purified with column chromatography (ethyl acetate) to give colorless amorphous, which was dissolved in ethyl acetate (50 ml), and to the mixture was added 4N hydrochloric acid ethyl acetate solution (0.5 ml). The resulting precipitate was filtered and recrystallized from ethyl acetate-methanol to give (E)-N-[4-[N-[2-(3,4-dimethoxyphenyl)ethyl]-N-methylaminomethyl]phenyl]-3-(4-methylphenyl)cinnamamide hydrochloride (Compound 63) (245 mg) as colorless crystals.

mp 214–217° C.; Elemental Analysis for $C_{34}H_{36}N_2O_3.1.0HCl$; Calcd: C, 73.30; H, 6.69; N, 5.03; Cl, 6.36. Found: C, 73.00; H, 6.66; N, 4.99; Cl, 6.20. IR (KBr) cm$^{-1}$: 3427, 2941, 1682, 1601, 1518, 1417, 1344, 1259, 1174, 1026, 793; $^1$H NMR (200 MHz, DMSO-d$_6$) δ: 2.37 (3H, s), 2.66–2.75 (3H, m), 2.95–3.40 (4H, m), 3.73 (3H, s), 3.75 (3H, s), 4.15–4.28 (1H, m), 4.32–4.46 (1H, m), 6.77 (1H, dd, J=1.8, 8.2 Hz), 6.84–6.94 (2H, m), 7.02 (1H, d, J=16.0 Hz), 7.31 (2H, d, J=7.8 Hz), 7.48–7.75 (8H, m), 7.79–7.93 (3H, m), 10.56 (2H, s).

WORKING EXAMPLE 64 (Production of Compound 64)

In DMF (3 ml) was dissolved (E)-N-[4-(chloromethyl)phenyl]-3- (4-methylphenyl)cinnamamide (200 mg), and to the solution were added methylaminoacetonitrile hydrochloride (77 mg) and potassium carbonate (382 mg). The mixture was stirred at room temperature for 14 hours, and to the mixture was added water (50 ml). The mixture was extracted with ethyl acetate. The organic layer was washed with saturated sodium chloride solution, dried with anhydrous sodium sulfate, and concentrated under reduced pressure. The residue was recrystallized from ethyl acetatediisopropylether to give (E)-N-[4-[N-(cyanomethyl)-N-methylaminomethyl]phenyl]-3-(4-methylphenyl)cinnamamide (Compound 64) (129 mg) as colorless crystals.

mp 163–165° C.; Elemental Analysis for $C_{26}H_{25}N_3O.0.1H_2O$; Calcd: C, 78.60; H, 6.39; N, 10.58. Found: C, 78.44; H, 6.32; N, 10.35. IR (KBr) cm$^{-1}$: 3250, 3055, 1662, 1626, 1599, 1535, 1516, 1412, 1344, 1184, 982, 822, 791; $^1$H NMR (200 MHz, CDCl$_3$) δ: 2.42 (3H, s), 2.44 (3H, s), 3.46 (2H, s), 3.59 (2H, s), 6.61 (1H, d, J=15.4 Hz), 7.23–7.65 (12H, m), 7.74 (1H, s), 7.83 (1H, d, J=15.4 Hz).

WORKING EXAMPLE 65 (Production of Compound 65)

In DMF (3 ml) was dissolved (E)-N-[4-(chloromethyl)phenyl]-3-(4-methylphenyl)cinnamamide (200 mg), and to the solution were added imidazole (49 mg) and potassium carbonate (382 mg). The mixture was stirred at room temperature for 18 hours, and to the mixture was added water. The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give (E)-N-[4-[(imidazol-1-yl)methyl]phenyl]-3-(4-methylphenyl)-cinnamamide (Compound 65) (90 mg) as colorless crystals.

mp 198–200° C.; Elemental Analysis for $C_{26}H_{23}N_3O.0.3H_2O$; Calcd: C, 78.29; H, 5.96; N, 10.53. Found: C, 78.26; H, 5.92; N, 10.17. IR (KBr) cm$^{-1}$: 3026, 1674, 1628, 1601, 1539, 1518, 1416, 1342, 1182, 1080, 787; $^1$H NMR (200 MHz, CDCl$_3$) δ: 2.41 (3H, s), 5.08 (2H, s), 6.67 (1H, d, J=15.4 Hz), 6.91 (1H, s), 7.09–7.16 (3H, m), 7.23–7.30 (2H, m), 7.35–7.66 (8H, m), 7.72 (1H, s), 7.82 (1H, d, J=15.4 Hz), 8.00 (1H, br s).

WORKING EXAMPLE 66 (Production of Compound 66)

In DMF (3 ml) was dissolved (E)-N-[4-(chloromethyl)phenyl]-3-(4-methylphenyl)cinnamamide (200 mg), and to the solution were added 3-(hydroxymethyl)piperidine (191 mg). The mixture was stirred at room temperature for 72 hours, and to the mixture was added water (50 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give (E)-N-[4-[3-(hydroxymethyl)piperidinomethyl]phenyl]-3-(4-methylphenyl)cinnamamide (Compound 66) (160 mg) as colorless crystals.

mp 153–154° C.; Elemental Analysis for C$_{29}$H$_{32}$N$_2$O$_2$.0.1H$_2$O; Calcd: C, 78.74; H, 7.34; N, 6.33. Found: C, 78.51; H, 7.32; N, 6.25. IR (KBr) cm$^{-1}$: 3290, 2924, 1664, 1626, 1603, 1543, 1514, 1412, 1346, 1186, 789; $^1$H NMR (200 MHz, CDCl$_3$) δ: 1.50–1.90 (3H, m), 2.05–2.35 (4H, m), 2.41 (3H, s), 2.50–2.63 (1H, m), 2.70–2.80 (1H, m), 3.46 (2H, s), 3.50–3.71 (2H, m), 6.65 (1H, d, J=15.6 Hz), 7.23–7.31 (4H, m), 7.36–7.61 (7H, m), 7.70–7.87 (3H, m).

WORKING EXAMPLE 67 (Production of Compound 67)

In DMF (3 ml) was dissolved (E)-N-[4-(chloromethyl)phenyl]-3-(4-methylphenyl)cinnamamide (200 mg), and to the mixture was added 3-hydroxypiperidine(168 mg). The mixture was stirred at room temperature for 13 hours, and to the mixture was added water (50 ml). The mixture was extracted with ethyl acetate. The organic layer was washed with saturated sodium chloride solution, dried with anhydrous sodium sulfate, and concentrated under reduced pressure. The residue was recrystallized from ethyl acetatediisopropylether to give (E)-N-[4-(3-hydroxypiperidinomethyl)phenyl]-3-(4-methylphenyl)cinnamamide (Compound 67) (174 mg) as colorless crystals.

mp 132–134° C.; Elemental Analysis for C$_{28}$H$_{30}$N$_2$O$_2$; Calcd: C, 78.84; H, 7.09; N, 6.57. Found: C, 78.58; H, 7.08; N, 6.54. IR (KBr) cm$^{-1}$: 3427, 2937, 1660, 1628, 1601, 1539, 1412, 1344, 1184, 791; $^1$H NMR (200 MHz, DMSO-d$_6$) δ: 1.28–1.90 (6H, m), 2.36 (3H, s), 2.59–2.68 (1H, m), 2.72–2.85 (1H, m), 3.33 (2H, s), 4.56 (1H, d, J=4.8 Hz), 6.93 (1H, d, J=15.8 Hz), 7.20–7.35 (4H, m), 7.46–7.71 (8H, m), 7.89 (1H, s), 10.19 (1H, s).

WORKING EXAMPLE 68 (Production of Compound 68)

In DMF (3 ml) was dissolved (E)-N-[4-(chloromethyl)phenyl]-3-(4-methylphenyl)cinnamamide (200 mg), and to the mixture was added 2-piperidinemethanol (191mg). The mixture was stirred at room temperature for 13 hours, and to the mixture was added water (50 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give (E)-N-[4-[2-(hydroxy-methyl)piperidinomethyl]phenyl]-3-(4-methylphenyl)cinnamamide (Compound 68) (120 mg) as colorless crystals.

mp 137–139° C.; Elemental Analysis for C$_{29}$H$_{32}$N$_2$O$_2$; Calcd: C, 79.06; H, 7.32; N, 6.36. Found: C, 78.73; H, 7.38; N, 6.37. IR (KBr) cm$^{-1}$: 3325, 2922, 1664, 1630, 1601, 1531, 1412, 1338, 1174, 974, 793; $^1$H NMR (200 MHz, CDCl) δ: 1.30–1.80 (6H, m), 2.10–2.25 (1H, m), 2.40–2.57 (1H, m), 2.41 (3H, s), 2.82–2.93 (1H, m), 3.33 (1H, d, J=13.5 Hz), 3.53 (1H, dd, J=4.0, 10.8 Hz), 3.88 (1H, dd, J=4.0, 10.8 Hz), 4.04 (1H, d, J=13.5 Hz), 6.61 (1H, d, J=15.4 Hz), 7.23–7.33 (4H, m), 7.37–7.62 (8H, m), 7.74 (1H, s), 7.82 (1H, d, J=15.4 Hz).

WORKING EXAMPLE 69 (Production of Compound 69)

In DMF (3 ml) was dissolved (E)-N-[4-(chloromethyl)phenyl]-3-(4-methylphenyl)cinnamamide (200 mg), and to the mixture was added 2-(2-hydroxyethyl)piperidine (214 mg). The mixture was stirred at room temperature for 18 hours, and to the mixture was added water (50 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give (E)-N-[4-[2-(2-hydroxyethyl)piperidinomethyl]phenyl]-3-(4-methylphenyl)cinnamamide (Compound 69) (202 mg) as colorless crystals.

mp 142–143° C.; Elemental Analysis for C$_{30}$H$_{34}$N$_2$O$_2$; Calcd: C, 79.26; H, 7.54; N, 6.16. Found: C, 79.00; H, 7.27; N, 6.19. IR (KBr) cm$^{-1}$: 3300, 2935, 1666, 1628, 1603, 1541, 1516, 1412, 1344, 1182, 789; $^1$H NMR (200 MHz, CDCL3) δ: 1.30–2.13 (8H, m), 2.20–2.35 (1H, m), 2.41 (3H, s), 2.73–2.87 (1H, m), 2.92–3.07 (1H, m), 3.48 (1H, d, J=13.0 Hz), 3.70–3.83 (1H, m), 3.90–4.02 (1H, m), 4.14 (1H, d, J=13.0 Hz), 6.65 (1H, d, J=15.4 Hz), 7.23–7.33 (4H, m), 7.38–7.64 (7H, m), 7.72–7.87 (3H, m).

WORKING EXAMPLE 70 (Production of Compound 70)

In THF (10 ml) was dissolved 3-(4-methylphenyl)cinnamic acid (0.48 g), and to the solution were added oxalyl chloride (0.35 ml) and a drop of DMF. The mixture was stirred at room temperature for 1 hour and concentrated under reduced pressure. The residue was dissolved in THF (20 ml), and to the solution were added 1-(4-aminobenzyl)piperidine (0.38 g) and triethylamine (0.34 ml) at room temperature. The reaction mixture was stirred at room temperature for 2 hours, and to the mixture was added water (150 ml). The mixture was extracted with ethyl acetate. The organic layer was washed with saturated sodium chloride solution, dried with anhydrous magnesium sulfate and concentrated under reduced pressure. The residue was recrystallized from ethyl acetate-diisopropylether to give (E)-N-[4-(piperidinomethyl)-phenyl]-3-(4-methylphenyl)-cinnamamide (Compound 70) (0.60 g) as pale yellow crystals.

mp 154–156° C.; Elemental Analysis for C$_{28}$H$_{30}$N$_2$O.0.4H$_2$O; Calcd: C, 80.50; H, 7.43; N, 6.71. Found: C, 80.60; H, 7.28; N, 6.52. $^1$H NMR (200 MHz, CDCl$_3$) δ: 1.44 (2H, m), 1.58 (4H, m), 2.39 (4H, m), 2.41 (3H, s), 3.47 (2H, s), 6.61 (1H, d, J=15.6 Hz), 7.25–7.60 (12H, m), 7.73 (1H, s), 7.82 (1H, d, J=15.6 Hz).

WORKING EXAMPLE 71 (Production of Compound 71)

In THF (10 ml) was dissolved 3-(2-methylphenyl)cinnamic acid (0.48 g), and to the solution were added oxalyl chloride (0.35 ml) and a drop of DMF. The mixture was stirred at room temperature for 1 hour and concentrated under reduced pressure. The residue was dissolved in THF (20 ml), and to the solution were added 1-(4-aminobenzyl)piperidine (0.38 g) and triethylamine (0.34 ml) at room temperature. The reaction mixture was stirred at room temperature for 2 hours, and to the mixture was added water (50 ml). The mixture was extracted with ethyl acetate. The organic layer was washed with saturated sodium chloride solution, dried with anhydrous magnesium sulfate and concentrated under reduced pressure. The residue was washed with ethyl acetate-diisopropylether to give (E)-N-[4-(piperidinomethyl)phenyl]-3-(2-methyl-phenyl)-cinnamamide (Compound 71) (0.75 g) as pale yellow amorphous. Elemental Analysis for C$_{28}$H$_{30}$N$_2$O.0.5H$_2$O; Calcd: C, 80.16; H, 7.45; N, 6.68. Found: C, 80.15; H, 7.38; N, 6.64. $^1$H NMR (200 MHz, CDCl$_3$) δ: 1.45 (2H, m), 1.58 (4H, m), 2.27 (3H, s), 2.39 (2H, m), 3.47 (2H, s), 6.58 (1H, d, J=15.4 Hz), 7.24–7.35 (7H, m), 7.39–7.58 (6H, m), 7.80 (1H, d, J=15.6 Hz).

WORKING EXAMPLE 72 (Production of Compound 72)

In DMF (4 ml) was dissolved (E)-N-[4-(piperidinomethyl)phenyl]-3-(4-methylphenyl)cinnamamide (0.41 g), and to the mixture was added methyl iodide (0.43 g). The mixture was stirred at room temperature for 20 hours and concentrated under reduced pressure. The residue was crystallized from ethyl acetate to give (E)-1-methyl-1-[4-(3-(4-methyl-phenyl)cinnamamido)benzyl]-piperidinium iodide (Compound 72) (0.51 g) as pale yellow crystals.

mp 176–178° C.; Elemental Analysis for $C_{29}H_{33}N_2OI.1.5H_2O$; Calcd: C, 60.10; H, 6.26; N, 4.83. Found: C, 60.19; H, 6.25; N, 4.95. $^1H$ NMR (200 MHz, DMSO-$d_6$) δ: 1.62 (2H, m), 1.88 (4H, m), 2.37 (3H, s), 2.93 (3H, s), 3.36 (4H, m), 4.55 (2H, s), 6.97 (1H, d, J=15.8 Hz), 7.31 (2H, d, J=7.6 Hz), 7.50–7.90 (11H, m), 10.44 (1H, s).

WORKING EXAMPLE 73 (Production of Compound 73)

In DMF (6 ml) was dissolved (E)-N-[4-(piperidinomethyl)phenyl]-3-(2-methylphenyl)cinnamamide (0.62 g), and to the mixture was added methyl iodide (0.64 g). The mixture was stirred at room temperature for 20 hours and concentrated under reduced pressure. The residue was solidified with ethyl acetate to give (E)-1-methyl-1-[4-(3-(2-methylphenyl)cinnamamido)benzyl]-piperidinium iodide (Compound 73) (0.79 g) as pale yellow amorphous.

Elemental Analysis for $C_{29}H_{33}N_2OI.1.5H_2O$; Calcd: C, 60.10; H, 6.26; N, 4.83. Found: C, 60.00; H, 6.11; N, 5.00. $^1H$ NMR (200 MHz, DMSO-$d_6$) δ: 1.62 (2H, m), 1.88 (4H, m), 2.27 (3H, s), 2.93 (3H, s), 3.32 (4H, m), 4.56 (2H, s), 6.94 (1H, d, J=15.6 Hz), 7.27–7.73 (11H, m), 7.84 (2H, d, J=8.4 Hz), 10.40 (1H, s).

WORKING EXAMPLE 74 (Production of Compound 74)

In THF (10 ml) was dissolved 3-(2,5-dimethylphenyl)cinnamic acid (0.50 g), and to the solution were added oxalyl chloride (0.35 ml) and a drop of DMF. The mixture was stirred at room temperature for 1 hour and concentrated under reduced pressure. The residue was dissolved in THF (20 ml), and to the solution were added 1-(4-aminobenzyl)piperidine (0.38 g) and triethylamine (0.34 ml) at room temperature. The reaction mixture was stirred at room temperature for 2 hours, and to the mixture was added water (50 ml). The mixture was extracted with ethyl acetate. The organic layer was washed with saturated sodium chloride solution, dried with anhydrous magnesium sulfate and concentrated under reduced pressure. The residue was washed with ethyl acetate-diisopropylether to give (E)-N-[4-(piperidinomethyl)phenyl]-3-(2,5-dimethylphenyl)cinnamamide (Compound 74) (0.75 g) as pale yellow amorphous.

Elemental Analysis for $C_{29}H_{32}N_2O.0.5H_2O$; Calcd: C, 80.33; H, 7.67; N, 6.46. Found: C, 80.25; H, 7.34; N, 6.68. $^1H$ NMR (200 MHz, CDCl$_3$) δ: 1.44 (2H, m), 1.61 (4H, m), 2.22 (3H, s), 2.36 (3H, s), 2.47 (4H, m), 3.55 (2H, s), 6.61 (1H, d, J=15.4 Hz), 7.05–7.20 (3H, m), 7.28–7.60 (8H, m), 7.71 (1H, s), 7.79 (1H, d. J=15.4 Hz).

WORKING EXAMPLE 75 (Production of Compound 75)

In THF (10 ml) was dissolved 3-(3-nitrophenyl)cinnamic acid (0.54 g), and to the solution were added oxalyl chloride (0.35 ml) and a drop of DMF. The mixture was stirred at room temperature for 1 hour and concentrated under reduced pressure. The residue was dissolved in THF (20 ml), and to the solution were added 1-(4-aminobenzyl)piperidine (0.38 g) and triethylamine (0.34 ml) at room temperature. The reaction mixture was stirred at room temperature for 2 hours, and to the mixture was added water (50 ml). The mixture was extracted with ethyl acetate. The organic layer was washed with saturated sodium chloride solution, dried with anhydrous magnesium sulfate and concentrated under reduced pressure. The residue was recrystallized from ethyl acetate to give (E)-N-[4-(piperidinomethyl)phenyl]-3-(3-nitrophenyl)cinnamamide (Compound 75) (0.65 g) as pale yellow crystals.

mp 178–179° C.; Elemental Analysis for $C_{27}H_{27}N_3O_3.0.5H_2O$; Calcd: C, 71.98; H, 6.26; N, 9.33. Found: C, 71.69; H, 6.38; N, 9.44. $^1H$ NMR (200 MHz, DMSO-$d_6$) δ: 1.51 (6H, m), 2.33 (4H, m), 3.39 (2H, s), 6.96 (1H, d, J=15.8 Hz), 7.24 (2H, d, J=8.0 Hz), 7.59–7.83 (7H, m), 8.02 (1H, s), 8.18–8.30 (2H, m), 8.52 (1H, s), 10.18 (1H, s).

WORKING EXAMPLE 76 (Production of Compound 76)

In DMF (6 ml) was dissolved (E)-N-[4-(piperidinomethyl)phenyl]-3-(2,5-dimethylphenyl)cinnamamide (0.60 g), and to the mixture was added methyl iodide (0.60 g). The mixture was stirred at room temperature for 20 hours and concentrated under reduced pressure. The residue was crystallized from ethyl acetate to give (E)-1-methyl-1-[4-(3-(2,5-dimethylphenyl)cinnamamido)benzyl]piperidinium iodide (Compound 76) (0.66 g) as pale yellow crystals.

mp 145–147C.; Elemental Analysis for $C_{30}H_{35}N_2OI.1.5H_2O$; Calcd: C, 60.71; H, 6.45; N, 4.72. Found: C, 61.06; H, 6.10; N, 4.74. $^1H$ NMR (200 MHz, DMSO-$d_6$) δ: 1.62 (2H, m), 1.88 (4H, m), 2.22 (3H, s), 2.33 (3H, s), 2.93 (3H, s), 3.33 (4H, m), 4.55 (2H, s), 6.92 (1H, d, J=15.8 Hz), 7.07 (1H, s), 7.15 (2H, ABq, J=7.6 Hz), 7.37 (1H, d, J=7.4 Hz), 7.48–7.60 (5H, m), 7.67 (1H, d, J=15.6 Hz), 7.84 (2H, d, J=8.4 Hz), 10.39 (1H, s).

WORKING EXAMPLE 77 (Production of Compound 77)

In DMF (6 ml) was dissolved (E)-N-[4-(piperidinomethyl)phenyl]-3-(3-nitrophenyl)cinnamamide (0.59 g), and to the mixture was added methyl iodide (0.57 g). The mixture was stirred at room temperature for 20 hours and concentrated under reduced pressure. The residue was crystallized from ethyl acetate to give (E)-1-methyl-1-[4-(3-(3-nitrophenyl)cinnamamido)benzyl]-piperidinium iodide (Compound 77) (0.75 g) as pale yellow crystals.

mp 188–190° C.; Elemental Analysis for $C_{28}H_{30}N_3O_3I.1.5H_2O$; Calcd: C, 55.09; H, 5.45; N, 6.88. Found: C, 54.91; H, 5.40; N, 7.23. $^1H$ NMR (200 MHz, DMSO-$d_6$) δ: 1.65 (2H, m), 1.90 (4H, m), 2.94 (3H, s), 3.35 (4H, m), 4.56 (2H, s), 6.99 (1H, d, J=15.8 Hz), 7.49–7.88 (9H, m), 8.04 (1H, s), 8.18–8.29 (2H, m), 8.53 (1H, s), 10.45 (1H, s).

WORKING EXAMPLE 78 (Production of Compound 78)

In toluene(10 ml) was dissolved (E)-N-[4-(chloromethyl)phenyl]-3-(4-methylphenyl)cinnamamide (300 mg), and to the mixture was added tributylphosphine (248 μl). The mixture was stirred at 80° C. for 3 days and cooled to room temperature. The resulting precipitate was filtered and recrystallized from ethyl acetate-methanol to give (E)tributyl[4-[3-(4-methylphenyl)cinnamamido]benzyl] phosphonium chloride (Compound 78) (389 mg) as colorless crystals.

mp 216–217° C.; Elemental Analysis for $C_{35}H_{47}NOClP$; Calcd: C, 74.51; H, 8.40; N, 2.48. Found: C, 74.40; H, 8.33; N, 2.63. IR (KBr) cm$^{-1}$ : 3429, 2966, 1674, 1630, 1601, 1537, 1516, 1344, 1180, 789; $^1$H NMR (200 MHz, DMSO-d$_6$) δ: 0.85–1.00 (9H, m), 1.30–1.60 (12H, m), 2.05–2.25 (6H, m), 2.37 (3H, s), 3.79 (2H, d, J=15.2 Hz), 7.05 (1H, d, J=15.8 Hz), 7.25–7.35 (4H, m), 7.48–7.90 (9H, m), 10.61 (1H, s).

WORKING EXAMPLE 79 (Production of Compound 79)

In THF (10 ml) was dissolved (E)-3-(4-methylphenyl) cinnamic acid (400 mg), and to the solution were added oxalyl chloride (220 μl) and a drop of DMF. The mixture was stirred at room temperature for 1 hour and concentrated under reduced pressure. The residue was dissolved in THF (10 ml), and to the mixture was dropwise added a solution of (4-aminophenyl) (2-pyridyl)methanol (370 mg) and triethylamine (471 μl) in THF (15 ml) at 0° C. The reaction mixture was stirred at room temperature for 20 hours, and to the mixture was added water (50 ml). The mixture was extracted with ethyl acetate. The organic layer was washed with saturated sodium chloride solution, dried with anhydrous sodium sulfate, and concentrated under reduced pressure. The residue was recrystallized from ethyl acetate-hexane to give (E)-N-[4-[hydroxy(2-pyridyl)methyl] phenyl]-3-(4-methylphenyl)cinnamamide (Compound 79) (517 mg) as colorless crystals.

mp 162–165° C.; Elemental Analysis for $C_{28}H_{24}N_2O_2 \cdot 0.1H_2O$; Calcd: C, 79.63; H, 5.78; N, 6.63. Found: C, 79.53; H, 5.73; N, 6.58. IR (KBr) cm$^{-1}$: 3257, 1659, 1626, 1597, 1531,1410, 1342, 1250, 1182, 787, 758; $^1$H NMR (200 MHz, CDCl$_3$) δ: 2.41 (3H, s), 5.27–5.36 (1H, m), 5.70–5.77 (1H, m), 6.60 (1H, d, J=15.4 Hz), 7.12–7.86 (17H, m), 8.57 (1H, d, J=4.4 Hz).

WORKING EXAMPLE 80 (Production of Compound 80)

In THF (10 ml) was dissolved (E)-N-[4-[hydroxy(2-pyridyl)methyl]phenyl]-3-(4-methylphenyl)cinnamamide (200 mg), and to the mixture was added 70% mCPBA (152 mg). The mixture was stirred at room temperature for 6 hours, and to the solution were added saturated sodium thiosulfate solution (10 ml) and saturated potassium carbonate (10 ml). The mixture was stirred at room temperature for 30 minutes and extracted with ethyl acetate. The organic layer was washed with saturated sodium chloride solution, dried with anhydrous sodium sulfate, and concentrated under reduced pressure. The residue was recrystallized from ethyl acetate-methanol to give (E)-N-[4-[hydroxy(1-oxido-2-pyridyl)methyl]phenyl]3-(4-methylphenyl)cinnamamide (Compound 80) (123 mg) as colorless crystals.

mp 165–167° C.; Elemental Analysis for $C_{28}H_{24}N_2O_3$; Calcd: C, 77.04; H, 5.54; N, 6.42. Found: C, 76.85; H, 5.55; N, 6.42. IR (KBr) cm$^{-1}$: 3288, 1668, 1628, 1601, 1539,1516, 1433, 1412, 1340, 1184, 791, 768; $^1$H NMR (200 MHz, CDCl$_3$) δ: 2.40 (3H, s), 6.05 (1H, d, J=4.4 Hz), 6.37 (1H, d, J=4.4 Hz), 6.65 (1H, d, J=15.8 Hz), 6.99–7.06 (1H, m), 7.20–7.31 (4H, m), 7.36–7.87 (12H, m), 8.20–8.26 (1H, m).

WORKING EXAMPLE 81 (Production of Compound 81)

To 3-phenylcinnamic acid (0.62 g) were added thionyl chloride (5 ml) and dimethylformamide (catalytic amount), and the mixture was refluxed for 4 hours. The solvent was evaporated, and the residue was dissolved in tetrahydrofuran. The mixture was dropwise added to a suspension of 1-(4-aminobenzyl)piperidine (0.5 g) and diisopropylethylamine (1.2 ml) in tetrahydrofuran (5 ml) under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (methanol/triethylamine/ethyl acetate). The resulting crude crystals was recrystallized from ethyl acetate-hexane to give 1-(4-(3-phenylcinnamoylamino) benzyl)piperidine (Compound 81) (0.45 g) as pale yellow crystals.

mp 159–160° C.; $^1$H-NMR(δ ppm, CDCl$_3$): 1.37–1.48 (2H, m), 1.49–1.63 (4H, m), 2.34–2.42 (4H, m), 3.45 (2H, s), 6.62 (1H, d, J=15.4 Hz), 7.23–7.63 (13H, m), 7.76 (1H, s), 7.83 (1H, d, J=15.4 Hz). IR(KBr) ν: 2934, 1659, 1624 cm$^{-1}$. Anal. for $C_{27}H_{28}N_2O \cdot 0.5H_2O$: Calcd. C, 79.97; H, 7.21; N, 6.91. Found C, 81.09; H, 7.02; N, 6.94.

WORKING EXAMPLE 82 (Production of Compound 82)

A solution of N-(4-chloromethylphenyl)-7-(4-methylphenyl)-2,3-dihydro-1-benzoxepine-4-carboxamide (0.15 g) and sodium phenyl sulfide (0.05 g) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give 7-(4-methylphenyl)-N-(4-(phenylthiomethyl)phenyl)-2,3-dihydro-1-benzoxepine-4-carboxamide (Compound 82) (0.13 g) as colorless crystals.

mp 176–177° C.; $^1$H-NMR(δ ppm, CDCl$_3$): 2.39 (3H, s), 3.07 (2H, t, J=4.5 Hz), 4.10 (2H, s), 4.35 (2H, t, J=4.5 Hz), 7.06 (1H, d, J=8.2 Hz), 7.18–7.33 (9H, m), 7.43–7.53 (6H, m), 7.58 (1H, s). IR(KBr) ν: 1652, 1515 cm$^{-1}$. Anal. for $C_{31}H_{27}NO_2S$: Calcd. C, 77.96; H, 5.70; N, 2.93. Found C, 77.72; H, 5.57; N, 3.07.

WORKING EXAMPLE 83 (Production of Compound 83)

A suspension of 1-(4-(3-bromocinnamoylamino)benzyl) piperidine (0.4 g), 4-fluorophenyl borate (0.14 g), 1M potassium carbonate (2 ml) and ethanol (1 ml) in toluene (5 ml) was stirred under argon atmosphere at room temperature for 30 minutes. To the suspension was added tetrakistriphenylphosphinepalladium (0.05 g), and the mixture was refluxed over night. The mixture was extracted with ethyl acetate, and the organic layer was washed with water and saturated sodium chloride solution, and dried with anhydrous magnesium sulfate. Under reduced pressure, the solvent was evaporated, and the residue was purified with silica gel column (methanol/triethylamine/ethyl acetate) to give crude crystals, which were recrystallized from ethyl acetate-hexane to give 1-(4-(3-(4-fluoro-phenyl)cinnamoylamino) benzyl)piperidine (Compound 83) (0.35 g) as colorless crystals.

mp 166–167° C.; $^1$H-NMR(δ ppm, CDCl$_3$): 1.38–1.50 (2H, m), 1.52–1.65 (4H, m), 2.34–2.39 (4H, m), 3.45 (2H, s), 6.61 (1H, d, J=15.4 Hz), 7.10–7.19 (2H, m), 7.30 (2H, d, J=8.0 Hz), 7.40–7.58 (8H, m), 7.68 (1H, s), 7.81 (1H, d, J=15.4 Hz). IR(KBr) ν: 3262, 2936, 1663 cm$^{-1}$. Anal. for $C_{27}H_{27}FN_2O.0.2H_2O$: Calcd. C, 77.56; H, 6.61; N, 6.70. Found C, 77.72; H, 6.49; N, 6.79.

WORKING EXAMPLE 84 (Production of Compound 84)

A suspension of 1-(4-(3-bromocinnamoyl amino)benzyl)piperidine (0.4 g), 4-methoxyphenyl borate (0.14 g), 1M potassium carbonate (2 ml) and ethanol (1 ml) in toluene (5 ml) was stirred under argon atmosphere at room temperature for 30 minutes. To the suspension was added tetrakistriphenylphosphinepalladium (0.05 g), and the mixture was refluxed over night. The mixture was extracted with ethyl acetate, and the organic layer was washed with water and saturated sodium chloride solution, and dried with anhydrous magnesium sulfate. Under reduced pressure, the solvent was evaporated, and the residue was purified with silica gel column (methanol/triethylamine/ethyl acetate) to give crude crystals, which were recrystallized from ethyl acetate-hexane to give 1-(4-(3-(4-methoxyphenyl)-cinnamoylamino)benzyl)piperidine (Compound 84) (0.38 g) as colorless crystals.

mp 150–151° C.; $^1$H-NMR(δ ppm, CDCl$_3$): 1.38–1.50 (2H, m), 1.51–1.62 (4H, m), 2.35–2.40 (4H, m), 3.46 (2H, s), 3.87 (3H, s), 6.61 (1H, d, J=15.4 Hz), 7.00 (2H, d, J=9.0 Hz), 7.29–7.36 (3H, m), 7.43–7.58 (7H, m), 7.71 (1H, s), 7.82 (1H, d, J=15.4 Hz). IR(KBr) ν: 3264, 2936, 1663 cm$^{-1}$. Anal. for $C_{28}H_{30}N_2O_2$: Calcd. C, 78.84; H, 7.09; N, 6.57. Found C, 79.07; H, 7.12; N, 6.69.

WORKING EXAMPLE 85 (Production of Compound 85)

A solution of 1-(4-(3-phenylcinnamoylamino)benzyl)piperidine (0.32 g) and methyl iodide (0.15 ml) in dimethylformamide (5 ml) was stirred over night under nitrogen atmosphere at room temperature. The solvent was evaporated, and to the residue was added ethyl acetate. Precipitated crude crystal was filtered, which were recrystallized from ethanol to give 1-methyl-1-(4-(3-phenylcinnamoylamino)-benzyl)piperidinium iodide (Compound 85) (0.26 g) as colorless crystals.

mp 194–195° C.; $^1$H-NMR(δ ppm, DMSO-d$_6$): 1.45–1.65 (2H, m), 1.75–1.95 (4H, m), 2.92 (3H, s), 3.24–3.28 (4H, m), 4.54 (2H, s), 6.97 (1H, d, J=15.8 Hz), 7.41–7.93 (14H, m), 10.44 (1H,s). IR(KBr) ν: 3241, 1682 cm$^{-1}$. Anal. for $C_{28}H_{31}IN_2O$: Calcd. C, 62.46; H, 5.80; N, 5.20. Found C, 62.19; H, 5.74; N, 5.10.

WORKING EXAMPLE 86 (Production of Compound 86)

A solution of N-(4-chloromethylphenyl)-7-(4-methylphenyl)-2,3-dihydro-1-benzoxepine-4-carboxamide (0.15 g) and sodium benzyl sulfide (0.055 g) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-(benzylthiomethyl)phenyl)-7-(4-methylphenyl)-2,3-dihydro-1-benzoxepine-4-carboxamide (Compound 86) (0.17 g) as colorless crystals.

mp 145–146° C.; $^1$H-NMR(δ ppm, CDCl$_3$): 2.39 (3H, s), 3.07 (2H, t, J=4.7 Hz), 3.59 (2H, s), 3.60 (2H, s), 4.35 (2H, t, J=4.7 Hz), 7.06 (1H, d, J=8.0 Hz), 7.22–7.32 (9H, m), 7.43–7.57 (6H, m), 7.61 (1H, s). IR(KBr) ν: 3028, 1646, 1515 cm$^{-1}$. Anal.for $C_{32}H_{29}NO_2S.0.5H_2O$: Calcd. C, 76.77; H, 6.04; N, 2.80. Found C, 77.07; H, 5.96; N, 2.95.

WORKING EXAMPLE 87 (Production of Compound 87)

A solution of Compound 83 (0.25 g) and methyl iodide (0.2 ml) in dimethylformamide (5 ml) was stirred at room temperature over night. The solvent was evaporated, and to the residue was added ethyl acetate. Precipitated crude crystal was filtered, which were recrystallized from ethanol to give 1-methyl-1-(4-(3-(4-fluorophenyl)cinnamoylamino)benzyl)piperidinium iodide (Compound 87) (0.27 g) as pale brown crystals.

mp 204–205° C.; $^1$H-NMR(δ ppm, DMSO-d$_6$): 1.42–1.75 (2H, m), 1.78–1.95 (4H, m), 2.91 (3H, s), 3.22–3.32 (4H, m), 4.52 (2H, s), 6.95 (1H, d, J=15.8 Hz), 7.29–7.38 (2H, m), 7.48–7.91 (11H, m), 10.44 (1H, s). IR(KBr) ν: 3237, 1682 cm$^{-1}$. Anal.for $C_{28}H_{30}FIN_2O.0.5H_2O$: Calcd. C, 59.47; H, 5.53; N, 4.95. Found C, 59.49; H, 5.35; N, 4.98.

WORKING EXAMPLE 88 (Production of Compound 88)

A solution of 1-(4-(3-(4-methoxyphenyl)cinnamoylamino)benzyl)piperidine (0.32 g) and methyl iodide (0.2 ml) in dimethylformamide (5 ml) was stirred at room temperature over night. The solvent was evaporated, and to the residue was added ethyl acetate. Precipitated crude crystal was filtered, which were recrystallized from ethanol-hexane to give 1-methyl-1-(4-(3-(4-methoxyphenyl)cinnamoylamino)benzyl)piperidinium iodide (Compound 88) (0.33 g) as pale brown crystals.

mp 208–209° C.; $^1$H-NMR(δ ppm, DMSO-d$_6$): 1.45–1.68 (2H, m), 1.78–1.95 (4H, m), 2.91 (3H, s), 3.24–3.34 (4H, m), 3.82 (3H, s), 4.53 (2H, s), 6.95 (1H, d, J=15.8 Hz), 7.06 (2H, d, J=8.6 Hz), 7.43–7.57 (4H, m), 7.61–7.74 (4H, m), 7.84 (2H, d, J=8.6 Hz), 7.88 (1H, s), 10.45 (1H, s). IR(KBr) ν: 3243, 1682 cm$^{-1}$. Anal. for $C_{29}H_{33}IN_2O_2$: Calcd. C, 61.27; H, 5.85; N, 4.93. Found C, 60.87; H, 5.83; N, 4.88.

WORKING EXAMPLE 89 (Production of Compound 89)

To 3,4-dihydro-7-phenylnaphthalene-2-carboxylic acid (0.25 g) were added thionyl chloride (5 ml) and dimethylformamide (catalytic amount), and the mixture was refluxed for 3 hours. The solvent was evaporated, and the residue was dissolved in tetrahydrofuran. The mixture was dropwise added to a suspension of 2-(4-aminobenzyl)-1,3-dimethyl-1,3,2-diazaphosphorane-2-oxide (0.25 g) and diisopropylethylamine (0.5 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated. Precipitated crude crystal was recrystallized from ethanol-hexane to give 2-(4-(3,4-dihydro-7-phenyl-naphthalene-2-carbonylamino)benzyl)-1,3-dimethyl-1,3,2-diazaphosphorinane-2-oxide (Compound 89) (0.35 g) as colorless crystals.

mp 249–250° C.; $^1$H-NMR(δ ppm, CDCl$_3$): 1.10–1.30 (1H, m), 1.65–1.85 (1H, m), 2.65 (3H, s), 2.69 (3H, s), 2.73–3.07 (8H, m), 3.17 (2H, d, J=17.4 Hz), 7.18 (2H, dd, J=2.6, 8.8 Hz), 7.29–7.60 (11H, m), 7.70 (1H, s). IR(KBr) v: 3283, 2940, 2886, 2832, 1655 cm$^{-1}$. Anal. for $C_{29}H_{32}N_3O_2P.0.2H_2O$: Calcd. C, 71.21; H, 6.68; N, 8.59. Found C, 71.12; H, 6.57; N, 8.52.

WORKING EXAMPLE 90 (Production of Compound 90)

To 3,4-dihydro-7-phenylnaphthalene-2-carboxylic acid (0.35 g) were added thionyl chloride (10 ml) and dimethylformamide (catalytic amount), and the mixture was refluxed for 2.5 hours. The solvent was evaporated, and the residue was dissolved in tetrahydrofuran. The mixture was dropwise added a suspension of 2-(4-aminobenzyl)-1,3-dimethyl-1,3,2-diazaphosphorane-2-oxide (0.33 g) and diisopropylethylamine (0.75 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated. Precipitated crude crystal was recrystallized from ethanol-hexane to give 2-(4-(3,4-dihydro-7-phenyl-naphthalene-2-carbonylamino) benzyl)-1,3-dimethyl-1,3,2-diaza-phosphorane- 2-oxide (Compound 90) (0.24 g) as colorless crystals.

mp 212–213° C.; $^1$H-NMR($\delta$ ppm, CDCl$_3$): 2.61 (3H, s), 2.65–2.76 (2H, m), 2.66 (3H, s), 2.94–3.07 (2H, m), 3.22 (2H, d, J=18.6 Hz), 7.19 (2H, dd, J=2.6, 8.6 Hz), 7.29–7.60 (11H, m), 7.72 (1H, s). IR(KBr) v: 3254, 2928, 2897, 1655 cm$^{-1}$. Anal. for $C_{28}H_{30}N_3O_2P.0.5H_2O$: Calcd. C, 69.98; H, 6.50; N, 8.74. Found C, 70.27; H, 6.32; N, 8.53.

WORKING EXAMPLE 91 (Production of Compound 91)

To a solution of 2-(4-methylphenyl)-6,7-dihydro-5H-benzocycloheptene-8-carboxylic acid (0.25 g) in dichloromethane (5 ml) were added oxalyl chloride (0.4 ml) and dimethylformamide (catalytic amount) under ice-cooling, and the mixture was stirred at 40° C. for 1 hour. The solvent was evaporated, and the residue was dissolved in tetrahydrofuran. The mixture was dropwise added to a solution of 1-(4-aminobenzyl)piperidine (0.17 g) and diisopropylethylamine (0.5 ml) in tetrahydrofuran (10 ml), under ice-cooling. Under nitrogen atmosphere, the mixture was stirred at room temperature over night. The solvent was evaporated, and to the residue was added water. The mixture was extracted with dichloromethane, and the organic layer was washed with water and dried with anhydrous magnesium sulfate. Under reduced pressure, the solvent was evaporated, and precipitated crude crystal was recrystallized from dichloromethane-hexane to give 2-(4-methylphenyl)-N-(4-piperidinomethylphenyl)-6,7-dihydro-5H-benzocycloheptene-8-carboxamide (Compound 91) (0.36 g) as colorless crystals.

mp 192–193° C.; $^1$H-NMR($\delta$ ppm, CDCl$_3$): 1.38–1.50 (2H, m), 1.50–1.63 (4H, m), 2.13–2.22 (2H, m), 2.35–2.39 (4H, m), 2.40 (3H, s), 2.72 (2H, t, J=6.4 Hz), 2.85–2.91 (2H, m), 3.46 (2H, s), 7.21–7.33 (5H, m), 7.41–7.57 (6H, m), 7.63 (1H, s). IR(KBr) v: 3352, 2932, 1647 cm$^{-1}$. Anal. for $C_{31}H_{34}N_2O.0.2H_2O$: Calcd. C, 81.97; H, 7.63; N, 6.17. Found C, 81.88; H, 7.52; N, 6.22.

WORKING EXAMPLE 92 (Production of Compound 92)

A solution of 2-(4-methylphenyl)-N-(4-piperidinomethylphenyl)-6,7-dihydro-5H-benzocycloheptene-8-carboxamide (0.26 g) and methyl iodide (0.15 ml) in dimethylformamide (15 ml) was stirred at room temperature over night. The solvent was evaporated, and to the residue was added ethyl acetate. Precipitated crude crystal was filtered, which were recrystallized from ethanol-ethyl acetate to give 1-(N-(2-(4-methylphenyl)-6,7-dihydro-5H-benzocycloheptene-8-carbonyl)-4-aminobenzyl)-1-methylpiperidinium iodide (Compound 92) (0.3 g) as colorless crystals.

mp 220–221° C.(dec.).; $^1$H-NMR($\delta$ ppm, DMSO-d$_6$): 1.45–1.65 (2H, m), 1.80–1.94 (4H, m), 1.99–2.09 (2H, m), 2.35 (3H, s), 2.64 (2H, t, J=6.1Hz), 2.83–2.88 (2H, m), 2.91 (3H, s), 3.23–3.29 (4H, m), 4.53 (2H, s), 7.26–7.38 (4H, m), 7.48–7.68 (6H, m), 7.87 (2H, d, J=8.6 Hz), 10.23 (1H, s). IR(KBr) v: 3285, 2946, 1651 cm$^{-1}$. Anal. for $C_{32}H_{37}IN_2O.0.5H_2O$: Calcd. C, 63.89; H, 6.37; N, 4.66. Found C, 63.94; H, 6.33; N, 4.60.

WORKING EXAMPLE 93 (Production of Compound 93)

To a solution of 7-(4-methylphenyl)-N-(4-hydroxymethylphenyl)-2,3-dihydro-1-benzothiepine-4-carboxamide (0.2 g), triethylamine (0.21 ml) and dimethylaminopyridine (catalytic amount) in tetrahydrofuran (10 ml) was dropwise added methane-sulfonylchloride (0.06 ml) under ice-cooling, and the mixture was stirred for 10 minutes. To the mixture was added piperidine (0.15 ml), and the mixture was stirred at room temperature for 2 hours. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (methanol/triethylamine/ethyl acetate) to give crude crystals, which were recrystallized from ethyl acetate-hexane to give 7-(4-methylphenyl)-N-(4-piperidinomethylphenyl)-2,3-dihydro-1-benzothiepine-4-carboxamide (Compound 93) (0.19 g) as colorless crystals.

mp 203–204° C.; $^1$H-NMR($\delta$ ppm, CDCl$_3$): 1.35–1.50 (2H, m), 1.55–1.63 (4H, m), 2.38–2.40 (4H, m), 2.40 (3H, s), 3.08 (2H, t, J=5.7 Hz), 3.29 (2H, t, J=5.7 Hz), 3.47 (2H, s), 7.24–7.46 (7H, m), 7.50–7.58 (5H, m), 7.68 (1H, s). IR(KBr) v: 2934, 1651 cm$^{-1}$. Anal. for $C_{30}H_{32}N_2OS.0.2H_2O$: Calcd. C, 76.30; H, 6.92; N, 5.93. Found C, 76.27; H, 6.77; N, 6.06.

WORKING EXAMPLE 94 (Production of Compound 94)

A solution of 7-(4-methylphenyl)-N-(4-piperidinomethyl-phenyl)-2,3-dihydro-1-benzothiepine-4-carboxamide (0.08 g) and methyl iodide (0.013 ml) in dimethylformamide (20 ml) was stirred at room temperature over night. The solvent was evaporated, and to the residue was added ethyl acetate. Precipitated crude crystal was filtered, which were recrystallized from ethanol-hexane to give 1-(N-(7-(4-methylphenyl)-2,3-dihydro-1-benzothiepine-4-carbonyl)-4-aminobenzyl)-1-methylpiperidinium iodide (Compound 94) (0.077 g) as colorless crystals.

mp 196–197° C.; $^1$H-NMR($\delta$ ppm, DMSO-d$_6$): 1.45–1.65 (2H, m), 1.80–1.95 (4H, m), 2.35 (3H, s), 2.91 (3H, s), 2.99–3.05 (2H, m), 3.15–3.29 (6H, m), 4.53 (2H, s), 7.29 (2H, d, J=8.2 Hz), 7.46–7.63 (7H, m), 7.82–7.89 (3H, m), 10.34 (1H, s). IR(KBr) v: 3284, 2947, 1652 cm$^1$. Anal. for $C_{31}H_{35}IN_2OS.0.5H_2O$: Calcd. C, 60.09; H, 5.86; N, 4.52. Found C, 60.03; H, 5.57; N, 4.44.

WORKING EXAMPLE 95 (Production of Compound 95)

To a suspension of 7-(4-methylphenyl)-2,3-dihydro-1-benzoxepine-4-carboxylic acid (1.0 g) in dichloromethane (30 ml) were added oxalyl chloride (0.93 ml) and dimethylformamide (catalytic amount), under ice-cooling, and the mixture was stirred at room temperature for 2 hours. The solvent was evaporated, and the residue was dissolved in tetrahydrofuran. The mixture was dropwise added to a solution of 1-(4-amino-benzyl)piperidine (0.75 g) and triethylamine (1.5 ml) in tetra-hydrofuran (50 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals which were recrystallized from ethyl acetate-hexane to give 7-(4-methyl-phenyl)-N-(4-((piperidinomethyl)phenyl)-2,3-dihydro-1-benzoxepine-4-carboxamide (Compound 95) (1.45 g) as colorless crystals.

mp 188–189° C.; $^1$H-NMR($\delta$ ppm, CDCl$_3$): 1.40–1.47 (2H, m), 1.52–1.60 (4H, m), 2.34–2.39 (4H, m), 2.39 (3H, s), 3.07 (2H, t, J=4.4 Hz), 3.46 (2H, s), 4.36 (2H, t, J=4.4 Hz), 7.06 (1H, d, J=8.4 Hz), 7.22–7.33 (5H, m), 7.43–7.58 (6H, m). IR(KBr) $\nu$: 2935, 1652 cm$^{-1}$. Anal. for C$_{30}$H$_{32}$N$_2$O$_2$: Calcd. C, 79.61; H, 7.13; N, 6.19. Found C, 79.53; H, 6.91; N, 6.22.

WORKING EXAMPLE 96 (Production of Compound 96)

A solution of 7-(4-methylphenyl)-N-(4-(piperidinomethyl)phenyl)-2,3-dihydro-1-benzoxepine-4-carboxamide (1.4 g) and methyl iodide (0.58 ml) in dimethylformamide (50 ml) was stirred at room temperature over night. The solvent was evaporated, and to the residue was added ethyl acetate. Precipitated crude crystal was filtered, which were recrystallized from ethanol-ethyl acetate to give 1-(N-(7-(4-methylphenyl)-2,3-dihydro-1-benzoxepin-4-carbonyl) -4-aminobenzyl) -1-methylpiperidinium iodide (Compound 96) (1.6 g) as colorless crystals.

mp 227–228° C.(dec.).; $^1$H-NMR($\delta$ ppm, DMSO-d$_6$): 1.45–1.70 (2H, m), 1.70–1.95 (4H, m), 2.34 (3H, s), 2.91 (3H, s), 3.00 (2H, br), 3.24–3.34 (4H, m), 4.31 (2H, br), 4.53 (2H, s), 7.06 (1H, d, J=8.4 Hz), 7.27 (2H, d, J=8.0 Hz), 7.36 (1H, s), 7.48–7.59 (5H, m), 7.75 (1H, s), 7.86 (2H, d, J=8.8 Hz), 10.19 (1H, s). IR(KBr) $\nu$: 3289, 2938, 1649 cm$^{-1}$. Anal. for C$_{31}$H$_{35}$IN$_2$O$_2$: Calcd. C, 62.63; H, 5.93; N, 4.71. Found C, 62.43; H, 5.91; N, 4.52.

WORKING EXAMPLE 97 (Production of Compound 97)

A solution of N- (4-chloromethylphenyl) -7- (4-methylphenyl)-2,3-dihydro-1-benzoxepine-4-carboxamide (0.15 g) and 1-methylpiperidine (0.14 ml) in dimethylformamide (15 ml) was stirred at room temperature over night. The solvent was evaporated, and to the residue was added ethyl acetate. Precipitated crude crystal was filtered, which were recrystallized from ethanol-diethylether to give 1-(N-(7-(4-methylphenyl) -2,3-dihydro-1-benzoxepin-4-carbonyl) -4-aminobenzyl) - 1 -methylpiperidinium chloride (Compound 97) (0.15 g) as colorless crystals.

mp 231–232° C.; $^1$H-NMR($\delta$ ppm, DMSO-d$_6$): 1.45–1.65 (2H, m), 1.80–1.95 (4H, m), 2.34 (3H, s), 2.91 (3H, s), 2.97–3.05 (2H, m), 3.23–3.30 (4H, m), 4.25–4.35 (2H, m), 4.53 (2H, s), 7.06 (1H, d, J=8.4 Hz), 7.27 (2H, d, J=8.4 Hz), 7.38 (1H, s), 7.48–7.59 (5H, m), 7.75 (1H, s), 7.86 (2H, d, J=8.8 Hz), 10.23 (1H, s). IR(KBr) $\nu$: 3227, 2969, 1665 cm$^{-1}$. Anal. for C$_{31}$H$_{35}$ClN$_2$O$_2$.0.5H$_2$O: Calcd. C, 72.71; H, 7.09; N, 5.47. Found C, 72.85; H, 6.93; N, 5.48.

WORKING EXAMPLE 98 (Production of Compound 98)

A solution of N-(4-chloromethylphenyl)-7-(4-methylphenyl)-2,3-dihydro-1-benzoxepine-4-carboxamide (0.18 g) and 1-ethylpiperidine (0.31 ml) in dimethylformamide (5 ml) were stirred at 50° C. over night. The solvent was evaporated, and to the residue was added ethyl acetate. Precipitated crude crystal was filtered, which were recrystallized from ethanol-ethyl acetate to give 1-(N-(7-(4-methylphenyl)-2,3-dihydro-1-benzoxepin-4-carbonyl)-4-amino-benzyl)-1-ethylpiperidinium chloride (Compound 98) (0.17 g) as colorless crystals.

mp 209–210° C.; $^1$H-NMR($\delta$ ppm, DMSO-d$_6$): 1.34 (3H, t, J=6.9 Hz), 1.38–1.66 (2H, m), 1.80–1.99 (4H, m), 2.34 (3H, s), 3.00 (2H, t, J=4.2 Hz), 3.13–3.31 (6H, m), 4.30 (2H, t, J=4.2 Hz), 4.50 (2H, s), 7.06 (1H, d, J=8.4 Hz), 7.27 (2H, d, J=8.0 Hz), 7.39 (1H, s), 7.46–7.59 (5H, m), 7.76 (1H, d, J=2.2 Hz), 7.87 (2H, d, J=8.8 Hz), 10.24 (1H, s). IR(KBr) $\nu$: 3202, 2946, 1645 cm$^{-1}$. Anal. for C$_{32}$H$_{37}$ClN$_2$O$_2$.0.3H$_2$O: Calcd. C, 73.56; H, 7.25; N, 5.36. Found C, 73.59; H, 7.26; N, 5.32.

WORKING EXAMPLE 99 (Production of Compound 99)

To a suspension of 7-(4-methylphenyl)-2,3-dihydro-1-benzoxepine-4-carboxylic acid (0.15 g) in dichloromethane (5 ml) were added oxalyl chloride (0.14 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 1-(2-(4-aminophenyl)ethyl)piperidine (0.11 g) and triethylamine (0.23 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals which were recrystallized from ethyl acetate-hexane to give N-(4-(2-piperidinoethyl)phenyl)-7-(4-methylphenyl)-2,3-dihydro-1-benzoxepine-4-carboxamide (Compound 99) (0.19 g) as colorless crystals.

mp 201–202° C.; $^1$H-NMR($\delta$ ppm, CDCl$_3$): 1.45–1.48 (2H, m), 1.50–1.65 (4H, m), 2.39 (3H, s), 2.47–2.58 (6H, m), 2.76–2.84 (2H, m), 3.07 (2H, t, J=4.4 Hz), 4.36 (2H, t, J=4.4 Hz), 7.05 (1H, d, J=8.0 Hz), 7.17–7.26 (4H, m), 7.43–7.51 (7H, m). IR(KBr) $\nu$: 2933, 1652 cm$^{-1}$. Anal. for C$_{31}$H$_{34}$N$_2$O$_2$: Calcd. C, 79.79; H, 7.34; N, 6.00. Found C, 79.63; H, 7.42; N, 6.07.

WORKING EXAMPLE 100 (Production of Compound 100)

A solution of N-(4-(2-piperidinoethyl)phenyl)-7-(4-methylphenyl)-2,3-dihydro-1-benzoxepine-4-carboxamide (0.09 g) and methyl iodide (0.06 ml) in dimethylformamide (10 ml) was stirred at room temperature over night. The solvent was evaporated, and to the residue was added ethyl acetate. Precipitated crude crystal was filtered, which were recrystallized from ethanol-hexane to give N-((7-(4-methylphenyl)-2,3-dihydro-1-benzoxepin-4-carbonyl)-2-(4-aminophenyl)ethyl)-N-methylpiperidinium iodide (Compound 100) (0.12 g) as pale yellow crystals.

mp 168–169° C.; $^1$H-NMR($\delta$ ppm, CDCl$_3$): 1.65–1.95 (6H, m), 2.35 (3H, s), 2.95–3.05 (4H, m), 3.25 (3H, s), 3.61–3.85 (6H, m), 4.29 (2H, t, J=4.2 Hz), 7.01 (1H, d, J=8.4 Hz), 7.17–7.26 (4H, m), 7.40–7.50 (4H, m), 7.58 (2H, d, J=8.4 Hz), 7.70 (1H, d, J=2.2 Hz), 8.49 (1H, br). IR(KBr) $\nu$: 2949, 1656 cm$^{-1}$. Anal. for C$_{32}$H$_{37}$IN$_2$O$_2$.0.5H$_2$O: Calcd. C, 62.24; H, 6.20; N, 4.54. Found C, 61.92; H, 6.17; N, 4.57.

WORKING EXAMPLE 101 (Production of Compound 101)

To a suspension of 7-(4-methylphenyl)-2-phenyl-2,3-dihydro-1-benzoxepine-4-carboxylic acid (0.1 g) in dichloro-methane (10 ml) were added oxalyl chloride (0.1 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-(N-methyl-N-(tetrahydropyran-4-yl)aminomethyl)aniline (0.06 g) and triethylamine (0.12 ml) in tetrahydrofuran (5 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate) to give crude crystals, which were recrystallized from ethyl acetate-hexane to give 7-(4-methylphenyl)-2-phenyl-N-(4-((N-tetrahydropyran-4-yl-N-methylamino)methyl)phenyl)-2,3-dihydro-1-benzoxepine-4-carboxamide (Compound 101) (0.11 g) as colorless crystals.

mp 178–179° C.; $^1$H-NMR($\delta$ ppm, CDCl$_3$): 1.63–1.74 (4H, m), 2.20 (3H, s), 2.40 (3H, s), 2.56–2.66 (1H, m), 3.15–3.43 (4H, m), 3.56 (2H, s), 4.01–4.05 (2H, m), 5.09 (1H, dd, J=2.2, 8.4 Hz), 7.10 (1H, d, J=8.4 Hz), 7.17–7.57 (16H, m). IR(KBr) $\nu$: 2949, 2844, 1652 cm$^{-1}$. Anal. for C$_{37}$H$_{38}$N$_2$O$_3$: Calcd. C, 79.54; H, 6.86; N, 5.01. Found C, 79.28; H, 6.96; N, 4.97.

WORKING EXAMPLE 102 (Production of Compound 102)

To a suspension of 7-(4-methylphenyl)-2-phenyl-2,3-dihydro-1-benzoxepine-4-carboxylic acid (0.1 g) in dichloro-methane (10 ml) were added oxalyl chloride (0.1 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 1-(4-amino-benzyl)piperidine (0.06 g) and triethylamine (0.12 ml) in tetrahydrofuran (5 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate) to give crude crystals, which were recrystallized from ethyl acetatehexane to give 7-(4-methylphenyl)-2-phenyl-N-(4-(piperidinomethyl)phenyl)-2,3-dihydro-1-benzoxepine-4-carboxamide (Compound 102) (0.12 g) as colorless crystals.

mp 210–211° C.; $^1$H-NMR($\delta$ ppm, CDCl$_3$): 1.40–1.47 (2H, m), 1.52–1.62 (4H, m), 2.34–2.40 (4H, m), 2.40 (3H, s), 3.23–3.31 (2H, m), 3.45 (2H, s), 5.09 (1H, dd, J=2.0, 8.8 Hz), 7.10 (1H, d, J=8.4 Hz), 7.23–7.56 (16H, m). IR(KBr) $\nu$: 2935, 1652 cm$^{-1}$. Anal. for C$_{36}$H$_{36}$N$_2$O$_2$: Calcd. C, 81.79; H, 6.86; N, 5.30. Found C, 81.45; H, 6.82; N, 5.28.

WORKING EXAMPLE 103 (Production of Compound 103)

A solution of 7-(4-methylphenyl)-2-phenyl-N-(4-(piperidinomethyl)phenyl)-2,3-dihydro-1-benzoxepine-4-carboxamide (0.08 g) and methyl iodide (0.05 ml) in dimethylformamide (15 ml) was stirred at room temperature over night. The solvent was evaporated, and to the residue was added ethyl acetate. Precipitated crude crystal was filtered, which were recrystallized from ethanol-ethyl acetate to give 1-(N-(7-(4-methylphenyl)-2-phenyl-2,3-dihydro-1-benzoxepin-4-carbonyl)-4-aminobenzyl)-1-methylpiperidinium iodide (Compound 103) (0.057 g) as colorless crystals.

mp 232–233° C.(dec.).; $^1$H-NMR($\delta$ ppm, DMSO-d$_6$): 1.45–1.70 (2H, m), 1.75–1.95 (4H, m), 2.35 (3H, s), 2.91 (3H, s), 3.25–3.44 (6H, m), 4.53 (2H, s), 5.12 (1H, t, J=5.0 Hz), 7.09 (1H, d, J=8.4 Hz), 7.28 (2H, d, J=8.2 Hz), 7.37–7.61 (11H, m), 7.81–7.87 (3H, m), 10.20 (1H, s). IR(KBr) $\nu$: 2949, 1650 cm$^{-1}$. Anal. for C$_{37}$H$_{39}$IN$_2$O$_2$.0.2H$_2$O: Calcd. C, 65.91; H, 5.89; N, 4.15. Found C, 65.80; H, 5.84; N, 4.17.

WORKING EXAMPLE 104 (Production of Compound 104)

To a suspension of 7-(4-methylphenyl)-2-methyl-2,3-dihydro-1-benzoxepine-4-carboxylic acid (0.1g) in dichloro-methane (5 ml) were added oxalyl chloride (0.1 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-(N-methyl-N-(tetrahydropyran-4-yl)aminomethyl)aniline (0.08 g) and triethylamine (0.14 ml) in tetrahydrofuran (5 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give 7-(4-methylphenyl)- 2-methyl-N-(4-((N-tetrahydropyran-4-yl-N-methylamino)methyl)phenyl)-2,3-dihydro-1-benzoxepine-4-carboxamide (Compound 104) (0.12 g) as colorless crystals.

mp 170–171° C.; $^1$H-NMR($\delta$ ppm, CDCl$_3$): 1.54 (3H, d, J=6.4 Hz), 1.60–1.78 (4H, m), 2.22 (3H, s), 2.39 (3H, s), 2.63–2.68 (1H, m), 2.85 (1H, ddd, J=2.6, 9.2, 17.6 Hz), 3.14 (1H, d, J=17.6 Hz), 3.37 (2H, dt, J=2.8, 11.3 Hz), 3.58 (2H, s), 4.01–4.07 (2H, m), 4.24–4.30 (1H, m), 7.05 (1H, d, J=8.4 Hz), 7.22–7.34 (4H, m), 7.43–7.56 (7H, m). IR(KBr) $\nu$: 2951, 2845, 1651 cm$^{-1}$. Anal. for C$_{32}$H$_{36}$N$_2$O$_3$: Calcd. C, 77.39; H, 7.31; N, 5.64. Found C, 77.21; H, 7.43; N, 5.51.

WORKING EXAMPLE 105 (Production of Compound 105)

To a suspension of 7-(4-methylphenyl)-2-methyl-2,3-dihydro-1-benzoxepine-4-carboxylic acid (0.1 g) in dichloro-methane (5 ml) were added oxalyl chloride (0.1 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 1-(4-aminobenzyl)piperidine (0.07 g) and triethylamine (0.14 ml) in tetrahydrofuran (5 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give 7-(4-methylphenyl)-2-methyl-N-(4-(piperidinomethyl)phenyl)-2,3-dihydro-1-benzoxepine-4-carboxamide (Compound 105) (0.12 g) as colorless crystals.

mp 175–176° C.; $^1$H-NMR($\delta$ ppm, CDCl$_3$): 1.40–1.45 (2H, m), 1.54 (3H, d, J=6.2 Hz), 1.53–1.61 (4H, m), 2.30–2.40 (4H, m), 2.39 (3H, s), 2.85 (1H, ddd, J=2.6, 8.8, 18.0 Hz), 3.14 (1H, d, J=18.0 Hz), 3.47 (2H, s), 4.23–4.30 (1H, m), 7.05 (1H, d, J=8.8 Hz), 7.16–7.36 (4H, m), 7.43–7.55 (7H, m). IR(KBr) v: 2936, 1651 cm$^{-1}$. Anal. for C$_{31}$H$_{34}$N$_2$O$_2$: Calcd. C, 79.79; H, 7.34; N, 6.00. Found C, 79.53; H, 7.35; N, 5.82.

WORKING EXAMPLE 106 (Production of Compound 106)

To a solution of N-(4-(cyclohexylthiomethyl)phenyl)-7-(4-methylphenyl)-2,3-dihydro-1-benzoxepine-4-carboxamide (0.19 g) in dichloromethane (5 ml) was added 70% m-chloroperbenzoic acid (0.097 g) under ice-cooling, and the mixture was stirred for 10 minutes. To the mixture was added sodium thiosulfate solution, and the mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (methanol/dichloromethane) to give crude crystals, which were recrystallized from ethanol to give N-(4-(cyclohexylsulfinylmethyl)phenyl)-7-(4-methylphenyl)-2,3-dihydro-1-benzoxepine-4-carboxamide (Compound 106) (0.048 g) as colorless crystals.

mp 257–258° C.(dec.).; $^1$H-NMR($\delta$ ppm, CDCl$_3$): 1.19–1.69 (6H, m), 1.81–1.85 (3H, m), 2.01–2.08 (1H, m), 2.40 (3H, s), 2.40–2.49 (1H, m), 3.08 (2H, t, J=4.6 Hz), 3.90 (2H, dd, J=13.2, 24.2 Hz), 4.35 (2H, t, J=4.6 Hz), 7.06 (1H, d, J=8.6 Hz), 7.23–7.28 (4H, m), 7.44–7.54 (4H, m), 7.60 (2H, d, J=8.4 Hz), 8.07 (1H,s). IR(KBr) v: 2930, 2853, 1659 cm$^{-1}$. Anal. for C$_{31}$H$_{33}$NO$_3$S.0.3H$_2$O: Calcd. C, 73.72; H, 6.71; N, 2.77. Found C, 73.66; H, 6.70; N, 2.80.

WORKING EXAMPLE 107 (Production of Compound 107)

To a solution of N-(4-(cyclohexylsulfinylmethyl)phenyl)-7-(4-methylphenyl)-2,3-dihydro-1-benzoxepine-4-carboxamide (0.13 g) in chloroform (45 ml) was added 70% m-chloroperbenzoic acid (mCPBA) (0.097 g) under ice-cooling, and the mixture was stirred at room temperature for 30 minutes. To the mixture was added sodium thiosulfate solution, and the mixture was washed with sodium hydrogen carbonate solution and water, and dried with anhydrous magnesium sulfate. Under reduced pressure, the solvent was evaporated to give crude crystals, which were recrystallized from ethanol-hexane to give N-(4-(cyclohexylsulfonylmethyl)phenyl)-7-(4-methylphenyl)-2,3-dihydro-1-benzoxepine-4-carboxamide (Compound 107) (0.11 g) as colorless crystals.

mp 250–251° C.; $^1$H-NMR($\delta$ ppm, CDCl$_3$): 1.18–1.26 (4H, m), 1.52–1.71 (2H, m), 1.87–1.94 (2H, m), 2.09–2.17 (2H, m), 2.40 (3H, s), 2.65–2.83 (1H, m), 3.08 (2H, t, J=4.6 Hz), 4.18 (2H, s), 4.37 (2H, t, J=4.6 Hz), 7.07 (1H, d, J=8.4 Hz), 7.23–7.27 (2H, m), 7.38–7.53 (6H, m), 7.65 (2H, d, J=8.6 Hz), 7.70 (1H, s). IR(KBr) v: 2932, 2857, 1667 cm$^{-1}$. Anal. for C$_{31}$H$_{33}$NO$_4$S. 0.2H$_2$O: Calcd. C, 71.70; H, 6.48; N, 2.70. Found C, 71.70; H, 6.54; N, 2.79.

WORKING EXAMPLE 108 (Production of Compound 108)

To a solution of 7-(4-methylphenyl)-N-(4-(phenylthiomethyl)phenyl)-2,3-dihydro-1-benzoxepine-4-carboxamide (0.1 g) in dichloromethane (30 ml) was added 70% m-chloroperbenzoic acid (0.046 g) at the temperature ranging from -20 to -10° C., and the mixture was stirred for 30 minutes. To the mixture was added sodium thiosulfate solution, and the mixture was concentrated and extracted with ethyl acetate. The organic layer was washed with sodium hydrogen carbonate solution, water and saturated sodium chloride solution, and dried with anhydrous magnesium sulfate. Under reduced pressure, the solvent was evaporated to give crude crystals, which were recrystallized from ethyl acetate-hexane to give 7-(4-methylphenyl)-N-(4-(phenylsulfinylmethyl)phenyl)-2,3-dihydro-1-benzoxepine-4-carboxamide (Compound 108) (0.11 g) as colorless crystals.

mp 127–128° C.; $^1$H-NMR($\delta$ ppm, CDCl$_3$): 2.39 (3H, s), 3.06 (2H, t, J=4.6 Hz), 4.01 (2H, s), 4.34 (2H, t, J=4.6 Hz), 6.95 (2H, d, J=8.8 Hz), 7.05 (1H, d, J=8.0 Hz), 7.22–7.26 (3H, m), 7.37–7.53 (10H, m), 7.85 (1H, s). IR(KBr) v: 3026, 2925, 1652 cm$^{-1}$. Anal. for C$_{31}$H$_{27}$NO$_3$S: Calcd. C, 75.43; H, 5.51; N, 2.84. Found C, 75.14; H, 5.55; N, 2.99.

WORKING EXAMPLE 109 (Production of Compound 109)

To a solution of N-(4-(benzylthiomethyl)phenyl)-7-(4-methylphenyl)-2,3-dihydro-1-benzoxepine-4-carboxamide (0.12 g) in dichloromethane (25 ml) was added 70% m-chloroperbenzoic acid (0.06 g) at the temperature ranging from -20 to -10° C., and the mixture was stirred for 10 minutes. To the mixture was added sodium thiosulfate solution, and the mixture was concentrated and extracted with ethyl acetate. The organic layer was washed with sodium hydrogen carbonate solution, water and saturated sodium chloride solution, and dried with anhydrous magnesium sulfate. Under reduced pressure, the solvent was evaporated to give crude crystals, which were recrystallized from ethyl acetate-hexane to give N-(4-(benzylsulfinylmethyl)phenyl)-7-(4-methylphenyl)-2,3-dihydro-1-benzoxepine-4-carboxamide (Compound 109) (0.08 g) as colorless crystals.

mp 208–209° C.; $^1$H-NMR($\delta$ ppm, CDCl$_3$): 2.39 (3H, s), 3.07 (2H, t, J=4.5 Hz), 3.76–3.94 (4H, m), 4.35 (2H, t, J=4.5 Hz), 7.06 (1H, d, J=8.2 Hz), 7.23–7.27 (6H, m), 7.35–7.53 (7H, m), 7.61 (2H, d, J=8.4 Hz), 7.93 (1H, s). IR(KBr) v: 3030, 1662 cm$^{-1}$. Anal. for C$_{32}$H$_{29}$NO$_3$S.0.2H$_2$O: Calcd. C, 75.18; H, 5.80; N, 2.74. Found C, 75.35; H, 5.81; N, 2.87.

WORKING EXAMPLE 110 (Production of Compound 110)

To a suspension of 7-(4-methylphenyl)-2,3-dihydro-1-benzoxepine-4-carboxylic acid (0.1 g) in dichloromethane (5 ml) were added oxalyl chloride (0.1 ml) and dimethylformamide (catalytic amount) under ice-cooling, and the mixture was stirred at room temperature for 2 hours. The solvent was evaporated, and the residue was dissolved in tetrahydrofuran. The mixture was added dropwise to a solution of 4-aminobenzyl 4-methylphenyl sulfone (0.11 g) and triethylamine (0.15 ml) intetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((4-methylphenyl)sulfonyl)-methylphenyl)-7-(4-methylphenyl)-2,3-dihydro-1-benzoxepine-4-carboxamide (Compound 110) (0.13 g) as colorless crystals.

mp 230–231° C.; $^1$H-NMR($\delta$ ppm, CDCl$_3$): 2.40 (3H, s), 2.43 (3H, s), 3.07 (2H, t, J=4.5 Hz), 4.27 (2H, s), 4.36 (2H, t, J=4.5 Hz), 7.04–7.10 (3H, m), 7.23–7.26 (5H, m), 7.43–7.55 (8H, m), 7.63 (1H, s). IR(KBr) v: 3027, 2884, 1663 cm$^{-1}$. Anal. for $C_{32}H_{29}NO_4S \cdot 0.2H_2O$: Calcd. C, 72.90; H, 5.62; N, 2.66. Found C, 72.74; H, 5.73; N, 2.76.

WORKING EXAMPLE 111 (Production of Compound 111)

A solution of N-(4-chloromethylphenyl)-7-(4-methylphenyl)-2,3-dihydro-1-benzoxepine-4-carboxamide (0.1 g) and N-methylcyclopentylamine (0.07 g) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethanolhexane to give N-(4-((N-cyclopentyl-N-methyl)aminomethyl)phenyl)-7-(4-methylphenyl)-2,3-dihydro-1-benzoxepine-4-carboxamide (Compound 111) (0.1 g) as colorless crystals.

mp 171–172° C.; $^1$H-NMR($\delta$ ppm, CDCl$_3$): 1.45–1.75 (6H, m), 1.80–1.95 (2H, m), 2.13 (3H, s), 2.39 (3H, s), 2.70–2.80 (1H, m), 3.08 (2H, t, J=4.6 Hz), 3.50 (2H, s), 4.35 (2H, t, J=4.6 Hz), 7.06 (1H, d, J=8.0 Hz), 7.22–7.33 (4H, m), 7.43–7.58 (7H, m). IR(KBr) v: 3340, 2958, 1646 cm$^{-1}$. Anal. for $C_{31}H_{34}N_2O_2 \cdot 0.2H_2O$: Calcd. C, 79.18; H, 7.37; N, 5.96. Found C, 79.15; H, 7.18; N, 5.96.

WORKING EXAMPLE 112 (Production of Compound 112)

To a solution of N-(4-hydroxymethylphenyl)-7-(4-methylphenyl)-2,3-dihydro-1-benzoxepine-4-carboxamide (0.15 g), triethylamine (0.14 ml) and 4-dimethylaminopyridine (catalytic amount) in dichloromethane was dropwise added methanesulfonyl chloride (0.04 ml) under ice-cooling, and the mixture was stirred for 15 minutes. To the mixture was added N-methylcyclohexylamine (0.15 ml), and the mixture was stirred at room temperature over night. The solvent was evaporated, and the residue was purified with silica gel column (ethyl acetate/methanol/triethylamine) to give crude crystals, which were recrystallized from ethyl acetate-hexane to give N-(4-((N-cyclohexyl-N-methyl)aminomethyl)phenyl)-7-(4-methylphenyl)-2,3-dihydro-1-benzoxepine-4-carboxamide (Compound 112) (0.03 g) as colorless crystals.

mp 176–177° C.; $^1$H-NMR($\delta$ ppm, CDCl$_3$): 1.15–1.35 (6H, m), 1.70–1.95 (4H, m), 2.23 (3H, s), 2.39 (3H, s), 2.39–2.55 (1H, m), 3.08 (2H, t, J=4.6 Hz), 3.59 (2H, s), 4.37 (2H, t, J=4.6 Hz), 7.06 (1H, d, J=8.0 Hz), 7.23–7.35 (5H, m), 7.44–7.58 (7H, m). IR(KBr) v: 2930, 2853, 1651 cm$^{-1}$. Anal. for $C_{32}H_{36}N_2O_2 \cdot 0.4H_2O$: Calcd. C, 78.78; H, 7.60; N, 5.74. Found C, 78.97; H, 7.49; N, 5.94.

WORKING EXAMPLE 113 (Production of Compound 113)

A solution of N-(4-chloromethylphenyl)-7-(4-methylphenyl)-2,3-dihydro-1-benzoxepine-4-carboxamide (0.09 g), N-methylcycloheptylamine (0.04 g) and potassium carbonate (0.1 g) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((N-cycloheptyl-N-methyl)aminomethyl)phenyl)-7-(4-methylphenyl)-2,3-dihydro-1-benzoxepine-4-carboxamide (Compound 113) (0.08 g) as colorless crystals.

mp 167–168° C.; $^1$H-NMR ($\delta$ ppm, CDCl$_3$): 1.35–1.55 (8H, m), 1.55–1.80 (2H, m), 1.80–1.95 (2H, m), 2.16 (3H, s), 2.39 (3H, s), 2.55–2.70 (1H, m), 3.08 (2H, t, J=4.6 Hz), 3.49 (2H, s), 4.35 (2H, t, J=4.6 Hz), 7.05 (1H, d, J=8.4 Hz), 7.22–7.33 (4H, m), 7.43–7.58 (7H, m). IR(KBr) v: 2927, 1650 cm$^{-1}$. Anal. for $C_{33}H_{38}N_2O_2 \cdot 0.1H_2O$: Calcd. C, 79.83; H, 7.76; N, 5.64. Found C, 79.62; H, 7.43; N, 5.53.

WORKING EXAMPLE 114 (Production of Compound 114)

A solution of N-(4-chloromethylphenyl)-7-(4-methylphenyl)-2,3-dihydro-1-benzoxepine-4-carboxamide (0.15 g) and cyclohexylamine (0.17 ml) in dimethylformamide (10 ml) was stirred at room temperature for 2.5 hours. The solvent was evaporated, and the residue was purified with silica gel column (ethyl acetate/methanol/triethylamine) to give crude crystals, which were recrystallized from ethanolhexane to give N-(4-((cyclohexylamino)methyl)phenyl)-7-(4-methylphenyl)-2,3-dihydro-1-benzoxepine-4-carboxamide (Compound 114) (0.09 g) as colorless crystals.

mp 183–184° C.; $^1$H-NMR($\delta$ ppm, CDCl$_3$): 1.17–1.30 (6H, m), 1.58–1.82 (4H, m), 2.39 (3H, s), 2.45–2.60 (1H, m), 3.08 (2H, t, J=4.6 Hz), 3.81 (2H, s), 4.35 (2H, t, J=4.6 Hz), 7.05 (1H, d, J=8.4 Hz), 7.22–7.34 (5H, m), 7.43–7.55 (6H, m), 7.72 (1H, s). IR(KBr) v: 2928, 2853, 1647 cm$^{-1}$. Anal. for $C_{31}H_{34}N_2O_2 \cdot 0.5H_2O$: Calcd. C, 78.28; H, 7.42; N, 5.89. Found C, 78.56; H, 7.12; N, 6.01.

WORKING EXAMPLE 115 (Production of Compound 115)

A solution of N-(4-chloromethylphenyl)-7-(4-methylphenyl)-2,3-dihydro-1-benzoxepine-4-carboxamide (0.15 g) and aniline (0.1 ml) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give crude crystals, which were recrystallized from ethanol-hexane to give N-(4-((phenylamino)methyl)phenyl)-7-(4-methylphenyl)-2,3-dihydro-1-benzoxepine-4-carboxamide (Compound 115) (0.1 g) as colorless crystals.

mp 157–158° C.; $^1$H-NMR($\delta$ ppm, CDCl$_3$): 2.39 (3H, s), 3.07 (2H, t, J=4.8 Hz), 4.31 (2H, s), 4.35 (2H, t, J=4.8 Hz), 6.62–6.76 (3H, m), 7.06 (1H, d, J=8.4 Hz), 7.18–7.22 (5H, m), 7.36 (2H, d, J=8.4 Hz), 7.43–7.60 (6H, m). IR(KBr) $\nu$: 1652, 1602 cm$^{-1}$. Anal. for C$_{31}$H$_{28}$N$_2$O$_2$: Calcd. C, 80.84; H, 6.13; N, 6.08. Found C, 80.57; H, 6.09; N, 6.06.

WORKING EXAMPLE 116 (Production of Compound 116)

A suspension of N-(4-chloromethylphenyl)-7-(4-methylphenyl)-2,3-dihydro-1-benzoxepine-4-carboxamide (0.15 g), N-methylaniline (0.06 ml) and potassium carbonate (0.15 g) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((N-methyl-N-phenyl)aminomethyl)phenyl)-7-(4-methylphenyl)-2,3-dihydro-1-benzoxepine-4-carboxamide (Compound 116) (0.15 g) as colorless crystals.

mp 164–165° C.; $^1$H-NMR($\delta$ ppm, CDCl$_3$): 2.39 (3H, s), 3.00 (3H, s), 3.06 (2H, t, J=4.6 Hz), 4.34 (2H, t, J=4.6 Hz), 4.51 (2H, s), 6.68–6.77 (3H, m), 7.05 (1H, d, J=8.4 Hz), 7.19–7.26 (6H, m), 7.43–7.54 (6H, m), 7.60 (1H, s). IR(KBr) $\nu$: 3344, 3020, 1644 cm$^{-1}$. Anal. for C$_{32}$H$_{30}$N$_2$O$_2$: Calcd. C, 80.98; H, 6.37; N, 5.90. Found C, 80.64; H, 6.32; N, 5.85.

WORKING EXAMPLE 117 (Production of Compound 117)

A suspension of N-(4-chloromethylphenyl)-7-(4-methylphenyl)-2,3-dihydro-1-benzoxepine-4-carboxamide (0.1 g), benzylamine hydrochloride (0.5 g) and potassium carbonate (0.6 g) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/methanol/triethylamine) to give crude crystals, which were recrystallized from ethyl acetate-hexane to give N-(4-((benzylamino)methyl)phenyl)-7-(4-methylphenyl)-2,3-dihydro-1-benzoxepine-4-carboxamide (Compound 117) (0.08 g) as colorless crystals.

mp 147–148° C.; $^1$H-NMR($\delta$ ppm, CDCl$_3$): 2.39 (3H, s), 3.08 (2H, t, J=4.6 Hz), 3.80 (2H, s), 3.81 (2H, s), 4.35 (2H, t, J=4.6 Hz), 7.06 (1H, d, J=8.4 Hz), 7.22–7.36 (9H, m), 7.43–7.61 (7H, m). IR(KBr) $\delta$: 3028, 1652 cm$^{-1}$. Anal. for C$_{32}$H$_{30}$N$_2$O$_2$.0.1H$_2$O: Calcd. C, 80.68; H, 6.39; N, 5.88. Found C, 80.43; H, 6.23; N, 5.95.

WORKING EXAMPLE 118 (Production of Compound 118)

A suspension of N-(4-chloromethylphenyl)-7-(4-methylphenyl)-2,3-dihydro-1-benzoxepine-4-carboxamide (0.1 g), N-methylbenzylamine (0.05 ml) and potassium carbonate (0.1 g) in dimethylformamide (5 ml) was stirred at room temperature for 2 hours. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((N-benzyl-N-methyl)aminomethyl)phenyl)-7-(4-methylphenyl)-2,3-dihydro-1-benzoxepine-4-carboxamide (Compound 118) (0.09 g) as colorless crystals.

mp 157–158° C.; $^1$H-NMR($\delta$ ppm, CDCl$_3$): 2.18 (3H, s), 2.39 (3H, s), 3.06 (2H, t, J=4.6 Hz), 3.50 (2H, s), 3.52 (2H, s), 4.34 (2H, t, J=4.6 Hz), 7.05 (1H, d, J=8.0 Hz), 7.22–7.30 (3H, m), 7.33–7.37 (5H, m), 7.43–7.57 (7H, m), 7.63 (1H, s). IR(KBr) $\nu$: 3336, 1643 cm$^{-1}$. Anal. for C$_{33}$H$_{32}$N$_2$O$_2$.0.2H$_2$O: Calcd. C, 80.52; H, 6.63; N, 5.69. Found C, 80.61; H, 6.49; N, 5.54.

WORKING EXAMPLE 119 (Production of Compound 119)

A solution of N-(4-chloromethylphenyl)-7-(4-methylphenyl)-2,3-dihydro-1-benzoxepine-4-carboxamide (0.1 g) and diisopropylamine (0.1 ml) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((diisopropylamino)methyl)-phenyl)-7-(4-methylphenyl)-2,3-dihydro-1-benzoxepine-4-carboxamide (Compound 119) (0.11 g) as colorless crystals.

mp 152–153° C.; $^1$H-NMR($\delta$ ppm, CDCl$_3$): 1.02 (12H, d, J=6.6 Hz), 2.39 (3H, s), 2.98–3.10 (4H, m), 3.62 (2H, s), 4.35 (2H, t, J=4.8 Hz), 7.05 (1H, d, J=8.6 Hz), 7.24 (2H, d, J=8.0 Hz), 7.35–7.55 (9H, m). IR(KBr) $\nu$: 2964, 1646 cm$^{-1}$. Anal. for C$_{31}$H$_{36}$N$_2$O$_2$: Calcd. C, 79.45; H, 7.74; N, 5.98. Found C, 79.18: H, 7.66; N, 5.93.

WORKING EXAMPLE 120 (Production of Compound 120)

A solution of N-(4-chloromethylphenyl)-7-(4-methylphenyl)-2,3-dihydro-1-benzoxepine-4-carboxamide (0.1 g) and N-ethylcyclohexylamine (0.11 ml) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((N-cyclohexyl-N-ethyl)aminomethyl)phenyl)-7-(4-methylphenyl)-2,3-dihydro-1-benzoxepine-4-carboxamide (Compound 120) (0.1 g) as colorless crystals.

mp 166–167° C.; $^1$H-NMR($\delta$ ppm, CDCl$_3$): 0.98 (3H, t, J=7.2 Hz), 1.02–1.26 (6H, m), 1.60–1.80 (4H, m), 2.39 (3H, s), 2.48–2.59 (3H, m), 3.08 (2H, t, J=4.5 Hz), 3.59 (2H, s), 4.36 (2H, t, J=4.5 Hz), 7.05 (1H, d, J=8.4 Hz), 7.24 (2H, d, J=7.6 Hz), 7.35 (2H, d, J=8.4 Hz), 7.43–7.56 (7H, m). IR(KBr) $\nu$: 2929, 1648 cm$^{-1}$. Anal. for C$_{33}$H$_{38}$N$_2$O$_2$.0.2H$_2$O: Calcd. C, 79.55; H, 7.77; N, 5.62. Found C, 79.65; H, 7.63; N, 5.66.

WORKING EXAMPLE 121 (Production of Compound 121)

A suspension of N-(4-chloromethylphenyl)-7-(4-methylphenyl)-2,3-dihydro-1-benzoxepine-4-carboxamide (0.1 g), 4-ethyl-amino-1-benzylpiperidine (0.11 g) and potassium carbonate (0.05 g) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from diethyl ether-hexane to give N-(4-((N-(1-benzylpiperidin-4-yl)-N-ethyl)aminomethyl)phenyl)-7-(4-methylphenyl)-2,3-dihydro-1-benzoxepine-4-carboxamide (Compound 121) (0.13 g) as colorless crystals.

mp 121–122° C.; $^1$H-NMR($\delta$ ppm, CDCl$_3$): 0.98 (3H, t, J=7.1 Hz), 1.55–1.75 (4H, m), 1.87–2.00 (2H, m), 2.39 (3H, s), 2.49–2.60 (3H, m), 2.90–2.96 (2H, m), 3.08 (2H, t, J=4.4 Hz), 3.48 (2H, s), 3.60 (2H, s), 4.36 (2H, t, J=4.4 Hz), 7.06 (1H, d, J=8.2 Hz), 7.23–7.35 (9H, m), 7.44–7.55 (7H, m). IR(KBr) $\nu$: 2939, 1652 cm$^{-1}$. Anal. for C$_{39}$H$_{43}$N$_3$O$_2$: Calcd. C, 79.97; H, 7.40; N, 7.17. Found C, 79.95; H, 7.50; N, 7.28.

WORKING EXAMPLE 122 (Production of Compound 122)

A suspension of N-(4-chloromethylphenyl)-7-(4-methylphenyl)-2,3-dihydro-1-benzoxepine-4-carboxamide (0.1 g), amino-methylcyclohexane (0.05 g) and potassium carbonate (0.1 g) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/methanol/triethylamine) to give crude crystals, which were recrystallized from ethyl acetate-hexane to give N-(4-((cyclohexylmethyl)aminomethyl)phenyl)-7-(4-methylphenyl)-2,3-dihydro-1-benzoxepine-4-carboxamide (Compound 122) (0.06 g) as colorless crystals.

mp 154–155° C.; $^1$H-NMR($\delta$ ppm, CDCl$_3$): 0.88–0.99 (2H, m), 1.17–1.26 (4H, m), 1.43–1.56 (1H, m), 1.65–1.78 (4H, m), 2.39 (3H, s), 2.45 (2H, d, J=6.6 Hz), 3.07 (2H, t, J=4.5 Hz), 3.76 (2H, s), 4.35 (2H, t, J=4.5 Hz), 7.05 (1H, d, J=8.4 Hz), 7.22–7.33 (5H, m), 7.43–7.61 (6H, m). IR(KBr) $\nu$: 3357, 2918, 1648 cm$^{-1}$. Anal. for C$_{32}$H$_{36}$N$_2$O$_2$.0.2H$_2$O: Calcd. C, 79.37; H, 7.58; N, 5.78. Found C, 79.58; H, 7.50; N, 5.80.

WORKING EXAMPLE 123 (Production of Compound 123)

A solution of N-(4-chloromethylphenyl)-7-(4-methylphenyl)-2,3-dihydro-1-benzoxepine-4-carboxamide (0.1 g) and 1-methyl-4-methylaminopiperidine (0.1 ml) in dimethylformamide (5 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((N-methyl-N-(1-methylpiperidin-4-yl))aminomethyl)phenyl)-7-(4-methylphenyl)-2,3-dihydro-1-benzoxepine-4-carboxamide (Compound 123) (0.03 g) as colorless crystals.

mp 183–184° C.; $^1$H-NMR($\delta$ ppm, CDCl$_3$): 1.67–2.05 (6H, m), 2.20 (3H, s), 2.28 (3H, s), 2.39 (3H, s), 2.38–2.45 (1H, m), 2.91–2.96 (1H, m), 3.08 (2H, t, J=4.6 Hz), 3.56 (2H, s), 4.36 (2H, t, J=4.5 Hz), 7.06 (1H, d, J=8.0 Hz), 7.22–7.33 (4H, m), 7.44–7.59 (7H, m). IR(KBr) $\nu$: 2939, 2785, 1652 cm$^{-1}$. Anal. for C$_{32}$H$_{37}$N$_3$O$_2$: Calcd. C, 77.54; H, 7.52; N, 8.48. Found C, 77.34; H, 7.57; N, 8.56.

WORKING EXAMPLE 124 (Production of Compound 124)

To a solution of 7-(4-(4-methylpiperazin-1-yl)phenyl)-2,3-dihydro-1-benzoxepine-4-carboxylic acid (0.12 g), 4-(N-methyl-N-(tetrahydropyran-4-yl)aminomethyl)aniline (0.08 g) and 1-hydroxybenzotriazole(0.05 g) in dimethylformamide (15 ml) was added 1-ethyl-3-(3-dimethylaminopropyl) carbodiimide hydro-chloride (0.1 g), under ice-cooling. Under nitrogen atmosphere, the mixture was cooled to room temperature. To the mixture were added 4-dimethylaminopyridine (catalytic amount) and triethylamine (0.14 ml), and the mixture was stirred overnight. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/methanol/triethylamine) to give crude crystals, which were recrystallized from ethyl acetate-hexane to give 7-(4-(4-methylpiperazin-1-yl)phenyl)-N-(4-((N-tetrahydropyran-4-yl-N-methylamino)methyl)phenyl)-2,3-dihydro-1-benzoxepine-4-carboxamide (Compound 124) (0.15 g) as colorless crystals.

mp 220–221° C.; $^1$H -NMR($\delta$ ppm, CDCl$_3$): 1.64–1.75 (4H, m), 2.22 (3H, s), 2.37 (3H, s), 2.58–2.71 (5H, m), 3.08 (2H, t, J=4.6 Hz), 3.25–3.32 (4H, m), 3.37 (2H, dt, J=2.8, 11.4 Hz), 3.58 (2H, s), 4.01–4.07 (2H, m), 4.35 (2H, t, J=4.6 Hz), 6.97–7.06 (3H, m), 7.32 (2H, d, J=8.4 Hz), 7.41–7.58 (7H, m). IR(KBr) $\nu$: 2946, 2841, 1663 cm$^{-1}$. Anal. for C$_{35}$H$_{42}$N$_4$O$_3$.0.5H$_2$O: Calcd. C, 73.01; H, 7.53; N, 9.73. Found C, 73.25; H, 7.46; N, 9.72.

WORKING EXAMPLE 125 (Production of Compound 125)

A solution of N-(4-((N-(1-t-butoxycarbonylpiperidin-4-yl)-N-methylamino)methyl)phenyl)-7-(4-methylphenyl)-2,3-dihydro-1-benzoxepine-4-carboxamide (0.14 g) and trifluoro-acetic acid (5 ml) in dichloromethane (20 ml) was stirred at room temperature for 1.5 hours. The reaction mixture was neutralized with sodium hydrogen carbonate solution, and the solvent was evaporated. To the residue was added water, and the mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethanol-hexane to give N-(4-((N-methyl-N-(piperidin-4-yl))aminomethyl)phenyl)-7-(4-methylphenyl)-2,3-dihydro-1-benzoxepine-4-carboxamide (Compound 125) (0.08 g) as colorless crystals.

mp 129–130° C.; $^1$H-NMR($\delta$ ppm, CDCl$_3$): 1.68–1.95 (4H, m), 2.22 (3H, s), 2.39 (3H, s), 2.61–2.79 (3H, m), 3.08 (2H, t, J=4.5 Hz), 3.25–3.33 (2H, m), 3.58 (2H, s), 4.36 (2H, t, J=4.5 Hz), 7.06 (1H, d, J=8.4 Hz), 7.23–7.33 (4H, m), 7.44–7.60 (7H, m). IR(KBr) $\nu$: 2929, 1683 cm$^{-1}$.

WORKING EXAMPLE 126 (Production of Compound 126) and

WORKING EXAMPLE 127 (Production of Compound 127)

A suspension of N-(4-chloromethylphenyl)-7-(4-methylphenyl)-2,3-dihydro-1-benzoxepine-4-carboxamide (0.1 g), N,4-dimethylcyclohexylamine hydrochloride (0.08 g) and potassium carbonate (0.17 g) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate)to give each of crude crystals, which was recrystallized from ethyl acetate-hexane to give each isomer of N-(4-((N-methyl-N-(4-methylcyclohexyl))amino-methyl)phenyl)-7-(4-methylphenyl)-2,3-dihydro-1-benzoxepine-4-carboxamide (Compound 126 (0.05 g), Compound 127(0.03 g)) as colorless crystals.

(Compound 126):

mp 144–145° C.; $^1$H-NMR($\delta$ ppm, CDCl$_3$): 0.96 (3H, d, J=6.8 Hz), 1.40–1.80 (9H, m), 2.17 (3H, s), 2.20–2.40 (1H, m), 2.39 (3H, s), 3.08 (2H, t, J=4.5 Hz), 3.55 (2H, s), 4.36 (2H, t, J=4.5 Hz), 7.05 (1H, d, J=8.4 Hz), 7.22–7.34 (4H, m), 7.43–7.58 (7H, m). IR(KBr) $\nu$: 2927, 1650 cm$^{-1}$. Anal. for C$_{33}$H$_{36}$N$_2$O$_2$.0.2H$_2$O: Calcd. C, 79.55; H, 7.77; N, 5.62. Found C, 79.59; H, 7.68; N, 5.84.

(Compound 127):

mp 183–184° C.; $^1$H-NMR($\delta$ ppm, CDCl$_3$): 0.87 (3H, d, J=6.6 Hz), 0.89–1.02 (2H, m), 1.26–1.89 (7H, m), 2.20 (3H, s), 2.20–2.40 (1H, m), 2.39 (3H, s), 3.08 (2H, t, J=4.6 Hz), 3.56 (2H, s), 4.36 (2H, t, J=4.6 Hz), 7.06 (1H, d, J=8.4 Hz), 7.22–7.34 (5H, m), 7.44–7.55 (6H, m). IR(KBr) $\nu$: 2925, 1654 cm$^{-1}$. Anal. for C$_{33}$H$_{38}$N$_2$O$_2$.0.2H$_2$O: Calcd. C, 79.55; H, 7.77; N, 5.62. Found C, 79.48; H, 7.70; N, 5.83.

WORKING EXAMPLE 128 (Production of Compound 128)

To a suspension of 7-(4-methylphenyl)-2,3-dihydro-1-benzoxepine-4-carboxylic acid (0.15 g) in dichloromethane (7 ml) were added oxalyl chloride (0.14 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-(N-methyl-N-(tetrahydropyran-4-yl) aminomethyl)aniline (0.12 g) and triethylamine (0.23 ml) in tetrahydrofuran (10 ml), underice-cooling. Undernitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-(N-methyl-(N-tetrahydropyran-4-yl)aminomethyl)phenyl)-7-(4-methylphenyl)-2,3-dihydro-1-benzoxepine-4-carboxamide (Compound 128) (0.19 g) as colorless crystals.

mp 162–163° C.; $^1$H-NMR($\delta$ ppm, CDCl$_3$): 1.59–1.74 (4H, m), 2.20 (3H, s), 2.39 (3H, s), 2.58–2.66 (1H, m), 3.07 (2H, t, J=4.5 Hz), 3.37 (2H, dt, J=2.8, 11.0 Hz), 3.56 (2H, s), 4.01–4.06 (2H, m), 4.35 (2H, t, J=4.5 Hz), 7.05 (1H, d, J=8.4 Hz), 7.22–7.33 (4H, m), 7.43–7.56 (6H, m), 7.62 (1H, s). IR(KBr) $\nu$: 3296, 2950, 1654 cm$^{-1}$. Anal. for C$_{31}$H$_{34}$N$_2$O$_3$.0.2H$_2$O: Calcd. C, 76.58; H, 7.13; N, 5.76. Found C, 76.51; H, 7.07; N, 5.53.

WORKING EXAMPLE 129 (Production of Compound 129)

To a suspension of 7-(4-methylphenyl)-2,3-dihydro-1-benzoxepine-4-carboxylic acid (0.15 g) in dichloromethane (5 ml) were added oxalyl chloride (0.14 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-(N-methyl-N-(tetrahydropyran-3-yl) aminomethyl)aniline (0.13 g) and triethylamine (0.23 ml) in tetrahydrofuran (10 ml), under ice-cooling, and the mixture was stirred under nitrogen atmosphere at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate) to give crude crystals, which were recrystallized from ethyl acetate-hexane to give N-(4-((N-tetrahydropyran-3-yl-N-methyl)aminomethyl)-phenyl)-7-(4-methylphenyl)-2,3-dihydro-1-benzoxepine-4-carboxamide (Compound 129) (0.18 g) as colorless crystals.

mp 158–159° C.; $^1$H-NMR($\delta$ ppm, CDCl$_3$): 1.57–1.75 (3H, m), 2.00–2.05 (1H, m), 2.21 (3H, s), 2.39 (3H, s), 2.55–2.68 (1H, m), 3.08 (2H, t, J=4.7 Hz), 3.22–3.39 (2H, m), 3.59 (2H, s), 3.84–3.90 (1H, m), 4.04–4.07 (1H, m), 4.37 (2H, t, J=4.7 Hz), 7.06 (1H, d, J=8.0 Hz), 7.23–7.32 (4H, m), 7.44–7.55 (7H, m). IR(KBr) $\nu$: 2941, 1652 cm$^{-1}$. Anal. for C$_{31}$H$_{34}$N$_2$O$_3$: Calcd. C, 77.15; H, 7.10; N, 5.80. Found C, 77.12; H, 7.02; N, 5.88.

WORKING EXAMPLE 130 (Production of Compound 130)

To a suspension of 7-(4-methylphenyl)-2,3-dihydro-1-benzoxepine-4-carboxylic acid (0.15 g) in dichloromethane (7 ml) were added oxalyl chloride (0.14 ml) and dimethylformamide (catalytic amount), under ice-cooling, and the mixture was stirred at room temperature for 2 hours. The solvent was evaporated, and the residue was dissolved in tetrahydrofuran. The mixture was dropwise added to a solution of 4-((N-indan-2-yl-N-methyl)aminomethyl)aniline (0.14 g) and triethyl-amine (0.23 ml) in tetrahydrofuran (15 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-ethanol-hexane to give N-(4-((N-indan-2-yl-N-methyl) amino-methyl)phenyl)-7-(4-methylphenyl)-2,3-dihydro-1-benzoxepine-4-carboxamide (Compound 130) (0.23 g) as colorless crystals.

mp 204–205° C.; $^1$H-NMR($\delta$ ppm, CDCl$_3$): 2.19 (3H, s), 2.39 (3H, s), 2.94–3.18 (6H, m), 3.41–3.48 (1H, m), 3.57 (2H, s), 4.36 (2H, t, J=4.7 Hz), 7.06 (1H, d, J=8.4 Hz), 7.16–7.22 (6H, m), 7.33–7.57 (9H, m). IR(KBr) $\nu$: 1654 cm$^{-1}$. Anal. for $C_{35}H_{34}N_2O_2 \cdot 0.2H_2O$: Calcd. C, 81.11; H, 6.69; N, 5.41. Found C, 81.06; H, 6.57; N, 5.49.

WORKING EXAMPLE 131 (Production of Compound 131)

To a suspension of 7-(4-methylphenyl)-2,3-dihydro-1-benzoxepine-4-carboxylic acid (0.15 g) in dichloromethane (6 ml) were added oxalyl chloride (0.14 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of (E)-4-((N-4-t-butylcyclohexyl-N-methyl)aminomethyl)aniline (0.15 g) and triethylamine (0.23 ml) in tetrahydrofuran (10 ml), under ice-cooling. Undernitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give (E)-N-(4-((N-(4-t-butylcyclohexyl)-N-methyl)aminomethyl)phenyl)-7-(4-methylphenyl)-2,3-dihydro-1-benzoxepine-4-carboxamide (Compound 131) (0.22 g) as colorless crystals.

mp 225–226° C.; $^1$H-NMR($\delta$ ppm, CDCl$_3$): 0.84 (9H, s), 0.95–1.05 (2H, m), 1.22–1.33 (2H, m), 1.82–1.95 (5H, m), 2.20 (3H, s), 2.30–2.45 (1H, m), 2.39 (3H, s), 3.08 (2H, t, J=4.6 Hz), 3.55 (2H, s), 4.36 (2H, t, J=4.6 Hz), 7.06 (1H, d, J=8.0 Hz), 7.22–7.34 (4H, m), 7.44–7.55 (7H, m). IR(KBr) v: 2943, 1652 cm$^{-1}$. Anal. for $C_{36}H_{44}N_2O_2$: Calcd. C, 80.56; H, 8.26; N, 5.22. Found C, 80.30; H, 8.42; N, 5.32.

WORKING EXAMPLE 132 (Production of Compound 132)

To a suspension of 7-(4-methylphenyl)-2,3-dihydro-1-benzoxepine-4-carboxylic acid (0.15 g) in dichloromethane (6 ml) were added oxalyl chloride (0.14 ml) and dimethylformamide (catalytic amount), under ice-cooling, and the mixture was stirred at room temperature for 2 hours. The solvent was evaporated, and the residue was dissolved in tetrahydrofuran. The mixture was dropwise added to a solution of (Z)-4-((N-4-t-butylcyclohexyl-N-methyl)aminomethyl)aniline (0.15 g) and triethylamine (0.23 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from diethyl ether-hexane to give (Z)-N-(4-((N-(4-t-butylcyclohexyl)-N-methyl)aminomethyl)phenyl)-7-(4-methylphenyl)-2,3-dihydro-1-benzoxepine-4-carboxamide (Compound 132) (0.2 g) as colorless crystals.

mp 169–170° C.; $^1$H-NMR($\delta$ ppm, CDCl$_3$): 0.89 (9H, s), 1.05–1.20 (1H, m), 1.36–1.50 (6H, m), 2.06 (3H, s), 2.06–2.14 (2H, m), 2.30–2.32 (1H, m), 2.39 (3H, s), 3.09 (2H, t, J=4.8 Hz), 3.50 (2H, s), 4.37 (2H, t, J=4.8 Hz), 7.06 (1H, d, J=8.4 Hz), 7.23–7.35 (4H, m), 7.44–7.54 (7H, m). IR(KBr) v: 2941, 1648 cm$^{-1}$. Anal. for $C_{36}H_{44}N_2O_2 \cdot 0.2H_2O$: Calcd. C, 80.02; H, 8.28; N, 5.18. Found C, 80.23; H, 8.30; N, 5.22.

WORKING EXAMPLE 133 (Production of Compound 133)

To a suspension of 7-(4-methylphenyl)-2,3-dihydro-1-benzoxepine-4-carboxylic acid (0.15 g) in dichloromethane (6 ml) were added oxalyl chloride (0.14 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-((N-(3,5-dimethylcyclohexyl)-N-methyl)aminomethyl)aniline (0.13 g) and triethylamine (0.23 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from diethyl ether-hexane to give N-(4-((N-methyl-N-(3,5-dimethylcyclohexyl))aminomethyl)phenyl)-7-(4-methylphenyl)-2,3-dihydro-1-benzoxepine-4-carboxamide (Compound 133) (0.22 g) as colorless crystals.

mp 135–136° C.; $^1$H-NMR($\delta$ ppm, CDCl$_3$): 0.45–0.68 (1H, m), 0.84 (3H, s), 0.87 (3H, s), 0.96–1.03 (2H, m), 1.65–2.05 (5H, m), 2.06 (3H, s), 2.39 (3H, s), 2.39–2.42 (1H, m), 3.08 (2H, t, J=4.7 Hz), 3.50 (2H, s), 4.36 (2H, t, J=4.7 Hz), 7.06 (1H, d, J=8.4 Hz), 7.16–7.32 (4H, m), 7.44–7.54 (7H, m). IR(KBr) v: 2947, 1652 cm$^{-1}$. Anal. for $C_{34}H_{40}N_2O_2$: Calcd. C, 80.28; H, 7.93; N, 5.51. Found C, 80.19; H, 7.95; N, 5.54.

WORKING EXAMPLE 134 (Production of Compound 134)

To a suspension of 7-(4-methylphenyl)-2,3-dihydro-1-benzoxepine-4-carboxylic acid (0.15 g) in dichloromethane (6 ml) were added oxalyl chloride (0.14 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-((N-(3,5-dimethylcyclohexyl)-N-methyl)aminomethyl)aniline (0.13 g) and triethylamine (0.23 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((N-methyl-N-(3,5-dimethylcyclohexyl))aminomethyl)phenyl)-7-(4-methylphenyl)-2,3-dihydro-1-benzoxepine-4-carboxamide (Compound 134) (0.2 g) as colorless crystals.

mp 173–174° C.; $^1$H-NMR($\delta$ppm, CDCl$_3$): 0.43–0.60 (1H, m), 0.81–0.99 (2H, m), 0.91 (3H, s), 0.95 (3H, s), 1.30–1.58 (3H, m), 1.79–1.84 (2H, m), 2.19 (3H, s), 2.39 (3H, s), 2.48–2.60 (1H, m), 3.08 (2H, t, J=4.6 Hz), 3.55 (2H, s), 4.36 (2H, t, J=4.6 Hz), 7.06 (1H, d, J=8.4 Hz), 7.22–7.33 (4H, m), 7.44–7.55 (7H, m). IR(KBr) v: 2950, 1652 cm$^{-1}$. Anal. for $C_{34}H_{40}N_2O_2 \cdot 0.2H_2O$: Calcd. C, 79.71; H, 7.95; N, 5.47. Found C, 79.83; H, 7.83; N, 5.54.

WORKING EXAMPLE 135 (Production of Compound 135)

To a suspension of 7-(4-methylphenyl)-2,3-dihydro-1-benzoxepine-4-carboxylic acid (0.12 g) in dichloromethane (5 ml) were added oxalyl chloride (0.11 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-((N-(3,5-dimethylcyclohexyl)-N-methyl)aminomethyl)aniline (0.1 g) and triethylamine (0.17 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate) to give crude crystals, which were recrystallized from diethyl ether-hexane to give N-(4-((N-methyl-N-(3,5-dimethylcyclohexyl))aminomethyl)phenyl)-7-(4-methylphenyl)-2,3-dihydro-1-benzoxepine-4-carboxamide (Compound 135) (0.08 g) as pale yellow crystals.

mp 99–100° C.; $^1$H-NMR($\delta$ ppm, CDCl$_3$): 0.82–1.13 (8H, m), 1.40–1.53 (2H, m), 1.64–1.85 (3H, m), 2.08–2.18 (1H, m), 2.18 (3H, s), 2.39 (3H, s), 2.69–2.81 (1H, m), 3.08 (2H, t, J=4.8 Hz), 3.54 (2H,s), 4.35 (2H, t, J=4.8 Hz), 7.05 (1H, d, J=8.2 Hz), 7.22–7.33 (4H, m), 7.43–7.58 (7H, m). IR(KBr) $\nu$: 2923, 1652 cm$^{-1}$. Anal. for C$_{34}$H$_{40}$N$_2$O$_2$.0.5H$_2$O: Calcd. C, 78.88; H, 7.98; N, 5.41. Found C, 78.88; H, 7.74; N, 5.50.

WORKING EXAMPLE 136 (Production of Compound 136)

To a suspension of 7-(4-methylphenyl)-2,3-dihydro-1-benzoxepine-4-carboxylic acid (0.15 g) in dichloromethane (5 ml) were added oxalyl chloride (0.14 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-((N-methyl-N-n-propyl)aminomethyl)aniline (0.1 g) and triethylamine (0.23 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/methanol/triethylamine) to give crude crystals, which were recrystallized from diethyl ether-hexane to give N-(4-((N-methyl-N-n-propyl)aminomethyl)phenyl)-7-(4-methylphenyl)-2,3-dihydro-1-benzoxepine-4-carboxamide (Compound 136) (0.1 g) as colorless crystals.

mp 142–143° C.; $^1$H-NMR($\delta$ ppm, CDCl$_3$): 0.90 (3H, t, J=7.3 Hz), 1.48–1.59 (2H, m), 2.19 (3H, s), 2.29–2.37 (2H, m), 2.39 (3H, s), 3.08 (2H, t, J=4.4 Hz), 3.47 (2H, s), 4.36 (2H, t, J=4.4 Hz), 7.06 (2H, d, J=8.4 Hz), 7.22–7.33 (4H, m), 7.43–7.57 (7H, m). IR(KBr) $\nu$: 2962, 1652, 1517 cm$^{-1}$. Anal. for C$_{29}$H$_{32}$N$_2$O$_2$.0.2 H$_2$O: Calcd. C, 78.42; H, 7.35; N, 6.31. Found C, 78.41; H, 7.21; N, 6.26.

WORKING EXAMPLE 137 (Production of Compound 137)

A solution of N-(4-chloromethylphenyl)-7-(4-methylphenyl)-2,3-dihydro-1-benzoxepine-4-carboxamide (0.1 g) and N-methyl-n-butylamine (0.06 g) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((N-n-butyl-N-methyl)aminomethyl)phenyl)-7-(4-methylphenyl)-2,3-dihydro-1-benzoxepine-4-carboxamide (Compound 137) (0.09 g) as colorless crystals.

mp 138–139° C.; $^1$H-NMR($\delta$ ppm, CDCl$_3$): 0.91 (3H, t, J=7.2 Hz), 1.27–1.55 (4H, m), 2.19 (3H, s), 2.33–2.39 (2H, m), 2.39 (3H, s), 3.08 (2H, t, J=4.5 Hz), 3.47 (2H, s), 4.36 (2H, t, J=4.5 Hz), 7.06 (1H, d, J=8.2 Hz), 7.22–7.33 (4H, m), 7.44–7.58 (7H, m). IR(KBr) $\nu$: 2956, 2931, 1652 cm$^{-1}$. Anal. for C$_{30}$H$_{34}$N$_2$O$_2$.0.2H$_2$O: Calcd. C, 78.64; H, 7.57; N, 6.11. Found C, 78.83; H, 7.44; N, 6.19.

WORKING EXAMPLE 138 (Production of Compound 138)

To a suspension of 7-(4-methylphenyl)-2,3-dihydro-1-benzoxepine-4-carboxylic acid (0.15 g) in dichloromethane (5 ml) were added oxalyl chloride (0.14 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-((N-isopropyl-N-methyl)aminomethyl)aniline (0.1 g) and triethylamine (0.23 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((N-isopropyl-N-methyl)-aminomethyl)phenyl)-7-(4-methylphenyl)-2,3-dihydro-1-benzoxepine-4-carboxamide (Compound 138) (0.18 g) as colorless crystals.

mp 181–182° C.; $^1$H-NMR($\delta$ ppm, CDCl$_3$): 1.07 (6H, d, J=6.6 Hz), 2.15 (3H, s), 2.39 (3H, s), 2.83–2.96 (1H, m), 3.08 (2H, t, J=4.7 Hz), 3.49 (2H, s), 4.36 (2H, t, J=4.7 Hz), 7.06 (1H, d, J=8.4 Hz), 7.22–7.34 (4H, m), 7.44–7.55 (7H, m). IR(KBr) $\nu$: 2968, 1652 cm$^{-1}$. Anal. for C$_{29}$H$_{32}$N$_2$O$_2$: Calcd. C, 79.06; H, 7.32; N, 6.36. Found C, 78.87; H, 7.30; N, 6.33.

WORKING EXAMPLE 139 (Production of Compound 139)

To a suspension of 7-(4-methylphenyl)-2,3-dihydro-1-benzoxepine-4-carboxylic acid (0.15 g) in dichloromethane (5 ml) were added oxalyl chloride (0.14 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-((N-sec-butyl-N-methyl)aminomethyl)aniline (0.12 g) and triethylamine (0.23 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate.

Under reduced pressure, the solvent was evaporated, and the residue was purified with silica gel column (ethyl acetate) to give crude crystals, which were recrystallized from ethyl acetate-hexane to give N-(4-((N-sec-butyl-N-methyl) aminomethyl)phenyl)-7-(4-methylphenyl)-2,3-dihydro-1-benzoxepine-4-carboxamide (Compound 139) (0.12 g) as colorless crystals.

mp 152–153° C.; $^1$H-NMR($\delta$ ppm, CDCl$_3$): 0.89–1.01 (6H, m), 1.22–1.39 (1H, m), 1.50–1.67 (1H, m), 2.13 (3H, s), 2.39 (3H, s), 2.54–2.65 (1H, m), 3.08 (2H, t, J=4.7 Hz), 3.44 (1H, d, J=13.2 Hz), 3.56 (1H, d, J=13.2 Hz), 4.36 (2H, t, J=4.7 Hz), 7.06 (2H, d, J=8.0 Hz), 7.22–7.35 (4H, m), 7.44–7.54 (7H, m). IR(neat) v: 2964, 1652 cm$^{-1}$. Anal. for C$_{30}$H$_{34}$N$_2$O$_2$·0.2H$_2$O: Calcd. C, 78.64; H, 7.57; N, 6.11. Found C, 78.88; H, 7.39; N, 6.16.

WORKING EXAMPLE 140 (Production of Compound 140)

A solution of N-(4-chloromethylphenyl)-7-(4-methylphenyl)-2,3-dihydro-1-benzoxepine-4-carboxamide (0.1 g) and N-methylisobutylamine (0.06 g) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((N-isobutyl-N-methyl) aminomethyl)phenyl)-7-(4-methyl-phenyl)-2,3-dihydro-1-benzoxepine-4-carboxamide (Compound 140) (0.08 g) as colorless crystals.

mp 137–138° C.; $^1$H-NMR($\delta$ ppm, CDCl$_3$): 0.90 (6H, d, J=6.6 Hz), 1.78–1.88 (1H, m), 2.10 (2H, d, J=7.4 Hz), 2.16 (3H, s), 2.39 (3H, s), 3.08 (2H, t, J=4.6 Hz), 3.44 (2H, s), 4.36 (2H, t, J=4.6 Hz), 7.06 (1H, d, J=8.0 Hz), 7.23–7.34 (4H,m), 7.44–7.57 (7H, m). IR(KBr) v: 2954, 1652 cm$^{-1}$. Anal. for C$_{30}$H$_{34}$N$_2$O$_2$: Calcd. C, 79.26; H, 7.54; N, 6.16. Found C, 78.99; H, 7.38; N, 6.21.

WORKING EXAMPLE 141 (Production of Compound 141)

To a suspension of 7-(4-methylphenyl)-2,3-dihydro-1-benzoxepine-4-carboxylic acid (0.1 g) in dichloromethane (5 ml) were added oxalyl chloride (0.1 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-((N-t-butyl-N-methyl)amino-methyl)aniline (0.08 g) and triethylamine (0.12 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((N-t-butyl-N-methyl)amino-methyl) phenyl)-7-(4-methylphenyl)-2,3-dihydro-1-benzoxepine-4-carboxamide (Compound 141) (0.12 g) as colorless crystals.

mp 122–123° C.; $^1$H-NMR($\delta$ ppm, CDCl$_3$): 1.16 (9H, s), 2.09 (3H, s), 2.39 (3H, s), 3.08 (2H, t, J=4.7 Hz), 3.49 (2H, s), 4.36 (2H, t, J=4.7 Hz), 7.06 (1H, d, J=8.4 Hz), 7.23–7.36 (4H, m), 7.44–7.54 (7H, m). IR(KBr) v: 2971, 1651, 1599, 1516 cm$^{-1}$. Anal. for C$_{30}$H$_{34}$N$_2$O$_2$: Calcd. C, 79.26; H, 7.54; N, 6.16. Found C, 79.16; H, 7.55; N, 5.98.

WORKING EXAMPLE 142 (Production of Compound 142)

To a suspension of 7-(4-methylphenyl)-2,3-dihydro-1-benzoxepine-4-carboxylic acid (0.1 g) in dichloromethane (5 ml) were added oxalyl chloride (0.1 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-((N-methyl-N-(pentan-3-yl))aminomethyl) aniline (0.08 g) and triethylamine (0.12 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((N-methyl-N-(pentan-3-yl))aminomethyl)phenyl)-7-(4-methylphenyl)-2,3-dihydro-1-benzoxepine-4-carboxamide (Compound 142) (0.12 g) as colorless crystals.

mp 133–134° C.; $^1$H-NMR($\delta$ ppm, CDCl$_3$): 0.94 (6H, t, J=7.5 Hz), 1.26–1.53 (4H, m), 2.13 (3H, s), 2.24–2.31 (1H, m), 2.40 (3H, s), 3.09 (2H, t, J=4.4 Hz), 3.55 (2H, s), 4.37 (2H, t, J=4.4 Hz), 7.06 (1H, d, J=8.4 Hz), 7.17–7.36 (4H, m), 7.44–7.54 (7H, m). IR(KBr) v: 2930, 1649, 1597, 1518 cm$^{-1}$. Anal. for C$_{31}$H$_{36}$N$_2$O$_2$: Calcd. C, 79.45; H, 7.74; N, 5.98. Found C, 79.06; H, 7.56; N, 5.98.

WORKING EXAMPLE 143 (Production of Compound 143)

To a suspension of 7-(4-methylphenyl)-2,3-dihydro-1-benzoxepine-4-carboxylic acid (0.1 g) in dichloromethane (5 ml) were added oxalyl chloride (0.1 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-((N-methyl-N-(norbornan-2-yl))aminomethyl) aniline (0.09 g) and triethylamine (0.12 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane). The purified product was dissolved in ethyl acetate (10 ml), and to the mixture was added 4N hydrochloric acid-ethyl acetate solution (0.2 ml) under ice-cooling. The solvent was evaporated to give crude crystals, which were recrystallized from ethanol-hexane to give N-(4-((N-methyl-N-(norbornan-2-yl))aminomethyl)-phenyl)-7-(4-methylphenyl)-2,3-dihydro-1-benzoxepine-4-carboxamide hydrochloride (Compound 143) (0.16 g) as colorless crystals.

mp 268–269° C.(dec.).; $^1$H-NMR($\delta$ ppm, DMSO-d$_6$): 1.24–1.55 (6H, m), 1.99–2.15 (3H, m), 2.28 (1H, br), 2.34 (3H, s), 2.51–2.63 (3H, m), 2.82 (1H, br), 3.00 (2H, br), 4.04–4.45 (4H, m), 7.06 (1H, d, J=8.4 Hz), 7.33 (2H, d, J=7.8 Hz), 7.38 (1H, s), 7.48–7.59 (5H, m), 7.75–7.85 (3H, m), 9.52 (0.5H, br), 9.83 (0.5H, br), 10.18 (1H, s). IR(KBr) v: 2957, 2492, 1661 cm$^{-1}$. Anal. for $C_{33}H_{37}ClN_2O_2 \cdot 0.2H_2O$: Calcd. C, 74.40; H, 7.08; N, 5.26. Found C, 74.34; H, 7.05; N, 5.19.

WORKING EXAMPLE 144 (Production of Compound 144)

To a suspension of 7-(4-methylphenyl)-2,3-dihydro-1-benzoxepine-4-carboxylic acid (0.15 g) in dichloromethane (5 ml) were added oxalyl chloride (0.14 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-(2-(N-cyclohexyl-N-methyl)aminoethyl) aniline (0.15 g) and triethylamine (0.23 ml) in tetrahydrofuran (15 ml),underice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-(2-((N-cyclohexyl-N-methyl)amino) ethyl)phenyl)-7-(4-methylphenyl)-2,3-dihydro-1-benzoxepine-4-carboxamide (Compound 144) (0.23 g) as colorless crystals.

mp 154–155° C.; $^1$H-NMR($\delta$ ppm, CDCl$_3$): 1.18–1.30 (6H, m), 1.65–1.80 (4H, m), 2.35 (3H, s), 2.39 (3H, s), 2.39–2.50 (1H, m), 2.66–2.73 (4H, m), 3.08 (2H, t, J=4.6 Hz), 4.36 (2H, t, J=4.6 Hz), 7.06 (1H, d, J=8.4 Hz), 7.18–7.26 (4H, m), 7.44–7.55 (7H, m). IR(KBr) v: 2929, 2854, 1648 cm$^{-1}$. Anal. for $C_{33}H_{38}N_2O_2 \cdot 0.3H_2O$: Calcd. C, 79.26; H, 7.78; N, 5.60. Found C, 79.26; H, 7.48; N, 5.62.

WORKING EXAMPLE 145 (Production of Compound 145)

To a suspension of 7-(4-methylphenyl)-2,3-dihydro-1-benzoxepine-4-carboxylic acid (0.1 g) in dichloromethane (5 ml) were added oxalyl chloride (0.1 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-(1-hydroxy-2-piperidino-ethyl)aniline (0.09 g) and triethylamine (0.12 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-(1-hydroxy-2-piperidinoethyl)phenyl)-7-(4-methylphenyl)-2,3-dihydro-1-benzoxepine-4-carboxamide (Compound 145) (0.14 g) as colorless crystals.

mp 212–213° C.; $^1$H-NMR($\delta$ ppm, CDCl$_3$): 1.44–1.52 (2H, m), 1.56–1.69 (4H, m), 2.32–2.47 (4H, m), 2.40 (3H, s), 2.65–2.74 (2H, m), 3.08 (2H, t, J=4.5 Hz), 4.37 (2H, t, J=4.5 Hz), 4.72 (1H, dd, J=3.8, 10.0 Hz), 7.06 (1H, d, J=8.4 Hz), 7.25 (2H, d, J=7.4 Hz), 7.35–7.59 (9H, m). IR(KBr) v: 2936, 1651, 1520 cm$^{-1}$. Anal. for $C_{31}H_{34}N_2O_3$: Calcd. C, 77.15; H, 7.10; N, 5.80. Found C, 76.95; H, 7.34; N, 5.69.

WORKING EXAMPLE 146 (Production of Compound 146)

To a solution of 7-(3-pyridyl)-2,3-dihydro-1-benzoxepine-4-carboxylic acid (0.15 g), 4-(N-methyl-N-(tetra-hydropyran-4-yl)aminomethyl)aniline (0.12 g) and triethylamine (0.16 ml) in dimethylformamide (50 ml) was added diethyl cyano-phosphate (0.1 ml) under ice-cooling, and the mixture was stirred under nitrogen atmosphere at room temperature over night. The solvent was evaporated, and the residue was purified with silica gel column (methanol/ethyl acetate/triethylamine) to give crude crystals, which were recrystallized from ethanol-hexane to give 7-(3-pyridyl)-N-(4-((N-tetrahydropyran-4-yl-N-methylamino)-methyl)phenyl)-2,3-dihydro-1-benzoxepine-4-carboxamide (Compound 146) (0.06 g) as colorless crystals.

mp 158–159° C.; $^1$H-NMR($\delta$ ppm, CDCl$_3$): 1.64–1.71 (4H, m), 2.23 (3H, s), 2.65–2.75 (1H, m), 3.11 (2H, t, J=4.8 Hz), 3.37 (2H, dt, J=2.4, 11.0 Hz), 3.60 (2H, s), 4.01–4.07 (2H, m), 4.38 (2H, t, J=4.8 Hz), 7.12 (1H, d, J=8.4 Hz), 7.31–7.40 (3H, m), 7.44–7.58 (4H, m), 7.66 (1H, br), 7.84 (1H, d, J=7.6 Hz), 8.58 (1H, d, J=4.8 Hz), 8.82 (1H, d, J=2.2 Hz). IR(KBr) v: 2949, 2845, 1661 cm$^{-1}$. Anal. for $C_{29}H_{31}N_3O_3 \cdot 0.5H_2O$: Calcd. C, 72.78; H, 6.74; N, 8.78. Found C, 72.72; H, 6.72; N, 8.95.

WORKING EXAMPLE 147 (Production of Compound 147)

To a solution of 7-(4-pyridyl)-2,3-dihydro-1-benzoxepine-4-carboxylic acid (0.15 g), 4-(N-methyl-N-(tetrahydropyran-4-yl)aminomethyl)aniline (0.12 g) and triethylamine (0.16 ml) in dimethylformamide (50 ml) was added diethyl cyano-phosphate (O.1 ml) under ice-cooling, and the mixture was stirred under nitrogen atmosphere at room temperature over night. The solvent was evaporated, and the residue was purified with silica gel column (methanol/ethyl acetate/triethylamine) to give crude crystals, which were recrystallized from ethanol-hexane to give 7-(4-pyridyl)-N-(4-((N-tetrahydropyran-4-yl-N-methylamino)methyl)phenyl)-2,3-dihydro-1-benzoxepine-4-carboxamide (Compound 147) (0.07 g) as pale brown crystals.

mp 186–187° C.; $^1$H-NMR($\delta$ ppm, CDCl$_3$): 1.67–1.73 (4H, m), 2.23 (3H, s), 2.60–2.75 (1H, m), 3.11 (2H, t, J=4.6 Hz), 3.37 (2H, dt, J=3.0, 11.0 Hz), 3.60 (2H, s), 4.01–4.07 (2H, m), 4.38 (2H, t, J=4.6 Hz), 7.12 (1H, d, J=8.0 Hz), 7.34 (2H, d, J=8.4 Hz), 7.45–7.51 (3H, m), 7.55–7.59 (3H, m), 7.82 (1H, br), 8.64 (2H, d, J=5.8 Hz). IR(KBr) v: 2948, 1659 cm$^{-1}$. Anal. for $C_{29}H_{31}N_3O_3 \cdot 0.5H_2O$: Calcd. C, 72.78; H, 6.74; N, 8.78. Found C, 72.64; H, 6.51; N, 8.85.

WORKING EXAMPLE 148 (Production of Compound 148)

To a solution of 7-(2-furyl)-2,3-dihydro-1-benzoxepine-4-carboxylic acid (0.15 g), 4-(N-methyl-N-(tetrahydropyran-4-yl)aminomethyl)aniline (0.15 g) and triethylamine (0.25 ml) in dimethylformamide (10 ml) was added diethyl cyanophosphate (0.13 ml) under ice-cooling, and the mixture was stirred under nitrogen atmosphere at room temperature over night. The solvent was evaporated, and the residue was purified with silica gel column (methanol/ethyl acetate/triethylamine) to give crude crystals, which were recrystallized from ethyl acetatehexane to give 7-(2-furyl)-N-(4-((N-tetrahydropyran-4-yl-N-methylamino)methyl)phenyl)-2,3-dihydro-1-benzoxepine-4-carboxamide (Compound 148) (0.1 g) as brown crystals.

mp 166–167° C.(dec.).; ¹H-NMR(δ ppm, CDCl₃): 1.64–1.78 (4H, m), 2.22 (3H, s), 2.60–2.75 (1H, m), 3.06 (2H, t, J=4.6 Hz), 3.37 (2H, dt, J=3.0, 11.1 Hz), 3.59 (2H, s), 4.02–4.07 (2H, m), 4.33 (2H, t, J=4.6 Hz), 6.46 (1H, dd, J=1.8, 3.3 Hz), 6.56 (1H, d, J=3.3 Hz), 7.01 (2H, d, J=8.4 Hz), 7.21 (1H, s), 7.32 (2H, d, J=8.6 Hz), 7.44 (1H, d, J=1.8 Hz), 7.50–7.62 (4H, m), 7.73 (1H, s). IR(KBr) v: 2951, 1659 cm⁻¹. Anal. for $C_{28}H_{30}N_2O_4 \cdot 0.5H_2O$: Calcd. C, 71.93; H, 6.68; N, 5.99. Found C, 71.97; H, 6.52; N, 6.08.

WORKING EXAMPLE 149 (Production of Compound 149)

To a solution of 7-(4-dimethylaminophenyl)-2,3-dihydro-1-benzoxepine-4-carboxylic acid (0.15 g), 4-(N-methyl-N-(tetrahydropyran-4-yl)aminomethyl)aniline (0.11 g) and triethylamine (0.2 ml) in dimethylformamide (15 ml) was added diethyl cyano-phosphate (0.11 ml) under ice-cooling, and the mixture was stirred under nitrogen atmosphere at room temperature over night. The solvent was evaporated, and the residue was purified with silica gel column (methanol/ethyl acetate/triethylamine) to give crude crystals, which were recrystallized from ethyl acetate-hexane to give 7-(4-dimethylaminophenyl)-N-(4-((N-tetrahydropyran-4-yl-N-methylamino)methyl)phenyl)-2,3-dihydro-1-benzoxepine-4-carboxamide (Compound 149) (0.07 g) as pale brown crystals.

mp 208–209° C.(dec.).; ¹H-NMR(δ ppm, CDCl₃): 1.63–1.78 (4H, m), 2.20 (3H, s), 2.59–2.70 (1H, m), 2.98 (6H, s), 3.04 (2H, t, J=4.5 Hz), 3.36 (2H, dt, J=2.6, 11.0 Hz), 3.56 (2H, s), 4.00–4.06 (2H, m), 4.31 (2H, t, J=4.5 Hz), 6.78 (2H, d, J=8.8 Hz), 7.01 (1H, d, J=8.0 Hz), 7.24–7.31 (3H, m), 7.39–7.46 (4H, m), 7.55 (2H, d, J=8.4 Hz), 7.79 (1H, s). IR(KBr) v: 2949, 2845, 1659 cm⁻¹. Anal. for $C_{32}H_{37}N_3O_3 \cdot 0.3H_2O$: Calcd. C, 74.33; H, 7.33; N, 8.13. Found C, 74.11; H, 7.22; N, 8.21.

WORKING EXAMPLE 150 (Production of Compound 150)

To a solution of 7-(4-(pyrrolidin-1-yl)phenyl)-2,3-dihydro-1-benzoxepine-4-carboxylic acid (0.15 g), 4-(N-methyl-N-(tetrahydropyran-4-yl)aminomethyl)aniline (0.1 g) and 1-hydroxybenzotriazole (0.07 g) in dimethylformamide (10 ml) was added 1-ethyl-3-(3-dimethylaminopropyl) carbodiimide hydro-chloride (0.13 g) under ice-cooling, and the mixture was stirred under nitrogen atmosphere at room temperature for 3 hours. To the mixture were added 4-dimethylaminopyridine (catalytic amount) and 1,8-diazabicyclo[5.4.0]-7-undecene (0.2 ml), and the mixture was stirred over night. The solvent was evaporated, and the residue was purified with silica gel column (methanol/ethyl acetate/triethylamine) to give crude crystals, which were recrystallized from ethanol-hexane to give 7-(4-(pyrrolidin-1-yl)phenyl)-N-(4-((N-tetrahydropyran-4-yl-N-methylamino)-methyl)phenyl)-2,3-dihydro-1-benzoxepine-4-carboxamide (Compound 150) (0.08 g) as colorless crystals.

mp 210–211° C.; ¹H-NMR(δ ppm, CDCl₃): 1.69–1.78 (8H, m), 1.99–2.06 (4H, m), 2.21 (3H, s), 2.55–2.70 (1H, m), 3.07 (2H, t, J=4.5 Hz), 3.30–3.38 (4H, m), 3.38–3.57 (2H, m), 3.57 (2H, s), 4.01–4.06 (2H, m), 4.35 (2H, t, J=4.5 Hz), 6.63 (2H, d, J=8.8 Hz), 7.02 (1H, d, J=8.4 Hz), 7.31 (2H, d, J=8.4 Hz), 7.40–7.48 (4H, m), 7.54 (2H, d, J=8.4 Hz), 7.61 (1H, s). IR(KBr) v: 2951, 2841, 1653 cm⁻¹. Anal. for $C_{34}H_{39}N_3O_3$: Calcd. C, 75.95; H, 7.31; N, 7.81. Found C, 75.70; H, 7.10; N, 7.83.

WORKING EXAMPLE 151 (Production of Compound 151)

To a solution of 7-(4-piperidinophenyl)-2,3-dihydro-1-benzoxepine-4-carboxylic acid (0.15 g), 4-(N-methyl-N-(tetrahydropyran-4-yl)aminomethyl)aniline (0.1 g) and 1-hydroxy-benzotriazole (0.07 g) in dimethylformamide (10 ml) was added 1-ethyl-3-(3-dimethylaminopropyl)-carbodiimide hydrochloride (0.13 g) under ice-cooling. Under nitrogen atmosphere, the mixture was warmed to room temperature. To the mixture were added 4-dimethylaminopyridine (catalytic amount) and triethylamine (0.18 ml), and the mixture was stirred over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give 7-(4-piperidinophenyl)-N-(4-((N-methyl-N-tetrahydro-pyran-4-yl)amino)methyl)phenyl)-2,3-dihydro-1-benzoxepine-4-carboxamide (Compound 151) (0.18 g) as colorless crystals.

mp 197–198° C.; ¹H-NMR(δ ppm, CDCl₃): 1.58–1.70 (2H, m), 1.70–1.73 (4H, m), 2.21 (3H, s), 2.55–2.70 (1H, m), 3.08 (2H, t, J=4.6 Hz), 3.18–3.23 (4H, m), 3.37 (2H, dt, J=2.4, 11.0 Hz), 3.57 (2H. s), 4.01–4.07 (2H, m), 4.35 (2H, t, J=4.6 Hz), 6.63 (2H, d, J=8.8 Hz), 6.97–7.05 (3H, m), 7.31 (2H, d, J=8.4 Hz), 7.43–7.57 (7H, m). IR(KBr) v: 2938, 2847, 1651 cm⁻¹. Anal. for $C_{35}H_{41}N_3O_3 \cdot 0.5H_2O$: Calcd. C, 74.97; H, 7.55; N, 7.49. Found C, 75.26; H, 7.53; N, 7.63.

WORKING EXAMPLE 152 (Production of Compound 152)

To a solution of 7-(4-morpholinophenyl)-2,3-dihydro-1-benzoxepine-4-carboxylic acid (0.15 g), 4-(N-methyl-N-(tetrahydropyran-4-yl)aminomethyl)aniline (0.1 g) and 1-hydroxybenzotriazole (0.06 g) in dimethylformamide (15 ml) was added 1-ethyl-3-(3-dimethylaminopropyl)-carbodiimide hydrochloride (0.12 g) under ice-cooling. Under nitrogen atmosphere, the mixture was warmed to room temperature. To the mixture were added 4-dimethylaminopyridine (catalytic amount) and triethylamine (0.18 ml), and the mixture was stirred over night. The mixture was poured into water and was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((N-methyl-N-(tetrahydropyran-4-yl)aminomethyl)phenyl)-7-(4-morpholinophenyl)-2,3-dihydro-1-benzoxepine-4-carboxamide (Compound 152) (0.17 g) as pale brown crystals.

mp 238–239° C.(dec.).; ¹H-NMR(δ ppm, CDCl₃): 1.58–1.77 (4H, m), 2.21 (3H, s), 2.55–2.75 (1H, m), 3.08 (2H, t, J=4.6 Hz), 3.19–3.24 (4H, m), 3.37 (2H, dt, J=3.0, 11.3 Hz), 3.57 (2H, s), 3.87–3.91 (4H, m), 4.01–4.11 (2H, m), 4.36 (2H, t, J=4.6 Hz), 6.98 (2H, d, J=9.0 Hz), 7.05 (1H, d, J=8.4 Hz), 7.27–7.34 (3H, m), 7.42–7.57 (6H, m). IR(KBr) v: 2961, 2847, 1660 cm⁻¹. Anal. for $C_{34}H_{39}N_3O_4 \cdot 0.5H_2O$: Calcd. C, 72.57; H, 7.16; N, 7.47. Found C, 72.79; H, 7.08; N, 7.35.

WORKING EXAMPLE 153 (Production of Compound 153)

To a solution of 7-(4-(1-imidazolyl)phenyl)-2,3-dihydro-1-benzoxepine-4-carboxylic acid (0.13 g), 4-(N-methyl-N-(tetrahydropyran-4-yl)aminomethyl)aniline (0.11 g) and 1-hydroxybenzotriazole (0.07 g) in dimethylformamide (20 ml) was added 1-ethyl-3-(3-dimethylaminopropyl)

carbodiimide hydrochloride (0.13 g) under ice-cooling. Under nitrogen atmosphere, the mixture was warmed to room temperature. To the mixture were added 4-dimethylaminopyridine (catalytic amount) and triethylamine (0.2 ml), and the mixture was stirred over night. The solvent was evaporated, and the residue was extracted with ethyl acetate. The organic layer was washed with saturated sodium chloride solution and dried with anhydrous magnesium sulfate. Under reduced pressure, the solvent was evaporated, and the residue was purified with silica gel column (ethyl acetate/methanol/triethylamine) to give crude crystals, which were recrystallized from ethanolhexane to give 7-(4-(1-imidazolyl)phenyl)-N-(4-((N-tetrahydropyran-4-yl-N-methylamino)methyl)phenyl)-2,3-dihydro-1-benzoxepine-4-carboxamide (Compound 153) (0.11 g) as pale yellow crystals.

mp 194–195° C.; $^1$H-NMR($\delta$ ppm, CDCl$_3$): 1.63–1.80 (4H, m), 2.21 (3H, s), 2.59–2.70 (1H, m), 3.10 (2H, t, J=4.6 Hz), 3.37 (2H, dt, J=2.6, 11.8 Hz), 3.58 (2H, s), 4.00–4.08 (2H, m), 4.39 (2H, t, J=4.6 Hz), 7.11 (1H, d, J=8.2 Hz), 7.23–7.24 (1H, m), 7.30–7.34 (4H, m), 7.42–7.46 (3H, m), 7.51 (1H, s), 7.57 (2H, d, J=8.6 Hz), 7.65 (2H, d, J=8.6 Hz), 7.84 (1H, br), 7.91 (1H, s). IR(KBr) $\nu$: 2949, 2843, 1651 cm$^{-1}$. Anal. for C$_{33}$H$_{34}$N$_4$O$_3$.0.2H$_2$O: Calcd. C, 73.64; H, 6.44; N, 10.41. Found C, 73.63; H, 6.23; N, 10.46.

WORKING EXAMPLE 154 (Production of Compound 154)

To a solution of 7-(4-dimethylaminophenyl)-2,3-dihydro-1-benzoxepine-4-carboxylic acid (0.1 g), 1-(4-aminobenzyl) phosphorinane-1-oxide (0.08 g) and 1-hydroxybenzotriazole (0.05 g) in dimethylformamide (7 ml) was added 1-ethyl-3-(3-dimethylaminopropyl)carbodiimide hydrochloride (0.1 g) under ice-cooling. Under nitrogen atmosphere, the mixture was warmed to room temperature. To the mixture were added 4-dimethylaminopyridine (catalytic amount) and triethylamine (0.15 ml), and the mixture was stirred over night. The solvent was evaporated, and the residue was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/methanol/triethylamine) to give crude crystals, which were recrystallized from ethanolhexane to give 7-(4-dimethylaminophenyl)-N-(4-((1-oxophosphorinan-1-yl)methyl)phenyl)-2,3-dihydro-1-benzoxepine-4-carboxamide (Compound 154) (0.12 g) as colorless crystals.

mp 293–294° C.(dec.).; $^1$H-NMR($\delta$ ppm, CDCl$_3$): 1.35–1.55 (2H, m), 1.60–1.75 (6H, m), 1.75–2.05 (2H, m), 3.00 (6H, s), 3.09 (2H, t, J=4.7 Hz), 3.13 (2H, d, J=13.6 Hz), 4.35 (2H, t, J=4.7 Hz), 6.80 (2H, d, J=8.8 Hz), 7.03 (1H, d, J=8.4 Hz), 7.21–7.27 (3H, m), 7.41–7.51 (4H, m), 7.60 (2H, d, J=8.2 Hz), 8.24 (1H, br). IR(KBr) $\nu$: 2940, 1665 cm$^{-1}$. Anal. for C$_{31}$H$_{35}$N$_2$O$_3$P: Calcd. C, 72.35; H, 6.86; N, 5.44. Found C, 72.00; H, 6.84; N, 5.45.

WORKING EXAMPLE 155 (Production of Compound 155)

To a solution of 7-(4-dimethylaminophenyl)-N-(4-((1-oxophosphorinan-1-yl)methyl)phenyl)-2,3-dihydro-1-benzoxepine-4-carboxamide (0.1 g) in ethanol was added 4N hydrochloric acid-ethyl acetate (0.2 ml) under ice-cooling. The solvent was evaporated, and the residue was crystallized from ethanol and diethylether to give 7-(4-dimethylaminophenyl)-N-(4-((1-oxophosphorinan-1-yl) methyl)phenyl)-2,3-dihydro-1-benzoxepine-4-carboxamide hydrochloride (Compound 155) (0.1 g) as colorless crystals.

mp 162–163° C.; $^1$H-NMR($\delta$ ppm, DMSO-d$_6$): 1.40–1.50 (2H,m), 1.50–1.90 (8H,m), 2.99 (2H, br), 3.04 (6H, s), 3.16 (2H, d, J=13.6 Hz), 4.30 (2H, br), 7.05 (1H, d, J=8.8 Hz), 7.20–7.25 (4H, m), 7.35 (1H, s), 7.54 (1H, dd, J=2.2, 8.2, 8.8 Hz), 7.63–7.69 (4H, m), 7.74 (1H, d, J=2.2 Hz), 9.97 (1H, s). Anal. for C$_{31}$H$_{35}$N$_2$O$_3$P.HCl.2H$_2$O: Calcd. C, 63.42; H, 6.87; N, 4.77. Found C, 63.45; H, 6.99; N, 4.39.

WORKING EXAMPLE 156 (Production of Compound 156)

In methanol (100 ml) and ethyl acetate (150 ml) was dissolved N-(4-(1-(tert-butoxycarbonyl)piperidin-2-ylcarbonyl)phenyl)-7-(4-methylphenyl)-2,3-dihydro-1-benzoxepine-4-carboxamide (1.0 g), and to the mixture was added hydrochloric acid (17 ml). The mixture was stirred at room temperature for 2 hours, concentrated and neutralized with sodium hydrogen carbonate solution. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethanol-ethyl acetate-hexane to give N-(4-(piperidin-2-ylcarbonyl)phenyl)-7-(4-methylphenyl)-2,3-dihydro-1-benzoxepine-4-carboxamide (Compound 156) (0.6 g) as colorless crystals.

mp 195–196° C.(dec.).; $^1$H-NMR($\delta$ ppm, CDCl$_3$): 1.26–1.49 (2H, m), 1.50–1.70 (2H, m), 1.87–1.94 (2H, m), 2.39 (3H, s), 2.79 (1H, t, J=12.0 Hz), 3.08 (2H, t, J=4.4 Hz), 3.26 (1H, d, J=12.0 Hz), 4.26–4.37 (3H, m), 7.06 (1H, d, J=8.4 Hz), 7.24 (2H, d, J=8.4 Hz), 7.30 (1H, s), 7.43–7.53 (4H, m), 7.71 (2H, d, J=8.8 Hz), 7.90–7.95 (3H, m). IR(KBr) $\nu$: 2934, 1674 cm$^{-1}$. Anal. for C$_{30}$H$_{30}$N$_2$O$_3$.0.3H$_2$O: Calcd. C, 76.34; H, 6.53; N, 5.94. Found C, 76.35; H, 6.44; N, 5.88.

WORKING EXAMPLE 157 (Production of Compound 157)

In dichloromethane (35 ml) was dissolved N-(4-(piperidin-2-ylcarbonyl)phenyl)-7-(4-methylphenyl)-2,3-dihydro-1-benzoxepine-4-carboxamide (0.3 g), and to the solution were added methyl iodide (0.08 ml) and diisopropylethylamine (0.17 ml). The mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/methanol/triethylamine) to give crude crystals, which were recrystallized from ethyl acetate-hexane to give N-(4-(1-methylpiperidin-2-ylcarbonyl) phenyl)-7-(4-methylphenyl)-2,3-dihydro-1-benzoxepine-4-carboxamide (Compound 157) (0.17 g) as colorless crystals.

mp 162–163. $^1$H-NMR($\delta$ ppm, CDCl$_3$): 1.27–1.45 (2H, m), 1.50–1.90 (4H, m), 2.04–2.20 (1H, m), 2.21 (3H, s), 2.39 (3H, s), 3.00–3.05 (1H, m), 3.08 (2H, t, J=4.6 Hz), 3.48 (1H, d, J=7.6 Hz), 4.36 (2H, t, J=4.6 Hz), 7.06 (1H, d, J=8.0 Hz), 7.25 (2H, d, J=12.4 Hz), 7.43–7.51 (4H, m), 7.69 (2H, d, J=8.8 Hz), 7.81 (1H, s), 8.18 (2H, d, J=8.4 Hz). IR(KBr) $\nu$: 2940, 1667 cm$^{-1}$. Anal. for C$_{31}$H$_{32}$N$_2$O$_3$: Calcd. C, 77.47; H, 6.71; N, 5.83. Found C, 77.22; H, 6.71; N, 5.63.

WORKING EXAMPLE 158 (Production of Compound 158)

In methanol (40 ml) was dissolved N-(4-(1-methylpiperidin-2-ylcarbonyl)phenyl)-7-(4-methylphenyl)-

2,3-dihydro-1-benzoxepine-4-carboxamide (0.1 g) under ice-cooling, and to the mixture was added sodium boron hydride (10 mg). The mixture was stirred for 15 minutes, and to the mixture was added water. The mixture was concentrated and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/methanol/triethylamine) to give crude crystals, which were recrystallized from ethanol-ethyl acetate-hexane to give N-(4-(hydroxy(1-methylpiperidin-2-yl)methyl)phenyl)-7-(4-methylphenyl)-2,3-dihydro-1-benzoxepine-4-carboxamide (Compound 158) (0.07 g) as colorless crystals.

mp 195–196. $^1$H-NMR($\delta$ ppm, CDCl$_3$): 0.95–1.05 (2H, m), 1.25–1.40 (2H, m), 2.04–2.30 (4H, m), 2.39 (3H, s), 2.50 (3H, s), 2.95–3.01 (1H, m), 3.08 (2H, t, J=4.6 Hz), 4.36 (2H, t, J=4.6 Hz), 5.16 (1H, d, J=3.0 Hz), 7.06 (1H, d, J=8.4 Hz), 7.24 (2H, d, J=8.0 Hz), 7.33 (2H, d, J=8.4 Hz), 7.43–7.52 (4H, m), 7.56 (2H, d, J=8.4 Hz), 7.61 (1H, s). IR(KBr) ν: 3287, 2938, 1647 cm$^{-1}$. Anal. for C$_{31}$H$_{34}$N$_2$O$_3$.0.6H$_2$O: Calcd. C, 75.46; H, 7.19; N, 5.68. Found C, 75.36; H, 7.33; N, 5.76.

WORKING EXAMPLE 159 (Production of Compound 159)

Under nitrogen atmosphere, oxalyl chloride (0.31 ml) was added to a solution of 7-(4-methylphenyl)-2,3-dihydrobenzoxepine-4-carboxylic acid (0.65 g) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (15 ml). To the solution were added triethylamine (0.65 ml) and 2-(4-aminophenyl) pyridine (J. Chem. Soc., p.1511, 1960) (0.44 g) at 0° C., and the mixture was stirred at room temperature for 2 hours. The reaction mixture was added to vigorously stirred water to stop the reaction. The mixture was extracted with ethyl acetate. Precipitated crystal was collected by filtration to give N-[4-(2-pyridyl)phenyl]-7-(4-methylphenyl)-2,3-dihydro-1-benzoxepine-4-carboxamide (Compound 159) (185.9 mg) as colorless crystals. The mother liquor was concentrated and recrystallized from ethyl acetate-tetrahydrofuran to give N-[4-(2-pyridyl)-phenyl]-7-(4-methylphenyl)-2,3-dihydro-1-benzoxepine-4-carboxamide (Compound 159) (0.58 g) as pale yellow crystals.

m.p. 228–229° C.; $^1$H-NMR (200 MHz, CDCl$_3$) δ 2.39 (3H, s), 3.09 (2H, t, J=4.4 Hz), 4.36 (2H, t, J=4.4 Hz), 7.06 (1H, d, J=8.2 Hz), 7.16–7.32 (4H, m), 7.42–7.56 (4H, m), 7.68–7.82 (5H, m), 8.02 (2H, dd, J=8.8, 2.0 Hz), 8.65–8.73 (1H, dt, J=4.8, 1.4 Hz). IR (KBr) 3338, 1645, 1593, 1516, 1493, 1466, 1435, 1323, 1248, 810, 777 cm$^{-1}$; Elemental Analysis for C$_{29}$H$_{24}$N$_2$O$_2$; Calcd. C, 80.53; H, 5.59; N, 6.48: Found. C, 80.46; H, 5.62; N, 6.46.

WORKING EXAMPLE 160 (Production of Compound 160)

To a suspension of N-[4-(2-pyridyl)phenyl]-7-(4-methylphenyl)-2,3-dihydro-1-benzoxepine-4-carboxamide (400 mg) in dichloromethane (10 ml) was added 3-chloroperbenzoic acid (70%, 0.25 g) at 0° C., and the mixture was stirred at room temperature for 70 hours. To the mixture was added sodium thiosulfate solution, and the mixture was stirred for minutes. The mixture was extracted with dichloromethane. The organic layer was washed with saturated sodium bicarbonate solution and saturated sodium chloride solution, and dried with magnesium sulfate. The mixture was concentrated, purified with column chromatography (ethanol/ethyl acetate=1:1) to give crystals, which were dissolved in chloroform. The mixture was concentrated, and to the residue was added ethanol. Precipitated crystal was collected by filtration to give crystals, which were washed with ethanol to give N-[4-(1-oxidopyridin-2-yl)phenyl]-7-(4-methylphenyl)-2,3-dihydro-1-benzoxepine-4-carboxamide (Compound 160) (60 mg) as colorless crystals.

m.p. 254° C.(dec.); $^1$H-NMR (200 MHz, CDCl$_3$) δ 2.40 (3H, s), 3.06 (2H, t, J=4.4 Hz), 4.36 (2H, t, J=4.4 Hz), 7.00–7.14 (2H, m), 7.16–7.30 (4H, m), 7.38–7.51 (5H, m), 7.67 (2H, d, J=8.6 Hz), 7.78 (2H, d, J=8.8 Hz), 8.19 (1H, d, J=7.0 Hz), 8.38–8.48 (1H, m). IR (KBr) 3334, 3039, 1653, 1487, 1240, 814, 760 cm$^{-1}$; Elemental Analysis for C$_{29}$H$_{24}$N$_2$O$_3$.0.5H$_2$O; Calcd. C, 76.13; H, 5.51; N, 6.12: Found. C, 75.82; H, 5.27; N, 6.18.

WORKING EXAMPLE 161 (Production of Compound 161)

Under nitrogen atmosphere, oxalyl chloride (0.19 ml) was added to a solution of 7-(4-methylphenyl)-2,3-dihydro-1-benzoxepine-4-carboxylic acid (0.40 g) in tetra-hydrofuran (10 ml) at room temperature. To the mixture was added a drop of DMF, and the mixture was stirred for 1 hour. Under reduced pressure, the solvent was evaporated, and the residue was dissolved in tetrahydrofuran (6 ml). To the solution were added triethylamine (0.40 ml) and a solution of 2-(4-aminobenzyl)pyridine (0.29 g) in tetrahydrofuran (5 ml) at 0° C., and the mixture was stirred at room temperature for 2 hours. The reaction mixture was added to vigorously stirred water to stop the reaction. The mixture was extracted with ethyl acetate. The organic layer was washed with saturated sodium chloride solution, dried with magnesium sulfate, concentrated and recrystallized from ethyl acetate to give N-[4-(2-pyridylmethyl)phenyl]-7-(4-methylphenyl)-2,3-dihydro-1-benzoxepine-4-carboxamide (Compound 161) (303 mg) as colorless crystals.

m.p. 189–190° C.; $^1$H-NMR (200 MHz, CDCl$_3$) δ 2.39 (3H, s), 3.06 (2H, t, J=4.6 Hz), 4.14 (2H, s), 4.35 (2H, t, J=4.6 Hz), 7.03–7.16 (3H, m), 7.18–7.31 (5H, m), 7.40–7.64 (8H, m), 8.52–8.58 (1H, m). IR (KBr) 3338, 1645, 1510, 1493, 1414, 1313, 1252, 1234, 816, 750 cm$^{-1}$; Elemental Analysis for C$_{30}$H$_{26}$N$_2$O$_2$; Calcd. C, 80.69; H, 5.87; N, 6.27: Found. C, 80.63; H, 5.80; N, 6.37.

WORKING EXAMPLE 162 (Production of Compound 162)

To a solution of N-[4-(2-pyridylmethyl)phenyl]-7-(4-methylphenyl)-2,3-dihydro-1-benzoxepine-4-carboxamide (200 mg) in tetrahydrofuran (10 ml) was added 3-chloroperbenzoic acid (70%, 0.18 g) at 0° C., and the mixture was stirred at room temperature for 17 hours. To the reaction mixture was added sodium thio-sulfate solution, and the mixture was stirred for a few minutes. The mixture was extracted with ethyl acetate. The organic layer was washed with saturated sodium bicarbonate solution and saturated sodium chloride solution, dried with magnesium sulfate and concentrated to give crystals, which were collected by filtration and was recrystallized from ethanol to give N-[4-(1-oxidopyridin-2-ylmethyl)phenyl]-7-(4-methylphenyl)-2,3-dihydro-1-benzoxepine-4-carboxamide (Compound 162) (124 mg) as colorless crystals.

m.p. 188–190° C.; $^1$H-NMR (200 MHz, CDCl$_3$) δ 2.39 (3H, s), 3.09 (2H, t, J=4.6 Hz), 4.24 (2H, s), 4.36 (2H, t,

J=4.6 Hz), 6.90–7.01 (1H, m), 7.06 (1H, d, J=8.4 Hz), 7.11–7.16 (2H, m), 7.22–7.29 (5H, m), 7.43–7.51 (4H, m), 7.54–7.76 (3H, m), 8.24–8.31 (1H, m). IR (KBr) 3319, 1666, 1601, 1517, 1491, 1412, 1319, 1246, 813 cm$^{-1}$; Elemental Analysis for $C_{30}H_{26}N_2O_3 \cdot 0.3H_2O$; Calcd. C, 77.00; H, 5.73; N, 5.99: Found. C, 76.98; H, 5.59; N, 6.10.

WORKING EXAMPLE 163 (Production of Compound 163)

Under nitrogen atmosphere, oxalyl chloride (0.07 ml) was added to a solution of 7-(4-methylphenyl)-2,3-dihydro-1-benzoxepine-4-carboxylic acid (144.8 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.14 ml) and a solution of 4-aminobenzyldiethylphosphine oxide (120 mg) in tetrahydrofuran (5 ml) at 0° C. and the mixture was stirred at room temperature for 1 hour. The reaction mixture was added to vigorously stirred water to stop the reaction. The mixture was extracted with ethyl acetate. The organic layer was washed with saturated sodium chloride solution, dried with magnesium sulfate, concentrated and recrystallized from ethanol-tetrahydrofuran to give N-(4-diethylphosphorylmethylphenyl)-7-(4-methylphenyl)-2,3-dihydro-1-benzoxepine-4-carboxamide (Compound 163) (157 mg) as colorless crystals.

m.p. 240–241° C.; $^1$H-NMR (200 MHz, CDCl$_3$) δ 1.13 (6H, dt, J=16.4, 8.0 Hz), 1.53–1.72 (4H, m), 2.39 (3H, s), 3.06–3.13 (4H, m), 4.36 (2H, t, J=4.8 Hz), 7.06 (1H, d, J=8.4 Hz), 7.22–7.27 (5H, m), 7.44–7.52 (4H, m), 7.58 (2H, d, J=8.4 Hz), 7.98 (1H, s). IR (KBr) 3263, 1653, 1599, 1516, 1491, 1410, 1319, 1250, 1173, 1132, 843, 808 cm$^{-1}$; Elemental Analysis for $C_{29}H_{32}NO_3P$; Calcd. C, 73.55; H, 6.81; N, 2.96; P, 6.54: Found. C, 73.23; H, 6.64; N, 3.01; P, 6.63.

WORKING EXAMPLE 164 (Production of Compound 164)

Under nitrogen atmosphere, oxalyl chloride (0.28 ml) was added to a solution of 7-(4-methylphenyl)-2,3-dihydro-1-benzoxepine-4-carboxylic acid (0.60 g) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.60 ml) and 3-(4-aminophenyl)pyridine (J. Chem. Soc., p.1511, 1960) (0.40 g) at 0° C., and the mixture was stirred at room temperature for 2 hours. The reaction mixture was added to vigorously stirred water to stop the reaction. The mixture was extracted with ethyl acetate. The organic layer was washed with saturated sodium chloride solution, dried with magnesium sulfate, concentrated and recrystallized from ethanol to give N-[4-(3-pyridyl)phenyl]-7-(4-methylphenyl)-2,3-dihydro-1-benzoxepine-4-carboxamide (Compound 164) (750 mg) as yellow crystals.

m.p. 214–216° C.; $^1$H-NMR (200 MHz, CDCl$_3$) δ 2.39 (3H, s), 3.07–3.11 (2H, m), 4.34–4.39 (2H, m), 7.06 (1H, d, J=8.2 Hz), 7.18–7.63 (10H, m), 7.71–7.90 (4H, m), 8.57–8.59 (1H, m), 8.85 (1H, d, J=1.8 Hz). IR (KBr) 3313, 1666, 1524, 1493, 1321, 1244, 808 cm$^{-1}$; Elemental Analysis for $C_{29}H_{24}N_2O_2 \cdot 0.2H_2O$; Calcd. C, 79.87; H, 5.64; N, 6.42: Found. C, 80.00; H, 5.59; N, 6.00.

WORKING EXAMPLE 165 (Production of Compound 165)

To a solution of N-[4-(3-pyridyl)phenyl]-7-(4-methylphenyl)-2,3-dihydro-1-benzoxepine-4-carboxamide (400 mg) in tetrahydrofuran (50 ml) was added 3-chloroperbenzoic acid (70%, 0.34 g) at 0° C., and the mixture was stirred at room temperature for 68 hours. To the reaction mixture was added sodium thiosulfate solution, and the mixture was stirred for a few minutes and extracted with dichloromethane. The organic layer was washed with saturated sodium bicarbonate solution and saturated sodium chloride solution, dried with magnesium sulfate and concentrated. The residue was separated and purified with column chromatography (ethanol/ethyl acetate=1:1), and recrystallized from ethanol-chloroform to give N-[4-(1-oxidopyridin-3-yl)phenyl]-7-(4-methylphenyl)-2,3-dihydro-1-benzoxepine-4-carboxamide (Compound 165) (216 mg) as pale yellow crystals.

m.p. 262° C.(dec.); $^1$H-NMR (200 MHz, CDCl$_3$) δ 2.40 (3H, s), 3.10 (2H, t, J=4.4 Hz), 4.38 (2H, t, J=4.4 Hz), 7.07 (1H, d, J=8.4 Hz), 7.23–7.36 (4H, m), 7.42–7.58 (7H, m), 7.76 (2H, dd, J=8.8, 2.0 Hz), 7.88 (1H, br s), 8.16–8.20 (1H, m), 8.43–8.47 (1H, m). IR (KBr) 3313, 1655, 1599, 1525, 1491, 1244, 1203, 814 cm$^{-1}$; Elemental Analysis for $C_{29}H_{24}N_2O_3 \cdot 0.1H_2O$; Calcd. C, 77.35; H, 5.42; N, 6.22: Found. C, 77.13; H, 5.28; N, 6.21.

WORKING EXAMPLE 166 (Production of Compound 166)

Under nitrogen atmosphere, oxalyl chloride (0.19 ml) was added to a solution of 7-(4-methylphenyl)-2,3-dihydro-1-benzoxepine-4-carboxylic acid (0.40 g) in tetra-hydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added at 0° C. triethylamine (0.40 ml) and (4-aminophenyl)-(2-pyridyl)methanol (0.31 g), and the mixture was stirred at room temperature for 18 hours. The reaction mixture was added to vigorously stirred water to stop the reaction. The mixture was extracted with ethyl acetate. The organic layer was washed with saturated sodium chloride solution, dried with magnesium sulfate, concentrated and recrystallized from ethanol-ethyl acetate to give N-[4-[hydroxy(2-pyridyl)-methyl]phenyl]-7-(4-methylphenyl)-2,3-dihydro-1-benzoxepine-4-carboxamide (Compound 166) (549 mg) as pale yellow crystals.

m.p. 215–217° C.; $^1$H-NMR (200 MHz, CDCl$_3$) δ 2.39 (3H, s), 3.06 (2H, t, J=4.4 Hz), 4.34 (2H, t, J=4.4 Hz), 5.26–5.38 (1H, m), 5.70–5.78 (1H, m), 7.03–7.27 (6H, m), 7.33–7.79 (10H, m), 8.57 (1H, d, J=4.8 Hz). IR (KBr) 3392, 1651, 1537, 1514, 1493, 1319, 1248 cm$^{-1}$; Elemental Analysis for $C_{30}H_{26}N_2O_3 \cdot 0.2H_2O$; Calcd. C, 77.30; H, 5.71; N, 6.01: Found. C, 77.21; H, 5.75; N, 5.86.

WORKING EXAMPLE 167 (Production of Compound 167)

To a solution of N-[4-[hydroxy(2-pyridyl)methyl]-phenyl]-7-(4-methylphenyl)-2,3-dihydro-1-benzoxepine-4-carboxamide (351.3 mg) in tetrahydrofuran (20 ml) was added 3-chloroperbenzoic acid (70%, 0.28 g) at 0° C., and the mixture was stirred at room temperature for 16 hours. To the reaction mixture was added sodium thiosulfate solution, and the mixture was stirred for a few minutes. The mixture was extracted with ethyl acetate. The organic layer was washed with saturated sodium bicarbonate solution and saturated sodium chloride solution, dried with magnesium sulfate and concentrated. The residue was separated and purified with column chromatography (ethanol-diethylether=1:1), and recrystallized from ethanol to give N-[4-[hydroxy(1-oxidopyridin-2-yl)methyl]phenyl]-7-(4-methylphenyl)-2,3-dihydro-1-benzoxepine-4-carboxamide (Compound 167) (184 mg) as colorless crystals.

m.p. 208–210° C.; $^1$H-NMR (200 MHz, CDC$_3$) δ 2.40 (3H, s), 3.09 (2H, t, J=4.4 Hz), 4.37 (2H, t, J=4.5 Hz), 6.07 (1H, d, J=4.5 Hz), 6.41 (1H, d, J=4.6 Hz), 6.93–6.98 (1H, m), 7.06 (1H, d, J=8.4 Hz), 7.20–7.31 (5H, m), 7.41–7.55 (6H, m), 7.65 (2H, d, J=8.8 Hz), 7.73 (1H, br s), 8.24–8.28 (1H, m). IR (KBr) 3427, 1645, 1599, 1531, 1514, 1491, 1317, 1263 cm$^{-1}$; Elemental Analysis for C$_{30}$H$_{26}$N$_2$O$_4$.0.1H$_2$O; Calcd. C, 75.01; H, 5.50; N, 5.83: Found. C, 74.96; H, 5.36; N, 5.73.

WORKING EXAMPLE 168 (Production of Compound 168)

Under nitrogen atmosphere, oxalyl chloride (0. 2 ml) was added to a solution of 7-(4-methylphenyl)-2,3-dihydro-1-benzoxepine-4-carboxylic acid (400 mg) in tetra-hydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.4 ml) and 4-aminobenzyldipropylphosphine oxide (0.38 g) at 0° C., and the mixture was stirred at room temperature for 5 hours. The reaction mixture was added to vigorously stirred water to stop the reaction. The mixture was extracted with ethyl acetate. The organic layer was washed with saturated sodium chloride solution, dried with magnesium sulfate and concentrated. The residue was separated and purified with column chromatography (ethanol/ethyl acetate=1:5), and recrystallized from ethanol to give N-(4-dipropyl-phosphorylmethylphenyl)-7-(4-methylphenyl)-2,3-dihydro-1-benzoxepine-4-carboxamide (Compound 168) (456 mg) as colorless crystals.

m.p. 219–220° C.; $^1$H-NMR (200 MHz, CDCl$_3$) δ 0.84–0.98 (6H, m), 1.41–1.63 (8H, m), 2.39 (3H, s), 3.02 (2H, d, J=13.2 Hz), 3.09 (2H, t, J=4.4 Hz), 4.35 (2H, t, J=4.4 Hz), 7.06 (1H, d, J=8.0 Hz), 7.13–7.29 (5H, m), 7.44–7.48 (3H, m), 7.53 (1H, d, J=2.2 Hz), 7.61 (2H, d, J=8.0 Hz), 8.64 (1H, s). IR (KBr) 3386, 2960, 1653, 1518, 1491, 1319, 1248, 1185, 1128, 849 cm$^{-1}$; Elemental Analysis for C$_{31}$H$_{36}$NO$_3$P.0.3H$_2$O; Calcd. C, 73.44; H, 7.28; N, 2.76; P, 6.11: Found. C, 73.35; H, 7.40; N, 2.62; P, 6.35.

WORKING EXAMPLE 169 (Production of Compound 169)

Under nitrogen atmosphere, oxalyl chloride (0.17 ml) was added to a solution of 7-(4-methylphenyl)-2,3-dihydro-1-benzoxepine-4-carboxylic acid (350 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.35 ml) and (4-aminophenyl)(3-methoxy-pyridin-2-yl)methanol (316 mg) at 0° C., and the mixture was stirred at room temperature for 16 hours. The reaction mixture was added to vigorously stirred water to stop the reaction. The mixture was extracted with ethyl acetate. The organic layer was washed with saturated sodium chloride solution, dried with magnesium sulfate and concentrated. The residue was separated and purified with column chromatography (ethyl acetate), and recrystallized from tetrahydrofuran-hexane to give N-[4-[hydroxy(3-methoxy-pyridin-2-yl)methyl]phenyl]-7-(4-methylphenyl)-2,3-dihydro-1-benzoxepine-4-carboxamide (Compound 169) (509 mg) as colorless crystals.

m.p. 232–233° C.; $^1$H-NMR (200 MHz, CDCl$_3$) δ 2.39 (3H, s), 3.05 (2H, t, J=4.8 Hz), 3.77 (3H, s), 4.34 (2H, t, J=4.8 Hz), 5.51 (1H, d, J=6.8 Hz), 5.93 (1H, d, J=6.8 Hz), 7.05 (1H, d, J=8.0 Hz), 7.10–7.26 (5H, m), 7.34–7.54 (9H, m), 8.18 (1H, d, J=5.2 Hz). IR (KBr) 3354, 1651, 1518, 1491, 1412, 1311, 1279, 1240, 1211, 1022, 816 cm$^{-1}$; Elemental Analysis for C$_{31}$H$_{28}$N$_2$O$_4$; Calcd. C, 75.59; H, 5.73; N, 5.69: Found. C, 75.47: H, 5.61; N, 5.70.

WORKING EXAMPLE 170 (Production of Compound 170)

To a solution of N-[4-[hydroxy-(3-methoxypyridin-2-yl)methylphenyl]-7-(4-methylphenyl)-2,3-dihydro-1-benzoxepine-4-carboxamide (350 mg) in tetrahydrofuran (30 ml) was added 3-chloroperbenzoic acid (70%, 0.26 g) at 0 20 C., and the mixture was stirred at room temperature for 64 hours. To the mixture was added sodium thiosulfate, and the mixture was stirred for a few minutes and extracted with ethyl acetate. The organic layer was washed with saturated sodium bicarbonate solution and saturated sodium chloride solution, dried with magnesium sulfate and concentrated under reduced pressure. The residue was separated and purified with column chromatography (ethyl acetate→ethanol/ethyl acetate=1:4) recrystallized from tetra-hydrofuran-hexane to give N-[4-[hydroxy(3-methoxy-1-oxidopyridin-2-yl)methyl]phenyl]-7-(4-methylphenyl)-2,3-dihydro-1-benzoxepine-4-carboxamide (Compound 170) (168 mg) as colorless crystals.

m.p. 242° C.(dec.); $^1$H-NMR (200 MHz, CDCl$_3$) δ 2.39 (3H, s), 3.06 (2H, t, J=4.4 Hz), 3.97 (3H, s), 4.35 (2H, t, J=4.4 Hz), 6.34 (1H, d, J=11.4 Hz), 6.97 (1H, d, J=7.8 Hz), 7.05 (1H, d, J=8.2 Hz), 7.14–7.27 (4H, m), 7.42–7.53 (8H, m), 7.61 (1H, br s), 7.84 (1H, d, J=6.6 Hz), 7.87 (1H, d, J=11.2 Hz). IR (KBr) 3493, 3294, 2953, 1657, 1601, 1516, 1493, 1323, 1207, 1184, 1088, 1043, 817 cm$^{-1}$; Elemental Analysis for C$_{31}$H$_{28}$N$_2$O$_5$.0.2H$_2$O; Calcd. C, 72.70; H, 5.59; N, 5.47: Found. C, 72.53; H, 5.64; N, 5.36.

WORKING EXAMPLE 171 (Production of Compound 171)

Under nitrogen atmosphere, oxalyl chloride (0.12 ml) was added to a solution of 7-(4-methylphenyl)-2,3-dihydro-1-benzoxepine-4-carboxylic acid (250 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.25 ml) and 1-(4-aminobenzyl)-phosphorane-1-oxide (204.8 mg) at 0° C., and the mixture was stirred at room temperature 18 hours. The reaction mixture was added to vigorously stirred water to stop the reaction. The mixture was extracted with ethyl acetate, and the organic layer was washed with saturated sodium chloride solution, concentrated and recrystallized from ethanol to give N-(4-(tetramethylene)phosphorylmethylphenyl)-7-(4-methylphenyl)-2,3-dihydrobenzoxepine-4-carboxamide (Compound 171) (316 mg) as colorless crystals.

m.p. 273–275° C.; $^1$H-NMR (200 MHz, CDCl$_3$) δ 1.43–1.97 (8H, m), 2.40 (3H, s), 3.09 (2H, t, J=4.4 Hz), 3.20 (2H, d, J=14.4 Hz), 4.40 (2H, t, J=4.4 Hz), 7.06 (1H, d, J=8.4 Hz), 7.18–7.29 (5H, m), 7.44–7.54 (4H, m), 7.60 (2H, d, J=8.0 Hz), 8.12–8.23 (1H, m). IR (KBr) 3223, 2952, 1653, 1518, 1491, 1321, 1254, 1186, 810 cm$^{-1}$; Elemental Analysis for C$_{29}$H$_{30}$NO$_3$P; Calcd. C, 73.87; H, 6.41; N, 2.97; P, 6.57: Found. C, 73.79; H, 6.33; N, 3.00; P, 6.59.

WORKING EXAMPLE 172 (Production of Compound 172)

Under nitrogen atmosphere, oxalyl chloride (0.47 ml) was added to a solution of 7-(4-methylphenyl)-2,3-dihydro-1-benzoxepine-4-carboxylic acid (1.0 g) in tetrahydrofuran (20 ml) at room temperature. To the mixture was added a drop of DMF, and the mixture was stirred for 1 hour. Under reduced pressure, the solvent was evaporated, and the residue was dissolved in tetrahydrofuran (20 ml) at 0° C. To the solution were added triethylamine (1.0 ml) and 2-(4-aminobenzyl)-3-methoxymethoxypyridine (0.96 g), and the mixture was stirred at room temperature for 4 hours. The reaction mixture was added to vigorously stirred water to stop the reaction. The mixture was extracted with ethyl acetate. The organic layer was washed with saturated sodium chloride solution, dried with magnesium sulfate and concentrated. The residue was separated and purified with column chromatography (ethyl acetate/hexane=2:1) to give N-[4-(3-methoxymethoxy-pyridin-2-ylmethyl)phenyl]-7-(4-methylphenyl)-2,3-dihydro-1-benzoxepine-4-carboxamide (Compound 172) (1.63 g) as orange crystals.

$^1$H-NMR (200 MHz, CDCl$_3$) δ 6 2.39 (3H, s), 3.03 (2H, t, J=4.4 Hz), 3.37 (3H, s), 4.18 (2H, s), 4.32 (2H, t, J=4.4 Hz), 5.17 (2H, s), 7.03 (1H, d, J=8.0 Hz), 7.10 (1H, dd, J=8.4, 4.8 Hz), 7.19–7.51 (12H, m), 7.62 (1H, br s), 8.20 (1H, dd, J=4.8, 1.2 Hz). IR (KBr) 3275, 2945, 1659, 1516, 1444, 1406, 1491, 1313, 1240, 1153, 982. 814 cm$^{-1}$;

WORKING EXAMPLE 173 (Production of Compound 173)

To a solution of N-[4-(3-methoxymethoxypyridin-2-ylmethyl)phenyl]-7-(4-methylphenyl)-2,3-dihydro-1-benzoxepine-4-carboxamide (300 mg) in tetrahydrofuran (10 ml) was added 3-chloroperbenzoic acid (70%, 0.22 g) at 0° C., and the mixture was stirred at room temperature for 18 hours. To the mixture was added sodium thiosulfate, and the mixture was stirred for a few minutes. The mixture was extracted with ethyl acetate, and the organic layer was washed with saturated sodium bicarbonate solution and saturated sodium chloride solution, dried with magnesium sulfate and concentrated under reduced pressure. The residue was separated and purified with column chromatography (ethanol/ethyl acetate=1:15→1:10), and recrystallized from ethanol to give N-[4-(1-oxido-3-methoxymethoxypyridin-2-ylmethyl)phenyl]-7-(4-methylphenyl)-2,3-dihydro-1-benzoxepine-4-carboxamide (Compound 173) (203 mg) as colorless crystals.

m.p. 206–208° C.; $^1$H-NMR (200 MHz, CDCl$_3$) δ 2.39 (3H, s), 3.06 (2H, t, J=4.6 Hz), 3.44 (3H, s), 4.35 (2H, t, J=4.6 Hz), 4.37 (2H, s), 5.24 (2H, s), 6.96–7.08 (3H, m), 7.19–7.27 (4H, m), 7.38–7.52 (7H, m), 7.62 (1H, br s), 7.99 (1H, dd, J=5.0, 2.2 Hz). IR (KBr) 3305, 1653, 1601, 1516, 1491, 1321, 1244, 1053, 818 cm$^{-1}$; Elemental Analysis for C$_{32}$H$_{30}$N$_2$O$_5$.0.2H$_2$O; Calcd. C, 73.04; H, 5.82; N, 5.32: Found. C, 72.96; H, 5.72; N, 5.30.

WORKING EXAMPLE 174 (Production of Compound 174)

To a solution of N-[4-(3-methoxymethoxypyridin-2-ylmethyl)phenyl]-7-(4-methylphenyl)-2,3-dihydro-1-benzoxepine-4-carboxamide (1.00 g) in ethanol(20 ml) was added concentrated hydrochloric acid (5.0 ml), and the mixture was stirred at room temperature for 4 days. To the mixture was added saturated sodium bicarbonate solution at 0° C. to make the solution pH 6–7, and precipitated crystal was collected by filtration to give N-[4-(3-hydroxypyridin-2-ylmethyl)phenyl]-7-(4-methylphenyl)-2,3-dihydro-1-benzoxepine-4-carboxamide (Compound 174) (693 mg) as pale yellow crystals.

m.p. 285–288° C.; $^1$H-NMR (200 MHz, DMSO-d$_6$) δ 2.34 (3H, s), 2.97 (2H, t, J=4.4 Hz), 4.00 (2H, s), 4.28 (2H, t, J=4.4 Hz), 7.02–7.32 (8H, m), 7.49–7.64 (5H, m), 7.73 (1H, d, J=2.2 Hz), 7.95 (1H, dd, J=4.4, 1.4 Hz), 9.86 (1H, br s). IR (KBr) 3390, 3028, 1651, 1510, 1408, 1284, 1236, 808 cm$^{-1}$; Elemental Analysis for C$_{30}$H$_{26}$N$_2$O$_3$.0.2H$_2$O; Calcd. C, 77.30; H, 5.71; N, 6.01: Found. C, 77.20; H, 5.63; N, 5.89.

WORKING EXAMPLE 175 (Production of Compound 175)

To a suspension of N-[4-(3-hydroxypyridin-2-ylmethyl)phenyl]-7-(4-methylphenyl)-2,3-dihydro-1-benzoxepine-4-carboxamide (400 mg) in tetrahydrofuran (30 ml) was added 3-chloroperbenzoic acid (70%, 0.32 g) at 0° C., and the mixture was stirred at room temperature for 15 hours. To the mixture was added sodium thiosulfate, and the mixture was stirred for a few minutes and extracted with ethyl acetate. The organic layer was washed with saturated sodium bicarbonate solution and saturated sodium chloride solution, dried with magnesium sulfate, concentrated under reduced pressure and recrystallized from ethanol to give N-[4-(1-oxido-3-hydroxypyridin-2-ylmethyl)phenyl]-7-(4-methylphenyl)-2,3-dihydro-1-benzoxepine-4-carboxamide (Compound 175) (262 mg) as pale yellow crystals.

m.p. 254° C.(dec.); $^1$H-NMR (200 MHz, DMSO-d$_6$) δ 2.34 (3H, s), 2.92–3.02 (2H, m), 4.14 (2H, s), 4.23–4.34 (2H, m), 6.87 (1H, d, J=7.4 Hz), 7.04 (1H, d, J=8.6 Hz), 7.11 (1H, dd, J=8.4, 6.6 Hz), 7.18–7.36 (5H, m), 7.48–7.61 (5H, m), 7.73 (1H, d, J=2.2 Hz), 7.83 (1H, dd, J=6.4, 1.0 Hz), 9.88 (1H, s). IR (KBr) 3180, 3102, 1651, 1601, 1537, 1516, 1493, 1437, 1227, 1036, 816 cm$^{-1}$; Elemental Analysis for C$_{30}$H$_{26}$N$_2$O$_4$.0.2H$_2$O; Calcd. C, 74.73; H, 5.52; N, 5.81: Found. C, 74.63; H, 5.35; N, 5.55.

WORKING EXAMPLE 176 (Production of Compound 176)

Under nitrogen atmosphere, oxalyl chloride (0.12 ml) was added to a solution of 7-(4-methylphenyl)-2,3-dihydro-1-benzoxepine-4-carboxylic acid (250 mg) in tetrahydrofuran (10 ml) at room temperature. To the mixture was added a drop of DMF, and the mixture was stirred for 1 hour. Under reduced pressure, the solvent was evaporated. The residue was dissolved in tetrahydrofuran (15 ml), and to the solution were added triethylamine (0.25 ml) and 1-(4-aminobenzyl) phosphorinane-1-oxide (219.0 mg) at 0° C. The mixture was stirred at room temperature for 4 hours, added to vigorously stirred water to stop the reaction and extracted with chloroform. The organic layer was washed with saturated sodium chloride solution, dried with magnesium sulfate, concentrated and recrystallized from ethanol to give N-(4-(pentamethylene)phosphorylmethylphenyl)-7-(4-methylphenyl)-2,3-dihydro-1-benzoxepine-4-carboxamide (Compound 176) (253 mg) as colorless crystals.

m.p. 283–286° C.; $^1$H-NMR (200 MHz, CDCl$_3$) δ 1.32–2.09 (10H, m), 2.39 (3H, s), 3.04–3.18 (4H, m), 4.36 (2H, t, J=4.6 Hz), 7.06 (1H, d, J=8.4 Hz), 7.19–7.29 (5H, m), 7.44–7.48 (3H, m), 7.53 (1H, d, J=2.6 Hz), 7.59 (2H, d, J=8.4 Hz), 8.09 (1H, br s). IR (KBr) 3217, 2927, 1655, 1599, 1516, 1493, 1321, 1255, 1236, 1167, 1134, 847, 810 cm$^{-1}$; Elemental Analysis for C$_{30}$H$_{32}$NO$_3$P; Calcd. C, 74.21; H, 6.64; N, 2.88; P, 6.38: Found. C, 73.96; H, 6.53; N, 3.11; P, 6.56.

WORKING EXAMPLE 177 (Production of Compound 177)

Under nitrogen atmosphere, oxalyl chloride (0.06 ml) was added to a solution of 7-(4-ethylphenyl)-2,3-dihydro-1-benzoxepine-4-carboxylic acid (120 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.12 ml) and 4-[N-methyl-N-(tetrahydro-pyran-4-yl)aminomethyl]aniline (99 mg) at 0° C., and the mixture was stirred at room temperature for 3 hours. The reaction mixture was added to vigorously stirred water to stop the reaction. The mixture was extracted with ethyl acetate. The organic layer was washed with saturated sodium chloride solution, dried with magnesium sulfate and concentrated. The residue was purified with column chromatography (ethanol/ethyl acetate=1:5) and recrystallized from ethyl acetate to give N-[4-[N-methyl-N-(tetrahydropyran-4-yl)aminomethyl]phenyl]-7-(4-ethylphenyl)-2,3-dihydro-1-benzoxepine-4-carboxamide (Compound 177) (99 mg) as colorless crystals.

m.p. 181–182° C.; $^1$H-NMR (200 MHz, CDCl$_3$) δ 1.28 (3H, t, J=7.6 Hz), 1.60–1.82 (4H, m), 2.21 (3H, s), 2.57–2.61 (1H, m), 2.69 (2H, q, J=7.6 Hz), 3.09 (2H, t, J=4.6 Hz), 3.37 (2H, dt, J=3.3, 11.1 Hz), 3.58 (2H, s), 3.98–4.09 (2H, m), 4.37 (2H, t, J=4.6 Hz), 7.06 (1H, d, J=8.4 Hz), 7.23–7.36 (5H, m), 7.44–7.58 (7H, m). IR (KBr) 3305, 2960, 1647, 1539, 1514, 1491, 1321, 820 cm$^{-1}$; Elemental Analysis for C$_{32}$H$_{36}$N$_2$O$_3$; Calcd. C, 77.39; H, 7.31; N, 5.64: Found. C, 77.38; H, 7.24; N, 5.66.

WORKING EXAMPLE 178 (Production of Compound 178)

Under nitrogen atmosphere, oxalyl chloride (0.06 ml) was added to a solution of 7-(4-ethylphenyl)-2,3-dihydro-1-benzoxepine-4-carboxylic acid (120 mg) in tetrahydrofuran (10 ml) at room temperature. To the mixture was added a drop of DMF, and the mixture was stirred for 1 hour. Under reduced pressure, the solvent was evaporated. The residue was dissolved in tetrahydrofuran (20 ml), and to the solution were added triethylamine (0.12 ml) and 1-(4-aminobenzyl)phosphorinane-1-oxide (100 mg) at 0° C., and the mixture was stirred at room temperature for 5 hours. The reaction mixture was added to vigorously stirred water to stop the reaction, and the mixture was extracted with chloroform. The organic layer was washed with saturated sodium chloride solution, dried with magnesium sulfate and concentrated. The residue was purified with column chromatography (ethanol/ethyl acetate=1:5→1:4) and recrystallized from ethanol to give N-(4-(pentamethylene)phosphorylmethylphenyl)-7-(4-ethylphenyl)-2,3-dihydro-1-benzoxepine-4-carboxamide (Compound 178) (88 mg) as colorless crystals.

m.p. 287–288° C.; $^1$H-NMR (200 MHz, CDCl$_3$) δ 1.28 (3H, t, J=7.4 Hz), 1.42–2.16 (10H, m), 2.70 (2H, q, J=7.4 Hz), 3.05–3.19 (4H, m), 4.37 (2H, t, J=4.6 Hz), 7.06 (1H, d, J=8.4 Hz), 7.21–7.31 (5H, m), 7.43–7.62 (6H, m), 7.84 (1H, br s). IR (KBr) 3392, 1655, 1599, 1533, 1516, 1493, 1321, 1255, 1167, 847, 824 cm$^{-1}$; Elemental Analysis for C$_{31}$H$_{34}$NO$_3$P; Calcd. C, 74.53; H, 6.86; N, 2.80; P, 6.20: Found. C, 74.23; H, 6.78: N, 2.89; P, 6.07.

WORKING EXAMPLE 179 (Production of Compound 179)

Under nitrogen atmosphere, oxalyl chloride (0.06 ml) was added to a solution of 7-(4-tert-butylphenyl)-2,3-dihydro-1-benzoxepine-4-carboxylic acid (130 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.12 ml) and 4-(N-methyl-N-(tetrahydro-pyran-4-yl)aminomethyl]aniline (98 mg) at 0° C., and the mixture was stirred at room temperature for 3 hours. The reaction mixture was added to vigorously stirred water to stop the reaction. The mixture was extracted with ethyl acetate. The organic layer was washed with saturated sodium chloride solution, dried with magnesium sulfate and concentrated. The residue was purified with column chromatography (ethanol/ethyl acetate=1:4) and recrystallized from ethyl acetate to give N-[4-[N-methyl-N-(tetrahydropyran-4-yl)aminomethyl]phenyl]-7-(4-tert-butylphenyl)-2,3-dihydro-1-benzoxepine-4-carboxamide (Compound 179) (126 mg) as colorless crystals.

m.p. 193–194° C.; $^1$H-NMR (200 MHz, CDCl$_3$) δ 1.37 (9H, s), 1.60–1.82 (4H, m), 2.21 (3H, s), 2.56–2.75 (1H, m), 3.09 (2H, t, J=4.6 Hz), 3.29–3.45 (2H, m), 3.58 (2H, s), 3.97–4.09 (2H, m), 4.37 (2H, t, J=4.6 Hz), 7.06 (1H, d, J=8.0 Hz), 7.23–7.35 (3H, m), 7.41–7.58 (9H, m). IR (KBr) 3342, 2949, 1647, 1512, 1406, 1313, 1240, 1136, 822 cm$^{-1}$; Elemental Analysis for C$_{34}$H$_{40}$N$_2$O$_3$; Calcd. C, 77.83; H, 7.68; N, 5.34: Found. C, 77.69; H, 7.71; N, 5.39.

WORKING EXAMPLE 180 (Production of Compound 180)

Under nitrogen atmosphere, oxalyl chloride (0.06 ml) was added to a solution of 7-(4-tert-butylphenyl)-2,3-dihydro-1-benzoxepine-4-carboxylic acid (130 mg) in tetrahydrofuran (10 ml) at room temperature. To the mixture was added a drop of DMF, and the mixture was stirred for 1 hour. Under reduced pressure, the solvent was evaporated. The residue was dissolved in dichloromethane (10 ml), and to the solution were added triethylamine (0.12 ml) and 1-(4-aminobenzyl)phosphorinane-1-oxide (99 mg) at 0° C., and the mixture was stirred at room temperature for 4 hours. The reaction mixture was added to vigorously stirred water to stop the reaction, and the mixture was extracted with dichloromethane. The organic layer was washed with saturated sodium chloride solution, dried with magnesium sulfate and concentrated. The residue was purified with column chromatography (ethanol/ethyl acetate=1:4) and recrystallized from ethanol to give N-(4-(pentamethylene)phosphorylmethylphenyl)-7-(4-tert-butylphenyl)-2,3-dihydro-1-benzoxepine-4-carboxamide (Compound 180) (106 mg) as colorless crystals.

m.p. 292–294° C.; $^1$H-NMR (200 MHz, CDCl$_3$) δ 1.36 (9H, s), 1.39–2.10 (10 H, m), 3.04–3.19 (4H, m), 4.36 (2H, t, J=4.6 Hz), 7.06 (1H, d, J=8.2 Hz), 7.19–7.30 (3H, m), 7.41–7.63 (8H, m), 8.24 (1H, br s). IR (KBr) 3236, 1664, 1516, 1491, 1311, 1252, 1232, 1163, 1132, 845, 824 cm$^{-1}$; Elemental Analysis for C$_{33}$H$_{38}$NO$_3$P; Calcd. C, 75.12; H, 7.26; N, 2.65; P, 5.87: Found. C, 74.82; H, 7.25; N, 2.73; P, 5.99.

WORKING EXAMPLE 181 (Production of Compound 181)

Under nitrogen atmosphere, oxalyl chloride (0.06 ml) was added to a solution of 7-(4-chlorophenyl)-2,3-dihydro-1-benzoxepine-4-carboxylic acid (120 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.12 ml) and 4-[N-methyl-N-(tetrahydropyran-4-yl)aminomethyl]aniline (97 mg) at 0° C., and the mixture was stirred at room temperature for 3 hours. The reaction mixture was added to vigorously stirred water to stop the reaction. The mixture was extracted with ethyl acetate. The organic layer was washed with saturated sodium chloride solution, dried with magnesium sulfate and concentrated. The residue was purified with column chromatography (ethanol/ethyl acetate=1:4) and recrystallized from ethyl acetatediethylether to give N-[4-[N-methyl-N-(tetrahydropyran-4-yl)aminomethyl]-phenyl]-7-(4-chlorophenyl)-2,3-dihydro-1-benzoxepine-4-carboxamide (Compound 181) (67 mg) as colorless crystals.

m.p. 191–192° C.; $^1$H-NMR (200 MHz, CDCl$_3$) δ 1.61–1.83 (4H, m), 2.21 (3H, s), 2.54–2.74 (1H, m), 3.09 (2H, t, J=4.7 Hz), 3.31–3.44 (2H, m), 3.58 (2H, s), 3.97–4.09 (2H, m), 4.37 (2H, t, J=4.7 Hz), 7.08 (1H, d, J=8.2 Hz), 7.23–7.58 (12H, m). IR (KBr) 3309, 1643, 1520, 1485, 1319, 1246, 816 cm$^{-1}$; Elemental Analysis for C$_{30}$H$_{31}$N$_2$O$_3$Cl; Calcd. C, 71.63; H, 6.21; N, 5.57; Cl, 7.05: Found. C, 71.32; H, 6.21; N, 5.60 ; Cl, 6.81.

WORKING EXAMPLE 182 (Production of Compound 182)

Under nitrogen atmosphere, oxalyl chloride (0.06 ml) was added to a solution of 7-(4-chlorophenyl)-2,3-dihydro-1-benzoxepine-4-carboxylic acid (120 mg) in tetrahydrofuran (10 ml) at room temperature. To the mixture was added a drop of DMF, and the mixture was stirred for 1 hour. Under reduced pressure, the solvent was evaporated. The residue was dissolved in dichloromethane (10 ml). To the solution were added triethylamine (0.12 ml) and 1-(4-aminobenzyl)phosphorinane-1-oxide (98 mg) at 0° C., and the mixture was stirred at room temperature for 3 hours. The reaction mixture was added to vigorously stirred water to stop the reaction, and the mixture was extracted with dichloromethane. The organic layer was washed with saturated sodium chloride solution, dried with magnesium sulfate and concentrated. The residue was purified with column chromatography (ethanol/ethyl acetate=1:4) and recrystallized from ethanol to give N-(4-pentamethylenephosphorylmethylphenyl)-7-(4-chlorophenyl)-2,3-dihydro-1-benzoxepine-4-carboxamide (Compound 182) (69 mg) as colorless crystals.

m.p. 270–272° C.; $^1$H-NMR (200 MHz, CDCl$_3$) δ 1.31–2.10 (10H, m), 3.04–3.18 (4H, m), 4.37 (2H, t, J=4.6 Hz), 7.07 (1H, d, J=8.4 Hz), 7.19–7.29 (3H, m), 7.38–7.52 (6H, m), 7.58 (2H, d, J=8.4 Hz), 8.07 (1H, br s). IR (KBr) 3230, 2935, 1655, 1599, 1516, 1483, 1317, 1254, 1230, 1157, 824 cm$^{-1}$; Elemental Analysis for C$_{29}$H$_{29}$NO$_3$ClP.0.5H$_2$O; Calcd. C, 67.64; H, 5.87; N, 2.72; Cl, 6.88; P, 6.01: Found. C, 67.55; H, 5.81; N, 2.79; Cl, 6.67; P, 6.11.

WORKING EXAMPLE 183 (Production of Compound 183)

Under nitrogen atmosphere, oxalyl chloride (0.05 ml) was added to a solution of 7-(4-trifluoromethylphenyl)-2,3-dihydro-1-benzoxepine-4-carboxylic acid (130 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.1 ml) and 4-[N-methyl-N-(tetrahydropyran-4-yl)amino-methyl]aniline (95 mg) at 0° C., and the mixture was stirred at room temperature for 3 hours. The reaction mixture was added to vigorously stirred water to stop the reaction. The mixture was extracted with ethyl acetate. The organic layer was washed with saturated sodium chloride solution, dried with magnesium sulfate and concentrated. The residue was purified with column chromatography (ethanol/ethyl acetate=1:4) and recrystallized from ethyl acetate-hexane to give N-[4-[N-methyl-N-(tetrahydropyran-4-yl)aminomethyl]phenyl]-7-(4-trifluoromethylphenyl)-2,3-dihydro-1-benzoxepine-4-carboxamide (Compound 183) (91mg) as colorless crystals.

m.p. 205–209° C.; $^1$H-NMR (200 MHz, CDCl$_3$) δ 1.69–1.82 (4H, m), 2.21 (3H, s), 2.55–2.74 (1H, m), 3.10 (2H, t, J=4.7 Hz), 3.31–3.44 (2H, m), 3.58 (2H, s), 3.99–4.11 (2H, m), 4.39 (2H, t, J=4.7 Hz), 7.11 (1H, d, J=8.4 Hz), 7.25–7.34 (3H, m), 7.46–7.58 (5H, m), 7.62–7.71 (4H, m). IR (KBr) 3315, 2958, 2846, 1643, 1522, 1327, 1165, 1115, 1072, 835, 822 cm$^{-1}$; Elemental Analysis for C$_{31}$H$_{33}$N$_2$O$_3$F$_3$; Calcd. C, 69.39; H, 5.82; N, 5.22; F, 10.62; Found. C, 69.21; H, 5.79; N, 5.24; F, 10.60.

WORKING EXAMPLE 184 (Production of Compound 184)

Under nitrogen atmosphere, oxalyl chloride (0.05 ml) was added to a solution of 7-(4-trifluoromethylphenyl)-2,3-dihydro-1-benzoxepine-4-carboxylic acid (130 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.1 ml) and 1-(4-aminobenzyl)phosphorinane-1-oxide (94.5 mg) at 0° C., and the mixture was stirred at room temperature for 3 hours. The reaction mixture was added to vigorously stirred water to stop the reaction. The mixture was extracted with ethyl acetate. The organic layer was washed with saturated sodium chloride solution, dried with magnesium sulfate and concentrated. The residue wag purified with column chromatography (ethanol/ethyl acetate=1:4) and recrystallized from ethyl acetate-hexane to give N-(4-(pentamethylene)phosphorylmethylphenyl)-7-(4-trifluoromethylphenyl)-2,3-dihydro-1-benzoxepine-4-carboxamide (Compound 184) (111 mg) as colorless crystals.

m.p. 269° C.(dec.); $^1$H-NMR (200 MHz, CDCl$_3$) δ 1.19–2.08 (10H, m), 3.03–3.16 (4H, m), 4.38 (2H, t, J=4.6 Hz), 7.10 (1H, d, J=8.4 Hz), 7.15–7.30 (3H, m), 7.48 (1H, dd, J=8.4, 2.2 Hz), 7.52–7.73 (7H, m), 8.39–8.46 (1H, m). IR (KBr) 3221, 2937, 1657, 1533, 1516, 1327, 1257, 1167, 1128, 1072, 849, 825 cm$^{-1}$; Elemental Analysis for C$_{30}$H$_{29}$NO$_3$F$_3$P.0. 2H$_2$O; Calcd. C, 66.34; H, 5.46; N, 2.58: Found. C, 66.21; H, 5.62; N, 2.61.

WORKING EXAMPLE 185 (Production of Compound 185)

Under nitrogen atmosphere, oxalyl chloride (0.08 ml) was added to a solution of 7-(4-ethoxyphenyl)-2,3-dihydro-1-benzoxepine-4-carboxylic acid (154.8 mg) in tetrahydrofuran (10 ml) at room temperature. To the mixture was added a drop of DMF, and the mixture was stirred for 1 hour. Under reduced pressure, the solvent was evaporated. The residue was dissolved in tetrahydrofuran (20 ml), and to the solution were added triethylamine (0.2 ml) and 4-[N-methyl-N-(tetrahydropyran-4-yl)aminomethyl]aniline (121 mg) at 0° C., and the mixture was stirred at room temperature for 3 hours. The reaction mixture was added to vigorously stirred water to stop the reaction. The mixture was extracted with ethyl acetate. The organic layer was washed with saturated sodium chloride solution, dried with magnesium sulfate and concentrated. The residue was purified with column chromatography (ethanol/ethyl acetate=1:4) and recrystallized from ethanol to give 7-(4-ethoxyphenyl)-N-[4-[N-methyl-N-(tetrahydropyran-4-yl)aminomethyl]phenyl]-2,3-dihydro-1-benzoxepine-4-carboxamide (Compound 185) (202 mg) as colorless crystals.

m.p. 174–176° C.; $^1$H-NMR (200 MHz, CDCl$_3$) δ 1.44 (3H, t, J=7.0 Hz), 1.62–1.82 (4H, m), 2.21 (3H, s), 2.55–2.72 (1H, m), 3.08 (2H, t, J=4.8 Hz), 3.31–3.44 (2H, m), 3.57 (2H, s), 3.97–4.10 (2H, m), 4.08 (2H, q, J=7.0 Hz), 4.36 (2H, t, J=4.8 Hz), 6.96 (2H, d, J=8.8 Hz), 7.05 (1H, d, J=8.4 Hz), 7.24–7.58 (10H, m). IR (KBr) 3327, 2947, 1645, 1608, 1514, 1495, 1240, 1180, 1051, 822 cm$^{-1}$; Elemental Analysis for C$_{32}$H$_{36}$N$_2$O$_4$; Calcd. C, 74.97; H, 7.08; N, 5.46: Found. C, 74.88; H, 7.27; N, 5.50.

WORKING EXAMPLE 186 (Production of Compound 186)

Under nitrogen atmosphere, oxalyl chloride (0.06 ml) was added to a solution of 7-(4-trifluoromethoxyphenyl)-2,3-dihydro-1-benzoxepine-4-carboxylic acid (150 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.12 ml) and 4-[N-methyl-N-(tetrahydropyran-4-yl)aminomethyl]aniline (104 mg) at 0° C., and the mixture was stirred at room temperature for 3 hours. The reaction mixture was added to vigorously stirred water to stop the reaction. The mixture was extracted with ethyl acetate. The organic layer was washed with saturated sodium chloride solution, dried with magnesium sulfate and concentrated. The residue was separated and purified with column chromatography (ethanol/ethyl acetate=1:4), and recrystallized from ethyl acetate-hexane to give N-[4-[N-methyl-N-(tetrahydropyran-4-yl)aminomethyl]phenyl]-7-(4-trifluoromethoxyphenyl)-2,3-dihydro-1-benzoxepine-4-carboxamide (Compound 186) (143 mg) as colorless crystals.

m.p. 187–188° C.; $^1$H-NMR (200 MHz, CDCl$_3$) δ 1.62–1.82 (4H, m), 2.21 (3H, s), 2.55–2.74 (1H, m), 3.10 (2H, t, J=4.7 Hz), 3.29–3.45 (2H, m), 3.57 (2H, s), 3.99–4.10 (2H, m), 4.38 (2H, t, J=4.7 Hz), 7.09 (1H, d, J=8.4 Hz), 7.22–7.35 (3H, m), 7.40–7.60 (9H, m). IR (KBr) 3319, 2960, 2845, 1643, 1520, 1493, 1319, 1261, 1205, 1163, 835, 810 cm$^{-1}$; Elemental Analysis for C$_{31}$H$_{31}$N$_2$O$_4$F$_3$; Calcd. C, 67.38; H, 5.65; N, 5.07; F, 10.31: Found. C, 67.39; H, 5.38; N, 5.07; F, 10.18.

WORKING EXAMPLE 187 (Production of Compound 187)

Under nitrogen atmosphere, oxalyl chloride (0.07 ml) was added to a solution of (E)-3-(4-methylphenyl)cinnamic acid (125 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.14 ml) and (4-aminobenzyl)diethylphosphine oxide (120 mg) in tetrahydrofuran (5 ml) at 0° C., and the mixture was stirred at room temperature for 1.5 hours. The reaction mixture was added to vigorously stirred water to stop the reaction. The mixture was extracted with ethyl acetate. The organic layer was washed with saturated sodium chloride solution, dried with magnesium sulfate, concentrated and recrystallized from ethanol-ethyl acetate to give (E)-N-(4-diethylphosphorylmethylphenyl)-3-(4-methylphenyl)cinnamamide (Compound 187) (125 mg) as pale yellow crystals.

m.p. 197–198° C.; $^1$H-NMR (200 MHz, CDCl$_3$) δ 1.13 (6H, dt, J=16.6, 8.0 Hz), 1.55–1.71 (4H, m), 2.41 (3H, m), 3.08 (2H, d, J=13.2 Hz), 6.81 (1H, d, J=15.4 Hz), 7.15–7.30 (4H, m), 7.41–7.62 (7H, m), 7.74–7.84 (2H, m), 8.93–9.02 (1H, m). IR (KBr) 3242, 1678, 1630, 1603, 1541, 1514, 1409, 1344, 1250, 1165, 1130, 985, 847, 791 cm$^{-1}$; Elemental Analysis for C$_{27}$H$_{30}$NO$_2$P.0. 3H$_2$O; Calcd. C, 74,22; H, 7.06; N, 3.21; P, 7.09: Found. C, 73.96; H, 6.77; N, 3.34; P, 7.01.

WORKING EXAMPLE 188 (Production of Compound 188)

Under nitrogen atmosphere, oxalyl chloride (0.27 ml) was added to a solution of (E)-3-(4-methylphenyl)cinnamic acid (0.50 g) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.60 ml) and 2-(4-aminophenyl)pyridine (0.39 g), and the mixture was stirred at room temperature for 2 hours. The reaction mixture was added to vigorously stirred water to stop the reaction. The mixture was extracted with ethyl acetate. The organic layer was washed with saturated sodium chloride solution, dried with magnesium sulfate, concentrated under reduced pressure and recrystallized from tetrahydrofuran-hexane (1:1) to give (E)-N-[4-(2-pyridyl)-phenyl]-3-(4-methylphenyl)cinnamamide (Compound 188) (561 mg) as pale yellow crystals.

m.p. 220–222° C.; $^1$H-NMR (200 MHz, CDCl$_3$) δ 2.42 (3H, s), 6.63 (1H, d, J=15.4 Hz), 7.18–7.31 (3H, m), 7.44–7.63 (6H, m), 7.70–7.83 (5H, m), 7.85 (1H, d, J=15.4 Hz), 8.02 (2H, d, J=8.8 Hz), 8.66–8.72 (1H, m). IR (KBr) 3286, 1657, 1622, 1597, 1524, 1462, 1333, 1180, 970, 787 cm$^{-1}$; Elemental Analysis for C$_{27}$H$_{22}$N$_2$O.0.1H$_2$O; Calcd. C, 82.67; H, 5.70; N, 7.14: Found. C, 82.45; H, 5.70; N, 7.13.

WORKING EXAMPLE 189 (Production of Compound 189)

To a solution of (E)-N-[4-(2-pyridyl)phenyl]-3-(4-methylphenyl)cinnamamide (350 mg) in tetrahydrofuran (10 ml) and dichloromethane (30 ml) was added 3-chloroperbenzoic acid (70%, 0.27 g) at 0° C., and the mixture was stirred at room temperature for 2 days. To the reaction mixture was added sodium thiosulfate solution, and the mixture was stirred for a few minutes and extracted with dichloromethane. The organic layer was washed with saturated sodium bicarbonate solution and saturated sodium chloride solution, dried with magnesium sulfate and concentrated. The residue was purified with column chromatography (ethanol/ethyl acetate=1:1) concentrated to give crystals, which were recrystallized from ethanol-chloroform to give (E)-N-[4-(1-oxidopyridin-2-yl)phenyl]-3-(4-methylphenyl)cinnamamide (Compound 189) (188 mg) as pale yellow crystals.

m.p. 240–241° C.; $^1$H-NMR (200 MHz, CDCl$_3$) δ 2.43 (3H, s), 6.63 (1H, d, J=15.4 Hz), 6.98–7.07 (1H, m), 7.24–7.35 (4H, m), 7.37–7.68 (10H, m), 7.78 (1H, d, J=15.4 Hz), 8.33–8.36 (1H, m), 8.58–8.66 (1H, m). IR (KBr) 3300, 1680, 1630, 1595, 1529, 1475, 1342, 1225, 970, 837, 766 cm$^{-1}$; Elemental Analysis for C$_{27}$H$_{22}$N$_2$O$_2$; Calcd. C, 79.78; H, 5.46; N, 6.89: Found. C, 79.71; H, 5.39 : N, 6.93.

WORKING EXAMPLE 190 (Production of Compound 190)

Under nitrogen atmosphere, oxalyl chloride (0.22 ml) was added to a solution of (E)-3-(4-methylphenyl)cinnamic acid (0.40 g) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.50 ml) and 2-(4-amino-benzyl)pyridine (0.34 g) in tetrahydrofuran (5 ml) at 0° C., and the mixture was stirred at room temperature for 2 hours. The reaction mixture was added to vigorously stirred water to stop the reaction. The mixture was extracted with ethyl acetate. The organic layer was washed with saturated sodium chloride solution, dried with magnesium sulfate, concentrated and recrystallized from ethyl acetate-hexane to give (E)-N-[4-(2-pyridylmethyl) phenyl]-3-(4-methylphenyl)-cinnamamide (Compound 190) (490 mg) as yellow crystals.

m.p. 169–171° C.; $^1$H-NMR (200 MHz, CDCl$_3$) δ 2.41 (3H, s), 4.14 (2H, s), 6.60 (1H, d, J=15.4 Hz), 7.10–7.15 (2H, m), 7.22–7.28 (4H, m), 7.42–7.63 (9H, m), 7.71 (1H, br s), 7.80 (1H, d, J=15.4 Hz), 8.53–8.58 (1H, m). IR (KBr) 3238, 1673, 1630, 1601, 1539, 1512, 1348, 1248, 1174, 976, 791, 760 cm$^{-1}$; Elemental Analysis for C$_{28}$H$_{24}$N$_2$O.0.1H$_2$O; Calcd. C, 82.77; H, 6.00; N, 6.89: Found. C, 82.73; H, 5.89; N, 6.97.

WORKING EXAMPLE 191 (Production of Compound 191)

To a solution of (E)-N-[4-(2-pyridylmethyl)phenyl]-3-(4-methylphenyl)cinnamamide (302 mg) in tetrahydrofuran (10 ml) was added 3-chloroperbenzoic acid (70%, 0.27 g) at 0° C., and the mixture was stirred at room temperature for 18 hours. To the reaction mixture was added sodium thiosulfate solution, and the mixture was stirred for a few minutes. The mixture was extracted with ethyl acetate. The organic layer was washed with saturated sodium bicarbonate solution and saturated sodium chloride solution, dried with magnesium sulfate and concentrated. The residue was recrystallized from ethanol to give (E)-N-[4-(1-oxidopyridin-2-ylmethyl) phenyl]-3-(4-methylphenyl)cinnamamide (Compound 191) (180 mg) as pale yellow crystals.

m.p. 183–185° C.; $^1$H-NMR (200 MHz, CDCl$_3$) δ 2.41 (3H, s), 4.24 (2H, s), 6.64 (1H, d, J=15.4 Hz), 6.96–7.01 (1H, m), 7.12–7.17 (2H, m), 7.22–7.30 (4H, m), 7.40–7.51 (4H, m), 7.54–7.63 (3H, m), 7.66–7.74 (2H, m), 7.82 (1H, d, J=15.4 Hz), 8.29–8.31 (1H, m). IR (KBr) 3255, 1684, 1605, 1541, 1514, 1412, 1346, 1244, 839, 785 cm$^{-1}$; Elemental Analysis for C$_{28}$H$_{24}$N$_2$O$_2$; Calcd. C, 79.98; H, 5.75; N, 6.66: Found. C, 80.18; H, 5.63; N, 6.69.

WORKING EXAMPLE 192 (Production of Compound 192)

Under nitrogen atmosphere, oxalyl chloride (0.27 ml) was added to a solution of (E)-3-(4-methylphenyl)cinnamic acid (0.50 g) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.60 ml) and 3-(4-aminophenyl)pyridine (0.39 g) at 0° C., and the mixture was stirred at room temperature for 18 hours. The reaction mixture was added to vigorously stirred water to stop the reaction. The mixture was extracted with ethyl acetate. The organic layer was washed with saturated sodium chloride solution, dried with magnesium sulfate and concentrated. The residue was purified with column chromatography (ethyl acetate) to give yellow crystals, which were recrystallized from tetra-hydrofuran-ethanol to give (E)-N-[4-(3-pyridyl)phenyl]-3-(4-methylphenyl) cinnamamide (Compound 192) (447 mg) as pale yellow crystals.

m.p. 213–214° C.; $^1$H-NMR (200 MHz, CDCl$_3$) δ 2.15 (3H, s), 6.65 (1H, d, J=15.4 Hz), 7.26–7.64 (11H, m), 7.75–7.90 (5H, m), 8.59 (1H, dd, J=4.8, 1.8 Hz), 8.85 (1H, d, J=1.8 Hz). IR (KBr) 3344, 1660, 1626, 1525, 1481, 1335, 1171, 978, 795 cm$^{-1}$; Elemental Analysis for C$_{27}$H$_{22}$N$_2$O; Calcd. C, 83.05; H, 5.68; N, 7.17: Found. C, 83.01; H, 5.82; N, 7.23.

WORKING EXAMPLE 193 (Production of Compound 193)

To a solution of (E)-N-[4-(3-pyridyl)phenyl]-3-(4-methylphenyl)cinnamamide (250 mg) in tetrahydrofuran (20 ml) was added 3-chloroperbenzoic acid (70%, 0.24 g) at 0° C., and the mixture was stirred at room temperature for 18 hours. To the reaction mixture was added sodium thiosulfate solution, and the mixture was stirred for a few minutes and extracted with dichloromethane. The organic layer was washed with saturated sodium bicarbonate solution and saturated sodium chloride solution, dried with magnesium sulfate and concentrated. The residue was recrystallized from ethanol-tetrahydrofuran-acetone to give (E)-N-[4-(1-oxidopyridin-3-yl)phenyl]-3-(4-methylphenyl) cinnamamide (Compound 193) (208 mg) as pale yellow crystals. $^1$H-NMR (200 MHz, DMSO-d$_6$) δ 2.38 (3H, s), 6.95 (1H, d, J=15.7 Hz), 7.31 (2H, d, J=8.1 Hz), 7.45–7.57 (2H, m), 7.59–7.94 (12H, m), 8.19 (1H, d, J=6.5 Hz), 8.58 (1H, s). IR (KBr) 3423, 1672, 1597, 1531, 1477, 1340, 1201, 901, 835, 793 cm$^{-1}$;

WORKING EXAMPLE 194 (Production of Compound 194)

Under nitrogen atmosphere, oxalyl chloride (0.19 ml) was added to a solution of (E)-3-(4-methylphenyl)cinnamic acid (340 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.4 ml) and 4-aminobenzyl-dipropylphosphine oxide (0.38 g) at 0° C., and the mixture was stirred at room temperature for 18 hours. The reaction mixture was added to vigorously stirred water to stop the reaction. The mixture was extracted with ethyl acetate. The organic layer was concentrated. The residue was recrystallized from ethanol to give (E)-N-(4-dipropylphosphorylmethylphenyl)-3-(4-methylphenyl) cinnamamide (Compound 194) (489 mg) as colorless crystals.

m.p. 225–227° C.; $^1$H-NMR (200 MHz, DMSO-d$_6$) δ 0.87–1.00 (6H, m), 1.37–1.63 (8H, m), 2.37 (3H, s), 3.07 (2H, d, J=15.0 Hz), 6.93 (1H, d, J=16.0 Hz), 7.16–7.25 (2H, m), 7.30 (2H, d, J=8.0 Hz), 7.50–7.71 (9H, m), 7.89 (1H, br s). IR (KBr) 3232, 1676, 1624, 1605, 1545, 1512, 1338, 1151 cm$^{-1}$; Elemental Analysis for C$_{29}$H$_{34}$NO$_2$P; Calcd. C, 75.79; H, 7.46; N, 3.05; P, 6.74: Found. C, 75.60; H, 7.68; N, 2.99; P, 6.83.

WORKING EXAMPLE 195 (Production of Compound 195)

Under nitrogen atmosphere, oxalyl chloride (0.11 ml) was added to a solution of (E)-3-(4-methylphenyl)cinnamic acid (200 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.25 ml) and 1-(4-aminobenzyl)phosphorane-1-oxide (193 mg) at 0° C., and the mixture was stirred at room temperature for 18 hours. The reaction mixture was added to vigorously stirred water to stop the reaction. The mixture was extracted with ethyl acetate. The organic layer was washed with saturated sodium chloride solution and concentrated. The residue was recrystallized from ethanol to give (E)-N-(4-(tetramethylene)phosphoryl-methylphenyl)-3-(4-methylphenyl)cinnamamide (Compound 195) (221 mg) as colorless crystals.

m.p. 273–275° C.; $^1$H-NMR (200 MHz, CDCl$_3$) δ 1.48–2.04 (8H, m), 2.41 (3H, s), 3.19 (2H, d, J=13.6 Hz), 6.78 (1H, d, J=15.8 Hz), 7.14–7.31 (4H, m), 7.43–7.59 (7H, m), 7.73–7.76 (1H, m), 7.79 (1H, d, J=15.8 Hz), 8.75–8.84 (1H, m). IR (KBr) 3232, 1676, 1628, 1603, 1543, 1512, 1410, 1341, 1171, 985, 868, 793 cm$^{-1}$; Elemental Analysis for C$_{27}$H$_{28}$NO$_2$P.0.3H$_2$O; Calcd. C, 74.56; H, 6.62; N, 3.22; P, 7.12: Found. C, 74.36; H, 6.64; N, 3.20; P, 7.06.

WORKING EXAMPLE 196 (Production of Compound 196)

Under nitrogen atmosphere, oxalyl chloride (0.12 ml) was added to a solution of (E)-3-(4-methylphenyl)cinnamic acid (220 mg) in tetrahydrofuran (10 ml) at room temperature. To the mixture was added a drop of DMF, and the mixture was stirred for 1 hour. Under reduced pressure, the solvent was evaporated. The residue was dissolved in tetrahydrofuran (20 ml), and to the solution were added triethylamine (0.26 ml) and 1-(4-amino-benzyl)phosphorinane-1-oxide (226 mg) at 0° C. The mixture was stirred at room temperature for 20 hours. The reaction mixture was added to vigorously stirred water to stop the reaction, and the mixture was extracted with chloroform. The organic layer was washed with saturated sodium chloride solution, dried with magnesium sulfate and concentrated. The residue was recrystallized from ethanol to give (E)-N-(4-(pentamethylene)phosphorylmethylphenyl)-3-(4-methylphenyl)cinnamamide (Compound 196) (271 mg) as colorless crystals.

m.p. 273–276° C.; $^1$H-NMR (200 MHz, CDCl$_3$) δ 1.43–2.08 (10H, m), 2.41 (3H, s), 3.13 (2H, d, J=12.8 Hz), 6.81 (1H, d, J=15.8 Hz), 7.14–7.30 (4H, m), 7.41–7.61 (7H, m), 7.76 (1H, s), 7.80 (1H, d, J=15.8 Hz), 8.72–8.87 (1H, m). IR (KBr) 3242, 1676, 1628, 1603, 1539, 1514, 1344, 1174, 1155, 1126, 991, 789 cm$^{-1}$; Elemental Analysis for C$_{28}$H$_{30}$NO$_2$P.1.5H$_2$O; Calcd. C, 71.47; H, 7.06; N, 2.98; P, 6.58: Found. C, 71.53; H, 6.99; N, 2.87; P, 6.76.

WORKING EXAMPLE 197 (Production of Compound 197)

Under nitrogen atmosphere, oxalyl chloride (0.20 ml) was added to a solution of 6-(4-methylphenyl)-2H-1-benzopyran-3-carboxylic acid (300 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.31 ml) and 1-(4-aminobenzyl)piperidine (0.24 g) at 0° C., and the mixture was stirred at room temperature for 3 hours. The reaction mixture was added to vigorously stirred water to stop the reaction. The mixture was extracted with ethyl acetate. The organic layer was concentrated. The residue was separated and purified with column chromatography (ethanol/ethyl acetate=1:5) to give N-[4-(1-piperidinylmethyl)phenyl]-6-(4-methylphenyl)-2H-1-benzopyran-3-carboxamide (Compound 197) (324 mg) as yellow crystals.

m.p. 196–197° C.; $^1$H-NMR (200 MHz, CDCl$_3$) δ 1.41–1.71 (6H, m), 2.34–2.43 (7H, m), 3.46 (2H, s), 5.12 (2H, d, J=1.4 Hz), 6.95 (1H, d, J=8.0 Hz), 7.14 (1H, br s), 7.23–7.29 (3H, m), 7.31–7.38 (2H, m), 7.40–7.46 (6H, m). IR (KBr) 3361, 1643, 1601, 1529, 1485, 1317, 1254, 810 cm$^{-1}$; Elemental Analysis for C$_{29}$H$_{30}$N$_2$O$_2$.0.1H$_2$O; Calcd. C, 79.10; H, 6.91; N, 6.36: Found. C, 78.85; H, 6.90; N, 6.26.

WORKING EXAMPLE 198 (Production of Compound 198)

To a solution of N-[4-(1-piperidinylmethyl)phenyl]-6-(4-methylphenyl)-2H-1-benzopyran-3-carboxamide (200 mg) in DMF (3 ml) was added methyl iodide (0.1 ml) at room temperature, and the mixture was stirred for 20 hours. To the mixture was added ethyl acetate. Precipitated crystal was collected by filtration and recrystallized from chloroform-ethanol to give 1-[4-[N-[6-(4-methylphenyl)-2H-1-benzopyran-3-carbonyl]-amino]benzyl]-1-methylpiperidinium iodide (Compound 198) (188 mg) as yellow crystals.

m.p. 210° C.(dec.); $^1$H-NMR (200 MHz, CDCl$_3$) δ 1.62–2.01 (6H, m), 2.36 (3H, s), 3.06 (3H, br s), 3.34–3.49 (2H, m), 3.60–3.76 (2H, m), 4.97 (2H, br s), 5.04 (2H, br s), 6.85 (1H, d, J=8.4 Hz), 7.17 (2H, d, J=8.2 Hz), 7.37–7.42 (3H, m), 7.47–7.52 (3H, m), 7.83–7.91 (3H, m), 9.00 (1H, br s). IR (KBr) 3246, 1668, 1527, 1483, 1319, 1248, 808 cm$^{-1}$; Elemental Analysis for C$_{30}$H$_{33}$N$_2$O$_2$I.0.2H$_2$O; Calcd. C, 61.69; H, 5.76; N, 4.80: Found. C, 61.53; H, 5.72; N, 4.85.

WORKING EXAMPLE 199 (Production of Compound 199)

Under nitrogen atmosphere, oxalyl chloride (0.26 ml) was added to a solution of 6-(4-methylphenyl)-2H-1-benzopyran-3-carboxylic acid (0.52 g) in tetrahydrofuran (10 ml) at room temperature. To the mixture was added a drop of DMF, and the mixture was stirred for 1 hour. Under reduced pressure, the solvent was evaporated. The residue was dissolved in tetrahydrofuran (6 ml), and to the solution were added triethylamine (0.60 ml) and 2-(4-aminobenzyl)pyridine (0.40 g) in tetrahydrofuran (5 ml), and the mixture was stirred at room temperature for 3 hours. The reaction mixture was added to vigorously stirred water to stop the reaction. The mixture was extracted with ethyl acetate. The organic layer was washed with saturated sodium chloride solution, dried with magnesium sulfate and concentrated under reduced pressure. The residue was separated and purified with column chromatography (ethyl acetate/hexane=2:1) and concentrated to give crystals, which were recrystallized from ethanol-ethyl acetate) to give N-[4-(2-pyridylmethyl)phenyl]-6-(4-methylphenyl)-2H-1-benzopyran-3-carboxamide (Compound 199) (353.2 mg) as yellow crystals, which were similarly recrystallized to give the second crystals (208 mg).

m.p. 184–187° C.; $^1$H-NMR (200 MHz, CDCl$_3$) δ 2.39 (3H, m), 4.14 (2H, s), 5.10 (2H, d, J=1.4 Hz), 6.93 (1H, d, J=8.4 Hz), 7.09–7.15 (3H, m), 7.19–7.32 (5H, m), 7.37–7.66 (7H, m), 8.53–8.57 (1H, m). IR (KBr) 3296, 1639, 1599, 1531, 1514, 1473, 1325, 1259 cm$^{-1}$; Elemental Analysis for C$_{29}$H$_{24}$N$_2$O$_2$; Calcd. C, 80.53; H, 5.59; N, 6.48: Found. C, 80.24; H, 5.75; N, 6.43.

WORKING EXAMPLE 200 (Production of Compound 200)

To a solution of N-[4-(2-pyridylmethyl)phenyl]-6-(4-methylphenyl)-2H-1-benzopyran-3-carboxamide (250 mg) in tetrahydrofuran (10 ml) was added 3-chloroperbenzoic acid (70%, 0.21 g) at 0° C., and the mixture was stirred at room temperature for 14 hours. To the reaction mixture was added sodium thiosulfate solution, and the mixture was stirred for a few minutes. The mixture was extracted with ethyl acetate. The organic layer was washed with saturated sodium bicarbonate solution and saturated sodium chloride solution, dried with magnesium sulfate and concentrated. The residue was separated and purified with column chromatography (ethanol/ethyl acetate=1:3) concentrated to give crystals, which were recrystallized from chloroform-ethanol to give N-[4-(1-oxidopyridin-2-ylmethyl)phenyl]-6-(4-methylphenyl)-2H-1-benzopyran-3-carboxamide (Compound 200) (191 mg) as pale yellow crystals.

m.p. 261–263° C.; $^1$H-NMR (200 MHz, CDCl$_3$) δ 2.40 (3H, s), 4.25 (2H, s), 5.11 (2H, s), 6.92–7.01 (2H, m), 7.13–7.67 (14H, m), 8.29 (1H, t, J=4.2 Hz). IR (KBr) 3302, 1660, 1605, 1537, 1520, 1250 cm$^{-1}$; Elemental Analysis for C$_{29}$H$_{24}$N$_2$O$_3$; Calcd. C, 77.66; H, 5.39; N, 6.25: Found. C, 77.90; H, 5.37; N, 6.21.

WORKING EXAMPLE 201 (Production of Compound 201)

Under nitrogen atmosphere, oxalyl chloride (0.19 ml) was added to a solution of 6-(4-methylphenyl)-2H-1-benzopyran-3-carboxylic acid (380 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.4 ml) and 4-aminobenzyldipropylphosphine oxide (0.38 g) at 0° C., and the mixture was stirred at room temperature for 3 hours. The reaction mixture was added to vigorously stirred water to stop the reaction. The mixture was extracted with ethyl acetate. The organic layer was concentrated, and the residue was recrystallized from ethanol to give N-(4-dipropylphosphoryl-methylphenyl)-6-(4-methylphenyl)-2H-1-benzopyran-3-carboxamide (Compound 201) (460 mg) as pale yellow crystals.

m.p. 192–194° C.; $^1$H-NMR (200 MHz, CDCl$_3$) δ 0.83–0.97 (6H, m), 1.39–1.68 (8H, m), 2.39 (3H, s), 3.05 (2H, d, J=13.2 Hz), 5.12 (2H, d, J=0.8 Hz), 6.94 (1H, d, J=8.4 Hz), 7.11–7.28 (4H, m), 7.31–7.50 (5H, m), 7.61 (2H, d, J=8.4 Hz), 9.13–9.24 (1H, m). IR (KBr) 3265, 1664, 1628, 1603, 1539, 1514, 1487, 1325, 1252, 1167, 851 cm$^{-1}$; Elemental Analysis for C$_{30}$H$_{34}$NO$_3$P; Calcd. C, 73.90; H, 7.03; N, 2.87; P, 6.35: Found. C, 73.95; H, 6.87; N, 2.84; P, 6.41.

WORKING EXAMPLE 202 (Production of Compound 202)

Under nitrogen atmosphere, oxalyl chloride (0.19 ml) was added to a solution of 6-(4-methylphenyl)-2-methyl-2H-1-benzopyran-3-carboxylic acid (400 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.4 ml) and (4-aminophenyl)-(2-pyridyl)methanol (310 mg) at 0° C., and the mixture was stirred at room temperature for 20 hours. The reaction mixture was added to vigorously stirred water to stop the reaction. was extracted with ethyl acetate. The organic layer was washed with saturated sodium chloride solution, dried with magnesium sulfate and concentrated. Precipitated crystal was recrystallized from tetrahydrofuran-hexane to give N-[4-[hydroxy(2-pyridyl)methyl]-phenyl]-6-(4-methylphenyl)-2-methyl-2H-1-benzopyran-3-carboxamide (Compound 202) (470 mg) as yellow crystals.

m.p. 202–205° C.; $^1$H-NMR (200 MHz, CDCl$_3$) δ 1.47 (3H, d, J=6.6 Hz), 2.39 (3H, s), 5.29–5.38 (1H, m), 5.48 (1H, q, J=6.6 Hz), 5.74 (1H, br s), 6.94 (1H, d, J=8.0 Hz), 7.08–7.26 (5H, m), 7.33–7.67 (10H, m), 8.57 (1H, d, J=4.6 Hz). IR (KBr) 3255, 1647, 1597, 1518, 1485, 1412, 1317, 1255, 812, 756 cm$^{-1}$; Elemental Analysis for C$_{30}$H$_{26}$N$_2$O$_3$.0.2H$_2$O; Calcd. C, 77.30; H, 5.70; N, 6.01: Found. C, 77.31; H, 5.60; N, 6.21.

WORKING EXAMPLE 203 (Production of Compound 203)

To a solution of N-[4-[hydroxy(2-pyridyl)methyl]phenyl]-6-(4-methylphenyl)-2-methyl-2H-1-benzopyran-3-carboxamide (300 mg) in tetrahydrofuran (10 ml) was added 3-chloroperbenzoic acid (70%, 0.24 g) at 0° C., and the mixture was stirred at room temperature for 24hours. To the mixture was added sodium thiosulfate, and the mixture was stirred for a few minutes. was extracted with ethyl acetate. The organic layer was washed with saturated sodium bicarbonate solution and saturated sodium chloride solution, dried with magnesium sulfate and concentrated. The residue was separated and purified with column chromatography (ethanol/ethyl acetate=1:2) to give crystals, which were recrystallized from ethanol-ethyl acetate to give N-[4-[hydroxy(1-oxidopyridin-2-yl)-methyl]phenyl]-6-(4-methylphenyl)-2-methyl-2H-1-benzopyran-3-carboxamide (Compound 203) (129 mg) as pale yellow crystals.

m.p. 230–232° C.; $^1$H-NMR (200 MHz, CDCl$_3$) δ 1.49 (3H, d, J=6.6 Hz), 2.40 (3H, s), 5.50 (1H, q, J=6.6 Hz), 6.07 (1H, d, J=4.5 Hz), 6.40 (1H, d, J=4.5 Hz), 6.93–6.97 (2H, m), 7.12 (1H, s), 7.22–7.29 (4H, m), 7.35 (1H, d, J=2.2 Hz), 7.42–7.50 (5H, m), 7.64 (2H, d, J=8.4 Hz), 7.73 (1H, br s), 8.24–8.28 (1H, m). IR (KBr) 3311, 1664, 1603, 1535, 1485, 1321, 1252, 812 cm$^{-1}$; Elemental Analysis for C$_{30}$H$_{26}$N$_2$O$_4$.0.3H$_2$O; Calcd. C, 74.46; H, 5.54; N, 5.79: Found. C, 74.41; H, 5.46; N, 5.78.

WORKING EXAMPLE 204 (Production of Compound 204)

Under nitrogen atmosphere, oxalyl chloride (0.11 ml) was added to a solution of 6-(4-methylphenyl)-2H-1-benzopyran-3-carboxylic acid (230 mg) in tetrahydrofuran (10 ml) at room temperature. To the mixture was added a drop of DMF, and the mixture was stirred for 1 hour. Under reduced pressure, the solvent was evaporated. The residue was dissolved in tetra-hydrofuran (20 ml), and to the solution were added triethylamine (0.25 ml) and 1-(4-aminobenzyl)phosphorane-1-oxide (200 mg) at 0° C., and the mixture was stirred at room temperature for 20 hours. The reaction mixture was added to vigorously stirred water to stop the reaction. Precipitated crystal was collected by filtration to give N-(4-tetramethylenephosphorylmethylphenyl)-6-(4-methylphenyl)-2H-1-benzopyran-3-carboxamide (Compound 204) (181 mg) as colorless crystals.

m.p.>300° C.; $^1$H-NMR (200 MHz, CDCl$_3$) δ 1.49–2.04 (8H, m), 2.40 (3H, s), 3.22 (2H, d, J=14.4 Hz), 5.12 (2H, s), 6.94 (1H, d, J=8.4 Hz), 7.21–7.29 (4H, m), 7.34–7.50 (5H, m), 7.58 (2H, d, J=8.4 Hz), 8.04–8.07 (1H, m). IR (KBr) 3236, 1657, 1601, 1535, 1518, 1487, 1323, 1255, 1180, 810 cm$^{-1}$; Elemental Analysis for $C_{28}H_{28}NO_3P.0.3H_2O$; Calcd. C, 72.65; H, 6.23; N, 3.03; P, 6.69: Found. C, 72.30; H, 5.90; N, 3.00; P, 6.98.

WORKING EXAMPLE 205 (Production of Compound 205)

Under nitrogen atmosphere, oxalyl chloride (0.12 ml) was added to a solution of 6-(4-methylphenyl)-2H-1-benzopyran-3-carboxylic acid (240 mg) in tetrahydrofuran (10 ml) at room temperature. To the mixture was added a drop of DMF, and the mixture was stirred for 1 hour. Under reduced pressure, the solvent was evaporated. The residue was dissolved in tetra-hydrofuran (20 ml), and to the solution were added triethylamine (0.25 ml) and 1-(4-aminobenzyl)phosphorinane-1-oxide (221 mg) at 0° C., and the mixture was stirred at room temperature for 3 hours. The reaction mixture was added to vigorously stirred water to stop the reaction. The mixture was extracted with chloroform. The organic layer was washed with saturated sodium chloride solution, dried with magnesium sulfate and concentrated under reduced pressure. The residue was recrystallized from ethanol to give N-(4-(pentamethylene)phosphorylmethylphenyl)-6-(4-methylphenyl)-2H-1-benzopyran-3-carboxamide (Compound 205) (257 mg) as yellow crystals.

m.p. 268° C.(dec.); $^1$H-NMR (200 MHz, CDCl$_3$) δ 1.39–2.15 (10H, m), 2.40 (3H, s), 3.14 (2H, d, J=12.8 Hz), 5.12 (2H, s), 6.94 (1H, d, J=8.0 Hz), 7.18–7.49 (9H, m), 7.59 (2H, d, J=8.4 Hz), 8.54 (1H, br s). IR (KBr) 3296, 1660, 1533, 1514, 1323, 1255, 1163, 845, 812 cm$^{-1}$; Elemental Analysis for $C_{29}H_{30}NO_3P$; Calcd. C, 73.87; H, 6.41; N, 2.97; P, 6.57: Found. C, 74.20; H, 6.39; N, 2.78; P, 6.45.

WORKING EXAMPLE 206 (Production of Compound 206)

Under nitrogen atmosphere, oxalyl chloride (0.06 ml) was added to a solution of 6-(4-methylphenyl)-2H-1-benzopyran-3-carboxylic acid (120 mg) in tetrahydrofuran (10 ml) at room temperature. To the mixture was added a drop of DMF, and the mixture was stirred for 1 hour. Under reduced pressure, the solvent was evaporated. The residue was dissolved in tetra-hydrofuran (20 ml). To the solution were added triethylamine (0.2 ml) and 4-[N-methyl-N-(tetrahydropyran-4-yl)aminomethyl]-aniline (109 mg) at 0° C., and the mixture was stirred at room temperature for 4 hours. The reaction mixture was added to vigorously stirred water to stop the reaction. The mixture was extracted with ethyl acetate. The organic layer was washed with saturated sodium chloride solution, dried with magnesium sulfate and concentrated under reduced pressure. The residue was separated and purified with column chromatography (ethanol/ethyl acetate=1:4), and recrystallized from ethyl acetate-hexane to give N-[4-[N-methyl-N-(tetrahydro-pyran-4-yl)aminomethyl]-phenyl]-6-(4-methylphenyl)-2H-1-benzopyran-3-carboxamide (Compound 206) (117 mg) as pale yellow crystals.

m.p. 143–145° C.; $^1$H-NMR (200 MHz, CDCl$_3$) δ 1.62–1.84 (4H, m), 2.21 (3H, s), 2.40 (3H, s), 2.56–2.74 (1H, m), 3.28–3.45 (2H, m), 3.57 (2H, s), 3.98–4.11 (2H, m), 5.12 (2H, d, J=1.0 Hz), 6.94 (1H, d, J=8.4 Hz), 7.15 (1H, br s), 7.21–7.37 (5H, m), 7.39–7.59 (6H, m). IR (KBr) 3280, 2937, 2848, 1649, 1597, 1539, 1489, 1336, 1257, 1138, 1007, 810 cm$^{-1}$; Elemental Analysis for $C_{30}H_{32}N_2O_3$; Calcd. C, 76.90; H, 6.88; N, 5.98: Found. C, 76.56; H, 6.87; N, 6.00.

WORKING EXAMPLE 207 (Production of Compound 207)

Under nitrogen atmosphere, oxalyl chloride (0.06 ml) was added to a solution of 6-(4-methylphenyl)-2H-1-benzopyran-3-carboxylic acid (120m) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (20 ml). To the solution were added triethylamine (0.13 ml) and 4-[N-methyl-N-(tetrahydrothiopyran-4-yl)amino-methyl]aniline (117 mg) at 0° C., and the mixture was stirred at room temperature for 4 hours. The reaction mixture was added to vigorously stirred water to stop the reaction. The mixture was extracted with ethyl acetate. The organic layer was washed with saturated sodium chloride solution, dried with magnesium sulfate and concentrated under reduced pressure. The residue was separated and purified with column chromatography (ethanol/ethyl acetate=1:4), and recrystallized from ethyl acetate-hexane to give N-[4-[N-methyl-N-(tetrahydrothiopyran-4-yl)aminomethyl]phenyl]-6-(4-methylphenyl)-2H-1-benzopyran-3-carboxamide (Compound 207) (125 mg) as pale yellow crystals.

m.p. 169–171° C.; $^1$H-NMR (200 MHz, CDCl$_3$) δ 1.63–1.80 (2H, m), 2.09–2.24 (2H, m), 2.21 (3H, s), 2.40 (3H, s), 2.42–2.56 (1H, m), 2.64–2.74 (4H, m), 3.57 (2H, s), 5.12 (2H, d, J=1.0 Hz), 6.94 (1H, d, J=8.8 Hz), 7.15 (1H, br s), 7.23–7.36 (5H, m), 7.39–7.57 (6H, m). IR (KBr) 3286, 2922, 1649, 1597, 1539, 1336, 1319, 1261, 808 cm$^{-1}$; $C_{30}H_{32}N_2O_2S$; Calcd. C, 74.35; H, 6.65; N, 5.78; S, 6.62: Found. C, 74.25; H, 6.47; N, 5.91; S, 6.52.

WORKING EXAMPLE 208 (Production of Compound 208)

To a solution of (E)-3-[5-(4-methylphenyl)thiophen-2-yl]acrylic acid (400 mg) in tetrahydrofuran (10 ml) was added oxalyl chloride (0.22 ml) at room temperature. To the mixture was added a drop of DMF, and the mixture was stirred for 1 hour. Under reduced pressure, the solvent was evaporated, and the residue was dissolved in tetrahydrofuran (20 ml). To the solution were added triethylamine (0.46 ml) and 4-[N-methyl-N-(tetrahydropyran-4-yl)aminomethyl]aniline (0.40 g) at 0° C., and the mixture was stirred at room temperature for 18 hours. The reaction mixture was added to vigorously stirred water to stop the reaction. The mixture was extracted with chloroform. The organic layer was washed with saturated sodium chloride solution, dried with magnesium sulfate and concentrated under reduced pressure. The residue was recrystallized from ethanol to give (E)-N-[4-[N-methyl-N-(tetrahydropyran-4-yl)aminomethyl]phenyl]-3-[5-(4-methylphenyl)thiophen-2-yl]-acrylic amide (Compound 208) (293 mg) as yellow crystal.

m.p. 199–201° C.; $^1$H-NMR (200 MHz, CD$_3$OD) δ 1.57–1.95 (4H, m), 2.32 (3H, s), 2.36 (3H, s), 2.74–2.96 (1H, m), 3.32–3.47 (2H, m), 3.76 (2H, s), 3.96–4.09 (2H, m), 6.55 (1H, d, J=15.2 Hz), 7.23 (2H, d, J=8.4 Hz), 7.29–7.36 (4H, m), 7.56 (2H, d, J=8.0 Hz), 7.66 (2H, d, J=8.4 Hz), 7.75 (1H, d, J=15.2 Hz). IR (KBr) 3359, 1668, 1608, 1554, 1512, 1363, 802 cm$^{-1}$; Elemental Analysis for $C_{27}H_{30}N_2O_2S.1.2H_2O$; Calcd. C, 69.26; H, 6.97; N, 5.98: Found. C, 69.28; H, 6.90; N, 6.06.

WORKING EXAMPLE 209 (Production of Compound 209)

To a solution of (E)-3-[5-(4-methylphenyl)thiophen-2-yl]acrylic acid (150 mg) in tetrahydrofuran (10 ml) was added oxalyl chloride (0.1 ml) at room temperature. To the mixture was added a drop of DMF, and the mixture was stirred for 1 hour. Under reduced pressure, the solvent was evaporated, and the residue was dissolved in tetrahydrofuran (30 ml). To the solution were added triethylamine (0.2 ml) and 1-(4-aminobenzyl)phosphorinane-1-oxide (150 mg) at 0° C., and the mixture was stirred at room temperature for 16 hours. The reaction mixture was added to vigorously stirred water to stop the reaction. The mixture was extracted with ethyl acetate. The organic layer was washed with saturated sodium chloride solution, dried with magnesium sulfate and concentrated under reduced pressure. The residue was recrystallized from ethanol to give (E)-N-(4-pentamethylenephosphorylmethylphenyl)-3-[5-(4-methylphenyl)-thiophen-2-yl]acrylic amide (Compound 209) (172 mg) as yellow crystals.

m.p. 294–297° C.; $^1$H-NMR (200 MHz, CDCl$_3$) δ 1.35–2.13 (10H, m), 2.29 (3H, s), 3.06 (2H, d, J=13.0 Hz), 6.36–6.48 (1H, m), 7.06–7.17 (6H, m), 7.38–7.49 (4H, m), 7.73 (1H, d, J=15.0 Hz). IR (KBr) 3048, 1672, 1606, 1541, 1512, 1348, 1151, 804 cm$^{-1}$; Elemental Analysis for C$_{26}$H$_{28}$NO$_2$SP; Calcd. C, 69.47; H, 6.28; N, 3.12; P, 6.89: Found. C, 69.48; H, 6.23; N, 3.20; P, 7.17.

WORKING EXAMPLE 210 (Production of Compound 210)

To a solution of (E)-3-[5-(4-methylphenyl)furan-2-yl]acrylic acid (200 mg), 4-[N-methyl-N-(tetrahydropyran-4-yl)aminomethyl]aniline (212 mg) and triethylamine (0.15 ml) in DMF (10 ml) was added diethyl cyanophosphate (0.16 ml) at 0° C., and the mixture was stirred at room temperature for 3 hours. To the mixture was added ethyl acetate, and the mixture was washed with water and saturated sodium chloride solution, dried with magnesium sulfate and concentrated. The residue was separated and purified with column chromatography (ethanol/ethyl acetate=1:50→1:25→1:10) to give (E)-N-[4-[N-methyl-N-(tetrahydropyran-4-yl)aminomethyl]phenyl]-3-[5-(4-methylphenyl)furan-2-yl]acrylic amide (Compound 210) (87 mg) as brown amorphous.

$^1$H-NMR (200 MHz, CDCl$_3$) δ 1.53–1.85 (4H, m), 2.21 (3H, s), 2.38(3H, s), 2.54–2.72 (1H, m), 3.31–3.44 (2H, m), 3.56 (2H, s), 3.98–4.11 (2H, m), 6.52 (1H, d, J=15.4 Hz), 6.67–6.69 (2H, m), 7.22 (2H, d, J=8.0 Hz), 7.29 (2H, d, J=8.4 Hz), 7.41 (1H, s), 7.48–7.64 (5H, m).

WORKING EXAMPLE 211 (Production of Compound 211)

To a solution of (E)-3-[5-(4-methylphenyl)furan-2-yl]acrylic acid (150 mg), 1-(4-aminobenzyl)phosphorinane-1-oxide (161 mg) and triethylamine (0.11 ml) in DMF (10 ml) was added diethyl cyanophosphate (0.12 ml) at 0° C., and the mixture was stirred at room temperature for 3 hours. To the mixture was added ethyl acetate, and the mixture was washed with water and saturated sodium chloride solution, dried with magnesium sulfate and concentrated. The residue was separated and purified with column chromatography (ethanol/ethyl acetate=1:10→1:5→1:4) to give (E)-N-(4-(pentamethylene)phosphorylmethylphenyl)-3-[5-(4-methylphenyl)furan-2-yl]acrylic amide (Compound 211) (53 mg) as brown crystals.

$^1$H-NMR (200 MHz, CDCl$_3$) δ 1.43–2.09 (10H, m), 2.39 (3H, s), 3.15 (2H, d, J=13.2 Hz), 6.58–6.70 (3H, m), 7.16–7.29 (4H, m), 7.48–7.65 (5H, m), 8.24–8.35 (1H, m). IR (KBr) 3292, 1672, 1614, 1541, 1512, 1489, 1412, 1335, 1244, 1120, 787 cm$^{-1}$;

WORKING EXAMPLE 212 (Production of Compound 212)

Under nitrogen atmosphere, oxalyl chloride (0.16 ml) was added to a solution of (E)-3-[4-(4-methylphenyl)thiophen-2-yl]acrylic acid (300 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (10 ml). To the solution were added triethylamine (0.4 ml) and 4-[N-methyl-N-(tetrahydro-pyran-4-yl)aminomethyl]-aniline (298 mg) at 0° C., and the mixture was stirred at room temperature for 3 hours. The reaction mixture was added to vigorously stirred water to stop the reaction. The mixture was extracted with chloroform. The organic layer was washed with saturated sodium chloride solution, dried with magnesium sulfate and concentrated under reduced pressure. The residue was separated and purified with column chromatography (ethanol/ethyl acetate:1:4), and recrystallized from ethanol to give pale yellow crystals, which were recrystallized from tetrahydrofuran-hexane to give (E)-N-[4-[N-methyl-N-(tetrahydropyran- 4-yl)aminomethyl]phenyl]-3-[4-(4-methylphenyl)thiophen-2-yl]acrylamide (Compound 212) (261 mg) as pale yellow crystals.

m.p. 188–190° C.; $^1$H-NMR (200 MHz, CDCl$_3$) δ 1.45–1.83 (4H, m), 2.20 (3H, s), 2.38 (3H, s), 2.55–2.73 (1H, m), 3.31–3.44 (2H, m), 3.56 (2H, s), 3.99–4.10 (2H, m), 6.38 (1H, d, J=15.2 Hz), 7.20–7.32 (5H, m), 7.41–7.58 (6H, m), 7.89 (1H, d, J=15.2 Hz). IR (KBr) 3329, 2954, 1668, 1608, 1554, 1512, 1412, 1360, 1342, 1254, 1174, 1159, 984, 816 cm$^{-1}$; Elemental Analysis for C$_{27}$H$_{30}$N$_2$O$_2$S1.0H$_2$O; Calcd. C, 69.80; H, 6.94; N, 6.03: Found. C, 69.94; H, 6.85; N, 5.98.

WORKING EXAMPLE 213 (Production of Compound 213)

Under nitrogen atmosphere, oxalyl chloride (0.08 ml) was added to a solution of (E)-3-[4-(4-methylphenyl)thiophen-2-yl]acrylic acid (150 mg) in tetrahydrofuran (10 ml) at room temperature. To the mixture was added a drop of DMF, and the mixture was stirred for 1 hour. Under reduced pressure, the solvent was evaporated, and the residue was dissolved in tetrahydrofuran (20 ml). To the solution were added triethylamine (0.2 ml) and 1-(4-aminobenzyl)-phosphorinane-1-oxide (150 mg) at 0° C., and the mixture was stirred at room temperature for 4 hours. The reaction mixture was added to vigorously stirred water to stop the reaction. The mixture was extracted with ethyl acetate. The organic layer was washed with saturated sodium chloride solution, dried with magnesium sulfate and concentrated under reduced pressure. The residue was recrystallized from ethanol to give (E)-N-(4-(penta-methylene)phosphorylmethylphenyl)-3-[4-(4-methylphenyl)thiophen-2-yl]acrylic amide (Compound 213) (138 mg) as pale yellow crystals.

m.p. 279° C.(dec.); $^1$H-NMR (200 MHz, CDCl$_3$) δ 1.49–2.23 (1OH, m), 2.38 (3H, s), 3.15 (2H, d, J=12.8 Hz), 6.61 (1H, d, J=15.2 Hz), 7.13–7.28 (4H, m), 7.38–7.57 (6H, m), 7.86 (1H, d, J=15.2 Hz), 9.09–9.20 (1H, m).

IR (KBr) 3392, 2935, 1672, 1618, 1543, 1512, 1336, 1250, 1161, 818 cm$^{-1}$; Elemental Analysis for C$_{26}$H$_{28}$NO$_2$SP.0.3H$_2$O; Calcd. C, 68.64; H, 6.34; N, 3.08; P, 6.81: Found. C, 68.44; H, 6.30; N, 3.06; P, 6.65.

WORKING EXAMPLE 214 (Production of Compound 214)

Under nitrogen atmosphere, oxalyl chloride (0.12 ml) was added to a solution of 2-(4-methylphenyl)-7,8-dihydro-6H- cyclohepta[b]thiophene-5-carboxylic acid (250 mg) in tetrahydrofuran (10 ml) at room temperature. To the mixture was added a drop of DMF, and the mixture was stirred for 2 hours. Under reduced pressure, the solvent was evaporated, and the residue was dissolved in tetrahydrofuran (20 ml). To the solution were added triethylamine (0.25 ml) and 4-[N-methyl-N-(tetrahydropyran-4-yl)aminomethyl] aniline (215 mg) at 0° C., and the mixture was stirred at room temperature for 4 hours. The reaction mixture was added to vigorously stirred water to stop the reaction. The mixture was extracted with chloroform. The organic layer was washed with saturated sodium chloride solution, dried with magnesium sulfate and concentrated. The residue was purified with column chromatography (ethanol/ethyl acetate=1:4) and recrystallized from ethanol to give N-[4-[N-methyl-N-(tetrahydropyran-4-yl)aminomethyl]phenyl]-2-(4-methylphenyl)-7,8-dihydro-6H-cyclohepta[b] thiophene-5-carboxamide (Compound 214) (319 mg) as colorless crystals.

m.p. 201–203° C.; $^1$H-NMR (200 MHz, CDCl$_3$) δ 1.62–1.84 (4H, m), 2.06–2.18 (2H, m), 2.21 (3H, s), 2.36 (3H, s), 2.53–2.71 (1H, m), 2.79–2.87 (2H, m), 3.06–3.15 (2H, m), 3.31–3.44 (2H, m), 3.57 (2H, s), 3.97–4.08 (2H, m), 7.08 (1H, s), 7.14–7.22 (3H, m), 7.30 (2H, d, J=8.8 Hz), 7.43 (2H, d, J=8.0 Hz), 7.50–7.56 (3H, m). IR (KBr) 3311, 2943, 1649, 1518, 1408, 1311, 810 cm$^{-1}$; Elemental Analysis for C$_{30}$H$_{34}$N$_2$O$_2$S; Calcd. C, 74.04; H, 7.04; N, 5.76; S, 6.59: Found. C, 73.92; H, 6.85; N, 5.70; S, 6.53.

WORKING EXAMPLE 215 (Production of Compound 215)

To a solution of (E)-3-[5-(4-methylphenyl)pyridin-3-yl] acrylic acid (150 mg), 4-[N-methyl-N-(tetrahydropyran-4-yl)aminomethyl]aniline (168 mg) and triethylamine (0.10 ml) in DMF (10 ml) was added diethyl cyanophosphate (0.12 ml) at 0° C., and the mixture was stirred at room temperature for 3 hours and concentrated under reduced pressure. To the residue was added water, the mixture was extracted with chloroform. The organic layer was washed with saturated sodium chloride solution, dried with magnesium sulfate and concentrated under reduced pressure. The residue was separated and purified with column chromatography (ethanol/ethyl acetate=1:2) to give (E)-N-[4-[N-methyl-N-(tetrahydropyran-4-yl)aminomethyl]phenyl]-3-[5-(4-methylphenyl)pyridin-3-yl]acrylic amide (Compound 215) (24 mg) as yellow solid.

$^1$H-NMR (200 MHz, CDCl$_3$) δ 1.66–1.83 (4H, m), 2.21 (3H, s), 2.43 (3H, s), 2.53–2.74 (1H, m), 3.30–3.45 (2H, m), 3.57 (2H, s), 3.99–4.10 (2H, m), 6.69 (1H, d, J=15.5 Hz), 7.24–7.37 (4H, m), 7.41–7.63 (5H, m), 7.82 (1H, d, J=15.5 Hz), 7.95–8.01 (1H, m), 8.74 (1H, d, J=1.8 Hz), 8.81 (1H, d, J=2.2 Hz). IR (KBr) 3242, 3190, 1678, 1606, 1545, 1514, 1348, 976, 816 cm$^{-1}$.

WORKING EXAMPLE 216 (Production of Compound 216)

To a solution of 6-(4-methylphenyl)-2-methylquinoline-3-carboxylic acid (120 mg) and 1-hydroxybenzotriazole (88 mg) in DMF (5 ml) was added 1-ethyl-3-(3'-dimethylaminopropyl)carbodiimide hydrochloride (125 mg) at room temperature, and the mixture was stirred for 2 hours. To the mixture was added a solution of 4-[N-methyl-N-(tetrahydropyran-4-yl)aminomethyl]aniline (105 mg) and triethylamine (0.2 ml) in DMF (5 ml), and the mixture was stirred for 18 hours and concentrated under reduced pressure. To the residue was added water, and the mixture was extracted with chloroform. The organic layer was washed with saturated sodium chloride solution, dried with magnesium sulfate and concentrated under reduced pressure. The residue was separated and purified with column chromatography (ethanol/ethyl acetate=1:2), and recrystallized from ethyl acetate-hexane to give N-[4-[N-methyl-N-(tetrahydropyran-4-yl)aminomethyl]phenyl]-6-(4-methylphenyl)-2-methylquinoline-3-carboxamide (Compound 216) (82 mg) as pale yellow crystals.

m.p. 157–160° C.; $^1$H-NMR (200 MHz, CDCl$_3$) δ 1.49–1.85 (4H, m), 2.23 (3H, s), 2.43 (3H, s), 2.54–2.76 (1H, m), 2.89 (3H, s), 3.31–3.47 (2H, m), 3.60 (2H, s), 4.00–4.11 (2H, m), 7.25–7.41 (4H, m), 7.55–7.71 (4H, m), 7.83 (1H, br s), 7.88 (1H, d, J=1.8 Hz), 8.01 (1H, dd, J=8.8, 1.8 Hz), 8.09 (1H, d, J=8.8 Hz), 8.21 (1H, s). IR (KBr) 3311, 2958, 1657, 1520, 1313, 110, 847, 812 cm$^{-1}$; Elemental Analysis for C$_{31}$H$_{33}$N$_3$O$_2$·0.3H$_2$O; Calcd. C, 76.76; H, 6.98; N, 8.66: Found. C, 76.68; H, 7.07; N, 8.80.

WORKING EXAMPLE 217 (Production of Compound 217)

In THF (20 ml) was dissolved 7-phenyl-3,4-dihydronaphthalene-2-carboxylic acid (1.00 g), and to the solution were added oxalyl chloride (523 μl) and a drop of DMF. The mixture was stirred at room temperature for 1 hour and concentrated under reduced pressure. The residue was dissolved in THF (20 ml), and to the solution were added 1-(3-aminobenzyl)piperidine (837 mg) and triethylamine (673 μl) at room temperature. The reaction mixture was stirred at room temperature for 2 hours, and to the mixture was added water (100 ml). The mixture was extracted with ethyl acetate. The organic layer was washed with saturated sodium chloride solution, dried with anhydrous sodium sulfate, and concentrated under reduced pressure. The residue was recrystallized from ethyl acetate-diisopropylether to give 7-phenyl-N-[3-(piperidinomethyl)phenyl]-3,4-dihydronaphthalene-2-carboxamide (Compound 217) (1.29 g) as pale yellow crystals.

mp 152–153° C.; Elemental Analysis for C$_{29}$H$_{30}$N$_2$O·0.1H$_2$O; Calcd: C, 82.08; H, 7.17; N, 6.60. Found: C, 81.97; H, 7.27; N, 6.47. IR (KBr) cm$^{-1}$: 3373, 2933, 1645, 1543, 1487, 1439, 770, 696 $^1$H NMR (200 MHz, CDCl$_3$) δ: 1.35–1.70 (6H, m), 2.32–2.45 (4H, m), 2.65–2.80 (2H, m), 2.92–3.03 (2H, m), 3.48 (2H, s), 7.08 (1H, d, J=7.6 Hz), 7.25–7.50 (10H, m), 7.52–7.67 (3H, m).

WORKING EXAMPLE 218 (Production of Compound 218)

In DMF (3 ml) was dissolved 7-phenyl-N-[3-(piperidinomethyl)phenyl]-3,4-dihydronaphthalene-2-carboxamide (200 mg), and to the mixture was added methyl iodide (88 μl). The mixture was stirred at room temperature for 15 hours and concentrated under reduced pressure. The residue was recrystallized from methanol-ethyl acetate to give 1-methyl-1-[3-(7-phenyl-3,4-dihydronaphthalene-2-carboxamido)benzyl]-piperidinium iodide (Compound 218) (211 mg) as colorless crystals.

mp 208–209° C.; Elemental Analysis for C$_{30}$H$_{33}$N$_2$OI; Calcd: C, 63.83; H, 5.89; N, 4.96. Found: C, 63.58; H, 5.89; N, 4.95. IR (KBr) cm$^{-1}$: 3450, 1657, 1520, 1483, 1439, 1250, 1215, 766, 702; $^1$H NMR (200 MHz, DMSO-d$_6$) δ: 1.40–2.00 (6H, m), 2.55–2.70 (2H, m), 2.80–3.00 (5H, m), 3.20–3.40 (4H, m), 4.57 (2H, s), 7.20–7.82 (12H, m), 8.03 (1H, s), 10.14 (1H, s).

WORKING EXAMPLE 219 (Production of Compound 219)

To a solution of 2-(4-methylphenyl)-6,7-dihydro-5H-benzocycloheptene-8-carboxylic acid (0.2 g) in dichloromethane (5 ml) were added oxalyl chloride (0.19 ml) and dimethylformamide (catalytic amount) under ice-cooling, and the mixture was stirred at room temperature for 2 hours. The solvent was evaporated, and the residue was dissolved in tetrahydrofuran. The mixture was added to a solution of 4-(N-methyl-N-(tetrahydropyran-4-yl)aminomethyl)aniline (0.17 g) and triethylamine (0.3 ml) in tetrahydrofuran (10 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and precipitated crude crystal was recrystallized from ethyl acetate-hexane to give 2-(4-methylphenyl)-N-(4-((N-tetrahydropyran-4-yl-N-methyl-amino)methyl)phenyl)-6,7-dihydro-5H-benzocycloheptene-8-carboxamide (Compound 219) (0.29 g) as colorless crystals.

mp 161–162° C.; $^1$H-NMR($\delta$ ppm, CDCl$_3$): 1.59–1.77 (4H, m), 2.13–2.21 (2H, m), 2.21 (3H, s), 2.40 (3H, s), 2.55–2.75 (3H, m), 2.86–2.92 (2H, m), 3.37 (2H, dt, J=2.8, 10.9 Hz), 3.57 (2H, s), 4.01–4.07 (2H, m), 7.21–7.33 (4H, m), 7.41–7.58 (7H, m), 7.63 (1H, s). IR(KBr) $\nu$: 2938, 1651 cm$^{-1}$. Anal. for $C_{32}H_{36}N_2O_2$: Calcd. C,79.97; H,7.55; N,5.83. Found C,79.63; H,7.43; N,5.64.

WORKING EXAMPLE 220 (Production of Compound 220)

A solution of 2-(4-methylphenyl)-N-(4-((N-tetrahydropyran-4-yl-N-methylamino)methyl)phenyl)-6,7-dihydro-5H-benzocycloheptene-8-carboxamide (0.11 g) and methyl iodide (0.02 ml) in dimethylformamide (4 ml) was stirred at room temperature over night. The solvent was evaporated, and to the residue was added ethyl acetate. Precipitated crude crystal was filtered, which was recrystallized from ethanol-ethyl acetate to give N,N-dimethyl-N-(4-((2-(4-methylphenyl)-6,7-dihydro-5H-benzocyclohepten-8-yl)carbonyl)aminobenzyl)-N-(4-tetrahydropyranyl)ammonium iodide (Compound 220) (0.13 g) as pale yellow crystals.

mp 157–158° C.; $^1$H-NMR($\delta$ ppm, DMSO-d$_6$): 1.80–2.20 (6H, m), 2.35 (3H, s), 2.64 (2H, t, J=6.6 Hz), 2.80–2.88 (2H, m), 2.88 (6H, s), 3.33–3.40 (2H, m), 3.50–3.65 (1H, m), 4.02–4.09 (2H, m), 4.47 (2H, s), 7.26–7.37 (4H, m), 7.50–7.60 (5H, m), 7.66 (1H, s), 7.88 (2H, d, J=8.8 Hz), 10.22 (1H, s). IR(KBr) $\nu$: 1659 cm$^{-1}$. Anal. for $C_{33}H_{39}IN_2O_2 \cdot 0.5H_2O$: Calcd. C,62.76; H,6.38; N,4.44. Found C,62.69; H,6.38; N,4.21.

WORKING EXAMPLE 221 (Production of Compound 221)

A solution of 7-(4-piperidinophenyl)-N-(4-((N-tetrahydropyran-4-yl-N-methylamino)methyl)phenyl)-2,3-dihydro-1-benzoxepine-4-carboxamide (0.2 g) and methyl iodide (0.025 ml) in dimethylformamide (5 ml) was stirred at room temperature over night. The solvent was evaporated, and to the residue was added ethyl acetate. Precipitated crude crystal was filtered, which were recrystallized from ethanol-ethyl acetate to give dimethyl(N-(7-(4-piperidinophenyl)-2,3-dihydro-1-benzoxepin-4-carbonyl)-4-aminobenzyl)-4-tetrahydropyranylammonium iodide (Compound 221) (0.1 g) as yellow crystals.

mp 189–190° C.; $^1$H-NMR($\delta$ ppm, DMSO-d$_6$): 1.50–1.70 (6H,m), 1.75–2.00(2H, m), 2.05–2.25 (2H, m), 2.88 (6H, s), 2.99 (2H, br), 3.16–3.19 (4H, m), 3.26–3.33 (2H, m), 3.50–1.70 (1H, m), 4.01–4.15 (2H, m), 4.29 (2H, br), 4.47 (2H, s), 7.00 (2H, d, J=8.8 Hz), 7.03 (1H, d, J=8.4 Hz), 7.35 (1H, s), 7.50–7.57 (5H, m), 7.68 (1H, d, J=2.6 Hz), 7.86 (2H, d, J=8.4 Hz), 10.19 (1H, s). IR(KBr) $\nu$: 2936, 1659 cm$^{-1}$. Anal. for $C_{36}H_{44}IN_3O_3 \cdot H_2O$: Calcd. C,60.76; H,6.51; N,5.90. Found C,60.57; H,6.60; N,5.85.

WORKING EXAMPLE 222 (Production of Compound 222)

To a suspension of 7-(4-methylphenyl)-2,3-dihydro-1-benzoxepine-4-carboxylic acid (0.3 g) in dichloromethane (10 ml) were added oxalyl chloride (0.28 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 4-(N-methyl-N-(tetrahydrothiopyran-4-yl)-aminomethyl)aniline (0.26 g) and triethylamine (0.5 ml) in tetrahydrofuran (20 ml), under ice-cooling. Under nitrogen atmosphere, the mixture was stirred at room temperature for 7 hours. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate) to give crude crystals, which were recrystallized from ethyl acetate-hexane to give N-(4-((N-tetrahydrothiopyran-4-yl-N-methyl)amino-methyl)phenyl)-7-(4-methylphenyl)-2,3-dihydro-1-benzoxepine-4-carboxamide (Compound 222) (0.47 g) as colorless crystals.

mp 180–181° C.; $^1$H-NMR($\delta$ ppm, CDC$_3$): 1.60–1.85 (2H, m), 2.10–2.15 (2H, m), 2.21 (3H, s), 2.39 (3H, s), 2.40–2.50 (1H, m), 2.66–2.72 (4H, m), 3.08 (2H, t, J=4.6 Hz), 3.57 (2H, s), 4.36 (2H, t, J=4.6 Hz), 7.06 (1H, d, J=8.4 Hz), 7.24 (2H, d, J=8.0 Hz), 7.31 (2H, d, J=8.4 Hz), 7.43–7.57 (7H, m). IR(KBr) $\nu$: 2934, 1653 cm$^{-1}$; Anal. for $C_{31}H_{34}N_2O_2S$: Calcd. C,74.66; H,6.87; N,5.62. Found C,74.46; H,6.72; N,5.42.

WORKING EXAMPLE 223 (Production of Compound 223)

A solution of N-(4-((N-tetrahydrothiopyran- 4-yl-N-methyl)aminomethyl)phenyl)-7-(4-methylphenyl)-2,3-dihydro-1-benzoxepine-4-carboxamide (0.11 g) and methyl iodide (0.025 ml) in dimethylformamide (5 ml) was stirred at room temperature over night. The solvent was evaporated, and the residue was purified with silica gel column (chloroform/methanol) to give dimethyl-(N-(7-(4-methylphenyl)-2,3-dihydro-1-benzoxepin-4-carbonyl)-4-aminobenzyl)-4-tetrahydrothiopyranylammonium iodide (Compound 223) (0.09 g) as colorless crystals.

mp 185–186° C.(dec.). $^1$H-NMR($\delta$ ppm, DMSO-d$_6$): 1.75–2.00 (2H, m), 2.34 (3H, s), 2.55–2.75 (4H, m), 2.75–2.85 (2H, m), 2.90 (6H, s), 3.00 (2H, br), 3.14–3.25 (1H, m), 4.31 (2H, br), 4.47 (2H, s), 7.07 (1H, d, J=8.4 Hz), 7.27 (2H, d, J=7.8 Hz), 7.36 (1H, s), 7.50–7.59 (5H, m), 7.74 (1H, d, J=2.2 Hz), 7.86 (2H, d, J=8.8 Hz), 10.19 (1H, s). IR(KBr) $\nu$: 2901, 1659 cm$^{-1}$. Anal. for $C_{32}H_{37}N_2O_2SI \cdot H_2O$: Calcd. C,58.36; H,5.97; N,4.25. Found C,58.62; H,6.04; N,4.29.

WORKING EXAMPLE 224 (Production of Compound 224)

To a solution of 2-(4-piperidinophenyl)-6,7-dihydro-5H-benzocycloheptene-8-carboxylic acid (0.45 g), 4-(N- methyl-N-(tetrahydropyran-4-yl)aminomethyl)aniline (0.31 g) and 1-hydroxybenzotriazole (0.18 g) in dimethylformamide (20 ml) was added 1-ethyl-3-(3-dimethylaminopropyl)carbodiimide hydro-chloride (0.37 g) under ice-cooling. Under nitrogen atmosphere, the mixture was warmed to room temperature. To the mixture were added 4-dimethylaminopyridine (catalytic amount) and triethylamine (0.54 ml), and the mixture was stirred over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/methanol/triethylamine) to give crude crystals, which were recrystallized from ethyl acetate-hexane to give 2-(4-piperidinophenyl)-N-(4-((N-tetrahydropyran-4-yl-N-methylamino)methyl)phenyl)-6,7-dihydro-5H-benzocyclohepten-8-carboxamide (Compound 224) (0.44 g) as pale orange crystals.

mp 170–171° C.; $^1$H-NMR($\delta$ ppm, CDCl$_3$): 1.59–1.65 (2H, m), 1.65–1.80 (8H, m), 2.05–2.21 (2H, m), 2.21 (3H, s), 2.55–2.68 (1H, m), 2.71 (2H, t, J=6.3 Hz), 2.84–2.90 (2H, m), 3.19–3.24 (4H, m), 3.37 (2H, dt, J=2.8, 11.2 Hz), 4.01–4.11 (2H, m), 7.00 (2H, d, J=8.8 Hz), 7.20 (1H, d, J=7.6 Hz), 7.31 (2H, d, J=8.4 Hz), 7.41–7.51 (4H, m), 7.56 (2H, d, J=8.4 Hz), 7.63 (1H, s). IR(KBr) v: 2936, 1661 cm$^{-1}$. Anal. for C$_{36}$H$_{43}$N$_3$O$_2$.0.2H$_2$O: Calcd. C,78.14; H,7.91; N,7.59. Found C,78.09; H,7.93; N,7.55.

WORKING EXAMPLE 225 (Production of Compound 225)

A solution of 2-(4-piperidinophenyl)-N-(4-((N-tetrahydropyran-4-yl-N-methylamino)methyl)phenyl)-6,7-dihydro-5H-benzocycloheptene-8-carboxamide (0.2 g) and methyl iodide (0.025 ml) in dimethylformamide (10 ml) was stirred at room temperature over night. The solvent was evaporated, and the residue was purified with silica gel column (chloroform/methanol) to give crude crystals, which were recrystallized from ethanol-hexane to give dimethyl-(N-(2-(4-piperidinophenyl)-6,7-dihydro-5H-benzocycloheptene-8-carbonyl)-4-aminobenzyl)-4-tetrahydropyranylammonium iodide (Compound 225) (0.15 g) as pale brown crystals.

mp 177–178 C.; $^1$H-NMR($\delta$ ppm, DMSO-d$_6$): 1.50–1.70 (6H, m), 1.80–1.95 (2H, m), 2.00–2.10 (2H, m), 2.10–2.20 (2H, m), 2.60–2.70 (2H, m), 2.75–2.87 (2H, m), 2.88 (6H, s), 3.14–3.24 (6H, m), 3.53–3.65 (1H, m), 4.00–4.15 (2H, m), 4.46 (2H, s), 7.00 (2H, d, J=8.8 Hz), 7.26 (1H, d, J=8.0 Hz), 7.36 (1H, s), 7.46–7.62 (6H, m), 7.87 (2H, d, J=8.8 Hz), 10.22 (1H, s). IR(KBr) v: 2934, 1655 cm$^{-1}$. Anal. for C$_{37}$H$_{46}$N$_{13}$O$_2$.H$_2$O: Calcd. C,62.62; H,6.82; N,5.92. Found C,62.32; H,6.71; N,5.92.

WORKING EXAMPLE 226 (Production of Compound 226)

Under nitrogen atmosphere, oxalyl chloride (0.05 ml) was added to a solution of 7-(4-methylthiophenyl)-2,3-dihydro-1-benzoxepine-4-carboxylic acid (80.6 mg) in tetrahydrofuran (10 ml) at room temperature. To the mixture was added a drop of DMF, and the mixture was stirred for 1 hour. Under reduced pressure, the solvent was evaporated. The residue was dissolved in tetrahydrofuran (20 ml). To the solution were added triethylamine (0.1 ml) and 4-[N-methyl-N-(tetrahydropyran-4-yl)aminomethyl]aniline (62.5 mg) at 0° C., and the mixture was stirred at room temperature for 3 hours. The reaction mixture was added to vigorously stirred water to stop the reaction. The mixture was extracted with ethyl acetate. The organic layer was washed with saturated sodium chloride solution, dried with magnesium sulfate and concentrated. The residue was purified with column chromatography (ethanol/ethyl acetate=1:4) and recrystallized from ethanol to give N-[4-[N-methyl-N-(tetrahydropyran-4-yl)aminomethyl]-phenyl]-7-(4-methylthiophenyl)-2,3-dihydro-1-benzoxepine-4-carboxamide (Compound 226) (85 mg) as colorless crystals.

m.p. 180–186° C.; $^1$H-NMR (200 MHz, CDCl$_3$) $\delta$ 1.53–1.81 (4H, m), 2.21 (3H, s), 2.52 (3H, s), 2.54–2.73 (1H, m), 3.08 (2H, t, J=4.6 Hz), 3.31–3.43 (2H, m), 3.57 (2H, s), 3.98–4.10 (2H, m), 4.36 (2H, t, J=4.6 Hz), 7.06 (1H, d, J=8.4 Hz), 7.23–7.36 (4H, m), 7.41–7.63 (8H, m). IR (KBr) 3319, 2947, 1645, 1516, 1485, 1315, 1248, 1140, 1086, 812 cm$^{-1}$; Elemental Analysis for C$_{31}$H$_{34}$N$_2$O$_3$S.0.2H$_2$O; Calcd. C, 71.84; H, 6.69; N, 5.40; S, 6.19: Found. C, 71.75; H, 6.70; N, 5.38; S, 6.24.

REFERENCE EXAMPLE 49

To 3-bromocinnamic acid (2.0 g) were added thionyl chloride (25 ml) and dimethylformamide (catalytic amount), and the mixture was refluxed for 1.5 hours. The solvent was evaporated, and the residue was dissolved in tetrahydrofuran. The mixture was dropwise added to a suspension of 1-(4-aminobenzyl)piperidine (1.7 g) and diisopropylethylamine (4 ml) in tetrahydrofuran (5 ml) under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (methanol/triethylamine/ethyl acetate) to give crude crystals, which were recrystallized from ethyl acetate-hexane to give 1-(4-(3-bromocinnamoylamino)benzyl)piperidine (1.8 g) as colorless crystals.

mp 144–145° C.; $^1$H-NMR($\delta$ ppm, CDCl$_3$): 1.37–1.49 (2H, m), 1.52–1.63 (4H, m), 2.34–2.39 (4H, m), 3.45 (2H, s), 6.54 (1H, d, J=15.5 Hz), 7.21–7.33 (3H, m), 7.41–7.57 (5H, m), 7.67 (1H, d, J=15.5 Hz), 7.69 (1H, s). IR(KBr) v: 3270, 2934, 1663 cm$^{31\ 1}$. Anal. for C$_{21}$H$_{23}$BrN$_2$O.0.2H$_2$O: Calcd. C,62.60; H,5.85; N,6.95. Found C,62.67; H,5.79; N,6.93.

REFERENCE EXAMPLE 50

To 3-phenylcinnamic acid (0.24 g) were added thionyl chloride (10 ml) and dimethylformamide (catalytic amount), and the mixture was refluxed for 2 hours. The solvent was evaporated, and the residue was dissolved in tetrahydrofuran. The mixture was dropwise added to a suspension of 2-(4-aminobenzyl)-1,3,2-dioxaphosphorinane-2-oxide (0.2 g) and diisopropylethylamine (0.8 ml) in tetrahydrofuran (20 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and precipitated crude crystal was recrystallized from ethanol-hexane to give 2-(4-(3-phenylcinnamoylamino)benzyl)-1,3,2-dioxaphosphorinane-2-oxide (0.32 g) as colorless crystals.

mp 204–205r° C.; $^1$H-NMR($\delta$ ppm, CDCl$_3$): 1.84–1.88 (2H, m), 3.24 (2H, d, J=21.2 Hz), 4.07–4.22 (2H, m), 4.34–4.44 (2H, m), 6.74 (1H, d, J=15.8 Hz), 7.23 (2H, dd, J=2.6, 8.8 Hz), 7.38–7.63 (10H, m), 7.77 (1H, s), 7.81 (1H, d, J=15.8 Hz), 8.16 (1H, br). IR(KBr) ν: 3059, 1680 cm$^{-1}$. Anal. for $C_{25}H_{24}NO_4P$: Calcd. C,69.28; H,5.58; N,3.23. Found C,68.82; H,5.58; N,3.30.

REFERENCE EXAMPLE 51

To a suspension of 7-(4-methylphenyl)-2,3-dihydro-1-benzoxepine-4-carboxylic acid (0.15 g) in dichloromethane (7 ml) were added oxalyl chloride (0.14 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of 2-(4-aminobenzyl)-1,3,2-dioxaphosphorinane-2-oxide (0.13 g) and triethylamine (0.23 ml) in tetrahydrofuran (20 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-ethanol-hexane to give 2-(4-(7-(4-methylphenyl)-2,3-dihydro-1-benzoxepin-4-carbonylamino)benzyl)-1,3,2-dioxaphosphorinane-2-oxide (0.23 g) as colorless crystals.

mp 268–269° C.; $^1$H-NMR(δ ppm, CDCl$_3$): 1.75–1.87 (2H, m), 2.40 (3H, s), 3.09 (2H, t, J=4.5 Hz), 3.24 (2H, d, J=21.6 Hz), 4.02–4.19 (2H, m), 4.34–4.50 (4H, m), 7.06 (1H, d, J=8.4 Hz), 7.23–7.32 (4H, m), 7.44–7.60 (6H, m), 7.81 (1H, s). IR(KBr) ν: 1652 cm$^{-1}$. Anal. for $C_{28}H_{26}NO_5P$: Calcd. C,68.70; H,5.77; N,2.86. Found C,68.54; H,5.71; N,2.86.

REFERENCE EXAMPLE 52

A suspension of N-(4-chloromethylphenyl)-7-(4-methylphenyl)-2,3-dihydro-1-benzoxepine-4-carboxamide (0.18 g), 1-t-butoxycarbonyl-4-methylaminopiperidine (0.19 g) and potassium carbonate (0.18 g) in dimethylformamide (10 ml) was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-((N-(1-t-butoxycarbonylpiperidin-4-yl)-N-methyl)aminomethyl)phenyl)-7-(4-methylphenyl)-2,3-dihydro-1-benzoxepine-4-carboxamide (0.25 g) as colorless crystals.

mp 203–204° C.; $^1$H-NMR(δ ppm, CDCl$_3$): 1.37–1.70 (4H, m), 1.46 (9H, s), 1.77–1.83 (2H, m), 2.19 (3H, s), 2.39 (3H, s), 2.52–2.74 (3H, m), 3.08 (2H, t, J=4.6 Hz), 3.56 (2H, s), 4.18 (1H, br), 4.36 (2H, t, J=4.6 Hz), 7.06 (1H, d, J=8.4 Hz), 7.22–7.33 (5H, m), 7.43–7.61 (6H, m). IR(KBr) ν: 2977, 2933, 1695, 1668 cm$^{31}$ $^1$. Anal. for $C_{36}H_{43}N_3O_4$: Calcd. C,74.33; H,7.45; N,7.22. Found C,74.00; H,7.41; N,7.26.

REFERENCE EXAMPLE 53

To a suspension of 7-(4-methylphenyl)-2,3-dihydro-1-benzoxepine-4-carboxylic acid (0.6 g) in dichloromethane (25 ml) were added oxalyl chloride (0.56 ml) and dimethylformamide (catalytic amount) under ice-cooling, and the mixture was stirred at room temperature for 2 hours. The solvent was evaporated, and the residue was dissolved in tetrahydrofuran. The mixture was dropwise added to a solution of (4-aminophenyl)[1-(tert-butoxycarbonyl)piperidin-2-yl]methanone (0. 72 g) and triethylamine (0.9 ml) in tetrahydrofuran (50 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give crude crystals, which were recrystallized from ethyl acetate-hexane to give N-(4-(1-(tertbutoxycarbonyl)piperidin-2-ylcarbonyl)-phenyl)-7-(4-methylphenyl)-2,3-dihydro-1-benzoxepine-4-carboxamide (1.1 g) as pale yellow crystals.

mp 223–224° C.; $^1$H-NMR(δ ppm, CDCl$_3$): 1.44 (9H, br), 1.44–1.65 (4H, m), 1.70–1.95 (1H, m), 2.00–2.20 (1H, m), 2.39 (3H, s), 3.08 (2H, t, J=4.4 Hz), 5.60 (1H, br), 7.06 (1H, d, J=8.4 Hz), 7.25 (2H, d, J=11.8 Hz), 7.44–7.53 (4H, m), 7.65 (1H, br), 7.69 (1H, br), 7.82 (1H, br), 7.94 (2H, d, J=8.8 Hz). IR(KBr) ν: 2942, 1678 cm$^{-1}$. Anal. for $C_{35}H_{38}N_2O_5 \cdot 0.3H_2O$: Calcd. C,73.48; H,6.80; N,4.90. Found C,73.51; H,6.60; N,4.68.

REFERENCE EXAMPLE 54

To a mixture of 3-bromobenzaldehyde (10 g) and methoxy-carbonylmethylenetriphenylphosphine (20 g) was added toluene (150 ml), and the mixture was refluxed under nitrogen atmosphere for 2 hours. The solvent was evaporated, and the organic layer was washed with water and saturated sodium chloride solution, and dried with anhydrous magnesium sulfate. Under reduced pressure, the solvent was evaporated, and the residue was purified with silica gel column (ethyl acetate/hexane) to give methyl 3-bromocinnamate (10.7 g) as colorless crystals.

$^1$H-NMR(δ ppm, CDCl$_3$): 3.82 (3H, s), 6.44 (1H, d, J=16.0 Hz), 7.27 (1H, d, J=15.6 Hz), 7.43–7.54 (2H, m), 7.62 (1H, d, J=16.0 Hz), 7.66–7.68 (1H, m). IR(KBr) ν: 1734, 1717 cm$^{-1}$. Anal. for $C_{10}H_9BrO_2$: Calcd. C,49.82; H,3.76. Found C,49.90; H,3.90.

REFERENCE EXAMPLE 55

In a solution of methanol (200 ml) and 2N sodium hydroxide (50 ml) was dissolved methyl 3-bromocinnamate (10.7 g), and the mixture was stirred at room temperature over night, concentrated and neutralized with 1N hydrochloric acid. The mixture was extracted with ethyl acetate. The organic layer was washed with water and saturated sodium chloride solution, and dried with anhydrous magnesium sulfate. Under reduced pressure, the solvent was evaporated to give 3-bromophenylcinnamic acid (9.2 g) as colorless crystals.

$^1$H-NMR(δ ppm, CDCl$_3$): 6.45 (1H, d, J=15.8 Hz), 7.28 (1H, t, J=7.7 Hz), 7.45–7.56 (2H, m), 7.67–7.75 (2H, m). IR(KBr) ν: 1688 cm$^{-1}$. Anal. for $C_9H_7BrO_2$: Calcd. C,47.61; H,3.11. Found C,47.57; H,3.10.

REFERENCE EXAMPLE 56

A suspension of methyl 3-bromocinnamate (3.8 g), phenyl borate (2.0 g), 1M potassium carbonate (20 ml) and ethanol (10 ml) in toluene(100 ml) was stirred under argon atmosphere at room temperature for 30 minutes. To the reaction mixture was added tetrakistriphenylphosphine-palladium (0.9 g), and the mixture was refluxed over night and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give colorless crystals (3.6 g), 1.8 g of which was dissolved in a solution of methanol (100 ml) and 1N sodium hydroxide (20 ml). The mixture was stirred at room temperature over night, concentrated, neutralized with 1N hydrochloric acid and extracted with ethyl acetate. The organic layer was washed with water and saturated sodium chloride solution, and dried with anhydrous magnesium sulfate. Under reduced pressure, the solvent was evaporated to give 3-phenylcinnamic acid (1.5 g) as colorless crystals.

$^1$H-NMR($\delta$ ppm, CDCl$_3$): 6.54 (1H, d, J=16.0 Hz), 7.39–7.67 (8H, m), 7.76–7.77 (1H,m), 7.87 (1H,d,J=16.0 Hz). IR(KBr) $\nu$ 1709 cm$^{-1}$. Anal. for C$_{15}$H$_{12}$O$_2$: Calcd. C,80.34; H,5.39. Found C,80.62; H,5.40.

REFERENCE EXAMPLE 57

To 4-nitrobenzylphosphonic acid (0.5 g) were added thionyl chloride (5 ml) and dimethylformamide (catalytic amount), and the mixture was refluxed under nitrogen atmosphere for 4 hours. The solvent was evaporated, and to the residue was added toluene. The solvent was evaporated. The residue was dissolved in tetrahydrofuran (15 ml), and the mixture was cooled to −78° C. under nitrogen atmosphere. To the mixture was dropwise added dimethylpropanediamine (0.3 ml) dissolved in tetrahydrofuran (2 ml) and then triethylamine (1.6 ml), and the mixture was gradually warmed to room temperature and stirred at room temperature over night. The solvent was evaporated, and the residue was purified with silica gel column (ethyl acetate/methanol/triethylamine) to give colorless crystals, which were dissolved in ethanol (15 ml). To the mixture was added 10% palladium on carbon (0.04 g), and catalytic hydrogenation was carried out at room temperature for 3.5 hours. The catalyst was filtered off, and the solvent was evaporated to give 2-(4-aminobenzyl)-1,3-dimethyl-1,3,2-diazaphosphorinane-2-oxide (0.3 g) as colorless crystals.

$^1$H-NMR($\delta$ ppm, CDCl$_3$): 1.09–1.27 (1H, m), 1.68–1.85 (1H, m), 2.65 (3H, s), 2.69 (3H, s), 2.72–3.01 (4H, m), 3.08 (2H, d, J=17.4 Hz), 6.65 (2H, d, J=8.1 Hz), 6.96 (2H, dd, J=2.4, 8.1 Hz). IR(KBr) $\nu$: 3339, 2897, 1615 cm$^{-1}$. Anal. for C$_{12}$H$_{20}$N$_3$OP.0.3H$_2$O: Calcd. C, 55.72; H, 8.03; N, 16.24. Found C, 55.69; H, 7.98; N, 16.13.

REFERENCE EXAMPLE 58

To 4-nitrobenzylphosphonic acid (0.5 g) were added thionyl chloride (5 ml) and dimethylformamide (catalytic amount), and the mixture was refluxed for 3 hours under nitrogen atmosphere. The solvent was evaporated, and to the residue was added toluene. The solvent was evaporated. The residue was dissolved in tetrahydrofuran (5 ml), and the mixture was cooled to −78° C. under nitrogen atmosphere. To the mixture was dropwise added dimethylethylenediamine (0.25 ml) dissolved in tetrahydrofuran (2 ml), and then triethylamine (1.5 ml), and the mixture was gradually warmed to room temperature and stirred at room temperature over night. The solvent was evaporated, and the residue was purified with silica gel column (ethyl acetate/methanol/triethylamine) to give colorless crystals, which were dissolved in ethanol (15 ml). To the mixture was added 10% palladium on carbon (0.05 g), and catalytic hydrogenation was carried out at room temperature for 3 hours. The catalyst was filtered off, and the solvent was evaporated to give 2-(4-aminobenzyl)-1,3-dimethyl-1,3,2-diazaphosphorane-2-oxide (0.3 g) as yellow crystals.

$^1$H-NMR($\delta$ ppm, CDCl$_3$): 2.61 (3H, s), 2.63–2.71 (2H, m), 2.66 (3H, s), 3.00–3.07 (2H, m), 3.13 (2H, d, J=18.2 Hz), 6.63 (2H, d, J=8.5 Hz), 6.97 (2H, dd, J=2.4, 8.5 Hz). IR(KBr) $\nu$: 3341, 2895, 1632 cm$^{-1}$. Anal. for C$_{11}$H$_{18}$N$_3$OP.0.5H$_2$O: Calcd. C, 53.22; H, 7.71; N, 16.93. Found C, 53.23; H, 7.53; N, 16.83.

REFERENCE EXAMPLE 59

A suspension of $^3$-bromo-6,7,8,9-tetrahydro-5H-benzocycloheptan-5-one (4.6 g; L. A. M. Cornelius and D. W. Combs, Synth. Commun. (1994), 24(19), 2777–2788), 4-methylphenyl borate (3.8 g), 2M potassium carbonate (30 ml) and ethanol (30 ml) in toluene (100 ml) was stirred under argon atmosphere at room temperature for 30 minutes. To the reaction mixture was added tetrakistriphenylphosphinepalladium (1.5 g), and the mixture was refluxed over night and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give pale brown oil (5.7 g), to which were added sodium methoxide (6.2 g) and dimethyl carbonate (100 ml). The mixture was refluxed under nitrogen atmosphere for 8 hours and poured into 1N hydrochloric acid under ice-cooling. The mixture was extracted with ethyl acetate. The organic layer was washed with water and saturated sodium chloride solution, and dried with anhydrous magnesium sulfate. The solvent was evaporated, and the residue was purified with silica gel column (ethyl acetate/hexane) to give brown oil (5.5 g), which was dissolved in dichloromethane (20 ml). To the mixture was dropwise added sodium boron hydride dissolved in methanol, under ice-cooling. After starting materials disappeared, water was added to the reaction mixture, and the mixture was concentrated and extracted with ethyl acetate. The organic layer was washed with water and saturated sodium chloride solution, and dried with anhydrous magnesium sulfate. The solvent was evaporated, and to the residue were added iN sodium hydroxide (40 ml), methanol (40 ml) and diethylether (100 ml). The mixture was heated to 50° C. for 30 minutes and concentrated. To the residue was added 1N sodium hydroxide, and the mixture was extracted with water, washed with ethyl acetate and acidified with hydrochloric acid. The mixture was extracted with ethyl acetate. The organic layer was washed with water and saturated sodium chloride solution, and dried with anhydrous magnesium sulfate. The solvent was evaporated, and the residue was dissolved in Diglyme(20 ml). To the mixture was added hydrochloric acid (5 ml), and the mixture was heated to 100° C. for 6 hours and poured into water. The mixture was extracted with ethyl acetate. The organic layer was washed with water and saturated sodium chloride solution, and dried with anhydrous magnesium sulfate. The solvent was evaporated to give 2-(4-methylphenyl)-6,7-dihydro-5H-benzocycloheptene-8-carboxylic acid (0.3 g) as colorless crystals.

$^1$H-NMR($\delta$ ppm, CDCl$_3$): 2.07–2.16 (2H, m), 2.40 (3H, s), 2.70 (2H, t, J=6.6 Hz), 2.86–2.91 (2H, m), 7.21–7.28 (3H, m), 7.44–7.56 (4H, m), 7.91 (1H, s). IR(KBr) $\nu$: 2930, 1678 cm$^{-1}$. Anal. for C$_{19}$H$_{18}$O$_2$: Calcd. C, 81.99; H, 6.52. Found C, 81.64; H, 6.41.

REFERENCE EXAMPLE 60

In dimethylformamide (100 ml) was added 4-bromothiophenol (25 g). To the solution were added ethyl 4-bromobutyrate (30 g) and potassium carbonate (36 g), and the mixture was stirred at room temperature over night. The solvent was evaporated, and to the residue was added water. The mixture was extracted with ethyl acetate. The organic layer was washed with and saturated sodium chloride solution, and dried with anhydrous magnesium sulfate. The solvent was evaporated, and to the residue were added 1N sodium hydroxide (240 ml) and methanol (120 ml). The mixture was stirred at room temperature over night and concentrated. The residue was dissolved in water, and the mixture was washed with ethyl acetate. The aqueous layer was acidified with hydrochloric acid under ice-cooling. The mixture was extracted with ethyl acetate. The organic layer was washed with and saturated sodium chloride solution, and dried with anhydrous magnesium sulfate. The solvent was evaporated to give colorless crystals (32 g), to which was added polyphosphoric acid (250 g), and the mixture was stirred at 100° C. for 1 hour and poured into ice-water. The mixture was extracted with ethyl acetate. The organic layer was washed with water, sodium hydrogen carbonate solution, water and saturated sodium chloride solution, and dried with anhydrous magnesium sulfate. The solvent was evaporated to give brown crystals (13.6 g), to which were added sodium methoxide (14.2 g) and dimethyl carbonate (200 ml), and the mixture was refluxed under nitrogen atmosphere for 8 hours. Under ice-cooling, the mixture was poured into 1N hydrochloric acid. The mixture was extracted with ethyl acetate. The organic layer was washed with and saturated sodium chloride solution, and dried with anhydrous magnesium sulfate. the solvent was evaporated to give brown crystals (11.5 g), which were dissolved in dichloromethane (100 ml). To the mixture was dropwise added sodium boron hydride dissolved in methanol, under ice-cooling. After starting materials disappeared, water was added to the reaction mixture, and the mixture was concentrated and extracted with ethyl acetate. The organic layer was washed with and saturated sodium chloride solution, and dried with anhydrous magnesium sulfate. The solvent was evaporated, and to the residue were added 1N sodium hydroxide (100 ml), methanol (100 ml) and diethylether (500 ml). The mixture was stirred at room temperature for 1.5 hours and concentrated. To the residue was added 1N sodium hydroxide, and the mixture was extracted with water, washed with diethylether and acidified with hydrochloric acid. The mixture was extracted with ethyl acetate. The organic layer was washed with and saturated sodium chloride solution, and dried with anhydrous magnesium sulfate. The solvent was evaporated, and the residue was dissolved in Diglyme (100 ml). To the mixture was added hydrochloric acid (20 ml), and the mixture was heated to 110° C. for 2.5 hours and poured into water. The mixture was extracted with ethyl acetate. The organic layer was washed with and saturated sodium chloride solution, and dried with anhydrous magnesium sulfate. The solvent was evaporated to give colorless crystal (1.1 g), 1 g of which was suspended dichloromethane (15 ml). To the suspension were added oxalyl chloride (1 ml) and dimethylformamide (catalytic amount) under ice-cooling, and the mixture was stirred at room temperature for 2.5 hours. The solvent was evaporated, and the residue was dissolved in tetrahydrofuran. The mixture was dropwise added to a solution of 4-(tertbutyldimethylsilyloxy)aniline (0.76 g) and triethylamine (1.6 ml) in tetrahydrofuran (20 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give brown oil (1.8 g), to which were added 4-methylphenyl borate (0.5 g), 1M potassium carbonate (15 ml), ethanol (15 ml) and toluene(500 ml), and the mixture was stirred under argon atmosphere at room temperature for 30 minutes. To the mixture was added tetrakistriphenylphosphinepalladium (0.2 g), and the mixture was refluxed over night. The mixture was extracted with ethyl acetate, and the organic layer was washed with water and saturated sodium chloride solution, and dried with anhydrous magnesium sulfate. Under reduced pressure, the solvent was evaporated, and the residue was purified with silica gel column (ethyl acetate/hexane) to give colorless crystals (1.3 g), which were dissolved in ethyl acetate (50 ml). To the mixture was added hydrochloric acid (5 ml), and the mixture was stirred at room temperature for 1.5 hours, washed with sodium hydrogen carbonate solution, water, saturated sodium chloride solution, and dried with anhydrous magnesium sulfate. Under reduced pressure, the solvent was evaporated to give 7-(4-methylphenyl)-N-(4-hydroxymethylphenyl)-2,3-dihydro-1-benzothiepine-4-carboxamide (1.0 g) as colorless crystals.

$^1$H-NMR($\delta$ ppm, CDCl$_3$): 2.40 (3H, s), 3.08 (2H, t, J=5.8 Hz), 3.29 (2H, t, J=5.8 Hz), 4.69 (2H, s), 7.24–7.28 (2H, m), 7.35–7.62 (10H, m), 7.71 (1H, br). IR(KBr) v: 3314, 2928, 1649 cm$^{-1}$. Anal. for C$_{25}$H$_{23}$NO$_2$S.0.2H$_2$O: Calcd. C, 74.12; H, 5.82; N, 3.46. Found C, 74.10; H, 5.65; N, 3.47.

REFERENCE EXAMPLE 61

In dimethylformamide (100 ml) was dissolved 4-bromophenol (17.3 g). To the solution were added ethyl 4-bromobutyrate (21.2 g) and potassium carbonate (25 g), and the mixture was stirred at room temperature over night. The solvent was evaporated, and to the residue was added water. The mixture was extracted with ethyl acetate. The organic layer was washed with and saturated sodium chloride solution, and dried with anhydrous magnesium sulfate. The solvent was evaporated, and to the residue were added 3N sodium hydroxide (100 ml)and methanol (60 ml). The mixture was stirred at 70° C. for 30 minutes and concentrated. The residue was dissolved in water, and the mixture was washed with diethylether. The aqueous layer was acidified with hydrochloric acid under ice-cooling, and the mixture was extracted with ethyl acetate. The organic layer was washed with and saturated sodium chloride solution, and dried with anhydrous magnesium sulfate. The solvent was evaporated to give colorless crystal (23.9 g), to 10 g of which was added polyphosphoric acid (120 g). The mixture was stirred at 100° C. for45 minutes and poured into ice-water. The mixture was extracted with ethyl acetate. The organic layer was washed with water, sodium hydrogen carbonate solution, water and saturated sodium chloride solution, and dried with anhydrous magnesium sulfate. The solvent was evaporated, and the residue was purified with silica gel column (ethyl acetate/hexane) to give 7-bromo-2, 3,4,5-tetrahydrobenzoxepin-5-one as yellow oil (6.5 g).

$^1$H-NMR($\delta$ ppm, CDCl$_3$): 2.15–2.29 (2H, m), 2.89 (2H, t, J=7.0 Hz), 4.24 (2H, t, J=6.6 Hz), 6.97 (1H, d, J=8.8 Hz), 7.50 (1H, dd, J=2.6, 8.1 Hz), 7.87 (1H, d, J=2.6 Hz). IR(neat) v: 2969, 1686 cm$^{-1}$.

REFERENCE EXAMPLE 62

To 7-bromo-2,3,4,5-tetrahydrobenzoxepin-5-one (6.5 g) were added 4-methylphenyl borate (4.1 g), 2M potassium carbonate (30 ml), ethanol (30 ml) and toluene (100 ml), and the mixture was stirred under argon atmosphere at room temperature for 30 minutes. To the mixture was added tetrakistriphenylphosphinepalladium (1.3 g), and the mixture was refluxed over night and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give pale yellow crystal (5.7 g), to 3.6 g of which was added sodium methoxide (3.9 g) and dimethyl carbonate (50 ml). Under nitrogen atmosphere, the mixture was refluxed for 8 hours and poured into 1N hydrochloric acid under ice-cooling. The mixture was extracted with ethyl acetate. The organic layer was washed with and saturated sodium chloride solution, and dried with anhydrous magnesium sulfate, and the solvent was evaporated. The residue was purified with silica gel column (ethyl acetate/hexane) to give colorless crystal (3.5 g), 1.8 g of which was dissolved in dichloromethane (25 ml). To the mixture was dropwise added sodium boron hydride dissolved in methanol, under ice-cooling. After starting materials disappeared, water was added to the reaction mixture, and the mixture was concentrated and extracted with ethyl acetate. The organic layer was washed with and saturated sodium chloride solution, and dried with anhydrous magnesium sulfate, and the solvent was evaporated. To the residue were added 1N sodium hydroxide (50 ml), methanol (25 ml) and diethylether (25 ml), and the mixture was stirred at room temperature for 30 minutes and concentrated. To the mixture was added 1N sodium hydroxide, and the mixture was extracted with water, washed with diethylether and acidified with hydrochloric acid. The mixture was extracted with ethyl acetate. The organic layer was washed with and saturated sodium chloride solution, and dried with anhydrous magnesium sulfate. The solvent was evaporated, and the residue was dissolved in Diglyme (25 ml). To the mixture was added hydrochloric acid (5 ml), and the mixture was heated at 100° C. for 40 minutes and poured into water. The mixture was extracted with ethyl acetate. The organic layer was washed with and saturated sodium chloride solution, and dried with anhydrous magnesium sulfate. The solvent was evaporated to give 7-(4-methylphenyl)-2,3-dihydro-1-benzoxepine-4-carboxylic acid (1.2 g) as colorless crystals.

mp 255–256° C.; $^1$H-NMR((δ ppm, CDCl$_3$): 2.40 (3H, s), 3.02 (2H, t, J=4.6 Hz), 4.33 (2H, t, J=4.6 Hz), 7.05 (1H, d, J=8.6 Hz), 7.24 (2H, d, J=8.2 Hz), 7.46 (2H, d, J=8.2 Hz), 7.47–7.56 (2H, m), 7.78 (1H, s). IR(KBr) ν: 2996, 1694 cm$^{-1}$. Anal. for C$_{18}$H$_{16}$O$_3$: Calcd. C, 77.12; H, 5.75. Found C, 76.91; H, 5.75.

REFERENCE EXAMPLE 63

In dichloromethane (10 ml) was suspended 7-(4-methylphenyl)-2,3-dihydro-1-benzoxepine-4-carboxylic acid (1.0 g) and to the suspension were added oxalyl chloride (1 ml) and dimethylformamide (catalytic amount) under ice-cooling. The mixture was stirred at room temperature for 3 hours. The solvent was evaporated, and the residue was dissolved in tetrahydrofuran. The mixture was dropwise added to a solution of 4-(tert-butyldimethyl-silyloxy)aniline (0.93 g) and triethylamine (1.5 ml) in tetrahydrofuran (15 ml), under ice-cooling. Under nitrogen atmosphere, the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give colorless oil (1.88 g), which was dissolved in ethyl acetate (20 ml). To the mixture was added hydrochloric acid (5 ml), and the mixture was stirred at room temperature 1.5 hours. The mixture was washed with sodium hydrogen carbonate solution, water and saturated sodium chloride solution, and dried with anhydrous magnesium sulfate. Under reduced pressure, the solvent was evaporated, and the residue was purified with silica gel column (ethyl acetate/hexane) to give colorless crystals (0.9 g), which was suspended in dichloromethane (60 ml). To the suspension were added lithium chloride (0.1 g) and triethylamine (1 ml). To the mixture was dropwise added methanesulfonylchloride (0.3 ml) under ice-cooling, and the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate) to give N-(4-chloromethylphenyl)-7-(4-methylphenyl)-2,3-dihydro-1-benzoxepine-4-carboxamide (0.4 g).

$^1$H-NMR(δ ppm, CDCl$_3$): 2.39 (3H, s), 3.08 (2H, t, J=4.6 Hz), 4.36 (2H, t, J=4.6 Hz), 4.59 (2H, s), 7.06 (1H, d, J=8.4 Hz), 7.22–7.26 (2H, m), 7.36–7.53 (6H, m), 7.60 (2H, d, J=8.4 Hz), 7.65 (1H, s). IR(KBr) ν: 3025, 1649 cm$^{-1}$.

REFERENCE EXAMPLE 64

In tetrahydrofuran (50 ml) were suspended p-nitrophenethylbromide (2.3 g) and sodium iodide (1.5 g). To the suspension was added piperidine (4 ml), and the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated to give yellow oil (2.3 g), which was dissolved in ethanol (50 ml). To the mixture was added 10% palladium on carbon (0.23 g), and catalytic hydrogenation was carried out at room temperature over night. The catalyst was filtered off, and the solvent was evaporated to give 1-(2-(4-aminophenyl)ethyl)piperidine (2.0 g) as yellow oil.

$^1$H-NMR(δ ppm, CDCl$_3$): 1.43–1.50 (2H, m), 1.56–1.67 (4H, m), 2.42–2.53 (6H, m), 2.67–2.75 (2H, m), 3.55 (2H, br), 6.62 (2H, d, J=8.4 Hz), 6.99 (2H, d, J=8.4 Hz). IR(neat) ν: 2935, 1623 cm$^{-1}$.

REFERENCE EXAMPLE 65

To 5'-bromo-2'-hydroxyacetophenone (10 g) were added 4-methylphenylborate (6.7 g), 2M potassium carbonate (70 ml), ethanol (70 ml) and toluene (200 ml), and the mixture was stirred under argon atmosphere at room temperature for 30 minutes. To the mixture was added tetrakistriphenylphosphinepalladium (2.1 g), and the mixture was ref luxed over night. The mixture was extracted with ethyl acetate, and the organic layer was washed with water and saturated sodium chloride solution, and dried with anhydrous magnesium sulfate. Under reduced pressure, the solvent was evaporated, and the residue was purified with silica gel column (ethyl acetate/hexane) to give pale yellow crystal (7.4 g), 2.3 g of which was dissolved in pyridine (15 ml). To the mixture was added benzoyl chloride (1.4 ml), and the mixture was stirred at room temperature for 30 minutes. The solvent was evaporated, and to the residue was added water. The mixture was extracted with ethyl acetate, and the organic layer was washed with water and saturated sodium chloride solution, and dried with anhydrous magnesium sulfate. Under reduced pressure, the solvent was evaporated to give colorless crystals (3.0 g), 2.9 g of which was dissolved in pyridine (25 ml). To the mixture was added potassium hydroxide (0.7 g) little by little at 50° C. The mixture was stirred at 50° C. for 1 hour, and the solvent was evaporated. To the residue was added 10% acetic acid under ice-cooling, and the mixture was extracted with ethyl acetate. The organic layer was washed with water and saturated sodium chloride solution, and dried with anhydrous magnesium sulfate. Under reduced pressure, the solvent was evaporated to give yellow crystal (2.3 g), to which was added sulfuric acid (0.37 ml) and acetic acid (15 ml). The mixture was refluxed for 1 hour and poured into ice-water. The mixture was extracted with ethyl acetate. The organic layer was washed with water and saturated sodium chloride solution, and dried with anhydrous magnesium sulfate. Under reduced pressure, the solvent was evaporated to give colorless crystal (2.1 g), which was dissolved in dimethylsulfoxide (150 ml). To the mixture was dropwise added a solution which was prepared by adding a solution of trimethylsulfoxonium iodide (2.3 g) in dimethylsulfoxide (60 ml) dropwise to a suspension of sodium hydride (60%, 0.44 g) in dimethylsulfoxide (10 ml) and stirring the mixture under nitrogen atmosphere at room temperature for 40 minutes. The mixture was stirred at room temperature for 3 hours and further stirred at 50° C. for 2 hours. The mixture was poured into water, and the mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give pale yellow crystals (1.7 g), to which were added tributyltin hydride (2.1 ml), 2,2'-azobis (isobutyronitrile) (0.64 g) and toluene (50 ml). The mixture was stirred under nitrogen atmosphere at 100° C. for 1 hour, washed with water and saturated sodium chloride solution, and dried with anhydrous magnesium sulfate. Under reduced pressure, the solvent was evaporated, and the residue was purified with silica gel column (ethyl acetate/hexane) to give colorless crystals (0.65 g), to which were added sodium methoxide (0.54 g) and dimethyl carbonate (25 ml). The mixture was refluxed under nitrogen atmosphere for 8 hours and poured into 1N hydrochloric acid under ice-cooling. The mixture was extracted with ethyl acetate. The organic layer was washed with and saturated sodium chloride solution, and dried with anhydrous magnesium sulfate. The solvent was evaporated to give pale brown oil (0.76 g), which was dissolved in dichloromethane (50 ml). To the mixture was dropwise added the solution of sodium boron hydride in methanol at −10° C. After starting materials disappeared, water was added to the reaction mixture, and the mixture was concentrated extracted with ethyl acetate. The organic layer was washed with and saturated sodium chloride solution, and dried with anhydrous magnesium sulfate, and the solvent was evaporated. To the residue were added 1N sodium hydroxide (20 ml) and methanol (200 ml), and the mixture was stirred at room temperature for 3 hours, concentrated and acidified with hydrochloric acid. The mixture was extracted with ethyl acetate. The organic layer was washed with and saturated sodium chloride solution, and dried with anhydrous magnesium sulfate, and the solvent was evaporated. The residue was dissolved in Diglyme (50 ml), and to the mixture was added hydrochloric acid (10 ml). The mixture was stirred at 100° C. for 30 minutes and poured into water. The mixture was extracted with ethyl acetate. The organic layer was washed with and saturated sodium chloride solution, and dried with anhydrous magnesium sulfate. The solvent was evaporated to give 7-(4-methylphenyl)-2-phenyl-2,3-dihydro-1-benzoxepine-4-carboxylic acid (0.4 g) as colorless crystals.

mp 296–297° C.; $^1$H-NMR($\delta$ ppm, CDCl$_3$): 2.40 (3H, s), 3.10–3.39 (2H, m), 5.02 (1H, dd, J=1.8, 8.8 Hz), 7.10 (1H, d, J=8.4 Hz), 7.12–7.27 (2H, m), 7.35–7.53 (8H, m), 7.58 (1H, d, J=2.2 Hz), 7.86 (1H, d, J=2.0 Hz). IR(KBr) $\nu$: 1673 cm$^{-1}$. Anal. for C$_{24}$H$_{20}$O$_3$.0.1H$_2$O: Calcd. C, 80.47; H, 5.68. Found C, 80.41; H, 5.73.

REFERENCE EXAMPLE 66

In 1,2-dichloroethane (100 ml) were suspended p-nitrobenzylamine hydrochloride (7.5 g), 4H-tetrahydropyran-4-one (4.0 g) and triethylamine (5.6 ml), and to the suspension was added sodium triacetoxy boron hydride (11.8 g) under ice-cooling. The mixture was stirred under nitrogen atmosphere at room temperature for 5 hours. To the mixture were added 37% formalin (3.6 ml) and sodium triacetoxy boron hydride (11.8 g) under ice-cooling, and the mixture was stirred under nitrogen atmosphere at room temperature for 4 hours. The solvent was evaporated, and the residue was neutralized with sodium hydroxide. The mixture was extracted with ethyl acetate. The organic layer was washed with water and saturated sodium chloride solution, and dried with anhydrous magnesium sulfate. Under reduced pressure, the solvent was evaporated to give brown oil (10 g), to which were added reduced iron (9 g) and acetic acid (200 ml). The mixture was stirred at room temperature over night. The solvent was evaporated, and to the residue was added ethyl acetate. The precipitate was filtered off, and the filtrate was washed with sodium hydrogen carbonate solution, water and saturated sodium chloride solution, and dried with anhydrous magnesium sulfate. Under reduced pressure, the solvent was evaporated to give 4-(N-methyl-N-(tetrahydro-pyran-4-yl)aminomethyl) aniline (7.3 g) as colorless crystals.

mp 93–94° C.; $^1$H-NMR($\delta$ ppm, CDCl$_3$): 1.65–1.76 (4H, m), 2.19 (3H, s), 2.58–2.68 (1H, m), 3.36 (2H, dt, J=3.2, 11.3 Hz), 3.48 (2H, s), 3.60 (2H, br), 4.00–4.05 (2H, m), 6.65 (2H, d, J=8.4 Hz), 7.09 (2H, d, J=8.4 Hz). IR(KBr) $\nu$: 2952, 2844, 2788, 1613 cm$^{-1}$. Anal. for C$_{13}$H$_{20}$N$_2$O.0.1H$_2$O: Calcd. C, 70.30; H, 9.17; N, 12.61. Found C, 70.21; H, 8.85; N, 12.64.

REFERENCE EXAMPLE 67

In methanol (20 ml) was dissolved ethyl levulinate (10 g), and to the mixture was added sodium boron hydride (0.7 g) at −78° C. The mixture was warmed to room temperature, and to the mixture was added ammonium chloride solution. The mixture was concentrated, extracted with diethylether, and dried with anhydrous magnesium sulfate. The solvent was evaporated to give colorless oil (9.3 g), which was dissolved in tetrahydrofuran (50 ml). To the mixture was added triethylamine (10.6 ml) under ice-cooling, and to the mixture was dropwise added methane-sulfonylchloride (4.9 ml). The mixture was warmed to room temperature, and the solvent was evaporated. To the residue were added sodium iodide (11.4 g) and acetone (50 ml), and the mixture was stirred at 50° C. for 2 hours. The solvent was evaporated, and to the residue was added ethyl acetate. The precipitate was filtered off, and the solvent was evaporated. The residue was purified with silica gel column (ethyl acetate/hexane) to give colorless oil (7.0 g), which was dissolved in dimethylformamide (20 ml). The mixture was dropwise added to a solution of methyl 5-bromosalicylate (1.8 g) and sodium hydride (60%, 0.33 g) in dimethylformamide (20 ml), under ice-cooling, and the mixture was stirred at 50° C. over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give colorless oil (1.1 g), which was dissolved in tetrahydrofuran (20 ml). The mixture was dropwise added to a solution of lithium diisopropylamine, which was prepared by diisopropylamine (0.37 g) and a solution of n-butyl lithium in hexane (1.6M, 2.1 ml), in tetrahydrofuran, at −78° C. The mixture was stirred at room temperature under argon atmosphere over night and poured into water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give colorless oil (0.3 g), which was dissolved in dichloromethane (25 ml). The mixture was dropwise added to a solution of sodium boron hydride in methanol at −10° C. After starting materials disappeared, water was added to the reaction mixture, and the mixture was concentrated and extracted with ethyl acetate. The organic layer was washed with and saturated sodium chloride solution, and dried with anhydrous magnesium sulfate. The solvent was evaporated, and the residue was dissolved in dichloromethane (25 ml). To the mixture was added triethylamine (0.74 ml), and to the mixture was dropwise added methanesulfonylchloride (0.15 ml) under ice-cooling. The mixture was stirred at room temperature under nitrogen atmosphere over night, washed with water and dried with anhydrous magnesium sulfate. The solvent was evaporated, and the residue was purified with silica gel column (ethyl acetate/hexane) to give colorless crystals (0.2 g), to which were added 4-methylphenyl borate (0.1 g), 1M potassium carbonate (2.5 ml), ethanol (2.5 ml) and toluene (15 ml). The mixture was stirred under argon atmosphere at room temperature for 30 minutes, and to the mixture was added tetrakistriphenylphosphinepalladium (0.03 g). The mixture was refluxed over night and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give colorless crystals (0.2 g), to which were added 1N sodium hydroxide (5 ml) and methanol (50 ml). The mixture was ref luxed for 30 minutes, concentrated, acidified with hydrochloric acid and extracted with ethyl acetate. The organic layer was washed with and saturated sodium chloride solution, and dried with anhydrous magnesium sulfate. The solvent was evaporated to give 7-(4-methylphenyl)-2-methyl-2,3-dihydro-1-benzoxepine-4-carboxylic acid (0.2 g) as colorless crystals.

mp 224–225° C.; $^1$H-NMR($\delta$ ppm, CDCl$_3$): 1.53 (3H, d, J=6.2 Hz), 2.40 (3H, s), 2.81 (1H, ddd, J=2.2, 8.8, 18.0 Hz), 3.08 (1H, d, J=18.0 Hz), 4.17–4.27 (1H, m), 7.04 (1H, d, J=8.2 Hz), 7.24 (2H, d, J=7.4 Hz), 7.44–7.52 (4H, m), 7.77 (1H, d, J=2.2 Hz). IR(KBr) v: 2973, 1674 cm$^{-1}$. Anal. for C$_{19}$H$_{18}$O$_3$: Calcd. C, 77.53; H, 6.16. Found C, 77.60; H, 6.14.

REFERENCE EXAMPLE 68

In ethanol (10 ml) and ethyl acetate (60 ml) was dissolved 4-methylphenyl 4-nitrobenzyl sulfone (0.5 g; G. Bram et al., Synthesis, 1987, 56–59). To the mixture was added 10% palladium on carbon (0.05 g) and catalytic hydrogenation was carried out at room temperature over night. The catalyst was filtered off, and the solvent was evaporated to give 4-aminobenzyl 4-methylphenyl sulfone (0.4 g) as colorless crystals.

$^1$H-NMR($\delta$ ppm, CDCl$_3$): 2.42 (3H, s), 4.18 (2H, s), 6.56 (2H, d, J=8.4 Hz), 6.86 (2H, d, J=8.4 Hz), 7.24 (2H, d, J=8.2 Hz), 7.52 (2H, d, J=8.2 Hz). IR(KBr) v: 3443, 3370, 2926, 1612 cm$^{-1}$. Anal. for C$_{14}$H$_{15}$NOS, 0.2H$_2$O: Calcd. C, 63.47; H, 5.86; N, 5.29. Found C, 63.63; H, 5.86; N, 5.09.

REFERENCE EXAMPLE 69

In 1,2-dichloroethane (50 ml) were suspended cyclopentanone (1 g), methylamine hydrochloride (1.6 g) and triethylamine (3.4 ml), and to the suspension was added sodium triacetoxy boron hydride (3.5 g) under ice-cooling. Under nitrogen atmosphere, the mixture was stirred at room temperature over night. The mixture was neutralized with sodium hydroxide, concentrated and extracted with water. The aqueous layer was washed with ethyl acetate. The aqueous layer was saturated with sodium chloride and extracted with diethylether. The organic layer was dried with anhydrous magnesium sulfate. Under reduced pressure, the solvent was evaporated to give N-methylcyclopentylamine (0.5 g) as colorless oil.

$^1$H-NMR($\delta$ ppm, CDCl$_3$): 1.21–1.86 (8H, m), 2.40 (3H, s), 2.94–3.01 (1H, m).

REFERENCE EXAMPLE 70

In 1,2-dichloroethane (50 ml) were suspended cycloheptanone (2 g), methylamine hydrochloride (3 g) and triethylamine (6.2 ml), and to the suspension was added sodium triacetoxy boron hydride (5.3 g) under ice-cooling. Under nitrogen atmosphere, the mixture was stirred at room temperature over night. The solvent was evaporated, and the residue was neutralized with sodium hydroxide. The mixture was extracted with ethyl acetate. The organic layer was washed with saturated sodium chloride solution and dried with anhydrous magnesium sulfate. Under reduced pressure, the solvent was evaporated to give N-methylcycloheptylamine (1.8 g) as colorless oil.

$^1$H-NMR($\delta$ ppm, CDCl$_3$): 1.26–1.70 (10H, m), 1.77–1.89 (2H, m), 2.40 (3H, s), 2.47–2.58 (1H, m). IR(KBr) v: 2933, 2860 cm$^{-1}$.

REFERENCE EXAMPLE 71

In tetrahydrofuran (100 ml) were added 4-amino-1-benzyl-piperidine (10 g) and triethylamine (36 ml), and to the mixture was dropwise added acetyl chloride (4.1 ml) under ice-cooling. The mixture was stirred at room temperature for 1 hour, and the solvent was evaporated. To the residue was added water, and the mixture was extracted with ethyl acetate. The organic layer was washed with saturated sodium chloride solution and dried with anhydrous magnesium sulfate. Under reduced pressure, the solvent was evaporated to give colorless crystal (2.6 g), which was dissolved in tetrahydrofuran (10 ml). Under ice-cooling, borane methylsulfide (2.2 ml) was dropwise added to the solution. Under nitrogen atmosphere, the mixture was refluxed for 5 hours. Under ice-cooling, methanol (10 ml) was added to the mixture, and the mixture was stirred at room temperature for 1 hour. To the mixture was added 4N hydrochloric acid-ethyl acetate, and the mixture was refluxed for 1 hour. The solvent was evaporated, and to the residue was added 1N sodium hydroxide. The mixture was extracted with ethyl acetate. The organic layer was washed with water and saturated sodium chloride solution, and dried with anhydrous magnesium sulfate. Under reduced pressure, the solvent was evaporated to give 4-ethylamino-1-benzylpiperidine (1.2 g) as colorless oil.

$^1$H-NMR($\delta$ ppm, CDCl$_3$): 1.10 (3H, t, J=7.2 Hz), 1.28–1.47 (2H, m), 1.82–1.88 (2H, m), 1.95–2.07 (2H, m), 2.40–2.51 (1H, m), 2.66 (2H, q, J=7.2 Hz), 2.82–2.88 (2H, m), 3.50 (2H, s), 7.20–7.33 (5H, m).

REFERENCE EXAMPLE 72

To a mixture of ethyl 7-bromo-2,3-dihydro-1-benzoxepine-4-carboxylate (0.5 g), 4-(4-methylpiperazin-1-yl)phenyl borate (0.44 g), 1M potassium carbonate (6 ml) and ethanol (6 ml) was added toluene (50 ml), and the mixture was stirred under argon atmosphere at room temperature for 30 minutes. To the mixture was added tetrakistriphenylphosphinepalladium (0.07 g), and the mixture was refluxed over night and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate) to give colorless crystals (0.39 g), which were dissolved in 1N sodium hydroxide (15 ml) and methanol (100 ml). The mixture was refluxed for 2 hours, concentrated and neutralized with hydrochloric acid to precipitate 7-(4-(4-methylpiperazin-1-yl)phenyl)-2,3-dihydro-1-benzoxepine-4-carboxylic acid (0.33 g) as colorless crystals.

mp 278–279° C.(dec.). $^1$H-NMR($\delta$ ppm, DMSO-d$_6$): 2.24 (3H, s), 2.45–2.52 (4H, m), 2.87 (2H, t, J=4.0 Hz), 3.15–3.20 (4H, m), 4.23 (2H, t, J=4.8 Hz), 6.97–7.01 (3H, m), 7.49–7.62 (4H, m), 7.70 (1H, d, J=2.2 Hz). IR(KBr) v: 1692 cm$^{-1}$. Anal. for C$_{22}$H$_{24}$N$_2$O$_3$.0.5H$_2$O: Calcd. C, 70.76; H, 6.75; N, 7.50. Found C, 70.87; H, 6.50; N, 7.56.

REFERENCE EXAMPLE 73

In 1,2-dichloroethane (35 ml) were suspended 4-methylcyclohexanone (2.5 g), methylamine hydrochloride (1.6 g) and triethylamine (3.3 ml), and to the suspension was added sodium triacetoxy boron hydride (6.6 g) under ice-cooling. The mixture was stirred under nitrogen atmosphere at room temperature over night. The solvent was evaporated, and the residue was neutralized with sodium hydroxide. The mixture was extracted with ethyl acetate. The organic layer was washed with saturated sodium chloride solution and dried with anhydrous magnesium sulfate. Under reduced pressure, the solvent was evaporated. To the residue was added 4N hydrochloric acid-ethyl acetate, and the solvent was evaporated to give N, 4-dimethyl-cyclohexylamine hydrochloride (2.6 g) as colorless crystals.

$^1$H-NMR($\delta$ ppm, CDCl$_3$): 0.90 (1.5H, d, J=6.6 Hz), 1.01 (1.5H, d, J=6.6 Hz), 1.45–2.10 (8H, m), 2.19–2.26 (1H, m), 2.61–2.68 (3H, m), 3.03 (1H, br). Anal. for C$_8$H$_{18}$ClN: Calcd. C, 58.70; H, 11.08; N, 8.56. Found C, 58.42; H, 10.91; N, 8.48.

REFERENCE EXAMPLE 74

In 1,2-dichloroethane (25 ml) were suspended p-nitrobenzylamine hydrochloride (1.2 g), tetrahydropyran-3-one (0.6 g; Numata et al., JP-A-63-170372) and triethylamine (0.9 ml), and to the suspension was added sodium triacetoxy boron hydride (1.8 g) under ice-cooling. Under nitrogen atmosphere, the mixture was stirred at room temperature over night. Under ice-cooling, to the mixture were added 37% formalin (0.6 ml) and sodium triacetoxy boron hydride (1.8 g). Under nitrogen atmosphere, the mixture was stirred at room temperature over night, and the solvent was evaporated. The residue was neutralized with sodium hydroxide, and the mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give pale yellow oil (1.0 g), to which was added reduced iron (0.6 g) and acetic acid (50 ml). The mixture was stirred at room temperature over night. The solvent was evaporated, and to the residue was added ethyl acetate. The precipitate was filtered off, and the filtrate was washed with sodium hydrogen carbonate solution, water and saturated sodium chloride solution, and dried with anhydrous magnesium sulfate. Under reduced pressure, the solvent was evaporated to give 4-(N-methyl-N-(tetrahydropyran-3-yl)aminomethyl)aniline (0.3 g) as brown oil.

$^1$H-NMR($\delta$ ppm, CDCl$_3$): 1.46–1.75 (3H, m), 1.95–2.01 (1H, m), 2.19 (3H, s), 2.55–2.68 (1H, m), 3.21–3.40 (2H, m), 3.49 (2H, s), 3.59 (2H, br), 3.83–3.89 (1H, m), 4.00–4.08 (1H, m), 6.64 (2H, d, J=8.4 Hz), 7.07 (2H, d, J=8.4 Hz). IR(neat) v: 2941, 2846, 1615 cm$^{-1}$.

REFERENCE EXAMPLE 75

In 1,2-dichloroethane (50 ml) were suspended 2-aminoindane hydrochloride (1.0 g), p-nitrobenzaldehyde (0.9 g) and triethylamine (0.9 ml), and to the mixture was added sodium triacetoxy boron hydride (1.8 g) under ice-cooling. Under nitrogen atmosphere, the mixture was stirred at room temperature over night. Under ice-cooling, to the mixture were added 37% formalin (0. 6 ml) and sodium triacetoxy boron hydride (1.8 g). Under nitrogen atmosphere, the mixture was stirred at room temperature over night, and the solvent was evaporated. The residue was neutralized with sodium hydroxide, and the mixture was extracted with ethyl acetate. The organic layer was washed with water and saturated sodium chloride solution, and dried with anhydrous magnesium sulfate. Under reduced pressure, the solvent was evaporated to give colorless crystals (1.7 g), which was dissolved in ethanol (50 ml) and ethyl acetate (50 ml). To the mixture was added 10% palladium on carbon (0.15 g), and catalytic hydrogenation was carried out at room temperature for 1 hour. The catalyst was filtered off, and the solvent was evaporated. The residue was purified with silica gel column (ethyl acetate) to give 4-((N-indan-2-yl-N-methyl)aminomethyl)aniline (0.6 g) as colorless crystals.

mp 95–96° C.; $^1$H-NMR($\delta$ ppm, CDCl$_3$): 2.17 (3H, s), 2.91–3.16 (4H, m), 3.32–3.43 (1H, m), 3.47 (2H, s), 3.61 (2H, br), 6.66 (2H, d, J=8.8 Hz), 7.10–7.22 (6H, m). IR(KBr) v: 2782, 1623 cm$^{-1}$. Anal. for C$_{17}$H$_{20}$N$_2$.0.2H$_2$O: Calcd. C, 79.77; H, 8.03; N, 10.94. Found C, 79.87; H, 8.04; N, 10.75.

REFERENCE EXAMPLE 76

In 1,2-dichloroethane (50 ml) were suspended p-nitrobenzylamine hydrochloride (1.9 g), 4-t-butylcyclohexanone (1.5 g) and triethylamine (1.4 ml), and to the suspension was added sodium triacetoxy boron hydride (3 g) under ice-cooling. Under nitrogen atmosphere, the mixture was stirred at room temperature over night. Under ice-cooling, to the mixture were added 37% formalin (0.9 ml) and sodium triacetoxy boron hydride (3 g). Under nitrogen atmosphere, the mixture was stirred at room temperature over night, and the solvent was evaporated. The residue was neutralized with sodium hydroxide, and the mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane)y to give (E)-N-(4-t-butylcyclohexyl)-N-methyl-N-(4-nitro-benzyl)amine (0.3 g) as colorless crystals and (Z)-N-(4-t-butylcyclohexyl)-N-methyl-N-(4-nitrobenzyl)amine (2.4 g) as yellow oil. (E)-N-(4-t-butylcyclohexyl)-N-methyl-N-(4-nitrobenzyl)amine:

mp 96–97° C.; $^1$H-NMR($\delta$ ppm, CDCl$_3$): 0.85 (9H, s), 0.94–1.05 (3H, m), 1.20–1.40 (2H, m), 1.80–2.00 (4H, m), 2.19 (3H, s), 2.29–2.44 (1H, m), 3.65 (2H, s), 7.51 (2H, d, J=8.4 Hz), 8.17 (2H, d, J=8.4 Hz). IR(KBr) v: 2941, 1604, 1513 cm$^{-1}$. Anal. for C$_{18}$H$_{28}$N$_2$O$_2$: Calcd. C, 71.02; H, 9.27; N, 9.20. Found C, 70.77; H, 9.26; N, 9.32.

(Z)-N-(4-t-butylcyclohexyl)-N-methyl-N-(4-nitrobenzyl) amine:

$^1$H-NMR($\delta$ ppm, CDCl$_3$): 0.89 (9H, s), 1.15–1.20 (1H, m), 1.30–1.54 (6H, m), 1.97–2.10 (2H, m), 2.08 (3H, s), 2.38 (1H, br), 3.61 (2H, s), 7.52 (2H, d, J=8.4 Hz), 8.18 (2H, d, J=8.4 Hz). IR(neat) v: 2943, 1606, 1521 cm$^{-1}$.

REFERENCE EXAMPLE 77

In ethanol (25 ml) and ethyl acetate (25 ml) was dissolved (E)-N-(4-t-butylcyclohexyl)-N-methyl-N-(4-nitrobenzyl) amine (0.3 g). To the mixture was added 10% palladium on carbon (0.03 g) and catalytic hydrogenation was carried out at room temperature for 1 hour. The catalyst was filtered off, and the solvent was evaporated. The residue was purified with silica gel column (ethyl acetate/methanol/triethylamine) to give (E)-4-((N-4-t-butylcyclohexyl-N-methyl)aminomethyl)aniline (0.2 g) as colorless crystals.

mp 87–88° C.; $^1$H-NMR($\delta$ ppm, CDCl$_3$): 0.84 (9H, s), 0.93–1.03 (2H, m), 1.15–1.40 (2H, m), 1.81–1.96 (5H, m), 2.19 (3H, s), 2.30–2.45 (1H, m), 3.48 (2H, s), 3.60 (2H, br), 6.65 (2H, d, J=8.4 Hz), 7.10 (2H, d, J=8.4 Hz). IR(KBr) v: 2927, 1614, 1517 cm$^{-1}$. Anal. for C$_{18}$H$_{30}$N$_2$.0.2H$_2$O: Calcd. C, 77.75; H, 11.02; N, 10.07. Found C, 77.87; H, 10.93; N, 10.16.

REFERENCE EXAMPLE 78

In acetic acid (70 ml) was dissolved (Z)-N-(4-t-butylcyclohexyl)-N-methyl-N-(4-nitrobenzyl)amine (1.2 g), and to the mixture was added reduced iron (1.1 g). The mixture was stirred at room temperature over night. The solvent was evaporated, and to the residue was added ethyl acetate. The precipitate was filtered off, and the filtrate was washed with sodium hydrogen carbonate solution, water and saturated sodium chloride solution, and dried with anhydrous magnesium sulfate. Under reduced pressure, the solvent was evaporated, and the residue was purified with silica gel column (ethyl acetate to give (Z)-4-((N-4-t-butylcyclohexyl-N-methyl)aminomethyl)aniline (0.7 g) as yellow oil.

$^1$H-NMR($\delta$ ppm, CDCl$_3$): 0.87 (9H, s), 1.00–1.20 (1H, m), 1.25–1.56 (6H, m), 2.04 (3H, s), 2.04–2.13 (2H, m), 2.26–2.29 (1H, m), 3.40 (2H, s), 3.58 (2H, br), 6.65 (2H, d, J=8.4 Hz), 7.10 (2H, d, J=8.4 Hz). IR(neat) v: 2941, 1623, 1515 cm$^{-1}$.

REFERENCE EXAMPLE 79

In 1,2-dichloroethane (70 ml) were suspended p-nitrobenzylamine hydrochloride (3.8 g), 3,5-dimethylcyclohexanone (2.5 g) and triethylamine (2.8 ml). Under ice-cooling, to the mixture was added sodium triacetoxy boron hydride (5.9 g). Under nitrogen atmosphere, the mixture was stirred at room temperature over night. Under ice-cooling, to the mixture were added 37% formalin (1.8 ml) and sodium triacetoxy boron hydride (5.9 g). Under nitrogen atmosphere, the mixture was stirred at room temperature over night. The solvent was evaporated, and the residue was neutralized with sodium hydroxide. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give 3 isomers of N-methyl-N-(3,5-dimethylcyclohexyl)-N-(4-nitrobenzyl)amine (4.3 g; (31-a), 0.7 g; (31-b), 0.2 g; (31-c)) as each yellow oil.

31-a: $^1$H-NMR($\delta$ ppm, CDCl$_3$): 0.53–0.74 (1H, m), 0.84 (3H, s), 0.87 (3H, s), 0.93–1.07 (2H, m), 1.73–1.99 (5H, m), 2.06 (3H, s), 2.49 (1H, t, J=2.8 Hz), 3.60 (2H, s), 7.50 (2H, d, J=8.8 Hz), 8.17 (2H, d, J=8.8 Hz). IR(neat) v: 2949, 1606, 1521 cm$^{-1}$.

31-b: $^1$H-NMR($\delta$ ppm, CDCl$_3$): 0.51 (1H, q, J=12.0 Hz), 0.80–1.02 (2H, m), 0.92 (3H, s), 0.95 (3H, s), 1.34–1.53 (2H, m), 1.58–1.66 (1H, m), 1.78–1.84 (2H, m), 2.19 (3H, s), 2.53 (1H, tt, J=3.3, 11.7 Hz), 3.65 (2H, s), 7.51 (2H, d, J=8.8 Hz), 8.17 (2H, d, J=8.8 Hz). IR(neat) v: 2949, 1606, 1519 cm$^{-1}$.

31-c: $^1$H-NMR($\delta$ ppm, CDCl$_3$): 0.80–1.13 (8H, m), 1.38–1.52 (2H, m), 1.62–1.68 (2H, m), 1.80–1.86 (1H, m), 2.08–2.17 (1H, m), 2.18 (3H, s), 2.74 (1H, tt, J=3.5, 11.9 Hz), 3.64 (2H, s), 7.51 (2H, d, J=8.4 Hz), 8.17 (2H, d, J=8.4 Hz). IR(neat) v: 2920, 1606, 1521 cm$^{-1}$.

REFERENCE EXAMPLE 80

In ethanol (50 ml) and ethyl acetate (50 ml) was dissolved N-methyl-N-(3,5-dimethylcyclohexyl)-N-(4-nitrobenzyl) amine (2.0 g; (31-a)). To the mixture was added 10% palladium on carbon (0.2 g) and catalytic hydrogenation was carried out at room temperature for 1 hour. The catalyst was filtered off, and the solvent was evaporated. The residue was purified with silica gel column (ethyl acetate/methanol/triethylamine) to give 4-((N-(3,5-dimethylcyclohexyl)-N-methyl)aminomethyl)aniline (0.2 g) as pale yellow oil.

$^1$H-NMR($\delta$ ppm, CDCl$_3$): 0.58 (1H, q, J=11.7 Hz), 0.83 (3H, s), 0.86 (3H, s), 0.93–1.00 (2H, m), 1.69–2.04 (5H, m), 2.04 (3H, s), 2.24–2.40 (1H, m), 3.41 (2H, s), 3.50 (2H, br), 6.64 (2H, d, J=8.6 Hz), 7.08 (2H, d, J=8.6 Hz). IR(neat) v: 2947, 1623 cm$^{-1}$.

REFERENCE EXAMPLE 81

In acetic acid (30 ml) was dissolved N-methyl-N-(3,5-dimethylcyclohexyl)-N-(4-nitrobenzyl)amine (0.7 g; (31-b)), and to the mixture was added reduced iron (0.7 g). The mixture was stirred at room temperature over night. The solvent was evaporated, and to the residue was added ethyl acetate. The precipitate was filtered off, and the filtrate was washed with sodium hydrogen carbonate solution, water and saturated sodium chloride solution, and dried with anhydrous magnesium sulfate. Under reduced pressure, the solvent was evaporated, and the residue was purified with silica gel column (ethyl acetate/methanol/triethylamine) to give 4-((N-(3,5-dimethylcyclohexyl)-N-methyl)aminomethyl) aniline (0.4 g) as yellow oil.

$^1$H-NMR($\delta$ ppm, CDCl$_3$): 0.50 (1H, q, J=12.0 Hz), 0.80–1.03 (1H, m), 0.91 (3H, s), 0.94 (3H, s), 1.22–1.50

(3H, m), 1.55–1.64 (1H, m), 1.78–1.84 (2H, m), 2.17 (3H, s), 2.53 (1H, tt, J=3.3, 11.8 Hz), 3.46 (2H, s), 3.58 (2H, br), 6.64 (2H, d, J=8.6 Hz), 7.09 (2H, d, J=8.6 Hz). IR(neat) v: 2949, 1621 cm$^{-1}$.

REFERENCE EXAMPLE 82

In acetic acid (15 ml) was dissolved N-methyl-N-(3,5-dimethylcyclohexyl)-N-(4-nitrobenzyl)amine (0.2 g; (31-c)), and to the mixture was added reduced iron (0.2 g). The mixture was stirred at room temperature over night. The solvent was evaporated, and to the residue was added ethyl acetate. The precipitate was filtered off, and the filtrate was washed with sodium hydrogen carbonate solution, water and saturated sodium chloride solution, and dried with anhydrous magnesium sulfate. Under reduced pressure, the solvent was evaporated, and the residue was purified with silica gel column (ethyl acetate/methanol/triethyl-amine) to give 4-((N-(3,5-dimethylcyclohexyl)-N-methyl)aminomethyl) aniline (0.1 g) as brown oil.

$^{1}$H-NMR(δ ppm, CDCl$_3$): 0.87–1.15 (7H, m), 1.35–1.55 (2H, m), 1.60–1.70 (2H, m), 1.75–1.90 (1H, m), 2.05–2.19 (2H, m), 2.17 (3H, s), 2.75 (1H, tt, J=3.3, 12.1 Hz), 3.45 (2H, s), 3.60 (2H, br), 6.64 (2H, d, J=8.3 Hz), 7.09 (2H, d, J=8.3 Hz).

REFERENCE EXAMPLE 83

In 1,2-dichloroethane (50 ml) were dissolved n-propylamine (1.1 g) and p-nitrobenzaldehyde (2.3 g). Under ice-cooling, to the mixture was added sodium triacetoxy boron hydride (4.5 g). Under nitrogen atmosphere, the mixture was stirred at room temperature over night. Under ice-cooling, to the mixture were added 37% formalin (1.7 ml) and sodium triacetoxy boron hydride (4.5 g). Under nitrogen atmosphere, the mixture was stirred at room temperature over night, and the solvent was evaporated. The residue was neutralized with sodium hydroxide, and the mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give pale yellow oil (2.3 g), which was dissolved in tetrahydrofuran (10 ml). The mixture was dropwise added to a solution, which was prepared by adding dropwise lithium aluminum hydride (0.5 g) to a solution of titanium tetrachloride (2 ml) in tetrahydrofuran (50 ml), under ice-cooling, and stirring the mixture at room temperature for 15 minutes, under ice-cooling. The mixture was stirred at room temperature for 30 minutes, and to the mixture were added water (50 ml) and ammonia solution (50 ml). The mixture was concentrated and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/methanol/triethylamine) to give 4-((N-methyl-N-n-propyl) aminomethyl)aniline (0.25 g) as yellow oil.

$^{1}$H-NMR(δ ppm, CDCl$_3$): 0.88 (3H, t, J=7.3 Hz), 1.43–1.61 (2H, m), 2.16 (3H, s), 2.30 (2H, t, J=7.7 Hz), 3.37 (2H, s), 3.59 (2H, br), 6.64 (2H, d, J=8.0 Hz), 7.08 (2H, d, J=8.0 Hz). IR(neat) v: 2960, 1623, 1517 cm$^{-1}$.

REFERENCE EXAMPLE 84

In 1,2-dichloroethane (50 ml) were dissolved isopropylamine (1 g) and p-nitrobenzaldehyde (2.3 g), and to the mixture was added sodium triacetoxy boron hydride (4.5 g) under ice-cooling. Under nitrogen atmosphere, the mixture was stirred at room temperature over night. Under ice-cooling, to the mixture were added 37% formalin (1.5 ml) and sodium triacetoxy boron hydride (4.5 g). Under nitrogen atmosphere, the mixture was stirred at room temperature over night. The solvent was evaporated, and the residue was neutralized with sodium hydroxide. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give yellow oil (2.8 g), 1.5 g of which was dissolved in ethanol (25 ml) and ethyl acetate (25 ml). To the mixture was added 10% palladium on carbon (0.15 g), and catalytic hydrogenation was carried out at room temperature for 1 hour. The catalyst was filtered off, and the solvent was evaporated. The residue was purified with silica gel column (ethyl acetate/methanol/ triethylamine) to give 4-((N-isopropyl-N-methyl) aminomethyl)aniline (0.17 g) as pale yellow oil.

$^{1}$H-NMR(δ ppm, CDCl$_3$): 1.05 (6H, d, J=6.6 Hz), 2.13 (3H, s), 2.81–2.95 (1H, m), 3.40 (2H, s), 3.60 (2H, br), 6.65 (2H, d, J=8.4 Hz), 7.10 (2H, d, J=8.4 Hz). IR(neat) v: 2966, 1623, 1517 cm$^{-1}$.

REFERENCE EXAMPLE 85

In 1,2-dichloroethane (50 ml) were dissolved 1-methylpropylamine (1.3 g) and p-nitrobenzaldehyde (2.3 g), and to the mixture was added sodium triacetoxy boron hydride (4.5 g) under ice-cooling. Under nitrogen atmosphere, the mixture was stirred at room temperature over night. Under ice-cooling, to the mixture were added 37% formalin (1.7 ml) and sodium triacetoxy boron hydride (4.5 g). Under nitrogen atmosphere, the mixture was stirred at room temperature over night. The solvent was evaporated, and the residue was neutralized with sodium hydroxide. The mixture was extracted with ethyl acetate. The organic layer was washed with water and saturated sodium chloride solution, and dried with anhydrous magnesium sulfate. Under reduced pressure, the solvent was evaporated to give brown oil (3.4 g), 2.0 g of which was dissolved in tetrahydrofuran (20 ml). The mixture was dropwise added to a solution, which was prepared by adding dropwise lithium-aluminum hydride (0.7 g) to a solution of titanium tetrachloride (3 ml) in tetrahydrofuran (50 ml) under ice-cooling and stirring the mixture at room temperature for 15 minutes, under ice-cooling. The mixture was stirred at room temperature over night, and, to the mixture were added water (75 ml) and ammonia solution (75 ml). The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/methanol/triethylamine) to give 4-((N-sec-butyl-N-methyl)aminomethyl)aniline (0.8 g) as yellow oil.

$^{1}$H-NMR(δ ppm, CDCl$_3$): 0.87–0.99 (6H, m), 1.22–1.37 (1H, m), 1.53–1.63 (1H, m), 2.11 (3H, s), 2.53–2.63 (1H, m), 3.34 (1H, d, J=12.8 Hz), 3.46 (1H, d, J=12.8 Hz), 3.57 (2H, br), 6.64 (2H, d, J=8.4 Hz), 7.11 (2H, d, J=8.4 Hz). IR(neat) v: 2962, 2933, 2873, 1617, 1517 cm$^{-1}$.

REFERENCE EXAMPLE 86

In 1,2-dichloroethane (70 ml) were dissolved t-butylamine (1.6 g) and p-nitrobenzaldehyde (3.0 g), and to the mixture was added sodium triacetoxy boron hydride (5.9 g) under ice-cooling. Under nitrogen atmosphere, the mixture was stirred at room temperature over night. Under ice-cooling, to the mixture were added 37% formalin (2 ml) and sodium triacetoxy boron hydride (5.9 g). Under nitrogen atmosphere, the mixture was stirred at room temperature over night. The solvent was evaporated, and the residue was neutralized with sodium hydroxide. The mixture was extracted with ethyl acetate. The organic layer was washed with water and saturated sodium chloride solution, and dried with anhydrous magnesium sulfate. Under reduced pressure, the solvent was evaporated, to give brown oil (4.4 g), which was dissolved in acetic acid (50 ml). To the mixture was added reduced iron (3.2 g), and the mixture was stirred at room temperature over night. The solvent was evaporated, and to the residue was added ethyl acetate. The precipitate was filtered off, and the filtrate was washed with sodium hydrogen carbonate solution, water and saturated sodium chloride solution, and dried with anhydrous magnesium sulfate. Under reduced pressure, the solvent was evaporated to give 4-((N-t-butyl-N-methyl)aminomethyl)aniline (2.2 g) as brown oil.

$^1$H-NMR($\delta$ ppm, CDCl$_3$): 1.14 (9H, s), 2.07 (3H, s), 3.38 (2H, s), 3.57 (2H, br), 6.64 (2H, d, J=8.4 Hz), 7.11 (2H, d, J=8.4 Hz). IR(neat) v: 2971, 1622, 1516 cm$^{-1}$.

REFERENCE EXAMPLE 87

In 1,2-dichloroethane (70 ml) were suspended p-nitrobenzylamine hydrochloride (3.8 g) and 3-pentanone (1.7 g), and to the suspension was added triethylamine (2.8 ml). Under ice-cooling, to the mixture was added sodium triacetoxy boron hydride (5.9 g). Under nitrogen atmosphere, the mixture was stirred at room temperature over night. Under ice-cooling, to the mixture were added 37% formalin (1.8 ml) and sodium triacetoxy boron hydride (5.9 g). Under nitrogen atmosphere, the mixture was stirred at room temperature over night. The solvent was evaporated, and the residue was neutralized with sodium hydroxide. The mixture was extracted with ethyl acetate. The organic layer was washed with water and saturated sodium chloride solution, and dried with anhydrous magnesium sulfate. Under reduced pressure, the solvent was evaporated to give pale yellow oil (4.6 g), which was dissolved in acetic acid (100 ml). To the mixture was added reduced iron (4.7 g), and the mixture was stirred at room temperature over night. The solvent was evaporated, and to the residue was added ethyl acetate. The precipitate was filtered off, and the filtrate was washed with sodium hydrogen carbonate solution, water and saturated sodium chloride solution, and dried with anhydrous magnesium sulfate. Under reduced pressure, the solvent was evaporated to give 4-((N-methyl-N-(pentan-3-yl))-aminomethyl)aniline (3.3 g) as pale brown oil.

$^1$H-NMR($\delta$ ppm, CDCl$_3$): 0.92 (6H, t, J=7.3 Hz), 1.20–1.59 (4H, m), 2.10 (3H, s), 2.18–2.29 (1H, m), 3.44 (2H, s), 3.57 (2H, br), 6.64 (2H, d, J=8.4 Hz), 7.11 (2H, d, J=8.4 Hz). IR(neat) v: 2959, 1622, 1516 cm$^{-1}$.

REFERENCE EXAMPLE 88

In 1,2-dichloroethane (70 ml) were suspended p-nitrobenzylamine hydrochloride (3.8 g) and norcamphor (2.2 g), and to the suspension was added triethylamine (2.8 ml). Under ice-cooling, to the mixture was added sodium triacetoxy boron hydride (5.9 g). Under nitrogen atmosphere, the mixture was stirred at room temperature over night. Under ice-cooling, to the mixture were added 37% formalin (1.8 ml) and sodium triacetoxy boron hydride (5.9 g). Under nitrogen atmosphere, the mixture was stirred at room temperature over night. The solvent was evaporated, and the residue was neutralized with sodium hydroxide. The mixture was extracted with ethyl acetate. The organic layer was washed with water and saturated sodium chloride solution, and dried with anhydrous magnesium sulfate. Under reduced pressure, the solvent was evaporated to give pale yellow oil (5.2 g), which was dissolved in acetic acid (100 ml). To the mixture was added reduced iron (5 g), and the mixture was stirred at room temperature over night. The solvent was evaporated, and to the residue was added ethyl acetate. The precipitate was filtered off, and the filtrate was washed with sodium hydrogen carbonate solution, water and saturated sodium chloride solution, and dried with anhydrous magnesium sulfate. Under reduced pressure, the solvent was evaporated to give 4-((N-methyl-N-(norbornan-2-yl))amino-methyl)aniline (4.0 g) as pale brown oil.

$^1$H-NMR($\delta$ ppm, CDCl$_3$): 0.94–1.04 (1H, m), 1.22–1.55 (5H, m), 1.68–1.97 (2H, m), 2.00 (3H, s), 2.16 (1H, br), 2.37 (2H, br), 3.22 (1H, d, J=12.8 Hz), 3.42 (1H, d, J=12.8 Hz), 3.58 (2H, br), 6.64 (2H, d, J=8.4 Hz), 7.09 (2H, d, J=8.4 Hz). IR(neat) v: 2949, 1622, 1516 cm$^{-1}$.

REFERENCE EXAMPLE 89

To a mixture of p-nitrophenethylbromide (2.3 g), N-methylcyclohexylamine (2.8 g), potassium carbonate (6.6 g) and sodium iodide (1.5 g) was added dimethylformamide (50 ml), and the mixture was stirred at 50° C. over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/methanol/triethylamine) to give yellow oil (2.2 g), which was dissolved in ethanol (50 ml). To the mixture was added 10% palladium on carbon (0.2 g), and catalytic hydrogenation was carried out at room temperature over night. The catalyst was filtered off, and the solvent was evaporated to give 4-(2-(N-cyclohexyl-N-methyl)aminoethyl)aniline (1.9 g) as pale yellow oil.

$^1$H-NMR($\delta$ ppm, CDCl$_3$): 1.05–1.30 (6H, m), 1.60–1.79 (4H, m), 2.33 (3H, s), 2.33–2.45 (1H, m), 2.61–2.63 (4H, m), 3.55 (2H, br), 6.63 (2H, d, J=8.4 Hz), 6.99 (2H, d, J=8.4 Hz). IR(neat) v: 2929, 1625, 1517 cm$^{-1}$.

REFERENCE EXAMPLE 90

In ethanol (15 ml) were dissolved p-nitrostyreneoxide (0.5 g; E. Borredon et al., J. Org. Che., 1990, 55, 501–504) and piperidine (0.36 ml), and the mixture was refluxed for 1 hour. The solvent was evaporated to give yellow crystals (0.53 g), which was dissolved in ethanol (50 ml). To the mixture was added 5% palladium on carbon (0.05 g), and catalytic hydrogenation was carried out at room temperature 1.5 hours. The catalyst was filtered off, and the solvent was evaporated,4-(1-hydroxy-2-piperidinoethyl)aniline (0.4 g) as colorless crystals.

mp 75–76° C.; $^1$H-NMR($\delta$ ppm, CDCl$_3$): 1.40–1.50 (2H, m), 1.55–1.70 (4H, m), 2.31–2.41 (4H, m), 2.62–2.75 (2H, m), 3.61 (2H, br), 4.61 (1H, dd, J=6.2, 8.0 Hz), 6.66 (2H, d, J=8.4 Hz), 7.15 (2H, d, J=8.4 Hz). IR(KBr) v: 2936, 1622, 1518 cm$^{-1}$. Anal. for C$_{13}$H$_{20}$N$_2$O: Calcd. C, 70.87; H, 9.15; N, 12.72. Found C, 71.02; H, 9.10; N, 13.01.

REFERENCE EXAMPLE 91

In dimethylformamide (50 ml) were dissolved methyl 5-bromosalicylate (5 g), ethyl 4-bromobutyrate (4.2 g) and potassium carbonate (7.5 g), and the mixture was stirred at room temperature over night. The solvent was evaporated, and to the residue was added water. The mixture was extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give colorless oil (6.5 g), which was dissolved in tetrahydrofuran (20 ml). The mixture was dropwise added to a solution of lithium diisopropylamine in tetrahydrofuran prepared by diisopropylamine (3.2 ml) and n-butyllithium in hexane (1.6M, 13 ml), at −78° C. The mixture was stirred at room temperature under argon atmosphere over night and poured into water. The mixture was extracted with ethyl acetate. The organic layer was washed with water and saturated sodium chloride solution, and dried with anhydrous magnesium sulfate. Under reduced pressure, the solvent was evaporated to give oil, which was dissolved in dichloromethane (100 ml). The mixture was dropwise added to a solution of sodium boron hydride in methanol at −15° C. After starting materials disappeared, water was added to the reaction mixture, and the mixture was concentrated and extracted with ethyl acetate. The organic layer was washed with and saturated sodium chloride solution, and dried with anhydrous magnesium sulfate. The solvent was evaporated, and the residue was dissolved in dichloromethane (100 ml). To the mixture was added triethylamine (7.9 ml), and to the mixture was dropwise added methanesulfonylchloride (2.2 ml) under ice-cooling. The mixture was stirred at room temperature under nitrogen atmosphere over night, and to the mixture was added water. The mixture was concentrated and extracted with ethyl acetate. The organic layer was washed with and saturated sodium chloride solution, and dried with anhydrous magnesium sulfate. The solvent was evaporated, and the residue was purified with silica gel column (ethyl acetate/hexane) to give ethyl 7-bromo-2,3-dihydro-1-benzoxepine-4-carboxylate (2.3 g) as colorless crystals.

mp 86–87° C.; $^1$H-NMR($\delta$ ppm, CDCl$_3$): 1.35 (3H, t, J=7.2 Hz), 2.98 (2H, t, J=4.7 Hz), 4.23–4.33 (4H, m), 6.86 (1H, d, J=8.8 Hz), 7.32 (1H, dd, J=2.6, 8.8 Hz), 7.46–7.47 (2H, m).

REFERENCE EXAMPLE 92

To a mixture of ethyl 7-bromo-2,3-dihydro-1-benzoxepine-4-carboxylate (0.5 g), diethyl (3-pyridyl)-borane (0.26 g), 1M potassium carbonate (6 ml) and ethanol (6 ml) was added toluene (50 ml), and the mixture was stirred under argon atmosphere at room temperature for 30 minutes. To the mixture was added tetrakistriphenylphosphinepalladium (0.07 g), and the mixture was refluxed over night. The mixture was extracted with ethyl acetate, and the organic layer was washed with water and saturated sodium chloride solution, and dried with anhydrous magnesium sulfate. Under reduced pressure, the solvent was evaporated, and the residue was purified with silica gel column (ethyl acetate/hexane) to give colorless crystals (0.28 g), which were dissolved in 1N sodium hydroxide (10 ml) and methanol (50 ml). The mixture was stirred at room temperature over night, concentrated and neutralized with hydrochloric acid to precipitate 7-(3-pyridyl)-2,3-dihydro-1-benzoxepine-4-carboxylic acid (0.3 g) as colorless crystals.

mp>300° C.; $^1$H-NMR($\delta$ ppm, DMSO-d$_6$): 2.89 (2H, t, J=4.6 Hz), 4.27 (2H, t, J=4.6 Hz), 7.09 (1H, d, J=8.4 Hz), 7.46 (1H, dd, J=4.6, 7.8 Hz), 7.64–7.69 (2H,m), 7.90 (1H, d, J=2.2 Hz), 8.10 (1H, dt, J=7.8, 1.5 Hz), 8.54 (1H, dd, J=1.5, 4.6 Hz), 8.92 (1H, d, J=2.2 Hz). IR(KBr) $\nu$: 1699 cm$^{-1}$. Anal. for C$_{16}$H$_{13}$NO$_3$.0.2H$_2$O: Calcd. C, 70.94; H, 4.99; N, 5.17. Found C, 70.71; H, 5.00; N, 5.17.

REFERENCE EXAMPLE 93

To a mixture of ethyl 7-bromo-2,3-dihydro-1-benzoxepine-4-carboxylate (1.0 g), 4-pyridyl borate (0.46 g), 1M potassium carbonate (11 ml) and ethanol (11 ml) was added toluene (80 ml), and the mixture was stirred under argon atmosphere at room temperature for 30 minutes. To the mixture was added tetrakistriphenylphosphinepalladium (0.16 g), and the mixture was refluxed over night and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give colorless oil (0.52 g), which was dissolved in 1N sodium hydroxide (18 ml) and methanol (100 ml). The mixture was stirred at room temperature over night, concentrated and neutralized with hydrochloric acid to precipitate 7-(4-pyridyl)-2,3-dihydro-1-benzoxepine-4-carboxylic acid (0.34 g) as colorless crystals.

mp 277–278° C.(dec.). $^1$H-NMR($\delta$ ppm, DMSO-d$_6$): 2.89 (2H, t, J=4.8 Hz), 4.28 (2H, t, J=4.8 Hz), 7.10 (1H, d, J=8.6 Hz), 7.68 (1H, s), 7.74–7.79 (3H, m), 8.02 (1H, d, J=2.2 Hz), 8.61 (2H, d, J=5.6 Hz). Anal. for C$_{16}$H$_{13}$NO$_3$.0.1H$_2$O: Calcd. C, 71.42; H, 4.94; N, 5.21. Found C, 71.30; H, 4.80; N, 5.05.

REFERENCE EXAMPLE 94

To a mixture of ethyl 7-bromo-2,3-dihydro-1-benzoxepine-4-carboxylate (0.5 g), 2-furyl borate (0.22 g), 1M potassium carbonate (6 ml) and ethanol (6 ml) was added toluene (50 ml) and, the mixture was stirred under argon atmosphere at room temperature for 30 minutes. To the mixture was added tetrakistriphenylphosphinepalladium (0.07 g), and the mixture was refluxed over night and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give colorless crystals (0.37 g), which were dissolved in 1N sodium hydroxide (10 ml) and methanol (50 ml). The mixture was stirred at room temperature over night, concentrated and acidified with hydrochloric acid. The mixture was extracted with ethyl acetate. The organic layer was washed with water and saturated sodium chloride solution, and dried with anhydrous magnesium sulfate. Under reduced pressure, the solvent was evaporated to give 7-(2-furyl)-2,3-dihydro-1-benzoxepine-4-carboxylic acid (0.3 g) as colorless crystals.

mp 234–235° C.(dec.). $^1$H-NMR($\delta$ ppm, CDCl$_3$): 3.02 (2H, t, J=4.7 Hz), 4.32 (2H, t, J=4.7 Hz), 6.47 (1H, dd, J=1.5, 3.2 Hz), 6.58 (1H, dd, J=0.7, 3.2 Hz), 7.02 (1H, d, J=8.6 Hz), 7.46 (1H, dd, J=0.7, 1.5 Hz), 7.57 (1H, dd, J=2.2, 8.6 Hz), 7.68 (1H, d, J=2.2 Hz), 7.77 (1H, s). IR(KBr) $\nu$: 1686 cm$^{-1}$. Anal. for C$_{15}$H$_{12}$O$_4$: Calcd. C, 70.31; H, 4.72. Found C, 70.31; H, 4.73.

REFERENCE EXAMPLE 95

To a mixture of ethyl 7-bromo-2,3-dihydro-1-benzoxepine-4-carboxylate (0.5 g), 4-dimethylaminophenyl borate (0.3 g), 1M potassium carbonate (6 ml) and ethanol (6 ml) was added toluene (50 ml), and the mixture was stirred under argon atmosphere at room temperature for 30 minutes. To the mixture was added tetrakistriphenylphosphinepalladium (0.07 g), and the mixture was ref luxed over night and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/ hexane) to give pale yellow crystals (0.45 g), which were dissolved in 1N sodium hydroxide (15 ml), methanol (100 ml) and tetrahydrofuran (25 ml). The mixture was stirred at room temperature over night, concentrated and neutralized with hydrochloric acid to precipitate 7-(4-dimethylaminophenyl)-2,3-dihydro-1-benzoxepine-4-carboxylic acid (0.4 g) as pale yellow crystals.

mp 281–282° C.(dec.). $^1$H-NMR($\delta$ ppm, DMSO-d$_6$): 2.87 (2H, t, J=4.6 Hz), 2.93 (6H, s), 4.23 (2H, t, J=4.6 Hz), 6.78 (2H, d, J=8.8 Hz), 6.99 (1H, d, J=8.4 Hz), 7.47–7.54 (3H, m), 7.62 (1H, s), 7.67 (1H, d, J=2.2 Hz). IR(KBr) $\nu$: 1676 cm$^{-1}$. Anal. for C$_{19}$H$_{19}$NO$_3$: Calcd. C, 73.77; H, 6.19; N, 4.53. Found C, 73.57; H, 6.22; N, 4.64.

REFERENCE EXAMPLE 96

To a mixture of ethyl 7-bromo-2,3-dihydro-1-benzoxepine-4-carboxylate (0.5 g),4-(pyrrolidin-1-yl) phenylborate (0.35 g), 1M potassium carbonate (6 ml) and ethanol (6 ml) was added toluene (50 ml), and the mixture was stirred under argon atmosphere at room temperature for 30 minutes. To the mixture was added tetrakistriphenylphosphinepalladium (0.07 g), and the mixture was refluxed over night and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/ hexane) to give pale yellow crystals (0.55 g), which were dissolved in 1N sodium hydroxide (15 ml), methanol (25 ml) and tetrahydrofuran (25 ml). The mixture was stirred at room temperature over night, concentrated and neutralized with hydrochloric acid to precipitate 7-(4-(pyrrolidin-1-yl) phenyl)-2,3-dihydro-1-benzoxepine-4-carboxylic acid (0.5 g) as pale yellow crystals.

mp 266–267° C.(dec.). $^1$H-NMR($\delta$ ppm, DMSO-d$_6$): 1.94–2.00 (4H, m), 2.87 (2H, t, J=4.4 Hz), 3.25–3.30 (4H, m), 4.22 (2H, t, J=4.4 Hz), 6.59 (2H, d, J=8.8 Hz), 6.98 (1H, d, J=8.4 Hz), 7.45–7.52 (3H, m), 7.61 (1H, s), 7.65 (1H, d, J=2.2 Hz). IR(KBr) $\nu$: 1678 cm$^{-1}$. Anal. for C$_{21}$H$_{21}$NO$_3$.0.2H$_2$O: Calcd. C, 74.40; H, 6.36; N, 4.13. Found C, 74.49; H, 6.39; N, 4.47.

REFERENCE EXAMPLE 97

To a mixture of ethyl 7-bromo-2,3-dihydro-1-benzoxepine-4-carboxylate (0.5 g), 4-piperidinophenyl borate (0.38 g), 1M potassium carbonate (6 ml) and ethanol (6 ml) was added toluene (50 ml), and the mixture was stirred under argon atmosphere at room temperature for 30 minutes. To the mixture was added tetrakistriphenylphosphinepalladium (0.07 g), and the mixture was refluxed over night and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/ hexane) to give colorless crystals (0.62 g), which were dissolved in 1N sodium hydroxide (10 ml), methanol (25 ml) and tetrahydrofuran (25 ml). The mixture was stirred at room temperature over night, concentrated and neutralized with hydrochloric acid to precipitate 7-(4-piperidinophenyl)-2,3-dihydro-1-benzoxepine-4-carboxylic acid (0.6 g) as pale yellow crystals.

mp 262–263° C.(dec.). $^1$H-NMR($\delta$ ppm, DMSO-d$_6$): 1.50–1.75 (6H, m), 2.87 (2H, t, J=4.8 Hz), 3.15–3.19 (4H, m), 4.23 (2H, t, J=4.8 Hz), 6.96 (2H, d, J=8.8 Hz), 7.00 (1H, d, J=8.4 Hz), 7.51 (1H, dd, J=2.4, 8.4 Hz), 7.52 (2H, d, J=8.8 Hz), 7.62 (1H, s), 7.68 (1H, d, J=2.4 Hz). IR(KBr) $\nu$: 2932, 1690 cm$^{-1}$.

REFERENCE EXAMPLE 98

To a mixture of ethyl 7-bromo-2,3-dihydro-1-benzoxepine-4-carboxylate (0.5 g), 4-morpholinophenyl borate (0.39 g), 1M potassium carbonate (6 ml) and ethanol (6 ml) was added toluene (50 ml), and the mixture was stirred under argon atmosphere at room temperature for 30 minutes. To the mixture was added tetrakistriphenylphosphinepalladium (0.07 g), and the mixture was refluxed for 4 hours and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/ hexane) to give colorless crystals (0.54 g), which were dissolved in 1N sodium hydroxide (15 ml), methanol (100 ml) and tetrahydrofuran (100 ml). The mixture was stirred at room temperature over night, concentrated and neutralized with hydrochloric acid to precipitate 7-(4-morpholinophenyl)-2,3-dihydro-1-benzoxepine-4-carboxylic acid (0.44 g) as colorless crystals.

mp 291–292° C.(dec.). $^1$H-NMR($\delta$ ppm, DMSO-d$_6$): 2.87 (2H, t, J=4.8 Hz), 3.12–3.17 (4H, m), 3.73–3.78 (4H, m), 4.23 (2H, t, J=4.8 Hz), 7.00 (3H, d, J=8.4 Hz), 7.51 (1H, dd, J=2.4, 8.4 Hz), 7.56 (2H, d, J=8.8 Hz), 7.60 (1H, s), 7.69 (1H, d, J=2.4 Hz). Anal. for C$_{21}$H$_{21}$NO$_4$: Calcd. C, 71.78: H, 6.02: N, 3.99. Found C, 71.42; H, 6.19; N, 4.16.

REFERENCE EXAMPLE 99

To a mixture of ethyl 7-bromo-2,3-dihydro-1-benzoxepine-4-carboxylate (0.5 g), 4-(1-imidazolyl)phenyl borate (0.38 g), 1M potassium carbonate (7 ml) and ethanol (7 ml) was added toluene (50 ml), and the mixture was stirred under argon atmosphere at room temperature for 30 minutes. To the mixture was added tetrakistriphenylphosphinepalladium (0. 07 g), and the mixture was refluxed for 4 hours and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate) to give colorless crystals (0.53 g), which were dissolved in 1N sodium hydroxide (10 ml) and methanol (50 ml). The mixture was stirred at room temperature over night, concentrated and neutralized with hydrochloric acid to precipitate 7-(4-(1-imidazolyl)phenyl)-2,3-dihydro-1-benzoxepine-4-carboxylic acid (0.44 g) as colorless crystals.

mp>300° C.; $^1$H-NMR($\delta$ ppm, DMSO-d$_6$): 2.89 (2H, t, J=4.5 Hz), 4.26 (2H, t, J=4.5 Hz), 7.07 (1H, d, J=8.4 Hz), 7.13 (1H, s), 7.55–7.68 (3H, m), 7.73 (2H, d, J=8.8 Hz), 7.81 (1H, s), 7.85 (2H, d, J=8.8 Hz), 8.33 (1H, s). Anal. for C$_{20}$H16N$_2$O$_3$.0.3H$_2$O: Calcd. C, 71.12; H, 4.95; N, 8.29. Found C, 71.15; H, 4.84; N, 8.21.

REFERENCE EXAMPLE 100

In 1,2-dichloroethane (100 ml) was suspended p-nitrobenzylamine hydrochloride (8.1 g), 4H-tetrahydrothiopyran-4-one (5.0 g) and triethylamine (6 ml), and to the suspension was added sodium triacetoxy boron hydride (12.8 g) under ice-cooling. Under nitrogen atmosphere, the mixture was stirred at room temperature for 9 hours. Under ice-cooling, to the mixture were added 37% formalin (3.9 ml) and sodium triacetoxy boron hydride (12.8 g). Under nitrogen atmosphere, the mixture was stirred at room temperature over night. The solvent was evaporated, and the residue was neutralized with sodium hydroxide. The mixture was extracted with ethyl acetate. The organic layer was washed with water and saturated sodium chloride solution, and dried with anhydrous magnesium sulfate. Under reduced pressure, the solvent was evaporated to give yellow oil (11.5 g), to which were added reduced iron (12 g) and acetic acid (200 ml). The mixture was stirred at room temperature over night. The solvent was evaporated, and to the residue was added ethyl acetate. The precipitate was filtered off, and the filtrate was washed with sodium hydrogen carbonate solution, water and saturated sodium chloride solution, and dried with anhydrous magnesium sulfate. Under reduced pressure, the solvent was evaporated, and the residue was purified with silica gel column (ethyl acetate/methanol/triethylamine) to give 4-(N-methyl-N-(tetrahydrothiopyran-4-yl)aminomethyl)aniline (8.8 g) as pale yellow crystals.

mp 88–89° C.; $^1$H-NMR($\delta$ ppm, CDCl$_3$): 1.65–1.84 (2H, m), 2.10–2.18 (2H, m), 2.19 (3H, s), 2.45 (1H, tt, J=3.2, 13.0 Hz), 2.65–2.71 (4H, m), 3.47 (2H, s), 3.61 (2H, br), 6.64 (2H, d, J=8.4 Hz), 7.08 (2H, d, J=8.4 Hz). IR(KBr) v: 2932, 1620 cm$^{-1}$. Anal. for $C_{13}H_{20}N_2S$: Calcd. C, 66.06; H, 8.53; N, 11.85. Found C, 66.03; H, 8.35; N, 11.78.

REFERENCE EXAMPLE 101

A mixture of sodium methoxide (12.5 g) and dimethyl carbonate (150 ml) was added to 3-bromo-6,7,8,9-tetrahydro-5H-benzocycloheptan-5-one (10.8 g), and the mixture was refluxed for 8 hours under nitrogen atmosphere. Under ice-cooling, the mixture was poured into 1N hydrochloric acid, and the mixture was extracted with ethyl acetate. The organic layer was washed with and saturated sodium chloride solution, and dried with anhydrous magnesium sulfate. The solvent was evaporated to give brown oil (13.1 g), which was dissolved in dichloromethane (150 ml). To the mixture was dropwise added sodium boron hydride dissolved in methanol, under ice-cooling. After starting materials disappeared, water was added to the reaction mixture, and the mixture was concentrated and extracted with ethyl acetate. The organic layer was washed with and saturated sodium chloride solution, and dried with anhydrous magnesium sulfate. The solvent was evaporated, and the residue was dissolved in dichloromethane (150 ml). To the mixture was added triethylamine (29 ml), and to the mixture was dropwise added methane-sulfonylchloride (5.3 ml) under ice-cooling. The mixture was stirred at room temperature under nitrogen atmosphere over night, and to the mixture was added water. The mixture was concentrated and extracted with ethyl acetate. The organic layer was washed with and saturated sodium chloride solution, and dried with anhydrous magnesium sulfate. The solvent was evaporated, and the residue was purified with silica gel column (ethyl acetate/hexane) to give methyl 2-bromo-6,7-dihydro-5H-benzo-cycloheptene-8-carboxylate (1.7 g) as colorless crystals.

mp 83–84° C.; $^1$H-NMR($\delta$ ppm, CDCl$_3$): 1.97–2.10 (2H, m), 2.62 (2H, t, J=6.6 Hz), 2.72–2.78 (2H, m), 3.82 (3H, s), 7.02 (1H, d, J=8.0 Hz), 7.32 (1H, dd, J=2.2, 8.0 Hz), 7.45 (1H, d, J=2.2 Hz), 7.60 (1H,s). IR(KBr) v: 2946, 1713 cm$^{-1}$.

Anal. for $C_{13}H_{13}BrO_2$: Calcd. C, 55.54; H, 4.66. Found C, 55.56; H, 4.75.

REFERENCE EXAMPLE 102

To a mixture of methyl 2-bromo-6,7-dihydro-5H-benzocycloheptene-8-carboxylate (0.5 g), 4-piperidinophenyl borate (0.4 g), 1M potassium carbonate (6 ml) and ethanol (6 ml) was added toluene (50 ml), and the mixture was stirred under argon atmosphere at room temperature for 30 minutes. To the mixture was added tetrakistriphenylphosphinepalladium (0.08 g), and the mixture was refluxed over night and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate/hexane) to give colorless crystals (0.45 g), which were dissolved in 1N sodium hydroxide (15 ml), methanol (50 ml) and tetrahydrofuran (50 ml). The mixture was refluxed at room temperature for 2 hours, concentrated and neutralized with hydrochloric acid to precipitate 2-(4-piperidinophenyl)-6,7-dihydro-5H-benzocycloheptene-8-carboxylic acid (0.46 g) as colorless crystals.

mp 219–220° C.(dec.). $^1$H-NMR($\delta$ ppm, DMSO-d$_6$): 1.50–1.70(6H,m), 1.85–2.05(2H,m), 2.56 (2H, t, J=6.4 Hz), 2.80–2.82 (2H, s), 3.13–3.25 (4H, m), 6.99 (2H, d, J=8.7 Hz), 7.23 (1H, d, J=8.0 Hz), 7.47 (1H, dd, J=1.8, 8.0 Hz), 7.54 (2H, d, J=8.7 Hz), 7.60 (1H, d, J=1.8 Hz), 7.70 (1H, s). Anal. for $C_{23}H_{25}NO_2 \cdot 0.2H_2O$: Calcd. C, 78.69; H, 7.29; N, 3.99. Found C, 78.82; H, 7.38; N, 3.89.

REFERENCE EXAMPLE 103

To a mixture of N-t-butoxycarbonylpiperidin-4-one (3 g; M. S. Ashwood et al., J. Chem. Soc. Perkin Trans. 1, 1995, 641–644) and methylamine hydrochloride (1 g) were added triethylamine (2.1 ml) and 1,2-dichloroethane(50 ml). Under ice-cooling, to the mixture was added sodium triacetoxy boron hydride (4.5 g), and the mixture was stirred under nitrogen atmosphere at room temperature for 4 hours. The mixture was neutralized with sodium hydroxide, concentrated and extracted with ethyl acetate. The organic layer was washed with saturated sodium chloride solution and dried with anhydrous magnesium sulfate. Under reduced pressure, the solvent was evaporated to give 1-t-butoxycarbonyl-4-methylaminopiperidine (3.1 g) as colorless oil.

$^1$H-NMR($\delta$ ppm, CDCl$_3$): 1.13–1.33 (3H, m), 1.33–1.54 (3H, m), 1.45 (9H, s), 1.83–1.88 (2H, m), 2.44 (3H, s), 2.44–2.56 (1H, m), 2.73–2.87 (2H, m), 4.01 (1H, br).

REFERENCE EXAMPLE 104

In chlorobenzene (100 ml) was dissolved 2-bromo-4'-acetophenone (25.1 g), and the mixture was dropwise added to a suspension of hexamethylenetetramine (15.9 g) in chlorobenzene (100 ml). The mixture was stirred under nitrogen atmosphere at 60° C. for 4 hours and cooled to precipitate crystals, which were filtered and washed with ethanol and diethylether. The resulting crystals were added little by little to a mixture of 95% ethanol (100 ml) and hydrochloric acid (50 ml), and the mixture was stirred at room temperature over night. Precipitated crystal was filtered and washed with diethylether. To the crystal was added di-t-butyl bicarbonate (32 g), triethylamine (29 ml) and dichloromethane (500 ml), and the mixture was stirred at room temperature for 2 hours, washed with water, 10% citric acid and water, and dried with anhydrous magnesium sulfate. Under reduced pressure, the solvent was evaporated, and the residue was purified with silica gel column (ethyl acetate/hexane) to give yellow solid (24.9 g), 12 g of which was dissolved in ethanol (200 ml) and ethyl acetate (50 ml). To the mixture was added 10% palladium on carbon (1.2 g) and catalytic hydrogenation was carried out at room temperature for 6 hours. The catalyst was filtered off, and the solvent was evaporated to give colorless crystals (6.5 g), 4 g of which was dissolved in dimethylformamide (50 ml). To the mixture was added sodium hydride (60%, 1.4 g) at −3° C., and the mixture was stirred for 20 minutes. To the mixture was dropwise added 1,4-dibromobutane (2.1 ml), and the mixture was stirred under ice-cooling for 1.5 hours. To the mixture was ammonium chloride solution, and the mixture was extracted with ethyl acetate. The organic layer was washed with water and saturated sodium chloride solution, and dried with anhydrous magnesium sulfate. Under reduced pressure, the solvent was evaporated, (4-aminophenyl) [1-(tert-butoxycarbonyl)piperidin-2-yl] methanone (2.1 g) as pale yellow crystals.

mp 187–188° C. $^1$H-NMR(δ ppm, CDCl$_3$): 1.42 (9H, br), 1.43 (2H, br), 1.80 (1H, br), 2.05 (1H, br), 3.22 (1H, br), 3.95 (1H, br), 4.09 (2H, br), 5.55 (1H, br), 6.63 (2H, d, J=8.4 Hz), 7.79 (2H, d, J=8.4 Hz). IR(KBr) ν: 3362, 2942, 1682cm$^{-1}$. Anal. for C$_{17}$H$_{24}$N$_2$O$_3$.0.1H$_2$O: Calcd. C, 66.69; H, 7.97; N, 9.15. Found C, 66.60; H, 7.91; N, 8.87.

REFERENCE EXAMPLE 105

A mixture of 2-(4-nitrobenzyl)pyridine (J. Chem. Soc., p549, 1929) (1.50 g) and 5% Pd-C (0.15 g) in ethanol (30 ml) was vigorously stirred under hydrogen atmosphere for 8 hours, and the Pd-C was filtered off. The filtrate was concentrated under reduced pressure, and the residue was separated and purified with column chromatography (ethyl acetate/hexane=1:1→2:1) to give 2-(4-aminobenzyl)-pyridine (1.09 g) as yellow oil.

$^1$H-NMR (200 MHz, CDCl$_3$) δ 3.41–3.75 (2H, m), 4.05 (2H, s), 6.50–6.69 (2H, m), 6.97–7.16 (4H, m), 7.51–7.60 (1H, m), 8.48–8.57 (1H, m). IR (neat) 3338, 3213, 3008, 1622, 1593, 1516, 1471, 1433, 1281, 754 cm$^{-1}$.

REFERENCE EXAMPLE 106

Under nitrogen atmosphere, to a solution of ethyl magnesium chloride in tetrahydrofuran (1.58M, 95 ml) was added diethyl phosphite (6.91 g) under ice-cooling, and the mixture was stirred at room temperature for 1 hour. To the mixture was added benzyl bromide (7.2 ml), and the mixture was refluxed for 4 hours. The reaction mixture was vigorously stirred and concentrated hydrochloric acid-ice was added to the mixture to stop the reaction. The mixture was extracted with diethylether and concentrated. To the residue was added chloroform, and the mixture was washed with water and concentrated under reduced pressure. The residue was separated and purified with column chromatography (ethyl acetate/ethanol=3:1→2:1) to give benzyldiethylphosphine oxide (1.45 g) as colorless crystals.

$^1$H-NMR (200 MHz, CDCl$_3$) δ 1.17 (6H, dt, J=16.6, 8.0 Hz), 1.57–1.75 (4H, m), 3.14 (2H, d, J=14.4 Hz), 7.19–7.40 (4H, m). IR (KBr) 3396, 2974, 16445, 1495, 1458, 1410, 1242, 1159, 1124, 1034, 829, 789, 702 cm$^{-1}$.

REFERENCE EXAMPLE 107

To a mixture of nitric acid (0.4 ml) and concentrated sulfuric acid (3 ml) was added benzyldiethylphosphine oxide (1.05 g) at 0° C., and the mixture was stirred at 50° C. for 1 hour. The reaction mixture was added to ice-water, and ammonia solution was added to the solution to neutralize the solution, which was extracted with ethyl acetate. The organic layer was washed with saturated sodium chloride solution, dried with magnesium sulfate and concentrated. The residue was separated and purified with column chromatography (ethyl acetate/ethanol=3:2→1:1) to give 4-nitrobenzyldiethylphosphine oxide (518 mg) as pale yellow crystals.

$^1$H-NMR (200 MHz, CDCl$_3$) δ 1.18 (6H, dt, J=17.0, 8.0 Hz), 1.64–1.86 (4H, m), 3.23 (2H, d, J=13.6 Hz), 7.49 (2H, dd, J=8.8, 1.6 Hz), 8.20 (2H, d, J=8.8 Hz). IR (KBr) 1599, 1506, 1340, 1169, 864, 773, 694, 501 cm$^{-1}$.

REFERENCE EXAMPLE 108

A mixture of 4-nitrobenzyldiethylphosphine oxide (0.4 g) and 10% Pd-C (0.06 g) in ethanol (10 ml) was vigorously stirred under hydrogen atmosphere for 16 hours, and the Pd-C was filtered off. The filtrate was concentrated under reduced pressure to give 4-aminobenzyldiethylphosphine oxide (349 mg) as brown oil.

$^1$H-NMR (200 MHz, CDCl$_3$) δ 1.16 (6H, dt, J=16.6, 7.8 Hz), 1.56–1.76 (4H, m), 3.02 (2H, d, J=14.4 Hz), 6.64 (2H, d, J=8.4 Hz), 7.03 (2H, dd, J=8.4, 1.8 Hz). IR (neat) 3336, 1630, 1614, 1516, 1460, 1408, 1284, 1157, 1126, 841, 791, 768, 540 cm$^{-1}$.

REFERENCE EXAMPLE 109

Under nitrogen atmosphere, to a solution of propyl magnesium bromide in tetrahydrofuran (2M, 250 g) was added diethyl phosphite (18.0 g) under ice-cooling, and the mixture was stirred at room temperature for 3 hours. To the reaction mixture was added benzyl bromide (24.7 ml), and the mixture was refluxed for 5 hours. The reaction mixture was vigorously stirred and added to concentrated hydrochloric acid-ice to stop the reaction. The mixture was extracted with ethyl acetate and concentrated. The residue was separated and purified with column chromatography (ethyl acetate ethyl acetate/ethanol=3:1) to give benzyldipropylphosphine oxide (25.33 g) as colorless crystals.

$^1$H-NMR (200 MHz, CDCl$_3$) δ 0.94–1.09 (6H, m), 1.49–1.75 (8H, m), 3.15 (2H, d, J=14.6 Hz), 7.19–7.39 (5H, m). IR (KBr) 3425, 2964, 1645, 1603, 1497, 1456, 1242, 1161, 1126, 1080, 1030, 843 cm$^{-1}$.

REFERENCE EXAMPLE 110

To a mixture of nitric acid (3.6 ml) and concentrated sulfuric acid (22 ml) was added benzyldipropylphosphineoxide (10.75 g) at 0° C., and the mixture was stirred at 60° C. for 1.5 hours. The reaction mixture was added to ice-water, and ammonia solution was added to the mixture to neutralize the solution, which was extracted with ethyl acetate. The organic layer was washed with saturated sodium chloride solution, dried with magnesium sulfate and concentrated. The residue was separated and purified with column chromatography (ethyl acetate/ethanol=9:1→4:1) to give 4-nitrobenzyldipropylphosphine oxide (3.77 g) as pale yellow crystals.

$^1$H-NMR (200 MHz, CDCl$_3$) δ 0.96–1.09 (6H, m), 1.51–1.75 (8H, m), 3.20 (2H, d, J=13.6 Hz), 7.47 (2H, dd, J=8.8, 2.0 Hz), 8.21 (2H, d, J=8.8 Hz). IR (KBr) 1527, 1431, 1352, 1028 cm$^{-1}$.

REFERENCE EXAMPLE 111

A mixture of 4-nitrobenzyldipropylphosphine oxide (3.0 g) and 5% Pd-C (0.3 g)in ethanol (50 ml) was vigorously stirred under hydrogen atmosphere for 16 hours, and the Pd-C was filtered off. The filtrate was concentrated under reduced pressure. The residue was separated and purified with column chromatography (ethanol/ethyl acetate=1:5→1:4) and recrystallized from ethanol-ethyl acetate to give 4-aminobenzyldipropylphosphine oxide (1.78 g) as colorless crystals.

m.p. 104–106° C.; $^1$H-NMR (200 MHz, CDCl$_3$) δ 0.88–1.12 (6H, m), 1.43–1.72 (8H, m), 3.01 (2H, d, J=14.8 Hz), 3.52–3.76 (2H, m), 6.65 (2H, d, J=8.6 Hz), 7.01 (2H, dd, J=8.6, 2.0 Hz). IR (KBr) 3348, 3209, 2058, 1608, 1512, 1155, 1126, 852 cm$^{-1}$; Elemental Analysis for C$_{13}$H$_{22}$NOP; Calcd. C, 65.25; H, 9.27; N, 5.85; P, 12.94: Found. C, 65.16; H, 9.04; N, 5.91; P, 12.94.

REFERENCE EXAMPLE 112

Under nitrogen atmosphere, to a solution of 2-bromo-3-hydroxypyridine (10.00 g) in DMF (100 ml) was added sodium hydride (60% oil, 2.5 g) at 0° C., and the mixture was stirred for 30 minutes. To the reaction mixture was added methyl iodide (4.0 ml), and the mixture was stirred at room temperature for 2 hours. To the reaction mixture was added water, and the mixture was extracted with ethyl acetate. The organic layer was washed with saturated sodium chloride solution, dried with magnesium sulfate and concentrated. Under reduced pressure, the residue was separated and purified with column chromatography (ethyl acetate/hexane=1:2) to give 2-bromo-3-methoxypyridine (9.24 g) as colorless crystals.

m.p. 41–43° C.; $^1$H-NMR (200 MHz, CDCl$_3$) δ 3.92 (3H, s), 7.15 (1H, dd, J=8.0, 1.4 Hz), 7.24 (1H, dd, J=8.0, 4.4 Hz), 7.99 (1H, dd, J=4.4, 1.4 Hz). IR (KBr) 3055, 1562, 1468, 1414, 1298, 1205, 1078, 1049, 791, 667 cm$^{-1}$; Elemental Analysis for C$_6$H$_6$NO; Calcd. C, 38.33; H, 3.22 N, 7.45: Found. C, 38.35; H, 3.07; N, 7.28.

REFERENCE EXAMPLE 113

To a solution of 2-bromo-3-methoxypyridine (1.00 g) in diethylether (20 ml) was added a solution of n-butyllithium in hexane (1.6M, 3.7 ml) at −78° C., and the mixture was stirred for 1 hour to prepare the lithium salt, which was dropwise added to a solution of 4-nitrobenzaldehyde (0.81 g) in tetrahydrofuran (10 ml) cooled at −78° C. The mixture was stirred at −78° C. To the reaction mixture was added water to stop the reaction, and the mixture was extracted with ethyl acetate. The organic layer was washed with saturated sodium chloride solution, dried with magnesium sulfate and concentrated. Under reduced pressure, the residue was separated and purified with column chromatography (ethyl acetate/hexane=1:3→1:1) to give 3-methoxypyridin-2-yl)-(4-nitrophenyl)methanol (742 mg) as pale yellow crystals.

m.p. 137–138° C.; $^1$H-NMR (200 MHz, CDCl$_3$) δ 3.81 (3H, s), 5.64 (1H, d, J=6.8 Hz), 6.02 (1H, d, J=6.8 Hz), 7.17 (1H, dd, J=8.4, 1.4 Hz), 7.27 (1H, dd, J=8.4, 4.6 Hz), 7.58 (2H, dd, J=7.0, 2.0 Hz), 8.15 (2H, dd, J=7.0, 2.0 Hz), 8.21 (1H, dd, J=4.6, 1.4 Hz). IR (KBr) 3348, 1524, 1464, 1344, 1284, 1053, 1020, 837, 797, 744, 689 cm$^{-1}$; Elemental Analysis for C$_{13}$H$_{12}$N$_2$O$_4$; Calcd. C, 60.00; H, 4.65; N, 10.76: Found. C, 59.97; H, 4.57; N, 10.82.

REFERENCE EXAMPLE 114

A mixture of (3-methoxypyridin-2-yl)-(4-nitrophenyl) methanol (600 mg) and 5% Pd-C (0.06 g) in ethanol (20 ml) was vigorously stirred under hydrogen atmosphere for 3 hours, and the Pd-C was filtered off. The filtrate was concentrated under reduced pressure to give (4-aminophenyl)-(3-methoxypyridin-2-yl)-methanol (483 mg) as pale yellow crystals.

$^1$H-NMR (200 MHz, CDCl$_3$) δ 3.51–3.65 (2H, m), 3.75 (3H, s), 5.33 (1H, d, J=7.1 Hz), 5.85 (1H, d, J=7.1 Hz), 6.60 (2H, dd, J=6.6, 1.8 Hz), 7.08–7.23 (4H, m), 8.17 (1H, dd, J=4.6, 1.4 Hz). IR (KBr) 3458, 3463, 3323, 1626, 1614, 1518, 1454, 1427, 1279, 1178, 1038, 835, 804 cm$^{-1}$.

REFERENCE EXAMPLE 115

A solution of diethyl benzylphosphonate (25 g) in methanol (10 ml) and concentrated hydrochloric acid (500 ml) solution was refluxed for 4 days. The mixture was cooled to room temperature, and precipitated crystal was collected by filtration to give benzylphosphonic acid (11.17 g) as colorless crystals.

m.p. 171–173° C.; $^1$H-NMR (200 MHz, DMSO-d$_6$) δ 2.96 (2H, d, J=21.6 Hz), 7.13–7.34 (5H, m). IR (KBr) 2779, 2330, 1497, 1458, 1263, 1074, 993, 943, 781, 694, 527, 428 cm$^{-1}$. Elemental Analysis for C$_7$H$_9$O$_3$P; Calcd. C, 48.85; H, 5.27; P, 18.00: Found. C, 48.75; H, 5.01; P, 17.78.

REFERENCE EXAMPLE 116

Under nitrogen atmosphere, to a mixture of magnesium (3.39 g) and a piece of iodine in diethylether (16 ml) was dropwise added a solution of 1,4-dibromobutane (5.55 ml) and 1,2-dibromoethane (2 ml) in diethylether (80 ml) at 40° C. for 1 hour. The mixture was refluxed for 1 hour, cooled to room temperature and allowed to stand for 2 hours. The upper layer of diethylether was removed through cannula, to obtain the di-Grignard reagent, which was dissolved in dichloro-methane (210 ml). The resulting di-Grignard reagent as it is was used for the following reaction. To benzyl phosphonate (8.0 g) was added thionyl chloride (40 ml) and then 2 drops of DMF, and the mixture was refluxed for 4 hours and concentrated under reduced pressure. The residue was dissolved in dichloromethane (210 ml), and the mixture was cooled to 0° C. To the mixture was dropwise added a solution of the above di-Grignard reagent in dichloromethane, which was cooled to 0° C., through cannula for 1 hour, and the mixture was stirred at room temperature for 16 hours. To the reaction mixture were added 10% ammonium chloride solution (100 ml) and saturated sodium chloride solution, and the mixture was extracted with dichloromethane. The organic layer was washed with saturated sodium chloride solution, dried with magnesium sulfate and concentrated under reduced pressure. The residue was separated and purified with column chromatography (ethanol/ethyl acetate=1:4) to give 1-benzyl-phosphorane-1-oxide (4.83 g) as colorless crystals.

$^1$H-NMR (200 MHz, CDCl$_3$) δ 1.40–2.08 (8H, m), 3.27 (2H, d, J=15.0 Hz), 7.11–7.42 (5H, m). IR (KBr) 2951, 1643, 1495, 1454, 1406, 1265, 1236, 1165, 1120, 702 cm$^{-1}$.

REFERENCE EXAMPLE 117

To 1-benzylphosphorane-1-oxide (4.17 g) were added nitric acid (1.7 ml) and sulfuric acid (11 ml) at 0° C., and the mixture was stirred at 50–60° C. for 2 hours. The reaction mixture was added to crushed ice and neutralized with ammonia solution. The mixture was extracted with ethyl acetate. The organic layer was washed with saturated sodium chloride solution, dried with magnesium sulfate and concentrated. Under reduced pressure, The residue was separated and purified with column chromatography (ethanol/ethyl acetate=1:4→1:1) to give1-(4-nitro-benzyl) phosphorane-1-oxide (2.22 g) as yellow crystals.

$^1$H-NMR (200 MHz, CDCl$_3$) δ 1.55–2.13 (8H, m), 3.32 (2H, d, J=13.8 Hz), 7.50 (2H, dd, J=8.8, 1.8 Hz), 8.22 (2H, d, J=8.8 Hz). IR (KBr) 3402, 2954, 1514, 1346, 1171, 860, 700 cm$^{-1}$.

REFERENCE EXAMPLE 118

A mixture of 1-(4-nitrobenzyl)phosphorane-1-oxide (1.80 g) and 10% Pd-C (0.2 g) in ethanol (30 ml) was vigorously stirred under hydrogen atmosphere for 24 hours, and the catalyst was filtered off. The filtrate was concentrated and purified with column chromatography (ethanol/ethyl acetate=1:2) and recrystallized from ethanol-diethylether to give 1-(4-aminobenzyl)phosphorane-1-oxide (0.90 g) as colorless crystals.

$^1$H-NMR (200 MHz, CDCl$_3$) δ 1.32–2.02 (8H, m), 3.16 (2H, d, J=14.6 Hz), 3.52–3.74 (2H, m), 6.65 (2H, d, J=8.4 Hz), 7.04 (2H, dd, J=8.4, 2.2 Hz). IR (KBr) 3386, 3338, 3228, 1641, 1612, 1516, 1296, 1263, 1174, 1124, 833 cm$^{-1}$.

REFERENCE EXAMPLE 119

Under nitrogen atmosphere, to a solution of 2-bromo-3-methoxymethoxypyridine (10.00 g) in diethylether (150 ml) was added a solution of n-butyllithium in hexane (1.6M, 31.5 ml) at −78° C., and the mixture was stirred for 1 hour to prepare the lithium salt. The resulting lithium salt was dropwise added to a solution of 4-nitrobenzaldehyde (6.93 g) in tetrahydrofuran (100 ml) cooled at −78° C., and the mixture was stirred at the same temperature for 3 hours. To the reaction mixture was added water to stop the reaction, and the mixture was extracted with ethyl acetate. The organic layer was washed with saturated sodium chloride solution, dried with magnesium sulfate and concentrated under reduced pressure. The residue was separated and purified with column chromatography (ethyl acetate/hexane=1:3→1:2) to give (3-methoxymethoxypyridin-2-yl)-(4-nitrophenyl)-methanol (11.78 g) as yellow oil.

$^1$H-NMR (200 MHz, CDCl$_3$) δ 3.27 (3H, s), 5.12 (1H, d, J=7.0 Hz), 5.20 (1H, d, J=7.0 Hz), 5.70 (1H, d, J=7.0 Hz), 6.02 (1H, d, J=7.0 Hz), 7.25 (1H, dd, J=8.4, 4.4 Hz), 7.42 (1H, dd, J=8.4, 1.4 Hz), 7.58 (2H, d, J=8.8 Hz), 8.15 (2H, d, J=8.8 Hz), 8.27 (1H, dd, J=4.4, 1.4 Hz). IR (neat) 3390, 1522, 1448, 1348, 1155, 1084, 1055, 980, 824, 849, 800, 744, 700 cm$^{-1}$.

REFERENCE EXAMPLE 120

A mixture of (3-methoxymethoxypyridin-2-yl)-(4-nitrophenyl)methanol (11.78 g) and 10% Pd-C (1.2 g) in ethanol (100 ml) was vigorously stirred under hydrogen atmosphere for 24 hours. The catalyst was filtered of, and the filtrate was concentrated under reduced pressure. The residue was separated and purified with column chromatography (ethyl acetate/hexane=1:1→2:1) to give 2-(4-aminobenzyl)-3-methoxymethoxypyridine (2.92 g) as orange oil.

$^1$H-NMR (200 MHz, CDCl$_3$) δ 3.37 (3H, s), 4.08 (2H, s), 5.16 (2H, s), 6.59 (2H, dd, J=8.4, 2.0 Hz), 7.04–7.19 (3H, m), 7.33 (1H, dd, J=8.4, 1.2 Hz), 8.18 (1H, dd, J=4.8, 1.2 Hz). IR (neat) 3433, 3352, 3219, 1620, 1514, 1446, 1265, 1153, 1082, 985, 922, 798 cm$^{-1}$.

REFERENCE EXAMPLE 121

Under nitrogen atmosphere, to a mixture of magnesium (3.2 g) and a piece of iodine in diethylether (20 ml) was dropwise added to a solution of 1,5-dibromopentane (13.21 g) and 1,2-dibromoethane (1.21 ml) in diethylether (80 ml) at 40° C. for 1 hour. The mixture was refluxed for 1 hour, cooled to room temperature and allowed to stand for 2 hours. The upper layer of diethylether was removed through cannula, to obtain the di-Grignard reagent, which was dissolved in dichloromethane (250 ml). The resulting di-Grignard reagent as it is was used for the following reaction. To benzylphosphonic acid (10.0 g) was added thionyl chloride (30 ml) and then a drop of DMF, and the mixture was refluxed for 3 hours and concentrated under reduced pressure. The residue was dissolved in dichloromethane (210 ml), and the mixture was cooled to 0° C. To the mixture was dropwise added a solution of the above di-Grignard reagent in dichloromethane, which was cooled to 0° C., through cannula for 1 hour, and the mixture was stirred at room temperature for 20 hours. To the reaction mixture were added 10% ammonium chloride solution (100 ml) and saturated sodium chloride solution, and the mixture was extracted with dichloromethane. The organic layer was washed with saturated sodium chloride solution, dried with magnesium sulfate and concentrated under reduced pressure. The residue was separated and purified with column chromatography (ethanol/ethyl acetate=1:3→1:2) to give 1-benzylphosphorinane-1-oxide (5.39 g) as colorless crystals.

$^1$H-NMR (200 MHz, CDCl$_3$) δ 1.36–2.18 (10H, m), 3.17 (2H, d, J=14.0 Hz), 7.23–7.42 (5H, m). IR (KBr) 2939, 2912, 2886, 1493, 1452, 1404, 1232, 1161, 827, 700 cm$^{-1}$.

REFERENCE EXAMPLE 122

To a solution of diethyl benzylphosphonate (2.5 g) in tetrahydrofuran (500 ml) was added Red-Al (70% toluene solution) (3.8 g) at room temperature, and the mixture was stirred until gas production stopped. To the reaction mixture was added 1,5-dibromopentane (25.18 g), and the mixture was stirred at 50–60° C. for 16 hours. To the reaction mixture was added water (20 ml), and precipitate was removed by filtration. The filtrate was concentrated under reduced pressure, and the residue was separated and purified with column chromatography (ethyl acetate→ethanolethyl acetate=1:2) to give 1-benzylphosphorinane-1-oxide (8.41 g) as colorless crystals.

$^1$H-NMR (200 MHz, CDCl$_3$) δ 1.36–2.18 (10H, m), 3.17 (2H, d, J=14.0 Hz), 7.23–7.42 (5H, m). IR (KBr) 2939, 2912, 2886, 1493, 1452, 1404, 1232, 1161, 827, 700 cm$^{-1}$.

REFERENCE EXAMPLE 123

To 1-benzylphosphorinane-1-oxide (5.39 g) were added nitric acid (1.94 ml) and sulfuric acid (15 ml) at 0° C., and the mixture was stirred at 50–60° C. for 2hours. The reaction mixture was added to crushed ice-water, neutralized with ammonia solution and extracted with ethyl acetate. The organic layer was washed with saturated sodium chloride solution, dried with magnesium sulfate and concentrated under reduced pressure. The residue was separated and purified with column chromatography (ethanol/ethyl acetate=1:3→1:2) to give 1-(4-nitrobenzyl)-phosphorinane-1-oxide (2.47 g) as pale yellow crystals.

$^1$H-NMR (200 MHz, CDCl$_3$) δ 1.46–2.18 (10H, m), 3.28 (2H, d, J=13.6 Hz), 7.48 (2H, dd, J=8.8, 2.2 Hz), 8.21 (2H, d, J=8.8 Hz). IR (KBr) 2926, 1599, 1516, 1348, 1230, 1159, 1132, 864, 822, 696 cm$^{-1}$.

REFERENCE EXAMPLE 124

A mixture of 1-(4-nitrobenzyl)phosphorinane-1-oxide (2.25 g) and 10% Pd-C (0.2 g) in ethanol (30 ml) was vigorously stirred under hydrogen atmosphere for 24 hours. The catalyst was filtered off, and the filtrate was concentrated recrystallized from ethanol-diethylether to give 1-(4-aminobenzyl)-phosphorinane-1-oxide (1.5 g) as pale yellow crystals.

$^1$H-NMR (200 MHz, CDCl$_3$) δ 1.27–2.16 (10H, m), 3.06 (2H, d, J=13.8 Hz), 3.53–3.80 (2H, m), 6.65 (2H, d, J=8.3 Hz), 7.05 (2H, dd, J=8.3, 2.0 Hz). IR (KBr) 3386, 3334, 3224, 2939, 1639, 1612, 1514, 1296, 1225, 1153, 1120, 841 cm$^{-1}$.

REFERENCE EXAMPLE 125

Under argon atmosphere, to a solution of 4-ethylbromobenzene (10.0 g) in tetrahydrofuran (60 ml) was added n-butyllithium (1.6M hexane solution) (37.2 ml) at −78° C., and the mixture was stirred for 1 hour. To the reaction mixture was dropwise added a solution of tributyl borate (13.68 g) in tetrahydrofuran (30 ml), and the reaction mixture was warmed to room temperature and stirred at room temperature for 2 hours. To the reaction mixture was added 10% sulfuric acid (100 ml), and the mixture was stirred for 1 hour. The mixture was extracted with ethyl acetate. The organic layer was washed with saturated sodium chloride solution, dried with magnesium sulfate and concentrated under reduced pressure. The residue was dissolved in acetone (30 ml), and to the mixture was added 10% sulfuric acid (50 ml). The mixture was stirred at room temperature for 16 hours, and under reduced pressure acetone was evaporated. The mixture was extracted with ethyl acetate. The organic layer was washed with saturated sodium chloride solution, dried with magnesium sulfate and concentrated under reduced pressure. The residue was separated and purified with column chromatography (ethyl acetate/hexane=1:2) to give crude 4-ethylphenyl borate (0.91 g) as colorless solid. Under argon atmosphere, a solution of ethyl 7-bromo-2,3-dihydro-1-benzoxepine-4-carboxylate (500 mg), the above crude 4-ethylphenyl borate (0.32 g) and potassium carbonate (0.49 g) in toluene-ethanol-water (20-2-2 ml) was stirred at room temperature for 1 hour. To the reaction mixture was added tetrakistriphenyl-phosphinepalladium (0.06 g), and the mixture was refluxed for 18 hours and cooled to room temperature. The organic layer was washed with saturated sodium chloride solution, dried with magnesium sulfate and concentrated under reduced pressure. The residue was separated and purified with column chromatography (ethyl acetate/hexane=1:15) to give ethyl 7-(4-ethylphenyl)-2,3-dihydro-1-benzoxepine-4-carboxylate (464 mg) as colorless crystals.

m.p. 81–83° C.; $^1$H-NMR (200 MHz, CDCl$_3$) δ 1.28 (3H, t, J=7.6 Hz), 1.36 (3H, t, J=7.2 Hz), 2.69 (2H, q, J=7.6 Hz), 3.00 (2H, t, J=5.2 Hz), 4.29 (2H,q, J=7.2 Hz), 4.30 (2H, t, J=5.2 Hz), 7.04 (1H, d, J=8.4 Hz), 7.27 (2H, d, J=8.6 Hz), 7.44–7.51 (3H, m), 7.55 (1H, d, J=2.6 Hz), 7.65 (1H, br s). IR (KBr) 1699, 1493, 1302, 1254, 1213, 1012, 822 cm$^{-1}$. Elemental Analysis for C$_{21}$H$_{22}$O$_3$; Calcd. C, 78.23; H, 6.88: Found. C, 78.05; H, 6.61.

REFERENCE EXAMPLE 126

To a solution of ethyl 7-(4-ethylphenyl)-2,3-dihydro-1-benzoxepine-4-carboxylate (430 mg) in ethanol (20 ml) was added 1N sodium hydroxide (4.0 ml) at room temperature, and the mixture was stirred for 24 hours and concentrated under reduced pressure. To the residue was added 1N hydrochloric acid (15 ml), and the mixture was extracted with ethyl acetate. The organic layer was washed with saturated sodium chloride solution, dried with magnesium sulfate and concentrated to give crystals, which were collected by filtration to give 7-(4-ethylphenyl)-2,3-dihydro-1-benzoxepine-4-carboxylic acid (328 mg) as colorless crystals.

m.p. 241–243° C.; $^1$H-NMR (200 MHz, CDCl$_3$) δ 1.28 (3H, t, J=7.8 Hz), 2.70 (2H, q, J=7.8 Hz), 3.02 (2H, t, J=4.8 Hz), 4.33 (2H, t, J=4.8 Hz), 7.05 (1H, d, J=8.4 Hz), 7.27 (2H, d, J=8.0), 7.46–7.56 (4H, m), 7.78 (1H, br s). IR (KBr) 2966, 1689, 1491, 1437, 1263, 1230, 822 cm$^{-1}$. Elemental Analysis for C$_{19}$H$_{18}$O$_3$; Calcd. C, 77.53; H, 6.16: Found. C, 77.52; H, 6.27.

REFERENCE EXAMPLE 127

Under argon atmosphere, to a solution of 4-tert-butylbromobenzene (10.0 g) in diethylether (50 ml) was added n-butyllithium (1.6M, hexane solution) (32.3 ml) at −78° C., and the mixture was stirred for 1 hour. To the reaction mixture was dropwise added trimethyl boric acid (16 ml) in diethylether (30 ml), and the mixture was warmed to room temperature and stirred at room temperature 16 hours. To the reaction mixture were added 1N hydrochloric acid (50 ml) and water, and the mixture was extracted with ethyl acetate. The organic layer was washed with saturated sodium chloride solution, dried with magnesium sulfate and concentrated under reduced pressure. The residue was separated and purified with column chromatography (ethyl acetate/hexane=1:9) to give crude 4-tert-phenyl borate(0.84 g) as pale yellow oil. Under argon atmosphere, a solution of ethyl 7-bromo-2,3-dihydro-1-benzoxepine-4-carboxylate (500 mg), the above crude 4-tert-butylphenyl borate(0.59 g) and potassium carbonate (0.47 g) in toluene-ethanol-water (20-2-2 ml) was stirred at room temperature for 1 hour. To the reaction mixture was added tetrakistriphenylphosphine palladium (0.06 g), and the mixture was refluxed for 20 hours and cooled to room temperature. The organic layer was washed with saturated sodium chloride solution, dried with magnesium sulfate and concentrated under reduced pressure. The residue was separated and purified with column chromatography (ethyl acetate/hexane=1:19) to give ethyl 7-(4-tert-butyl-phenyl)-2,3-dihydro-1-benzoxepine-4-carboxylate (504 mg) as colorless oil.

$^1$H-NMR (200 MHz, CDCl$_3$) δ 1.36 (9H, s), 1.36 (3H, t, J=7.2 Hz), 3.00 (2H, t, J=4.7 Hz), 4.29 (2H, q, J=7.2 Hz), 4.30 (2H, t, J=4.7 Hz), 7.04 (1H, d, J=8.2 Hz), 7.42–7.56 (6H, m), 7.65 (1H, br s). IR (neat) 1731, 1491, 1298, 1246, 1211, 1184, 1090, 1018, 824 cm$^{-1}$.

REFERENCE EXAMPLE 128

To a solution of ethyl 7-(4-tert-butylphenyl)-2,3-dihydro-1-benzoxepine-4-carboxylate (503.8 mg) in ethanol (10 ml)was added 1N sodium hydroxide (2.0 m) at room temperature, and the mixture was stirred for 64 hours and concentrated under reduced pressure. To the residue was added 1N hydrochloric acid (15 ml), and the mixture was extracted with ethyl acetate. The organic layer was washed with saturated sodium chloride solution, dried with magnesium sulfate and concentrated. The resulting crystal was collected by filtration to give 7-(4-tert-butylphenyl)-2,3-dihydro-1-benzoxepine-4-carboxylic acid (396 mg) as colorless crystals.

m.p. 259–261° C.; $^1$H-NMR (200 MHz, CDCl) δ 1.37 (9H, s), 3.03 (2H, t, J=4.4 Hz), 4.34 (2H, t, J=4.4 Hz), 7.06 (1H, d, J=8.4 Hz), 7.41–7.58 (6H, m), 7.79 (1H, br s). IR (KBr) 2951, 1678, 1489, 1263, 829, 820 cm$^{-1}$; Elemental Analysis for C$_{21}$H$_{22}$O$_3$; Calcd. C, 78.23; H, 6.88: Found. C, 78.10; H, 6.81.

REFERENCE EXAMPLE 129

Under argon atmosphere, a solution of ethyl 7-bromo-2,3-dihydro-1-benzoxepine-4-carboxylate (500 mg), 4-chloro-phenyl borate (289 mg) and potassium carbonate (464 mg) in toluene-ethanol-water (20-2-2 ml) was stirred at room temperature for 1 hour. To the reaction mixture was added tetrakistriphenyl-phosphinepalladium (0.06 g), and the mixture was refluxed for 24 hours and cooled to room temperature. The organic layer was washed with saturated sodium chloride solution, dried with magnesium sulfate and concentrated under reduced pressure. The residue was separated and purified with column chromatography (ethyl acetate/hexane=1:19) to give ethyl 7-(4-chlorophenyl)-2,3-dihydro-1-benzoxepine-4-carboxylate (459 mg) as colorless crystals.

m.p. 131–134° C.; $^1$H-NMR (200 MHz, CDCl$_3$) δ 1.36 (3H, t, J=7.2 Hz), 3.01 (2H, t, J=5.0 Hz), 4.23–4.34 (4H, m), 7.05 (1H, d, J=8.4 Hz), 7.37–7.52 (6H, m), 7.64 (1H, s). IR (KBr) 1705, 1485, 1302, 1255, 1213, 820 cm$^{-1}$; Elemental Analysis for C$_{19}$H$_{17}$O$_3$Cl; Calcd. C, 69.41; H, 5.21; Cl, 10.78: Found. C, 69.16; H, 5.12; Cl, 10.85.

REFERENCE EXAMPLE 130

To a solution of ethyl 7-(4-chlorophenyl)-2,3-dihydro-1-benzoxepine-4-carboxylate (400 mg) in tetrahydrofuran-ethanol (10-10 ml) was added 1N sodium hydroxide (2.0 ml) at room temperature, and the mixture was stirred for 42 hours and concentrated under reduced pressure.

To the residue was added 1N hydrochloric acid (15 ml), and the mixture was extracted with ethyl acetate. The organic layer was washed with saturated sodium chloride solution, dried with magnesium sulfate and concentrated. The resulting crystal was collected by filtration to give 7-(4-chlorophenyl)-2,3-dihydro-1-benzoxepine-4-carboxylic acid (342 mg) as colorless crystals.

m.p. 263–264° C.; $^1$H-NMR (200 MHz, CDCl$_3$) δ 3.03 (2H, t, J=4.7 Hz), 4.34 (2H, t, J=4.7 Hz), 7.07 (1H, d, J=8.4 Hz), 7.35–7.55 (6H, m), 7.76 (1H, br s). IR (KBr) 2959, 1680, 1483, 1267, 1230, 818 cm$^{-1}$; Elemental Analysis for C$_{17}$H$_{13}$O$_3$Cl; Calcd. C, 69.89; H, 4.36; Cl, 11.79: Found. C, 67.55; H, 4.19; Cl, 11.46.

REFERENCE EXAMPLE 131

Under argon atmosphere, a solution of ethyl 7-bromo-2,3-dihydro-1-benzoxepine-4-carboxylate (500 mg), 4-trifluoromethylphenyl borate (351.5 mg) and potassium carbonate (0.47 g) in toluene-ethanol-water (20-2-2 ml) was stirred at room temperature for 1 hour. To the reaction mixture was added tetrakistriphenylphosphinepalladium (0.06 g), and the mixture was refluxed for 20 hours and cooled to room temperature. The organic layer was washed with saturated sodium chloride solution, dried with magnesium sulfate and concentrated under reduced pressure. The residue was separated and purified with column chromatography (ethyl acetate/hexane=1:10) to give ethyl 7-(4-trifluoromethylphenyl)-2,3-dihydro-1-benzoxepine-4-carboxylate (489 mg) as colorless crystals.

m.p. 107–110° C.; $^1$H-NMR (200 MHz, CDCl$_3$) δ 1.37 (3H, t, J=7.2 Hz), 2.99–3.05 (2H, m), 4.29 (2H, q, J=7.2 Hz), 4.33 (2H, t, J=4.8 Hz), 7.09 (1H, d, J=8.4 Hz), 7.49 (1H, dd, J=8.4, 2.4 Hz), 7.58 (1H, d, J=2.4 Hz), 7.62–7.73 (5H, m). IR (KBr) 1701, 1329, 1257, 1126, 1107, 1068, 1012, 822 cm$^{-1}$; Elemental Analysis for C$_{20}$H$_{17}$O$_3$F$_3$; Calcd. C, 66.30; H, 4.73; F, 15.73: Found. C, 66.40; H, 4.63; F, 15.44.

REFERENCE EXAMPLE 132

To a solution of ethyl 7-(4-trifluoromethylphenyl)-2,3-dihydro-1-benzoxepine-4-carboxylate (440 mg) in tetrahydrofuran-ethanol (10-10 ml) was added 1N sodium hydroxide (4.0 ml) at room temperature, and the mixture was stirred for 20 hours and concentrated under reduced pressure. To the residue was added 1N hydrochloric acid (5 ml), and the mixture was extracted with ethyl acetate. The organic layer was washed with saturated sodium chloride solution, dried with magnesium sulfate and concentrated. The resulting crystal was collected by filtration to give 7-(4-trifluoromethylphenyl)-2,3-dihydro-1-benzoxepine-4-carboxylic acid (392 mg) as colorless crystals.

m.p. 273–276° C.; $^1$H-NMR (200 MHz, DMSO-d$_6$) δ 2.89 (2H, t, J=4.4 Hz), 4.28 (2H, t, J=4.4 Hz), 7.09 (1H, d, J=8.4 Hz), 7.61–7.70 (2H, m), 7.78 (2H, d, J=8.4 Hz), 7.92–7.96 (3H, m). IR (KBr) 2979, 1689, 1329, 1263, 1134, 1072, 831 cm$^{-1}$; Elemental Analysis for C$_{18}$H$_{13}$O$_3$F$_3$; Calcd. C, 64.67; H, 3.92: Found. C, 64.62; H, 3.89.

REFERENCE EXAMPLE 133

Under argon atmosphere, to a solution of 4-bromophenetole (26.4 g) in tetrahydrofuran (200 ml) was dropwise added n-butyl-lithium (1.6M, hexane solution) (90.3 ml) at −78° C. for 50 minutes, and the mixture was stirred for 30 minutes. To the reaction mixture was dropwise added a solution of trimethyl borate (40.8 g) in tetrahydrofuran (40 ml) for 30 minutes, and the mixture was stirred for 30 minutes, warmed to room temperature, and further stirred for 1.5 hours. To the reaction mixture was added 10% sulfuric acid (182 ml) for 40 minutes or more, and the mixture was stirred 1.5 hours, extracted with ethyl acetate, washed with saturated sodium chloride solution, dried with magnesium sulfate and concentrated under reduced pressure. The residue was crystallized from diisopropylether-hexane to give 4-ethoxyphenyl borate (15.5 g) as colorless crystals. Under argon atmosphere, a solution of ethyl 7-bromo-2,3-dihydro-1-benzoxepine-4-carboxylate (504.5 mg), the above 4-ethoxyphenyl borate (310 mg) and potassium carbonate (0.47 g) in toluene-ethanol-water (20-2-2 ml) was stirred at room temperature for 1 hour. To the reaction mixture was added tetrakistriphenylphosphine-palladium (0.06 g), and the mixture was refluxed for 20 hours and cooled to room temperature. The organic layer was washed with saturated sodium chloride solution, dried with magnesium sulfate and concentrated under reduced pressure. The residue was separated and purified with column chromatography (ethyl acetate/hexane=1:9–1:5) to give ethyl 7-(4-ethoxyphenyl)-2,3-dihydro-1-benzoxepine-4-carboxylate (468 mg) as colorless crystals.

m.p. 124–127° C.; $^1$H-NMR (200 MHz, CDCl$_3$) δ 1.36 (3H, t, J=7.2 Hz), 1.44 (3H, t, J=7.0 Hz), 3.00 (2H, t, J=4.0 Hz), 4.08 (2H, q, J=7.0 Hz), 4.28 (2H, q, J=7.2 Hz), 4.30 (2H, t, J=4.0 Hz), 6.96 (2H, dd, J=6.6, 2.2 Hz), 7.02 (1H, d, J=8.4 Hz), 7.41 (1H, d, J=2.6 Hz), 7.44–7.51 (3H, m), 7.65 (1H, br s). IR (KBr) 1701, 1493, 1254, 1215, 1014, 824 cm$^{-1}$; Elemental Analysis for C$_{21}$H$_{22}$O$_4$; Calcd. C, 74.54; H, 6.55: Found. C, 74.42; H, 6.47.

REFERENCE EXAMPLE 134

To a solution of ethyl 7-(4-ethoxyphenyl)-2,3-dihydro-1-benzoxepine-4-carboxylate (447.8 mg) in ethanol (20 ml) was added 2N sodium hydroxide (2.0 ml) at room temperature, and the mixture was stirred for 20 hours and concentrated under reduced pressure. To the residue was added 1N hydrochloric acid (5 ml), and the mixture was extracted with ethyl acetate and concentrated. The resulting crystal was collected by filtration to give 7-(4-ethoxyphenyl)-2,3-dihydro-1-benzoxepine-4-carboxylic acid (380 mg) as colorless crystals.

m.p. 269–271° C.; $^1$H-NMR (200 MHz, DMSO-$d_6$) δ 1.35 (3H, t, J=7.0 Hz), 2.81–2.94 (2H, m), 4.06 (2H, q, J=7.0 Hz), 4.18–4.31 (2H, m), 6.94–7.00 (3H, m), 7.49–7.79 (5H, m). IR (KBr) 2980, 1678, 1610, 1493, 1431, 1265, 1232, 1182, 1049, 926, 829, 810 cm$^{-1}$; Elemental Analysis for $C_{19}H_{18}O_4$; Calcd. C, 73.53; H, 5.85: Found. C, 73.44; H, 5.77.

REFERENCE EXAMPLE 135

Under argon atmosphere, to a solution of 4-trifluoromethoxybromobenzene (10.0 g) in tetrahydrofuran (75 ml) was dropwise added n-butyllithium (1.6M, hexane solution) (28.5 ml) at –78° C. for 20 minutes, and the mixture was stirred for 40 minutes. To the reaction mixture was dropwise added a solution of trimethyl borate (12.9 g) in tetrahydrofuran (12 ml) for 15 minutes, and the mixture was stirred at –78° C. for 30 minutes and at room temperature for 1 hour. To the reaction mixture was added was dropwise added 10% sulfuric acid (57.6 ml) for 15 minutes, and the mixture was stirred for 2 hours, extracted with ethyl acetate, washed with saturated sodium chloride solution, dried with magnesium sulfate and concentrated under reduced pressure. The residue was crystallized from hexane to give 4-trifluoromethoxyphenyl borate (2. 7 g) as colorless crystals. Under argon atmosphere, a solution of ethyl 7-bromo-2,3-dihydro-1-benzoxepine-4-carboxylate (500 mg), the above 4-trifluoromethoxyphenyl borate (380 mg) and potassium carbonate (0.46 g) in toluene-ethanol-water (20-2-2 ml) was stirred at room temperature for 1 hour. To the reaction mixture was added tetrakistriphenylphosphine-palladium (0.06 g), and the mixture was refluxed for 18 hours and cooled to room temperature. The organic layer was washed with saturated sodium chloride solution, dried with magnesium sulfate and concentrated under reduced pressure. The residue was separated and purified with column chromatography (ethyl acetate/hexane=1:10) to give ethyl 7-(4-trifluoromethoxyphenyl)-2,3-dihydro-1-benzoxepine-4-carboxylate (379 mg) as colorless crystals.

m.p. 59–63° C.; $^1$H-NMR (200 MHz, CDCl$_3$) δ 1.36 (3H, t, J=7.1 Hz), 3.01 (2H, t, J=4.8 Hz), 4.24–4.34 (4H, m), 7.06 (1H, d, J=8.4 Hz), 7.22–7.31 (2H, m), 7.44 (1H, dd, J=8.4, 2.2 Hz), 7.52 (1H, d, J=2.2 Hz), 7.57 (2H, d, J=8.8 Hz), 7.64 (1H, br s). IR (KBr) 1701, 1489, 1304, 1257, 1227, 1211, 1182, 1134, 1014, 833, 808 cm$^{-1}$; Elemental Analysis for $C_{20}H_{17}O_4F_3$; Calcd. C, 63.49; H, 4.53: Found. C, 63.68; H, 4.47.

REFERENCE EXAMPLE 136

To a solution of ethyl 7-(4-trifluoromethoxyphenyl)-2,3-dihydro-1-benzoxepine-4-carboxylate (323.9 mg) in tetrahydrofuran-ethanol (5–5 ml) was added 1N sodium hydroxide (2.0 ml) at room temperature, and the mixture was stirred for 5 days and concentrated under reduced pressure. To the residue 1N hydrochloric acid (5 ml) was added, and the mixture was extracted with ethyl acetate. The organic layer was washed with saturated sodium chloride solution, dried with magnesium sulfate and concentrated. The resulting crystal was collected by filtration to give 7-(4-trifluoromethoxyphenyl)-2,3-dihydro-1-benzoxepine-4-carboxylic acid (282 mg) as colorless crystals.

m.p. 252–254° C.; $^1$H-NMR (200 MHz, CDCl$_3$) δ 3.03 (2H, t, J=4.6 Hz), 4.34 (2H, t, J=4.6 Hz), 7.08 (1H, d, J=8.4 Hz), 7.28 (2H, d, J=8.8 Hz), 7.47 (1H, dd, J=8.4, 2.2 Hz), 7.54 (1H, d, J=2.2 Hz), 7.59 (2H, d, J=8.8 Hz), 7.78 (1H, br s). IR (KBr) 2981, 1691, 1493, 1290, 1261, 1213, 1169, 835 cm$^{-1}$; Elemental Analysis for $C_{18}H_{13}O_4F_3$; Calcd. C, 61.72; H, 3.74; F, 16.27: Found. C, 61.61; H, 3.72; F, 16.06.

REFERENCE EXAMPLE 137

To a solution of 5-bromosalicylaldehyde (10.0 g) and tert-butyl acrylate (17.5 ml) in tert-butanol (100 ml) was added potassium tert-butoxide (1.67 g) at room temperature, and the mixture was refluxed for 66 hours and cooled to room temperature. To the mixture was added ethyl acetate, and the mixture was washed with water, 1N sodium hydroxide and saturated sodium chloride solution, dried with magnesium sulfate and concentrated. The residue was separated and purified with column chromatography (ethyl acetate/hexane=1:19) to give tert-butyl 6-bromo-2H-1-benzopyran-3-carboxylate (10.86 g) as pale yellow crystals.

m.p. 96–97° C.; $^1$H-NMR (200 MHz, CDCl$_3$) δ 1.53 (9H, s), 4.95 (2H, d, J=0.8 Hz), 6.72 (1H, d, J=8.4 Hz), 7.21–7.30 (3H, m). IR (KBr) 1699, 1479, 1331, 1288, 1159, 1088, 816 cm$^{-1}$; Elemental Analysis for $C_{14}H_{15}O_3Br$; Calcd. C, 54.04; H, 4.86; Br, 25.68: Found. C, 53.98; H, 4.86; Br, 25.90.

REFERENCE EXAMPLE 138

Under argon atmosphere, a solution of tert-butyl 6-bromo-2H-1-benzopyran-3-carboxylate (5.00 g), 4-methylphenyl borate (2.62 g) and potassium carbonate (4,44 g) in toluene-ethanol-water (160-16-16 ml) was stirred at room temperature for 1 hour. To the reaction mixture was added tetrakistriphenylphosphinepalladium (0.56 g), and the mixture was refluxed for 14 hours and cooled to room temperature. The organic layer was washed with saturated sodium chloride solution, dried with magnesium sulfate and concentrated. The residue was separated and purified with column chromatography (ethyl acetate/hexane=1:19) to give pale yellow crystals, which were recrystallized from ethanol to give tert-butyl 6-(4-methylphenyl)-2H-1-benzopyran-3-carboxylate (3.84 g) as pale yellow crystals.

m.p. 80–82° C.; $^1$H-NMR (200 MHz, CDCl$_3$) δ 1.54 (9H, s), 2.39 (3H, s), 4.98 (2H, d, J=1.4 Hz), 6.94 (1H, d, J=8.2 Hz), 7.23 (2H, d, J=8.0 Hz), 7.33 (1H, d, J=2.2 Hz), 7.36–7.45 (4H, m). IR (KBr) 1705, 1367, 1340, 1311, 1251, 1159, 1133, 1003, 808 cm$^{-1}$; Elemental Analysis for $C_{21}H_{22}O_3$; Calcd. C, 78.23; H, 6.88: Found. C, 78.07; H, 6.89.

REFERENCE EXAMPLE 139

To tert-butyl 6-(4-methylphenyl)-2H-1-benzopyran-3-carboxylate (3.00 g) was added 4N hydrochloric acid-ethyl acetate (10 ml) at room temperature, and the mixture was stirred for 16 hours. To the reaction mixture was added hexane, and crystal was collected by filtration and washed with hexane to give 6-(4-methylphenyl)-2H-1-benzopyran-3-carboxylic acid (2.14 g) as pale yellow crystals.

m.p. 236–237° C.; $^1$H-NMR (200 MHz, CDCl$_3$) δ 2.40 (3H, s), 5.05 (2H, d, J=1.4 Hz), 6.94 (1H, d, J=8.2 Hz), 7.23–7.27 (2H, m), 7.37 (1H, d, J=2.2 Hz), 7.41–7.52 (3H, m), 7.63 (1H, br s). IR (KBr) 3022, 1689, 1633, 1485, 1442, 1306, 1242, 812 cm$^{-1}$; Elemental Analysis for $C_{17}H_{14}O_3$; Calcd. C, 76.68; H, 5.30: Found. C, 76.51; H, 5.03.

REFERENCE EXAMPLE 140

To a solution of 5-bromo-salicylaldehyde (10.0 g) and ethyl crotonate (11.36 g) in tert-butanol (50 ml) was added potassium tert-butoxide (1.12 g) at room temperature, and the mixture was refluxed for 3 days. To the reaction mixture was added water, and the mixture was extracted with ethyl acetate. The organic layer was washed with saturated sodium chloride solution, dried with magnesium sulfate and concentrated. The residue was separated and purified with column chromatography (ethyl acetate/hexane=1:10→1:5) to give pale yellow liquid (5.75 g). The resulting compound was used for the following reaction without subjecting to further purification. Under nitrogen atmosphere, to a solution of the above crude product (5.5 g) and triethylamine (7.3 ml) in dichloro-methane (50 ml) was added methanesulfonyl chloride (2.0 ml) at 0° C., and the mixture was stirred at 0° C. for 10 minutes and then at room temperature for 18 hours. To the reaction mixture was added water, and the mixture was extracted with diethylether. The organic layer was washed with saturated sodium chloride solution, dried with magnesium sulfate and concentrated. The residue was separated and purified with column chromatography (ethyl acetate/hexane=1:15) to give crude product (4.85 g) as pale yellow oil. The resulting compound was used for the following reaction without subjecting to further purification. Under argon atmosphere, a solution of the above crude product (4.7 g), 4-methylphenyl borate (2.58 g) and potassium carbonate (4.4 g) in toluene-ethanol-water (160-16-16 ml) was stirred at room temperature for 1 hour. To the reaction mixture was added tetrakistriphenylphosphinepalladium (0.54 g), and the mixture was refluxed for 20 hours and cooled to room temperature. The organic layer was washed with saturated sodium chloride solution, dried with magnesium sulfate and concentrated. The residue was separated and purified with column chromatography (ethyl acetate/hexane=1:15) to give ethyl 6-(4-methylphenyl)-2-methyl-2H-1-benzopyran-3-carboxylate (3.63 g) as pale yellow crystals.

m.p. 82–84° C.; $^1$H-NMR (200 MHz, CDCl$_3$) δ 1.35 (3H, t, J=7.2 Hz), 1.40 (3H, d, J=6.6 Hz), 2.39 (3H, s), 4.29 (2H, q, J=7.2 Hz), 5.40 (1H, q, J=6.6 Hz), 6.92 (1H, d, J=8.4 Hz), 7.24 (2H, d, J=8.2 Hz), 7.36 (1H, d, J=2.2 Hz), 7.40–7.49 (4H, m). IR (KBr) 1699, 1485, 1296, 1244, 1217, 1190, 1136, 1047, 804, 764, 511 cm$^{-1}$; Elemental Analysis for C$_{20}$H$_{20}$O$_3$; Calcd. C, 77.90; H, 6.54: Found. C, 77.79; H, 6.46.

REFERENCE EXAMPLE 141

To a solution of ethyl 6-(4-methylphenyl)-2-methyl-2H-1-benzopyran-3-carboxylate (3.0 g) in ethanol-tetrahydrofuran (30-30 ml) was added 1N sodium hydroxide (12 ml) at room temperature, and the mixture was stirred for 16 hours. Under reduced pressure, the solvent was evaporated and acidified with 1N hydrochloric acid. The mixture was extracted with ethyl acetate. The organic layer was washed with saturated sodium chloride solution and dried with magnesium sulfate. Under reduced pressure, the solvent was evaporated to give 6-(4-methylphenyl)-2-methyl-2H-1-benzopyran-3-carboxylic acid (2.15 g) as yellow crystals.

m.p. 190–192° C.; $^1$H-NMR (200 MHz, CDCl$_3$) δ 1.43 (3H, d, J=6.6 Hz), 2.39 (3H, s), 5.40 (1H, q, J=6.6 Hz), 6.94 (1H, d, J=8.4 Hz), 7.24 (2H, d, J=8.0 Hz), 7.38 (1H, d, J=2.2 Hz), 7.44 (2H, d, J=8.0 Hz), 7.50 (1H, dd, J=8.4, 2.2 Hz), 7.60 (1H, s). IR (KBr) 2983, 1680, 1635, 1485, 1421, 1298, 1261, 1190, 808 cm$^{-1}$; Elemental Analysis for C$_{18}$H$_{16}$O$_3$; Calcd. C, 77.12; H, 5.75: Found. C, 77.25; H, 5.63.

REFERENCE EXAMPLE 142

A solution of 5-bromo-2-thiophenecarboxyaldehyde (6.08 g) and methyl (triphenylphosphoranilidene)acetate (11.12 g) in toluene (60 ml) was refluxed under nitrogen atmosphere for 2 hours and cooled. To the mixture was added water, and the mixture was extracted with ethyl acetate. The organic layer was washed with saturated sodium chloride solution, dried with magnesium sulfate and concentrated under reduced pressure. The residue was separated and purified with column chromatography (ethyl acetate/hexane=1:15→1:9) and recrystallized from ethyl acetate to give methyl (E)-3-(5-bromothiophen-2-yl)-acrylate (7.44 g) as pale yellow crystals.

m.p. 60–62° C.; $^1$H-NMR (200 MHz, CDCl$_3$) δ 3.79 (3H, s), 6.13 (1H, d, J=15.8 Hz), 6.96–7.05 (2H, m), 7.66 (1H, d, J=15.8 Hz). IR (KBr) 1724, 1624, 1417, 1257, 1203, 1165, 968, 802, 486 cm$^{-1}$; Elemental Analysis for C$_8$H$_7$O$_2$SBr; Calcd. C, 38.88; H, 2.86; S, 12.98; Br, 32.34: Found. C, 38.95; H, 2.83; S, 13.13; Br, 32.36.

REFERENCE EXAMPLE 143

Under argon atmosphere, a solution of methyl (E)-3-(5-bromothiophen-2-yl)acrylate (4.0 g), 4-methylphenyl borate (2.64 g) and potassium carbonate (4.48 g) in toluene-ethanol-water (160-16-16 ml) was stirred at room temperature for 1 hour. To the reaction mixture was added tetrakistriphenylphosphinepalladium (0.56 g), and the mixture was refluxed for 16 hours and cooled to room temperature. The organic layer was washed with saturated sodium chloride solution, dried with magnesium sulfate and concentrated under reduced pressure to give crude product (5.24 g). To a solution of the resulting carboxylic acid ester (5.24 g) in tetrahydrofuran (100 ml) was added 1N sodium hydroxide (20 ml) at room temperature, and the mixture was stirred for 5 days. To the reaction mixture was added water, and the mixture was washed with ethyl acetate. The aqueous layer was acidified with concentrated hydrochloric acid, and the mixture was extracted with ethyl acetate, washed with saturated sodium chloride solution, dried with magnesium sulfate and concentrated under reduced pressure to give (E)-3-[5-(4-methylphenyl)-thiophen-2-yl]acrylic acid (1.9 g) as yellow crystals.

m.p. 223–225° C.; $^1$H-NMR (200 MHz, CDCl$_3$) δ 2.38 (3H, s), 6.21 (1H, d, J=15.8 Hz), 7.16–7.27 (4H, m), 7.52 (2H, d, J=8.0 Hz), 7.84 (1H, d, J=15.8 Hz). IR (KBr) 2968, 1666, 1606, 1413, 1261, 1230, 804 cm$^{-1}$; Elemental Analysis for C$_{14}$H$_{12}$O$_2$S; Calcd. C, 38.83; H, 4.95; S, 13.12: Found. C, 68.76; H, 5.07; S, 13.28.

REFERENCE EXAMPLE 144

To a suspension of 5-bromo-2-furancarboxylic acid (5.00 g) and N-hydroxysuccinimide (3.31 g) in acetonitrile (50 ml) was added 1-ethyl-3-(3'-dimethylaminopropyl)-carbodiimide hydrochloride (5.52 g) at room temperature, and the mixture was stirred for 2 hours. To the reaction mixture was added a suspension of N,O-dimethylhydroxylamine hydrochloride (2.81 g) and triethylamine (10 ml) in acetonitrile (20 ml), and the mixture was stirred for 1 hour. To the reaction mixture were added 1,8-diazabicyclo-[5.4.0]-7-undecene (4.3 ml) and DMF (50 ml), and the mixture was stirred for 3 hours and concentrated under reduced pressure. To the residue was added water, and the mixture was extracted with ethyl acetate. The organic layer was washed with saturated sodium chloride solution, dried with magnesium sulfate and concentrated under reduced pressure. The residue was separated and purified with column chromatography (ethyl acetate/hexane=1:4→1:3→1:2) to give N-methyl-N-methoxy-5-bromofuran-2-carboxamide (2.77 g) as pale yellow oil.

$^1$H-NMR (200 MHz, CDCl$_3$) δ 3.34 (3H, s), 3.77 (3H, s), 6.45 (1H, d, J=3.6 Hz), 7.09 (1H, d, J=3.6 Hz). IR (neat) 2974, 2937, 1647, 1475, 1416, 1385, 1211, 1024, 985, 926, 796, 739 cm$^{-1}$.

REFERENCE EXAMPLE 145

Under argon atmosphere, a solution of N-methyl-N-methoxy-5-bromofuran-2-carboxamide (2.77 g), 4-methylphenyl borate (1.93 g) and potassium carbonate (3.27 g) in toluene-ethanol-water (110-11-11 ml) was stirred at room temperature for 1 hour. To the reaction mixture was added tetrakistriphenylphosphinepalladium (0.41 g), and the mixture was refluxed for 20 hours and cooled to room temperature. The organic layer was washed with saturated sodium chloride solution, dried with magnesium sulfate and concentrated under reduced pressure. The residue was separated and purified with column chromatography (ethyl acetate/hexane=1:5→1:2→1:1) to give N-methyl-N-methoxy-5-(4-methylphenyl)furan-2-carboxamide (2.65 g) as colorless crystals.

m.p. 54–58° C.; $^1$H-NMR (200 MHz, CDCl$_3$) δ 2.38 (3H, s), 3.38 (3H, s), 3.82 (3H, s), 6.69 (1H, d, J=3.8 Hz), 7.20–7.26 (3H, m), 7.68 (2H, d, J=8.6 Hz). IR (neat) 1632, 1487, 1381, 1032, 987, 798, 739, 557, 494 cm$^{-1}$; Elemental Analysis for C$_{14}$H$_{15}$NO$_3$; Calcd. C, 68.56; H, 6.16; N, 5.71: Found. C, 68.22; H, 6.02; N, 5.47.

REFERENCE EXAMPLE 146

Under nitrogen atmosphere, to a solution of N-methyl-N-methoxy-5-(4-methylphenyl)furan-2-carboxamide (2.5 g) in tetrahydrofuran (20 ml) was added duisobutylaluminum hydride (1.01M toluene solution) (15 ml) at −78° C., and the mixture was stirred at −78° C. for 10 minutes and then at 0° C. for 15 minutes. To the reaction mixture was added 1N hydrochloric acid to stop the reaction, and the mixture was extracted with ethyl acetate. The organic layer was washed with saturated sodium chloride solution, dried with magnesium sulfate and concentrated. The residue was separated and purified with column chromatography (ethyl acetate/hexane=1:5→1:4) to give crude product (1.49 g). A solution of the crude aldehyde (1.49 g) and methyl (triphenylphosphoranilidene)acetate (2.67 g) in toluene (30 ml) was refluxed under nitrogen atmosphere for 1 hour and cooled. To the mixture was added water, and the mixture was extracted with ethyl acetate. The organic layer was washed with saturated sodium chloride solution, dried with magnesium sulfate and concentrated under reduced pressure. The residue was separated and purified with column chromatography (ethyl acetate/hexane=1:9→1:5) to give methyl (E)-3-[5-(4-methylphenyl)furan-2-yl]acrylate (1.63 g) as pale yellow crystals.

m.p. 113–115° C.; $^1$H-NMR (200 MHz, CDCl$_3$) δ 2.38 (3H, s), 3.80 (3H, s), 6.39 (1H, d, J=15.5 Hz), 6.68 (2H, s), 7.22 (2H, d, J=8.4 Hz), 7.44 (1H, d, J=15.5 Hz), 7.62 (2H, d, J=8.4 Hz). IR (KBr) 1716, 1632, 1304, 1201, 1161, 798 cm$^{-1}$; Elemental Analysis for C$_{15}$H$_{14}$O$_3$; Calcd. C, 74.36; H, 5.82: Found. C, 74.36; H, 5.75.

REFERENCE EXAMPLE 147

To a solution of methyl (E)-3-[5-(4-methylphenyl)-furan-2-yl]acrylate (1.49 g) in tetrahydrofuran-ethanol (10-10 ml) was added 2N sodium hydroxide (4 ml) at room temperature, and the mixture was stirred for 24 hours. The reaction mixture was acidified with 1N hydrochloric acid, and the mixture was extracted with ethyl acetate. The organic layer was washed with saturated sodium chloride solution, dried with magnesium sulfate and concentrated under reduced pressure to give (E)-3-[5-(4-methylphenyl)-furan-2-yl]acrylic acid (0.93 g) as colorless crystals.

m.p. 183–184° C.; $^1$H-NMR (200 MHz, CDCl$_3$) δ 2.39 (3H, s), 6.39 (1H, d, J=15.4 Hz), 6.70 (1H, d, J=3.4 Hz), 6.75 (1H, d, J=3.4 Hz), 7.23 (2H, d, J=8.2 Hz), 7.52 (1H, d, J=15.4 Hz), 7.64 (1H, d, J=8.2 Hz). IR (KBr) 2964, 1678, 1624, 1419, 1308, 1261, 785 cm$^{-1}$; Elemental Analysis for C$_{14}$H$_{12}$O$_3$; Calcd. C, 73.67; H, 5.30: Found. C, 73.42; H, 5.15.

REFERENCE EXAMPLE 148

A solution of 4-bromo-2-thiophenecarboxyaldehyde (4.77 g) and methyl (triphenylphosphoranilidene)acetate (8.44 g) in toluene (50 ml) was refluxed under nitrogen atmosphere for 3 hours and cooled. To the mixture was added water, and the mixture was extracted with ethyl acetate. The organic layer was washed with saturated sodium chloride solution, dried with magnesium sulfate and concentrated under reduced pressure. The residue was separated and purified with column chromatography (ethyl acetate/hexane=1:15) to give methyl (E)-3-(4-bromothiophen-2-yl)acrylate (5.55 g) as pale yellow crystals.

m.p. 63–67° C.; $^1$H-NMR (200 MHz, CDCl$_3$) δ 3.80 (3H, s), 6.25 (1H, d, J=15.8 Hz), 7.16 (1H, d, J=0.8 Hz), 7.26 (1H, d, J=0.8 Hz), 7.68 (1H, d, J=15.8 Hz). IR (KBr) 1713, 1630, 1304, 1257, 1165, 958, 828 cm$^{-1}$; Elemental Analysis for C$_8$H$_7$O$_2$SBr; Calcd. C, 38.88; H, 2.86; S, 12.98; Br, 32.34: Found. C, 38.78; H, 2.83; S, 12.98; Br, 32.27.

REFERENCE EXAMPLE 149

Under argon atmosphere, a solution of methyl (E)-3-(4-bromothiophen-2-yl)acrylic acid (3.0 g), 4-methylphenyl borate (1.82 g) and potassium carbonate (3.36 g) in toluene-ethanol-water (120-12-12 ml) was stirred at room temperature for 1 hour. To the reaction mixture was added tetrakistriphenylphosphinepalladium (0.42 g), and the mixture was refluxed for 24 hours and cooled to room temperature. The organic layer was washed with saturated sodium chloride solution, dried with magnesium sulfate and concentrated under reduced pressure. The residue was separated and purified with column chromatography (ethyl acetate/hexane=1:9→1:5→1:2) to give methyl (E)-3-[4-(4-methylphenyl)thiophen-2-yl)acrylate (2.40 g) as pale yellow crystals.

m.p. 116–118° C.; $^1$H-NMR (200 MHz, CDCl$_3$) δ 2.38 (3H, s), 3.80 (3H, s), 6.27 (1H, d, J=15.8 Hz), 7.21 (2H, d, J=7.8 Hz), 7.43–7.50 (4H, m), 7.80 (1H, d, J=15.8 Hz). IR (KBr) 1713, 1622, 1506, 1423, 1302, 1240, 1192, 1159, 966, 847, 916, 760 cm$^{-1}$; Elemental Analysis for C$_{15}$H$_{14}$O$_2$S; Calcd. C, 69.74; H, 5.46; S, 12.41: Found. C, 69.54; H, 5.47; S, 12.24.

REFERENCE EXAMPLE 150

To a solution of methyl (E)-3-[4-(4-methylphenyl)-thiophen-2-yl)acrylate (2.40 g) in tetrahydrofuran (50 ml) was added 2N sodium hydroxide (6.0 ml) at room temperature, and the mixture was stirred for 6 days. Precipitated crystal was collected by filtration and washed with tetrahydrofuran. To the crystals was added 1N hydrochloric acid (20 ml), and the mixture was extracted with ethyl acetate. The organic layer was washed with saturated sodium chloride solution, dried with magnesium sulfate and concentrated under reduced pressure to give (E)-3-[4-(4-methylphenyl)thiophen-2-yl]acrylic acid (1.24 g) as pale yellow crystals.

m.p. 206–207° C.; $^1$H-NMR (200 MHz, CDCl$_3$) δ 2.38 (3H, s), 6.28 (1H, d, J=15.6 Hz), 7.23 (2H, d, J=8.0 Hz), 7.47 (2H, d, J=8.0 Hz), 7.49 (1H, s), 7.55 (1H, d, J=1.4 Hz), 7.90 (1H, d, J=15.6 Hz). IR (KBr) 2970, 2918, 1682, 1622, 1306, 1196, 966, 818, 764 cm$^{-1}$; Elemental Analysis for C$_{14}$H$_{12}$O$_2$S; Calcd. C, 68.83; H, 4.95; S, 13.12: Found. C, 68.66 : H, 4.77 : S, 13.08.

REFERENCE EXAMPLE 151

Under nitrogen atmosphere, to a solution of ethyl chloroformylbutyrate (25.0 g) in 1,2-dichloroethane (150 ml) was dropwise added a solution of tin tetrachloride (76.6 g) in 1,2-dichloroethane (50 ml) at 0° C. and then a solution of 2-bromothiophene (22.8 g) in 1,2-dichloroethane (20 ml), and the mixture was stirred at room temperature for 2 hours. The reaction mixture was vigorously stirred and added to ice-concentrated hydrochloric acid to stop the reaction. The mixture was stirred for 30 minutes and extracted with dichloromethane. The organic layer was washed with saturated sodium bicarbonate solution and saturated sodium chloride solution, dried with magnesium sulfate and concentrated. The residue was separated and purified with column chromatography (ethyl acetate/hexane=1:5) to give ethyl 5-(5-bromothiophen-2-yl)-5-oxovalerate (28.1 g) as colorless crystals.

m.p. 53–54° C.; $^1$H-NMR (200 MHz, CDCl$_3$) δ 1.26 (3H, t, J=7.2 Hz), 1.97–2.12 (2H, m), 2.41 (2H, t, J=7.2 Hz), 2.92 (2H, t, J=7.3 Hz), 4.14 (2H, q, J=7.2 Hz), 7.10 (1H, d, J=4.0 Hz), 7.47 (1H, d, J=4.0 Hz). IR (KBr) 1726, 1664, 1419, 1281, 1184, 980, 812 cm$^{-1}$; Elemental Analysis for C$_{11}$H$_{13}$O$_3$SBr; Calcd. C, 43.29; H, 4.29; S, 10.51; Br, 26.18: Found. C, 43.54; H, 4.20; S, 10.64; Br, 26.24.

REFERENCE EXAMPLE 152

Under argon atmosphere, a solution of ethyl 5-(5-bromothiophen-2-yl)-5-oxovalerate (10.09 g), 4-methylphenyl borate (5.39 g) and potassium carbonate (9.14 g) in toluene-ethanol-water (320-32-32 ml) was stirred at room temperature for 1 hour. To the reaction mixture was added tetrakistriphenylphosphinepalladium (1.14 g), and the mixture was refluxed for 8 hours and cooled to room temperature. The organic layer was washed with saturated sodium chloride solution, dried with magnesium sulfate and concentrated under reduced pressure. The residue was separated and purified with column chromatography (ethyl acetate/hexane=1:4→1:3→1:2→1:1) to give ethyl 5-[5-(4-methylphenyl)thiophen-2-yl]-5-oxovalerate (10.23 g) as colorless crystals.

m.p. 120–121° C.; $^1$H-NMR (200 MHz, CDCl$_3$) δ 1.26 (3H, t, J=7.2 Hz), 2.01–2.15 (2H, m), 2.38 (3H, s), 2.44 (2H, t, J=7.4 Hz), 2.97 (2H, t, J=7.2 Hz), 4.15 (2H, q, J=7.2 Hz), 7.22 (2H, d, J=7.9 Hz), 7.27 (1H, d, J=4.1 Hz), 7.55 (2H, d, J=7.9 Hz), 7.68 (1H, d, J=4.1 Hz). IR (KBr) 1722, 1647, 1448, 1286, 1173, 816 cm$^{-1}$; Elemental Analysis for C$_{18}$H$_{20}$O$_3$S; Calcd. C, 68.33; H, 6.37; S, 10.13: Found. C, 68.40; H, 6.26; S, 10.11.

REFERENCE EXAMPLE 153

To a solution of ethyl 5-[5-(4-methylphenyl)thiophen-2-yl]-5-oxovalerate (4.50 g) in trifluoroacetic acid (7.66 ml) was added triethylsilane(5.7 ml) at room temperature, and the mixture was stirred for 4 days. To the reaction mixture was added ethyl acetate, and the mixture was made alkaline with saturated sodium bicarbonate solution. The organic layer was washed with saturated sodium chloride solution, dried with magnesium sulfate and concentrated under reduced pressure. The residue was separated and purified with column chromatography (ethyl acetate/hexane=1:9) to give crude ethyl 5-[5-(4-methyl-phenyl)thiophen-2-yl] valerate. To a solution of the crude ethyl 5-[5-(4-methylphenyl)thiophen-2-yl]valerate in tetrahydrofuran (50 ml) was added 1N sodium hydroxide (20 ml) at room temperature, and the mixture was stirred for 24 hours. To the reaction mixture was added water, and the mixture was washed with diethylether. The aqueous layer was acidified with 1N hydrochloric acid, and the mixture was extracted with ethyl acetate. The organic layer was washed with saturated sodium chloride solution, dried with magnesium sulfate and concentrated under reduced pressure to precipitate crystals, which were collected by filtration and washed with hexane to give 5-[5-(4-methylphenyl)-thiophen-2-yl] valeric acid (2.88 g) as colorless crystals.

m.p. 124–127° C.; $^1$H-NMR (200 MHz, CDCl$_3$) δ 1.67–1.82 (4H, m), 2.35 (3H, s), 2.36–2.45 (2H, m), 2.78–2.90 (2H, m), 6.73 (1H, d, J=3.6 Hz), 7.07 (1H, d, J=3.6 Hz), 7.15 (2H, d, J=8.4 Hz), 7.44 (2H, d, J=8.4 Hz). IR (KBr) 2941, 1693, 1512, 1429, 1408, 1317, 1267, 1203, 945, 797, 771 cm$^{-1}$; Elemental Analysis for C$_{16}$H$_{18}$O$_2$S; Calcd. C, 70.04; H, 6.61; S, 11.69: Found. C, 69.79; H, 6.37; N, 11.62.

REFERENCE EXAMPLE 154

Under nitrogen atmosphere, to a solution of 5-[5-(4-methylphenyl)thiophen-2-yl]valeric acid (2.60 g) in tetrahydrofuran (30 ml) was added oxalyl chloride (1.24 ml) at room temperature and then a drop of DMF, and the mixture was stirred 1 hour. Under reduced pressure, the solvent was evaporated, and the residue was dissolved in dichloromethane(30 ml). To the mixture was added tin tetra-chloride (1.5 ml) at 0° C., and the mixture was stirred at room temperature for 3 hours. The reaction mixture was added to water to stop the reaction, and the mixture was extracted with ethyl acetate. The organic layer was washed with saturated sodium chloride solution, dried with magnesium sulfate and concentrated under reduced pressure. The residue was separated and purified with column chromatography (ethyl acetate/hexane=1:9→1:5) to give 2-(4-methylphenyl)-4-oxo-5,6,7,8-tetrahydro-4H-cyclohepta[b] thiophene (2.07 g) as pale yellow crystals.

m.p. 82–84° C.; $^1$H-NMR (200 MHz, CDCl$_3$) δ 1.82–2.06 (4H, m), 2.35 (3H, s), 2.71–2.78 (2H, m), 3.06–3.12 (2H, m), 7.17 (2H, d, J=8.2 Hz), 7.44 (2H, d, J=8.2 Hz), 7.57 (1H, s). IR (KBr) 2927, 1662, 1390, 1176, 810cm$^{-1}$; Elemental Analysis for C$_{16}$H$_{16}$OS; Calcd. C, 74.96; H, 6.29; S, 12.51: Found. C, 74.89 : H, 6.20 : S, 12.53.

REFERENCE EXAMPLE 155

To a solution of 2-(4-methylphenyl)-4-oxo-5,6,7,8-tetrahydro-4H-cyclohepta[b]thiophene (2.62 g) and dimethyl carbonate (2.6 ml) in tetrahydrofuran (50 ml) was added potassium tert-butoxide (1.38 g) at room temperature, and the mixture was refluxed for 1 hour. To the reaction mixture were added potassium tert-butoxide (1.4 g) and dimethyl carbonate (5 ml), and the mixture was refluxed for 2 hours and cooled to room temperature. To the mixture was added 1N hydrochloric acid (150 ml) at 0° C., and the mixture was extracted with ethyl acetate. The organic layer was washed with saturated sodium chloride solution, dried with magnesium sulfate and concentrated under reduced pressure to give crude products (3.30 g).

To the crude products (3.30 g) in dichloromethane (50 ml) was added sodium boron hydride (0.77 g) at room temperature and then methanol (8 ml) at –15° C. for 30 minutes, and the mixture was stirred for 2 hours. To the reaction mixture was added water, and the mixture was extracted with ethyl acetate. The organic layer was washed with saturated sodium chloride solution, dried with magnesium sulfate and concentrated under reduced pressure to give crude product (2.95 g). To a solution of the crude product (2.95 g) and triethylamine (7 ml) in dichloromethane (20 ml) was added methanesulfonyl chloride (1.2 ml) at 0° C., and the mixture was stirred at room temperature for 17 hours. To the reaction mixture was added water, and the mixture was extracted with ethyl acetate. The organic layer was washed with saturated sodium chloride solution, dried with magnesium sulfate and concentrated under reduced pressure. The concentrate was purified with column chromatography (ethyl acetate/hexane=1:9) to give methyl 2-(4-methyl-phenyl)-7,8-dihydro-6H-cyclohepta[b]thiophene-5-carboxylate (884 mg) as yellow crystals.

$^1$H-NMR (200 MHz, CDCl$_3$) δ 1.98–2.11 (2H, m), 2.36 (3H, s), 2.79 (2H, t, J=5.5 Hz), 3.09 (2H, t, J=5.6 Hz), 3.79 (3H, s), 7.08 (1H, s), 7.17 (2H, d, J=8.1 Hz), 7.42 (2H, d, J=8.1 Hz), 7.60 (1H, s).

REFERENCE EXAMPLE 156

To a solution of methyl 2-(4-methylphenyl)-7,8-dihydro-6H-cyclohepta[b]thiophene-5-carboxylate (803 mg) in ethanol-tetrahydrofuran (5-10 ml) was added 2N sodium hydroxide (2 ml) at room temperature, and the mixture was stirred for 5 days and concentrated under reduced pressure. To the residue was added 1N hydrochloric acid (10 ml), and the mixture was extracted with ethyl acetate. The organic layer was washed with saturated sodium chloride solution, dried with magnesium sulfate and concentrated under reduced pressure to precipitate crystals, which were collected by filtration and washed with diisopropylether to give 2-(4-methylphenyl)-7,8-dihydro-6H-cyclohepta[b]thiophene-5-carboxylic acid (650 mg) as pale yellow crystals.

m.p. 250–251° C.; $^1$H-NMR (200 MHz, CDCl$_3$) δ 2.00–2.14 (2H, m), 2.36 (3H, s), 2.75–2.85 (2H, m), 3.07–3.16 (2H, m), 7.10 (1H, s), 7.18 (2H, d, J=8.0 Hz), 7.43 (2H, d, J=8.0 Hz), 7.72 (1H, s). IR (KBr) 2910, 2831, 1670, 1614, 1423, 1287, 1242, 810cm$^{-1}$; Elemental Analysis for C$_{17}$H$_{16}$O$_2$S; Calcd. C, 71.80; H, 5.67; S, 11.28: Found. C, 71.74; H, 5.64; S, 11.06.

REFERENCE EXAMPLE 157

To a suspension of 5-bromonicotinic acid (5.0 g) and N-hydroxysuccinimide (4.27 g) in acetonitrile (60 ml) was added 1-ethyl-3-(3'-dimethylaminopropyl)carbodiimide hydrochloride (7.12 g) at room temperature, and the mixture was stirred for 30 minutes. To the reaction mixture were added N,O-dimethyl-hydroxylamine hydrochloride (2.66 g) and triethylamine (10 ml), and the mixture was stirred for 64 hours and concentrated under reduced pressure. To the residue was added water, and the mixture was extracted with ethyl acetate. The organic layer was washed with saturated sodium chloride solution, dried with magnesium sulfate and concentrated under reduced pressure. The residue was separated and purified with column chromatography (ethyl acetate/hexane=2:1) to give N-methyl-N-methoxy-5-bromopyridine-3-carboxamide (3.71 g) as pale yellow oil.

$^1$H-NMR (200 MHz, CDCl$_3$) δ 3.40 (3H, s), 3.58 (3H, s), 8.19 (1H, dd, J=2.2, 1.8 Hz), 8.76 (1H, d, J=2.2 Hz), 8.88 (1H, d, J=1.8 Hz). IR (neat) 1647, 1412, 1381, 1221, 1099, 1020, 982, 897, 773, 739, 969, 667, 575, 461 cm$^{-1}$.

REFERENCE EXAMPLE 158

Under argon atmosphere, a solution of N-methyl-N-methoxy-5-bromopyridine-3-carboxamide (3.70 g), 4-methyl-phenyl borate (2.26 g) and potassium carbonate (4.17 g) in toluene-ethanol-water (100-10-10 ml) was stirred at room temperature for 1 hour. To the reaction mixture was added tetrakistriphenylphosphinepalladium (0.52 g), and the mixture was refluxed for 16 hours and cooled to room temperature. The organic layer was washed with saturated sodium chloride solution, dried with magnesium sulfate and concentrated under reduced pressure. The residue was separated and purified with column chromatography (ethyl acetate/hexane=1:2→1:1) to give N-methyl-N-methoxy-5-(4-methylphenyl)pyridine-3-carboxamide (3.97 g) as yellow oil.

$^1$H-NMR (200 MHz, CDCl$_3$) δ 2.42 (3H, s), 3.42 (3H, s), 3.60 (3H, s), 7.30 (2H, d, J=8.3 Hz), 7.51 (2H, d, J=8.3 Hz), 8.20 (1H, t, J=2.1 Hz), 8.89–8.81 (2H, m). IR (neat) 1647, 1431, 1379, 1203, 982, 818, 743, 540, 426 cm$^{-1}$.

REFERENCE EXAMPLE 159

Under nitrogen atmosphere, to a solution of N-methyl-N-methoxy-5-(4-methylphenyl)pyridine-3-carboxamide (3.95 g) in tetrahydrofuran (30 ml) was dropwise added diisobutylaluminum hydride (1.0M toluene solution) (30 ml) at −78° C., and the mixture was stirred at the same temperature for 2 hours. To the reaction mixture was added 1N hydrochloric acid to stop the reaction. To the mixture was added ethyl acetate, and the mixture was made alkaline with 1N sodium hydroxide. The organic layer was washed with saturated sodium chloride solution, dried with magnesium sulfate and concentrated under reduced pressure. The residue was separated and purified with column chromatography (ethyl acetate/hexane=1:2→1:1) to give 5-(4-methylphenyl)pyridine-3-carboxyaldehyde (1.82 g) as colorless crystals.

m.p. 60–61° C.; $^1$H-NMR (200 MHz, CDCl$_3$) δ 2.43 (3H, s), 7.33 (2H, d, J=7.8 Hz), 7.54 (2H, d, J=7.8 Hz), 8.33 (1H, dd, J=2.2, 2.0 Hz), 9.03 (1H, d, J=2.0 Hz), 9.07 (1H, d, J=2.2 Hz), 10.19 (1H, s). IR (KBr) 1701, 1186, 818, 725, 806 cm$^{-1}$; Elemental Analysis for C$_{13}$H$_{11}$NO; Calcd. C, 79.17; H, 5.62; N, 7.10: Found. C, 79.24; H, 5.64; N, 7.01.

REFERENCE EXAMPLE 160

A solution of 5-(4-methylphenyl)pyridine-3-carboxyaldehyde (1.82 g) and methyl (triphenylphosphoranilidene)-acetate (3.46 g) in toluene (20 ml) was refluxed under nitrogen atmosphere for 4 hours and cooled. To the mixture was added water, and the mixture was extracted with ethyl acetate. The organic layer was washed with saturated sodium chloride solution, dried with magnesium sulfate and concentrated under reduced pressure. The residue was separated and purified with column chromatography (ethyl acetate/hexane=1:2→1:1) to give methyl (E)-3-[5-(4-methylphenyl)pyridin-3-yl]acrylate (2.34 g) as colorless crystals.

m.p. 141–144° C.; $^1$H-NMR (200 MHz, CDCl$_3$) δ 2.43 (3H, s), 3.84 (3H, s), 6.59 (1H, d, J=16.0 Hz), 7.32 (2H, d, J=7.9 Hz), 7.50 (2H, d, J=7.9 Hz), 7.76 (1H, d, J=16.0 Hz), 7.98 (1H, dd, J=2.2, 2.0 Hz), 8.70 (1H, d, J=2.0 Hz), 8.82 (1H, d, J=2.2 Hz). IR (KBr) 1718, 1639, 1431, 1335, 1196, 1176, 995, 816 cm$^{-1}$; Elemental Analysis for C$_{16}$H$_{15}$NO$_2$; Calcd. C, 75.87; H, 5.97; N, 5.53: Found. C, 75.82; H, 5.86; N, 5.47.

REFERENCE EXAMPLE 161

To a solution of methyl (E)-3-[5-(4-methylphenyl)-pyridin-3-yl]acrylate (2.25 g) in tetrahydrofuran (20 ml) was added 1N sodium hydroxide (11 ml) at room temperature, and the mixture was stirred for 5 days. To the reaction mixture was added 1N hydrochloric acid (12 ml), and the mixture was concentrated under reduced pressure to precipitate crystals, which were collected by filtration and washed with water and diethylether to give (E)-3-[5-(4-methylphenyl)pyridin-3-yl]acrylic acid (1.92 g) as colorless crystals.

m.p. 208–211° C.; $^1$H-NMR (200 MHz, DMSO-d$_6$) δ 2.37 (3H, s), 6.85 (1H, d, J=16.2 Hz), 7.33 (2H, d, J=8.6 Hz), 7.66–7.74 (3H, m), 8.40–8.45 (1H, m), 8.81 (1H, d, J=1.8 Hz), 8.89 (1H, d, J=2.2 Hz). IR (KBr) 3030, 1672, 1635, 1435, 1331, 1302, 987, 820 cm$^{-1}$; Elemental Analysis for C$_{15}$H$_{13}$NO$_2$; Calcd. C, 75.30; H, 5.48; N, 5.85: Found. C, 74.99; H, 5.39; N, 5.94.

REFERENCE EXAMPLE 162

To DMF (7.18 ml) was dropwise added phosphoryl chloride (8.64 ml) at 0° C., and the mixture was stirred at room temperature for 30 minutes. To the mixture was added methyl acetoacetate (10 ml) at 0° C., and the mixture was stirred at room temperature for 2hours. The mixture was cooled to 0° C., and to the mixture was added 4-bromoaniline (16.78 g), and the mixture was stirred at 90° C. for 4 hours. To the reaction mixture was added chloroform, and the mixture was neutralized with 8N sodium hydroxide. The organic layer was washed with water and saturated sodium chloride solution, dried with magnesium sulfate and concentrated under reduced pressure. The residue was separated and purified with column chromatography (ethyl acetate/hexane=1:2) and was recrystallized from ethyl acetate-hexane to give methyl 6-bromo-2-methylquinoline-3-carboxylate (6.02 g) as pale yellow crystals.

m.p. 150–151° C.; $^1$H-NMR (200 MHz, CDCl$_3$) δ 2.97 (3H, s), 3.99 (3H, s), 7.84 (1H, dd, J=9.0, 2.0 Hz), 7.92 (1H, d, J=9.0 Hz), 8.02 (1H, d, J=2.0 Hz), 8.65 (1H, s). IR (KBr) 1726, 1423, 1396, 1277, 1238, 1219, 1134, 1074, 829 cm$^{-1}$; Elemental Analysis for C$_{12}$H$_{10}$NO$_2$Br; Calcd. C, 51.45; H, 3.60; N, 5.00: Found. C, 51.57; H, 3.55; N, 5.17.

REFERENCE EXAMPLE 163

Under argon atmosphere, a solution of methyl 6-bromo-2-methylquinoline-3-carboxylate (1.22 g), 4-methylphenyl borate (0.65 g) and potassium carbonate (1.18 g) in toluene-ethanol-water (40-4-4 ml) was stirred at room temperature for 1 hour. To the reaction mixture was added tetrakistriphenylphosphinepalladium (0.15 g), and the mixture was refluxed for 18 hours and cooled to room temperature. The organic layer was washed with saturated sodium chloride solution, dried with magnesium sulfate and concentrated under reduced pressure. The residue was separated and purified with column chromatography (ethyl acetate/hexane=1:1) to give methyl 6-(4-methylphenyl)-2-methylquinoline-3-carboxylate (1.27 g) as colorless crystals.

m.p. 84–87° C.; $^1$H-NMR (200 MHz, CDCl$_3$) δ 2.43 (3H, s), 3.01 (3H, s), 4.00 (3H, s), 7.32 (2H, d, J=8.0 Hz), 7.61 (2H, d, J=8.0 Hz), 8.01–8.12 (3H, m), 8.79 (1H, s). IR (KBr) 1732, 1440, 1277, 1213, 1068, 814 cm$^{-1}$; Elemental Analysis for C$_{19}$H$_{17}$NO$_2$; Calcd. C, 78.33; H, 5.88; N, 4.81: Found. C, 77.98; H, 6.02; N, 4.75.

REFERENCE EXAMPLE 164

To a solution of methyl 6-(4-methylphenyl)-2-methylquinoline-3-carboxylate (0.99 g) in tetrahydrofurane-thanol (5–5 ml) was added 2N sodium hydroxide (2 ml) at room temperature, and the mixture was stirred for 2 days. To the reaction mixture was added 1N hydrochloric acid (4 ml), and the mixture was concentrated under reduced pressure to precipitate crystals, which were collected by filtration and washed with ethanol and diethylether to give 6-(4-methylphenyl)-2-methylquinoline-3-carboxylic acid (648 mg) as colorless crystals.

m.p. 273° C. (dec.); $^1$H-NMR (200 MHz, DMSO-d$_6$) δ 2.38 (3H, s), 2.89 (3H, s), 7.34 (2H, d, J=8.3 Hz), 7.74 (2H, d, J=8.3 Hz), 8.02 (1H, d, J=8.8 Hz), 8.15 (1H, dd, J=8.8, 2.1 Hz), 8.37 (1H, d, J=2.1 Hz), 8.90 (1H, s). IR (KBr) 2918, 1703, 1570, 1495, 1257, 1227, 1180, 1151, 1065, 812, 770 cm$^{-1}$; Elemental Analysis for C$_{18}$H$_{15}$NO$_2$; Calcd. C, 77.96; H, 5.45; N, 5.05: Found. C, 77.74; H, 5.34; N, 5.12.

REFERENCE EXAMPLE 165

Under argon atmosphere, a solution of ethyl 7-bromo-2,3-dihydro-1-benzoxepine-4-carboxylate (1.0 g), 4-methylthiophenyl borate (622 mg) and potassium carbonate (0.93 g) in toluene-ethanol-water (30-3-3 ml) was stirred at room temperature for 1 hour. To the reaction mixture was added tetrakistriphenyl-phosphinepalladium (117 mg), and the mixture was refluxed for 16 hours. To the reaction mixture was added tetrakistriphenyl-phosphinepalladium (0.13 g), and the mixture was refluxed for 24 hours and cooled to room temperature. The organic layer was washed with saturated sodium chloride solution, dried with magnesium sulfate and concentrated under reduced pressure. The residue was separated and purified with column chromatography (ethyl acetate/hexane=1:10) to give ethyl 7-(4-methylthiophenyl)-2,3-dihydro-1-benzoxepine-4-carboxylate (442 mg) as colorless crystals.

$^1$H-NMR (200 MHz, CDCl$_3$) δ 1.36 (3H, t, J=7.0 Hz), 2.52 (3H, s), 3.00 (2H, t, J=4.8 Hz), 4.29 (2H, q, J=7.0 Hz), 4.30 (2H, t, J=4.8 Hz), 7.04 (1H, d, J=8.4 Hz), 7.32 (2H, d, J=8.8 Hz), 7.42–7.54 (4H, m), 7.65 (1H, br s). IR (KBr) 1705, 1489, 1302, 1250, 1230, 1200, 1090, 1063, 1011, 813 cm$^{-1}$.

REFERENCE EXAMPLE 166

To a solution of ethyl 7-(4-methylthiophenyl)-2,3-dihydro-1-benzoxepine-4-carboxylate (132 mg) in ethanol-tetrahydrofuran (5 ml-5 ml) was added 1N sodium hydroxide (1.0 ml) at room temperature, and the mixture was stirred for 20 hours and concentrated under reduced pressure. To the residue was added 1N hydrochloric acid (2 ml) and the mixture was extracted with ethyl acetate. The organic layer was washed with saturated sodium chloride solution, dried with magnesium sulfate and concentrated under reduced pressure. The resulting crystal was collected by filtration to give 7-(4-methylthiophenyl)-2,3-dihydro-1-benzoxepine-4-carboxylic acid (113 mg) as colorless crystals.

$^1$H-NMR (200 MHz, DMSO-d$_6$) δ 2.51 (3H, s,), 2.89 (2H, t, J=4.4 Hz), 4.25 (2H, t, J=4.4 Hz), 7.04 (1H, d, J=8.4 Hz), 7.33 (2H, d, J=8.4 Hz), 7.58 (1H, dd, J=8.4, 2.4 Hz), 7.61–7.70 (3H, m), 7.80 (1H, d, J=2.4 Hz). IR (KBr) 2974, 1689, 1493, 1263, 1213, 1169, 1020, 833 cm$^{-1}$.

REFERENCE EXAMPLE 167

To a solution of 4-nitrobenzylalcohol (50 g, 0.326 mol) in ethyl acetate (EtOAc) (200 ml) were added 3,4-dihydropyran (35.7 ml, 0.392 mol) and CSA (camphor sulfonic acid) (379 mg, 1.63 mmol) under stirring at room temperature, and the mixture was stirred at room temperature for 1 hour. After the reaction completed, the reaction mixture was neutralized with saturated NaHCO$_3$ solution and separated ethyl acetate layer was dried with MgSO$_4$ and concentrated under reduced pressure. The residue was purified with silica gel column chromatography to give 4-(2-tetrahydropyranyloxymethyl)nitrobenzene (74.5 g, 96%) as syrup.

$^1$H-NMR (200 MHz, CDCl$_3$) δ 1.55–2.05 (6H, m), 3.51–3.62 (1H, m), 3.83–3.94 (1H, m) , 4.61 (1H, d, J=13.6 Hz), 4.74 (1H, t, J=3.2 Hz), 4.93 (1H, d, J=13.4 Hz), 7.51–7.56 (2H, d, J=8.8 Hz), 8.18–8.24 (2H, m).

REFERENCE EXAMPLE 168

To a solution of 4-(2-tetrahydropyranyloxymethyl) nitrobenzene (59.7 g, 0.256 mol) in ethanol (EtOH) (300 ml) was added under nitrogen atmosphere at room temperature 10% Pd/C (5.97 g), and catalytic hydrogenation was carried out. The mixture was stirred at room temperature for 24 hours. After the reaction completed, the catalyst was filtered off, and the organic layer was concentrated under reduced pressure. The residue was purified with silica gel column chromatography to give 4-(2-tetrahydropyranyloxymethyl) aniline (39.7 g, 76%) as syrup.

$^1$-NMR (200 MHz, CDCl$_3$) δ: 1.45–1.95 (6H, m), 3.00–3.60 (3H, br m), 3.87–4.14 (1H, m), 4.39 (1H, d, J=11.4 Hz), 4.68 (1H, d, J=11.4 Hz), 4.71 (1H, m), 6.65–6.69 (2H, m), 7.15–7.19 (2H, m).

REFERENCE EXAMPLE 169

To a solution of 2-(4-methylphenyl)-6,7-dihydro-5H-benzocycloheptene-8-carboxylic acid (35.0 g, 0.126 mol) in tetrahydrofuran (THF) (280 ml) were added (COCl)$_2$ (21.9 ml, 0.251 mol) and DMF (0.7 ml) at 0° C. Under nitrogen atmosphere, the mixture was stirred at room temperature for 4 hours. After the reaction completed, The solvent was evaporated, and to the residue was added THF (315 ml). To a solution of the acid chloride was added a solution of 4-(2-tetrahydropyranyloxymethyl)aniline (28.1 g, 0.138 mol) and triethylamine (Et$_3$N) (26.3 ml, 0.189 mol) in THF (105 ml) at 0° C., and the mixture was stirred under nitrogen atmosphere, at room temperature for 2 hours. After the reaction completed, to the mixture was added water, and the mixture was extracted with ethyl acetate. The organic layer was washed with saturated NaCl solution and dried with MgSO$_4$. The solvent was evaporated and the residue was dissolved in methanol (MeOH) (470 ml). To the mixture was dropwise added 6N HCl (5.9 ml) at room temperature, and the mixture was stirred for 1 hour. After the reaction completed, the mixture was neutralized with saturated NaHCO$_3$ solution, and the solvent was removed. The residue was washed with water and then acetone/isopropylether (10:1; 60 ml), and the resulting precipitate was filtered, which was dissolved in THF. The mixture was dried with MgSO$_4$, and the solvent was evaporated. The resulting powder was washed twice with hexane:ethyl acetate (10:1; 50 ml) to give N-(4-hydroxymethylphenyl)-3-(4-methylphenyl)-6,7-dihydro-5H-benzocycloheptene-6-carboxamide (26.8 g, 56%) as white powder.

$^1$H-NMR (200 MHz, CDCl$_3$) δ: 2.10–2.22 (2H, m), 2.39 (3H, s), 2.71 (2H, br t, J=6.4), 2.84–2.91 (2H, m), 4.67 (2H, s), 7.20–7.26 (2H, m), 7.33–7.51 (7H, m), 7.61 (2H, d, J=8.4), 7.71 (1H, br s).

REFERENCE EXAMPLE 170

To a solution of N-(4-hydroxymethylphenyl)-2-(4-methylphenyl)-6,7-dihydro-5H-benzocycloheptene-8-carboxamide (10.0 g, 26.1 mmol) and pyridine (0.1 ml) in chloroform (150 ml) was dropwise added a solution of thionyl chloride (3.4 ml, 39.2 mmol)in chloroform (90 ml), and the mixture was stirred under nitrogen atmosphere at room temperature for 17 hours. After the reaction completed, water was added to the mixture, and the mixture was extracted with chloroform. The organic layer was washed with saturated sodium chloride solution and dried with anhydrous magnesium sulfate. The solvent was evaporated, and the resulting powder was washed with hexane to give N-(4-chloromethylphenyl)-2-(4-methylphenyl)-6,7-dihydro-5H-benzocycloheptene-8-carboxamide (10.2 g, 97%) as colorless powder.

$^1$H-NMR (200 MHz, CDCl$_3$) δ: 2.05–2.21 (2H, m), 2.40 (3H, s), 2.71 (2H, br t, J=6.4), 2.84–2.91 (2H, m), 4.58 (2H, s), 7.20–7.27 (2H, m), 7.35–7.52 (7H, m), 7.59–7.65 (2H, m), 7.71 (1H, br s). Anal. for C$_{26}$H$_{24}$NOCl.0.25H$_2$O: Calcd: C; 76.83, H; 6.08, N; 3.45. Found: C; 76.55, H; 6.00, N; 3.53.

REFERENCE EXAMPLE 171

To a solution of tetrahydro-4H-pyran-4-one (60 g, 0.6 mol) and water (5 ml) in DMF (70 ml, 0.90 mol) was added formic acid (46 ml, 1.2 mol), and the mixture was stirred at 140° C. for 23 hours. After the reaction completed, reflux apparatus was changed to evaporation apparatus, crude amine was obtained by evaporation (74.6 g). b.p. 117–123° C. (27 mm).

To an aqueous solution (100 ml) of the crude amine (30 g) was dropwise added 6N HCl (5 drops), and the mixture was washed twice with dichloromethane. The aqueous layer was adjusted to pH 11 with sodium hydroxide. To the mixture was added NaCl, and the mixture was extracted with dichloromethane three times. The organic layer was dried with potassium carbonate, and the solvent was evaporated. The residue was purified with evaporation to give N,N-dimethyl-N-tetrahydropyran-4-ylamine (10.4 g, 29%) as colorless oil.

b.p. 75–82° C.(29 mm). $^1$H-NMR (200 MHz, CDCl$_3$) δ:1.40–1.82 (4H, m), 2.28 (6H, s), 2.25–2.40 (1H, m), 3.37 (2H, ddd, J=11.8, 11.8 and 2.2), 3.97–4.05 (2H, m).

REFERENCE EXAMPLE 172

To a suspension of 7-(4-methylphenyl)-2,3-dihydro-1-benzoxepine-4-carboxylic acid (0.6 g, 2.1 mmol) in tetrahydrofuran (10 ml) were added oxalyl chloride (0.33 ml, 4.3 mmol) and N,N-dimethylformamide (1 drop) at 0° C., and the mixture was stirred at room temperature for 2.5 hours. The solvent was evaporated, and the residue was dissolved in tetrahydrofuran (6 ml). To the mixture was dropwise added 4-(tert-butyldimethylsilyloxymethyl)aniline (0.56 g, 2.4 mmol) and triethylamine (0.36 ml, 2.6 mmol) in tetrahydrofuran (2 ml) at 0° C., and the mixture was stirred at room temperature for 16 hours. To the reaction mixture was added water, and the mixture was extracted with ethyl acetate. The extract was washed with saturated sodium chloride solution and dried with magnesium sulfate. The solvent was evaporated, and the residue was subjected to silica gel column chromatography. Crude amide (1.1 g) was obtained from fractions of hexane:ethyl acetate=5:1. This product was dissolved in acetone (8 ml), and to the mixture was dropwise added 6N hydrochloric acid. The mixture was stirred for 1 hour. To the mixture were added 1% sodium hydrogen carbonate (100 ml) and diisopropylether (100 ml), and precipitate was filtered, which were dissolved in acetone. The mixture was dried with magnesium sulfate, and the solvent was evaporated. The resulting powder was recrystallized from acetone-diisopropyl-ether to give N-(4-hydroxymethylphenyl)-7-(4-methylphenyl)-2,3-dihydro-1-benzoxepine-4-carboxamide (0.87 g) as colorless crystals.

$^1$H-NMR (CDCl$_3$) δ:2.39 (3H, s), 3.08 (2H, br t, J=4.4), 4.36 (2H, t, J=4.4), 4.68 (2H, s), 7.06 (2H, d, J=8.4), 7.18–7.61 (10H, m), 7.24 (2H, d, J=8.4). Anal. for C$_{25}$H$_{23}$NO$_3$: Calcd: C; 77.90, H; 6.01, N; 3.63. Found: C; 77.91, H; 6.10, N; 3.55.

REFERENCE EXAMPLE 173

To a solution of N-(4-hydroxymethylphenyl)-7-(4-methylphenyl)-2,3-dihydro-1-benzoxepine-4-carboxamide (412 mg, 1.07 mmol) and pyridine (1 drop) in chloroform (5 ml) was dropwise added thionyl chloride (0.14 ml, 1.61 mmol), and the mixture was stirred for 2 hours. The mixture was diluted with water and extracted with chloroform. The extract was washed with saturated sodium chloride solution and dried with magnesium sulfate. The solvent was evaporated, and the resulting powder was washed with hexane-ethyl acetate (1:1) to give N-(4-chloromethylphenyl)-7-(4-methylphenyl)-2,3-dihydro-1-benzoxepine-4-carboxamide (380 mg, 88%) as colorless powder.

m.p. 164° C.; $^1$H-NMR (CDCl$_3$) δ:3.29 (3H, s), 3.07 (2H, t, J=4.8), 4.36 (2H, t, J=4.8), 4.59 (2H, s), 7.05 (1H, d, J=8.2), 7.22–7.26 (2H, m), 7.36–7.52 (6H, m), 7.57–7.62 (3H, m). Anal. for C$_{25}$H$_{22}$NO$_2$Cl: Calcd: C; 74.34, H; 5.49, N; 3.47. Found: C; 74.00, H; 5.42, N; 3.29.

REFERENCE EXAMPLE 174

To a suspension of 1,4-cyclohexanedione monoethyleneketal (3.82 g, 24.6 mmol) and dimethylamine hydrochloride (2.00 g, 24.6 mmol) in 1,2-dichloroethane (50 ml) were dropwise added triethylamine (4.2 ml, 29.6 mmol) and DBU (1,8-diazabicyclo-[5.4.0]-7-undecene) (4.4 ml), and the mixture was stirred for 10 minutes. To the mixture was added triacetoxyborohydride (7.68 g, 34.4 mmol), and the mixture was stirred for 4.5 hours. Precipitate was filtered off, and the filtrate was concentrated to give crude product (6.34 g), which was dissolved in water (10 ml). To the mixture was dropwise added concentrated hydro-chloric acid (6 ml), and the mixture was stirred for 48 hours. The reaction mixture was diluted with water and washed twice with ether. The aqueous layer was made basic with sodium hydroxide and extracted with ether twice. The extract was washed with saturated sodium chloride solution, dried with potassium carbonate and purified by evaporation to give 4-dimethylaminocyclohexanone (0.59 g, 17%).

b.p.142–5° C.; $^1$H-NMR (CDCl$_3$) δ:1.69–2.13 (4H, m), 2.32 (6H, s), 2.20–2.41 (2H, m), 2.44–2.64 (3H, m).

REFERENCE EXAMPLE 175

To a solution of 7-(4-ethoxyphenyl)-2,3-dihydro-1-benzoxepine-4-carboxylic acid (2.38 g) in THF (50 ml) were added oxalyl chloride (1.4 ml) and DMF (2 drops) at room temperature, and the mixture was stirred for 1 hour. Under reduced pressure, the solvent was evaporated, and the residue was dissolved in THF (50 ml). To the mixture was dropwise added a solution of triethylamine (2.1 ml) and 4-aminobenzyloxy-tert-butyldimethylsilane (2.00 g) in THF (10 ml) at 0° C., and the mixture was stirred at room temperature for 18 hours. To the reaction mixture was added water, and the mixture was extracted with ethyl acetate. The organic layer was washed with saturated sodium chloride solution, dried with magnesium sulfate and concentrated under reduced pressure. The residue was separated and purified with column chromatography (ethyl acetate/hexane=1:4) to give pale yellow crystals (3.99 g), which were dissolved in acetone (50 ml). To the mixture was added 6N hydrochloric acid (1.3 ml) at room temperature, and the mixture was stirred for 1 hour. To the reaction mixture were added 5% sodium hydrogen carbonate solution (15 ml) and diisopropylether (100 ml). Precipitate was collected by filtration and washed with water and diisopropylether. The resulting solid was dissolved in THF, dried with magnesium sulfate and concentrated under reduced pressure to give crystals, which were recrystallized from THF to give 7-(4-ethoxyphenyl)-N-(4-hydroxymethylphenyl)-2,3-dihydro-1-benzoxepine-4-carboxamide (2.65 g) as colorless crystals.

m.p. 208–210° C.; $^1$H-NMR (200 MHz, DMSO-d$_6$) δ:1.35 (3H, t, J=7.0 Hz), 2.93–3.03 (2H, m), 4.06 (2H, q, J=7.0 Hz), 4.45 (2H, br s), 5.01–5.18 (1H, m), 6.98–7.05 (3H, m), 7.25–7.34 (3H, m), 7.49–7.71 (6H, m), 9.92 (1H, s). IR (KBr) ν: 3363, 3290, 1659, 1612, 1525, 1493, 1242, 1227, 825 cm$^{-1}$; Anal. for C$_{26}$H$_{25}$NO$_4$; Calcd: C, 75.16; H, 6.06; N, 3.37; Found: C, 75.16; H, 6.08; N, 3.31.

REFERENCE EXAMPLE 176

To a suspension of 7-(4-ethoxyphenyl)-N-(4-hydroxymethylphenyl)-2,3-dihydro-1-benzoxepine-4-carboxamide (2.55 g) and pyridine (2 drops) in chloroform (50 ml) was added thionyl chloride (0.8 ml) at room temperature, and the mixture was stirred for 20 hours. To the reaction mixture was added water and then THF, and the mixture was extracted with ethyl acetate. The organic layer was washed with saturated sodium chloride solution, dried with magnesium sulfate and concentrated under reduced pressure to give solid, which was dissolved in THF and ethyl acetate. The mixture was concentrated under reduced pressure to give crystals, which were collected by filtration and washed with diisopropylether to give N-(4-chloromethylphenyl)-7-(4-ethoxyphenyl)-2,3-dihydro-1-benzoxepine-4-carboxamide (2.42 g) as colorless crystals.

m.p. 187–189° C.; $^1$H-NMR (200 MHz, DMSO-d$_6$) δ: 1.35 (3H, t, J=7.0 Hz), 2.93–3.04 (2H, m), 4.06 (2H, q, J=7.0 Hz), 4.23–4.34 (2H, m), 4.74 (2H, s), 6.98–7.06 (3H, m), 7.35–7.42 (3H, m), 7.52 (1H, dd, J=8.4, 2.2 Hz), 7.59 (2H, d, J=8.8 Hz), 7.70–7.74 (3H, m), 10.04 (1H, s). IR (KBr) ν: 3400, 1659, 1610, 1525, 1493, 1242, 1047, 822 cm$^{-1}$; Anal. for C$_{26}$H$_{24}$NO$_3$Cl; Calcd: C, 71.97; H, 5.57; N, 3.23; Found: C, 71.96; H, 5.54; N, 3.04. Working Example 227 (Production of Compound 227)

To solution of 7-(4-ethoxyphenyl)-N-[4-[N-methyl-N-(tetrahydropyran-4-yl)aminomethyl]phenyl]-2,3-dihydro-1-benzoxepine-4-carboxamide (111 mg) in DMF (5 ml) was added methyl iodide (0.04 ml) at room temperature, and the mixture was stirred for 8 hours. Under reduced pressure, the mixture was concentrated, and to the residue was added ethyl acetate to precipitate solid, which was collected by filtration and recrystallized from ethanol-ethyl acetate to give dimethyl-[4-N-[7-(4-ethoxyphenyl)-2,3-dihydro-1-benzoxepin-4-carbonyl]aminobenzyl]-4-tetrahydropyranylammonium iodide (97 mg) as pale yellow crystals.

m.p. 152–158° C.; $^1$H-NMR (200 MHz, CDCl$_3$) δ: 1.41 (3H, t, J=7.0 Hz), 1.68–1.98 (2H, m), 2.10–2.26 (2H, m), 2.94 (6H, s), 2.98–3.08 (2H, m), 3.35–3.59 (3H, m), 3.96–4.16 (2H, m), 4.03 (2H, q, J=7.0 Hz), 4.19–4.31 (2H, m), 4.84 (2H, s), 6.91 (2H, d, J=8.8 Hz), 6.97 (1H, d, J=8.4 Hz), 7.38 (1H, dd, J=8.4, 2.2 Hz), 7.44–7.57 (5H, m), 7.69

(1H, d, J=2.2 Hz), 7.80 (2H, d, J=8.4 Hz), 8.01 (1H, s). IR (KBr) ν: 3440, 1657, 1605, 1520, 1491, 1317, 1240 cm$^{-1}$; Anal. for $C_{33}H_{39}N_2O_4I.1.00H_2O$; Calcd: C, 58.93; H, 6.14; N, 4.16; Found: C, 58.86; H, 6.18; N, 4.19.

WORKING EXAMPLE 228 (Production of Compound 228)

To a solution of 7-(4-ethylphenyl)-N-[4-[N-methyl-N-(tetrahydropyran-4-yl)aminomethyl]phenyl]-2,3-dihydro-1-benzoxepine-4-carboxamide (125 mg) in DMF (5 ml) was added methyl iodide (0.04 ml) at room temperature, and the mixture was stirred for 20 hours. Under reduced pressure, the mixture was concentrated, and to the residue was added ethyl acetate to precipitate solid, which was collected by filtration and recrystallized from acetone-diethylether→ethanol-diethyl-ether) to give dimethyl-[4-N-[7-(4-ethylphenyl)-2,3-dihydro-1-benzoxepin-4-carbonyl]aminobenzyl]-4-tetrahydropyranylammonium iodide (68 mg) as pale yellow crystals.

m.p. 156–160° C.; $^1$H-NMR (200 MHz, CDCl$_3$) δ: 1.25 (3H, t, J=7.6 Hz), 1.69–1.93 (2H, m), 2.13–2.28 (2H, m), 2.66 (2H, q, J=7.6 Hz), 2.95 (6H, s), 3.00–3.09 (2H, m), 3.39–3.56 (2H, m), 4.02–4.34 (5H, m), 4.86 (2H, s), 6.99 (1H, d, J=8.4 Hz), 7.18–7.28 (3H, m), 7.39–7.56 (5H, m), 7.69–7.73 (1H, m), 7.79 (2H, d, J=8.8 Hz), 8.78 (1H, s). IR (KBr) ν: 3429, 1657, 1301, 1520, 1491, 1412, 1319, 1244, 827 cm$^{-1}$; Anal. for $C_{33}H_{39}N_2O_3I.1.00H_2O$; Calcd: C, 60.37 : H, 6.29; N, 4.27; Found: C, 60.40; H, 6.24; N, 4.10.

WORKING EXAMPLE 229 (Production of Compound 229)

To a solution of N-[4-[N-methyl-N-(tetrahydropyran-4-yl)aminomethyl]phenyl]-7-(4-trifluoromethylphenyl)-2,3-dihydro-1-benzoxepine-4-carboxamide (113.6 mg) in DMF (5 ml) was added methyl iodide (0.04 ml) at room temperature, and the mixture was stirred for 24 hours. Under reduced pressure, the mixture was concentrated, and to the residue was added ethyl acetate to precipitate solid, which was collected by filtration and recrystallized from acetone-diethylether→ethanol-diethyl-ether) to give dimethyl-[4-N-[7-(4-trifluoromethylphenyl)-2,3-dihydro-1-benzoxepin-4-carbonyl]aminobenzyl]-4-tetrahydropyranylammonium iodide (99 mg) as pale yellow crystals.

m.p. 213° C. (dec.); $^1$H-NMR (200 MHz, DMSO-d$_6$) δ: 1.42–1.66 (2H, m), 1.75–1.88 (2H, m), 2.55 (6H, s), 2.62–2.72 (2H, m), 2.94–3.35 (3H, m), 3.68–3.81 (2H, m), 3.96–4.08 (2H, m), 4.13 (2H, s), 6.80 (1H, d, J=8.8 Hz), 7.05 (1H, s), 7.21 (2H, d, J=8.4 Hz), 7.34–7.40 (1H, m), 7.44–7.63 (7H, m), 9.89 (1H, s). IR (KBr) ν: 3277, 1649, 1510, 1520, 1491, 1325, 1255, 1120, 843 cm$^{-1}$; Anal. for $C_{32}H_{34}N_2O_3F_3I.0.2H_2O$; Calcd: C, 56.35; H, 5.08; N, 4.11; Found: C, 56.21; H, 5.16; N, 4.11.

REFERENCE EXAMPLE 177

In 1,2-dichloroethane(400 ml) was suspended p-nitrobenzylamine hydrochloride (30.8 g), 1,4-cyclohexane-dione monoethyleneketal (25.4 g) and triethylamine (23 ml), and to the suspension was added sodium triacetoxy boron hydride (50.9 g) under ice-cooling. Under nitrogen atmosphere, the mixture was stirred at room temperature for 2.5 hours. Under ice-cooling, 37% formalin (14.6 ml) and sodium triacetoxy boron hydride (50.9 g) were added to the mixture. Under nitrogen atmosphere, the mixture was stirred at room temperature overnight. The mixture was neutralized with sodium hydrogen carbonate and extracted with 1,2-dichloroethane. The organic layer was washed with sodium chloride solution and dried with anhydrous magnesium sulfate. Under reduced pressure, the solvent was evaporated to give yellow solid (47.5 g), 44 g of which was dissolved in (660 ml). To the mixture was added reduced iron (32 g) little by little, and the mixture was stirred at room temperature overnight. The solvent was evaporated, and to the residue was added ethyl acetate. The precipitate was filtered off, and the filtrate was made alkaline with potassium carbonate and extracted with ethyl acetate. The organic layer was washed with water and saturated sodium chloride solution and dried with anhydrous magnesium sulfate. Under reduced pressure, the solvent was evaporated, and the residue was purified with silica gel column chromatography (ethyl acetate/triethylamine/methanol) to give 4-((N-(4,4-ethylenedioxycyclohexyl)-N-methyl)aminomethyl)aniline (34.1 g) as brown oil.

$^1$H-NMR(CDCl$_3$) δ: 1.36–1.93 (8H, m), 2.17 (3H, s), 2.43–2.57 (1H, m), 3.46 (2H, s), 3.60 (2H, br), 3.94 (4H, s), 6.64 (2H, d, J=8.4 Hz), 7.09 (2H, d, J=8.4 Hz). IR(neat) ν: 2946, 1615 cm$^{-1}$.

WORKING EXAMPLE 230 (Production of Compound 230)

In dichloromethane (400 ml) was suspended 7-(4-methylphenyl)-2,3-dihydro-1-benzoxepine-4-carboxylic acid (17.0 g), and to the suspension were added oxalyl chloride (10.3 ml) and dimethylformamide (catalytic amount) under ice-cooling. The mixture was stirred at room temperature for 2 hours, and the solvent was evaporated. The residue was dissolved in tetrahydrofuran (300 ml), and the mixture was dropwise added to a solution of 4-((N-(4,4-ethylenedioxycyclohexyl)-N-methyl)aminomethyl)-aniline (16.75 g) and triethylamine (25 ml) in tetrahydrofuran (200 ml), under ice-cooling. Under nitrogen atmosphere, the mixture was stirred at room temperature overnight, and the solvent was evaporated. To the residue was added water, and the mixture was extracted with ethyl acetate. The organic layer was washed with water and saturated sodium chloride solution and dried with anhydrous magnesium sulfate. Under reduced pressure, the solvent was evaporated to give crude crystals, which were recrystallized from ethyl acetate to give N-(4-((N-(4,4-ethylenedioxycyclohexyl)-N-methyl)aminomethyl)phenyl)-7-(4-methylphenyl)-2,3-dihydro-1-benzoxepine-4-carboxamide (17.1 g) as colorless crystals.

mp 192–193° C.; $^1$H-NMR(CDCl$_3$) δ: 1.48–1.86 (8H, m), 2.20 (3H, s), 2.39 (3H, s), 2.45–2.60 (1H, m), 3.08 (2H, t, J=4.5 Hz), 3.56 (2H, s), 3.95 (4H, s), 4.36 (2H, t, J=4.5 Hz), 7.06 (1H, d, J=8.4 Hz), 7.23–7.33 (4H, m), 7.44–7.56 (7H, m). IR(KBr) ν: 2948, 1651 cm$^{-1}$. Anal. for $C_{34}H_{38}N_2O_4$: Calcd: C, 75.81; H, 7.11; N, 5.20. Found: C, 75.51; H, 6.99; N, 5.29.

WORKING EXAMPLE 231 (Production of Compound 231)

In acetic acid (100 ml) and 1N hydrochloric acid (200 ml) was dissolved N-(4-((N-(4,4-ethylenedioxycyclohexyl)-N-methyl)aminomethyl)phenyl)-7-(4-methylphenyl)-2,3-dihydro-1-benzoxepine-4-carboxamide (17.1 g), and the mixture was stirred at 100° C. for 1.5 hours and concentrated. The residue was neutralized with 1N sodium hydroxide and extracted with ethyl acetate. The organic layer was washed with water and saturated sodium chloride solution and dried with anhydrous magnesium sulfate. Under reduced pressure, the solvent was evaporated to give crude crystals, which were recrystallized from ethyl acetate-methanol to give N-(4-((N-(4-oxocyclohexyl)-N-methyl)

aminomethyl)-phenyl)-7-(4-methylphenyl)-2,3-dihydro-1-benzoxepine-4-carboxamide (12 g) as colorless crystals.

mp 149–150° C.; $^1$H-NMR(CDCl$_3$) δ: 1.78–2.13 (4H, m), 2.23 (3H, s), 2.25–2.35 (2H, m), 2.39 (3H, s), 2.45–2.57 (2H, m), 2.84–2.94 (1H, m), 3.08 (2H, t, J=4.4 Hz), 3.59 (2H, s), 4.35 (2H, t, J=4.4 Hz), 7.06 (1H, d, J=8.0Hz), 7.22–7.34 (4H, m), 7.43–7.57 (6H, m), 7.65 (1H, s). IR(KBr) v: 2946, 1713 cm$^{-1}$. Anal. for C$_{32}$H$_{34}$N$_2$O$_3$; Calcd: C, 77.70; H, 6.93; N, 5.66. Found: C, 77.45; H, 6.78; N, 5.65.

REFERENCE EXAMPLE 178

To a mixture of methyl 2-bromo-6,7-dihydro-5H-benzocycloheptene-8-carboxylate (0.5 g), 4-(1-pyrrolidinyl)phenyl borate(0.37 g), 1M potassium carbonate (6 ml) and ethanol(6 ml) was added toluene (50 ml), and the mixture was stirred under argon atmosphere at room temperature for 30 minutes. To the mixture was added tetrakistriphenylphosphinepalladium (0.08 g), and the mixture was refluxed for 6 hours and extracted with ethyl acetate. The organic layer was washed with water and saturated sodium chloride solution and dried with anhydrous magnesium sulfate. Under reduced pressure, the solvent was evaporated, and the residue was purified with silica gel column (ethyl acetate/hexane) to give colorless crystals (0.48 g), which were dissolved in 1N sodium hydroxide (15 ml), methanol (50 ml) and tetrahydrofuran (50 ml). The mixture was stirred at room temperature overnight, concentrated and neutralized with hydrochloric acid to precipitate 2-(4-(1-pyrrolidinyl)phenyl)-6,7-dihydro-5H-benzocycloheptene-8-carboxylic acid (0.46 g) as pale yellow crystals.

mp 242–243° C.(dec.). $^1$H-NMR(DMSO-d$_6$) δ: 1.93–2.00 (6H,m), 2.56 (2H, t, J=5.8 Hz), 2.76–2.82 (2H, m), 3.23–3.35 (4H, m), 6.60 (2H, d, J=8.8 Hz), 7.20 (1H, d, J=8.2 Hz), 7.44 (1H, dd, J=1.0, 8.2 Hz), 7.53 (2H, d, J=8.8 Hz), 7.56 (1H, d, J=1.0 Hz), 7.69 (1H, s). Anal. for C$_{22}$H$_{23}$NO$_2$.0.1H$_2$: Calcd: C, 78.82; H, 6.98; N, 4.18. Found: C, 78.92; H, 6.95; N, 4.15.

WORKING EXAMPLE 232 (Production of Compound 232)

To a solution of 2-(4-(1-pyrrolidinyl)phenyl)-6,7-dihydro-5H-benzocycloheptene-8-carboxylic acid (0.45 g), 4-(N-methyl-N-(tetrahydropyran-4-yl)aminomethyl)aniline (0.33 g) and 1-hydroxybenzotriazole (0.18 g) in dimethylformamide (20 ml) was added 1-ethyl-3-(3-dimethylaminopropyl)carbodiimide hydrochloride (0.39 g) under ice-cooling. Under nitrogen atmosphere, the reaction mixture was cooled to room temperature, and to the mixture were added 4-dimethylaminopyridine (catalytic amount) and triethylamine (0.56 ml). The mixture was stirred overnight, poured into water and extracted with ethyl acetate. The organic layer was washed with water and saturated sodium chloride solution and dried with anhydrous magnesium sulfate. Under reduced pressure, the solvent was evaporated, and the residue was purified with silica gel column (ethyl acetate/methanol/triethylamine) to give crude crystals, which were recrystallized from ethyl acetate-hexane to give 2-(4-(1-pyrrolidinyl)phenyl)-N-(4-((N-tetrahydropyran-4-yl-N-methyl)aminomethyl)phenyl)-6,7-dihydro-5H-benzocycloheptene-8-carboxamide (0.28 g) as colorless crystals.

mp 124–125° C.; $^1$H-NMR(CDCl$_3$) δ: 1.66–1.77 (4H, m), 1.99–2.06 (4H, m), 2.11–2.18 (2H, m), 2.21 (3H, s), 2.55–2.75 (3H, m), 2.84–2.90 (2H, m), 3.30–3.44 (6H, m), 3.58 (2H, s), 4.00–4.14 (2H, m), 6.64 (2H, d, J=9.0 Hz), 7.19 (1H, d, J=8.0 Hz), 7.31 (2H, d, J=8.5 Hz), 7.39–7.51 (4H, m), 7.57 (2H, d, J=8.5 Hz), 7.64 (1H, s). IR(KBr) v: 2946, 2843, 1651, 1611 cm$^{-1}$. Anal. for C$_{35}$H$_{41}$N$_3$O$_2$.0.2H$_2$O; Calcd: C, 77.95; H, 7.74; N, 7.79. Found: C, 77.76; H, 7.59; N, 7.79.

REFERENCE EXAMPLE 179

In 1,2-dichloroethane (50 ml) were dissolved p-nitrobenzaldehyde (5 g) and 3-amino-1-propanol (2.5 g), and to the mixture was added sodium triacetoxy boron hydride (9.8 g) under ice-cooling. Under nitrogen atmosphere, the mixture was stirred at room temperature for 5 hours. Under ice-cooling ,to the mixture was added 37% formalin(3 ml) and sodium triacetoxy boron hydride (9.8 g). Under nitrogen atmosphere, the mixture was stirred at room temperature overnight. To the mixture was added water, and the mixture was concentrated, neutralized with aqueous sodiumhydroxide and extracted with ethyl acetate. The organic layer was washed with water and sodium chloride solution and dried with anhydrous magnesium sulfate. Under reduced pressure, the solvent was evaporated, and the residue was purified with silica gel column (ethyl acetate/methanol/triethylamine) to give yellow oil (5.0 g), 2.5 g of which was dissolved in ethanol (50 ml) and catalytic hydrogenation was carried out with 5% palladium on carbon (0.2 g) for 1.5 hours. The catalyst was filtered off, and the solvent was evaporated. The residue was purified with silica gel column (ethyl acetate/methanol/triethylamine) to give 4-((N-3-hydroxypropyl-N-methyl)aminomethyl)-aniline (1.5 g) as pale yellow oil.

$^1$H-NMR(CDCl$_3$) δ: 1.67–1.78 (2H, m), 2.21 (3H, s), 2.62 (2H, t, J=5.5 Hz), 3.41 (2H, s), 3.65 (2H, br), 3.77 (2H, t, J=5.1 Hz), 6.65 (2H, d, J=8.4 Hz), 7.07 (2H, d, J=8.4 Hz). IR(neat) v: 3347, 2948, 2799, 1615 cm$^{-1}$.

WORKING EXAMPLE 233 (Production of Compound 233)

In dichloromethane (5 ml) was suspended 2-(4-methylphenyl)-6,7-dihydro-5H-benzocycloheptene-8-carboxylic acid (0.3 g), and to the suspension were added oxalyl chloride (0.28 ml) and dimethylformamide (catalytic amount) under ice-cooling. The mixture was stirred at room temperature for 1.5 hours, and the solvent was evaporated. The residue was dissolved in tetrahydrofuran (15 ml), and the mixture was dropwise added to a solution of 4-((N-3-hydroxypropyl-N-methyl)aminomethyl)aniline (0.23 g) and triethylamine (0.45 ml) in tetrahydrofuran (15 ml) under ice-cooling. Under nitrogen atmosphere, the mixture was stirred at room temperature overnight, and the solvent was evaporated. To the residue was added water, and the mixture was extracted with ethyl acetate. The organic layer was washed with water and saturated sodium chloride solution and dried with anhydrous magnesium sulfate. Under reduced pressure, the solvent was evaporated, and the residue was purified with silica gel column (ethyl acetate/methanol/triethylamine) to give crude crystals, which were recrystallized from ethyl acetate-hexane to give N-(4-((N-3-hydroxypropyl-N-methyl)aminomethyl)phenyl)-2-(4-methylphenyl)-6,7-dihydro-5H-benzocycloheptene-8-carboxamide (0.32 g) as colorless crystals.

mp 139–140° C.; $^1$H-NMR(CDCl$_3$) δ: 1.72–1.81 (2H, m), 2.13–2.19 (2H, m), 2.25. (3H, s), 2.40 (3H, s), 2.63–2.75 (4H, m), 2.86–2.92 (2H, m), 3.53 (2H, s), 3.79 (2H, t, J=5.4 Hz), 7.21–7.32 (3H, m), 7.42–7.52 (6H, m), 7.58 (2H, d, J=8.4 Hz), 7.66 (1H, s). IR(KBr) v: 2936, 1651 cm$^{-1}$. Anal. for C$_{30}$H$_{34}$N$_2$O$_2$.0.5H$_2$O: Calcd: C, 77.72; H, 7.61; N, 6.04. Found: C, 77.94; H, 7.62; N, 6.15.

WORKING EXAMPLE 234 (Production of Compound 234)

In dichloromethane(12 ml) was suspended 7-(4-methylphenyl)-2,3-dihydro-1-benzoxepine-4-carboxylic acid (0.4 g), and to the suspension were added oxalyl chloride (0.37 ml) and dimethylformamide (catalytic amount) under ice-cooling. The mixture was stirred at room temperature for 2 hours, and the solvent was evaporated. The residue was dissolved in tetrahydrofuran (15 ml), and the mixture was dropwise added to a solution of 4-((N-3-hydroxy-propyl-N-methyl)aminomethyl)aniline (0.33 g) and tri-ethylamine (0.6 ml) in tetrahydrofuran(15 ml) under ice-cooling. Under nitrogen atmosphere, the mixture was stirred at room temperature overnight, and the solvent was evaporated. To the residue was added water, and the mixture was extracted with ethyl acetate. The organic layer was washed with water and saturated sodium chloride solution and dried with anhydrous magnesium sulfate. Under reduced pressure, the solvent was evaporated, and the residue was purified with silica gel column (ethyl acetate/methanol/triethylamine) to give crude crystals, which were recrystallized from ethyl acetate-hexane to give N-(4-((N-3-hydroxypropyl-N-methyl)aminomethyl)phenyl)-7-(4-methylphenyl)-2,3-dihydro-1-benzoxepine-4-carboxamide (0.39 g) as colorless crystals.

mp 119–120° C.; $^1$H-NMR(CDCl$_3$) δ: 1.68–1.80 (2H, m), 2.24 (3H, s), 2.39 (3H, s), 2.65 (2H, t, J=5.8 Hz), 3.07 (2H, t, J=4.6 Hz), 3.52 (2H, s), 3.77 (2H, t, J=5.2 Hz), 4.35 (2H, t, J=4.6 Hz), 7.05 (1H, d, J=8.4 Hz), 7.22–7.31 (3H, m), 7.43–7.52 (5H, m), 7.57 (2H, d, J=8.4 Hz), 7.78 (1H,s). IR(KBr) ν: 3287, 2948, 1649 cm$^{-1}$. Anal. for C$_{29}$H$_{32}$N$_2$O$_3$.0.2H$_2$O: Calcd: C, 75.69; H, 7.10; N, 6.09. Found: C, 75.58; H, 6.93; N, 6.08.

WORKING EXAMPLE 235 (Production of Compound 235)

In dichloromethane (10 ml) was suspended 7-(4-methylphenyl)-2,3-dihydro-1-benzothiepine-4-carboxylic acid (0.3 g), and to the suspension were added oxalyl chloride (0.27 ml) and dimethylformamide (catalytic amount) under ice-cooling. The mixture was stirred at room temperature for 2 hours, and the solvent was evaporated. The residue was dissolved in tetrahydrofuran (15 ml), and the mixture was dropwise added to a solution of 4-(N-methyl-N-(tetrahydropyran-4-yl)aminomethyl)aniline (0.25 g) and triethylamine (0.42 ml) in tetrahydrofuran(15 ml) under ice-cooling. Under nitrogen atmosphere, the mixture was stirred at room temperature overnight, and the solvent was evaporated. To the residue was added water, and the mixture was extracted with ethyl acetate. The organic layer was washed with water and saturated sodium chloride solution and dried with anhydrous magnesium sulfate. Under reduced pressure, the solvent was evaporated to give crude crystals, which were recrystallized from ethyl acetate-hexane to give 7-(4-methylphenyl)-N-(4-((N-tetrahydropyran-4-yl-N-methyl)aminomethyl)phenyl)-2,3-dihydro-1-benzothiepine-4-carboxamide (0.45 g) as colorless crystals.

mp 177–178° C.; $^1$H-NMR(CDCl$_3$) δ: 1.63–1.77 (4H, m), 2.21 (3H, s), 2.40 (3H, s), 2.57–2.70 (1H, m), 3.08 (2H, t, J=5.8 Hz), 3.26–3.44 (4H, m), 3.57 (2H, s), 4.01–4.11 (2H, m), 7.24–7.34 (3H, m), 7.40–7.57 (8H, m), 7.70 (1H, s). IR(KBr) ν: 2949, 1651 cm$^{-1}$. Anal. for C$_{31}$H$_{34}$N$_2$O$_2$S.0.3H$_2$O: Calcd: C, 73.86; H, 6.92; N, 5.56. Found: C, 73.93; H, 6.73; N, 5.82.

WORKING EXAMPLE 236 (Production of Compound 236)

In dichloromethane (6 ml) was suspended 2-(4-methylphenyl)-6,7-dihydro-5H-benzocycloheptene-8-carboxylic acid (0.25 g), and to the suspension were added oxalyl chloride (0.24 ml) and dimethylformamide (catalytic amount) under ice-cooling. The mixture was stirred at room temperature for 1.5 hours, and the solvent was evaporated. The residue was dissolved in tetrahydrofuran (15 ml), and the mixture was dropwise added to a solution of 4-((N-methyl-N-(pentan-3-yl))aminomethyl)aniline (0.2 g) and triethylamine (0.38 ml) in tetrahydrofuran (15 ml) under ice-cooling. Under nitrogen atmosphere, the mixture was stirred at room temperature for 5 hours, and the solvent was evaporated. To the residue was added water, and the mixture was extracted with ethyl acetate. The organic layer was washed with water and saturated sodium chloride solution and dried with anhydrous magnesium sulfate. Under reduced pressure, the solvent was evaporated to give crude crystals, which were recrystallized from ethyl acetate-hexane to give N-(4-((N-methyl-N-(pentan-3-yl))aminomethyl)phenyl)-2-(4-methylphenyl)-6,7-dihydro-5H-benzocycloheptene-8-carboxamide (0.23 g) as colorless crystals.

mp 112–113° C.; $^1$H-NMR(CDCl$_3$) δ: 0.94 (6H, t, J=7.3 Hz), 1.26–1.54 (4H, m), 2.14 (3H, s), 2.14–2.32 (3H, m), 2.40 (3H, s), 2.72 (2H, t, J=6.4 Hz), 2.86–2.91 (2H, m), 3.55 (2H, s), 7.21–7.27 (3H, m), 7.31–7.56 (8H, m), 7.62 (1H, s). IR(KBr) ν: 2930, 1651 cm$^{-1}$. Anal. for C$_{32}$H$_{38}$N$_2$O: Calcd: C, 82.36; H, 8.21; N, 6.00. Found: C, 82.30; H, 8.05; N, 5.90.

REFERENCE EXAMPLE 180

To a mixture of 3-(4-methylphenyl)-6,7,8,9-tetrahydro-5H-benzocycloheptan-5-one (0.5 g), potassium carbonate (1.65 g) and 18-crown-6 (1.05 g) was added dimethylsulfoxide (10 ml). Under carbon dioxide atmosphere, the mixture was stirred at room temperature for 20 hours, poured into water, acidified with hydrochloric acid and extracted with ethyl acetate. The organic layer was washed with water and subjected to back extraction with sodium hydroxide and water. The aqueous layer was collected, acidified with hydrochloric acid and extracted with ethyl acetate. The organic layer was washed with water and saturated sodium chloride solution and dried with anhydrous magnesium sulfate. The solvent was evaporated to precipitate colorless crystals (0.42 g), which were filtered with hexane and dissolved in ethanol (40 ml). To the mixture was added sodium boron hydride (0.54 g), and the mixture was stirred at room temperature for 1 hour. To the mixture was added water, and the mixture was concentrated, was acidified with hydrochloric acid and extracted with ethyl acetate. The organic layer was washed with water and saturated sodium chloride solution and dried with anhydrous agnesium sulfate. The solvent was evaporated to give colorless crystals (0.41 g), which were dissolved in 80% formic acid (40 ml). The mixture was stirred at 100° C. for 2.5 hours and concentrated. To the residue was added water, and the mixture was extracted with ethyl acetate. The organic layer was washed with water and saturated sodium chloride solution and dried with anhydrous magnesium sulfate. The solvent was evaporated, and the residue was purified with silica gel column (ethyl acetate/hexane) to give 2-(4-methylphenyl)-6,7-dihydro-5H-benzocycloheptene-8-carboxylic acid (0.14 g) as colorless crystals.

$^1$H-NMR(CDCl$_3$) δ: 2.04–2.18 (2H, m), 2.40 (3H, s), 2.70 (2H, t, J=6.8 Hz), 2.86–2.91 (2H, m), 7.21–7.28 (3H, m), 7.44–7.56 (4H, m), 7.91 (1H, s).

REFERENCE EXAMPLE 181

In dimethylsulfoxide (15 ml) were dissolved 3-(4-methylphenyl)-6,7,8,9-tetrahydro-5H-benzocycloheptan-5- one (0.5 g) and 18-crown-6 (1.05 g). Under ice-cooling, potassium t-butoxide (1.65 g) was added to the solution. Under carbon dioxide atmosphere, the mixture was stirred at room temperature for 3 hours, poured into water, acidified with hydrochloric acid and extracted with ethyl acetate. The organic layer was washed with water and subjected to back extraction with sodium hydroxide and water. The aqueous layer was collected, acidified with hydrochloric acid and extracted with ethyl acetate. The organic layer was washed with water and saturated sodium chloride solution and dried with anhydrous magnesium sulfate. The solvent was evaporated to precipitate colorless crystals (0.47 g), which were filtered with hexane and dissolved in ethanol (40 ml). To the mixture was added sodium boron hydride (0.58 g), and the mixture was stirred at room temperature for 1 hour. To the mixture was added water, and the mixture was concentrated, acidified with hydrochloric acid and extracted with ethyl acetate. The organic layer was washed with water and saturated sodium chloride solution and dried with anhydrous magnesium sulfate. The solvent was evaporated to precipitate colorless crystals (0.46 g), which were filtered with hexane. To the crystals was added 80% formic acid (10 ml), and the mixture was refluxed for 1.5 hours. To the mixture was added water, and the mixture was extracted with ethyl acetate. The organic layer was washed with water and subjected to back extraction with sodium hydroxide and water. The aqueous layer was collected, acidified with hydrochloric acid and extracted with ethyl acetate. The organic layer was washed with water and saturated sodium chloride solution and dried with anhydrous magnesium sulfate. The solvent was evaporated to precipitate 2-(4-methylphenyl)-6,7-dihydro-5H-benzocycloheptene-8-carboxylic acid (0.22 g) as colorless crystals.

$^1$H-NMR(CDCl$_3$) δ: 2.04–2.16 (2H, m), 2.40 (3H, s), 2.69 (2H, t, J=6.7 Hz), 2.86–2.91 (2H, m), 7.21–7.278 (3H, m), 7.44–7.56 (4H, m), 7.89 (1H, s).

WORKING EXAMPLE 237 (Production of Compound 237)

In dimethylformamide (100 ml) was dissolved 7-(4-methylphenyl)-N-(4-((N-(4-oxocyclohexyl)-N-methyl)-aminomethyl)-phenyl)-2,3-dihydro-1-benzoxepine-4-carboxamide (7.5 g), and to the mixture was added methyl iodide (4.7 ml). Under nitrogen atmosphere, the mixture was stirred at room temperature overnight. The solvent was evaporated, and to the residue was added acetone to give dimethyl-(N-(7-(4-methylphenyl)-2,3-dihydro-1-benzoxepin-4-carbonyl)-4-aminobenzyl)-N-(4-oxocyclohexyl)ammonium iodide (8.9 g) as colorless crystals.

$^1$H-NMR(DMSO-d$_6$) δ: 2.09–2.24 (2H, m), 2.34 (3H, s), 2.41–2.61 (6H, m), 2.97 (6H, s), 2.97–3.00 (2H, m), 3.79–3.90 (1H, m), 4.31 (2H, t, J=4.4 Hz), 4.56 (2H, s), 7.07 (1H, d, J=8.4 Hz), 7.27 (2H, d, J=8.2 Hz), 7.37 (1H, s), 7.55–7.60 (5H, m), 7.75 (1H, d, J=2.2 Hz), 7.88 (2H, d, J=8.8 Hz), 10.20 (1H, s).

WORKING EXAMPLE 238 (Production of Compound 238)

In dimethylformamide (5 ml) was dissolved in 2-(4-(1-pyrrolidinyl)phenyl)-N-(4-((N-tetrahydropyran-4-yl-N-methyl)aminomethyl)phenyl)-6,7-dihydro-5H-benzocycloheptene-8-carboxamide (0.15 g), and to the mixture was added methyl iodide (0.02 ml). Under nitrogen atmosphere, the mixture was stirred at room temperature overnight. To the mixture was added ethyl acetate, and crude crystal was filtered. The crude crystal was recrystallized from ethanol-ethyl acetate to give dimethyl-(N-(2-(4-(1-pyrrolidinyl)phenyl)-6,7-dihydro-5H-benzocycloheptene-8-carbonyl)-4-aminobenzyl)-4-tetrahydropyranylammonium iodide (0.05 g) as pale brown powder.

$^1$H-NMR(DMSO-d$_6$) δ: 1.80–2.20 (10H, m), 2.63 (2H, t, J=5.6 Hz), 2.81–2.84 (2H, m), 2.88 (6H, s), 3.24–3.44 (6H, m), 3.54–3.65 (1H, m), 4.02–4.11 (2H, m), 4.46 (2H, s), 6.62 (2H, d, J=9.0 Hz), 7.25 (1H, d, J=7.8 Hz), 7.36–7.60 (7H, m), 7.88 (2H, d, J=8.4 Hz), 10.22 (1H, s). IR(KBr) ν: 2967, 1663, 1609 cm$^{-1}$. Anal. for C$_{36}$H$_{44}$IN$_3$O$_2$.H$_2$O: Calcd: C, 62.15; H, 6.66; N, 6.04. Found: C, 61.89; H, 6.30; N, 5.97.

WORKING EXAMPLE 239 (Production of Compound 239)

In dimethylformamide (5 ml) was dissolved N-(4-((N-3-hydroxypropyl-N-methyl)aminomethyl)phenyl)-2-(4-methylphenyl)-6,7-dihydro-5H-benzocycloheptene-8-carboxamide (0.2 g), and to the mixture was added methyl iodide (0.04 ml). Under nitrogen atmosphere, the mixture was stirred at room temperature overnight. The solvent was evaporated, and to the residue was added ethyl acetate to give crude crystals, which were filtered and recrystallized from ethanol-ethyl acetate to give N-(3-hydroxypropyl)-N,N-dimethyl-(N-(2-(4-methylphenyl)-6,7-dihydro-5H-benzocycloheptene-8-carbonyl)-4-aminobenzyl)ammonium iodide (0.05 g) as colorless crystals.

mp 210–213° C.; $^1$H-NMR(CDCl$_3$+CD$_3$OD) δ: 2.00–2.20 (4H, m), 2.40 (3H, s), 2.71 (2H, t, J=6.6 Hz), 2.87–2.92 (2H, m), 3.10 (6H, s), 3.54–3.65 (2H, m), 3.73 (2H, t, J=5.3 Hz), 4.63 (2H, s), 7.22–7.27 (3H, m), 7.43–7.58 (7H, m), 7.80 (2H, d, J=8.4 Hz), 9.21 (1H, s). IR(KBr) ν: 3337, 2934, 1653 cm$^{-1}$. Anal. for C$_{31}$H$_{37}$IN$_2$O$_2$.0.5H$_2$O: Calcd: C, 61.49; H, 6.33; N, 4.63. Found: C, 61.55; H, 6.22; N, 4.74.

WORKING EXAMPLE 240 (Production of Compound 240)

In dimethylformamide (5 ml) was dissolved N-(4-((N-3-hydroxypropyl-N-methyl)aminomethyl)phenyl)-7-(4-methylphenyl)-2,3-dihydro-1-benzoxepine-4-carboxamide (0.14 g), and to the mixture was added methyl iodide (0.04 ml). Under nitrogen atmosphere, the mixture was stirred at room temperature overnight. The solvent was evaporated, and to the residue was added ethyl acetate to give crude crystals, which were filtered and recrystallized from ethanol-ethyl acetate to give dimethyl-3-hydroxypropyl-(N-(7-(4-methylphenyl)-2,3-dihydro-1-benzoxepin-4-carbonyl)-4-aminobenzyl)ammonium iodide (0.15 g) as colorless crystals.

mp 216–219° C.; $^1$H-NMR(CDCl$_3$+CD$_3$OD) δ: 2.00–2.20 (2H, m), 2.40 (3H, s), 3.06–3.10 (2H, m), 3.10 (6H, s), 3.51–3.61 (2H, m), 3.73 (2H, t, J=5.4 Hz), 4.37 (2H, t, J=4.6 Hz), 4.61 (2H, s), 7.07 (1H, d, J=8.4 Hz), 7.25 (2H, d, J=8.2 Hz), 7.46–7.59 (7H, m), 7.81 (2H, d, J=8.2 Hz), 9.54 (1H, s). IR(KBr) ν: 3306, 1651 cm$^1$. Anal. for C$_{30}$H$_{35}$IN$_2$O$_3$.0.5H$_2$O: Calcd: C, 59.31; H, 5.97; N, 4.61. Found: C, 59.36; H, 5.95; N, 4.75.

WORKING EXAMPLE 241 (Production of Compound 241)

In dimethylformamide (5 ml) was dissolved 7-(4-methylphenyl)-N-(4-((N-tetrahydropyran-4-yl-N-methyl)-aminomethyl)-phenyl)-2,3-dihydro-1-benzothiepine-4-carboxamide (0.19 g), and to the mixture was added methyl iodide (0.03 ml). Under nitrogen atmosphere, the mixture as stirred at room temperature overnight. The solvent was evaporated, and to the residue was added ethyl acetate to give crude crystals, which were filtered and recrystallized from ethanol-hexane to give dimethyl-(N-(7-(4-methylphenyl)-2,3-dihydro-1-benzothiepine-4-carbonyl)-4-aminobenzyl)-N-(4-tetrahydropyranyl)ammonium iodide (0.2 g) as colorless crystals.

mp 220–222° C.(dec.). $^1$H-NMR(DMSO-d$_6$) δ: 1.78–1.95 (2H, m), 2.05–2.20 (2H, m), 2.35 (3H, s), 2.88 (6H, s), 2.95–3.05 (2H, m), 3.21–3.32 (4H, m), 3.50–3.65 (1H, m), 4.05–4.15 (2H, m), 4.46 (2H, s), 7.29 (2H, d, J=8.0 Hz), 7.46–7.63 (7H, m), 7.81–7.90 (3H, m), 10.34 (1H, s). IR(KBr) ν: 2924, 1657 cm$^{-1}$.

WORKING EXAMPLE 242 (Production of Compound 242)

In dimethylformamide (5 ml) was dissolved N-(4-((N-methyl-N-(pentan-3-yl))aminomethyl)phenyl)-2-(4-methylphenyl)-6,7-dihydro-5H-benzocycloheptene-8-carboxamide (0.17 g), and to the mixture was added methyl iodide (0.08 ml). Under nitrogen atmosphere, the mixture was stirred at 45° C. overnight. The solvent was evaporated, and to the residue was added ethyl acetate to give crude crystals, which were filtered and recrystallized from ethanol-ethyl acetate to give dimethyl-(N-(2-(4-methylphenyl)-6,7-dihydro-5H-benzocycloheptene-8-carbonyl)-4-aminobenzyl)-N-(pentan-3-yl)ammonium iodide (0.15 g) as colorless crystals.

mp 190–194° C.(dec.). $^1$H-NMR(CDCl$_3$) δ: 1.15 (6H, t, J=7.4 Hz), 1.67–1.82 (2H, m), 2.05–2.25 (4H, m), 2.39 (3H, s), 2.73 (2H, t, J=6.6 Hz), 2.80–2.90 (2H, m), 3.11 (6H, s), 3.40–3.51 (1H, m), 4.91 (2H, s), 7.18–7.26 (3H, m), 7.44 (1H, dd, J=1.8, 8.4 Hz), 7.49 (2H, d, J=8.4 Hz), 7.57–7.62 (4H, m), 7.80 (2H, d, J=8.4 Hz), 8.35 (1H,s). IR(KBr) ν: 2936, 1659 cm$^{-1}$. Anal. for C$_{33}$H$_{41}$IN$_2$O.0.5H$_2$O: Calcd: C, 64.18; H, 6.85; N, 4.54. Found: C, 63.84; H, 6.73; N, 4.47.

REFERENCE EXAMPLE 182

In DMF (50 ml) was dissolved N-cyclohexyl-N-methylamine (12.5 g, 0.11 mol), and to the solution were added potassium carbonate (27.6 g, 0.20 mol) and 4-nitrobenzylbromide (21.6 g, 0.10 mol). The mixture was stirred at room temperature for 5 hours. Under reduced pressure, the reaction mixture was concentrated. To the residue was added ethyl acetate, and the mixture was extracted with water. The ethyl acetate layer was washed with saturated sodium chloride solution, dried with MgSO$_4$ and concentrated under reduced pressure. The residue was purified with silica gel column chromatography (ethyl acetate/hexane) to give N-cyclohexyl-N-methyl-N-(4-nitrobenzyl)amine (24.8 g).

$^1$H-NMR (200 MHz, CDCl$_3$) δ: 1.0–1.95 (10H, m), 2.19 (3H, s), 3.66 (2H, s) , 7.51 (2H, d, J=8.8 Hz), 8.17 (2H, d, J=8.8 Hz).

REFERENCE EXAMPLE 183

To a solution of N-cyclohexyl-N-methyl-N-(4-nitrobenzyl)amine (12.4 g, 50.0 mmol) in methanol(250 ml) were added nickel bromide (1.09 g, 5.0 mmol) and then sodium boron hydride (7.57 g, 200 mmol) at 0° C., and the mixture was stirred at room temperature for 30 minutes. To the mixture were added nickel bromide (0.55 g, 2.5 mmol) and then sodium boron hydride (3.78 g, 100 mmol) at 0° C., and the mixture was stirred at room temperature for 30 minutes. To the reaction mixture was added water (100 ml), and the mixture was concentrated under reduced pressure. To the residue was added ethyl acetate, and insoluble material was filtered off with Celite. The filtrate was washed with ethyl acetate, and the ethyl acetate layer was dried with MgSO$_4$ and concentrated under reduced pressure. The residue was washed with hexane to give 4-(N-cyclohexyl-N-methylaminomethyl)aniline (3.99 g, 37%).

$^1$H-NMR (200 MHz, CDCl$_3$) δ: 1.0–1.95 (10H, m), 2.17 (3H, s), 2.3–2.55 (1H, m), 3.46 (2H, s), 3.59 (2H, br s) , 6.65 (2H, d, J=8.5 Hz), 7.10 (2H, d, J=8.5 Hz).

WORKING EXAMPLE 243 (Production of Compound 243)

To a solution of 7-(4-methylphenyl)-2,3-dihydro-1-benzoxepine-4-carboxylic acid (0.28 g), 4-(N-cyclohexyl-N-methylaminomethyl)aniline (0.24 g) and 1-hydroxybenzotriazole (0.15 g) in dimethylformamide (10 ml) was added 1-ethyl-3-(3-dimethylaminopropyl) carbodiimide hydrochloride (0.29 g) under ice-cooling. Under nitrogen atmosphere, the mixture was cooled to room temperature, and to the mixture were added 4-dimethylaminopyridine (3 mg) and triethylamine (0.42 ml). The mixture was stirred for 20 hours, poured into water, and extracted with ethyl acetate. The organic layer was washed with water and saturated sodium chloride solution and dried with anhydrous magnesium sulfate. Under reduced pressure, the solvent was evaporated, and the residue was washed with ethyl acetate and dried to give N-(4-(N-cyclohexyl-N-methylaminomethyl)phenyl)-7-(4-methylphenyl)-2,3-dihydro-1-benzoxepine-4-carboxamide (0.40 g).

$^1$H-NMR(CDCl$_3$) δ: 1.0–1.95 (10H, m), 2.20 (3H, s), 2.35–2.55 (1H, m), 2.40 (3H, s), 3.0–3.15 (2H, m), 3.56 (2H, s), 4.3–4.45 (2H, m), 7.06 (1H, d, J=8.4 Hz), 7.2–7.6 (11H, m).

WORKING EXAMPLE 244 (Production of Compound 244)

In dimethylformamide (7 ml) was dissolved N-(4-(N-cyclohexyl-N-methylaminomethyl)phenyl)-7-(4-methylphenyl)-2,3-dihydro-1-benzoxepine-4-carboxamide (0.15 g), and to the mixture was added methyl iodide (0.06 ml). Under nitrogen atmosphere, the mixture was stirred at room temperature for 20 hours. The solvent was evaporated, and to the residue was added ethyl acetate to give crude crystals, which were filtered and recrystallized from ethanol to give N-cyclohexyl-N,N-dimethyl-N-((7-(4-methylphenyl)-2,3-dihydro-1-benzoxepin-4-carbonyl)-4-aminobenzyl)ammonium iodide (0.15 g).

$^1$H-NMR(CDCl$_3$) δ: 1.0–1.8 (6H, m), 1.9–2.05 (2H, m), 2.25–2.45 (2H, m), 2.36 (3H, s), 2.95–3.15 (8H, m), 3.45–3.7 (1H, m), 4.2–4.35 (2H, m), 4.83 (2H, s), 6.99 (1H, d, J=8.4 Hz), 7.21 (2H, d, J=7.6 Hz), 7.35–7.6 (6H, m), 7.74 (1H, d, J=2.2 Hz), 7.85 (2H, d, J=8.6 Hz), 8.79 (1H, s). IR(KBr) ν: 1659, 1609, 1593, 1518, 1493 cm$^{-1}$.

WORKING EXAMPLE 245 (Production of Compound 245)

In dimethylformamide (5 ml) was dissolved N-(4-(N-methyl-N-(tetrahydropyran-4-yl)aminomethyl)phenyl)-7-(4-morpholino-phenyl)-2,3-dihydro-1-benzoxepine-4-carboxamide (0.20 g), and to the mixture was added methyl iodide (0.03 ml). Under nitrogen atmosphere, the mixture was stirred at room temperature for 32 hours. The solvent was evaporated, and the residue was purified with silica gel column chromatography (dichloromethane/methanol). The desired fraction was concentrated, and to the residue was added ethyl acetate. Insoluble material was filtered and recrystallized from ethanol to give dimethyl-N-(7-(4-morpholinophenyl)-2,3-dihydro-1-benzoxepin-4-carbonyl)-4-aminobenzyl-N-(4-tetrahydropyranyl)ammonium iodide (0.18 g).

$^1$H-NMR(CDCl$_3$) δ: 1.6–2.0 (2H, m), 2.1–2.3 (2H, m), 2.92 (6H, s), 2.95–3.2 (6H, m), 3.35–3.55 (2H, m), 3.8–3.9 (4H, m), 4.0–4.35 (5H, m), 4.84 (2H, s), 6.85–7.05 (3H, m), 7.35–7.85 (9H, m), 8.92 (1H, s). IR(KBr) v: 1659, 1609, 1520, 1495 cm$^{-1}$.

REFERENCE EXAMPLE 184

In tetrahydrofuran(100 ml) was dissolved 1,2-methlenedioxy-4-bromobenzene (24.0 g), and to the mixture was dropwise added n-butyllithium (1.6M hexane solution, 82 ml) at −55° C. or less. The mixture was stirred at −70° C. or less for 30 minutes. The resulting solution was dropwise added to a solution of trimethyl borate (18.6 g) in tetrahydrofuran (50 ml) at −60° C. or less through cannula, and the mixture was stirred at −70° C. or less for 1 hour and then for 2 hours while warming the mixture to room temperature. To the reaction mixture were added 1N hydrochloric acid (130 ml) and diethylether (150 ml), and the organic layer was separated. The organic layer was washed with water and saturated sodium chloride solution and dried with anhydrous magnesium sulfate. Under reduced pressure, the solvent was evaporated. The residue was washed with diisopropylether to give 3,4-methlenedioxyphenyl borate (6.79 g).

$^1$H-NMR(DMSO-d$_6$) δ: 5.99 (2H, s), 6.8–6.95 (1H, m), 7.25–7.45 (2H, m).

REFERENCE EXAMPLE 185

To a mixture of methyl 7-bromo-2,3-dihydro-1-benzoxepine-4-carboxylate (0.57 g), 3,4-methlenedioxyphenyl borate(0.47 g) and sodium carbonate (0.42 g) were added water (2 ml) and 1,2-dimethoxyethane (12 ml). Under argon atmosphere, the mixture was stirred at room temperature for 30 minutes, and to the mixture was added tetrakistriphenylphosphinepalladium (0.16 g). The mixture was stirred at 80° C. for 14 hours and extracted with ethyl acetate. The organic layer was washed with water and saturated sodium chloride solution and dried with anhydrous magnesium sulfate. Under reduced pressure, the solvent was evaporated, and the residue was purified with silica gel column (ethyl acetate/hexane) to give methyl 7-(3,4-methlenedioxyphenyl)-2,3-dihydro-1-benzoxepine-4-carboxylate (0.43 g).

$^1$H-NMR(CDCl$_3$) δ: 2.95–3.10 (2H, m), 3.83 (3H, s), 4.25–4.35 (2H, m), 6.01 (2H, s), 6.87 (1H, d, J=8.6 Hz), 6.95–7.10 (3H, m), 7.40 (1H, dd, J=8.4, 2.4 Hz), 7.47 (1H, d, J=2.2 Hz), 7.65 (1H, s).

REFERENCE EXAMPLE 186

To methyl 7-(3,4-methlenedioxyphenyl)-2,3-dihydro-1-benzoxepine-4-carboxylate (0.40 g) were added methanol (5 ml) and 1N sodium hydroxide (3.7 ml), and the mixture was stirred at room temperature for 20 hours. To the mixture was added 1N hydrochloric acid (3.7 ml). and the mixture was concentrated under reduced pressure. Precipitate was washed with water and diethylether and dried under reduced pressure to give 7-(3,4-methylene-dioxyphenyl)-2,3-dihydro-1-benzoxepine-4-carboxylic acid (0.32 g).

$^1$H-NMR(DMSO-d$_6$) δ: 2.80–2.95 (2H, m), 4.15–4.35 (2H, m), 6.05 (2H, s), 6.97 (1H, d, J=8.lHz), 7.01 (1H, d, J=8.4 Hz), 7.16 (1H, dd, J=8.1, 1.7 Hz), 7.29 (1H, d, J=1.7 Hz), 7.53 (2H, dd, J=8.4, 2.3 Hz), 7.63 (1H, s), 7.74 (1H, d, J=2.3 Hz).

WORKING EXAMPLE 246 (Production of Compound 246)

To a solution of 7-(3,4-methlenedioxyphenyl)-2,3-dihydro-1-benzoxepine-4-carboxylic acid (0.14 g), 4-(N-methyl-N-(tetrahydropyran-4-yl)aminomethyl)aniline (0.11 g) and 1-hydroxy-benzotriazole (0.15 g) in dimethylformamide (10 ml) was added 1-ethyl-3-(3-dimethylaminopropyl) carbodiimide hydrochloride (0.13 g) under ice-cooling. Under nitrogen atmosphere, the reaction mixture was warmed to room temperature. To the mixture were added 4-dimethylaminopyridine (3 mg) and triethylamine (0.19 ml), and the mixture was stirred for 18 hours, poured into water, and extracted with ethyl acetate. The organic layer was washed with water and saturated sodium chloride solution, and dried with anhydrous magnesium sulfate. Under reduced pressure, the solvent was evaporated, and the residue was purified with silica gel column (ethyl acetate) to give 7-(3,4-methlenedioxyphenyl)-4-(N-methyl-N-(tetrahydropyran-4-yl)aminomethyl)phenyl)-2,3-dihydro-1-benzoxepine-4-carboxamide (0.19 g).

1H-NMR(CDCl$_3$) δ: 1.55–1.85 (4H, m), 2.21 (3H, s), 2.55–2.80 (1H, m), 3.00–3.15 (2H, m), 3.30–3.45 (2H, m), 3.58 (2H, s), 3.95–4.15 (2H, m), 4.30–4.45 (2H, m), 6.01 (2H, s), 6.88 (1H, d, J=8.6 Hz), 6.95–7.10 (3H, m), 7.20–7.65 (7H, m). IR(KBr) v: 1653, 1597, 1514, 1483 cm$^{-1}$.

WORKING EXAMPLE 247 (Production of Compound 247)

In dimethylformamide (5 ml) was dissolved 7-(3,4-methlenedioxyphenyl)-4-(N-methyl-N-(tetrahydropyran-4-yl)aminomethyl)phenyl)-2,3-dihydro-1-benzoxepine-4-carboxamide (95 mg), and to the mixture was added methyl iodide (0.012 ml). Under nitrogen atmosphere, the mixture was stirred at room temperature for 18 hours. The solvent was evaporated, and to the residue was added ethyl acetate. Insoluble material was filtered and recrystallized from ethanol to give dimethyl-N-(7-(3,4-methylenedioxyphenyl)-2,3-dihydro-1-benzoxepin-4-carbonyl)-4-aminobenzyl-N-(4-tetrahydropyranyl)ammonium iodide (101 mg).

$^1$H-NMR(CDCl$_3$) δ: 1.7–2.0 (2H, m), 2.15–2.3 (2H, m), 2.85–3.1 (8H, m), 3.4–3.55 (2H, m), 4.0–4.35 (5H, m), 4.85 (2H, s), 5.96 (2H, s), 6.81 (1H, d, J=7.8 Hz), 6.9–7.1 (3H, m), 7.25–7.7 (5H, m), 7.83 (2H, d, J=8.2 Hz), 8.89 (1H, s). IR(KBr) v: 1659, 1609, 1520, 1495 cm$^{-1}$.

WORKING EXAMPLE 248 (Production of Compound 248)

In aqueous methanol was dissolved N,N-dimethyl-N-(4-(((2-(4-methylphenyl)-6,7-dihydro-5H-benzocyclohepten-8-yl)carbonyl)amino)benzyl)-N-(4-tetrahydropyranyl) ammonium iodide (19 g), and the mixture was subjected to ion exchange resin (DOWEXI-x8, 100–200 mesh, Cl$^-$ type) column, which was eluted with aqueous methanol. The solvent of the desired fractions was evaporated, and to the residue was added acetone to give crude crystals, which were recrystallized from ethanol to give N,N-dimethyl-N-(4-(((2-(4-methylphenyl)-6,7-dihydro-5H-benzocyclohepten-8-yl)carbonyl)amino)benzyl)-N-(4-tetrahydropyranyl)ammonium chloride (10.1 g) as colorless crystals.

mp 226–232° C.(dec.). $^1$H-NMR(CDCl$_3$+CD$_3$OD) δ: 1.80–2.00 (2H, m), 2.07–2.26 (4H, m), 2.39 (3H, s), 2.72 (2H, t, J=6.6 Hz), 2.85–2.91 (2H, m), 3.00 (6H, s), 3.54 (2H, t, J=11.3 Hz), 4.00–4.21 (3H, m), 4.70 (2H, s), 7.21–7.29 (3H, m), 7.42–7.56 (7H, m), 7.81 (2H, d, J=8.4 Hz), 9.06 (1H, s). IR(KBr) ν: 2934, 1655 cm$^{-1}$. Anal. for C$_{33}$H$_{39}$ClN$_2$O$_2$: Calcd: C, 74.62; H, 7.40; N, 5.27; Cl, 6.67. Found: C, 74.35; H, 7.33; N, 5.20; Cl, 6.80.

WORKING EXAMPLE 248a (Production of Compound 248)

To a solution of N-(4-chloromethylphenyl)-2-(4-methylphenyl)-6,7-dihydro-5H-benzocycloheptene-8-carboxamide (9.38 g, 23.3 mmol) in DMF (50 ml) was dropwise added a solution of N,N-dimethyl-N-tetrahydropyran-4-ylamine (4.5 g, 35.0 mmol) in DMF (50 ml). Under nitrogen atmosphere, the mixture was stirred for 23 hours. The solvent was evaporated to give powder, which was washed with acetone and dried. The resulting colorless powder was recrystallized from ethanol to give N,N-dimethyl-N-(4-(((2-(4-methylphenyl)-6,7-dihydro-5H-benzocyclohepten-8-yl)carbonyl)amino)benzyl)-N-(4-tetrahydropyranyl)ammonium chloride (Compound 248) (10.6 g, 86%) as colorless powder.

WORKING EXAMPLE 249 (Production of Compound 249)

In aqueous acetonitrile was dissolved N,N-dimethyl-N-(4-(((7-(4-methylphenyl)-2,3-dihydro-1-benzoxepin-4-yl)carbonyl)amino)benzyl)-N-(4-oxocyclohexyl)ammonium iodide (22.8 g), and the mixture was subjected to ion exchange resin (DOWEX-SBR, Cl$^-$ type) column, which was eluted with aqueous acetonitrile. The solvent of the desired fractions was evaporated, and the residue was dissolved in water. The mixture was subjected to freeze-drying to give N,N-dimethyl-N-(4-(((7-(4-methylphenyl)-2,3-dihydro-1-benzoxepin-4-yl)carbonyl)amino)benzyl)-N-(4-oxocyclohexyl)ammonium chloride (Compound 249) (16.1 g) as colorless powder.

$^1$H-NMR(DMSO-d$_6$) δ: 2.05–2.25 (2H, m), 2.34 (3H, s), 2.41–2.61 (6H, m), 2.97 (6H, s), 2.97–3.00 (2H, m), 3.75–3.90 (1H, m), 4.30 (2H, t, J=4.4 Hz), 4.57 (2H, s), 7.06 (1H, d, J=8.4 Hz), 7.27 (2H, d, J=7.8 Hz), 7.45 (1H, s), 7.53–7.60 (5H, m), 7.78 (1H, d, J=2.2 Hz), 7.92 (2H, d, J=8.4 Hz), 10.34 (1H, s). IR(KBr) ν: 3025, 2967, 1717, 1655 cm$^{-1}$. Anal. for C$_{33}$H$_{37}$ClN$_2$O$_3$·0.5H$_2$O: Calcd: C, 71.53; H, 6.91; N, 5.06; Cl, 6.40. Found: C, 71.21; H, 6.94; N, 4.94; Cl, 6.24.

WORKING EXAMPLE 249a (Production of Compound 249)

To a solution of N-(4-chloromethylphenyl)-7-(4-methylphenyl)-2,3-dihydro-1-benzoxepine-4-carboxamide (214 mg, 0.530 mmol) in N,N-dimethylformamide (1 ml) was dropwise added a solution of 4-dimethylaminocyclohexanone (112 mg, 0.795 mmol) in N,N-dimethylformamide (1 ml). Under nitrogen atmosphere, the mixture was stirred for 14 hours. The solvent was evaporated to give crude product, which was washed with ether to give N,N-dimethyl-N-(4-(((7-(4-methylphenyl)-2,3-dihydro-1-benzoxepin-4-yl)carbonyl)amino)benzyl)-N-(4-oxocyclohexyl)ammonium chloride (Compound 249) (305 mg) as colorless powder.

WORKING EXAMPLE 250 (Production of Compound 250)

To a solution of N-(4-chloromethylphenyl)-7-(4-ethoxyphenyl)-2,3-dihydro-1-benzoxepine-4-carboxamide (2.38 g) in DMF (20 ml) was added N,N-dimethyl-N-tetrahydropyran-4-ylamine (1.42 g) at room temperature, and the mixture was stirred for 14 hours. To the reaction mixture was added ethyl acetate (100 ml) to precipitate crystals, which were collected by filtration. The crystal was washed with ethyl acetate to give crude product as pale yellow crystals, which were recrystallized from ethanol to give as N-(4-(((7-(4-ethoxyphenyl)-2,3-dihydro-1-benzoxepin-4-yl)carbonyl)amino)benzyl)-N,N-dimethyl-N-(4-tetrahydropyranyl)ammonium chloride (Compound 250) (1.29 g) colorless crystals.

m.p. 200–204° C.; $^1$H-NMR (200 MHz, DMSO-d$_6$) δ: 1.35 (3H, t, J=7.0 Hz), 1.75–1.98 (2H, m), 2.06–2.24 (2H, m), 2.88 (6H, s), 2.94–3.05 (2H, m), 3.28–3.43 (2H, m), 3.49–3.69 (1H, m), 3.99–4.13 (2H, m), 4.07 (2H, q, J=7.0 Hz), 4.23–4.35 (2H, m), 4.47 (2H, s), 6.98–7.07 (3H, m), 7.37 (1H, s), 7.50–7.61 (5H, m), 7.72 (1H, d, J=2.2 Hz), 7.87 (2H, d, J=8.4 Hz), 10.22 (1H, s). IR (KBr) ν: 3425, 1647, 1603, 1520, 1489, 1407, 1317, 1294, 1240, 831 cm$^{-1}$; Anal. for C$_{33}$H$_{39}$N$_2$O$_4$Cl; Calcd: C, 70.38; H, 6.98; N, 4.97; Cl, 6.30 Found: C, 70.49; H, 7.08; N, 4.94; Cl, 6.19.

WORKING EXAMPLE 250a (Production of Compound 250)

In aqueous methanol was dissolved N-(4-(((7-(4-ethoxyphenyl)-2,3-dihydro-1-benzoxepin-4-yl)carbonyl)-amino)benzyl)-N,N-dimethyl-N-(4-tetrahydropyranyl) ammonium iodide (26.6 g), and the mixture was subjected to ion exchange resin (DOWEX-SBR, Cl$^-$ type) column, which was eluted with aqueous methanol. The solvent of the desired fractions was evaporated, and to the residue was added acetone to give crude crystals, which were recrystallized from ethanol to give N-(4-(((7-(4-ethoxyphenyl)-2,3-dihydro-1-benzoxepin-4-yl)carbonyl)amino)benzyl)-N,N-dimethyl-N-(4-tetrahydropyranyl)ammonium chloride (Compound 250) (16.6 g) as colorless crystals.

WORKING EXAMPLE 251 (Production of Compound 251)

To a solution of N-(4-((N-tetrahydrothiopyran-4-yl-N-methyl)aminomethyl)phenyl)-7-(4-methylphenyl)-2,3-dihydro-1-benzoxepine-4-carboxamide (0.2 g) in dichloromethane (10 ml) was added mCPBA (0.1 g) at –10 to –20° C., and the mixture was stirred for 30 minutes. To the mixture was added sodium thiosulfate solution, and the mixture was concentrated and extracted with ethyl acetate. The organic layer was washed with sodium hydrogen carbonate solution, water and saturated brine and dried with anhydrous magnesium sulfate. Under reduced pressure, the solvent was evaporated, and the residue was purified with silica gel column (methanol/triethylamine/ethyl acetate) to give N-(4-((N-(1-oxotetrahydrothiopyran-4-yl)-N-methyl) aminomethyl)phenyl)7-(4-methylphenyl)-2,3-dihydro-1-benzoxepine-4-carboxamide (Compound 251) (E,Z mixture: 0.12 g) as colorless powder.

$^1$H-NMR(δ ppm, CDCl$_3$) 1.80–1.97 (2H, m), 2.17 (1.4H, S), 2.28 (1.6H, s), 2.37–2.51 (3H, m), 2.39 (3H, S), 2.56–2.73 (2H, m), 3.08 (2H, t, J=4.7 Hz), 3.15–3.28 (2H, m), 3.54 (0.9H, s), 3.63 (1.1H, s), 4.36 (2H, t, J=4.7 Hz), 7.06 (1H, d, J=8.4 Hz), 7.23–7.34 (4H, m), 7.44–7.57 (6H, m), 7.64 (1H, s). IR(KBr) ν: 3279, 2946, 1651 cm$^{-1}$. Anal. Calcd. for C$_{31}$H$_{34}$N$_2$O$_3$S: C, 72.34; H, 6.66; N, 5.44. Found C, 72.31; H, 6.66; N, 5.35.

WORKING EXAMPLE 252 (Production of Compound 252)

To a suspension of 2-(4-methylphenyl)-6,7-dihydro-5H-benzocycloheptene-8-carboxylic acid (0.15 g) in dichloromethane (5 ml) were added under ice-cooling oxalyl chloride (0.15 ml) and dimethylformamide (catalytic amount), and the mixture was stirred at room temperature for 2 hours. The solvent was evaporated, and the residue was dissolved in tetrahydrofuran (15 ml). The mixture was added dropwise, under ice-cooling, to a mixture of 1-(4-aminobenzyl)phosphorinane-1-oxide (0.13 g) and triethylamine (0.23 ml) in tetrahydrofuran (15 ml). Under nitrogen atmosphere, the mixture was stirred at room temperature overnight. The mixture was poured into water and extracted with ethyl acetate. The organic layer was washed with water and saturated brine, and dried with anhydrous magnesium sulfate. Under reduced pressure, the solvent was evaporated to give crude crystals, which were recrystallized from ethanol/hexane to give 2-(4-methylphenyl)-N-(4-((1-oxophosphorinane-1-yl)methyl)-phenyl)-6,7-dihydro-5H-benzocycloheptene-8-carboxamide (Compound 252) (0.16 g) as colorless crystals.

mp 282–283° C.(dec.). $^1$H-NMR($\delta$ ppm, CDCl$_3$) 1.40–1.60 (2H, m), 1.70–1.80 (6H, m), 1.80–2.20 (4H, m), 2.40 (3H, s), 2.72 (2H, t, J=6.6 Hz), 2.86–2.95 (2H, m), 3.16 (2H, d, J=13.6 Hz), 7.15–7.26 (4H, m), 7.42–7.52 (5H, m), 7.60 (2H, d, J=8.0 Hz), 7.80 (1H, s). IR(KBr) $\nu$: 2932, 1659 cm$^{-1}$. Anal. Calcd. for C$_{31}$H$_{34}$NO$_2$P.0.2H$_2$O: C, 76.43; H, 7.12; N, 2.87. Found C, 76.20; H, 7.31; N, 3.00.

WORKING EXAMPLE 253 (Production of Compound 253)

To a suspension of 2-(4-methylphenyl)-6,7-dihydro-5H-benzocycloheptene-8-carboxylic acid (0.3 g) in dichloromethane (5 ml) were added under ice-cooling oxalyl chloride (0.3 ml) and dimethylformamide (catalytic amount), and the mixture was stirred at room temperature for 2 hours. The solvent was evaporated, and the residue was dissolved in tetrahydrofuran (10 ml). The mixture was added dropwise, under ice-cooling, to a mixture of 4-(N-methyl-N-(tetrahydrothiopyran-4-yl)-aminomethyl)aniline (0.27 g) and triethylamine (0.45 ml) in tetrahydrofuran (10 ml). Under nitrogen atmosphere, the mixture was stirred at room temperature for 4 hours. The solvent was evaporated, and to the residue was added water. The mixture was extracted with ethyl acetate, and the organic layer was washed with water and saturated brine, and dried with anhydrous magnesium sulfate. Under reduced pressure, the solvent was evaporated to give crude crystals, which were recrystallized from ethyl acetate/hexane to give N-(4-((N-tetrahydrothiopyran-4-yl-N-methyl)aminomethyl)phenyl)-2-(4-methylphenyl)-6,7-dihydro-5H-benzocycloheptene-8-carboxamide (Compound 253) (0.45 g) as colorless crystals.

mp 177–178° C.; $^1$H-NMR($\delta$ ppm, CDCl$_3$) 1.65–1.85 (2H, m), 2.14–2.20 (2H, m), 2.22 (3H, s), 2.40 (3H, s), 2.47–2.53 (1H, m), 2.68–2.72 (6H, m), 2.86–2.92 (2H, m), 3.58 (2H, s), 7.21–7.27 (2H, m), 7.31 (2H, d, J=8.4 Hz), 7.42–7.52 (5H, m), 7.56 (2H, d, J=8.4 Hz), 7.63 (1H, s). IR(KBr) $\nu$: 2932, 1651 cm$^{-1}$; Anal. Calcd. for C$_{32}$H$_{36}$N$_2$OS.0.2H$_2$O: C, 76.82; H, 7.33; N, 5.60. Found C, 76.89; H, 7.35; N, 5.64.

WORKING EXAMPLE 254 (Production of Compound 254a and 254b)

To a solution of N-(4-((N-tetrahydrothiopyran- 4-yl-N-methyl)aminomethyl)phenyl)-2-(4-methylphenyl)-6,7-dihydro-5H-benzocycloheptene-8-carboxamide (0.3 g) in dichloromethane (20 ml) was added mCPBA (0.18 g) at −10 to −20° C., and the mixture was stirred for 1.5 hours. To the mixture was added sodium thiosulfate solution, and the mixture was concentrated and extracted with ethyl acetate. The organic layer was washed with sodium hydrogen carbonate solution, water and saturated brine, and dried with anhydrous magnesium sulfate. Under reduced pressure, the solvent was evaporated, and the residue was purified with silica gel column (methanol/triethylamine/ethyl acetate) to give two kinds of crude crystals, each of which was recrystallized from ethyl acetate/ethanol/hexane to give (E) or (Z)-N-(4-((N-(1-oxotetrahydrothiopyran-4-yl)-N-methyl) aminomethyl)phenyl)-2-(4-methylphenyl)-6,7-dihydro-5H-benzocycloheptene-8-carboxamide (Compound 254a) (76 mg) and (Z) or (E)-N-(4-((N-(1-oxotetrahydrothiopyran-4-yl)-N-methyl)aminomethyl)phenyl)-2-(4-methylphenyl)-6, 7-dihydro-5H-benzocycloheptene-8-carboxamide (Compound 254b) (0.11 g) as colorless crystals, respectively.

Compound 254a:

mp 218–219° C.; $^1$H-NMR($\delta$ ppm, CDCl$_3$) 1.80–2.00 (2H, m), 2.10–2.20 (2H, m), 2.19 (3H, s), 2.25–2.39 (2H, m), 2.40 (3H, S), 2.61–2.76 (5H, m), 2.86–2.92 (2H, m), 3.23–3.33 (2H, m), 3.57 (2H, s), 7.22–7.31 (4H, m), 7.42–7.52 (5H, m), 7.58 (2H, d, J=8.4 Hz), 7.66 (1H, s). Anal. Calcd. for C$_{32}$H$_{36}$N$_2$O$_2$S.0.2H$_2$O: C, 74.44; H, 7.11; N, 5.43. Found C, 74.43; H, 7.18; N, 5.66.

Compound 254b:

mp 216–218° C.; $^1$H-NMR($\delta$ ppm, CDCl$_3$) 1.80–2.00 (3H, m), 2.10–2.25 (3H, m), 2.35 (3H, s), 2.40 (3H, S), 2.44–2.53 (2H, m), 2.69–2.76 (3H, m), 2.86–2.92 (2H, m), 3.07–3.17 (2H, m), 3.71 (2H, s), 7.22–7.27 (2H, m), 7.35–7.52 (7H, m), 7.60 (2H, d, J=8.4 Hz), 7.73 (1H, s).

WORKING EXAMPLE 255 (Production of Compound 255)

In dichloromethane (5 ml) was suspended 2-(4-methylphenyl)-6,7-dihydro-5H-benzocycloheptene-8-carboxylic acid (0.3 g), and to the mixture were added, under ice-cooling, oxalyl chloride (0.3 ml) and dimethylformamide (catalytic amount). The mixture was stirred at room temperature for 2 hours, and the solvent was evaporated. The residue was dissolved in tetrahydrofuran (15 ml), and the solution was added dropwise, under ice-cooling, to a solution of 4-(N-ethyl-N-(tetrahydropyran-4-yl)aminomethyl) aniline (0.27 g) and triethylamine (0.45 ml) in tetrahydrofuran (10 ml). Under nitrogen atmosphere, the mixture was stirred at room temperature overnight. The solvent was evaporated, and to the residue was added water. The mixture was extracted with ethyl acetate, and the organic layer was with water and saturated brine, and dried with anhydrous magnesium sulfate. Under reduced pressure, the solvent was evaporated, and the residue was purified with silica gel column (ethyl acetate) to give crude crystals, which were recrystallized from ethyl acetate/hexane to give N-(4-((N-ethyl-N-tetrahydropyran-4-yl)aminomethyl)phenyl)-2-(4-methylphenyl)-6,7-dihydro-5H-benzocycloheptene-8-carboxamide (Compound 255) (0.38 g) as colorless crystals.

mp 122–123° C.; $^1$H-NMR($\delta$ ppm, CDCl$_3$) 1.01 (3H, t, J=7.1 Hz), 1.62–1.72 (4H, m), 2.13–2.19 (2H, m), 2.40 (3H, s), 2.57 (2H, q, J=7.1 Hz), 2.69–2.76 (3H, m), 2.86–2.92 (2H, m), 3.34 (2H, dt, J=3.4, 10.9 Hz), 3.62 (2H, s), 3.97–4.04 (2H, m), 7.21–7.28 (3H, m), 7.35 (2H, d, J=8.6 Hz), 7.42–7.57 (6H, m), 7.62 (1H, s). IR(KBr) $\nu$: 2936, 1651 cm$^{-1}$. Anal. Calcd. for C$_{33}$H$_{38}$N$_2$O: C, 80.13; H, 7.74; N, 5.66. Found C, 79.96; H, 7.77; N, 5.38.

WORKING EXAMPLE 256 (Production of Compound 256)

To a suspension of 7-(4-methylphenyl)-2,3-dihydro-1-benzothiepine-4-carboxylic acid (0.3 g) in dichloromethane (6 ml) were added, under ice-cooling, oxalyl chloride (0.25 ml) and dimethylformamide (catalytic amount), and the mixture was stirred at room temperature for 1.5 hours. The solvent was evaporated, and the residue was dissolved in tetrahydrofuran (15 ml). The mixture was added dropwise, under ice-cooling, to a solution of 4-((N-methyl-N-(pentan-3-yl).)aminomethyl)-aniline (0.23 g) and triethylamine (0.42 ml) in tetrahydrofuran (15 ml). Under nitrogen atmosphere, the mixture was stirred at room temperature overnight. The solvent was evaporated, and to the residue was added water. The mixture was extracted with ethyl acetate, and the organic layer was with water and saturated brine, and dried with anhydrous magnesium sulfate. Under reduced pressure, the solvent was evaporated to give crude crystals, which were recrystallized from ethyl acetate/hexane to give N-(4-((N-methyl-N-(pentan-3-yl)amino)methyl)-phenyl)-7-(4-methylphenyl)-2,3-dihydro-1-benzothiepine-4-carboxamide (Compound 256) (0.34 g) as colorless crystals.

mp 136–137° C.; $^1$H-NMR($\delta$ ppm, CDCl$_3$) 0.94 (6H, t, J=7.3 Hz), 1.26–1.54 (4H, m), 2.13 (3H, s), 2.17–2.32 (1H, m), 2.40 (3H, s), 3.08 (2H, t, J=5.9 Hz), 3.29 (2H, t, J=5.9 Hz), 3.55 (2H, s), 7.24–7.28 (2H, m), 7.31–7.40 (3H, m), 7.44–7.57 (6H, m), 7.66 (1H, s). IR(KBr) v: 2959, 2928, 1651 cm$^{-1}$. Anal. Calcd. for C$_{31}$H$_{36}$N$_2$OS: C, 76.82; H, 7.49; N, 5.78. Found C, 76.77; H, 7.21; N, 5.63.

WORKING EXAMPLE 257 (Production of Compound 257)

In dichloromethane (5 ml) was suspended 7-(4-methylphenyl)-2,3-dihydro-1-benzoxepine-4-carboxylic acid (0.25 g), and to the mixture were added, under ice-cooling, oxalyl chloride (0.23 ml) and dimethylformamide (catalytic amount). The mixture was stirred at room temperature for 2 hours, and the solvent was evaporated. The residue was dissolved in tetrahydrofuran (20 ml), and the mixture was added dropwise, under ice-cooling, to a solution of 2-(N-(4-aminobenzyl)-N-methylamino)-1,3-propanediol (0.21 g) and triethylamine (0.37 ml) in tetrahydrofuran (10 ml). Under nitrogen atmosphere, the mixture was stirred at room temperature overnight. The solvent was evaporated, and to the residue was added water. The mixture was extracted with ethyl acetate, and the organic layer was with water and saturated brine, and dried with anhydrous magnesium sulfate. Under reduced pressure, the solvent was evaporated, and the residue was purified with silica gel column (methanol/triethylamine/ethyl acetate) to give crude crystals, which were recrystallized from ethyl acetate/ethanol/hexane to give N-(4-((N-bis(hydroxymethyl)methyl-N-methyl)aminomethyl)phenyl)-7-(4-methylphenyl)-2,3-dihydro-1-benzoxepine-4-carboxamide (Compound 257) (0.22 g) as colorless crystals.

mp 199–201° C.; $^1$H-NMR($\delta$ ppm, CDCl$_3$) 2.30 (3H, s), 2.39 (3H, s), 2.96–3.03 (1H, m), 3.08 (2H, t, J=4.5 Hz), 3.61–3.73 (4H, m), 3.78 (2H, s), 4.36 (2H, t, J=4.5 Hz), 7.06 (1H, d, J=8.4 Hz), 7.23–7.32 (4H, m), 7.44–7.58 (6H, m), 7.62 (1H, s). IR(KBr) v: 3260, 2928, 1653 cm$^{-1}$. Anal. Calcd. for C$_{29}$H$_{32}$N$_2$O$_4$.0.2H$_2$O: C, 73.15; H, 6.86; N, 5.88. Found C, 73.20; H, 6.86; N, 5.91.

WORKING EXAMPLE 258 (Production of Compound 258)

In dichloromethane (5 ml) was suspended 7-(4-methylphenyl)-2,3-dihydro-1-benzoxepine-4-carboxylic acid (0.3 g), and to the mixture were added, under ice-cooling, oxalyl chloride (0.28 ml) and dimethylformamide (catalytic amount). The mixture was stirred at room temperature for 2 hours, and the solvent was evaporated. The residue was dissolved in tetrahydrofuran (20 ml), and the mixture was added dropwise, under ice-cooling, to a solution of N-(4-aminobenzyl)sarcosine methyl ester (0.25 g) and triethylamine (0.45 ml) in tetrahydrofuran (10 ml). Under nitrogen atmosphere, the mixture was stirred at room temperature overnight. The solvent was evaporated, and to the residue was added water. The mixture was extracted with ethyl acetate, and the organic layer was with water and saturated brine, and dried with anhydrous magnesium sulfate. Under reduced pressure, the solvent was evaporated, and the residue was purified with silica gel column (ethyl acetate/hexane) to give crude crystals, which were recrystallized from ethyl acetate/hexane to give N-(4-((N-methoxycarbonylmethyl-N-methyl)aminomethyl)-phenyl)-7-(4-methylphenyl)-2,3-dihydro-1-benzoxepine-4-carboxamide (Compound 258) (0.38 g) as colorless crystals.

mp 135–136° C.; $^1$H-NMR($\delta$ ppm, CDCl$_3$) 2.39 (3H, s), 2.39 (3H, s), 3.08 (2H, t, J=4.4 Hz), 3.26 (2H, s), 3.65 (2H, s), 3.72 (3H, s), 4.36 (2H, t, J=4.4 Hz), 7.06 (1H, d, J=8.4 Hz), 7.22–7.36 (4H, m), 7.43–7.60 (7H, m). IR(KBr) v: 3262, 2951, 1740 cm$^{-1}$. Anal. Calcd. for C$_{29}$H$_{30}$N$_2$O$_4$: C, 74.02; H, 6.43; N, 5.95. Found C, 74.07; H, 6.47; N, 5.94.

WORKING EXAMPLE 259 (Production of Compound 259)

In methanol (20 ml) and THF (10 ml) was dissolved N-(4-((N-methoxycarbonylmethyl-N-methyl)aminomethyl)-phenyl)-7-(4-methylphenyl)-2,3-dihydro-1-benzoxepine-4-carboxamide (0.24 g), and to the mixture was added 1N sodium hydroxide solution (3.0 ml). The mixture was stirred at room temperature overnight and concentrated. The residue was neutralized with 1N hydrochloric acid, and precipitated materials were filtered and dissolved in methanol. The mixture was filtered, and to the filtrate was added 4N hydrochloric acid-ethyl acetate. The solvent was evaporated, and the residue was purified with methanol/diethylether to give N-(4-((N-carboxymethyl-N-methyl)aminomethyl)phenyl)- 7-(4-methylphenyl)-2,3-dihydro-1-benzoxepine-4-carboxamide hydrochloride (Compound 259) (0.21 g) as pale yellow amorphous.

$^1$H-NMR($\delta$ ppm, DMSO-d$_6$) 2.34 (3H, s), 2.76 (3H, s), 2.99 (2H, br), 3.36 (2H, br), 4.02 (2H, s), 4.30 (2H, br), 7.06 (1H, d, J=8.4 Hz), 7.27 (2H, d, J=7.8 Hz), 7.38 (1H, s), 7.48 (2H, d, J=8.6 Hz), 7.55–7.59 (3H, m), 7.76 (1H, d, J=2.2 Hz), 7.82 (2H, d, J=8.6 Hz), 10.18 (1H, s). IR(KBr) v: 1744 cm$^{-1}$. Anal. Calcd. for C$_{28}$H$_{29}$ClN$_2$O$_4$.0.5H$_2$O:] C, 66.99; H, 6.02; N, 5.58. Found C, 66.93; H, 5.87; N, 5.11.

WORKING EXAMPLE 260 (Production of Compound 260)

In dichloromethane (10 ml) was suspended 7-(4-methylphenyl)-2,3-dihydro-1-benzothiepine-4-carboxylic acid (0.3 g), and to the mixture were added, under ice-cooling, oxalyl chloride (0.25 ml) and dimethylformamide (catalytic amount). The mixture was stirred at room temperature for 2 hours, and the solvent was evaporated. The residue was dissolved in tetrahydrofuran (20 ml), and the mixture was added dropwise, under ice-cooling, to a solution of N-(4-aminobenzyl)sarcosine methyl ester (0.23 g) and triethylamine (0.42 ml) in tetrahydrofuran (10 ml). Under nitrogen atmosphere, the mixture was stirred at room temperature overnight. The solvent was evaporated, and to the residue was added water. The mixture was extracted with ethyl acetate, and the organic layer was with water and saturated brine, and dried with anhydrous magnesium sulfate. Under reduced pressure, the solvent was evaporated to give crude crystals, which were recrystallized from ethyl acetate/hexane to give N-(4-((N-methoxycarbonylmethyl-N-methyl)aminomethyl)phenyl)-7-(4-methylphenyl)-2,3-dihydro-1-benzothiepine-4-carboxamide (Compound 260) (0.43 g) as colorless crystals.

mp 148–150° C.; $^1$H-NMR($\delta$ ppm, CDCl$_3$) 2.39 (3H, s), 2.40 (3H, s), 3.08 (2H, t, J=6.0 Hz), 3.26 (2H, s), 3.29 (2H, t, J=6.0 Hz), 3.66 (2H, s), 3.72 (3H, s), 7.24–7.58 (11 H, m), 7.67 (1H, s). IR(KBr) v: 1738 cm$^{-1}$. Anal. Calcd. for C$_{29}$H$_{30}$N$_2$O$_3$S: C, 71.58; H, 6.21; N, 5.76. Found C, 71.75; H, 5.95; N, 5.60.

WORKING EXAMPLE 261 (Production of Compound 261)

In methanol (20 ml) and THF (10 ml) was dissolved N-(4-((N-methoxycarbonylmethyl-N-methyl)aminomethyl)phenyl)-7-(4-methylphenyl)-2,3-dihydro-1-benzothiepine-4-carboxamide (0.23 g), and to the mixture was added 1N sodium hydroxide solution (2.4 ml). The mixture was stirred at room temperature overnight, concentrated and neutralized with 1N hydrochloric acid. Precipitated materials were filtered, washed with water and recrystallized from ethanol/hexane to give N-(4-((N-carboxymethyl-N-methyl)aminomethyl)phenyl)-7-(4-methyl-phenyl)-2,3-dihydro-1-benzothiepine-4-carboxamide (Compound 261) (0.16 g) as colorless crystals.

mp 243–245° C.; $^1$H-NMR($\delta$ ppm, DMSO-d$_6$) 2.34 (6H, br), 3.00 (2H, br), 3.16 (2H, br), 3.22 (2H, br), 3.80 (2H, br), 7.20–7.35 (4H, m), 7.45–7.72 (7H, m), 7.82 (1H, s), 10.14 (1H, s). Anal. Calcd. for C$_{28}$H$_{28}$N$_2$O$_3$S.0.5H$_2$O: C, 69.83; H, 6.07; N, 5.82. Found C, 69.62; H, 5.92; N, 5.58.

WORKING EXAMPLE 262 (Production of Compound 262)

In dichloromethane (5 ml) was suspended 7-(4-methylphenyl)-2,3-dihydro-1-benzothiepine-4-carboxylic acid (0.2 g), and to the mixture were added, under ice-cooling, oxalyl chloride (0.18 ml) and dimethylformamide (catalytic amount). The mixture was stirred at room temperature for 2 hours, and the solvent was evaporated. The residue was dissolved in tetrahydrofuran (20 ml), and the mixture was added dropwise, under ice-cooling, to a solution of 1-(N-(4-aminobenzyl)-N-methylamino)-3-propanol (0.15 g) and triethylamine (0.28 ml) in tetrahydrofuran (10 ml). Under nitrogen atmosphere, the mixture was stirred at room temperature overnight. The solvent was evaporated, and to the residue was added water. The mixture was extracted with ethyl acetate, and the organic layer was with water and saturated brine, and dried with anhydrous magnesium sulfate. Under reduced pressure, the solvent was evaporated, and the residue was purified with silica gel column (methanol/triethylamine/ethyl acetate) to give crude crystals, which were recrystallized from ethyl acetate/hexane to give N-(4-((N-3-hydroxypropyl-N-methyl)aminomethyl)phenyl)-7-(4-methylphenyl)-2,3-dihydro-1-benzothiepine-4-carboxamide (Compound 262) (0.16 g) as colorless crystals.

mp 147–148° C.; $^1$H-NMR($\delta$ ppm, CDCl$_3$) 1.69–1.80 (2H, m), 2.25 (3H, s), 2.40 (3H, s), 2.67 (2H, t, J=5.6 Hz), 3.08 (2H, t, J=5.9 Hz), 3.28 (2H, t, J=5.9 Hz), 3.53 (2H, s), 3.78 (2H, t, J=5.3 Hz), 7.24–7.32 (3H, m), 7.41–7.50 (4H, m), 7.53–7.60 (4H, m), 7.81 (1H, s). IR(KBr) v: 3266, 2948, 1649 cm$^{-1}$. Anal. Calcd. for C$_{29}$H$_{32}$N$_2$O$_2$S.0.3H$_2$O: C, 72.86; H, 6.87; N, 5.86. Found C, 72.90; H, 6.70; N, 6.05.

WORKING EXAMPLE 263 (Production of Compound 263)

In dichloromethane (5 ml) was suspended 7-(4-methylphenyl)-2,3-dihydro-1-benzoxepine-4-carboxylic acid (0.2 g), and to the mixture were added, under ice-cooling, oxalyl chloride (0.19 ml) and dimethylformamide (catalytic amount). The mixture was stirred at room temperature for 2 hours, and the solvent was evaporated. The residue was dissolved in tetrahydrofuran (20 ml), and the mixture was added dropwise, under ice-cooling, to a solution of 4-((N-3-methoxypropyl-N-methyl)aminomethyl) aniline (0.16 g) and triethylamine (0.3 ml) in tetrahydrofuran (10 ml). Under nitrogen atmosphere, the mixture was stirred at room temperature overnight. The solvent was evaporated, and to the residue was added water. The mixture was extracted with ethyl acetate, and the organic layer was with water and saturated brine, and dried with anhydrous magnesium sulfate. Under reduced pressure, the solvent was evaporated to give crude crystals, which were recrystallized from ethyl acetate/hexane to give N-(4-((N-3-methoxypropyl-N-methyl)aminomethyl)phenyl)-7-(4-methyl-phenyl)-2,3-dihydro-1-benzoxepine-4-carboxamide (Compound 263) (0.28 g) as colorless crystals.

mp 121–123° C.; $^1$H-NMR($\delta$ ppm, CDCl$_3$) 1.75–1.84 (2H, m), 2.19 (3H, s), 2.40 (3H, s), 2.45 (2H, t, J=7.3 Hz), 3.09 (2H, t, J=4.6 Hz), 3.33 (3H, s), 3.43 (2H, t, J=6.6 Hz), 3.47 (2H, s), 4.37 (2H, t, J=4.6 Hz), 7.06 (1H, d, J=8.2 Hz), 7.23–7.33 (4H, m), 7.44–7.56 (7H, m). IR(KBr) v: 2934, 1653 cm$^{-1}$. Anal. Calcd. for C$_{30}$H$_{34}$N$_2$O$_3$: C, 76.57; H, 7.28; N, 5.95. Found C, 76.41; H, 7.24; N, 6.02.

WORKING EXAMPLE 264 (Production of Compound 264)

In dichloromethane (5 ml) was suspended 7-(4-methylphenyl)-2,3-dihydro-1-benzothiepine-4-carboxylic acid (0.15 g), and to the mixture were added, under ice-cooling, oxalyl chloride (0.15 ml) and dimethylformamide (catalytic amount). The mixture was stirred at room temperature for 2 hours, and the solvent was evaporated. The residue was dissolved in tetrahydrofuran (15 ml), and the mixture was added dropwise, under ice-cooling, to a solution of 4-((N-3-methoxypropyl-N-methyl)aminomethyl) aniline (0.12 g) and triethylamine (0.21 ml) in tetrahydrofuran (10 ml). Under nitrogen atmosphere, the mixture was stirred at room temperature overnight. The solvent was evaporated, and to the residue was added water. The mixture was extracted with ethyl acetate, and the organic layer was with water and saturated brine, and dried with anhydrous magnesium sulfate. Under reduced pressure, the solvent was evaporated to give crude crystals, which were recrystallized from ethyl acetate/hexane to give N-(4-((N-3-methoxypropyl-N-methyl)aminomethyl)phenyl)-7-(4-methylphenyl)-2,3-dihydro-1-benzothiepine-4-carboxamide (Compound 264) (0.18 g) as colorless crystals.

mp 128–129° C.; $^1$H-NMR(($\delta$ ppm, CDCl$_3$) 1.70–1.87 (2H, m), 2.19 (3H, s), 2.40 (3H, s), 2.45 (2H, t, J=8.4 Hz), 3.08 (2H, t, J=5.6 Hz), 3.29 (2H, t, J=5.6 Hz), 3.33 (3H, s), 3.43 (2H, t, J=6.4 Hz), 3.47 (2H, s), 7.24–7.33 (3H, m), 7.40–7.58 (8H, m), 7.68 (1H, s). IR(KBr) v: 2924, 1651 cm$^{-1}$. Anal. Calcd. for C$_{30}$H$_{34}$N$_2$O$_2$S: C, 74.04; H, 7.04; N, 5.76. Found C, 73.80; H, 6.95; N, 5.87.

WORKING EXAMPLE 265 (Production of Compound 265)

In dichloromethane (5 ml) was suspended 2-(4-methylphenyl)-6,7-dihydro-5H-benzocycloheptene-8-carboxylic acid (0.2 g), and to the mixture were added, under ice-cooling, oxalyl chloride (0.19 ml) and dimethylformamide (catalytic amount). The mixture was stirred at room temperature for 2 hours, and the solvent was evaporated. The residue was dissolved in tetrahydrofuran (15 ml), and the mixture was added dropwise, under ice-cooling, to a solution of (4-aminophenyl)-(2-pyridyl)methanol (0.15 g) and triethylamine (0.3 ml) in tetrahydrofuran (15 ml). Under nitrogen atmosphere, the mixture was stirred at room temperature overnight. The solvent was evaporated, and to the residue was added water. The mixture was extracted with ethyl acetate, and the organic layer was washed with water and saturated brine, and dried with anhydrous magnesium sulfate. Under reduced pressure, the solvent was evaporated to give crude crystals, which were recrystallized from ethyl acetate/hexane to give 2-(4-methylphenyl)-N-(4-hydroxy(2-pyridyl)methylphenyl)-6,7-dihydro-5H-benzocycloheptene-8-carboxamide (Compound 265) (0.30 g) as colorless crystals.

mp 195–196° C.; $^1$H-NMR($\delta$ ppm, CDCl$_3$) 2.12–2.18 (2H, m), 2.39 (3H, s), 2.71 (2H, t, J=6.2 Hz), 2.85–2.91 (2H, m), 5.31 (1H, d, J=3.8 Hz), 5.75 (1H, d, J=3.8 Hz), 7.12–7.26 (4H, m), 7.35–7.67 (11H, nm), 8.57 (1H, d, J=5.4 Hz). IR(KBr) $\nu$: 2930, 1651 cm$^{-1}$. Anal. Calcd. for C$_{31}$H$_{28}$N$_2$O$_2$.0.2H$_2$O: C, 80.21; H, 6.17; N, 6.04. Found C, 80.15; H, 6.05; N, 6.13.

WORKING EXAMPLE 266 (Production of Compound 266)

In dichloromethane (25 ml) was dissolved 2-(4-methylphenyl)-N-(4-hydroxy(2-pyridyl)methylphenyl)-6,7-dihydro-5H-benzocycloheptene-8-carboxamide (0.2 g), and to the mixture was added, under ice-cooling, mCPBA (0.14 g). The mixture was stirred at room temperature overnight, and to the mixture was added sodium thiosulfate solution. The mixture was concentrated and extracted with ethyl acetate. The organic layer was washed with sodium hydrogen carbonate solution, water and saturated brine, and dried with anhydrous magnesium sulfate. Under reduced pressure, the solvent was evaporated, and the residue was purified with silica gel column (methanol/triethylamine/ethyl acetate) to give crude crystals, which were recrystallized from ethyl acetate/hexane to give 2-(4-methylphenyl)-N-(4-hydroxy(1-oxidepyridin-2-yl)methyl-phenyl)-6,7-dihydro-5H-benzocycloheptene-8-carboxamide (Compound 266) (0.12 g) as colorless crystals.

mp 127–128° C.; $^1$H-NMR($\delta$ ppm, CDCl$_3$) 2.14–2.20 (2H, m), 2.40 (3H, s), 2.73 (2H, t, J=6.4 Hz), 2.87–2.92 (2H, m), 6.07 (1H, s), 6.40 (1H, br), 6.93–6.98 (1H, m), 7.22–7.28 (4H, m), 7.43–7.53 (7H, m), 7.67 (2H, d, J=8.8 Hz), 7.75 (1H, s), 8.24–8.28 (1H, m). IR(KBr) $\nu$: 2928, 1651 cm$^{-1}$. Anal. Calcd. for C$_{31}$H$_{28}$N$_2$O$_3$.0.5H$_2$O: C, 76.68; H, 6.02; N, 5.77. Found C, 76.59; H, 6.00; N, 5.65.

WORKING EXAMPLE 267 (Production of Compound 267)

In dimethylformamide (5 ml) was dissolved N-(4-(piperidin-2-ylcarbonyl)phenyl)-7-(4-methylphenyl)-2,3-dihydro-1-benzoxepine-4-carboxamide (0.2 g), and to the mixture were added sodium hydrogen carbonate (0.05 g) and methyl iodide (0.1 ml). Under nitrogen atmosphere, the mixture was stirred at room temperature overnight. The solvent was evaporated, and to the residue was added ethyl acetate to give crude crystals, which were recrystallized from ethanol/ethyl acetate to give N,N-dimethyl-2-(4-((7-(4-methylphenyl)-2,3-dihydro-1-benzoxepine-4-carbonyl)amino)benzoyl)piperidinium iodide (Compound 267) (0.16 g) as colorless powder.

mp 236–237° C.(dec.). $^1$H-NMR($\delta$ ppm, CDCl$_3$) 1.75–2.10 (4H, m), 2.15–2.38 (2H, m), 2.38 (3H, s), 3.07 (2H, t, J=4.6 Hz), 3.43 (3H, s), 3.53 (3H, s), 3.62–3.68 (1H, m), 4.34 (2H, t, J=4.6 Hz), 4.68 (1H, br), 6.41–6.45 (1H, m), 7.03 (1H, d, J=8.4 Hz), 7.22 (2H, d, J=8.0 Hz), 7.43–7.52 (4H, m), 7.73 (1H, d, J=2.2 Hz), 7.95 (2H, d, J=9.2 Hz), 8.34 (2H, d, J=8.8 Hz), 8.59 (1H, s). IR(KBr) $\nu$: 2955, 1674 cm$^{-1}$. Anal. Calcd. for C$_{32}$H$_{35}$IN$_2$O$_3$.0.5H$_2$O: C, 60.86; H, 5.75; N, 4.44. Found C, 60.89; H, 5.49; N, 4.52.

WORKING EXAMPLE 268 (Production of Compound 268)

To a solution of 2-methyl-6-(4-methylphenyl)-quinoline-3-carboxylic acid (120 mg) and 1-hydroxybenzotriazole (88 mg) in DMF (5 ml) was added at room temperature 1-ethyl-3-(3'-dimethylaminopropyl)carbodiimide hydrochloride (125 mg), and the mixture was stirred for 1 hour. To the mixture was added a solution of 1-(4-aminobenzyl)phosphorinane-1-oxide (109 mg) and triethylamine (0.1 ml) in DMF (3 ml), and the mixture was stirred for 3 days. Under reduced pressure, the mixture was concentrated, and to the residue was added water. The mixture was extracted with chloroform, and the organic layer was washed with saturated brine and dried with magnesium sulfate. Under reduced pressure, the mixture was concentrated, and the residue was separated and purified with column chromatography (ethanol/ethyl acetate=1:2) and recrystallized from (ethanol/ethyl acetate) to give pale yellow crystals of 2-methyl-6-(4-methylphenyl)-N-(pentamethylenephosphorylmethylphenyl)quinoline-3-carboxamide (Compound 268) (116.1 mg).

m.p. 273–275° C.; $^1$H-NMR (200 MHz, CDCl$_3$) $\delta$ 1.01–1.84 (10H, m), 2.44 (3H, s), 2.90 (3H, s), 3.04 (2H, d, J=12.6 Hz), 7.17–7.25 (2H, m), 7.32 (2H, d, J=7.9 Hz), 7.61 (2H, d, J=7.9 Hz), 7.69 (2H, d, J=8.2 Hz), 7.99–8.13 (3H, m), 8.30 (1H, s), 9.44 (1H, br s). IR (KBr) 3024, 1664, 1601, 1539, 1516, 1319, 1159, 847, 816 cm$^{-1}$; Anal. Calcd. for C$_{30}$H$_{31}$N$_2$O$_2$P.0.3H$_2$O; Calcd. C, 73.84; H, 6.53; N, 5.74; P, 6.35. Found. C, 73.67; H, 6.58; N, 5.67; P, 6.27.

WORKING EXAMPLE 269 (Production of Compound 269)

Under nitrogen atmosphere, to a solution of (E)-3-[5-(4-isopropylphenyl)thiophen-2-yl]acrylic acid (130 mg) in THF (10 ml) was added at room temperature oxalyl chloride (0.07 ml) and then a drop of DMF, and the mixture was stirred for 1 hour. Under reduced pressure, the solvent was evaporated, and the residue was dissolved in THF (20 ml). To the mixture were added 1-(4-aminobenzyl)phosphorinane-1-oxide (117 mg) and triethylamine (0.15 ml) at 0° C., and the mixture was stirred at room temperature for 4 hours. The mixture was added to vigorously stirred water to stop the reaction and extracted with ethyl acetate. The organic layer was washed with saturated brine, dried with magnesium sulfate, concentrated and purified with column chromatography (ethanol/ethyl acetate=1:4) and recrystallized from ethanol/ethyl acetate to give yellow crystals of (E)-3-[5-(4-methylphenyl)thiophen-2-yl]-N-(pentaethylenephosphorylmethylphenyl)acrylamide (Compound 269) (60.5 mg).

m.p. 295° C.(dec.) $^1$H-NMR (200 MHz, CDCl$_3$) $\delta$ 1.28 (6H, d, J=7.0 Hz), 1.51–2.10 (10H, m), 2.89–3.00 (1H, m), 3.15 (2H, d, J=13.2 Hz), 6.48 (1H, d, J=15.0 Hz), 7.15–7.33 (6H, m), 7.50–7.62 (4H, m), 7.82 (1H, d, J=15.0 Hz), 8.37–8.59 (1H, m). IR (KBr) 3057, 1672, 1618, 1543, 1510, 1412, 1356, 1327, 1250, 1232, 1165, 960, 852, 829, 793 cm$^{-1}$; Anal. Calcd. For C$_{28}$H$_{32}$NO$_2$SP; Calcd. C, 70.41; H, 6.75; N, 2.93. Found. C, 70.06; H, 6.82; N, 2.98.

WORKING EXAMPLE 270 (Production of Compound 270)

Under nitrogen atmosphere, to a solution of (E)-3-[5-(4-tert-butylphenyl)thiophen-2-yl]acrylic acid (120 mg) in THF (10 ml) were added at room temperature oxalyl chloride (0.06 ml) and a drop of DMF, and the mixture was stirred for 1 hour. Under reduced pressure, the solvent was evaporated, and the residue was dissolved in THF (20 ml). To the mixture were added at 0° C. 1-(4-aminobenzyl)phosphorinane-1-oxide (104 mg) and triethylamine (0.12 ml), and the mixture was stirred at room temperature for 18 hours. The mixture was added to vigorously stirred water to stop the reaction and extracted with ethyl acetate. The organic layer was washed with saturated brine and dried with magnesium sulfate. Under reduced pressure, the mixture was concentrated, and the residue was purified with column chromatography (ethanol/ethyl acetate=1:4) and recrystallized from ethanol to give yellow crystals of (E)-N-(4-pentamethylene phosphorylmethylphenyl)-3-[5-(4-tert-butylphenyl)thiophen-2-yl]acrylamide (Compound 270) (82.1mg).

m.p. >300° C.; $^1$H-NMR (200 MHz, CDCl$_3$) δ 1.35 (9H, s), 1.50–2.22 (10H, m), 3.15 (2H, d, J=13.2 Hz), 6.53 (1H, d, J=15.4 Hz), 7.12–7.30 (4H, m), 7.42 (2H, d, J=8.4 Hz), 7.49–7.60 (4H, m), 7.82 (1H, d, J=15.4 Hz), 8.79–8.98 (1H, m). IR (KBr) 3238, 1672, 1618, 1543, 1514, 1358, 1252, 1167, 852, 793 cm$^{-1}$; Anal. Calcd. For C$_{29}$H$_{34}$NO$_2$SP; Calcd. C, 70.85; H, 6.97; N, 2.85; P, 6.30. Found. C, 70.61; H, 6.90; N, 2.89; P, 6.17.

WORKING EXAMPLE 271 (Production of Compound 271)

Under nitrogen atmosphere, to a solution of 2-(4-methylphenyl)benzofuran-5-carboxylic acid (130 mg) in THF (10 ml) were added at room temperature oxalyl chloride (0.07 ml) and a drop of DMF, and the mixture was stirred for 1 hour. Under reduced pressure, the solvent was evaporated, and the residue was dissolved in THF (20 ml). To the mixture were added at 0° C. 1-(4-aminobenzyl)phosphorinane-1-oxide (126 mg) and triethyl-amine (0.15 ml), and the mixture was stirred at room temperature for 3 hour. The mixture was added to vigorously stirred water to stop the reaction and extracted with ethyl acetate. The organic layer was washed with saturated brine, dried with magnesium sulfate and concentrated. The resulting crystals were recrystallized from ethanol to give colorless crystals of 2-(4-methylphenyl)-N-(4-pentamethylenephosphorylmethylphenyl)benzofuran-5-carboxamide (Compound 271) (134.6 mg).

m.p. 297–296° C.; $^1$H-NMR (200 MHz, CDCl$_3$) δ 1.42–2.16 (10H, m), 2.42 (3H, s), 3.17 (2H, d, J=13.2 Hz), 7.04 (1H, s), 7.24–7.33 (4H, m), 7.58 (1H, d, J=8.6 Hz), 7.67 (2H, d, J=8.4 Hz), 7.76–7.85 (3H, m), 8.14 (1H, d, J=1.8 Hz), 8.15–8.19 (1H, m). IR (KBr) 3390, 2929, 1657, 1524, 1323, 1230, 1161, 1132, 849, 824, 800, 760 cm$^{-1}$; Anal. Calcd. For C$_{28}$H$_{28}$NO$_3$P; Calcd. C, 73.51; H, 6.17; N, 3.06. Found. C, 73.45 : H, 5.89 : N, 2.83.

WORKING EXAMPLE 272 (Production of Compound 272)

To a solution of 2-(4-methylphenyl)benzofuran-6-carboxylic acid (130 mg) in THF (10 ml) were added oxalyl chloride (0.07 ml) and a drop of dimethylformamide at room temperature, and the mixture was stirred for 1 hour. Under reduced pressure, the solvent was evaporated, and the residue was dissolved in THF (20 ml). To the mixture were added at 0° C. 1-(4-aminobenzyl)phosphorinane-1-oxide (126 mg) and triethylamine (0.15 ml), and the mixture was stirred at room temperature for 20 hours. The mixture was added to vigorously stirred water to stop the reaction and extracted with dichloromethane, and the organic layer was washed with saturated brine. Under reduced pressure, the mixture was concentrated, and the residue was recrystallized from ethanol to give pale yellow crystals of 2-(4-methylphenyl)-N-(4-pentamethylenephosphorylmethylphenyl)benzofuran-6-carboxamide (Compound 272) (149.9 mg).

m.p. >300° C.; IR (KBr) 3224, 1651, 1535, 1512, 1323, 1165, 845, 820 cm$^{-1}$; Anal. Calcd. For C$_{28}$H$_{28}$NO$_3$P; Calcd. C, 73.51; H, 6.17; N, 3.06. Found. C, 73.50; H, 6.17; N, 2.92.

WORKING EXAMPLE 273 (Production of Compound 273)

To a solution of 7-(4-methylsulfonylphenyl)-2,3-dihydro-1-benzoxepine-4-carboxylic acid (100 mg) in THF (10 ml) were added at room temperature oxalyl chloride (0.05 ml) and a drop of DMF, and the mixture was stirred for 1 hour. Under reduced pressure, the solvent was evaporated, and the residue was dissolved in THF (20 ml). To the mixture were added at 0° C. 4-[N-methyl-N-(tetrahydropyran-4-yl)-aminomethyl]aniline (71 mg) and triethylamine (0.1 ml), and the mixture was stirred at room temperature for 16 hours. The mixture was added to vigorously stirred water to stop the reaction and extracted with ethyl acetate. The organic layer was washed with saturated brine and dried with magnesium sulfate. Under reduced pressure, the mixture was concentrated, and the residue was purified with column chromatography (ethanol/ethyl acetate=1:3) and recrystallized from ethanol to give colorless crystals of 7-(4-methylsulfonylphenyl)-N-[4-[N-methyl-N-(tetrahydropyran-4-yl)aminomethyl]phenyl]-2,3-dihydro-1-benzoxepine-4-carboxamide (Compound 273) (123 mg).

m.p. 233–235° C.; $^1$H-NMR (200 MHz, CDCl$_3$) δ 1.62–1.82 (4H, m), 2.21 (3H, s), 2.56–2.73 (1H, m), 3.04–3.15 (2H, m), 3.10 (3H, s), 3.31–3.43 (2H, m), 3.57 (2H, s), 3.99–4.09 (2H, m), 4.39 (2H, t, J=4.5 Hz), 7.12 (1H, d, J=8.4 Hz), 7.24–7.35 (3H, m), 7.46–7.60 (5H, m), 7.74 (2H, d, J=8.6 Hz), 8.00 (2H, d, J=8.6 Hz). IR (KBr) 3292, 1645, 1524, 1308, 1144 cm$^{-1}$; Anal. Calcd. for C$_{31}$H$_{34}$N$_2$O$_5$S; Calcd. C, 68.11; H, 6.27; N, 5.12; S, 5.87. Found. C, 67.94; H, 6.40; N, 5.09; S, 5.90.

WORKING EXAMPLE 274 (Production of Compound 274)

Under nitrogen atmosphere, to a solution of (E)-3-[5-(4-isopropylphenyl)thiophen-2-yl]acrylic acid (130 mg) in THF (10 ml) were added at room temperature oxalyl chloride (0.07 ml) and a drop of DMF, and the mixture was stirred for 1 hour. Under reduced pressure, the solvent was evaporated, and the residue was dissolved in THF (20 ml). To the mixture were added at 0° C. 4-[N-methyl-N-(tetrahydropyran-4-yl)aminomethyl]aniline (116 mg) and triethylamine (0. 15 ml), and the mixture was stirred at room temperature for 4 hour. The mixture was added to vigorously stirred water to stop the reaction and extracted with ethyl acetate. The organic layer was washed with saturated brine, dried with magnesium sulfate, concentrated and purified with column chromatography (ethanol/ethyl acetate=1:4) and recrystallized from ethyl acetate/hexane to give yellow crystals of (E)-3-(5-(4-isopropylphenyl)thiophen-2-yl]-N-[4-[N-methyl-N-(tetrahydropyran-4-yl)aminomethyl]-phenyl]acrylamide (Compound 274) (162.9 mg).

m.p. 187–189° C.; $^1$H-NMR (200 MHz, CDCl$_3$) δ 1.27 (6H, d, J=6.8 Hz), 1.54–1.84 (4H, m), 2.21 (3H, s), 2.55–2.72 (1H, m), 2.84–3.01 (1H, m), 3.30–3.44 (2H, m), 3.56 (2H, s), 3.97–4.10 (2H, m), 6.31 (1H, d, J=15.4 Hz), 7.19–7.35 (7H, m), 7.49–7.61 (4H, m), 7.84 (1H, d, J=15.4 Hz). IR (KBr) 3315, 1664, 1606, 1535, 1512, 1408, 1335, 1169, 829, 804 cm$^{-1}$; Anal. Calcd. for C$_{29}$H$_{34}$N$_2$O$_2$S; Calcd. C, 73.38; H, 7.22; N, 5.90; S, 6.76. Found. C, 73.12; H, 7.34; N, 5.88; S, 6.83.

WORKING EXAMPLE 275 (Production of Compound 275)

A solution of 7-(4-methylthiophenyl)-N-[4-[N-methyl-N-(4-tetrahydropyran-4-yl)aminomethyl]phenyl]-2,3-dihydro-1-benzoxepine-4-carboxamide (110 mg) and sodium periodate (48 mg) in methanol/water (40/15 ml) was stirred at room temperature for 2 days. Under reduced pressure, the mixture was concentrated, and to the residue was added water. The mixture was extracted with chloroform. The organic layer was washed with saturated brine and dried with magnesium sulfate. Under reduced pressure, the mixture was concentrated, and the residue was purified with column chromatography (ethanol/ethyl acetate=1:1) and recrystallized from ethanol/ethyl acetate to give colorless crystals of 7-(4-methylsulfinylphenyl)-N-[4-[N-methyl-N-(4-tetrahydropyran-4-yl)aminomethyl]phenyl]-2,3-dihydro-1-benzoxepine-4-carboxamide (Compound 275) (15.5 mg).

$^1$H-NMR (200 MHz, CDCl$_3$) δ 1.52–1.83 (4H, m), 2.21 (3H, s), 2.52–2.74 (1H, m), 2.77 (3H, s), 3.10 (2H, t, J=4.4 Hz), 3.29–3.43 (2H, m), 3.57 (2H, s), 3.98–4.10 (2H, m), 4.39 (2H, t, J=4.4 Hz), 7.11 (1H, d, J=8.0 Hz), 7.23–7.35 (3H, m), 7.44–7.63 (5H, m), 7.71 (4H, s). IR (KBr) 3327, 1649, 1515, 1410, 1315, 1240, 1038, 822 cm$^{-1}$.

WORKING EXAMPLE 276 (Production of Compound 276)

Under nitrogen atmosphere, to a solution of (E)-3-[5-(4-tert-butylphenyl) thiophen-2-yl]acrylic acid (130 mg) in THF (10 ml) were added at room temperature oxalyl chloride (0.06 ml) and a drop of DMF, and the mixture was stirred for 1 hour. Under reduced pressure, the solvent was evaporated, and the residue was dissolved in THF (20 ml). To the mixture were added at 0° C. 4-[N-methyl-N-(tetrahydropyran-4-yl)aminomethyl]aniline (109 mg) and triethylamine (0. 13 ml) and the mixture was stirred at room temperature for 6 days. The mixture was added to vigorously stirred water to stop the reaction and extracted with ethyl acetate. The organic layer was washed with saturated brine, dried with magnesium sulfate and concentrated. The residue was purified with column chromatography (ethanol/ethyl acetate=1:4) and recrystallized from ethyl acetate/hexane to give yellow crystals of (E)-3-[5-(4-tert-butylphenyl) thiophen-2-yl]-N-[4-[N-methyl-N-(tetrahydropyran-4-yl) aminomethyl]phenyl]acrylamide (Compound 276) (107.3 mg).

m.p. 216–220° C.; $^1$H-NMR (200 MHz, CDCl$_3$) δ 1.35 (9H, s), 1.50–1.86 (4H, m), 2.21 (3H, s), 2.51–2.76 (1H, m), 3.30–3.45 (2H, m), 3.57 (2H, s), 3.99–4.10 (2H, m), 6.32 (1H, d, J=14.8 Hz), 7.21–7.35 (5H, m), 7.43 (2H, d, J=8.4 Hz), 7.51–7.61 (4H, m), 7.84 (1H, d, J=14.8 Hz). IR (KBr) 3320, 1666, 1606, 1535, 1335, 831 cm$^{-1}$; Anal. Calcd. for C$_{30}$H$_{36}$N$_2$O$_2$S.0.1H$_2$O; Calcd. C, 73.46; H, 7.44; N, 5.71. Found. C, 73.41; H, 7.41; N, 5.83.

WORKING EXAMPLE 277 (Production of Compound 277)

Under nitrogen atmosphere, to a solution of 2-(4-methylphenyl)benzofuran-5-carboxylic acid (200 mg) in THF (10 ml) were added at room temperature oxalyl chloride (0.1 ml) and a drop of DMF, and the mixture was stirred for 1 hour. Under reduced pressure, the solvent was evaporated, and the residue was dissolved in THF (20 ml). To the mixture were added at 0° C. 4-[N-methyl-N-(tetrahydropyran-4-yl)aminomethyl]aniline (192 mg) and triethylamine (0. 22 ml), and the mixture was stirred at room temperature for 18 hours. The mixture was added to vigorously stirred water to stop the reaction and extracted with chloroform. The organic layer was washed with saturated brine, dried with magnesium sulfate and concentrated. The resulting crystals were recrystallized from ethanol to give colorless crystals of 2-(4-methylphenyl)-N-[4-(N-methyl-N-(tetrahydropyran-4-yl)aminomethyl)phenyl]benzofuran-5-carboxamide (Compound 277) (295.8 mg).

m.p. 233–236° C.; $^1$H-NMR (200 MHz, CDCl$_3$) δ 1.62–1.83 (4H, m), 2.22 (3H, s), 2.42 (3H, s), 2.57–2.72 (1H, m), 3.32–3.44 (2H, m), 3.59 (2H, s), 3.99–4.09 (2H, m), 7.03 (1H, s), 7.31–7.36 (4H, m), 7.56–7.64 (3H, m), 7.76–7.82 (3H, m), 7.87 (1H, s), 8.11 (1H, d, J=1.4 Hz). IR (KBr) 3388, 2943, 1647, 1597, 1525, 1408, 1319, 1148, 794 cm$^{-1}$; Anal. Calcd. For C$_{29}$H$_{30}$N$_2$O$_3$; Calcd. C, 76.63; H, 6.65; N, 6.16, Found. C, 76.61; H, 6.47; N, 6.00.

WORKING EXAMPLE 278 (Production of Compound 278)

To a solution of 2-(4-methylphenyl)benzofuran-6-carboxylic acid (200 mg) in THF (10 ml) were added at room temperature oxalyl chloride (0.1 ml) and a drop of DMF, and the mixture was stirred for 1 hour. Under reduced pressure, the solvent was evaporated, and the residue was dissolved in THF (20 ml). To the mixture were added at 0° C. 4-[N-methyl-N-(tetrahydropyran-4-yl)aminomethyl] aniline (192 mg) and triethylamine (0.22 ml), and the mixture was stirred at room temperature for 4 hour. The mixture was added to vigorously stirred water to stop the reaction and extracted with dichloromethane. The organic layer was washed with saturated brine and dried with magnesium sulfate. Under reduced pressure, the mixture was concentrated, and the residue was purified with column chromatography (ethanol/ethyl acetate=1:4→1:2→2:1) and recrystallized from ethanol to give pale yellow crystals of 2-(4-methylphenyl)-N-[4-[N-methyl-N-(tetrahydropyran-4-yl)aminomethyl]phenyl]benzofuran-6-carboxamide (Compound 278) (280 mg).

m.p. 224–227° C.; $^1$H-NMR (200 MHz, CDCl$_3$) δ 1.41–1.82 (4H, m), 2.22 (3H, s), 2.42 (3H, s), 2.56–2.74 (1H, m), 3.32–3.44 (2H, m), 3.59 (2H, s), 3.98–4.12 (2H, m), 7.02 (1H, s), 7.25–7.37 (4H, m), 7.61–7.66 (3H, m), 7.72–7.81 (3H, m), 7.92 (1H, s), 8.07 (1H, s). IR (KBr) 3304, 1647, 1520, 1313, 822 cm$^{-1}$; Anal. Calcd. for C$_{29}$H$_{30}$N$_2$O$_3$; Calcd. C, 76.63; H, 6.65; N, 6.16. Found. C, 76.79; H, 6.39; N, 6.13.

WORKING EXAMPLE 279 (Production of Compound 279)

To a solution of (E)-3-[5-(4-methylphenyl)thiophen-2-yl]-N-[4-[N-methyl-N-(tetrahydropyran-4-yl)aminomethyl] phenyl]acrylamide (100 mg) in DMF (3 ml) was added at room temperature methyl iodide (0.5 ml), and the mixture was stirred for 2 days. Under reduced pressure, the mixture was concentrated, and to the residue was added acetonitrile. The resulting crystals were collected by filtration to give yellow crystals of N,N-dimethyl-N-[4-[[(E)-3-[5-(4-methylphenyl)thiophen-2-yl]-2-propenoyl]amino]benzyl]-4-tetrahydropyranyl ammonium iodide (Compound 279) (101.1 mg).

m.p. 212–216° C.; $^1$H-NMR (200 MHz, DMSO-d$_6$) δ 1.74–1.99 (2H, m), 2.09–2.22 (2H, m), 2.34 (3H, s), 2.87 (6H, br s), 3.24–3.42 (2H, m), 3.48–3.66 (1H, m), 4.00–4.11 (2H, m), 4.46 (2H, s), 6.58 (1H, d, J=15.4 Hz), 7.27 (2H, d, J=7.9 Hz), 7.44–7.58 (4H, m), 7.61 (2H, d, J=7.9 Hz), 7.76 (1H, d, J=15.4 Hz), 7.82 (2H, d, J=8.8 Hz), 10.43 (1H, s). IR (KBr) 3165, 1675, 1606, 1525, 1155, 814 cm$^{-1}$; Anal. Calcd. for C$_{28}$H$_{33}$N$_2$O$_2$SI.0.5H$_2$O; Calcd. C, 56.28; H, 5.74; N, 4.69. Found. C, 56.04; H, 5.71; N, 4.71.

WORKING EXAMPLE 280 (Production of Compound 280)

To a solution of (E)-N-[4-[N-methyl-N-(tetrahydropyran-4-yl)aminomethyl]phenyl]-3-[5-(4-isopropylphenyl)thiophen-2-yl]acrylamide (80 mg) in DMF (5 ml) was added at room temperature methyl iodide (0.04 ml), and the mixture was stirred for 3 days. Under reduced pressure, the solvent was evaporated, and to the residue was added acetonitrile. The resulting crystals were collected by filtration to give yellow crystals of N,N-dimethyl-N-[4-[[(E)-3-[5-(4-isopropylphenyl)thiophen-2-yl]-2-propenoyl]amino]benzyl]-4-tetrahydropyranyl ammonium iodide (Compound 280) (76.9 mg).

m.p. 217–220° C.; $^1$H-NMR (200 MHz, DMSO-d$_6$) δ 1.23 (6H, d, J=7.0 Hz), 1.72–2.01 (2H, m), 2.08–2.23 (2H, m), 2.79–3.01 (1H, m), 2.87 (6H, s), 3.25–3.44 (2H, m), 3.49–3.68 (1H, m), 3.99–4.12 (2H, m), 4.46 (2H, s), 6.58 (1H, d, J=15.4 Hz), 7.33 (2H, d J=8.5 Hz), 7.44–7.57 (4H, m), 7.63 (2H, d, J=8.5 Hz), 7.76 (1H, d, J=15.4 Hz), 7.82 (2H, d, J=8.8 Hz), 10.42 (1H, s). IR (KBr) 3298, 1654, 1608, 1527, 1452, 1417, 1323, 1252, 1163, 843, 802 cm$^1$; Anal. Calcd. for C$_{30}$H$_{37}$N$_2$O$_2$SI; Calcd. C, 58.44; H, 6.05; N, 4.54. Found. C, 58.24; H, 5.83; N, 4.27.

WORKING EXAMPLE 281 (Production of Compound 281)

To a solution of 2-(4-methylphenyl)-N-[4-(N-methyl-N-(tetrahydropyran-4-yl)aminomethyl)phenyl]-benzofuran-5-carboxamide (120 mg) in DMF (20 ml) was added at room temperature methyl iodide (0.04 ml), and the mixture was stirred for 24 hours. Under reduced pressure, the solvent was evaporated, and to the residue was added ethanol. The resulting crystals were collected by filtration to give yellow crystals of N,N-dimethyl-N-[4-[[2-(4-methylphenyl)benzofuran-5-carbonyl]amino]-benzyl]-4-tetrahydropyranyl ammonium iodide (Compound 281) (142.1mg).

m.p. 208–212° C.; $^1$H-NMR (200 MHz, DMSO-d$_6$) δ 1.71–2.01 (2H, m), 2.12–2.23 (2H, m), 2.39 (3H, s), 2.89 (6H, s), 3.10–3.43 (2H, m), 3.48–3.69 (1H, m), 4.03–4.15 (2H, m), 4.48 (2H, s), 7.36 (2H, d, J=8.0 Hz), 7.53–7.59 (3H, m), 7.77 (1H, d J=8.4 Hz), 7.85–7.99 (5H, m), 8.29 (1H, d, J=1.8 Hz), 10.52 (1H, s). IR (KBr) 3277, 1643, 1595, 1525, 1468, 1416, 1325, 842, 820, 789, 762 cm$^{-1}$; Anal. Calcd. for C$_{30}$H$_{33}$N$_2$O$_3$I.1.0H$_2$O; Calcd. C, 58.64; H, 5.74; N, 4.56. Found. C, 58.98; H, 5.62; N, 4.55.

WORKING EXAMPLE 282 (Production of Compound 282)

To a solution of 7-(4-methoxyphenyl)-2,3-dihydro-1-benzothiepine-4-carboxylic acid (150 mg) in THF (10 ml) were added at room temperature oxalyl chloride (0.13 ml) and a drop of DMF, and the mixture was stirred for 1 hour. Under reduced pressure, the solvent was evaporated, and the residue was dissolved in THF (20 ml). To the mixture were added at 0° C. 4-[N-methyl-N-(tetrahydropyran-4-yl)aminomethyl]aniline (116 mg) and triethylamine (0.2 ml), and the mixture was stirred at room temperature for 4 hours. The mixture was added to vigorously stirred water to stop the reaction and extracted with ethyl acetate. The organic layer was washed with saturated brine and dried with magnesium sulfate. Under reduced pressure, the mixture was concentrated, and the residue was purified with column chromatography (ethanol/ethyl acetate=1:4) and recrystallized from ethanol/diethylether to give pale yellow crystals of 7-(4-methoxyphenyl)-N-[4-[N-methyl-N-(tetrahydropyran-4-yl)aminomethyl]phenyl]-2,3-dihydro-1-benzothiepine-4-carboxamide (Compound 282) (128.5 mg).

m.p.162'164° C.; $^1$H-NMR (200 MHz, CDCl$_3$) δ 1.61–1.83 (4H, m), 2.21 (3H, s), 2.55–2.72 (1H, m), 3.05–3.10 (2H, m), 3.26–3.44 (4H, m), 3.57 (2H, s), 3.86 (3H, s), 3.96–4.09 (2H, m), 6.98 (2H, d, J=8.8 Hz), 7.32 (2H, d, J=8.4 Hz), 7.35–7.43 (2H, m), 7.48–7.57 (6H, m), 7.68 (1H, br s). IR (KBr) 3332, 1647, 1515, 1248, 818 cm$^{-1}$; Anal. Calcd. for C$_{31}$H$_{34}$N$_2$O$_3$S; Calcd. C, 72.34; H, 6.66; N, 5.44. Found. C, 72.25; H, 6.67; N, 5.43.

WORKING EXAMPLE 283 (Production of Compound 283)

To a solution of 7-(4-methoxyphenyl)-2,3-dihydro-1-benzothiepine-4-carboxylic acid (200 mg) in THF (10 ml) were added at room temperature oxalyl chloride (0.30 ml) and a drop of DMF, and the mixture was stirred for 1 hour. Under reduced pressure, the solvent was evaporated, and the residue was dissolved in THF (20 ml). To the mixture were added at 0° C. 4-[N-(4,4-ethylenedioxycyclohexyl)-N-methylaminomethyl]aniline (0.20 g) and triethylamine (0.3 ml), and the mixture was stirred at room temperature for 4 hours. The mixture was added to vigorously stirred water to stop the reaction and extracted with ethyl acetate. The organic layer was washed with saturated brine and dried with magnesium sulfate. Under reduced pressure, the mixture was concentrated, and the residue solid was recrystallized from acetone/diethylether to give pale yellow crystals of N-[4-[N-(4,4-ethylenedioxycyclohexyl)-N-methylaminomethyl]phenyl]-7-(4-methoxyphenyl)-2,3-dihydro-1-benzothiepine-4-carboxamide (Compound 283) (226.4 mg).

m.p. 198–201° C.; $^1$H-NMR (200 MHz, CDCl$_3$) δ 1.45–1.91 (8H, m), 2.21 (3H, s), 2.44–2.65 (1H, m), 3.03–3.10 (2H, m), 3.26–3.31 (2H, m), 3.57 (2H, s), 3.86 (3H, s), 3.95 (4H, s), 6.98 (2H, d, J=8.8 Hz), 7.32 (2H, d, J=8.4 Hz), 7.37–7.43 (2H, m), 7.46–7.60 (6H, m), 7.68 (1H, br s). IR (KBr) 3359, 1651, 1514, 1252, 1103, 1030, 926, 830 cm$^{-1}$; Anal. Calcd. for C$_{34}$H$_{38}$N$_2$O$_4$S.0.3H$_2$O; Calcd. C, 70.88; H, 6.75; N, 4.86. Found. C, 70.86; H, 6.70; N, 4.77.

WORKING EXAMPLE 284 (Production of Compound 284)

To a solution of N-[4-[N-(4,4-ethylenedioxycyclohexyl)-N-methylaminomethyl]phenyl]-7-(4-methoxyphenyl)-2,3-dihydro-1-benzothiepine-4-carboxamide (130 mg) in THF (15 ml) was added at room temperature 6N hydrochloric acid (1 ml), and the mixture was stirred for 66 hours. To the mixture was added sodium bicarbonate solution, and extracted with ethyl acetate. The organic layer was washed with saturated brine and magnesium sulfate. Under reduced pressure, the mixture was concentrated, and the resulting solid was recrystallized from ethyl acetate/hexane to give pale yellow crystals of 7-(4-methoxyphenyl)-N-[4-[N-methyl-N-(4-oxocyclohexyl) aminomethyl]phenyl]-2,3-dihydro-1-benzothiepine-4-carboxamide (Compound 284) (78.3 mg).

m.p. 133–139° C.; $^1$H-NMR (200 MHz, CDCl$_3$) δ 1.74–2.19 (4H, m), 2.23 (3H, s), 2.30–2.59 (4H, m), 2.81–2.97 (1H, m), 3.04–3.10 (2H, m), 3.26–3.32 (2H, m), 3.60 (2H, s), 3.86 (3H, s), 6.98 (2H, d, J=9.2 Hz), 7.33 (2H, d, J=8.4 Hz), 7.38–7.43 (2H, m), 7.48–7.58 (6H, m), 7.71 (1H, br s). IR (KBr) 3273, 1711, 1651, 1605, 1515, 1408, 1317, 1248, 1180, 820 cm$^{-1}$; Anal. Calcd. for C$_{32}$H$_{34}$N$_2$O$_3$S.0.2H$_2$O ; Calcd. C, 72.48; H, 6.54; N, 5.28. Found. C, 72.33; H, 6.42; N, 5.13.

WORKING EXAMPLE 285 (Production of Compound 285)

To a solution of 7- (4-morpholinophenyl) -2,3-dihydro-1-benzothiepine-4-carboxylic acid (150 mg) and 1-hydroxybenzotriazole (0.11 g) in DMF (5 ml) was added at room temperature 1-ethyl-3-(3-dimethylaminopropyl)carbodiimide hydrochloride (0.16 g), and the mixture was stirred for 1 hour. To the mixture was added a solution of 4-[N-methyl-N-(tetrahydropyran-4-yl)aminomethyl]aniline (135 mg) and triethylamine (0.11 ml) in DMF (5 ml), and the mixture was stirred for 18 hours. Under reduced pressure, the mixture was concentrated, and to the mixture was added water. The mixture was extracted with ethyl acetate, and the organic layer was washed with saturated brine and dried with magnesium sulfate. Under reduced pressure, the solvent was evaporated, and the residue was purified with column chromatography (ethanol/ethyl acetate=1:2) to give yellow crystals of N-[4-[N-methyl-N-(tetrahydropyran-4-yl)aminomethyl]phenyl]-7-(4-morpholinophenyl)-2,3-dihydro-1-benzothiepine-4-carboxamide (Compound 285) (113.9 mg).

m.p. 255–259° C.; $^1$H-NMR (200 MHz, CDCl$_3$) δ 1.63–1.84 (4H, m), 2.21 (3H, s), 2.55–2.76 (1H, m), 3.02–3.10 (2H, m), 3.19–3.46 (8H, m), 3.58 (2H, s), 3.85–3.93 (4H, m), 3.98–4.10 (2H, m), 6.99 (2H, d, J=9.2 Hz), 7.32 (2H, d, J=8.4 Hz), 7.37–7.45 (2H, m), 7.49–7.58 (6H, m), 7.67 (1H, br s). IR (KBr) 3288, 1653, 1606, 1522, 1232, 1119, 928, 816 cm$^{-1}$; Anal. Calcd. for C$_{34}$H$_{39}$N$_3$OS.0.5H$_2$O ; Calcd. C, 70.56; H, 6.97; N, 7.26. Found. C, 70.43; H, 6.83; N, 7.22.

WORKING EXAMPLE 286 (Production of Compound 286)

To a solution of 7-(3,4-methylenedioxyphenyl)-2,3-dihydro-1-benzothiepine-4-carboxylic acid (150 mg) in THF (10 ml) was added at room temperature oxalyl chloride (0.08 ml) and a drop of DMF, and the mixture was stirred for 1 hour. Under reduced pressure, the solvent was evaporated, and the residue was dissolved in THF (20 ml). To the mixture were added at 0° C. 4-[N-methyl-N-(tetrahydropyran-4-yl)aminomethyl]aniline (112 mg) and triethylamine (0.13 ml), and the mixture was stirred at room temperature for 18 hours. The mixture was added to vigorously stirred water to stop the reaction and extracted with ethyl acetate. The organic layer was washed with saturated brine and dried with magnesium sulfate. Under reduced pressure, the mixture was concentrated, and the residue was purified with column chromatography (ethanol/ethyl acetate=1:3) and recrystallized from ethanol to give colorless crystals of 7-(3,4-methylenedioxyphenyl)-N-[4-[N-methyl-N-(tetrahydropyran-4-yl)aminomethyl]phenyl]-2,3-dihydro-1-benzothiepine-4-carboxamide (Compound 286) (183.2 mg).

m.p. 193–194° C.; $^1$H-NMR (200 MHz, CDCl$_3$) δ 1.52–1.83 (4H, m), 2.21 (3H, s), 2.54–2.72 (1H, m), 3.04–3.10 (2H, m), 3.23–3.44 (4H, m), 3.57 (2H, s), 3.98–4.09 (2H, m), 6.01 (2H, s), 6.88 (1H, d, J=8.8 Hz), 7.01–7.07 (2H, m), 7.29–7.38 (4H, m), 7.46–7.58 (4H, m), 7.68 (1H, br s). IR (KBr) 3334, 1647, 1506, 1475, 1408, 1313, 1232, 1041, 818 cm$^{-1}$; Anal. Calcd. for C$_{31}$H$_{32}$N$_2$O$_4$S; Calcd. C, 70.43; H, 6.10; N, 5.30. Found. C, 70.28; H, 5.94; N, 5.14.

WORKING EXAMPLE 287 (Production of Compound 287)

To a solution of 7-(4-ethoxyphenyl)-2,3-dihydro-1-benzoxepine-4-carboxylic acid (200 mg) in THF (10 ml) were added at room temperature oxalyl chloride (0.11 ml) and a drop of DMF, and the mixture was stirred for 1 hour. Under reduced pressure, the mixture was concentrated, and the residue was dissolved in THF (20 ml). To the mixture was added a solution of added at 0° C. 4-[N-(4,4-ethylenedioxycyclohexyl)-N-methylaminomethyl]aniline (0.19 g) and triethylamine (0.18 ml) in THF (5 ml), and the mixture was stirred at room temperature for 16 hours. To the mixture was added water, and the mixture was extracted with ethyl acetate. The organic layer was washed with saturated brine and dried with magnesium sulfate. Under reduced pressure, the solvent was evaporated, and the residue was purified with column chromatography (ethanol/ethyl acetate=1:3) and recrystallized from ethyl acetate/diisopropylether) to give colorless crystals of 7-(4-ethoxyphenyl)-N-[4-[N-(4,4-ethylenedioxycyclohexyl)-N-methylaminomethyl]-phenyl]-2,3-dihydro-1-benzoxepine-4-carboxamide (Compound 287) (119.1 mg). The mother liquor was concentrated to give crude product (91.5 mg).

m.p. 172–174° C.; $^1$H-NMR (200 MHz, CDCl$_3$) δ 1.44 (3H, t, J=7.0 Hz), 1.51–1.88 (8H, m), 2.20 (3H, s), 2.44–2.64 (1H, m), 3.08 (2H, t, J=4.6 Hz), 3.56 (2H, s), 3.95 (4H, s), 4.08 (2H, q, J=7.0 Hz), 4.36 (2H, t, J=4.6 Hz), 6.96 (2H, d, J=9.0 Hz), 7.05 (1H, d, J=8.4 Hz), 7.32 (2H, d, J=8.4 Hz), 7.40–7.56 (8H, m). IR (KBr) 3350, 1651, 1515, 1493, 1242, 1101, 922, 829, 802 cm$^{-1}$; Anal. Calcd. for C$_{35}$H$_{40}$N$_2$O$_5$; Calcd. C, 73.92; H, 7.09; N, 4.93. Found. C, 73.82; H, 7.01; N, 4.90.

WORKING EXAMPLE 288 (Production of Compound 288)

To a solution of 7-(4-ethoxyphenyl)-N-[4-[N-(4,4-ethylenedioxycyclohexyl)-N-methylaminomethyl]phenyl]-2,3-dihydro-1-benzoxepine-4-carboxamide (151.5 mg) in THF (10 ml) was added at room temperature 3N hydrochloric acid (2 ml), and the mixture was stirred for 22 hours. To the mixture was added saturated sodium bicarbonate solution, and the mixture was extracted with ethyl acetate. The organic layer was washed with saturated brine and dried with magnesium sulfate. Under reduced pressure, the mixture was concentrated to give colorless solid, which was recrystallized from ethyl acetate/diisopropylether to give colorless crystals of 7-(4-ethoxyphenyl)-N-[4-[N-methyl-N-(4-oxocyclohexyl) aminomethyl]phenyl]-2,3-dihydro-1-benzoxepine-4-carboxamide (Compound 288) (103.5 mg).

m.p. 146–148° C.; $^1$H-NMR (200 MHz, CDCl$_3$) δ 1.44 (3H, t, J=7.0 Hz), 1.80–2.19 (4H, m), 2.23 (3H, s), 2.29–2.59 (4H, m), 2.83–2.98 (1H, m), 3.04–3.12 (2H, m), 3.61 (2H, s), 4.08 (2H, q, J=7.0 Hz), 4.34–4.39 (2H, m), 6.96 (2H, d, J=8.8 Hz), 7.05 (1H, d, J=8.4 Hz), 7.33 (2H, d, J=8.0 Hz), 7.41–7.57 (8H, m). IR (KBr) 3329, 1709, 1645, 1518, 1495, 1242, 825 cm$^{-1}$; Anal. Calcd. for C$_{33}$H$_{36}$N$_2$O$_4$.0.25H$_2$O; Calcd. C, 74.91; H, 6.95; N, 5.29. Found. C, 74.68; H, 6.92; N, 5.28.

WORKING EXAMPLE 289 (Production of Compound 289)

To a solution of 4-[1-(4-methylphenylsulfonyl)-piperidin-4-yl]-6,7-dihydro-5H-benzocycloheptene- 8-carboxylic acid (200 mg) in THF (10 ml) were added at room temperature oxalyl chloride (0.08 ml) and a drop of DMF, and the mixture was stirred for 1 hour. Under reduced pressure, the mixture was concentrated, and the residue was dissolved in THF (20 ml). To the mixture was added at 0° C. a solution of 4-[N-methyl-N-(tetrahydropyran-4-yl)aminomethyl]-aniline (114 mg) and triethylamine (0.2 ml) in THF (5 ml), and the mixture was stirred at room temperature for 3 hours. To the mixture was added water, and the mixture was extracted with ethyl acetate. The organic layer was washed with saturated brine and dried with magnesium sulfate. Under reduced pressure, the mixture was concentrated, and the residue was purified with column chromatography (ethanol/ethyl acetate=1:3) and recrystallized from ethanol to give colorless crystals of 4-[1-(4-methylphenylsulfonyl) piperidin-4-yl]-N-[4-[N-methyl-N-(tetrahydropyran-4-yl) aminomethyl]phenyl]-6,7-dihydro-5H-benzocycloheptene-8-carboxamide (Compound 289) (203.5 mg).

m.p. 175–176° C.; $^1$H-NMR(200 MHz, CDCl$_3$) δ 1.66–1.81 (4H,m), 1.83–1.92(4H, m), 2.04–2.17 (2H, m), 2.21 (3H, s), 2.26–2.43 (3H, m), 2.45 (3H, s), 2.65–2.71 (2H, m), 2.76–2.86 (2H, m), 3.30–3.45 (2H, m), 3.57 (2H, s), 3.87–4.10 (4H, m), 6.97–7.13 (3H, m), 7.29–7.37 (5H, m), 7.55 (2H, d, J=8.4 Hz), 7.58 (1H, s), 7.68 (2H, d, J=8.2 Hz). IR (KBr) 3346, 1647, 1518, 1344, 1159, 926, 725, 546 cm$^{-1}$; Anal. Calcd. for C$_{37}$H$_{45}$N$_3$O$_4$S; Calcd. C, 70.78; H, 7.22; N, 6.69. Found. C, 70.71; H, 7.14; N, 6.46.

WORKING EXAMPLE 290 (Production of Compound 290)

In THF (3.4 ml) was dissolved 7-(5-methyl-2-thienyl)-2,3-dihydro-1-benzoxepine-4-carboxylic acid (340 mg), and to the mixture were added oxalyl chloride (0.198 ml) and DMF (one drop) while stirring at room temperature. The mixture was stirred at room temperature for 2 hours. Under reduced pressure, the solvent was removed, and the resulting residue was dissolved in THF (5.1 ml). The mixture was added dropwise to a solution of 4-[N-methyl-N-(tetrahydropyran-4-yl)aminomethyl]aniline (308 mg) and triethylamine (0.473 ml) in THF (5.1 ml), under ice-cooling, and the mixture was stirred at room temperature for 13 hours. The mixture was poured into water, extracted with ethyl acetate, washed with saturated brine and dried with magnesium sulfate. Under reduced pressure, the solvent was removed, and the resulting residue was purified with silica gel column chromatography (ethyl acetate/ethanol=2/1) and recrystallized from hexane/ethyl acetate to give N-[4-[N-methyl-N-(tetrahydropyran-4-yl)aminomethyl]phenyl]-7-(5-methyl-2-thienyl)-2,3-dihydro-1-benzoxepine-4-carboxamide (Compound 290) (20 mg).

m.p. 129–130° C.; $^1$H-NMR (200 MHz, CDCl$_3$) δ 1.50–1.82 (4H, m), 2.21 (3H, s), 2.31 (3H, s), 2.65 (1H, m), 3.08 (2H, t, J=4.6 Hz), 3.37 (2H, dt, J=11.2, 3.2 Hz), 3.58 (2H, s), 4.04 (2H, m), 4.37 (2H, t, J=4.6 Hz), 6.92 (1H, d, J=5.2 Hz), 7.04 (1H, d, J=5.2 Hz), 7.18–7.52 (7H, m), 7.51–7.56 (2H, m); IR (KBr) 3294,1653,1597,1514,1498, 1456,1406,1315,1248,733 cm$^{-1}$.

WORKING EXAMPLE 291 (Production of Compound 291)

In THF (10 ml) was dissolved 7-(3-thienyl)-2,3-dihydro-1-benzoxepine-4-carboxylic acid (240 mg), and to the mixture were added oxalyl chloride (0.15 ml) and DMF (one drop) while stirring at room temperature, and the mixture was stirred at room temperature for 1.5 hours. Under reduced pressure, the solvent was removed, and the resulting residue in THF (6 ml) was added dropwise to a solution of 4-[N-methyl-N-(tetrahydropyran-4-yl)aminomethyl]aniline (247 mg) and triethylamine (0.35 ml) in THF (10 ml), under ice-cooling, and the mixture was stirred at room temperature for 14 hours. The mixture was poured into water, extracted with ethyl acetate, washed with saturated brine and dried with magnesium sulfate. Under reduced pressure, the solvent was removed, and the resulting residue was purified with silica gel column chromatography (ethyl acetate/ethanol=2/1) and recrystallized from hexane/ethyl acetate to give N-[4-[N-methyl-N-(tetrahydropyran-4-yl) aminomethyl]phenyl]-7-(3-thienyl)-2,3-dihydro-1-benzoxepine-4-carboxamide (Compound 291) (180 mg).

m.p. 194–195° C.; $^1$H-NMR (200 MHz, CDCl$_3$) δ 1.60–1.84 (4H, m),2.22 (3H, s),2.69 (1H, m), 3.09 (2H, t, J=4.6 Hz), 3.36 (2H, dt, J=11.2, 2.6 Hz), 3.60 (2H, s), 4.04 (2H, m), 4.34 (2H, t, J=4.6 Hz), 7.03 (1H, d, J=8.4 Hz), 7.25–7.42 (7H, m), 7.47 (1H, dd, J=8.4, 2.2 Hz), 7.54 (1H, s), 7.58 (1H, s), 7.67 (1H, s); IR (KBr) 3306,1645,1604, 1514,1496,1456,1408,1321,1230,781cm$^{-1}$; Anal. Calcd. for C$_{28}$H$_{30}$N$_2$O$_3$S; Calcd. C, 70.86; H, 6.37; N, 5.90. Found. C, 70.74; H, 6.16; N, 5.92.

WORKING EXAMPLE 292 (Production of Compound 292)

In THF 10 ml was dissolved in 7-(4-methyl-2-thienyl)-2,3-dihydro-1-benzoxepine-4-carboxylic acid (250 mg), and to the mixture were added oxalyl chloride (0.145 ml) and DMF (one drop) while stirring at room temperature, and the mixture was stirred at room temperature for 2 hours. Under reduced pressure, the solvent was removed, and the resulting residue in methylene chloride (10 ml) was added dropwise to a solution of 4-[N-methyl-N-(tetrahydropyran-4-yl) aminomethyl]aniline (250 mg) and triethylamine (0.35 ml) in THF(5 ml), under ice-cooling, and the mixture was stirred at room temperature for 13 hours. The mixture was poured into water, extracted with ethyl acetate, washed with saturated brine and dried with magnesium sulfate. Under reduced pressure, the solvent was removed, and the resulting residue was purified with silica gel column chromatography (ethyl acetate/ethanol=2/1) and recrystallized from hexane/ ethyl acetate to give N-[4-[N-methyl-N-(tetra-hydropyran-4-yl)aminomethyl]phenyl]-7-(4-methyl-2-thienyl)-2,3-dihydro-1-benzoxepine-4-carboxamide (Compound 292) (185 mg).

m.p. 147–148° C.; $^1$H-NMR (200 MHz, CDCl$_3$) δ 1.60–1.80 (4H, m), 2.21 (3H, s), 2.31 (3H, s), 2.64 (1H, m), 3.06 (2H, t, J=4.2 Hz), 3.37 (2H, dt, J=11.4, 2.8 Hz), 3.57 (2H, s), 4.04 (2H, m), 4.33 (2H, t, J=4.2 Hz), 6.82 (1H, d, J=1.2 Hz), 6.99 (1H, d, J=8.4 Hz), 7.04 (1H, d, J=1.2 Hz), 7.19 (1H, s), 7.41–7.57 (5H, m), 7.67 (1H, s); IR (KBr) 3292, 1653, 1597, , 1514, 1456, 1406, 1315, 1246, 733cm$^{-1}$; Anal. Calcd. for C$_{29}$H$_{32}$N$_2$O$_3$S.0.5H$_2$O; Calcd. C, 69.99; H, 6.68; N, 5.63. Found. C, 69.85; H, 6.43; N, 5.68.

WORKING EXAMPLE 293 (Production of Compound 293)

In THF (5.0 ml) was dissolved 7-(4-fluorophenyl)-2,3-dihydro-1-benzoxepine-4-carboxylic acid (137 mg), and to the mixture were added DMF (one drop) and oxalyl chloride (0.085 ml). The mixture was stirred at room temperature for 1 hour, and the solvent was removed under reduced pressure. The residue was dissolved in THF (5.0 ml), and to the mixture was added a solution of 4-[(N-methyl-N-tetrahydropyran-4-yl)aminomethyl]aniline (117 mg) and triethylamine (0.135 ml) in THF (5.0 ml). The mixture was stirred at room temperature for 1 hour, and to the mixture was added water (50 ml). The mixture was extracted with ethylacetate (100 ml and 50 ml), and the organic layer was dried with anhydrous magnesium sulfate. The solvent was removed under reduced pressure, and the residue was purified with silica gel column chromatography and recrystallized to give 7-(4-fluorophenyl)-N-[4-[(N-methyl-N-tetrahydropyran-4-yl)aminomethyl]-phenyl]-2,3-dihydro-1-benzoxepine-4-carboxamide (Compound 293) (149 mg, 64%) as pale yellow needle crystals.

mp 177–178° C.; IR (KBr) 3351, 2938, 1649, 1632, 1595, 1518, 1491, 1412, 1316, 1219, 829cm$^{-1}$. $^1$H NMR (200 MHz, CDCl$_3$) δ 1.69–1.77 (4H, m), 2.21 (3H, s), 2.60–2.70 (1H, m), 3.09 (2H, t, J=4.2 Hz), 3.37 (2H, td, J=11.1, 2.9 Hz), 3.58 (2H, s), 4.04 (2H, d, J=10.6 Hz), 4.37 (2H, t, J=4.7 Hz), 7.04–7.16 (3H, m), 7.29–7.56 (8H, m). Anal. Calcd. for C$_{30}$H$_{31}$FN$_2$O$_3$: C, 74.05, H, 6.42, N, 5.76. Found : C, 73.90, H, 6.35, N, 5.53.

WORKING EXAMPLE 294 (Production of Compound 294)

To a suspension of 6-(4-methylphenyl)-2H-thiochromene-3-carboxylic acid (0.36 g, 1.28 mmol) in dichloromethane (5 ml) were added at 0° C. oxalate chloride (0.33 ml, 3.84 mmol) and N,N-dimethylformamide (one drop), and the mixture was stirred at room temperature for 1 hour. The solvent was evaporated, and the residue was dissolved in tetrahydrofuran (3 ml). To the mixture was added dropwise a solution of aniline (0.31 g, 1.41 mmol) and triethylamine (0.54 ml, 3.84 mmol) in tetrahydrofuran (2 ml), and the mixture was stirred for 3 hours. To the mixture was added water, and the mixture was extracted with ethyl acetate. The organic layer was washed with saturated brine and dried with magnesium sulfate. The solvent was evaporated, and the resulting powder was washed with hexane to give 6-(4-methylphenyl)-N-(4-((N-methyl-N-tetrahydropyran-4-yl)amino)-methyl)phenyl-2H-thiochromene-3-carboxamide (Compound 294) (0.45 g, 72%) as pale yellow powder.

m.p. 200° C.; $^1$H-NMR (DMSO-d$_6$) δ: 7.32–7.36 (3H, m), 7.21–7.28 (4H, m), 7.07 (1H, d, J=8.2), 6.92–6.99 (4H, m), 3.50–3.66 (2H, m), 3.48 (2H, s), 3.20 (2H, s), 2.86–3.00 (2H, m), 2.20–2.37 (1H, m), 2.03 (3H, s), 1.78 (3H, s), 1.08–1.46 (4H, m). Anal. Calcd for C$_{30}$H$_{32}$N$_2$O$_2$S.0.25H$_2$O: C; 73.66, H; 6.70, N; 5.73. Found: C; 73.84, H; 6.60, N; 5.84.

WORKING EXAMPLE 295 (Production of Compound 295)

To a suspension of 6-(4-methylphenyl)-2H-thiochromene-3-carboxylic acid (226 mg, 0.785 mmol) in tetrahydrofuran (7 ml) were added oxalyl chloride (0.21 ml, 2.35 mmol) and N,N-dimethylformamide (one drop), and the mixture was stirred at room temperature for 1 hour. Under reduced pressure, the solvent was evaporated, and the residue was dissolved in tetrahydrofuran (5 ml). To the mixture was added dropwise a solution of (E)-4-((N-(4-hydroxycyclohexyl)-N-methyl)aminomethyl)aniline (202 mg, 0.864 mmol) and triethylamine (0.33 ml, 2.35 mmol) in tetrahydrofuran (2 ml), and the mixture was stirred for 15 hours. To the mixture was added water, and the mixture was extracted with ethyl acetate. The extract was washed with saturated brine and dried with magnesium sulfate. The solvent was evaporated, and the residue was purified with silica gel column chromatography [ethyl acetate:ethanol (2:1)] to give (E)-N-(4-((N-(4-hydroxycyclohexyl)-N-methyl)amino) methyl)phenyl-6-(4-methylphenyl)-2H-thiochromene-3-carboxamide (Compound 295) (160 mg, 41%), which was recrystallized from ethyl acetate/hexane to give yellow crystals.

m.p. 149° C.; $^1$H-NMR (CDCl$_3$) δ: 7.73 (1H, br s), 7.42–7.58 (6H, m), 7.22–7.38 (5H, m), 3.81 (2H, d, J=0.8), 3.59 (2H, s), 3.55–3.68 (1H, m), 2.42–2.61 (1H, m), 2.40 (3H, s), 2.21 (3H, s), 1.86–2.20 (4H, m), 1.23–1.57 (4H, m). Anal. Calcd for C$_{31}$H$_{34}$N$_2$O$_4$S.1.25H$_2$O: C; 71.44, H; 7.06, N; 5.37. Found: C; 71.12, H; 6.53, N;5.51.

WORKING EXAMPLE 296 (Production of Compound 296)

To a suspension of 6-(4-methylphenyl)-2H-thiochromene-3-carboxylic acid (204 mg, 0.708 mmol) in tetrahydrofuran (6 ml) were added oxalyl chloride (0.19 ml) and N,N-dimethylformamide (one drop), and the mixture was stirred at room temperature for 1 hour. Under reduced pressure, the solvent was evaporated, and the residue was dissolved in tetrahydrofuran (5 ml). To the mixture was added dropwise a solution of 4-((N-(2-methoxy-ethyl)-N-methyl)aminomethyl)aniline (153 mg, 0.802 mmol) and triethylamine (0.30 ml) in tetrahydrofuran (2 ml), and the mixture was stirred for 15 hours. To the mixture was added water, and the mixture was extracted with ethyl acetate. The extract was washed with saturated brine and dried with magnesium sulfate. The solvent was evaporated, and the residue was purified with silica gel column chromatography [ethyl acetate:ethanol (2:1)] to give N-(4-(N-(4-methoxyethyl)-N-methyl)aminomethyl)-phenyl-6-(4-methylphenyl)-2H-thiochromene-3-carboxamide (Compound 296) (170 mg, 52%), which was recrystallized from ethyl acetate/hexane to give yellow crystals.

m.p. 101° C.; $^1$H-NMR (CDCl$_3$) δ: 7.67 (1H, br s), 7.41–7.57 (6H, m), 7.20–7.38 (5H, m), 3.82 (2H, t, J=0.8), 3.56 (2H, s), 3.53 (2H, t, J=5.8), 3.35 (3H, s), 2.61 (2H, t, J=5.8), 2.40 (3H, s), 2.28 (3H, s). Anal. Calcd for C$_{28}$H$_{30}$N$_2$O$_2$S.0.25H$_2$O: C; 72.62, H; 6.64, N; 6.05. Found: C; 72.43, H; 6.39, N; 6.36.

WORKING EXAMPLE 297 (Production of Compound 297)

To a suspension of 7-(4-methylphenyl)-2,3-dihydro-1-benzothiepine-4-carboxylic acid (292 mg, 0.987 mmol) in tetrahydrofuran (10 ml) were added at 0° C. oxalyl chloride (0.26 ml) and N,N-dimethylformamide (one drop), and the mixture was stirred at room temperature for 1.5 hours. The solvent was evaporated, and the residue was dissolved in tetrahydrofuran (8 ml). To the residue was added dropwise a solution of 4-((N-(3-ethoxycarbonylethyl)-N-methyl)aminomethyl)aniline (233 mg, 0.987 mmol) and triethylamine (0.42 ml) in tetrahydrofuran (2 ml) at 0° C., and the mixture was stirred at room temperature for 17 hours. To the mixture was added water, and the mixture was extracted with ethyl acetate. The extract was washed with saturated brine and dried with magnesium sulfate. The solvent was evaporated, and the residue was purified with silica gel column chromatography [ethyl acetate] to give N-(4-(N-(3-ethoxycarbonylethyl)-N-methyl)aminomethyl)phenyl-7-(4-methylphenyl)-2,3-dihydro-1-benzothiepine-4-carboxamide (Compound 297) (408 mg, 80%), which was recrystallized from acetone/ethanol to give colorless crystals.

m.p. 124° C.; $^1$H-NMR (CDCl$_3$) δ: 7.89 (1H, br s), 7.38–7.58 (7H, m), 7.22–7.30 (4H, m), 4.14 (2H, q, J=7.4), 3.48 (2H, s), 3.25 (2H, dt, J=5.4, 1.4) 3.05 (2H, t, J=5.4), 2.74 (2H, t, J=6.8), 2.51 (2H, t, J=6.8), 2.39 (3H, s), 2.19

(3H, s), 1.25 (3H, t, J=7.4). Anal. Calcd for $C_{31}H_{34}N_2O_3S$: C; 72.34, H; 6.66, N; 5.44. Found: C; 72.32, H; 6.43, N; 5.45.

WORKING EXAMPLE 298 (Production of Compound 298)

To a suspension of 7-(4-methylphenyl)-2,3-dihydro-1-benzothiepine-4-carboxylic acid (222 mg, 0.750 mmol) in tetrahydrofuran (7 ml) was added at 0° C. oxalyl chloride (0.26 ml, 2.97 mmol) and N,N-dimethylformamide (one drop), and the mixture was stirred at room temperature for 2 hours. The solvent was evaporated, and the residue was dissolved in tetrahydrofuran (5 ml). To the residue was added dropwise a solution of aniline (149 mg, 0.825 mmol) and triethylamine (0.31 ml, 2.25 mmol) in tetrahydrofuran (2 ml) at 0° C., and the mixture was stirred at room temperature for 3 days. To the mixture was added water, and the mixture was extracted with ethyl acetate. The extract was washed with saturated brine and dried with magnesium sulfate. The solvent was evaporated, and the residue was purified with silica gel column chromatography [ethyl acetate:methanol:triethylamine (5:1:0.6)] to give N-(4-(N-(2-hydroxyethyl)-N-methyl)aminomethyl)phenyl-7-(4-methylphenyl)-2,3-dihydro-1-benzothiepine-4-carboxamide (Compound 298) (310 mg, 90%).

m.p. 138° C.; $^1$H-NMR (CDCl$_3$) δ: 7.74 (1H, br s), 7.40–7.59 (7H, m), 7.23–7.32 (4H, m), 3.64 (2H, t, J=5.2), 3.58 (2H, s), 3.28 (2H, t, J=5.6), 3.07 (2H, t, J=5.6), 2.62 (2H, t, J=5.2). Anal. Calcd for $C_{31}H_{34}N_2O_3S$: C; 72.34, H; 6.66, N; 5.44. Found: C; 72.32, H; 6.43, N; 5.45.

WORKING EXAMPLE 299 (Production of Compound 299)

To a suspension of 6-(4-methylphenyl)-2-pyridineacrylic acid (160 mg, 0.67 mmol) in DMF (5 ml) were added at 0° C. 1-hydroxybenzotriazole (99 mg, 0.73 mmol), 4-[N-methyl-N-(4-tetrahydropyranyl)aminomethyl]aniline (162 mg, 0.74 mmol), 1-ethyl-3-(3-dimethylaminopropyl) carbodiimide hydrochloride (192 mg, 1.00 mmol), triethylamine (0.28 ml, 2.01 mmol) and 4-dimethylaminopyridine (10 mg) in this order, and the mixture was stirred at room temperature for 17 hours. The mixture was concentrated under reduced pressure, and to the residue was added ethyl acetate (40 ml). The mixture was washed with water (5 ml, 3 ml×2), saturated sodium bicarbonate solution (3 ml×3) and saturated brine (3 ml) in this order. The organic layer was dried with anhydrous sodium sulfate and concentrated under reduced pressure, and the residue was purified with column chromatography (silica gel 15 g, ethylacetate/methanol=9/1). The desired fraction was concentrated under reduced pressure to give N-[4-[N-methyl-N-(4-tetrahydropyranyl) aminomethyl]phenyl]-6-(4-methylphenyl)-2-pyridineacrylamide (Compound 299) (259 mg, 0.59 mmol, 88%). IR (KBr): 1667, 1634, 1601, 1537, 1514 cm$^{-1}$. $^1$H-NMR (CDCl$_3$) δ: 1.55–1.85 (4H, m), 2.21 (3H, s), 2.43 (3H, s), 2.55–2.75 (1H, m), 3.30–3.45 (2H, m), 3.58 (2H, s), 3.95–4.10 (2H, m), 7.20–7.50 (5H, m), 7.45–7.85 (6H, m), 7.98 (2H, d, J=8.2 Hz).

WORKING EXAMPLE 300 (Production of Compound 300)

In DMF (5 ml) was dissolved 7-(3,4-methylenedioxyphenyl)-2,3-dihydro-1-benzoxepine-4-carboxylic acid, and to the mixture were added 1-hydroxybenzotriazole (67 mg, 0.50 mmol), 4-[N-methyl-N-(4-tetrahydropyranyl)-aminomethyl]aniline (109 mg, 0.49 mmol), 1-ethyl-3-(3-dimethylaminopropyl)-carbodiimide hydrochloride (130 mg, 0.68 mmol), triethylamine (0.189 ml, 1.36 mmol) and 4-dimethylaminopyridine (3 mg). The mixture was stirred at room temperature for 18 hours and concentrated under reduced pressure. To the residue was added ethyl acetate (60 m), and the mixture was washed with water (5 ml×3), saturated sodium bicarbonate solution (3 ml×3) and saturated brine (5 ml) in this order. The organic layer was dried with anhydrous sodium sulfate and concentrated under reduced pressure. The residue was purified with column chromatography (silica gel 15 g, ethyl acetate). The desired fraction was concentrated under reduced pressure, and to the residue was added ethyl acetate. Insoluble materials were filtered, and the insoluble materials were washed with ethyl acetate and dried under reduced pressure to give 7-(3,4-methylenedioxyphenyl)-N-[4-[N-methyl-N-(4-tetrahydropyranyl)aminomethyl]phenyl]-2,3-dihydro-1-benzoxepine-4-carboxamide (Compound 300) (187 mg, 0.36 mmol, 81%).

IR (KBr): 1653, 1597, 1514 cm$^{-1}$. $^1$H-NMR (CDCl$_3$) δ: 1.55–1.85 (4H, m), 2.21 (3H, s), 2.55–2.80 (1H, m), 3.00–3.15 (2H, m), 3.30–3.45 (2H, m), 3.58 (2H, s), 3.95–4.15 (2H, m), 4.30–4.45 (2H, m), 6.01 (2H, s), 6.88 (1H, d, J=8.6 Hz), 6.95–7.10 (3H, m), 7.20–7.65 (7H, m).

WORKING EXAMPLE 301 (Production of Compound 301)

In DMF (6 ml) was dissolved 7-morpholino-2,3-dihydro-1-benzoxepine-4-carboxylic acid (200 mg, 0.73 mmol), and to the mixture were added at 0° C. 1-hydroxybenzotriazole (108 mg, 0.80 mmol), 4-[N-methyl-N-(4-tetrahydropyranyl)-aminomethyl]aniline (176 mg, 0.80 mmol), 1-ethyl-3-(3-dimethylaminopropyl)carbodiimide hydrochloride (209 mg, 1.09 mmol), triethylamine (0.304 ml, 2.18 mmol) and 4-dimethylaminopyridine (3 mg). The mixture was stirred at room temperature for 13 hours and concentrated under reduced pressure. To the residue was added ethyl acetate (40 ml), and the mixture was washed with water (5 ml×3), saturated sodium bicarbonate solution (5 ml×3) and saturated brine (5 ml) in this order. The organic layer was dried with anhydrous sodium sulfate and concentrated under reduced pressure. The residue was purified with column chromatography (silica gel 15 g, ethyl acetate/methanol=1/0→9/1). The desired fraction was concentrated under reduced pressure, and to the residue was added diethylether. Insoluble materials were filtered, and the insoluble materials were washed with diethylether and dried under reduced pressure to give N-[4-[N-methyl-N-(4-tetrahydropyranyl)aminomethyl]phenyl]-7-morpholino-2,3-dihydro-1-benzoxepine-4-carboxamide (Compound 301) (248 mg, 0.52 mmol, 71%).

IR (KBr): 1655, 1597, 1507 cm$^{-1}$. $^1$H-NMR (CDCl$_3$) δ: 1.5–1.85 (4H, m), 2.21 (3H, s), 2.55–2.75 (1H, m), 3.0–3.15 (6H, m), 3.3–3.45 (2H, m), 3.57 (2H, s), 3.8–3.9 (4H, m), 3.95–4.1 (2H, m), 4.29 (2H, t, J=4.7 Hz), 6.8–7.0 (3H, m), 7.15–7.35 (3H, m), 7.5–7.6 (2H+1H(amide-H), m).

WORKING EXAMPLE 302 (Production of Compound 302)

In DMF (6 ml) was dissolved 7-(4-methylphenyl)-2,3-dihydro-1-benzoxepine-4-carboxylic acid (140 mg, 0.50 mmol), and to the mixture were added at 0° C. 1-hydroxybenzotriazole (74 mg, 0.55 mmol), 4-[N-(2-pyrimidinyl)-aminomethyl]aniline (100 mg, 0.50 mmol) and 1-ethyl-3-(3-dimethylaminopropyl)-carbodiimide hydrochloride (144 mg, 0.75 mmol). The mixture was stirred at room temperature for 22 hours and concentrated under reduced pressure. To the residue was added ethyl acetate (40 ml), and the mixture was washed with water (5 ml), saturated sodium bicarbonate solution (5 ml×3) and saturated brine (5 ml) in this order. The organic layer was dried with anhydrous sodium sulfate and concentrated to about 3 ml under reduced pressure. Precipitated insoluble materials were filtered and the insoluble materials were washed with ethyl acetate and dried under reduced pressure to give N-[4-[N-(2-pyrimidinyl)-aminomethyl]phenyl]- 7-(4-methylphenyl)-2,3-dihydro-1-benzoxepine-4-carboxamide (Compound 302) (129 mg, 0.28 mmol, 56%).

IR (KBr): 1647, 1591, 1518 cm$^{-1}$. $^1$H-NMR (DMSO-d$_6$) δ: 2.34 (3H, s), 2.9–3.05 (2H, m), 4.2–4.35 (2H, m), 4.46 (2H, d, J=6.6 Hz), 6.57 (1H, t, J=4.8 Hz), 7.04 (1H, d, J=8.4 Hz), 7.2–7.35 (5H, m), 7.5–7.75 (7H, m), 8.27 (2H, d, J=4.8 Hz), 9.91 (1H, s).

WORKING EXAMPLE 303 (Production of Compound 303)

To a mixture of 7-(2-methyl-1H-tetrazol-5-yl)-2,3-dihydro-1-benzoxepine-4-carboxylic acid (180 mg, 0.66 mmol), 4-[N-methyl-N-(tetrahydropyran-4-yl) aminomethyl]-aniline (160 mg, 0.73 mmol), 1-hydroxybenzotriazole (98 mg, 0.73 mmol) and DMF (10 ml) were added at 0° C. 1-[3-(dimethylamino)propyl]-3-ethylcarbodiimide hydrochloride (190 mg, 0.99 mmol) and triethylamine (0.276 ml, 1.98 mmol), and the mixture was stirred at room temperature for 24 hours. The mixture was concentrated under reduced pressure, and to the residue was added ethyl acetate (40 ml). The mixture was washed with saturated sodium bicarbonate solution (5 ml×3) and saturated brine (5 ml) in this order. The organic layer was dried with anhydrous sodium sulfate and concentrated under reduced pressure, and the residue was purified with column chromatography (silica gel 15 g, ethyl acetate). The desired fraction was concentrated under reduced pressure, and to the residue was added ethyl acetate. Insoluble materials were filtered, and the insoluble materials were washed with ethyl acetate and dried under reduced pressure to give 7-(2-methyl-1H-tetrazol-5-yl)-N-[4-[N-methyl-N-(tetrahydropyran-4-yl)aminomethyl]-phenyl]-2,3-dihydro-1-benzoxepine-4-carboxamide (Compound 303) (217 mg, 0.46 mmol, 69%).

IR (KBr): 1647, 1628, 1611, 1595, 1522 cm$^{-1}$. $^1$H-NMR (DMSO-d$_6$) δ: 1.35–1.8 (4H, m), 2.10 (3H, s), 2.4–2.7 (1H, m), 2.9–3.1 (2H, m), 3.15–3.4 (2H, m), 3.52 (2H, s), 3.8–4.0 (2H, m), 4.25–4.45 (2H, m), 4.42 (3H, s), 7.16 (1H, d, J=8.4 Hz), 7.26 (2H, d, J=8.4 Hz), 7.40 (1H, s), 7.66 (2H, d, J=8.4 Hz), 7.92 (1H, dd, J=1.9, 8.4 Hz), 8.19 (1H, d, J=1.9 Hz).

WORKING EXAMPLE 304 (Production of Compound 304)

To a mixture of 7-(1-methyl-1H-tetrazol-5-yl)-2,3-dihydro-1-benzoxepine-4-carboxylic acid (69 mg, 0.25 mmol), 4-[N-methyl-N-(tetrahydropyran-4-yl) aminomethyl]aniline (61 mg, 0.28 mmol), 1-hydroxybenzotriazole (38 mg, 0.28 mmol) and DMF (4 ml) were added at 0° C. 1-[3-(dimethylamino)-propyl]-3-ethylcarbodiimide hydrochloride (97 mg, 0.51 mmol) and triethylamine (0.106 ml, 0.76 mmol), and the mixture was stirred at room temperature for 2 days. The mixture was concentrated under reduced pressure, and to the residue was added ethyl acetate. The mixture was washed with saturated sodium bicarbonate solution. The organic layer was dried with anhydrous sodium sulfate and concentrated under reduced pressure. The residue was purified with column chromatography (silica gel 10 g, ethyl acetate). The desired fraction was concentrated under reduced pressure, and to the residue was added ethyl acetate. Insoluble materials were filtered and the insoluble materials were washed with ethyl acetate and dried under reduced pressure to give 7-(1-methyl-1H-tetrazol-5-yl)-N-[4-[N-methyl-N-(tetrahydropyran-4-yl)aminomethyl]-phenyl]-2,3-dihydro-1-benzoxepine-4-carboxamide (Compound 304) (84 mg, 0.18 mmol, 70%).

IR (KBr): 1649, 1630, 1597, 1518 cm$^{-1}$. $^1$H-NMR (DMSO-d$_6$) δ: 1.35–1.8 (4H, m), 2.10 (3H, s), 2.45–2.7 (1H, m), 2.95–3.1 (2H, m), 3.15–3.4 (2H, m), 3.51 (2H, s), 3.8–4.0 (2H, m), 4.20 (3H, s), 4.3–4.45 (2H, m), 7.22 (1H, d, J=8.4 Hz), 7.26 (2H, d, J=8.6 Hz), 7.35 (1H, s), 7.64 (2H, d, J=8.6 Hz), 7.76 (1H, dd, J=2.2, 8.4 Hz), 7.99 (1H, d, J=2.2 Hz).

WORKING EXAMPLE 305 (Production of Compound 305)

In DMF (12.0 ml) was dissolved 1-methyl-7-(4-methylphenyl)-2,3-dihydro-1-benzoazepine-4-carboxylic acid hydrochloride (386 mg), and to the mixture was added thionyl chloride (0.26 ml). The mixture was stirred at room temperature for 30 minutes, and the solvent was evaporated under reduced pressure. The residue was dissolved in dichloromethane (10.0 ml). Thus prepared acid chloride solution was added dropwise at 0° C. to a solution of 4-[[N-methyl-N-(tetrahydropyran-4-yl)amino]methyl]aniline (310 mg) and triethylamine (0.82 ml) in dichloromethane (4.0 ml). The mixture was stirred at 0° C. for 10 minutes and then at room temperature for 22 hours. To the mixture was added water (100 ml), and the mixture was extracted with dichloromethane (100 ml; twice). The organic layer was dried with anhydrous magnesium sulfate, and the solvent was evaporated under reduced pressure. The residue was purified with silica gel column chromatography (75 g, ethyl acetate:ethanol=9:1) and recrystallized from ethanol to give 1-methyl-7-(4-methylphenyl)-N-[4-[[N-methyl-N-(tetrahydropyran-4-yl)amino]methyl]phenyl]-2,3-dihydro-1-benzoazepine-4-carboxamide (Compound 305) (250 mg, 43%).

mp 178–181° C.; $^1$H NMR (200 MHz, CDCl$_3$) δ 1.64–1.76 (4H, m), 2.21 (3H, s), 2.38 (3H, s), 2.66 (1H, septet, J=5.3 Hz), 2.96 (2H, t, J=4.4 Hz), 3.09 (3H, s), 3.30–3.43 (2H +2H, m), 3.58 (2H, s), 4.01–4.06 (2H, m), 6.88 (1H, d, J=8.6 Hz), 7.23 (2H, d, J=8.0 Hz), 7.30 (2H, d, J=8.4 Hz), 7.42, (1H, s), 7.461 (2H, d, J=8.2 Hz), 7.466 (1H, dd, J=8.3, 2.3 Hz), 7.535 (2H, d, J=8.4 Hz), 7.539 (1H, d, J=2.6 Hz), 7.58 (1H, s). IR (KBr) 3337, 2949, 2851, 1653, 1516, 1501, 1341, 1304, 1238, 818, 521 cm$^{-1}$. Anal. Calcd. for C$_{32}$H$_{27}$N$_3$O$_2$: C, 77.54; H, 7.52; N, 8.48. Found: C, 77.51; H, 7.43; N, 8.44.

WORKING EXAMPLE 306 (Production of Compound 306)

In water:ethanol:toluene (1:1:10, 18.0 ml) were dissolved 4-ethoxyphenyl borate (252 mg) and 7-bromo-1-methyl-N-[4-[[N-methyl-N-(tetrahydropyran-4-yl)amino]-methyl] phenyl]-2,3-dihydro-1-benzoazepine-4-carboxamide (613 mg), and to the mixture was added potassium carbonate (420 mg). The mixture was stirred under argon atmosphere for 30 minutes, and to the mixture was added tetrakistriphenylphosphine palladium (59 mg). Under argon atmosphere, the mixture was refluxed for 17 hours. The mixture was diluted with ethyl acetate (200 ml) and washed with water (50 ml) and saturated brine (50 ml). The organic layer was dried with anhydrous magnesium sulfate, and the solvent was evaporated under reduced pressure. The residue was purified with silica gel column chromatography (75 g, ethyl acetate:ethanol=9:1) and recrystallized from ethanol to give 7-(4-ethoxyphenyl)-1-methyl-N-[4-[[N-methyl-N-(tetrahydropyran-4-yl)amino]methyl]phenyl]2,3-dihydro-1-benzoazepine-4-carboxamide (Compound 306) (230 mg, 35%).

mp 150.5–152° C.; $^1$H NMR (200 MHz, CDCl$_3$) δ 1.44 (3H, t, J=7.0 Hz), 1.64–1.77 (4H, m), 2.21 (3H, s), 2.57–2.72 (1H, m), 2.96 (2H, t, J=4.5 Hz), 3.08 (3H, s), 3.31–3.43 (2H+2H, m), 3.57 (2H, s), 4.01–4.09 (2H, m), 4.07 (2H, q, J=7.0 Hz), 6.88 (1H, d, J=8.4 Hz), 6.95 (2H, d, J=8.8 Hz), 7.30 (2H, d, J=8.6 Hz), 7.40–7.55 (1H+1H+1H+1H, concealed under 7.45 and 7.53), 7.47 (2H, d, J=9.0 Hz), 7.53 (2H, d, J=8.8 Hz). IR (KBr) 3372, 2955, 2847, 1680, 1605, 1595, 1518, 1503, 1314, 1240, 1194, 812 cm$^{-1}$. Anal. Calcd. for C$_{33}$H$_{39}$N$_3$O$_3$.0.5H$_2$O: C, 74.13; H, 7.54; N, 7.86. Found: C, 74.34; H, 7.31; N, 7.96.

WORKING EXAMPLE 307 (Production of Compound 307)

In water:ethanol:toluene (1:1:10, 18.0 ml) were dissolved 4-ethylphenyl borate (227 mg) and 7-bromo-1-methyl-N-[4-[[N-methyl-N-(tetrahydropyran-4-yl)amino]-methyllphenyl]-2,3-dihydro-1-benzoazepine-4-carboxamide (611 mg), and to the mixture was added potassium carbonate (418 mg). The mixture was stirred under argon atmosphere for 30 minutes, and to the mixture was added tetrakistriphenylphosphine palladium (59 mg). Under argon atmosphere, the mixture was ref luxed for 17 hours, and the mixture was diluted with ethyl acetate (200 ml) and washed with water (50 ml) and saturated brine (50 ml). The organic layer was dried with anhydrous magnesium sulfate, and the solvent was evaporated under reduced pressure. The residue was purified with silica gel column chromatography (75 g, ethyl acetate:ethanol=9:1) and recrystallized from ethanol to give 7-(4-ethylphenyl)-1-methyl-N-[4-[[N-methyl-N-(tetrahydropyran-4-yl)amino]methyl]phenyl]-2,3-dihydro-1-benzoazepine-4-carboxamide (Compound 307) (252 mg, 39%).

mp 164–165° C.; $^1$H NMR (200 MHz, CDCl$_3$) δ 1.27 (3H, t, J=7.6 Hz), 1.66–1.76 (4H, m), 2.21 (3H, s), 2.54–2.70 (1H, m), 2.69 (2H, q, J=7.7 Hz), 2.96 (2H, t, J=4.7 Hz), 3.09 (3H, s), 3.29–3.43 (4H, m), 3.57 (2H, s), 4.01–4.06 (2H, m), 6.89 (1H, d, J=8.6 Hz), 7.26 (2H, d, J=8.4 Hz), 7.30 (2H, d, J=8.8 Hz), 7.40 (1H, s), 7.48 (1H, dd, J=8.6, 2.2 Hz), 7.49 (2H, d, J=9.2 Hz), 7.54 (2H, d, J=8.8 Hz), 7.55 (1H, d, J=2.2 Hz), 1H was concealed under 7.40–7.56. IR (KBr) 3364, 2946, 2851, 1653, 1514, 1341, 1304, 1233, 1188, 824, 575, 519 cm$^{-1}$. Anal. Calcd. for C$_{33}$H$_{39}$N$_3$O$_2$: C, 77.76; H, 7.71; N, 8.24. Found: C, 77.81; H, 7.64; N, 8.27.

WORKING EXAMPLE 308 (Production of Compound 308)

In water:ethanol:toluene (1:1:10, 18.0 ml) were dissolved 4-trifluorophenyl borate (190 mg) and 7-bromo-1-methyl-N-[4-[[N-methyl-N-(tetrahydropyran-4-yl)-amino]methyl] phenyl]-2,3-dihydro-1-benzoazepine-4-carboxamide (403 mg), and to the mixture was added potassium carbonate (276 mg). The mixture was stirred under argon atmosphere for 30 minutes, and to the mixture was added tetrakistriphenylphosphine palladium (39 mg). Under argon atmosphere, the mixture was refluxed for 17 hours, and the mixture was diluted with ethyl acetate (200 ml) and washed with water (50 ml) and saturated brine (50 ml). The organic layer was dried with anhydrous magnesium sulfate, and the solvent was evaporated under reduced pressure. The residue was purified with silica gel column chromatography (75 g, ethyl acetate:ethanol=9:1) and recrystallized from ethanol to give 1-methyl-N-[4-[[N-methyl-N-(tetrahydropyran-4-yl) amino]-methyl]phenyl]-7-(4-trifluoromethylphenyl)-2,3-dihydro-1-benzoazepine-4-carboxamide (Compound 308) (177 mg, 39%).

mp 187.5–188.5° C.; $^1$H NMR (200 MHz, CDCl$_3$) δ 1.69–1.77 (4H, m), 2.21 (3H, s), 2.57–2.72 (1H, m), 2.98 (2H, t, J=4.6 Hz), 3.12 (3H, s), 3.37 (2H, td, J=11.2, 3.3 Hz), 3.38 (2H, t, J=4.7 Hz), 3.57 (2H, s), 4.01–4.06 (2H, m), 6.91 (1H, d, J=8.4 Hz), 7.30 (2H, d, J=8.4 Hz), 7.42 (1H, s), 7.49 (1H, dd, J=8.4, 2.2 Hz), 7.54 (2H, d, J=8.4 Hz), 7.55 (1H, s), 7.58 (1H, d, J=2.2 Hz), 7.66 (4H, s). IR (KBr) 2949, 2847, 1651, 1603, 1516, 1325, 1163, 1115, 1073, 847, 812cm$^{-1}$. Anal. Calcd. for C$_{32}$H$_{33}$F$_3$N$_3$O$_2$: C, 69.93; H, 6.24; N, 7.65. Found: C, 69.66; H, 6.20; N, 7.71.

WORKING EXAMPLE 309 (Production of Compound 309)

In water:ethanol:toluene (1:1:10, 18.0 ml) were dissolved 4-(4-morpholino)phenyl borate (208 mg) and 7-bromo-1-methyl-N-[4-[[N-methyl-N-(tetrahydropyran-4-yl)amino] methyl]phenyl]-2,3-dihydro-1-benzoazepine-4-carboxamide (406 mg), and to the mixture was added potassium carbonate (278 mg). The mixture was stirred under argon atmosphere for 30 minutes, and to the mixture was added tetrakistriphenylphosphine palladium (39 mg). Under argon atmosphere, the mixture was ref luxed for 17 hours, and the mixture was diluted with ethyl acetate (200 ml) and washed with water (50 ml) and saturated brine (50 ml). The organic layer was dried with anhydrous magnesium sulfate, and the solvent was evaporated under reduced pressure. The residue was purified with silica gel column chromatography (75 g, ethyl acetate:ethanol=9:1) and recrystallized from ethanol to give 1-methyl-N-[4-[[N-methyl-N-(tetrahydro-pyran-4-yl)amino]methyl]phenyl]-[4-(4-morpholino)-phenyl]- 2,3-dihydro-1-benzoazepine-4-carboxamide (Compound 309) (247 mg, 52%).

mp 209–211° C.; $^1$H NMR (200 MHz, CDCl$_3$) δ 1.64–1.77 (4H, m), 2.21 (3H, s), 2.57–2.75 (1H, m), 2.96 (2H, t, J=5.2 Hz), 3.09 (3H, s), 3.20 (2H, t, J=4.8 Hz), 3.18–3.22 (2H, m), 3.33–3.43 (4H, m), 3.58 (2H, s), 3.89 (4H, t, J=4.8 Hz), 4.01–4.06 (2H, m), 6.88 (1H, d, J=8.4 Hz), 6.97 (2H, d, J=8.8 Hz), 7.30 (2H, d, J=8.8 Hz), 7.41–7.56 (8H, m). IR (KBr) 2953, 2847, 1653, 1607, 1514, 1505, 1311, 1232, 1119, 926, 814, 735cm$^{-1}$. Anal. Calcd. for C$_{35}$H$_{42}$N$_4$O$_5$: C, 74.18; H, 7.47; N, 9.89. Found: C, 74.17; H, 7.39; N, 9.98.

REFERENCE EXAMPLE 187

In 1,2-dichloroethane (50 ml) were suspended p-nitrobenzylaminehydrochloride (3.77 g), 4H-tetrahydropyran-4-one (2 g) and triethylamine (2.8 ml), and to the mixture was added, under ice-cooling, triacetoxy sodium boron hydride (5.92 g). Under nitrogen atmosphere, the mixture was stirred at room temperature for 4 hours, and to the mixture were added, under ice-cooling, acetaldehyde (1.5 ml) and triacetoxy sodium boron hydride (5.92 g). Under nitrogen atmosphere, the mixture was stirred at room temperature overnight. The solvent was evaporated, and the residue was neutralized with sodium hydroxide solution. The mixture was extracted with ethyl acetate. The organic layer was washed with water and saturated brine and dried with anhydrous magnesium sulfate. Under reduced pressure, the solvent was evaporated, and the residue was purified with silica gel column (ethyl acetate/hexane) to give N-(4-nitrobenzyl)-N-(tetrahydropyran-4-yl)ethylamine (4.0 g) as yellow oil.

$^1$H-NMR($\delta$ ppm, CDCl$_3$) 1.01 (3H, t, J=6.9 Hz), 1.52–1.73 (4H, m), 2.59 (2H, q, J=6.9 Hz), 2.68–2.83 (1H, m), 3.34 (2H, dt, J=3.6, 11.2 Hz), 3.73 (2H, s), 3.99–4.06 (2H, m), 7.54 (2H, d, J=9.0 Hz), 8.16 (2H, d, J=9.0 Hz). IR(neat) $\nu$: 2951, 2841, 1599, 1520cm$^{-1}$.

REFERENCE EXAMPLE 188

In acetic acid (100 ml) was dissolved N-(4-nitrobenzyl)-N-(tetrahydropyran-4-yl)ethylamine (4.0 g), and to the mixture was added reduced iron (4.2 g). The mixture was stirred at room temperature overnight. The solvent was evaporated, and to the residue was added ethyl acetate. The precipitates were filtered off, and the filtrate was washed with sodium hydroxide solution, water and saturated brine, and dried with anhydrous magnesium sulfate. Under reduced pressure, the solvent was evaporated, and the residue was purified with silica gel column (methanol/triethylamine/ethyl acetate) to give 4-(N-ethyl-N-(tetrahydropyran-4-yl)aminomethyl) aniline (2.3 g) as red oil.

$^1$H-NMR($\delta$ ppm, CDCl$_3$) 1.00 (3H, t, J=7.1 Hz), 1.52–1.70 (4H, m), 2.54 (2H, q, J=7.1 Hz), 2.66–2.82 (1H, m), 3.26–3.39 (2H, m), 3.52 (2H, s), 3.59 (2H, br), 3.95–4.04 (2H, m), 6.64 (2H, d, J=8.5 Hz), 7.12 (2H, d, J=8.5 Hz).

REFERENCE EXAMPLE 189

In 1,2-dichloroethane (75 ml) were suspended p-nitrobenzaldehyde (5 g) and 2-amino-1,3-propanediol (3.0 g), and to the mixture was added, under ice-cooling, triacetoxy sodium boron hydride (9.8 g). Under nitrogen atmosphere, the mixture was stirred at room temperature for 3.5 hours. To the mixture were added, under ice-cooling, 37% formalin (3 ml) and triacetoxy sodium boron hydride (9.8 g), and the mixture was stirred, under nitrogen atmosphere, at room temperature overnight. To the mixture was added water, and the mixture was concentrated. The residue was neutralized with sodium hydroxide solution, saturated with sodium hydrochloride and extracted with ethyl acetate. The organic layer was dried with anhydrous magnesium sulfate, and the solvent was evaporated under reduced pressure. The residue was purified with silica gel column (ethyl acetate) to give 2-(N-methyl-N-(4-nitrobenzyl)amino)-1,3-propanediol (3.0 g) as pale yellow crystals.

mp 65–66° C.; $^1$H-NMR($\delta$ ppm, CDCl$_3$) 2.31 (3H, s), 2.93–3.06 (1H, m), 3.64–3.80 (4H, m), 3.92 (2H, s), 7.49 (2H, d, J=8.8 Hz), 8.20 (2H, d, J=8.8 Hz). IR(KBr) $\nu$: 3349, 2942, 2884, 1520cm$^{-1}$. Anal. Calcd. for C$_{11}$H$_{16}$N$_2$O$_4$: C, 54.99; H, 6.71; N, 11.66. Found: C, 55.14; H, 6.61; N, 11.55.

REFERENCE EXAMPLE 190

In ethanol (50 ml) was dissolved 2-(N-methyl-N-(4-nitrobenzyl)amino)-1,3-propanediol (2.9 g), and catalytic reduction was carried out with 5% palladium carbon (0.15 g) at room temperature for 2 hours. The catalyst was filtered off, and the solvent of the filtrate was evaporated. The residue was purified with silica gel column (methanol/triethylamine/ethyl acetate) to give 2-(N-(4-aminobenzyl)-N-methylamino)-1,3-propanediol (0.6 g) as pale yellow amorphous.

$^1$H-NMR($\delta$ ppm, CDCl$_3$) 2.26 (3H, s), 2.37 (2H, br), 2.91–2.99 (1H, m), 3.55–3.73 (6H, m), 6.65 (2H, d, J=8.4 Hz), 7.08 (2H, d, J=8.4 Hz). IR(KBr) $\nu$: 3347, 2942, 2880, 1615cm$^{-1}$. Anal. Calcd. for C$_{11}$H$_{18}$N$_2$O$_2$.0.1H$_2$O: C, 62.30; H, 8.65; N, 13.21. Found: C, 62.37; H, 8.79; N, 13.24.

REFERENCE EXAMPLE 191

In 1,2-dichloroethane (50 ml) were suspended p-nitrobenzaldehyde (5 g), sarcosine methyl ester hydrochloride (4.6 g) and triethylamine (4.6 ml), and to the mixture was added, under ice-cooling, triacetoxy sodium boron hydride (9.8 g). Under nitrogen atmosphere, the mixture was stirred at room temperature for 4 hours. To the mixture was added water, and the mixture was concentrated, neutralized with sodium hydroxide solution and extracted with ethyl acetate. The organic layer was washed with water and brine, and dried with anhydrous magnesium sulfate. Under reduced pressure, the solvent was evaporated, and the residue was purified with silica gel column (ethyl acetate/hexane) to give N-(4-nitrobenzyl)sarcosine methyl ester (6.3 g) as colorless oil.

$^1$H-NMR($\delta$ ppm, CDCl$_3$) 2.39 (3H, m), 3.33 (2H, s), 3.73 (3H, s), 3.80 (2H, s), 7.55 (2H, d, J=8.8 Hz), 8.19 (2H, d, J=8.8 Hz). IR(neat) $\nu$: 2951, 2847, 1748cm$^{-1}$.

REFERENCE EXAMPLE 192

In acetic acid (100 ml) was dissolved N-(4-nitrobenzyl) sarcosine methyl ester (5.96 g), and to the mixture was added little by little reduced iron (7 g). The mixture was stirred at room temperature overnight. The solvent was evaporated, and to the residue was added ethyl acetate. The precipitates were filtered off, and the filtrate was washed with sodium hydroxide solution, water and saturated brine, and dried with anhydrous magnesium sulfate. Under reduced pressure, the solvent was evaporated, and the resulting residue was purified with silica gel column chromatography (ethyl acetate/hexane) to give N-(4-aminobenzyl) sarcosine methyl ester (3.0 g) as red oil.

$^1$H-NMR($\delta$ ppm, CDCl$_3$) 2.36 (3H, m), 3.22 (2H, s), 3.55 (2H, s), 3.65 (2H, br), 3.70 (3H, s), 6.65 (2H, d, J=8.6 Hz), 7.11 (2H, d, J=8.6 Hz). IR(neat) $\nu$: 3364, 2949, 1744cm$^{-1}$.

REFERENCE EXAMPLE 193

In 1,2-dichloroethane (50 ml) were dissolved p-nitrobenzaldehyde (5 g) and 3-methoxypropylamine (3.1 g), and to the mixture was added, under ice-cooling, triacetoxy sodium boron hydride (9.8 g). Under nitrogen atmosphere, the mixture was stirred at room temperature for 3 hours, and to the mixture were added, under ice-cooling, 37% formalin (3 ml) and triacetoxy sodium boron hydride (9.8 g). Under nitrogen atmosphere, the mixture was stirred at room temperature for 3 hours, and to the mixture was added water. The mixture was concentrated, neutralized with sodium hydroxide solution and extracted with ethyl acetate. The organic layer was washed with water and subjected to back extraction with iN hydrochloric acid. The aqueous layer was washed with ethyl acetate, neutralized with 1N sodium hydroxide solution and extracted with ethyl acetate. The organic layer was washed with water and saturated brine, and dried with anhydrous magnesium sulfate. Under reduced pressure, the solvent was evaporated to give N-(3-methoxypropyl)-N-methyl-4-nitrobenzylamine (5.6 g) as yellow oil.

$^1$H-NMR($\delta$ ppm, CDCl$_3$) 1.72–1.85 (2H, m), 2.20 (3H, s), 2.47 (2H, t, J=7.3 Hz), 3.33 (3H, s), 3.43 (2H, t, J=6.4 Hz), 3.58 (2H, s), 7.50 (2H, d, J=9.0 Hz), 8.18 (2H, d, J=9.0 Hz). IR(neat) ν: 2805, 1605, 1520cm$^{-1}$.

REFERENCE EXAMPLE 194

In acetic acid (70 ml) was dissolved N-(3-methoxypropyl)-N-methyl-4-nitrobenzylamine (5.5 g), and to the mixture was added little by little reduced iron (6.4 g). The mixture was stirred at room temperature overnight. The solvent was evaporated, and to the residue was added ethyl acetate. The precipitates were filtered off, the filtrate was washed with sodium hydroxide solution, water and saturated brine, and dried with anhydrous magnesium sulfate. Under reduced pressure, the solvent was evaporated to give 4-((N-3-methoxypropyl-N-methyl)aminomethyl)aniline (4.4 g) as red oil.

$^1$H-NMR(δ ppm, CDCl$_3$) 1.71–1.85 (2H, m), 2.16 (3H, s), 2.42 (2H, t, J=7.4 Hz), 3.32 (3H, s), 3.37 (2H, s), 3.41 (2H, t, J=6.6 Hz), 3.61 (2H, br), 6.64 (2H, d, J=8.4 Hz), 7.08 (2H, d, J=8.4 Hz). IR(neat) ν: 2946, 2795, 1615cm$^{-1}$.

REFERENCE EXAMPLE 195

In ethanol (50 ml) was dissolved 7-(4-methylphenyl)-2,3,4,5-tetrahydro-1-benzoxepin-5-one (1 g), and to the mixture was added, under ice-cooling, sodium boron hydride (0.3 g). The mixture was stirred at room temperature for 30 minutes, and to the mixture was added water. The mixture was concentrated and extracted with ethyl acetate. The organic layer was washed with water and concentrated. The residue was dissolved in bis(2-methoxyethyl)ether (20 ml), and to the mixture was added hydrochloric acid (5 ml). The mixture was stirred at 75° C. for 1 hour, poured into water and extracted with ethyl acetate. The organic layer was washed with water and saturated brine, and dried with anhydrous magnesium sulfate. The solvent was evaporated, and the precipitated 7-(4-methylphenyl)-2,3-dihydro-1-benzoxepine (0.78 g) was filtered with hexane to give colorless crystals.

mp 98–100° C.; $^1$H-NMR(δ ppm, CDCl$_3$) 2.38 (3H, s), 2.65–2.74 (2H, m), 4.27 (2H, t, J=4.9 Hz), 6.01 (1H, dt, J=11.7, 4.4 Hz), 6.39 (1H, d, J=11.7 Hz), 7.01 (1H, d, J=8.0 Hz), 7.23 (2H, d, J=8.2 Hz), 7.31–7.38 (2H, m), 7.45 (2H, d, J=8.0 Hz). IR(KBr) ν: 3025, 1491cm$^{-1}$. Anal. Calcd. for C$_{17}$H$_{16}$O: C, 86.41; H, 6.82. Found: C, 86.17; H, 6.61.

REFERENCE EXAMPLE 196

Under ice-cooling, to dimethylformamide (0.2 ml) was added dropwise sulfuryl chloride (0.17 ml), and the mixture was stirred, under nitrogen atmosphere, at room temperature for 10 minutes. To the mixture was added 7-(4-methylphenyl)-2,3-dihydro-1-benzoxepine (0.3 g), and the mixture was stirred, under nitrogen atmosphere, at 90° C. for 3 hours. To the mixture was added ice-water, and the mixture was extracted with ethyl acetate. The organic layer was washed with water and saturated brine, and dried with anhydrous magnesium sulfate. The solvent was evaporated to give 7-(4-methylphenyl)-2,3-dihydro-1-benzoxepine-4-sulfonylchloride (0.36 g) as pale yellow crystals.

mp 162–166° C.; $^1$H-NMR(δ ppm, CDCl$_3$) 2.40 (3H, s), 3.27 (2H, t, J=4.7 Hz), 4.41 (2H, t, J=4.7 Hz), 7.11 (1H, d, J=9.6 Hz), 7.26 (2H, d, J=8.2 Hz), 7.44 (2H, d, J=8.2 Hz), 7.57–7.62 (2H, m), 7.70 (1H, s). IR(KBr) ν: 3027, 1634, 1493cm$^{-1}$. Anal. Calcd. for C$_{17}$H$_{15}$ClO$_3$S: C, 60.98; H, 4.52. Found: C, 61.14; H, 4.26.

REFERENCE EXAMPLE 197

Under argon atmosphere, a solution of ethyl (E)-3-(5-bromothiophen-2-yl)acrylate (1.00 g), 4-isopropylphenyl borate (0.86 g) and potassium carbonate (1.12 g) in toluene/ethanol/water (40/4/4 ml) was stirred at room temperature for 1 hour. To the mixture was added tetrakistriphenylphosphine palladium (0.14 g), and the mixture was refluxed for 18 hours and then cooled to room temperature. The organic layer was washed with saturated brine and dried with magnesium sulfate. Under reduced pressure, the mixture was concentrated, and the residue was purified with column chromatography (ethyl acetate/hexane=1:9) to give pale yellow crystals of methyl (E)-3-[5-(4-isopropylphenyl)-thiophen-2-yl]acrylate (0.83 g).

m.p. 117–119° C.; $^1$H-NMR (200 MHz, CDCl$_3$) δ 1.27 (6H, d, J=6.8 Hz), 2.94–3.00 (1H, m), 3.80 (3H, s), 6.22 (1H, d, J=15.8 Hz), 7.24–7.28 (4H, m), 7.54 (2H, d, J=7.8 Hz), 7.76 (1H, d, J=15.8 Hz). IR (KBr) 1718, 1622, 1436, 1306, 1230, 1203, 1165, 806 cm$^{-1}$; Anal. Calcd. for C$_{17}$H$_{18}$O$_2$S; Calcd. C, 71.30; H, 6.33; S, 11.20. Found. C, 71.22; H. 6.33; S, 11.23.

REFERENCE EXAMPLE 198

To a solution of methyl (E)-3-(5-(4-isopropylphenyl)-thiophen-2-yl]acrylate (0.75 mg) in THF/ethanol (10/10 ml) was added at room temperature 2N sodium hydroxide solution (2.0 ml), and the mixture was stirred for 20 hours. Under reduced pressure, the mixture was concentrated, and to the residue was added 1N hydrochloric acid (10 ml). The mixture was extracted with ethyl acetate, and the organic layer was washed with saturated brine, dried with magnesium sulfate and concentrated. The resulting crystals were collected by filtration to give pale yellow crystals of (E)-3-[5-(4-isopropylphenyl)thiophen-2-yl]acrylic acid (639.7 mg).

m.p. 216–219° C.; $^1$H-NMR (200 MHz, CDCl$_3$) δ 1.28 (6H, d, J=7.0 Hz), 2.86–3.01 (1H, m), 6.22 (1H, d, J=15.7 Hz), 7.23–7.33 (4H, m), 7.56 (2H, d, J=8.4 Hz), 7.85 (1H, d, J=15.7 Hz). IR (KBr) 2966, 1668, 1608, 1414, 1302, 1263, 1228, 804 cm$^{-1}$; Anal. Calcd. for C$_{16}$H$_{16}$O$_2$S; Calcd. C, 70.56; H, 5.92; S, 11.77. Found. C, 70.23; H, 5.94; S, 11.62.

REFERENCE EXAMPLE 199

Under argon atmosphere, a solution of methyl (E)-3-(5-bromothiophen-2-yl)acrylate (0.23 g), 4-tert-butylphenyl borate (0.3 g) and potassium carbonate (0.26 g) in toluene/ethanol/water (20/2/2 ml) was stirred at room temperature for 1 hour. To the mixture was added tetrakistriphenylphosphine palladium (32 mg), and the mixture was refluxed for 18 hours and then cooled to room temperature. To the organic layer was added ethyl acetate, and the mixture was washed with saturated brine and dried with magnesium sulfate. Under reduced pressure, the mixture was concentrated, and the residue was purified with column chromatography (ethyl acetate/hexane=1:9) to give pale yellow crystals of methyl (E)-3-[5-(4-tert-butylphenyl)thiophen-2-yl]acrylate (240 mg). This compound was used for the following reaction, without subjecting further purification.

$^1$H-NMR (200 MHz, CDCl$_3$) δ 1.34 (9H, s), 3.80 (3H, s), 6.22 (1H, d, J=15.8 Hz), 7.21–7.30 (2H, m), 7.42 (2H, d, J=8.7 Hz), 7.55 (2H, d, J=8.7 Hz), 7.76 (1H, d, J=15.8 Hz). IR (KBr) 1716, 1622, 1436, 1302, 1232, 1207, 1165, 972, 806 cm$^{-1}$.

REFERENCE EXAMPLE 200

To a solution of methyl (E)-3-[5-(4-tert-butylphenyl)-thiophen-2-yl]acrylate (190 mg) of THF/ethanol (15/15 ml)

was added at room temperature 2N sodium hydroxide solution (2.0 ml), and the mixture was stirred 18 hours. To the mixture was added 1N hydrochloric acid (5 ml), and the mixture was extracted with ethyl acetate. The organic layer was washed with saturated brine and dried with magnesium sulfate. Under reduced pressure, the mixture was concentrated, and the precipitated crystals were collected by filtration, which were washed with hexane to give yellow crystals of (E)-3-[5-(4-tert-butylphenyl)thiophen-2-yl] acrylic acid (149.7 mg). This compound was used for the following reaction, without subjecting further purification.

$^1$H-NMR (200 MHz, CDCl) δ 1.35 (9H, s), 6.22 (1H, d, J=15.6 Hz), 7.20–7.29 (2H, m), 7.43 (2H, d, J=8.8 Hz), 7.56 (2H, d, J=8.8 Hz), 7.85 (1H, d, J=15.6 Hz). IR (KBr) 2962, 1678, 1612, 1414, 1302, 1232, 806 cm$^{-1}$;

REFERENCE EXAMPLE 201

To a solution of 4'-methylacetophenone (10.0 g) in ethanol (100 ml) were added at room temperature an aqueous solution (50 ml) of hydroxyamine hydrochloride (7.77 g) and sodium acetate (9.63 g), and the mixture was refluxed for 24 hours and then cooled. The mixture was concentrated, and to the residue was added iN hydrochloric acid (150 ml). The mixture was extracted with ethyl acetate, washed with saturated brine and dried with magnesium sulfate. Under reduced pressure, the mixture was concentrated, and the residue was purified with column chromatography (ethyl acetate/hexane=1:3) to give colorless crystals of 4'-methylacetophenonoxime (10.89 g).

$^1$H-NMR (200 MHz, CDCl$_3$) δ 2.28 (3H, s), 2.37 (3H, s), 7.19 (2H, d, J=8.1 Hz), 7.53 (2H, d, J=8.1 Hz), 8.55–8.69 (1H, m).

REFERENCE EXAMPLE 202

To a solution of 4'-methylacetophenonoxime (10.46 g) in DMF (250 ml) was added at 0° C. sodium hydride (60%, 3.08 g), and the mixture was stirred at room temperature for 1 hour. To the mixture was added a solution of 4-fluorobenzaldehyde (9.57 g) in THF (300 ml), and the mixture was stirred for 5 days. To the mixture was added 1N hydrochloric acid (200 ml), and the mixture was extracted with ethyl acetate. The organic layer was washed with saturated brine and dried with magnesium sulfate. Under reduced pressure, the mixture was concentrated, and the residue was purified with column chromatography (ethyl acetate/hexane=1:5) to give colorless crystals of 4-(4'-methyl-α-methylbenzylideneaminoxy)benzaldehyde (11.23 g).

m.p. 96–98° C.; $^1$H-NMR (200 MHz, CDCl$_3$) δ 2.41 (3H, s), 2.47 (3H, s), 7.25 (2H, d, J=7.8 Hz), 7.43 (2H, d, J=8.8 Hz), 7.69 (2H, d, J=7.8 Hz), 7.88 (2H, d, J=8.8 Hz), 9.93 (1H, s). IR (KBr) 1699, 1597, 1576, 1498, 1232, 1207, 1149, 916, 820 cm$^{-1}$; Anal. Calcd. for C$_{16}$H$_{15}$NO$_2$; Calcd. C, 75.87; H, 5.97; N, 5.53. Found. C, 75.73; H, 6.04; N, 5.48.

REFERENCE EXAMPLE 203

A solution of 4-(4'-methyl-α-methylbenzylideneaminoxy)benzaldehyde (5.0 g) in 1N hydrochloric acid/acetic acid (80 ml) was stirred at 100–110° C. for 24 hours and then cooled to room temperature. To the mixture was added water, and the mixture was extracted with ethyl acetate. The organic layer was washed with saturated brine and dried with magnesium sulfate. Under reduced pressure, the mixture was concentrated, and the residue was purified with column chromatography (ethyl acetate/hexane=1:9) to give colorless crystals of 2-(4-methylphenyl)benzofuran-5-aldehyde (1.50 g).

m.p. 162–164° C.; $^1$H-NMR (200 MHz, CDCl$_3$) δ 2.41 (3H, s), 7.06 (1H, s), 7.28 (2H, d, J=8.0 Hz), 7.62 (1H, d, J=8.4 Hz), 7.77 (2H, d, J=8.0 Hz), 7.84 (1H, dd, J=8.4, 1.8 Hz), 8.11 (1H, d, J=1.8 Hz), 10.06 (1H, s). IR (KBr) 1697, 1292, 1271, 824, 798 cm$^{-1}$; Anal. Calcd. For C$_{16}$H$_{12}$O$_2$; Calcd. C, 81.34; H, 5.12. Found. C, 81.21; H, 5.11.

REFERENCE EXAMPLE 204

To a solution of 2-(4-methylphenyl)benzofuran-5-carbaldehyde (500 mg) and 1-methylcyclohexene (1.2 ml) in DMF (15 ml) was added a solution (9 ml) of sodium chlorite (80%, 1.5 g) and sodium dihydrogenphosphate (1.5 g) at room temperature, and the mixture was stirred for 3 hours. To the mixture was added 1N hydrochloric acid, and the mixture was extracted with ethyl acetate. The organic layer was washed with sodium thiosulfate and saturated brine, and dried with magnesium sulfate. Under reduced pressure, the mixture was concentrated, and the precipitated crystals were collected by filtration, which were washed with diethylether to give colorless crystals of 2-(4-methylphenyl)benzofuran-5-carboxylic acid (395 mg).

m.p. 279–283° C.; $^1$H-NMR (200 MHz, CDCl$_3$) δ 2.38 (3H, s), 7.34 (2H, d, J=8.2 Hz), 7.48 (1H, s), 7.70 (1H, d, J=8.8 Hz), 7.84 (2H, d, J=8.2 Hz), 7.92 (1H, dd, J=8.8, 1.2 Hz), 8.26 (1H, d, J=1.2 Hz). IR (KBr) 2989, 1689, 1416, 1291, 768 cm$^{-1}$; Anal. Calcd. for C$_{16}$H$_{12}$O$_3$; Calcd. C, 76.18; H, 4.79. Found. C, 76.11; H, 4.74.

REFERENCE EXAMPLE 205

To a solution of ethyl vanillate (2.50 g) and triethylamine (3.6 ml) in dichloromethane (50 ml) was added at 0° C. trifluoromethanesulfonic acid anhydride (2.6 ml), and the mixture was stirred for 1.5 hours. To the mixture was added water (15 ml), and the mixture was extracted with ethyl acetate. The organic layer was washed with saturated brine and dried with magnesium sulfate. Under reduced pressure, the mixture was concentrated, and the residue was purified with column chromatography (ethyl acetate/hexane=1:15) to give yellow oil of ethyl 3-methoxy-4-trifluoromethanesulfonyloxybenzoate (3.96 g).

$^1$H-NMR (200 MHz, CDCl$_3$) δ 1.41 (3H, t, J=7.1 Hz), 3.99 (3H, s), 4.41 (2H, q, J=7.1 Hz), 7.28 (1H, d, J=7.6 Hz), 7.67–7.72 (2H, m). IR (neat) 1726, 1606, 1502, 1466, 1427, 1292, 1246, 1207, 1142, 1109, 1030, 833, 768, 617 cm$^{-1}$.

REFERENCE EXAMPLE 206

To a solution of ethyl 3-methoxy-4-trifluoromethanesulfonyloxybenzoate (3.95 g), 4-methylphenylacetylene (1.54 g) and triethylamine (5.0 ml) in DMF (40 ml) was added bistriphenylphosphine palladium dichloride (0.25 g), and the mixture was stirred at 100° C. for 3 hours and then cooled to room temperature. To the mixture was added water, and the mixture was extracted with diethylether. The organic layer was washed with saturated brine and dried with magnesium sulfate. Under reduced pressure, the mixture was concentrated, and the residue was purified with column chromatography (ethyl acetate/hexane=1:9) and recrystallized from ethyl acetate/hexane to give pale yellow crystals of ethyl 3-methoxy-4-[2-(4-methylphenyl)ethynyl]-benzoate (2.02 g).

m.p. 71–73° C.; $^1$H-NMR (200 MHz, CDCl$_3$) δ 1.41 (3H, t, J=7.1 Hz), 2.37 (3H, s), 3.97 (3H, s), 4.39 (2H, q, J=7.1 Hz), 7.16 (2H, d, J=7.9 Hz), 7.47 (2H, d, J=7.9 Hz), 7.53

(1H, d, J=8.0 Hz), 7.57 (1H, d, J=1.6 Hz), 7.63 (1H, dd, J=8.0, 1.6 Hz). IR (KBr) 1711, 1410, 1294, 1236, 1099, 1036, 812, 762 cm$^{-1}$; Anal. Calcd. for $C_{19}H_{18}O_3$; Calcd. C, 77.53; H, 6.16. Found. C, 77.48; H, 6.01.

REFERENCE EXAMPLE 207

A mixture of ethyl 3-methoxy-4-(4-methylphenyl) ethynylbenzoate (1.5 g) and pyridinium chloride (9.0 g) was stirred at 200° C. for 2 hours, and then cooled to 100° C. To the mixture was added DMF (20 ml), and the mixture was cooled to room temperature. To the mixture was added 1N hydrochloric acid, and the mixture was extracted with ethyl acetate. The organic layer was washed with saturated brine and dried with magnesium sulfate. Under reduced pressure, the mixture was concentrated, and the precipitated crystals were collected by filtration, which were washed with diethylether and hexane to give pale yellow crystals of 2-(4-methylphenyl)benzofuran-6-carboxylic acid (0.84 g).

m.p. 270–272° C.; $^1$H-NMR (200 MHz, DMSO-d$_6$) δ 2.38 (3H, s), 7.35 (2H, d, J=8.2 Hz), 7.47 (1H, s), 7.72 (1H, d, J=8.0 Hz), 7.85–7.89 (3H, m), 8.11 (1H, s). IR (KBr) 2972, 1677, 1612, 1498, 1413, 1300, 1230, 798 cm$^{-1}$; Anal. Calcd. For $C_{16}H_{12}O_3$; Calcd. C, 76.18; H, 4.79. Found. C, 76.05; H, 4.54.

REFERENCE EXAMPLE 208

To a solution of ethyl 7-(4-methylthiophenyl)-2,3-dihydro-1-benzoxepine-4-carboxylate (198.5 mg) in THF (20 ml) was added at 0° C. 70% 3-chloroperbenzoic acid (317 mg), and the mixture was stirred at 0° C. for 30 minutes and then at room temperature for 1 hour. To the mixture was added sodium thiosulfate solution, and the mixture was stirred for a few minutes and then extracted with ethyl acetate. The organic layer was washed with saturated sodium bicarbonate solution and saturated brine, and dried with magnesium sulfate. Under reduced pressure, the mixture was concentrated, and the residue was purified with column chromatography (ethyl acetate/hexane=1:1) to give colorless crystals of ethyl 7-(4-methylsulfonylphenyl)-2,3-dihydro-1-benzoxepine-4-carboxylate (221.8 mg).

m.p. 150–153° C.; $^1$H-NMR (200 MHz, CDCl$_3$) δ 1.37 (3H, t, J=7.2 Hz), 3.03 (2H, t, J=4.5 Hz), 3.10 (3H, s), 4.30 (2H, q, J=7.2 Hz), 4.33 (2H, t, J=4.5 Hz), 7.10 (1H, d, J=8.4 Hz), 7.50 (1H, dd, J=8.4, 2.2 Hz), 7.60 (1H, d, J=2.2 Hz), 7.65 (1H, s), 7.75 (2H, d, J=8.4 Hz), 8.01 (2H, d, J=8.4 Hz). IR (KBr) 1693, 1595, 1485, 1302, 1252, 1230, 1213, 1146, 1092, 825 cm$^{-1}$; Anal. Calcd. for $C_{20}H_{20}O_5S$; Calcd. C, 64.50; H, 5.41; S, 8.61. Found. C, 64.36; H, 5.40; S, 8.53.

REFERENCE EXAMPLE 209

To a solution of ethyl 7-(4-methylsulfonylphenyl)-2,3-dihydro-1-benzoxepine-4-carboxylate (180 mg) in THF/ethanol (5/5 ml) was added at room temperature 1N sodium hydroxide solution (1 ml), and the mixture was stirred for 4 days. To the mixture was added 1N hydrochloric acid (10 ml), and the mixture was concentrated under reduced pressure. The residue was extracted with ethyl acetate. Under reduced pressure, the mixture was concentrated. The resulting crystals were collected by filtration, which were washed with water, ethanol and diethylether to give colorless crystals of 7-(4-methyl-sulfonylphenyl)-2,3-dihydrobenzoxepine-4-carboxylic acid (148.2 mg).

m.p. 275° C. (dec.); $^1$H-NMR (200 MHz, DMSO-d$_6$) δ 2.84–2.94 (2H, m), 3.25 (3H, s), 4.23–4.34 (2H, m), 7.10 (1H, d, J=8.4 Hz), 7.64–7.75 (2H, m), 7.92–8.04 (5H, m). IR (KBr) 3018, 1674, 1308, 1267, 1147, 829, 783, 760, 636, 546cm$^{-1}$; Anal. Calcd. for $C_{18}H_{16}O_5S\cdot 0.2H_2O$; Calcd. C, 62.13; H, 4.75; S, 9.21. Found. C, 62.19; H, 4.69; S, 9.06.

REFERENCE EXAMPLE 210

A mixture of 4-bromothiophenol (24,8 g), ethyl 4-bromobutyrate (30.7 g) and potassium carbonate (36.2 g) in DMF (100 ml) was stirred at room temperature overnight. Under reduced pressure, the solvent was evaporated, and to the residue was added water. The mixture was extracted with ethyl acetate, and the organic layer was washed with saturated brine and dried with magnesium sulfate. Under reduced pressure, the mixture was concentrated, and to the residue was were added methanol (120 ml) and 1N sodium hydroxidesolution(240 ml). The mixture was stirred at room temperature overnight, and to the mixture was added water. The mixture was washed with ethyl acetate, and to the aqueous layer was added concentrated hydrochloric acid to make the solution acidic. The mixture was extracted with ethyl acetate. The organic layer was washed with saturated brine and dried with magnesium sulfate. Under reduced pressure, the solvent was evaporated to colorless prism of 4-(4-bromophenylthio)butyric acid (31.8 g).

$^1$H-NMR(200 MHz, CDCl$_3$) δ 1.87–2.02 (2H, m), 2.53 (2H, t, J=7.1 Hz), 2.96 (2H, t, J=7.2 Hz), 7.21 (2H, d, J=8.8 Hz), 7.41 (2H, d, J=8.8 Hz). IR (KBr) 1699 cm$^{-1}$; Anal. Calcd. for $C_{10}H_{11}O_2BrS$; Calcd. C, 43.65; H, 4.03. Found. C, 43.70; H, 3.93.

REFERENCE EXAMPLE 211

A mixture of 4-(4-bromophenylthio)butyric acid (31.8 g) and polyphosphoric acid (250 g) was stirred at 100° C. for 1 hour. The mixture was added to ice/water and extracted with ethyl acetate. The organic layer was washed with saturated brine and dried with magnesium sulfate. Under reduced pressure, the solvent was evaporated to give brown prismof 7-bromo-2,3,4,5-tetrahydro-1-benzo-thiepin-5-one (13.6 g).

$^1$H-NMR(200 MHz, CDCl$_3$) δ 2.22–2.35(2H, m), 2.94–3.08(4H, m), 7.33 (1H, d, J=8.0 Hz), 7.44 (1H, dd, J=8.0, 2.6 Hz), 7.96 (1H, d, J=2.6 Hz). IR (KBr) 1682 cm$^{-1}$; Anal. Calcd. for $C_{10}H_9OBrS$; Calcd. C, 46.71; H, 3.53. Found. C, 46.71; H, 3.45.

REFERENCE EXAMPLE 212

To a solution of 7-bromo-2,3,4,5-tetrahydro-1-benzothiepin-5-one (13.5 g) in dimethyl carbonate (200 ml) was added at room temperature sodium methoxide (14.2 g), and the mixture was refluxed for 8 hours under nitrogen atmosphere. To the mixture was added 1N hydrochloric acid, and the mixture was extracted with ethyl acetate. The organic layer was washed with water and saturated brine, and dried with magnesium sulfate. Under reduced pressure, the solvent was evaporated to give brown prism of methyl 7-bromo-5-oxo-2,3,4,5-tetrahydro-1-benzothiepine-4-carboxylate (11.5 g).

$^1$H-NMR(200 MHz, CDCl$_3$) δ 2.40–2.84(6H, m), 3.16–3.27(2H, m), 3.75 (3H, s), 4.47–4.56 (1H, m), 7.33 (1H, d, J=8.4 Hz), 7.47 (1H, dd, J=8.4, 2.6 Hz), 7.99 (1H, d, J=2.6 Hz). IR (KBr) 1750 cm$^{-1}$; Anal. Calcd. for $C_{12}H_{11}O_3BrS$; Calcd. C, 45.73; H, 3.52. Found. C, 46.01; H. 3.48.

REFERENCE EXAMPLE 213

A solution of methyl 7-bromo-5-oxo-2,3,4,5-tetrahydro-1-benzothiepine-4-carboxylate (24.94 g) in THF (200 ml)

was cooled to −20° C., and to the mixture was added dropwise a solution of sodium boro hydride (2.99 g) in methanol (30 ml). While the temperature of the mixture was kept at −15 to 20° C., the mixture was stirred for 1 hour. To the mixture was added water, and the mixture was extracted with ethyl acetate. The organic layer was washed with saturated brine and dried with magnesium sulfate. Under reduced pressure, the solvent was evaporated, and the residue (24.38 g) was dissolved in THF (200 ml). To the mixture was added triethylamine (26 ml) and then to the mixture was added dropwise at 0° C. methanesulfonyl chloride (9.2 ml). The mixture was stirred at 0° C. for 30 minutes and then at room temperature for 15 hours. To the mixture was added dropwise 1,8-diaza-bicyclo[5,4,0]-7-undecene (17.9 g), and the mixture was stirred for 3 hours. To the mixture was added water, and the mixture was extracted with ethyl acetate. The organic layer was washed with water and saturated brine and dried with magnesium sulfate. Under reduced pressure, the mixture was concentrated, and the residue was purified with column chromatography (ethyl acetate/hexane=:10). Under reduced pressure, the mixture was concentrated, and the resulting crystals were recrystallized from ethyl acetate/hexane to give pale yellow crystals of methyl 7-bromo-2,3-dihydro-1-benzothiepine-4-carboxylate (11.00 g).

m.p. 94–95° C.; $^1$H-NMR (200 MHz, CDCl$_3$) 62.94–3.00 (2H, m), 3.15–3.21 (2H, m), 3.83 (3H, s), 7.28–7.33 (2H, m), 7.51 (1H, d, J=1.2 Hz), 7.70 (1H, s). Anal. Calcd. for C$_{12}$H$_{10}$O$_2$BrS; Calcd. C, 48.17; H, 3.71. Found. C, 48.37; H, 3.77.

REFERENCE EXAMPLE 214

Under argon atmosphere, a mixture of methyl 7-bromo-2,3-dihydro-1-benzothiepine-4-carboxylate (1.5 g), 4-methoxyphenyl borate (0.84 g) and potassium carbonate (1.39 g) in toluene/ethanol/water (50/5/5 ml) was stirred at room temperature for 1 hour. To the mixture was added tetrakistriphenylphosphine palladium (0.17 g), and the mixture was refluxed for 24 hours and then cooled. The mixture was extracted with ethyl acetate, washed with saturated brine and dried with magnesium sulfate. Under reduced pressure, the mixture was concentrated, and the residue was purified with column chromatography (ethyl acetate/hexane=1:15 1:9 1:4 1:2) to give pale yellow crystals of methyl 7-(4-methoxyphenyl)-2,3-dihydro-1-benzothiepine-4-carboxylate (1.40 g).

m.p. 117–120° C. $^1$H-NMR (200 MHz, CDCl$_3$) δ 2.97–3.04(2H, m), 3.19–3.25(2H, m), 3.84 (3H, s), 3.86 (3H, s), 6.98 (2H, d, J=8.8 Hz), 7.39 (1H, dd, J=8.0, 2.2 Hz), 7.48–7.54 (3H, m), 7.57 (1H, d, J=2.2 Hz), 7.88 (1H, br s). IR (KBr) 1716, 1630, 1606, 1520, 1479, 1431, 1281, 1250, 1221, 1186, 1020, 835, 814 cm$^{-1}$; Anal. Calcd. for C$_{19}$H$_{18}$O$_3$S; Calcd. C, 69.91; H, 5.56. Found. C, 70.22; H, 5.65.

REFERENCE EXAMPLE 215

To a solution of methyl 7-(4-methoxyphenyl)-2,3-dihydro-1-benzothiepine-4-carboxylate (0.50 g) in ethanol/THF (10/10 ml) was added at room temperature 1N sodium hydroxide solution (2 ml), and the mixture was stirred for 18 hours. To the mixture was added 1N hydrochloric acid (2 ml). Under reduced pressure, the mixture was concentrated. To the mixture was added water, and the precipitates were collected by filtration, which were washed with 2-propanol, diethylether and hexane to give pale yellow solid of 7-(4-methoxyphenyl)-2,3-dihydro-1-benzo-thiepine-4-carboxylic acid (508 mg). This compound was used for the following reaction, without subjecting further purification.

$^1$H-NMR (200 MHz, DMSO-d$_6$) δ 2.87 (2H, t, J=5.7 Hz), 3.11 (2H, t, J=5.7 Hz), 3.80 (3H, s), 7.01 (2H, d, J=8.8 Hz), 7.33–7.42 (2H, m), 7.50–7.55 (2H, m), 7.62 (2H, d, J=8.8 Hz). IR (KBr) 3356, 1633, 1608, 1518, 1358, 1246, 1178, 1020, 825 cm$^{-1}$;

REFERENCE EXAMPLE 216

Under argon atmosphere, a mixture of methyl 7-bromo-2,3-dihydro-1-benzothiepine-4-carboxylate (0.70 g), 4-morpholinophenyl borate (581.3 mg) and potassium carbonate (0.65 g) in toluene/ethanol/water (20/2/2 ml) was stirred at room temperature for 1 hour. To the mixture was added tetrakistriphenylphosphine palladium (0.14 g), and the mixture was refluxed for 20 hours and then cooled. The mixture was extracted with ethyl acetate, washed with saturated brine and dried with magnesium sulfate. Under reduced pressure, the mixture was concentrated, and the residue was purified with column chromatography (ethyl acetate/dichloromethane=1:4) to give yellow crystals of methyl 7-(4-morpholinophenyl)-2,3-dihydro-1-benzothiepine-4-carboxylate (664.4 mg).

m.p. 154–156° C.; $^1$H-NMR(200 MHz, CDCl$_3$) δ 2.97–3.02 (2H, m), 3.20–3.25 (6H, m), 3.84 (3H, s), 3.87–3.91 (4H, m), 6.98 (2H, d, J=8.8 Hz), 7.35–7.43 (1H, m), 7.49–7.58 (4H, m), 7.88 (1H, s). IR (KBr) 1709, 1606, 1520, 1448, 1274, 1242, 1232, 120, 926, 816 cm$^{-1}$; Anal. Calcd. for C$_{22}$H$_{23}$NO$_3$S; Calcd. C, 69.26; H, 6.08; N, 3.67. Found. C, 69.43; H, 6.01; N, 3.81.

REFERENCE EXAMPLE 217

To a solution of methyl 7-(4-morpholinophenyl)-2,3-dihydro-1-benzothiepine-4-carboxylate (0.55 g) in ethanol/THF (30/30 ml) was added at room temperature 1N sodium hydroxide solution (1.8 ml), and the mixture was stirred for 6 days and then refluxed for 2 hours. To the mixture was added 1N hydrochloric acid (1.8 ml). The resulting solid was collected by filtration, which was washed with ethanol and diethylether to give yellow powder of 7-(4-morpholinophenyl)-2,3-dihydro-1-benzo-thiepine-4-carboxylic acid (502.2 mg).

m.p. 280° C. (dec.); $^1$H-NMR (200 MHz, DMSO-d$_6$) δ 2.88 (2H, t, J=5.3 Hz), 3.05–3.25 (6H, m), 3.67–3.82 (4H, m), 7.02 (2H, d, J=8.7 Hz), 7.43–7.54 (2H, m), 7.61 (2H, d, J=8.7 Hz), 7.75 (1H, s), 7.81 (1H, s). IR (KBr) 2967, 1709, 1684, 1608, 1520, 1232, 1120, 926, 814 cm$^{-1}$; Anal. Calcd. for C$_{21}$H$_{21}$NO$_3$S; Calcd. C, 68.64; H, 5.76; N, 3.81. Found. C, 68.68; H, 5.62; N, 3.69.

REFERENCE EXAMPLE 218

Under argon atmosphere, a mixture of methyl 7-bromo-2,3-dihydro-1-benzothiepine-4-carboxylate (1.5 g), 3,4-methylenedioxyphenyl borate (0.92 g) and potassium carbonate (1.39 g) in toluene/ethanol/water (50/5/5 ml) was stirred at room temperature1 hours. To the mixture was added tetrakistriphenylphosphine palladium (0.29 g), and the mixture was refluxed for 16 hours and cooled. The mixture was extracted with ethyl acetate, washed with saturated brine and dried with magnesium sulfate. Under reduced pressure, the mixture was concentrated, and the residue was purified with column chromatography (ethyl acetate/hexane=1:2) to give pale yellow crystals of methyl 7-(3,4-methylenedioxyphenyl)-2,3-dihydro-1-benzo-thiepine-4-carboxylate (1.55 g).

m.p. 126–129° C.; $^1$H-NMR (200 MHz, CDCl$_3$) δ 2.97–3.06(2H, m), 3.19–3.24(2H, m), 3.84 (3H, s), 6.01 (2H, s), 6.88 (1H, d, J=8.8 Hz), 7.02–7.08 (2H, m), 7.35 (1H, dd, J=8.0, 1.8 Hz), 7.50 (1H, d, J=8.4 Hz), 7.53 (1H, d, J=1.8 Hz), 7.87 (1H, br s). IR (KBr) 1709, 1471, 1435, 1248, 1223, 1186, 1034, 928, 804 cm$^{-1}$; Anal. Calcd. for C$_{19}$H$_{16}$O$_4$S; Calcd. C, 67.04; H, 4.74. Found. C, 67.19; H, 4.61.

REFERENCE EXAMPLE 219

To a solution of methyl 7-(3,4-methylenedioxyphenyl)-2,3-dihydro-1-benzothiepine-4-carboxylate (0.6 g) in ethanol/THF (10/10 ml) was added at room temperature 1N sodium hydroxide solution (2 ml), and the mixture was stirred for 64 hours. To the mixture was added iN hydrochloric acid (3 ml), and the mixture was concentrated. The resulting solid was collected by filtration, which was washed with water, 2-propanol and diisopropylether to give pale yellow powder of 7-(3,4-methylenedioxyphenyl)-2,3-dihydro-1-benzothiepine-4-carboxylic acid (510.6 mg).

m.p. 227–229° C.; $^1$H-NMR (200 MHz, DMSO-d$_6$) δ 2.86–2.92 (2H, m), 3.14–3.20 (2H, m), 6.07 (2H, s), 6.99 (1H, d, J=8.2 Hz), 7.21 (1H, dd, J=8.2, 1.8 Hz), 7.33 (1H, d, J=1.8 Hz), 7.44–7.53 (2H, m), 7.77–7.82 (2H, m). IR (KBr) 2895, 1672, 1473, 1288, 1252, 1225, 1039, 933, 806 cm$^{-1}$; Anal. Calcd. for C$_{18}$H$_{14}$O$_4$S; Calcd. C, 66.24; H, 4.32. Found. C, 66.01; H, 4.44.

REFERENCE EXAMPLE 220

To a suspension of 4-phenylpiperidine (5.0 g) in acetonitrile (100 ml) was added triethylamine (8.64 ml) and then was added dropwise at 0° C. a solution of p-toluene-sulfonyl chloride (6.50 g) in acetonitrile (30 ml). The mixture was stirred at 0° C. for 2 hours. Under reduced pressure, the solvent was evaporated, and to the residue was water. The mixture was extracted with ethyl acetate, and the organic layer was washed with saturated brine and dried with magnesium sulfate. Under reduced pressure, the mixture was concentrated, and the resulting crystals were collected by filtration, which were washed with hexane to give colorless crystals of 1-(4-methylphenylsulfonyl)-4-phenylpiperidine (8.93 g).

m.p. 153–154° C.; $^1$H-NMR(200 MHz, CDCl$_3$) δ 1.83–1.95(4H, m), 2.26–2.43(3H, m), 2.45 (3H, s), 3.87–3.99 (2H, m), 7.13–7.30 (5H, m), 7.35 (2H, d, J=8.0 Hz), 7.69 (2H, d, J=8.0 Hz). IR (KBr) 1336, 1165, 1092, 933, 725, 700, 651, 577, 546 cm$^{-1}$; Anal. Calcd. for C$_{18}$H$_{21}$NO$_2$S; Calcd. C, 68.54; H, 6.71; N, 4.44. Found. C, 68.31; H, 6.64; N, 4.40.

REFERENCE EXAMPLE 221

To a solution of 1-(4-methylphenylsulfonyl)-4-phenylpiperidine (1.0 g) and 1,1-dichloromethylmethylether (0. 57 ml) in dichloromethane (5 ml) was added at 0° C. a solution of titanium tetrachloride (0.7 ml) in dichloromethane (5 ml), and the mixture was stirred at room temperature for 2 hours. The mixture was added to stirred ice/water to stop the reaction. The mixture was extracted with ethyl acetate. The organic layer was washed with sodium bicarbonate solution and saturated brine and dried with magnesium sulfate. Under reduced pressure, the mixture was concentrated, and the residue was purified with column chromatography (ethyl acetate/hexane=1:4→1:2) to give pale yellow crystals of 4-[1-(4-methylphenylsulfonyl) piperidin-4-yl]benzaldehyde (0.381 g). (469.4 mg of the starting materials were collected).

m.p. 134–137° C.; $^1$H-NMR (200 MHz, CDCl$_3$) δ 1.75–1.96 (4H, m), 2.29–2.58 (3H, m), 2.46 (3H, s), 3.90–4.03 (2H, m), 7.29–7.37 (4H, m), 7.69 (2H, d, J=8.4 Hz), 7.82 (2H, d, J=8.4 Hz), 9.97 ( 1H, s). IR (KBr) 1697, 1603, 1333, 1159, 937, 721, 581, 546 cm$^{-1}$; Anal. Calcd. for C$_{19}$H$_{21}$NO$_3$S; Calcd. C, 66.45; H, 6.16; N, 4.08. Found. C, 66.31; H, 6.08; N, 4.38.

REFERENCE EXAMPLE 222

To a suspension of (3-carboxypropyl) triphenylphosphonium bromide (16.5 g) in THF (170 ml) was added at room temperature potassium t-butoxide (8.63 g), and the mixture was stirred at 60° C. for 10 minutes and then cooled to room temperature. To the mixture was added a solution of 4-[1-(4-methylphenylsulfonyl)piperidin-4-yl] benzaldehyde (4.40 g) in THF (20 ml), and the mixture was stirred at 60° C. for 1 hour. To the mixture was added water (80 ml) and the mixture was extracted with toluene (80 ml). To the aqueous layer was added 1N hydrochloric acid to make the solution pH 3, and the mixture was extracted with ethyl acetate. The organic layer was washed three times with 2% sodium bicarbonate solution, and then with 1N hydrochloric acid and saturated brine (×3). Under reduced pressure, the mixture was concentrated, and the residue was dissolved in THF (150 ml). To the mixture was added Pd-C (0.5 g), and the mixture was stirred under hydrogen atmosphere for 5 hours. By filtration Pd-C was removed, and the filtrate was concentrated under reduced pressure. The resulting crystals were collected by filtration, which were washed with hexane to give colorless crystals of 5-[4-[1-(4-methylphenylsulfonyl)piperidin-4-yl]phenyl]pentanoic acid (4.63 g).

m.p. 164–170° C.; $^1$H-NMR(200 MHz, CDCl$_3$) δ 1.58–1.70(4H, m), 1.79–1.91(4H, m), 2.25–2.42 (5H, m), 2.45 (3H, s), 2.54–2.65 (2H, m), 3.84–3.97 (2H, m), 7.04 (2H, d, J=8.2 Hz), 7.10 (2H, d, J=8.2 Hz), 7.34 (2H, d, J=8.3 Hz), 7.68 (2H, d, J=8.3 Hz). IR (KBr) 2937, 1703, 1335, 1163, 926, 725, 546 cm$^{-1}$; Anal. Calcd. for C$_{23}$H$_{29}$NO$_4$S; Calcd. C, 66.48: H, 7.03; N, 3.37. Found. C, 66.66; H, 7.00; N, 3.50.

REFERENCE EXAMPLE 223

To a solution of 5-[4-[1-(4-methylphenylsulfonyl)-piperidin-4-yl]phenyl]pentanoic acid (0.50 g) in THF (10 ml) were added at room temperature oxalyl chloride (0.21 ml) and a drop of DMF, and the mixture was stirred for 1 hour. Under reduced pressure, the mixture was concentrated, and the residue was dissolved in dichloromethane (10 ml). To the mixture was added at 0° C. aluminum chloride (0.35 g), and the mixture was stirred at 0° C. for 30 minutes and then at room temperature for 5 minutes. The mixture was added to ice/water, and the mixture was extracted with ethyl acetate. The organic layer was washed with 1N hydrochloric acid, saturated sodium bicarbonate solution and saturated brine, and dried with magnesium sulfate. Under reduced pressure, the mixture was concentrated, and the residue was purified with column chromatography (ethyl acetate/hexane=1:2) to give colorless crystals of 3-[1-(4-methylphenylsulfonyl)-piperidin-4-yl]-6,7,8,9-tetrahydro-5H-benzocyclohepten-5-one (0.32 g).

m.p. 165–169° C.; $^1$H-NMR (200 MHz, CDCl$_3$) δ 1.74–1.93 (8H, m), 2.24–2.43 (3H, m), 2.46 (3H, s), 2.68–2.76 (2H, m), 2.85–2.95 (2H, m), 3.85–4.00 (2H, m), 7.14 (1H, d, J=8.0 Hz), 7.22 (1H, dd, J=8.0, 1.8 Hz), 7.35 (2H, d, J=8.2 Hz), 7.50 (1H, d, J=1.8 Hz), 7.68 (2H, d, J=8.2 Hz). IR (KBr) 1674, 1333, 1242, 1161, 1093, 933, 721, 546 cm$^{-1}$; Anal. Calcd. for C$_{23}$H$_{27}$NO$_3$S; Calcd. C, 69.49; H, 6.85; N, 3.52. Found. C, 69.10; H, 6.62; N, 3.71.

REFERENCE EXAMPLE 224

To a solution of 3-[1-(4-methylphenylsulfonyl)-piperidin-4-yl]-6,7,8,9-tetrahydro-5H-benzocyclohepten-5-one (3.25 g) in dimethyl carbonate (50 ml) was added at room temperature sodium methoxide (2.21 g), and the mixture was refluxed for 4.5 hours and cooled to room temperature. To the mixture was added 1N hydrochloric acid (100 ml), and the mixture was extracted with ethyl acetate. The organic layer was washed with saturated brine and dried with magnesium sulfate. Under reduced pressure, the mixture was concentrated to give crude product (3.91 g). The resulting crude product was dissolved in THF (150 ml), and to the mixture was added at −40° C. a solution of sodium boro hydride (0.31 g) in methanol (10 ml). The mixture was stirred at −10 to −20° C. for 1 hour. To the mixture was added a solution of sodium boro hydride (0.31 g) in methanol (10 ml), and the mixture was stirred for 1.5 hours. To the mixture was added acetone (2 ml), and the mixture was stirred for 30 minutes. To the mixture was added water, and the mixture was extracted with ethyl acetate. The organic layer was washed with saturated brine and dried with magnesium sulfate. Under reduced pressure, the mixture was concentrated, and the residue was dissolved in THF (40 ml). To the mixture was added triethylamine (3.42 ml). To the mixture was added at 0° C. methanesulfonyl chloride (0.95 ml), and the mixture was stirred at 0° C. for 30 minutes and then at room temperature for 30 minutes. To the mixture was added 1,8-diazabicyclo[5,4,0]-7-undecene (3.7 ml), and the mixture was stirred for 14 hours. To the mixture was added, and the mixture was extracted with ethyl acetate. The organic layer was washed with saturated brine and dried with magnesium sulfate. Under reduced pressure, the mixture was concentrated, and the residue was purified with column chromatography (ethyl acetate/hexane=1:2) to give colorless crystals of methyl 4-[1-(4-methylphenylsulfonyl)piperidin-4-yl]-6,7-dihydro-5H-benzocyclo-heptene-8-carboxylate (2.01 g).

m.p. 169–173° C.; $^1$H-NMR(200 MHz, CDCl$_3$) δ 1.75–1.92(2H, m), 1.95–2.09(2H, m), 2.26–2.43 (3H, m), 2.45 (3H, s), 2.62 (2H, t, J=6.2 Hz), 2.75–2.80 (2H, m), 3.81 (3H, s), 3.87–3.98 (2H, m), 6.98–7.10 (3H, m), 7.35 (2H, d, J=8.6 Hz), 7.65 (1H, s), 7.68 (2H, d, J=8.6 Hz). IR (KBr) 1709, 1433, 1336, 1234, 1198, 1161, 1092, 933, 721, 548 cm$^{-1}$; Anal. Calcd. for C$_{25}$H$_{29}$NO$_4$S; Calcd. C, 68.31; H, 6.65; N, 3.19. Found. C, 68.23; H, 6.60; N, 3.04.

REFERENCE EXAMPLE 225

To a solution of methyl 4-[1-(4-methylphenylsulfonyl)piperidin-4-yl]-6,7-dihydro-5H-benzocyclo-heptene-8-carboxylate (1.0 g) in ethanol/THF (20/40 ml) was added at room temperature 1N sodium hydroxide solution (2.7 ml), and the mixture was stirred for 13 hours. Under reduced pressure, the mixture was concentrated. To the mixture was added water, and the mixture was washed with ethyl acetate. To the aqueous layer was added 1N hydrochloric acid (5 ml), and the mixture was extracted with ethyl acetate/THF. The organic layer was washed with saturated brine and dried with magnesium sulfate. Under reduced pressure, the mixture was concentrated, and the resulting colorless crystals were collected by filtration, which were washed with hexane to give colorless crystals of 4-[1-(4-methylphenylsulfonyl)piperidin-4-yl]-6,7-dihydro-5H-benzocycloheptene-8-carboxylic acid (565.4 mg).

m.p. 255–257° C.; $^1$H-NMR (200 MHz, CDCl$_3$) δ 1.74–1.94 (4H, m), 1.96–2.11 (2H, m), 2.28–2.48 (3H, m), 2.46 (3H, s), 2.65 (2H, t, J=6.6 Hz), 2.78–2.84 (2H, m), 3.87–4.01 (2H, m), 7.00–7.12 (3H, m), 7.35 (2H, d, J=8.2 Hz), 7.72 (2H, d, J=8.2 Hz), 7.77 (1H, s). IR (KBr) 3008, 1674, 1352, 1294, 1273, 1255, 1163, 931, 721, 548 cm$^{-1}$; Anal. Calcd. for C$_{24}$H$_{27}$NO$_4$S; Calcd. C, 67.74; H, 6.40; N, 3.29. Found. C, 67.97; H, 6.69; N, 311.

REFERENCE EXAMPLE 226

In THF (126 ml) was dissolved 5-bromo-2-methylthiophene (10.5 g), and to the mixture was added dropwise at −78° C. 1.6N n-butyl lithium/hexane (40.8 ml). The mixture was stirred for 1 hour, and to the mixture was added dropwise a solution of trimethyl borate (18.5 g) in THF (40 ml). The mixture was stirred for 15 minutes and warmed to room temperature. To the mixture was added 10% sulfuric acid (63 ml), and the mixture was stirred for 15 minutes. The mixture was extracted with ethyl acetate, washed with saturated brine and dried with magnesium sulfate. Under reduced pressure, the solvent was removed, and the resulting residue was washed with isopropylether to give 5-methyl-2-thienyl borate (4.6 g).

$^1$H-NMR (200 MHz, CDCl$_3$) δ 2.59 (3H, s),6.93 (1H, d, J=3.4 Hz), 7.79 (1H, d, J=3.4 Hz).

REFERENCE EXAMPLE 227

In toluene/ethanol/water (10/1/1) (24 ml) was dissolved methyl 7-bromo-2,3-dihydro-1-benzoxepine-4-carboxylate (560 mg), and to the mixture were added 5-methyl-2-thienyl borate (875 mg) and potassium carbonate (1.56 g). The mixture was stirred at room temperature for 30 minutes. To the mixture was added tetrakistriphenylphosphine palladium (260 mg), and the mixture was stirred at 100° C. for 24 hours and cooled to room temperature. The mixture was extracted with ethyl acetate, washed with saturated brine and dried with magnesium sulfate. Under reduced pressure, the solvent was removed, and the resulting residue was purified with silica gel column chromatography (hexane/acetone=12/1) to give methyl 7-(5-methyl-2-thienyl)-2,3-dihydro-1-benzoxepine-4-carboxylate (345 mg).

$^1$H-NMR (200 MHz, CDCl$_3$) δ 2.28 (3H, s), 2.99 (2H, t, J=4.8 Hz), 3.83 (3H, s), 4.28 (2H, t, J=4.8 Hz), 6.82 (1H, d, J=1.2 Hz), 7.05 (1H, d, J=8.4 Hz), 7.45 (1H, dd, J=8.4, 2.4), 7.54 (1H, d, J=2.4 Hz), 7.61 (1H, s).

REFERENCE EXAMPLE 228

In THF (10.5 ml) and methanol (5.2 ml) was dissolved methyl 7-(5-methyl-2-thienyl)-2,3-dihydro-1-benzoxepine-4- carboxylate (525 mg), and to the mixture was added 1N sodium hydroxide (10.5 ml). The mixture was stirred at room temperature for 2 hours. Under reduced pressure, the organic solvent was removed, and to the residue was added ethyl acetate. The mixture was extracted with water, and to the aqueous layer was added 6N hydrochloric acid to make the solution pH 4–5, which was extracted with ethyl acetate, washed with saturated brine and dried with magnesium sulfate. Under reduced pressure, the solvent was removed to give 7-(5-methyl-2-thienyl)-2,3-dihydro-1-benzoxepine-4-carboxylic acid (410 mg).

$^1$H-NMR (200 MHz, DMSO-d$_6$) δ 2.23 (3H, s), 2.87 (2H, t, J=4.4 Hz), 4.24 (2H, t, J=4.4 Hz), 6.99 (1H, d, J=8.4 Hz), 7.07 (1H, s), 7.31 (1H, d, J=1.4 Hz), 7.49 (1H, dd, J=8.4, 2.2 Hz), 7.58 (1H, s), 7.74 (1H, d, J=2.2 Hz).

REFERENCE EXAMPLE 229

In toluene/ethanol/water (10/1/1) (12 ml) was dissolved methyl 7-bromo-2,3-dihydro-1-benzoxepine-4-carboxylate (700 mg), and to the mixture were added 3-thienyl borate (422 mg) and potassium carbonate (0.98 g). The mixture was stirred at room temperature for 30 minutes, and to the mixture was added tetrakistriphenylphosphine palladium (136 mg). The mixture was stirred at 100° C. for 13 hours and cooled to room temperature, and the mixture was extracted with ethyl acetate, washed with saturated brine and dried with magnesium sulfate. Under reduced pressure, the solvent was removed, and the resulting residue was purified with silica gel column chromatography (hexane/acetone=3/1) to give methyl 7-(3-thienyl)-2,3-dihydro-1-benzoxepine-4-carboxylate (610 mg).

$^1$H-NMR (200 MHz, CDCl$_3$) δ 3.00 (2H, t, J=4.2 Hz), 3.83 (3H, s), 4.30 (2H, t, J=4.2 Hz), 7.01 (1H, d, J=8.4 Hz), 7.33–7.40 (3H, m), 7.49 (1H, dd, J=8.4. 2.4), 7.66 (1H, d, J=2.4 Hz), 7.64 (1H, s).

REFERENCE EXAMPLE 230

In THF (24 ml) and methanol (6 ml) was dissolved methyl 7-(3-thienyl)-2,3-dihydro-1-benzoxepine-4-carboxylate (610 mg), and to the mixture was added 1N sodium hydroxide (12 ml). The mixture was stirred at room temperature for 3 hours. Under reduced pressure, the organic solvent was removed, and to the residue was added ethyl acetate. The mixture was extracted with water, and to the aqueous layer was added 6N hydrochloric acid to make the solution pH 4–5, which was extracted with ethyl acetate, washed with saturated brine and dried with magnesium sulfate. Under reduced pressure, the solvent was removed to give 7-(3-thienyl)-2,3-dihydro-1-benzoxepine-4-carboxylic acid (500 mg).

$^1$H-NMR (200 MHz, DMSO-d$_6$) δ 2.87 (2H, t, J=4.6 Hz), 4.24 (2H, t, J=4.6 Hz), 7.00 (1H, d, J=8.4 Hz), 7.60–7.85 (4H, m), 7.84–7.89 (2H, m).

REFERENCE EXAMPLE 231

In ether (160 ml) was dissolved 3-methylthiophene (20 g), and to the mixture was added N,N,N,N-tetramethylethylenediamine (26 g). To the mixture was added dropwise at room temperature 1.6N n-butyl lithium/hexane (140 ml), and the mixture was refluxed for 30 minutes. The mixture was cooled to −70° C., and to the mixture was added dropwise a solution of trimethyl borate (63.5 g) in THF (64 ml). The mixture was stirred for 30 minutes and warmed to room temperature. To the mixture was added 10% sulfuric acid (285 ml), and the mixture was stirred for 15 minutes. The mixture was washed with water and dried with magnesium sulfate. Under reduced pressure, the solvent was removed, and the resulting residue was washed with isopropylether to give 4-methyl-2-thienyl borate (6.0 g).

$^1$H-NMR(200 MHz, CDCl$_3$) δ 2.36 (3H, s), 7.35 (1H), 7.78 (1H, s)

REFERENCE EXAMPLE 232

In toluene/ethanol/water (10/1/1) (8.4 ml) was dissolved methyl 7-bromo-2,3-dihydro-1-benzoxepine-4-carboxylate (500 mg), and to the mixture were added 4-methyl-2-thienyl borate (334 mg) and potassium carbonate (651 g). The mixture was stirred at room temperature for 30 minutes, and to the mixture was added tetrakistriphenylphosphine palladium (97 mg). The mixture was stirred at 100° C. for 24 hours and cooled to room temperature. The mixture was extracted with ethyl acetate, washed with saturated brine and dried with magnesium sulfate. Under reduced pressure, the solvent was removed, and the resulting residue was purified with silica gel column chromatography (hexane/acetone=8/1) to give methyl 7-(4-methyl-2-thienyl)-2,3-dihydro-1-benzoxepine-4-carboxylate (432 mg).

$^1$H-NMR (200 MHz, CDCl$_3$) δ 2.28 (3H, s), 2.99 (2H, t, J=4.8 Hz), 3.83 (3H, s), 4.28 (2H, t, J=4.8 Hz),6.82 (1H, d, J=1.2 Hz), 7.05 (1H, d,,J=8.4 Hz), 7.45 (1H, dd, J=8.4,2.4 Hz), 7.54 (1H, d, J=2.4 Hz), 7.61 (1H, s).

REFERENCE EXAMPLE 233

In THF (10 ml) was dissolved methyl 7-(4-methyl-2-thienyl)-2,3-dihydro-1-benzoxepine-4-carboxylate (420 mg), and to the mixture was added 1N sodium hydroxide (8.4 ml). The mixture was stirred at room temperature for 15 hours. Under reduced pressure, the organic solvent was removed, and to the residue was added ethyl acetate. The mixture was extracted with water, and to the aqueous layer was added 6N hydrochloric acid to make the solution pH 4–5, which was extracted with ethyl acetate, washed with saturated brine and dried with magnesium sulfate. Under reduced pressure, the solvent was removed to give 7-(4-methyl-2-thienyl)-2,3-dihydro-1-benzoxepine-4-carboxylic acid (320 mg).

$^1$H-NMR (200 MHz, DMSO-d$_6$) δ 2.23 (3H, s), 2.87 (2H, t, J=4.4 Hz), 4.24 (2H, t, J=4.4 Hz), 6.99 (1H, d, J=8.4 Hz), 7.07 (1H, s), 7.31 (1H, d, J=1.4 Hz), 7.49 (1H, dd, J=8.4, 2.2 Hz), 7.58 (1H, s), 7.74 (1H, d, J=2.2 Hz).

REFERENCE EXAMPLE 234

To methyl 7-bromo-2,3-dihydro-1-benzoxepine-4-carboxylate (500 mg) were added 4-fluorophenyl borate (272 mg), potassium carbonate (537 mg), water (1.5 ml), ethanol (1.5 ml) and toluene (15 ml). Under argon atmosphere, the mixture was stirred at room temperature for 1 hour, and to the mixture was added tetrakistriphenylphosphine palladium (61 mg, 3 mol %). Under argon atmosphere, the mixture was ref luxed for 21 hours, and to the mixture was added ethyl acetate (100 ml). The mixture was washed with water (50 ml) and saturated brine (50 ml), and dried with anhydrous magnesium sulfate. Under reduced pressure, the solvent was removed, and the residue was purified with silica gel column chromatography to give methyl 7-(4-fluorophenyl)-2,3-dihydro-1-benzoxepine-4-carboxylate (310 mg, 59%) as pale yellow crystals.

$^1$H NMR (200 MHz, CDCl$_3$) δ 3.01 (2H, t, J=4.1 Hz), 3.83 (3H, s), 4.31 (2H, t, J=4.8 Hz), 7.03–7.17 (3H, m), 7.40–7.54 (4H, m), 7.66 (1H, s).

REFERENCE EXAMPLE 235

To methyl 7-(4-fluorophenyl)-2,3-dihydro-1-benzoxepine-4-carboxylate (0.27 g) were added THF (5.0 ml), ethanol (10.0 ml) and 2N sodium hydroxide solution (1.0 ml), and the mixture was stirred at room temperature for 19 hours. Under reduced pressure, the solvent was removed, and the residue was diluted with water (100 ml). The aqueous layer was made acidic with hydrochloric acid, and the mixture was extracted with ethyl acetate (100 ml). The organic layer was dried with anhydrous magnesium sulfate, and the solvent was removed under reduced pressure. The residue was crystallized and washed with hexane to give 7-(4-fluorophenyl)-2,3-dihydro-1-benzoxepine-4-carboxylic acid (0.22 g, 86%) as white crystals.

$^1$H NMR (200 MHz, CDCl$_3$) δ 3.03 (2H, t, J=4.8 Hz), 4.33 (2H, t, J=4.6 Hz), 7.05–7.17 (3H, m), 7.43–7.55 (4H, m), 7.76 (1H, s).

REFERENCE EXAMPLE 236

To 4-bromophenoxybutyric acid (75.0 g) was added polyphosphoric acid (873 g), and the mixture was stirred at 100° C. for 45 minutes. The mixture was poured into ice (about 1.5 kg), and the mixture was extracted with ethyl acetate (1.5 L and 0.5 L). The organic layer was washed with water (400 ml×3), 1N sodium hydroxide solution (400 ml×2), saturated sodium hydrogen carbonate solution (400 ml×2), water (400 ml×3) and saturated brine (400 ml×3), and dried with anhydrous magnesium sulfate. The solvent was removed under reduced pressure to give 7-bromo-2,3,4,5-tetrahydro-1-benzoxepin-5-one (38.6 g, 55%, 132.5° C./0.33 mmHg) as pale yellow oil.

REFERENCE EXAMPLE 237

To a solution of 5-bromo-2-fluorobenzaldehyde (0.49 g, 2.62 mmol) and ethyl 3-mercaptopropionate (0.37 ml, 2.88 mmol) in N,N-dimethylformamide (10 ml) was added potassium carbonate (0.90 g, 6.55 mmol), and the mixture was stirred at room temperature for 1 hour and then at 70° C. for 15 hours. The mixture was poured into ice-water, and made pH 4 with 1N hydrochloric acid. The aqueous layer was extracted with ethyl acetate, and the organic layer was washed with water and saturated brine, and dried with magnesium sulfate. The solvent was evaporated, and the residue was purified with silica gel column chromatography [hexane:ethyl acetate (5:1)] to give ethyl 6-bromo-2H-thiochromene-3-carboxylate (0.45 g, 58%) as yellow powder, a part of which was recrystallized from ethanol to give pale yellow needles.

m.p. 87° C.; $^1$H-NMR (CDCl$_3$) δ: 7.47 (1H, br s), 7.26–7.38 (2H, m), 7.14 (1H, d, J=8.0), 4.31 (2H, q, J=7.4), 3.73 (2H, d, J=1.2), 1.36 (3H, d, J=7.4). Anal. Calcd for C$_{12}$H$_{11}$BrO$_2$S: C; 48.17, H; 3.71. Found: C; 48.07, H; 3.77.

REFERENCE EXAMPLE 238

A solution of ethyl 6-bromo-2H-thiochromene-3-carboxylate (1.00 g, 3.34 mmol), 4-methylphenyl borate (0.55 g, 4.01 mmol) and tetrakistriphenylphosphine palladium (0.19 g, 0.167 mmol) in 2M sodium carbonate (3.5 ml), ethanol (3 ml) and toluene (25 ml) was stirred at 80° C. for 24 hours. To the mixture was added water, and the mixture was extracted with ethyl acetate. The organic layer was washed with 0.5N hydrochloric acid and saturated brine, and dried with magnesium sulfate. The solvent was evaporated, and the residue was purified with silica gel column chromatography [hexane:ethyl acetate (5:1)] to give ethyl 6-(4-methylphenyl)-2H-thiochromene-3-carboxylate (1.02 g, 99%) as yellow powder.

m.p. 87° C.; $^1$H-NMR (CDCl$_3$) δ: 7.62 (1H, br s), 7.40–7.46 (4H, m), 7.22–7.31 (3H, m), 4.31 (2H, q, J=7.0), 3.77 (2H, d, J=1.0), 2.40 (3H, s), 1.37 (3H, t, J=7.0). Anal. Calcd for C$_{19}$H$_{18}$O$_2$S: C; 73.52, H; 5.84. Found: C; 73.51, H; 5.65.

REFERENCE EXAMPLE 239

To a solution of ethyl 6-(4-methylphenyl)-2H-thiochromene-3-carboxylate (2.12 g, 6.84 mmol) in tetrahydrofuran (20 ml) and acetonitrile (20 ml) was added dropwise 1N sodium hydroxide (7 ml), and the mixture was stirred at 60° C. for 2.5 hours. The solvent was evaporated, and the residue was dissolved in diethylether. The mixture was extracted with water. The organic layer was extracted with 0.5N sodium hydroxide, and both of the aqueous layers were made pH 3 with 6N hydrochloric acid. The mixture was extracted with ethyl acetate, and the organic layer was washed with saturated brine and dried with magnesium sulfate. The solvent was evaporated to give 6-(4-methylphenyl)-2H-thiochromene-3-carboxylic acid (1.83 g, 95%) as yellow powder.

m.p. 244° C.; $^1$H-NMR (DMSO-d$_6$) δ: 7.44 (1H, d, J=1.8), 7.21–7.32 (4H, m), 7.05 (1H, d, J=8.4), 6.95 (2H, d, J=8.2), 3.41 (2H, d, J=1.0), 2.02 (3H, s). Anal. Calcd for C$_{17}$H$_{14}$O$_2$S.0.25H$_2$O: C; 71.18, H; 5.09. Found: C; 70.90, H; 4.80.

REFERENCE EXAMPLE 240

To asolution of 4-nitrobenzaldehyde (6.0 g, 37.7 mmol) and ethyl β-aminopropionate hydrochloride (6.1 g, 37.7 mmol) in 1,2-dichloroethane (120 ml) was added triethylamine (5.3 ml, 37.7 mmol) and at 0° C. was added little by little triacetoxy boro hydride (11.8 g, 52.8 mmol). The mixture was stirred at room temperature for 1 hour, and to the mixture was added 37% formalin (4.0 ml, 49.0 mmol) and then at 0° C. triacetoxy boro hydride (11.8 g, 52.8 mmol). The mixture was stirred at room temperature for 14 hours, and the mixture was neutralized with saturated sodium hydrogen carbonate and extracted with dichloromethane. The extract was washed with saturated brine and dried with magnesium sulfate. The solvent was evaporated to give crude product, which was purified with silica gel column chromatography [hexane:ethyl acetate (3:2)] to give ethyl 3-(N-methyl-N-(4-nitrobenzyl))aminopropionate (9.34 g, 93%) as pale yellow oil.

$^1$H-NMR (CDCl$_3$) δ: 8.17 (2H, dd, J=8.8, 1.8), 7.49 (2H, d, J=8.8), 4.15 (2H, q, J=7.4), 3.61 (2H, s), 2.76 (2H, t, J=7.2), 2.52 (2H, t, J=7.2), 2.22 (3H, s), 1.26 (3H, t, J=7.4). Anal. Calcd for C$_{13}$H$_{18}$N$_2$O$_4$: C; 58.63, H; 6.81, N; 10.52. Found: C; 58.24, H; 6.78, N; 10.23.

REFERENCE EXAMPLE 241

To a solution of 4-nitrobenzaldehyde (2.0 g, 13.2 mmol) and 2-methoxyethylamine (1.15 ml, 13.2 mmol) in 1,2-dichloroethane (40 ml) was added triethylamine (1.9 ml), and at 0° C. was added little by little triacetoxy boro hydride (4.1 g). The mixture was stirred at room temperature for 1 hour was stirred, and to the mixture was added 37% formalin (1.4 ml) and then at 0° C. triacetoxy boro hydride (4.1 g). The mixture was stirred at room temperature for 14 hours, neutralized with saturated sodium hydrogen carbonate solution and extracted with dichloromethane. The extract was washed with saturated brine and dried with magnesium sulfate. The solvent was evaporated to give crude product which was purified with silica gel column chromatography [hexane:ethyl acetate (1:2)] to give 4-((N-(2-methoxyethyl)-N-methyl)aminomethyl)nitrobenzene (2.75 g, 93%) as pale yellow oil.

$^1$H-NMR (CDCl$_3$) δ: 8.18 (2H, d, J=8.8), 7.53 (2H, d, J=8.8), 3.66 (2H, s), 3.53 (2H, t, J=5.6), 3.35 (3H, s), 2.63 (2H, t, J=5.6), 2.28 (3H, s). Anal. Calcd for C$_{14}$H$_{20}$N$_2$O$_3$: C; 63.62, H; 7.63, N; 10.60. Found: C; 63.54, H; 7.59, N; 10.51.

REFERENCE EXAMPLE 242

To a solution of 4-nitrobenzaldehyde (1.76 g, 11.7 mmol) and 4-aminocyclohexanol (1.34 g, 13.2 mmol) in 1,2-dichloroethane (30 ml) was added triethylamine (1.6 ml) and at 0° C. was added little by little triacetoxy boro hydride (3.7 g). The mixture was stirred at room temperature for 1 hour, and to the mixture was added 37% formalin (1.2 ml) and then at 0° C. triacetoxy boro hydride (3.7 g). The mixture was stirred at room temperature for 14 hours, neutralized with saturated sodium hydrogen carbonate and extracted with dichloromethane. The extract was washed with saturated brine and dried with magnesium sulfate. The solvent was evaporated to give crude product, which was purified with silica gel column chromatography [ethyl acetate:ethanol (2:1)] to give (E)-4-((N-(4-hydroxy-cyclohexyl)-N-methyl)aminomethyl)nitrobenzene (2.08 g, 67%) as pale yellow crystals, a part of which was recrystallized from ether/hexane to give pale yellow needles.

m.p. 87° C.; $^1$H-NMR (CDCl$_3$) δ: 8.17 (2H, d, J=8.6), 7.51 (2H, d, J=8.6), 3.51–3.65 (1H, m), 2.39–2.56 (1H, m), 2.18 (3H, s), 1.83–2.12 (4H, m), 1.20–1.51 (4H, m). Anal. Calcd for C$_{14}$H$_{20}$N$_2$O$_3$: C; 63.62, H; 7.63, N; 10.68. Found: C; 63.54, H; 7.59, N; 10.51.

REFERENCE EXAMPLE 243

To a solution of (E)-4-((N-(4-hydroxycyclohexyl)-N-methyl)aminomethyl)nitrobenzene (1.07 g, 4.05 mmol) in ethyl acetate (30 ml) was added 5%-Pd/C (0.43 g), and the mixture was stirred under hydrogen atmosphere for 3.5 hours. The mixture was filtered with sellaite, and the filtrate was concentrated. The resulting residue was purified with silica gel column chromatography [ethyl acetate:methanol:triethylamine (9:1:0.02) to give (E)-4-((N-(4-hydroxy-cyclohexyl)-N-methyl)aminomethyl)aniline (0.27 g, 28%) as yellow powder.

m.p. 105° C.; $^1$H-NMR (CDCl$_3$) δ: 7.09 (2H, d, J=8.6), 6.65 (2H, d, J=8.6), 3.46–3.70 (1H, m), 3.45 (2H, s), 2.35–2.53 (1H, m), 2.16 (3H, s), 1.84–2.10 (4H, m), 1.19–1.51 (4H, m).

REFERENCE EXAMPLE 244

To a solution of ethyl 3-(N-methyl-N-(4-nitrobenzyl)) aminopropionate (1.51 g, 5.68 mmol) in acetic acid (30 ml) was added iron (1.27 g, 22.7 mmol), and the mixture was stirred for 14 hours. The solvent was evaporated, and the precipitates were filtered with sellaite and washed with ethyl acetate. The filtrate was diluted with water, made basic with potassium carbonate and extracted with ethyl acetate. The extracted was washed with saturated brine and dried with magnesium sulfate. The solvent was evaporated, and the residue was purified with silica gel column chromatography [ethyl acetate:ethanol (2:1)] to give ethyl 3-(N-methyl-N-(4-aminobenzyl))aminopropianate (0.70 g, 52%) as brown oil.

$^1$H-NMR (CDCl$_3$) δ: 7.07 (2H, d, J=8.6), 6.64 (2H, d, J=8.6), 4.13 (2H, q, J=6.8), 3.41 (2H, s), 3.30–3.60 (2H, m), 2.73 (2H, t, J=7.4), 2.51 (2H, t, J=7.4), 2.19 (3H, s), 1.25 (3H, t, J=6.8).

REFERENCE EXAMPLE 245

To a solution of 4-((N-(2-methoxyethyl)-N-methyl) aminomethyl)nitrobenzene (1.1 g, 4.91 mmol) in acetic acid (20 ml) was added iron (1.1 g, 19.6 mmol), and the mixture was stirred for 15 hours. The solvent was evaporated, and the precipitates were filtered with sellaite and washed with ethyl acetate. The filtrate was diluted with water, made basic with potassium carbonate and extracted with ethyl acetate. The extract was washed with saturated brine and dried with magnesium sulfate. The solvent was evaporated, and the residue was purified with silica gel column chromatography [ethyl acetate:methanol:triethylamine (7:1:0.02)] to give 4-((N-(2-methoxyethyl)-N-methyl)aminomethyl)aniline (880 mg, 92%) as brown oil.

$^1$H-NMR (CDCl$_3$) δ: 7.09 (2H, d, J=8.4), 6.64 (2H, d, J=8.4), 3.50 (2H, t, J=5.8), 3.45 (2H, s), 3.33 (3H, s), 2.57 (2H, t, J=5.8), 2.24 (3H, s).

REFERENCE EXAMPLE 246

To a solution of 4-nitrobenzaldehyde (6.04 g, 40.0 mmol), N-methylethanolamine (3.00 g, 40.0 mmol) and triethylamine (5.6 ml, 40.0 mmol) in tetrahydrofuran (200 ml) was added triacetoxy boro hydride (26.8 g, 120 mmmol), and the mixture was stirred for 21 hours. The mixture was diluted with ethyl acetate, and washed with saturated sodium hydrogen carbonate and saturated brine. The extract was dried, and the solvent was evaporated to give crude product, which was purified with silica gel column chromatography [ethyl acetate:ethanol (4:1)] to give 4-((N-(2-hydroxyethyl)-N-methyl)nitrobenezene (7.08 g, 84%) as yellow oil.

$^1$H-NMR (CDCl$_3$) δ: 8.20 (2H, d, J=8.8), 7.50 (2H, d, J=8.8), 3.68 (2H, s), 3.68 (2H, t, J=5.6), 2.64 (2H, t, J=5.6), 2.52–2.70 (1H, m), 2.26 (3H, s).

REFERENCE EXAMPLE 247

To a solution of 4-((N-(2-hydroxyethyl)-N-methyl) aminomethyl)nitrobenzene (2.95 g, 14.1 mmol) in acetic acid (60 ml) was added iron (3.14 g, 56.2 mmol), and the mixture was stirred for 23 hours. The solvent was evaporated, and the precipitates were filtered with sellaite and washed with ethyl acetate. The filtrate was diluted with water, made pH 10 with potassium carbonate and extracted with ethyl acetate. The extract was washed with saturated brine and dried with magnesium sulfate. The solvent was evaporated, and the residue was purified with silica gel column chromatography [ethyl acetate:methanol:triethylamine (5:1:0.3)] to give 4-((N-(2-hydroxyethyl)-N-methyl) aminomethyl)aniline (1.25 g, 49%) as brown oil.

$^1$H-NMR (CDCl$_3$) δ: 7.07 (2H, d, J=8.4), 6.65 (2H, d, J=8.4), 3.61 (2H, t, J=5.2), 3.46 (2H, s), 2.57 (2H, t, J=5.2), 2.20 (3H, s).

REFERENCE EXAMPLE 248

To THF(60 ml) was added at −70° C. n-butyllithium (1.59M hexane solution, 63 ml, 100 mmol). To the mixture was added dropwise (taking about 1 hour) a solution of 2,6-dibromopyridine (23.69 g, 100 mmol) in THF (140 ml) at −60° C., and the mixture was stirred at −70° C. for 15 minutes. To the mixture was added DMF (12 ml), and the mixture was stirred at the same temperature for 15 minutes. To the mixture was added 20% ammonium chloride solution (100 ml), and the organic layer was separated. The aqueous layer extracted with ethyl acetate (100 ml), and the organic layer was mixed with the previous organic layer. The organic layer was dried with anhydrous sodium sulfate and concentrated under reduced pressure. The residue was purified with column chromatography (silica gel 150 g, ethyl acetate/hexane=1/20), and the desired fraction was concentrated under reduced pressure. To the residue was added diisopropylether (15 ml), and insoluble materials were filtered, which were washed with diisopropylether (5 ml×3) and dried under reduced pressure to give 6-bromo-2-pyridinecarbaldehyde (2.05 g, 11.0 mmol, 11%).

IR (KBr): 1732 cm$^{-1}$. $^1$H-NMR (CDCl$_3$) δ: 7.65–8.00 (3H, m), 10.01 (1H, s).

REFERENCE EXAMPLE 249

In THF (10 ml) was suspended sodiumhydride (60%, 440 mg, 11.0 mmol), and to the mixture was added at −30° C. a solution of diethylphosphonoethyl acetate (2.47 g, 11.0 mmol) in THF (10 ml). The mixture was stirred at the same temperature for 30 minutes, and to the mixture was added at −30° C. a solution of 6-bromo-2-pyridinecarbaldehyde (1.86 g, 10.0 mmol) in THF (10 ml). While warming the temperature of the mixture from −30° C. to −10° C., the mixture was stirred for 1.5 hours. To the mixture was added diethylether (40 ml), and the mixture was washed with water (20 ml, 5 ml×2) and saturated brine (5 ml). The organic layer was dried with anhydrous magnesium sulfate and concentrated under reduced pressure. To the residue was added hexane (10 ml), and the mixture was cooled to 0° C. The precipitated insoluble materials were filtered, which were washed with hexane cooled to 0° C., and dried under reduced pressure to give ethyl 6-bromo-2-pyridineacrylate (2.00 g, 7.81 mmol, 78%).

IR (KBr): 1717, 1703 cm$^{-1}$. $^1$H-NMR (CDCl$_3$) δ: 1.34 (3H, t, J=7.1 Hz), 4.28 (2H, q, J=7.1 Hz), 6.96 (1H, d, 15.8 Hz), 7.30–7.65 (4H, m).

REFERENCE EXAMPLE 250

In 1,2-dimethoxyethane (4 ml) were dissolved ethyl 6-bromo-2-pyridineacrylate (512 mg, 2.00 mmol) and 4-methylphenyl borate (299 mg, 2.20 mmol), and to the mixture were added sodium carbonate (424 mg, 4.00 mmol), water (2 ml) and tetrakis-(triphenylphosphine)palladium (116 mg, 0.10 mmol). The mixture was stirred at 80° C. for 10 hours. To complete the reaction, 4-tolyl borate (150 mg, 1.10 mmol) and tetrakis(triphenyl-phosphine)palladium (116 mg, 0.10 mmol) were added at 80° C. to the mixture, and the mixture was stirred for 14 hours. To the mixture was added ethyl acetate (30 ml), and the mixture was water (5 ml×2) and saturated brine (5 ml). The organic layer was dried with anhydrous magnesium sulfate and concentrated under reduced pressure. The residue was purified with column chromatography (silica gel 15 g, ethyl acetate/hexane=1/19), and the desired fraction was concentrated under reduced pressure to give ethyl 6-(4-methylphenyl)-2-pyridineacrylate (495 mg, 1.85 mmol, 93%).

IR (KBr): 1713 cm$^{-1}$. $^1$H-NMR (CDCl$_3$) δ: 1.36 (3H, t, J=7.1 Hz), 2.42 (3H, s), 4.30 (2H, q, J=7.1 Hz), 7.10 (1H, d, 15.6 Hz), 7.25–7.35 (3H, m), 7.65–7.85 (3H, m), 7.99 (2H, d, J=8.2 Hz).

REFERENCE EXAMPLE 251

In methanol (5 ml) was suspended ethyl 6-(4-methylphenyl)-2-pyridineacrylate (465 mg, 1.74 mmol), and to the mixture was added at 0° C. 1N sodium hydroxide solution (5.22 ml). The mixture was stirred at room temperature for 20 hours. To the mixture was added at 0° C. 1N hydrochloric acid (5.22 ml), and methanol was evaporated under reduced pressure. The aqueous layer extracted with ethyl acetate (30 ml, 20 ml). The organic layer was dried with anhydrous sodium sulfate and concentrated under reduced pressure. To the residue was added diisopropylether(5 ml), and Insoluble materials were filtered, which were washed with diisopropylether and dried under reduced pressure to give 6-(4-methylphenyl)-2-pyridineacrylic acid (344 mg, 1.44 mmol, 83%).

$^1$H-NMR (CDCl$_3$) δ: 2.43 (3H, s), 7.15 (1H, d, 15.5 Hz), 7.25–7.40 (1H, m), 7.31 (2H, d, J=8.5 Hz), 7.70–7.85 (2H, m), 7.84 (1H, d, J=15.5 Hz), 8.00 (2H, d, J=8.5 Hz).

REFERENCE EXAMPLE 252

In 1,2-dimethoxyethane(12 ml) were dissolved methyl 7-bromo-2,3-dihydro-1-benzoxepine-4-carboxylate (566 mg, 2.00 mmol) and 3,4-methylenedioxyphenyl borate (465 mg, 2.80 mmol). To the mixture were added sodium carbonate (424 mg, 4.00 mmol), water (2 ml) and tetrakis (triphenylphosphine)palladium (162 mg, 0.14 mmol), and the mixture was stirred at 80° C. for 14 hours. To the mixture was added ethyl acetate (30 ml), and the mixture was extracted with water (5 ml×2) and saturated brine (5 ml). The organic layer was dried with anhydrous magnesium sulfate and concentrated under reduced pressure. The residue was purified with column chromatography (silica gel 15 g, ethyl acetate/hexane=1/19), and the desired fraction was concentrated under reduced pressure. To the residue was added diisopropylether, and the insoluble materials were filtered, which were washed with diisopropylether and dried under reduced pressure to give methyl 7-(3,4-methylenedioxyphenyl)-2,3-dihydro-1-benzoxepine-4-carboxylate (434 mg, 1.34 mmol, 67%).

IR (KBr): 1705 cm$^{-1}$. $^1$H-NMR (CDCl$_3$) δ: 2.95–3.10 (2H, m), 3.83 (3H, s), 4.25–4.35 (2H, m), 6.01 (2H, s), 6.87 (1H, d, J=8.6 Hz), 6.95–7.10 (3H, m), 7.40 (1H, dd, J=8.4, 2.4 Hz), 7.47 (1H, d, J=2.2 Hz), 7.65 (1H, s).

REFERENCE EXAMPLE 253

In methanol (5 ml) was suspended 7-(3,4-methylenedioxy-phenyl)-2,3-dihydro-1-benzoxepine-4-carboxylate (399 mg, 1.23 mmol), and to the mixture was added 1N sodium hydroxide solution (3.69 ml). The mixture was stirred at room temperature for 20 hours, and to the mixture was added 1N hydrochloric acid (3.69 ml). The mixture was concentrated under reduced pressure, and to the residue was added water. Insoluble materials were filtered, which were washed with water and diethylether and dried under reduced pressure to give 7-(3,4-methylenedioxyphenyl)-2,3-dihydro-1-benzoxepine-4-carboxylic acid(321 mg, 1.03 mmol, 84%).

$^1$H-NMR (DMSO-d$_6$) δ: 2.80–2.95 (2H, m), 4.15–4.35 (2H, m), 6.05 (2H, s), 6.97 (1H, d, J=8.1 Hz), 7.01 (1H, d, J=8.4 Hz), 7.16 (1H, dd, J=8.1, 1.7 Hz), 7.29 (1H, d, J=1.7 Hz), 7.53 (1H, dd, J=8.4, 2.3 Hz), 7.63 (1H, s), 7.74 (1H, d, J=2.3 Hz).

REFERENCE EXAMPLE 254

In THF (100 ml) was dissolved 1,2-methylenedioxy-4-bromobenzene (24.00 g, 119 mmol), and to the mixture was added dropwise at −55° C. or less n-butyllithium (1.6M hexane solution, 82 ml, 131 mmol). The mixture was stirred at −70° C. for 30 minutes, and the resulting mixture was added dropwise at −60° C. or less to a solution of trimethyl borate (18.61 g, 179 mmol) in tetrahydrofuran (50 ml) with using cannula. The mixture was stirred at −70° C. for 1 hour and then for 2 hours with warming to room temperature. To the mixture were added 1N hydrochloric acid (130 ml) and diethylether (150 ml), and the organic layer was separated. The organic layer was washed with water (50×2 ml) and saturated brine (50 ml), dried with anhydrous magnesium sulfate and concentrated under reduced pressure. To the residue was added diisopropylether (40 ml), and insoluble materials were filtered, which were washed with diisopropylether (30 ml×4) and dried under reduced pressure to give 3,4-methylenedioxyphenyl borate (6.79 g, 40.9 mmol, 34%).

$^1$H-NMR (DMSO-d$_6$) δ: 5.99 (2H, s), 6.8–6.95 (1H, m), 7.25–7.45 (2H, m).

REFERENCE EXAMPLE 255

In methanol (250 ml) was suspended 5-nitrosalicylic acid (50.0 g, 273 mmol), and to the mixture was added sulfuric acid (6 ml). The mixture was stirred at 100° C. for 24 hours and the cooled to room temperature. The precipitated insoluble materials were filtered, which were washed with hydrous methanol (containing 20% of water) and methanol, and dried under reduced pressure to give methyl 5-nitrosalicylate (38.5 g, 195 mmol, 72%).

$^1$H-NMR (CDCl$_3$) δ: 4.04 (3H, s), 7.10 (1H, d, J=9.5 Hz), 8.35 (1H, dd, J=2.7, 9.5 Hz), 8.81 (1H, d, J=2.7 Hz), 11.45 (1H, s, OH).

REFERENCE EXAMPLE 256

In DMF (50 ml) was dissolved methyl 5-nitrosalicylate (1.97 g, 10.0 mmol), and to the mixture were added ethyl 4-bromobutyrate (1.57 ml, 11.0 mmol) and potassium carbonate (2.76 g, 20.0 mmol). The mixture was stirred at 110° C. for 5 hours, and the mixture was concentrated under reduced pressure. To the residue was added ethyl acetate, and the mixture was washed with water and 10% potassium carbonate solution. The organic layer was dried with anhydrous magnesium sulfate and concentrated under reduced pressure. The residue was purified with column chromatography (silica gel 30 g, ethyl acetate/hexane=1/5→1/3), and the desired fraction was concentrated under reduced pressure to give ethyl 4-(2-methoxycarbonyl-4-nitrophenoxy)butyrate (2.51 g, 8.06 mmol, 81%).

$^1$H-NMR (CDCl$_3$) δ: 1.26 (3H, t, J=7.2 Hz), 2.1–2.3 (2H, m), 2.60 (2H, t, J=7.1 Hz), 3.93 (3H, s), 4.15 (2H, q, J=7.2 Hz), 4.23 (2H, t, J=6.1 Hz), 7.06 (1H, d, J=9.4 Hz), 8.35 (1H, dd, J=2.8, 9.4 Hz), 8.71 (1H, d, J=2.8 Hz).

REFERENCE EXAMPLE 257

In THF (25 ml) was dissolved ethyl 4-(2-methoxycarbonyl-4-nitrophenoxy)butyrate (2.37 g, 7.61 mmol), and to the mixture was added 10% palladium-carbon (containing 50% water, 0.94 g). The mixture was subjected to catalytic reduction at room temperature for 4 hours. Insoluble materials were filtered off, and the filtrate was dried with anhydrous magnesium sulfate and concentrated under reduced pressure to give ethyl 4-(4-amino-2-methoxycarbonylphenoxy)butyrate (2.20 g).

IR (KBr): 1730 cm$^{-1}$. $^1$H-NMR (CDCl$_3$) δ: 1.25 (3H, t, J=7.2 Hz), 2.0–2.2 (2H, m), 2.56 (2H, t, J=7.3 Hz), 3.88 (3H, s), 4.00 (2H, t, J=6.0 Hz), 4.14 (2H, q, J=7.2 Hz), 6.75–6.9 (2H, m), 7.1–7.2 (1H, m).

REFERENCE EXAMPLE 258

A mixture of ethyl 4-(4-amino-2-methoxycarbonylphenoxy)butyrate (2.20 g), bis(2-chloroethyl)ether (0.915 ml, 7.81 mmol), potassiumcarbonate(3.24 g, 23.4 mmol), sodium iodide (2.34 g, 15.6 mmol) and DMF (20 ml) was stirred at 70° C. for 24 hours, and the mixture was concentrated under reduced pressure. To the residue was added water, and the mixture was extracted with ethyl acetate. The organic layer was dried with anhydrous sodium sulfate and concentrated under reduced pressure. The residue was purified with column chromatography (silica gel 30 g, ethyl acetate/hexane=1/4), and the desired fraction was concentrated under reduced pressure to give ethyl 4-(2-methoxycarbonyl-4-morpholinophenoxy)butyrate (2.18 g).

IR (KBr): 1732 cm$^{-1}$. $^1$H-NMR (CDCl$_3$) δ:1.25 (3H, t, J=7.1 Hz), 2.0–2.2 (2H, m), 2.57 (2H, t, J=7.1 Hz), 3.0–3.15 (4H, m), 3.8–3.9 (4H, m), 3.89 (3H, s), 4.04 (2H, t, J=6.0 Hz), 4.14 (2H, q, J=7.1 Hz), 6.92 (1H, d, J=9.0 Hz), 7.04 (1H, dd, J=3.1, 9.0 Hz), 7.36 (1H, d, J=3.1 Hz).

REFERENCE EXAMPLE 259

In THF (15 ml) was dissolved diisopropylamine (1.018 ml), and to the mixture was added dropwise at 0° C. n-butyl lithium (4.2 ml). The mixture was stirred at the same temperature for 30 minutes. To the mixture was added dropwise a solution of ethyl 4-(2-methoxycarbonyl-4-morpholinophenoxy)butyrate (1829 mg, 5.18 mmol) in THF (5 ml) at −78° C., ice bath was removed, and the mixture was stirred for 7 hours. To the mixture was added at 0° C. 10% ammonium chloride solution (30 ml), and the mixture was extracted with ethyl acetate (30 ml×3). The organic layer was dried with anhydrous sodium sulfate and concentrated under reduced pressure. The residue was purified with column chromatography (silica gel 50 g, ethyl acetate/hexane=1/5), and the desired fraction was concentrated under reduced pressure to give ethyl 7-morpholino-5-oxo-2,3,4,5-tetrahydro- 1-benzoxepine-4-carboxylate (924 mg, 2.89 mmol, 56%).

REFERENCE EXAMPLE 260

In THF (10 ml) was dissolved ethyl 7-morpholino-5-oxo-2,3,4,5-tetrahydro-1-benzoxepine-4-carboxylate (924 mg, 2.89 mmol), and to the mixture was added at −30° C. a solution of sodium boro hydride (164 mg, 4.34 mmol) in methanol (3 ml). The mixture was stirred at −20° C. to −15° C. for 30 minutes, and the mixture was cooled to −50° C., to which was added water (15 ml). The mixture was extracted with ethylacetate (15 ml×3), and the organic layer was dried with anhydrous magnesium sulfate and concentrated under reduced pressure. The residue was dissolved in THF (10 ml), and to the mixture were added at 0° C. triethylamine (2.02 ml, 14.5 mmol) andmethanesulfonylchloride (0.336 ml, 4.34 mmol). The mixture was stirred at room temperature for 17 hours and concentrated under reduced pressure. To the residue was added water (15 ml), and the mixture was extracted with ethyl acetate (20 ml×3). The organic layer was dried with anhydrous sodium sulfate and concentrated under reduced pressure. The residue was purified with column chromatography (silica gel 30 g, ethyl acetate/ hexane=1/5), and the desired fraction was concentrated under reduced pressure to give ethyl 7-morpholino-2,3-dihydro-1-benzoxepine-4-carboxylate (691 mg, 2.28 mmol, 79%).

IR (KBr): 1703 cm$^{-1}$. $^1$H-NMR (CDCl$_3$) δ: 1.35 (3H, t, J=7.2 Hz), 2.9–3.0 (2H, m), 3.05–3.15 (4H, m), 3.8–3.9 (4H, m), 4.22 (2H, t, J=4.8 Hz), 4.28 (2H, q, J=7.2 Hz), 6.8–7.0 (3H, m), 7.54 (1H, s).

REFERENCE EXAMPLE 261

In methanol (8 ml) was dissolved ethyl 7-morpholino-2,3-dihydro-1-benzoxepine-4-carboxylate (800 mg, 2.64 mmol), and to the mixture was added 1N sodium hydroxide solution (8 ml). The mixture was stirred at room temperature for 12 hours, and to the mixture was added 1N hydrochloric acid (8 ml). The organic solvent was evaporated under reduced pressure, and the precipitated insoluble materials were filtered, which were washed with water and diisopropylether and dried under reduced pressure to give 7-morpholino-2,3-dihydro-1-benzoxepine-4-carboxylic acid (649 mg, 2.36 mmol, 89%).

$^1$H-NMR (CDCl$_3$) δ: 2.97 (2H, t, J=4.5 Hz), 3.05–3.15 (4H, m), 3.8–3.95 (4H, m), 4.25 (2H, t, J=4.5 Hz), 6.8–7.0 (3H, m), 7.67 (1H, s).

REFERENCE EXAMPLE 262

A mixture of 4-nitrobenzylamine (6.09 g, 40.0 mmol), 2-chloropyrimidine (4.82 g, 42.1 mmol), triethylamine (11.2 ml, 80.4 mmol) and ethanol (120 ml) was stirred at 110° C. for 24 hours, and the mixture was concentrated under reduced pressure. To the residue was added water, and the mixture wasextractedwithethylacetate-THF. Theorganiclayerwas dried with anhydrous sodium sulfate and concentrated under reduced pressure. The residue was recrystallized from ethyl acetate-ethanol to give N-(4-nitrobenzyl)-N-(2-pyrimidinyl)amine (0.99 g, 4.3 mmol, 11%).

$^1$H-NMR (CDCl$_3$) δ: 4.77 (2H, d, J=6.4 Hz), 5.59 (1H, m), 6.62 (1H, t, J=4.9 Hz), 7.51 (2H, d, J=8.6 Hz), 8.19 (2H, d, J=8.6 Hz), 8.30 (2H, d, J=4.9 Hz).

REFERENCE EXAMPLE 263

In THF (20 ml) and methanol (20 ml) was dissolved N-(4-nitrobenzyl)-N-(2-pyrimidinyl)amine (921 mg, 4.00 mmol), and to the mixture were added at 0° C. nickel bromide (137 mg) and sodium boro hydride(955 mg). The mixture was stirred at room temperature for 30 minutes and concentrated under reduced pressure. To the residue were added ethyl acetate, THF and water, and the insoluble materials were filtered off. The aqueous layer was extracted with ethyl acetate-THF, and the organic layer was dried with anhydrous sodium sulfate and concentrated under reduced pressure. The residue was purified with column chromatography (silica gel 30 g, ethyl acetate/hexane=1/1), and the desired fraction was concentrated under reduced pressure. To the residue was added diethylether, and the insoluble materials were filtered, which were washed with diethylether and dried under reduced pressure to give 4-[N-(2-pyrimidinyl)aminomethyl]aniline (208 mg, 1.04 mmol, 26%).

$^1$H-NMR (CDCl$_3$) δ: 4.50 (2H, d, J=5.4 Hz), 5.32 (1H, m), 6.54 (1H, t, J=4.7 Hz), 6.66 (2H, d, J=8.3 Hz), 7.15 (2H, d, J=8.3 Hz), 8.29 (2H, d, J=4.7 Hz).

REFERENCE EXAMPLE 264

A mixture of methyl 7-bromo-2,3-dihydro-1-benzoxepine-4-carboxylate (1416 mg, 5.00 mmol), zinc cyanide (352 mg, 3.00 mmol), tetrakis(triphenylphosphine) palladium (347 mg, 0.30 mmol) and DMF(10 ml) was stirred at 80° C. for 3 hours. The mixture was concentrated under reduced pressure, and to the residue was added ethyl acetate. Insoluble materials were filtered off, which were washed with ethyl acetate. The filtrate was concentrated under reduced pressure. The resulting crude product was recrystallized from ethyl acetate to give methyl 7-cyano-2, 3-dihydro-1-benzoxepine-4-carboxylate (800 mg, 3.49 mmol, 70%).

IR (KBr): 2222, 1721 cm$^{-1}$. $^1$H-NMR (CDCl$_3$) δ: 2.95–3.1 (2H, m), 3.84 (3H, s), 4.3–4.4 (2H, m), 7.05 (1H, d, J=8.8 Hz), 7.50 (1H, dd, J=2.0, 8.8 Hz), 7.52 (1H, s), 7.66 (1H, d, J=2.0 Hz).

REFERENCE EXAMPLE 265

In toluene (15 ml) was suspended methyl 7-cyano-2,3-dihydro-1-benzoxepine-4-carboxylate (642 mg, 2.80 mmol), and to the mixture were added trimethylsilylazide (0.929 ml, 7.00 mmol) and dibutyl tin oxide (70 mg, 0.28 mmol). The mixture was stirred at 100° C. for 24 hours and concentrated under reduced pressure. To the residue was added methanol, and the mixture was concentrated under reduced pressure. To the residue was added ethyl acetate, and the mixture was extracted with saturated sodium bicarbonate solution (30 ml, 10 ml×2). To the aqueous layer was added 6N hydrochloric acid to make the solution about pH 1, and the mixture was extracted with ethyl acetate and THF ((30 ml50 ml) and (10 ml/10 ml)×2). The organic layer was dried with anhydrous magnesium sulfate and concentrated under reduced pressure, to the residue was added ethyl acetate. Insoluble materials were filtered, which were washed with ethyl acetate and dried under reduced pressure to give methyl 7-(1H-tetrazol-5-yl)-2,3-dihydro-1-benzoxepine-4-carboxylate (662 mg, 2.43 mmol, 87%).

$^1$H-NMR (DMSO-d$_6$) δ: 2.85–3.0 (2H, m), 3.78 (3H, s), 4.25–4.4 (2H, m), 7.21 (1H, d, J=8.6 Hz), 7.60 (1H, s), 7.94 (1H, dd, J=2.1, 8.6 Hz), 8.16 (1H, d, J=2.1 Hz).

REFERENCE EXAMPLE 266

In DMF (6 ml) was dissolved methyl 7-(1H-tetrazol-5-yl)-2,3-dihydro-1-benzoxepine-4-carboxylate (400 mg, 1.47 mmol),and to the mixture was added at 0° C. sodium hydride (60%, 90 mg, 2.3 mmol). The mixture was stirred at the same temperature for 15 minutes, and to the mixture was added at OC methyl iodide (0.28 ml, 4.4 mmol). While the temperature of the mixture was warmed from 0° C. to room temperature, the mixture was stirred for 3 hours. To the mixture was added at 0° C. water (30 ml), and the mixture was extracted with ethyl acetate. The organic layer was dried with anhydrous sodium sulfate and concentrated under reduced pressure. The residue was purified with column chromatography (silica gel 40 g, ethyl acetate/hexane=1/8→1/2), and the first eluted desired fraction was concentrated under reduced pressure to give methyl 7-(2-methyl-1H-tetrazol-5-yl)-2,3-dihydro-1-benzoxepine-4-carboxylate (334 mg, 1.17 mmol, 79%). The second eluted desired fraction was concentrated under reduced pressure to give methyl 7-(1-methyl-1H-tetrazol-5-yl)-2,3-dihydro-1-benzoxepine-4-carboxylate (76 mg, 0.27 mmol, 18%).

Methyl 7-(2-methyl-1H-tetrazol-5-yl)-2,3-dihydro-1-benzoxepine-4-carboxylate;

IR (KBr): 1705 cm$^{-1}$. $^1$H-NMR (CDCl$_3$) δ: 2.95–3.1 (2H, m), 3.83 (3H, s), 4.25–4.4 (2H, m), 4.39 (3H, s), 7.09 (1H, d, J=8.4 Hz), 7.69 (1H, s), 8.00 (1H, dd, J=2.2, 8.4 Hz), 8.15 (1H, d, J=2.2 Hz). Methyl 7-(1-methyl-1H-tetrazol-5-yl)-2, 3-dihydro-1-benzoxepine-4-carboxylate;

IR (KBr): 1705 cm$^{-1}$. $^1$H-NMR (CDCl$_3$) δ: 3.0–3.1 (2H, m), 3.84 (3H, s), 4.3–4.45 (2H, m), 4.20 (3H, s), 7.17 (1H, d, J=8.4 Hz), 7.61 (1H, s), 7.63 (1H, dd, J=2.2, 8.4 Hz), 7.75 (1H, d, J=2.2 Hz).

REFERENCE EXAMPLE 267

In methanol (7 ml) and THF (7 ml) was suspended methyl 7-(2-methyl-1H-tetrazol-5-yl)-2,3-dihydro-1-benzoxepine-4-carboxylate (324 mg, 1.13 mmol), and to the mixture was added 1N sodium hydroxide solution (3.4 ml). The mixture was stirred at 50° C. for 4 hours, and to the mixture was added, under ice-cooling, 1N hydrochloric acid (3.4 ml). The mixture was concentrated under reduced pressure, and to the residue was added water. Insoluble materials were filtered, which were washed with water and dried under reduced pressure to give 7-(2-methyl-1H-tetrazol-5-yl)-2,3-dihydro-1-benzoxepine-4-carboxylic acid (295 mg, 1.08 mmol, 96%).

REFERENCE EXAMPLE 268

In methanol (3 ml) and THF (3 ml) was dissolved methyl 7-(2-methyl-1H-tetrazol-5-yl)-2,3-dihydro-1-benzoxepine-4-carboxylate (76 mg, 0.27 mmol), and to the mixture was added 1N sodium hydroxide solution (0.8 ml). The mixture was stirred at 50° C. for 4 hours, and to the mixture was added, under ice-cooling, 1N hydrochloric acid (0.8 ml). The mixture was concentrated under reduced pressure, and to the residue was added water. Insoluble materials were filtered, which were washed with water and dried under reduced pressure to give 7-(1-methyl-1H-tetrazol-5-yl)-2,3-dihydro-1-benzoxepine-4-carboxylic acid (69 mg, 0.25 mmol, 95%).

REFERENCE EXAMPLE 269

In THF (500 ml) was dissolved 4-[(benzyloxy) carbonyl]-aminobutyric acid (25.0 g), and to the mixture was gradually added at −5° C. methyl iodide (37.4 g). Under nitrogen atmosphere, the mixture was stirred at 0° C. for 15 minutes and then at room temperature for 24 hours. To the mixture was added ethyl acetate (300 ml) and then water (800 ml). The mixture was made pH 11 with sodium hydroxide and washed with ether (400 ml×2). The aqueous layer was made pH 2 with concentrated hydrochloric acid and extracted with ethyl acetate (1000 ml and 500 ml×3). The organic layer was washed with 1M sodium thiosulf ate solution (300 ml) and dried with magnesium sulfate. The solvent was evaporated under reduced pressure to give 4-[(benzyloxy)carbonyl]-4-methyl-aminobutyric acid (26.3 g).

$^1$H NMR (200 MHz, CDCl$_3$) δ 1.88 (2H, m), 2.35–2.37 (2H, m), 2.93 (3H, s), 3.36 (2H, t, J=6.6 Hz), 5.13 (2H, s), 7.35 (5H, s).

REFERENCE EXAMPLE 270

To dichloromethane (1000 ml) was added at room temperature anhydrous magnesium sulfate (50.6 g) and then concentrated sulfuric acid (6.0 ml). The mixture was stirred at room temperature for 15 minutes, and to the mixture was added 4-[(benzyloxy)carbonyl]-4-methylaminobutyric acid (26.3 g) and then tert-butanol (50.5 ml). The mixture was sealed completely and stirred at room temperature for 18 hours. To the mixture was added saturated sodium hydrogen carbonate solution to dissolve all of the magnesium sulfate, and the mixture was stirred. The organic layer was separated, washed with saturated brine (400 ml) and dried with anhydrous magnesium sulfate. The solvent was evaporated under reduced pressure, and the residue was purified with silica gel column chromatography (250 g, hexane:ethyl acetate=5:1) to give tert-butyl 4-[(benzyloxy)-carbonyl]-4-methylaminobutyrate (17.2 g, 53%).

$^1$H NMR (200 MHz, CDCl$_3$) δ 1.44 (9H, s), 1.82 (2H, quint, J=6.6 Hz), 2.21 (2H, t, J=6.2 Hz), 2.93 (3H, s), 3.31 (2H, t, J=7.1 Hz), 5.13 (2H, s), 7.35 (5H, s).

REFERENCE EXAMPLE 271

In methanol (70 ml) was dissolved tert-butyl 4-[(benzyloxy)carbonyl]-4-methylaminobutyrate (6.06 g), and to the mixture was added 10% palladium-carbon (580 mg). Under hydrogen atmosphere, the mixture was stirred at room temperature for 3 hours, and 10% palladium-carbon was removed. The solvent was evaporated under reduced pressure to give tert-butyl 4-methylaminobutyrate (3.35 g, 98%). $^1$H NMR (200 MHz, CDCl$_3$) δ 1.45 (9H, s), 1.72 (1H, brs), 1.77 (2H, quint, J=7.2 Hz), 2.27 (2H, t, J=7.3 Hz), 2.43 (3H, s), 2.61 (2H, t, J=7.1 Hz).

REFERENCE EXAMPLE 272

In DMF (5.0 ml) was dissolved tert-butyl 4-methylaminobutyrate (1050 mg), and to the mixture was added at room temperature a solution of 5-bromo-2-fluorobenzaldehyde (1025 mg) in DMF (1.0 ml) and then potassium carbonate (837 mg). The mixture was stirred at 70° C. for 60 hours, and to the mixture was added at room temperature water (50 ml). The mixture was extracted with ethyl acetate (50 ml×3), and the organic layer was washed with saturated brine (50 ml×3) and dried with anhydrous magnesium sulfate. The solvent was evaporated under reduced pressure, and the residue was purified with silica gel column chromatography (75 g, hexane:ethyl acetate=10:1) to give tert-butyl 4-(4-bromo-2-formyl-N-methylanilino) butyrate (1620 mg, 90%).

$^1$H NMR (200 MHz, CDCl$_3$) δ 1.42 (9H, s), 1.88 (2H, quint, J=7.4 Hz), 2.22 (2H, t, J=7.3 Hz), 2.88 (3H, s), 3.14 (2H, t, J=7.3 Hz), 7.01 (1H, d, J=8.6 Hz), 7.55 (1H, dd, J=8.7, 2.5 Hz), 7.88 (1H, d, J=2.6 Hz), 10.19 (1H, s).

REFERENCE EXAMPLE 273

In tert-butanol (250 ml) was dissolved tert-butyl 4-(4-bromo-2-formyl-N-methylanilino)butyrate (4.54 g) and tert-butoxy potassium (1.43 g), and the mixture was refluxed for 1 hour and cooled. To the mixture was added water (500 ml), and the mixture was extracted with ethyl acetate (500 ml×2). The aqueous layer was made weakly acidic with 1N hydrochloric acid (about 12.5 ml), and the mixture was extracted with ethyl acetate (500 ml). Both of these organic layer was washed with saturated brine (250 ml) and dried with anhydrous magnesium sulfate. The solvent was evaporated under reduced pressure, and the residue was purified with silica gel column chromatography (200 g, hexane:ethyl acetate= 10:1→1:1) to give tert-butyl 7-bromo-1-methyl-2,3-dihydro-1-benzoazepine-4-carboxylate (3.33 g, 77%) and 7-bromo-1-methyl-2,3-dihydro-1H-1-benzoazepine-4-carboxylic acid (0.60 g, 17%).

tert-butyl 7-bromo-1-methyl-2,3-dihydro-1-benzoazepine-4-carboxylate.

$^1$HNMR (200 MHz, CDCl$_3$) δ 1.53 (9H, s), 2.80 (2H, t, J=4.8 Hz), 3.00 (3H, s), 3.21 (2H, t, J=4.7 Hz), 6.65 (1H, d, J=8.8 Hz), 7.25 (1H, dd, J=8.8, 2.2 Hz), 7.39 (1H, d, J=2.6 Hz), 7.46 (1H, s).

7-bromo-1-methyl-2,3-dihydro-1H-1-benzoazepine-4-carboxylic acid; $^1$H NMR (200 MHz, CDCl$_3$) δ 2.85 (2H, t, J=4.8 Hz), 3.03 (3H, s), 3.25 (2H, t, J=4.9 Hz), 6.67 (1H, d, J=9.2 Hz), 7.29 (1H, dd, J=8.8, 2.2 Hz), 7.44 (1H, d, J=2.6 Hz), 7.67 (1H, s).

REFERENCE EXAMPLE 274

In water:ethanol:toluene (1:1:10, 18.0 ml) were dissolved 4-methylphenyl borate (276 mg) and tert-butyl 7-bromo-1-methyl-2,3-dihydro-1-benzoazepine-4-carboxylate (571 mg), and to the mixture was added potassium carbonate (560 mg). The mixture was stirred under argon atmosphere for 30 minutes, and to the mixture was added tetrakistriphenylphosphine palladium (78 mg). Under argon atmosphere, the mixture was refluxed for 19.5 hours. The mixture was diluted with ethyl acetate (300 ml) and washed with water (100 ml) and saturated brine (100 ml). The organic layer was dried with anhydrous magnesium sulfate. The solvent was evaporated under reduced pressure, and the residue was purified with silica gel column chromatography (120 g, hexane→hexane:ethyl acetate=10:1) to give tert-butyl 1-methyl-7-(4-methylphenyl)-2,3-dihydro-1-benzoazepine-4-carboxylate (422 mg, 72%).

$^1$H NMR (200 MHz, CDCl$_3$) δ 1.54 (9H, s), 2.38 (3H, s), 2.83 (2H, t, J=4.9 Hz), 3.06 (3H, s), 3.28 (2H, t, J=4.9 Hz), 6.85 (1H, d, J=8.4 Hz), 7.23 (2H, d, J=8.0 Hz), 7.447 (1H, dd, J=8.6, 2.4 Hz), 7.463 (2H, d, J=8.2 Hz), 7.53 (1H, d, J=2.2 Hz), 7.67 (1H, s).

REFERENCE EXAMPLE 275

In ethyl acetate (7.0 ml) was dissolved tert-butyl 1-methyl-7-(4-methylphenyl)-2,3-dihydro-1-benzoazepine-4-carboxylate (490 mg), and to the mixture was added 4N hydrochloric acid (ethyl acetate) (7.0 ml). The mixture was stirred at room temperature for 20 hours. The solvent was evaporated under reduced pressure, and the residue was washed with hexane (10 ml×3) to give 1-methyl-7-(4-methylphenyl)-2,3-dihydro-1-benzoazepine-4-carboxylic acid hydrochloride (443 mg, 96%).

mp 249–252° C. (decomp.). $^1$H NMR (200 MHz, DMSO-d$_6$) δ 2.32 (3H, s), 2.75 (2H, t, J=4.6 Hz), 3.03 (3H, s), 3.25 (2H, t, J=4.9 Hz), 6.92 (1H, d, J=8.6 Hz), 7.22 (2H, d, J=8.2 Hz), 7.53 (1H, dd, J=8.8, 2.4 Hz), 7.55 (2H, d, J=8.2 Hz), 7.65 (1H, d, J=2.4 Hz), 7.68 (1H, s). IR (KBr) 3021, 2469, 1707, 1466, 1190, 1107, 810, 530 cm$^{-1}$. Anal. Calcd. for $C_{19}H_{19}NO_2 \cdot HCl \cdot 0.3H_2O$: C, 68.08; H, 6.19; N, 4.18. Found: C, 67.97; H, 6.13; N, 4.05.

REFERENCE EXAMPLE 276

In DMF (12.0 ml) was dissolved 7-bromo-1-methyl-2,3-dihydro-1-benzoazepine-4-carboxylic acid hydrochloride (600 mg), and to the mixture was added thionyl chloride (0.39 ml). The mixture was stirred at room temperature for 15 minutes. The solvent was evaporated under reduced pressure, and the residue was dissolved in dichloromethane (14.0 ml). The thus obtained acid chloride solution was added dropwise at 0° C. to a solution of 4-[[N-methyl-N-(tetrahydropyran-4-yl)amino]methyl]aniline (562 mg) and triethylamine (1.48 ml) in dichloromethane (5.5 ml). The mixture was stirred at 0° C. for 10 minutes and then at room temperature for 5 hours. To the mixture was added water (100 ml), and the mixture was extracted with dichloromethane (100 ml×3). The organic layer was dried with anhydrous magnesium sulfate. The solvent was evaporated under reduced pressure, and the residue was purified with silica gel column chromatography (150 g, ethyl acetate:ethanol=10:1) to give 7-bromo-1-methyl-N-[4-[[N-methyl-N-(tetrahydropyran-4-yl)amino]methyl]-phenyl]-2,3-dihydro-1-benzoazepine-4-carboxamide (767 mg, 75%).

mp 62–64° C.; $^1$H NMR (200 MHz, CDCl$_3$) δ 1.63–1.79 (4H, m), 2.21 (3H, s), 2.57–2.72 (1H, m), 2.94 (2H, t, J=4.2 Hz), 3.03 (3H, s), 3.27–3.44 (2H +2H, m), 3.57 (2H, s), 4.00–4.07 (2H, m), 6.70 (1H, d, J=8.8 Hz), 7.20 (1H, s), 7.26–7.303 (2H, m), 7.301 (1H, dd, J=8.6, 2.4 Hz), 7.42 (1H, d, J=2.6 Hz), 7.50–7.55 (1H+2H, m). IR (KBr) 3264, 2949, 2843, 1655, 1597, 1514, 1499, 1406, 1314, 1246, 1182, 810 cm$^{-1}$. Anal. Calcd. for $C_{25}H_{30}N_3O_2Br \cdot 0.25H_2O$: C, 61.41; H, 6.29; N, 8.59. Found: C, 61.45; H, 6.25; N, 8.32.

WORKING EXAMPLE 310 (Production of Compound 310)

In hydrous methanol was dissolved N,N-dimethyl-N-(4-(((7-(4-methylphenyl)-2,3-dihydro-1-benzoxepin-4-yl)carbonyl)amino)benzyl)tetrahydro-2H-pyran-4-aminium iodide (14.2 g), and the mixture was subjected to ion exchange resin (DOWEX SBR, 20–50 mesh, Cl$^-$ type) column and eluted with hydrous methanol. The solvent of the resulting fraction was evaporated, and to the residue was added acetone to give crude crystals, which were recrystallized from ethanol to give N,N-dimethyl-N-(4-(((7-(4-methylphenyl)-2,3-dihydro-1-benzoxepin-4-yl)carbonyl)amino)benzyl)tetrahydro-2H-pyran-4-aminium chloride (Compound 310) (10.4 g) as colorless crystals.

mp 232–237° C.(dec.). $^1$H-NMR(δ ppm, DMSO-d$_6$) 1.76–2.00 (2H, m), 2.14–2.20 (2H, m), 2.35 (3H, s), 2.89 (6H, s), 3.01 (2H, t, J=4.5 Hz), 3.29–3.46 (2H, m), 3.55–3.69 (1H, m), 4.04–4.09 (2H, m), 4.31 (2H, t, J=4.5 Hz), 4.50 (2H, s), 7.06 (1H, d, J=8.4 Hz), 7.27 (2H, d, J=8.4 Hz), 7.46 (1H, s), 7.53–7.59 (5H, m), 7.79 (1H, d, J=2.2 Hz), 7.92 (2H, d, J=8.4 Hz), 10.34 (1H, s). IR(KBr) ν: 2973, 2849, 1645, 1516cm$^{-1}$. Anal. Calcd. for $C_{32}H_{37}ClN_2O_3$:

C, 72.10; H, 7.00; N, 5.25; Cl,6.65. Found C, 72.03; H, 6.83; N, 5.38; Cl,6.47.

WORKING EXAMPLE 311 (Production of Compound 311)

In dichloromethane (5 ml) was suspended 7-(4-methylphenyl)-2,3-dihydro-1-benzoxepine-4-carboxylic acid (0.25 g), and to the mixture were added, under ice-cooling, oxalyl chloride (0.16 ml) and dimethylformamide (catalytic amount). The mixture was stirred at room temperature for 2 hours, and the solvent was evaporated. The residue was dissolved in tetrahydrofuran (20 ml), and the mixture was added dropwise to a solution of 4-((N,N-bis(2-methoxyethyl)amino)methyl)aniline (0.24 g) and triethylamine (0.4 ml) in tetrahydrofuran (10 ml) under ice-cooling. Under nitrogen atmosphere, the mixture was stirred at room temperature overnight, and the solvent was evaporated. To the residue was added water, and the mixture was extracted with ethyl acetate. The organic layer washed with water and saturated brine, and dried with anhydrous magnesium sulfate. Under reduced pressure, the solvent was evaporated, and the residue was purified with silica gel column (ethyl acetate) to give crude crystals, which were recrystallized from ethyl acetate-hexane to give N-(4-((N,N-bis(2-methoxyethyl)amino)methyl)phenyl)-7-(4-methylphenyl)-2,3-dihydro-1-benzoxepine-4-carboxamide (Compound 311) (0.25 g) as colorless crystals.

mp 110–112° C.; $^1$H-NMR(δ ppm, CDCl$_3$) 2.39 (3H, s), 2.74 (4H, t, J=6.0 Hz), 3.07 (2H, t, J=4.4 Hz), 3.32 (6H, s), 3.48 (4H, t, J=6.0 Hz), 3.69 (2H, s), 4.35 (2H, t, J=4.4 Hz), 7.05 (1H, d, J=8.0 Hz), 7.24 (2H, d, J=8.4 Hz), 7.33 (2H, d, J=8.8 Hz), 7.43–7.55 (6H, m), 7.61 (1H, s). IR(KBr) ν: 3287, 2876, 1651cm$^{-1}$. Anal. Calcd. for $C_{31}H_{36}N_2O_4$: C, 74.37; H, 7.25; N, 5.60. Found C, 74.33; H, 7.15; N, 5.45.

WORKING EXAMPLE 312 (Production of Compound 312)

In dichloromethane (5 ml) was suspended 7-(4-methylphenyl)-2,3-dihydro-1-benzoxepine-4-carboxylic acid (0.25 g), and to the mixture were added, under ice-cooling, oxalyl chloride (0.23 ml) and dimethylformamide (catalytic amount). The mixture was stirred at room temperature for 2 hours, and the solvent was evaporated. The residue was dissolved in tetrahydrofuran (20 ml), and the mixture was added dropwise to a solution of 4-((N-(3-ethoxypropyl)-N-methylamino)methyl)aniline dihydrochloride (0.3 g) and triethylamine (0.62 ml) in tetrahydrofuran (10 ml), under ice-cooling. Under nitrogen atmosphere, the mixture was stirred at room temperature overnight, and the solvent was evaporated. To the residue was added water, and the mixture was extracted with ethyl acetate. The organic layer washed with water and saturated brine, and dried with anhydrous magnesium sulfate. Under reduced pressure, the solvent was evaporated, and the residue was purified with silica gel column (methanol/triethylamine/ethyl acetate) to give crude crystals, which were recrystallized from ethyl acetate-hexane to give N-(4-((N-(3-ethoxypropyl)-N-methylamino)methyl)phenyl)-7-(4-methylphenyl)-2,3-dihydro- 1-benzoxepine-4-carboxamide (Compound 312) (0.3 g) as colorless crystals.

mp 119–122° C.; $^1$H-NMR($\delta$ ppm, CDC$_3$) 1.19 (3H, t, J=7.1 Hz), 1.65–1.85 (2H, m), 2.19 (3H, s), 2.39 (3H, s), 2.46 (2H, t, J=7.2 Hz), 3.08 (2H, t, J=4.8 Hz), 3.42–3.52 (6H, m), 4.36 (2H, t, J=4.8 Hz), 7.06 (1H, d, J=8.4 Hz), 7.24 (2H, d, J=8.0 Hz), 7.30 (2H, d, J=8.8 Hz), 7.44–7.58 (7H, m). IR(KBr) $\nu$: 2975, 2872, 1647, 1516cm$^{-1}$. Anal. Calcd. for C$_{31}$H$_{36}$N$_2$O$_3$: C, 76.83; H, 7.49; N, 5.78. Found C, 76.73; H, 7.31; N, 5.95.

WORKING EXAMPLE 313 (Production of Compound 313)

In THF (5 ml) was dissolved 7-(4-methylphenyl)-2,3-dihydro-1-benzoxepine-4-carboxylic acid (0.25 g), and to the mixture were added, under ice-cooling, oxalyl chloride (0.16 ml) and dimethylformamide (catalytic amount). The mixture was stirred at room temperature for 2 hours, and the solvent was evaporated. The residue was dissolved in tetrahydrofuran (15 ml), and the mixture was added dropwise to a solution of 4-((N-(1,3-dimethoxypropan-2-yl)-N-methylamino)methyl)aniline (0.23 g) and triethylamine (0.5 ml) in tetrahydrofuran (10 ml), under ice-cooling. Under nitrogen atmosphere, the mixture was stirred at room temperature overnight, andthe solventwas evaporated. To the residue was added water, and the mixture was extracted with ethyl acetate. The organic layer washed with water and saturated brine, and dried with anhydrous magnesium sulfate. Under reduced pressure, the solvent was evaporated, and the residue was purified with silica gel column (ethyl acetate/hexane) to give crude crystals, which were recrystallized from ethyl acetate-hexane to give N-(4-((N-(1,3-dimethoxypropan-2-yl)-N-methylamino)methyl)phenyl)-7-(4-methylphenyl)-2,3-dihydro-1-benzoxepine-4-carboxamide (Compound 313) (0.25 g) as colorless crystals.

mp 128–132° C.; $^1$H-NMR($\delta$ ppm, CDCl$_3$) 2.31 (3H, s), 2.39 (3H, S), 3.00–3.09 (3H, m), 3.35 (6H, s), 3.44–3.63 (4H, m), 3.71 (2H, s), 4.35 (2H, t, J=4.7 Hz), 7.05 (1H, d, J=8.4 Hz), 7.24 (2H, d, J=8.0 Hz), 7.33 (2H, d, J=8.8 Hz), 7.43–7.58 (7H, m). IR(KBr) $\nu$: 3285, 2882, 1651, 1516cm$^{-1}$. Anal. Calcd. for C$_{31}$H$_{36}$N$_2$O$_4$: C, 74.37; H, 7.25; N, 5.60. Found C, 74.17; H, 7.05; N, 5.75.

WORKING EXAMPLE 314 (Production of Compound 314)

In THF (5 ml) was dissolved 7-(4-methylphenyl)-2,3-dihydro-1-benzoxepine-4-carboxylic acid (0.25 g), and to the mixture were added, under ice-cooling, oxalyl chloride (0.16 ml) and dimethylformamide (catalytic amount). The mixture was stirred at room temperature for 2 hours, and the solvent was evaporated. The residue was dissolved in tetrahydrofuran (15 ml), and the mixture was added dropwise to a solution of 4-((N-(2-methoxyethyl)-N-methylamino)methyl)aniline (0.21 g) and triethylamine (0.37 ml) in tetrahydrofuran (10 ml), under ice-cooling. Under nitrogen atmosphere, the mixture was stirred at room temperature overnight, and the solvent was evaporated. To the residue was added water, and the mixture was extracted with ethyl acetate. The organic layer was washed with water and saturated brine, and dried with anhydrous magnesium sulfate. Under reduced pressure, the solvent was evaporated, and the residue was purified with silica gel column (methanol/triethylamine/ethyl acetate) to give crude crystals, which were recrystallized from ethyl acetate-hexane to give N-(4-((N-(2-methoxyethyl)-N-methylamino) methyl)phenyl)-7-(4-methylphenyl)-2,3-dihydro-1-benzoxepine-4-carboxamide (Compound 314) (0.24 g) as colorless crystals.

mp 121–122° C.; $^1$H-NMR($\delta$ ppm, CDCl$_3$) 2.26 (3H, s), 2.39 (3H, s), 2.60 (2H, t, J=5.8 Hz), 3.07 (2H, t, J=4.5 Hz), 3.35 (3H, s), 3.49–3.54 (4H, m), 4.35 (2H, t, J=4.5 Hz), 7.05 (1H, d, J=8.4 Hz), 7.24 (2H, d, J=8.8 Hz), 7.31 (2H, d, J=8.8 Hz), 7.43–7.56 (6H, m), 7.62 (1H, s). IR(KBr) $\nu$: 3287, 2926, 1651, 1516cm$^{-1}$. Anal. Calcd. for C$_{29}$H$_{32}$N$_2$O$_3$: C, 76.29; H, 7.06; N, 6.14. Found C, 75.99; H, 7.02; N, 6.22.

WORKING EXAMPLE 315 (Production of Compound 315)

In water/ethanol/toluene(1:1:10, 18.0 ml) were dissolved 4-trifluoromethoxyphenyl borate (208 mg) and 7-bromo-1-methyl-N-[4-[[N-methyl-N-(tetrahydro-2H-pyran-4-yl) amino]methyl]phenyl]-2,3-dihydro-1-benzazepine-4-carboxamide (407 mg), and to the mixture was added potassium carbonate (279 mg). Under argon atmosphere, the mixture was stirred for 30 minutes, and the mixture was added tetrakistriphenylphosphine palladium (39 mg). Under argon atmosphere, the mixture was refluxed for 16 hours, and the mixture was diluted with ethyl acetate (200 ml). The mixture was washed with water (50 ml) and saturated brine (50 ml), and the organic layer was dried with anhydrous magnesium sulfate. The solvent was evaporated under reduced pressure, and the residue was purified with silica gel column chromatography (75 g, ethyl acetate→ethyl acetate/ ethanol=20:1) and recrystallized from ethanol to give 1-methyl-N-[4-[[N-methyl-N-(tetrahydro-2H-pyran-4-yl) amino]methyl]phenyl]-7-(4-trifluoromethoxyphenyl)-2,3-dihydro-1-benzazepine-4-carboxamide (Compound 315) (148 mg, 31%).

mp 182–183° C.; $^1$H NMR (200 MHz, CDCl$_3$) $\delta$ 1.63–1.76 (4H, m), 2.20 (3H, s), 2.56–2.72 (1H, m), 2.96 (2H, t, J=4.6 Hz), 3.09 (3H, s), 3.30–3.43 (4H, m), 3.56 (2H, s), 4.01–4.06 (2H, m), 6.89 (1H, d, J=8.6 Hz), 7.25 (2H, d, J=8.2 Hz), 7.30 (2H, d, J=8.6 Hz), 7.40 (1H, s), 7.48 (1H, dd, J=8.6, 2.4 Hz), 7.51–7.58 (6H, m). IR (KBr) 2951, 2847, 1651, 1514, 1501, 1260, 1221, 1163, 806, 733 cm$^{-1}$. Anal. Calcd. for C$_{32}$H$_{34}$N$_3$O$_3$F$_3$: C, 67.95; H, 6.06; N, 7.43. Found: C, 67.74; H, 5.87; N, 7.68.

WORKING EXAMPLE 316 (Production of Compound 316)

In water/ethanol/toluene (1:1:10, 18.0 ml) were dissolved 4-(1-piperidinyl)phenyl borate (179 mg) and 7-bromo-1-methyl-N-[4-[[N-methyl-N-(tetrahydro-2H-pyran-4-yl) amino]methyl]phenyl]-2,3-dihydro-1-benzazepine-4-carboxamide (353 mg), and to the mixture was added potassium carbonate (242 mg). Under argon atmosphere, the mixture was stirred for 40 minutes, and to the mixture was added tetrakistriphenylphosphine palladium (34 mg). Under argon atmosphere, the mixture was ref luxed for 15 hours, and the mixture was dilute with ethyl acetate (200 ml). The mixture was washed with water (50 ml) and saturated brine (50 ml), and the organic layer was dried with anhydrous magnesium sulfate. The solvent was evaporated under reduced pressure, and the residue was purified with silica gel column chromatography (75 g, ethyl acetate/ethanol=9:1) and recrystallized from ethanol to give 1-methyl-N-[4-[[N-methyl-N-(tetrahydro-2H-pyran-4-yl)amino]methyl]-phenyl]-7-[4-(1-piperidinyl)phenyl]-2,3-dihydro-1-benzazepine-4-carboxamide (Compound 316) (79 mg, 19%).

mp 202–204° C.; $^1$H NMR (200 MHz, CDCl$_3$) $\delta$ 1.59–1.77 (10 H, m), 2.21 (3H, s), 2.57–2.73 (1H, m), 2.95 (2H, t, J=4.4 Hz), 3.07 (3H, s), 3.19 (4H, t, J=5.1 Hz), 3.31–3.43 (4H, m), 3.57 (2H, s), 4.01–4.06 (2H, m), 6.86

(1H, d, J=8.4 Hz), 6.99 (2H, d, J=8.8 Hz), 7.30 (2H, d, J=8.6 Hz), 7.39–7.50 (5H, m), 7.54 (2H, d, J=8.4 Hz), 7.57 (1H, s). IR (KBr) 2938, 2849, 1645, 1607, 1505, 1314, 1235, 910, 812, 733cm$^{-1}$. Anal. Calcd. for $C_{36}H_{44}N_4O_2$: C, 76.56; H, 7.85; N, 9.92. Found: C, 76.53; H, 7.79; N, 10.01.

WORKING EXAMPLE 317 (Production of Compound 317)

In water/ethanol/toluene (1:1:10, 60.0 ml) were dissolved 4-methylphenyl borate (658 mg) and 7-bromo-1-formyl-N-[4-[[N-methyl-N-(tetrahydro-2H-pyran-4-yl)amino]methyl]phenyl]- 2,3-dihydro-1-benzazepine-4-carboxamide (20 g), and to the mixture was added potassium carbonate (1.34 g). Under argon atmosphere, the mixture was stirred for 30 minutes, and to the mixture was added tetrakistriphenylphosphine palladium (186 mg). Under argon atmosphere, the mixture was ref luxed for 17 hours, and the mixture was dilute with ethyl acetate (750 ml). The mixture was washed with water (200 ml) and saturated brine (100 ml), and the organic layer was dried with anhydrous magnesium sulfate. The solvent was evaporated under reduced pressure, and the residue was purified with silica gel column chromatography (150 g, ethyl acetate ethyl acetate/ethanol= 20:1) and recrystallized from ethanol to give 1-formyl-7-(4-methylphenyl)-N-[4-[[N-methyl-N-(tetrahydro-2H-pyran-4-yl)amino]methyl]phenyl]-2,3-dihydro-1-benzazepine-4-carboxamide (Compound 317) (669 mg, 33%).

mp 229–230.5° C.; $^1$H NMR (200 MHz, CDCl$_3$) δ 1.69–1.79 (4H, m), 2.21 (3H, s), 2.41 (3H, s), 2.57–2.72 (1H, m), 3.04 (2H, t, J=4.9 Hz), 3.37 (2H, td, J=10.2, 3.1 Hz), 3.57 (2H, s), 3.93 (2H, t, J=5.5 Hz), 4.01–4.07 (2H, m), 7.21 (1H, d, J=8.2 Hz), 7.29 (2H, d, J=7.6 Hz), 7.32 (2H, d, J=8.4 Hz), 7.50 (2H, d, J=8.8 Hz), 7.54 (2H, d, J=8.8 Hz), 7.58 (1H, s), 7.59 (1H, dd, J=8.2, 2.2 Hz), 1H was concealed under 7.55–7.58, 7.71 (1H, d, J=2.2 Hz), 8.56 (1H, s). IR (KBr) 2946, 2847, 1667, 1597, 1516, 1497, 1360, 1316, 814, 733 cm$^{-1}$. Anal. Calcd. for $C_{32}H_{35}N_3O_3$: C, 75.41; H, 6.92; N, 8.25. Found: C, 75.45; H, 6.95; N, 8.18.

WORKING EXAMPLE 318 (Production of Compound 318)

To 1-formyl-7-(4-methylphenyl)-N-[4-[[N-methyl-N-(tetrahydro-2H-pyran-4-yl)amino]methyl]phenyl]-2,3-dihydro-1-benzazepine-4-carboxamide (1177 mg) was added 1N hydrochloric acid (20 ml), and the mixture was stirred at 100° C. for 1 hour. The mixture was dilute with ethyl acetate (50 ml) and made weakly basic with saturated sodium hydrogen carbonate solution (45 ml). To the mixture were added ethyl acetate (250 ml) and water (100 ml), and separated. The organic layer was dried with anhydrous magnesium sulfate. The solvent was evaporated under reduced pressure, and the residue was purified with silica gel column chromatography (75 g, ethyl acetate/ethanol=9:1) to give 7-(4-methylphenyl)-N-[4-[[N-methyl-N-(tetrahydro-2H-pyran-4-yl)amino]methyllphenyl]-2,3-dihydro-1-benzazepine-4-carboxamide (Compound 318) (804 mg, 72%) as amorphous.

$^1$H NMR (200 MHz, CDCl$_3$) δ 1.69–1.80 (4H, m), 2.21 (3H, s), 2.38 (3H, s), 2.58–2.72 (1H, m), 2.96 (2H, t, J=4.4 Hz), 3.37 (2H, td, J=11.4, 3.1 Hz), 3.47 (2H, t, J=4.8 Hz), 3.57 (2H, s), 4.01–4.07 (2H, m), 4.53–4.70 (1H, br), 6.71 (1H, d, J=8.4 Hz), 7.22 (2H, d, J=7.8 Hz), 7.28–7.32 (4H, m), 7.35 (1H, dd, J=8.4, 2.2 Hz), 7.42 (1H, s), 7.46 (1H, s), 7.48 (1H, d, J=2.0 Hz), 7.54 (2H, d, J=8.6 Hz). IR (KBr) 3330, 2949, 2847, 1651, 1609, 1514, 1507, 1408, 1316, 910, 812, 735 cm$^{-1}$. Anal. Calcd. for $C_{31}H_{35}N_3O_2$: C, 77.31; H. 7.32; N, 8.72. Found: C, 77.44; H. 7.12; N, 8.78.

WORKING EXAMPLE 319 (Production of Compound 319)

In dimethylformamide (5 ml) was dissolved 7-(4-ethoxyphenyl)-1-methyl-2,3-dihydro-1-benzazepine-4-carboxylic acid hydrochloride (0.5 g), and to the mixture was added, under ice-cooling, thionyl chloride (0.25 ml). The mixture was stirred at room temperature for 45 minutes, and the solvent was evaporated. The residue was dissolved in tetrahydrofuran (15 ml), and the mixture was added dropwise to a suspension of 4-((N-(3-ethoxypropyl)-N-methylamino)methyl)aniline dihydrochloride (0.41 g) and triethylamine (1.2 ml) in tetrahydrofuran (10 ml), under ice-cooling. Under nitrogen atmosphere, the mixture was stirred at room temperature overnight, and the solvent was evaporated. To the residue was added water, and the mixture was extracted with ethyl acetate. The organic layer was washed with water and saturated brine, and dried with anhydrous magnesium sulfate. Under reduced pressure, the solvent was evaporated, and the residue was purified with silica gel column (methanol/triethylamine/ethyl acetate) to give crude crystals, which were recrystallized from ethyl acetate-hexane to give N-(4-((N-(3-ethoxypropyl)-N-methylamino)methyl)phenyl)-7-(4-ethoxyphenyl)-1-methyl-2,3-dihydro-1-benzazepine-4-carboxamide (Compound 319) (0.39 g) as pale yellow crystals.

mp 129–131° C.; $^1$H-NMR(δ ppm, CDCl$_3$) 1.19 (3H, t, J=6.9 Hz), 1.44 (3H, t, J=7.1 Hz), 1.76–1.84 (2H, m), 2.19 (3H, s), 2.46 (2H, t, J=7.4 Hz), 2.97 (2H, t, J=4.6 Hz), 3.09 (3H, s), 3.35 (2H, t, J=4.8 Hz), 3.41–3.52 (6H, m), 4.07 (2H,q,J=7.1 Hz), 6.88 (1H, d, J=8.4 Hz), 6.95 (2H, d, J=8.8 Hz), 7.29 (2H, d, J=8.8 Hz), 7.40–7.55 (8H, m). IR(KBr) ν: 2978, 2868, 1651, 1607, 1516, 1503cm$^{-1}$. Anal. Calcd. for $C_{33}H_{41}N_3O_3$: C, 75.11; H, 7.83; N, 7.96. Found C, 74.90; H, 7.98; N, 7.97.

WORKING EXAMPLE 320 (Production of Compound 320)

In water/ethanol/toluene (1:1:10, 18.0 ml) were dissolved 4-ethylthiophenyl borate (264 mg) and 7-bromo-1-methyl-N-[4-[[N-methyl-N-(tetrahydro-2H-pyran-4-yl)amino]methyl]phenyl]-2,3-dihydro-1-benzazepine-4-carboxamide (439 mg), and to the mixture was added potassium carbonate (301 mg). Under argon atmosphere, the mixture was stirred for 30 minutes, and to the mixture was added tetrakistriphenylphosphine palladium (42 mg). Under argon atmosphere, the mixture was refluxed for 17.5 hours, and the mixture was dilute with ethyl acetate (200 ml). The mixture was washed with water (50 ml) and saturated brine (50 ml), and the organic layer was dried with anhydrous magnesium sulfate. The solvent was evaporated under reduced pressure, and the residue was purified with silica gel column chromatography (75 g, ethyl acetate→ethyl acetate/ethanol=9:1) and recrystallized from ethanol to give 7-(4-ethylthiophenyl)-1-methyl-N-[4-[[N-methyl-N-(tetrahydro-2H-pyran-4-yl)amino]methyl]phenyl]-2,3-dihydro-1-benzazepine-4-carboxamide (Compound 320) (168 mg, 34%).

mp 139–141° C.; $^1$H NMR (200 MHz, CDCl$_3$) δ 1.34 (3H, t, J=7.3 Hz), 1.63–1.76 (4H, m), 2.21 (3H, s), 2.57–2.72 (1H, m), 2.98 (2H, q, J=7.3 Hz), 2H around d 2.96 was concealed by d 2.98, 3.10 (3H, s), 3.31–3.43 (4H, m), 3.57 (2H, s), 4.00–4.07 (2H, m), 6.89 (1H, d, J=8.6 Hz), 7.28–7.40 (6H, m), 7.466 (1H, dd, J=8.5, 2.3 Hz), 7.473 (1H, s), 7.52–7.56 (4H, m). IR (KBr) 2948, 2845, 1645, 1597, 1514, 1489, 1408, 1314, 1244, 1188, 812 cm$^{-1}$. Anal. Calcd. for $C_{33}H_{39}N_3O_2S$: C, 73.16; H, 7.26; N, 7.76. Found: C, 72.96; H, 7.08; N, 7.64.

WORKING EXAMPLE 321 (Production of Compound 321)

In DMF (10.0 ml) was dissolved 7-(4-methylphenyl)-1-[(trifluoromethyl)sulfonyl]-2,3-dihydro-1-benzazepine-4-carboxylic acid (387 mg), and to the mixture was added thionyl chloride (0.175 ml). The mixture was stirred at room temperature for 1 hour, and excess thionyl chloride and DMF were evaporated under reduced pressure. The residue was dissolved in dichloromethane (10.0 ml), and the mixture was added dropwise to a solution of 4-[[N-methyl-N-(tetrahydro-2H-pyran-4-yl)amino]methyl]aniline dihydrochloride (331 mg) and triethylamine (0.98 ml) in dichloromethane (15.0 ml) at 0° C. The mixture was stirred at room temperature for 4 hours, and to the mixture was added water (50 ml). The mixture was extracted with dichloromethane (100 ml×3), and the organic layer was dried with anhydrous magnesium sulfate. The solvent was evaporated under reduced pressure, and the residue was purified with silica gel column chromatography (35 g, ethyl acetate→ethyl acetate/ethanol=9:1) and recrystallized from ethanol to give 7-(4-methylphenyl)-N-[4-[[N-methyl-N-methyl-N-(tetrahydro-2H-pyran-4-yl)amino]methyl]phenyl]-1-[(trifluoromethyl)sulfonyl]-2,3-dihydro-1-benzazepine-4-carboxamide (Compound 71) (251 mg, 43%).

mp 185–187° C.; $^1$H NMR (200 MHz, CDCl$_3$) δ 1.70–1.77 (4H, m), 2.21 (3H, s), 2.41 (3H, s), 2.57–2.72 (1H, m), 3.11 (2H, t, J=5.9 Hz), 3.37 (2H, td, J=11.3, 2.9 Hz), 3.58 (2H, s), 4.02–4.08 (4H, m), 7.26–7.35 (4H, m), 7.46–7.61 (8H, m), 7.64 (1H, s). IR (KBr) 1661, 1516, 1497, 1393, 1314, 1223, 1194, 1142, 812 cm$^{-1}$. Anal. Calcd. for C$_{32}$H$_{34}$F$_3$N$_3$O$_4$S: C, 62.63; H, 5.58; N, 6.85. Found: C, 62.58; H, 5.57; N. 6.91.

WORKING EXAMPLE 322 (Production of Compound 322)

To a solution of 7-(4-methylphenyl)-2,3-dihydrobenzoxepine-4-carboxylic acid (280 mg) and 2-[(4-aminophenyl)methylamino]pyridine (199 mg) in DMF (4 ml) was added, under ice-cooling, diethyl cyanophosphate (0.18 ml) and triethylamine (0.17 ml), and the mixture was stirred at 0° C. for 30 minutes and then at room temperature for 1 hour. To the mixture was added DMAP (1 piece), and the mixture was stirred at room temperature for 18 hours. Under ice-cooling, to the mixture was added sodium bicarbonate solution, and the mixture was extracted with ethyl acetate, washed with brine, dried (anhydrous magnesium sulfate) and concentrated. The residue was purified with silica gel column chromatography (ethyl acetate/hexane =1/1) and recrystallized from ethyl acetate/hexane to give N-[4-[(pyrid-2-yl)aminomethyl]phenyl]-7-(4-methylphenyl)-2,3-dihydro-1-benzoxepine-4-carboxamide (Compound 72) (97 mg) as colorless crystals.

m.p. 189–190° C.; $^1$H-NMR (200 MHz, CDCl$_3$) δ: 2.39 (3H, s), 3.07 (2H, t, J=4.6), 4.36 (2H, t, J=4.6), 4.49 (2H, d, J =4.6), 4.9–5.0 (1H, brm), 6.38 (1H, d, J=8.4), 6.60 (1H, dd, J=5.2, 7.2), 7.06 (1H, d, J=8.4), 7.2–7.6 (12H, m), 8.05–8.15 (1H, m). IR (KBr) 1651, 1597, 1522, 1491, 1439, 1316, 1254, 812, 772cm$^{-1}$. Anal. for C$_{30}$H$_{27}$N$_3$O$_2$.0.2H$_2$O; Calcd. C, 77.46; H, 5.94; N, 9.03: Found. C, 77.24; H, 5.96; N, 8.91.

REFERENCE EXAMPLE 277

A solution of p-nitrobenzyl bromide (10 g) in THF (50 ml) was added dropwise to a solution of bis(2-methoxyethyl) amine (6.8 g) and triethylamine (10 ml) in THF (50 ml). Under nitrogen atmosphere, the mixture was stirred at room temperature overnight, and the solvent was evaporated. To the residue was added water, and the mixture was extracted with ethyl acetate. The organic layer was washed with water and saturated brine, and dried with anhydrous magnesium sulfate. Under reduced pressure, the solvent was evaporated to give N,N-bis(2-methoxyethyl)-4-nitrobenzylamine (10.8 g) as yellow oil.

$^1$H-NMR(δ ppm, CDCl$_3$) 2.76 (4H, t, J=5.6 Hz), 3.31 (6H, s), 3.48 (4H, t, J=5.6 Hz), 3.83 (2H, s), 7.54 (2H, d, J=8.8 Hz), 8.17 (2H, d, J=8.8 Hz). IR(neat) v: 2878, 1599, 1520cm$^{-1}$.

REFERENCE EXAMPLE 278

In acetic acid (200 ml) was dissolved N,N-bis(2-methoxyethyl)-4-nitrobenzylamine (10.5 g), and to the mixture was added reduced iron (11 g) little by little. The mixture was stirred at room temperature overnight, and the solvent was evaporated. To the residue was added ethyl acetate and precipitates were filtered off. The filtrate was washed with sodium hydroxide solution, water and saturated brine, and dried with anhydrous magnesium sulfate. Under reduced pressure, the solvent was evaporated, and the residue was purified with silica gel column chromatography (ethyl acetate) to give 4-((N,N-bis(2-methoxyethyl)amino) methyl)aniline (6.2 g) as red oil.

$^1$H-NMR(δ ppm, CDCl$_3$) 2.71 (4H, t, J=6.3 Hz), 3.31 (6H, s), 3.46 (4H, t, J=6.3 Hz), 3.59 (2H, s), 6.63 (2H, d, J=8.4 Hz), 7.10 (2H, d, J=8.4 Hz). IR(neat) v: 3353, 2874, 2818, 1615cm$^{-1}$.

REFERENCE EXAMPLE 279

In 1,2-dichloroethane (50 ml) were dissolved p-nitrobenzaldehyde (5 g) and 3-ethoxypropylamine (3.75 g), and to the mixture was added, under ice-cooling, triacetoxy sodium boro hydride (9.8 g). Under nitrogen atmosphere, the mixture was stirred at room temperature overnight, and to the mixture were added, under ice-cooling, 37% formalin (3.5 ml) and triacetoxy sodium boro hydride (9.8 g). Under nitrogen atmosphere, the mixture was stirred at room temperature for 8 hours, and the solvent was evaporated. The residue was neutralized with 1N sodium hydroxide solution, and the mixture was extracted with ethyl acetate. The organic layer was washed with water and subjected to back extraction with 1N hydrochloric acid. The mixture was washed with ethyl acetate, neutralized with 1N sodium hydroxide and extracted with ethyl acetate. The organic layer was washed with water and saturated brine, and dried with anhydrous magnesium sulfate. Under reduced pressure, the solvent was evaporated to give N-(3-ethoxypropyl)-N-methyl-4-nitrobenzylamine (6.6 g) as yellow oil.

$^1$H-NMR(δ ppm, CDCl$_3$) 1.18 (3H, t, J=7.0 Hz), 1.72–1.86 (2H, m), 2.20 (3H, s), 2.48 (2H, t, J=7.6 Hz) 3.41–3.52 (4H, m), 3.58 (2H, s), 7.50 (2H, d, J=8.8 Hz), 8.17 (2H, d, J=8.8 Hz). IR(neat) v: 2859, 1520, 1346cm$^{-1}$.

REFERENCE EXAMPLE 280

In THF (60 ml) were suspended N-(3-ethoxypropyl)-N-methyl-4-nitrobenzylamine (6.0 g), iron chloride (III) (0.06 g) and active charcoal (0.6 g), and to the suspension was added dropwise hydrazine monohydrate (4.1 ml) at 60–65° C. The mixture was stirred at 65° C. for 4 hours, and to the mixture was added hydrazine monohydrate (15 ml). The mixture was stirred at 65° C. for 4 hours and filtered. The solvent of the filtrate was evaporated, and the residue was extracted with ethyl acetate. The organic layer was washed with saturated brine and dried with anhydrous magnesium sulfate, and the solvent was evaporated. The residue was dissolved in 2-propanol, and to the mixture was added hydrochloric acid (6 ml). The solvent was evaporated, and the precipitated 4-((N-(3-ethoxypropyl)-N-methylamino) methyl)aniline dihydrochloride (5.8 g) was filtered with ethyl acetate and washed with ethyl acetate-hexane to give yellow powder.

mp 173–175° C.; $^1$H-NMR($\delta$ ppm, CDCl$_3$+CD$_3$OD) 1.16 (3H, t, J=7.0 Hz), 2.18 (2H, br), 2.72 (3H, s), 3.05–3.29 (2H, m), 3.40–3.52 (4H, m), 4.22–4.43 (2H, m), 7.58 (2H, d, J=8.2 Hz), 7.78 (2H, d, J=8.2 Hz), 11.86 (1H, br). IR(KBr) v: 1651 cm$^{-1}$. Anal. Calcd. for C$_{13}$H$_{22}$N$_2$O.2HCl: C, 52.88; H, 8.19; N, 9.49. Found C, 52.61; H, 8.05; N, 9.55.

REFERENCE EXAMPLE 281

In 1,2-dichloroethane (50 ml) were suspended p-nitrobenzylamine hydrochloride (3 g), 1,3-dimethoxyacetone (1.9 g) and triethylamine (2.2 ml), and to the mixture was added, under ice-cooling, triacetoxy sodium boro hydride (4.7 g). Under nitrogen atmosphere, the mixture was stirred at room temperature for 5 hours, and to the mixture were added, under ice-cooling, 37% formalin (1.8 ml) and triacetoxy sodium boro hydride (5 g). Under nitrogen atmosphere, the mixture was stirred at room temperature overnight, and the solvent was evaporated. The residue was neutralized with 1N sodium hydroxide solution and extracted with ethyl acetate. The organic layer was washed with water and saturated brine, and dried with anhydrous magnesium sulfate. Under reduced pressure, the solvent was evaporated, and the residue was purified with silica gel column (ethyl acetate/hexane) to give N-(1,3-dimethoxypropan-2-yl)-N-methyl-4-nitrobenzylamine (3.2 g) as yellow oil.

$^1$H-NMR($\delta$ ppm, CDCl$_3$) 2.32 (3H, s), 2.97–3.09 (1H, m), 3.36 (6H, s) 3.44–3.63 (4H, m), 3.85 (2H, s), 7.53 (2H, d, J=9.0 Hz), 8.17 (2H, d, J=9.0 Hz). IR(neat) v: 2880, 1520, 1346cm$^{-1}$.

REFERENCE EXAMPLE 282

In acetic acid (100 ml) was dissolved N-(1,3-dimethoxypropan-2-yl)-N-methyl-4-nitrobenzylamine (3.1 g), and to the mixture was added reduced iron (3.2 g) little by little. The mixture was stirred at room temperature overnight, and the solvent was evaporated. To the residue was added ethyl acetate, and precipitates were filtered off. The filtrate was washed with sodium hydroxide solution, water and saturated brine, and dried with anhydrous magnesium sulfate. Under reduced pressure, the solvent was evaporated, and the residue dissolved in ethyl acetate. To the mixture was added 4N hydrochloric acid-ethyl acetate, and precipitates were filtered and washed with diethylether. The mixture was dissolved in water, and the mixture was neutralized with 1N sodium hydroxide solution and extracted with ethyl acetate. The organic layer was washed with water and saturated brine, and dried with anhydrous magnesium sulfate. Under reduced pressure, the solvent was evaporated to give 4-((N-(1,3-dimethoxypropan-2-yl)-N-methylamino) methyl)aniline (2.4 g) as red oil.

$^1$H-NMR($\delta$ ppm, CDCl$_3$) 2.29 (3H, s), 2.95–3.07 (1H, m), 3.34 (6H, s), 3.42–3.58 (4H, m), 3.61 (2H, s), 6.64 (2H, d, J=8.4 Hz), 7.11 (2H, d, J=8.4 Hz). IR(neat) v: 3357, 2880, 1615, 1518 cm$^{-1}$.

REFERENCE EXAMPLE 283

In 1,2-dichloroethane (50 ml) were dissolved p-nitrobenzaldehyde (5 g) and 2-methoxyethylamine (2.7 g), and to the mixture was added, under ice-cooling, triacetoxy sodium boro hydride (9.8 g). Under nitrogen atmosphere, the mixture was stirred at room temperature for 4 hours, and to the mixture were added, under ice-cooling, 37% formalin (3.8 ml) and triacetoxy sodium boro hydride (10 g). Under nitrogen atmosphere, the mixture was stirred at room temperature overnight, and the solvent was evaporated. The residue was neutralized with 1N sodium hydroxide solution and extracted with ethyl acetate. The organic layer was washed with water and saturated brine, and dried with anhydrous magnesium sulfate. Under reduced pressure, the solvent was evaporated, and the residue was purified with silica gel column (ethyl acetate/hexane) to give N-(2-methoxyethyl)-N-methyl-4-nitrobenzylamine (5.9 g) as yellow oil.

$^1$H-NMR($\delta$ ppm, CDCl$_3$) 2.28 (3H, s), 2.63 (2H, t, J=5.6 Hz), 3.35 (3H, s), 3.52 (2H, t, J=5.6 Hz), 3.65 (2H, s) 7.52 (2H, d, J=8.8 Hz), 8.18 (2H, d, J=8.8 Hz). IR(neat) v: 2814, 1605, 1520, 1346 cm$^{-1}$.

REFERENCE EXAMPLE 284

In acetic acid (100 ml) was dissolved N-(2-methoxyethyl)-N-methyl-4-nitrobenzylamine (5.9 g), and to the mixture was added reduced iron (7.5 g) little by little. The mixture was stirred at room temperature overnight, and the solvent was evaporated. To the residue was added ethyl acetate, and precipitates were filtered off. The filtrate was washed with sodium hydroxide solution, water and saturated brine, and dried with anhydrous magnesium sulfate. Under reduced pressure, the solvent was evaporated to give 4-((N-(2-methoxyethyl)-N-methylamino)methyl)aniline (3.4 g) as red oil.

$^1$H-NMR($\delta$ ppm, CDCl$_3$) 2.24 (3H, s), 2.57 (2H, t, J=6.0 Hz), 3.33 (3H, s), 3.44 (2H, s), 3.50 (2H, t, J=6.0 Hz), 6.64 (2H, d, J=8.4 Hz), 7.09 (2H, d, J=8.4 Hz). IR(neat) v: 3349, 2813, 1615, 1518cm$^{-1}$.

REFERENCE EXAMPLE 285

In THF (350 ml) was dissolved 5-bromoanthranilic acid (40.06 g), and the mixture was cooled to 0° C. To the mixture was added dropwise a solution of 10.0M borane dimethylsulfide in THF (54.5 ml), and the mixture was stirred at room temperature for 4.5 hours. The mixture was cooled to 0° C., and to the mixture was added dropwise 3N sodium hydroxide solution. The mixture was stirred at room temperature overnight, and to the mixture was added granulated sodium hydroxide to adjust the mixture to pH 11. The aqueous layer was saturated with potassium carbonate, and the THF layer was separated. The aqueous layer was extracted with ether (100 ml×5). The organic layers were combined and dried with magnesium sulfate. The solvent was evaporated under reduced pressure to give (2-amino-5-bromophenyl)methanol (36.66 g, 100%).

$^1$H NMR (200 MHz, CDCl$_3$) $\delta$ 4.62 (2H, s), 7.20 (1H, s), 7.23–7.26 (1H, m).

REFERENCE EXAMPLE 286

To acetone (300 ml) were added (2-amino-5-bromophenyl)methanol (23.32 g) and active manganese dioxide (58.5 g), and the mixture was stirred at room temperature for 17.5 hours and filtered. The solvent was evaporated under reduced pressure to give 2-amino-5-bromobenzaldehyde (16.41 g, 71%).

$^1$H NMR (200 MHz, CDCl$_3$) $\delta$ 6.10–6.20 (2H, br), 6.57 (1H, d, J=8.8 Hz), 7.38 (1H, dd, J=8.8, 2.4 Hz), 7.59 (1H, d, J=2.4 Hz), 9.81 (1H, s).

REFERENCE EXAMPLE 287

To acetic acid anhydride (34.8 ml) was added formic acid (17.0 ml) at 0° C., and the mixture was stirred at 60° C. for 2 hours, cooled and diluted with THF (200 ml). In THF (100 ml) was dissolved 2-amino-5-bromobenzaldehyde (16.40 g), and the mixture was added dropwise to the previously prepared solution of formic acid anhydride in THF at 0° C. The mixture was stirred at 0° C. for 2 hours, and the solvent was evaporated under reduced pressure. The residue was washed with hexane and filtered to give 4-bromo-2-formylphenylformamide (15.24 g, 82%).

$^1$H NMR (200 MHz, CDCl$_3$) δ 7.72 (1H, dd, J=8.8, 2.6 Hz), 7.83 (1H, d, J=2.6 Hz), 8.53 (1H, s), 8.68 (1H, d, J=9.2 Hz), 9.88 (1H, s), 10.94 (1H, br).

REFERENCE EXAMPLE 288

To 4-bromo-2-formylphenylformamide (18.07 g), ethyl 4-bromobutyrate (30.9 g) and potassium carbonate (21.9 g) was added DMF (160 ml), and the mixture was stirred at 70° C. for 24 hours. The mixture was dilute with ethyl acetate (1400 ml), washed with water (300 ml×3) and saturated brine (150 ml), and dried with magnesium sulfate. The solvent was evaporated under reduced pressure, and the residue was purified with silica gel column chromatography (300 g, hexane:ethyl acetate=4:1→1:1) to give ethyl 4-(4-bromo-2,N-diformylanilino)butyrate (21.56 g, 80%).

$^1$H NMR (200 MHz, CDCl$_3$) (syn:anti=5:2 or 2:5) δ 1.23 (2.1H, t, J=7.2 Hz), 1.25 (0.9H, t, J=7.2 Hz), 1.87 (2H, quint, J=7.5 Hz), 2.35 (1.4H, t, J=7.3 Hz), 2.36 (0.6H, t, J=6.8 Hz), 3.78 (0.6H, t, J=7.5 Hz), 3.85 (1.4H, t, J=7.6 Hz), 4.10 (1.4H, q, J=6.9 Hz), 4.15 (0.6H, q, J=7.2 Hz), 7.17 (0.3H, d, J=8.4 Hz), 7.24 (0.7H, d, J=8.6 Hz), 7.81 (0.3H, dd, J=8.4, 2.4 Hz), 7.82 (0.7H, dd, J=8.4, 2.4 Hz), 8.09 (0.3H, d, J=2.4 Hz), 8.10 (0.7H, d, J=2.4 Hz), 8.19 (0.7H, s), 8.39 (0.3H, s), 9.92 (0.3H, s), 10.04 (0.7H, s).

REFERENCE EXAMPLE 289

In t-butanol (500 ml) were dissolved ethyl 4-(4-bromo-2,N-diformylanilino)butyrate (15.32 g) and potassium t-butoxide (5.53 g), and the mixture was ref luxed for 30 minutes. To the mixture were added water (500 ml) and 1N hydrochloric acid (50 ml), and the mixture was extracted with ethyl acetate (1000 ml). Theorganiclayerwaswashed-withsaturatedbrine (200 ml) and dried with magnesium sulfate. The solvent was evaporated under reduced pressure, and the residue was purified with silica gel column chromatography (300 g, hexane:ethyl acetate=4:1→1:1) to give ethyl 7-bromo-1-formyl-2,3-dihydro-1-benzazepine-4-carboxylate (3.13 g, 22%) and 7-bromo-1-formyl-2,3-dihydro-1-benzazepine-4-carboxylic acid (1.39 g, 10%).

Ethyl 7-bromo-1-formyl-2,3-dihydro-1-benzazepine-4-carboxylate;

mp 150.5–152° C.; $^1$H NMR (200 MHz, CDCl$_3$) δ 1.34 (3H, t, J=7.1 Hz), 2.93 (2H, t, J=4.9 Hz), 3.80 (2H, t, J=5.7 Hz), 4.28 (2H, q, J=7.2 Hz), 7.00 (1H, d, J=8.4 Hz), 7.50 (1H, dd, J=8.4, 2.2 Hz), 7.57 (1H, s), 7.66 (1H, d, J=2.2 Hz), 8.46 (1H, s). IR (KBr) 1707, 1678, 1491, 1358, 1265, 1235, 1194, 1088 cm$^{-1}$. Anal. Calcd. for C$_{14}$H$_{14}$NO$_3$Br: C, 51.87; H, 4.35; N, 4.32. Found: C, 51.81; H, 4.35; N, 4.19.

7-Bromo-1-formyl-2,3-dihydro-1-benzazepine-4-carboxylic acid;

mp 248–249.5° C.; $^1$H NMR (200 MHz, DMSO-d$_6$) δ 2.73 (2H, td, J=5.1, 1.2 Hz), 3.67 (2H, t, J=5.9 Hz), 7.33 (1H, d, J=8.4 Hz), 7.57 (1H, s), 7.61 (1H, dd, J=8.4, 2.6 Hz), 7.91 (1H, d, J=2.4 Hz), 8.48 (1H, s). IR (KBr) 1665, 1491, 1431, 1360, 1300, 1281, 1252, 1196, 999, 918, 841, 754 cm$^{-1}$. Anal. Calcd. for C$_{12}$H$_{10}$NO$_3$Br: C, 48.67; H, 3.41; N, 4.73. Found: C, 48.70; H, 3.56; N, 4.54.

REFERENCE EXAMPLE 290

In 1N sodium hydroxide (13.0 ml) and THF:ethanol (1:1, 50 ml) was dissolved ethyl 7-bromo-1-formyl-2,3-dihydro-1-benzazepine-4-carboxylate (2.77 g), and the mixture was stirred at room temperature for 15 hours. To the mixture was added 1N hydrochloric acid (12.5 ml), and the mixture was concentrated. To the residue was added water (200 ml), and the mixture was adjusted to pH 2 with 1N hydrochloric acid. The mixture was extracted with ethyl acetate(300 ml×3), and the organic layer was dried with magnesium sulfate. The solvent was evaporated under reduced pressure to give 7-bromo-1-formyl-2,3-dihydro-1-benzazepine-4-carboxylic acid (2.52 g, 100%).

REFERENCE EXAMPLE 291

To a solution of 7-bromo-1-formyl-2,3-dihydro-1-benzazepine-4-carboxylic acid (3.28 g) in DMF (30 ml) was added dropwise thionyl chloride (2.0 ml) at 0° C., and the mixture was stirred at room temperature for 30 minutes. Under reduced pressure, thionyl chloride and DMF were evaporated, and the residue was dissolved in dichloromethane (40 ml). To a solution of 4-([N-methyl-N-(tetrahydro-2H-pyran-4-yl)amino]methyl]aniline (3.90 g) and triethylamine (11.6 ml) in dichloromethane (40 ml) was added dropwise the previously prepared chloride solution at 0° C., and the mixture was stirred at room temperature for 7 hours. The mixture was concentrated under reduced pressure, and the residue was diluted with ethyl acetate (400 ml), washed with water (100 ml×2) and saturated brine (50 ml), and dried with magnesium sulfate. The solvent was evaporated under reduced pressure, and the residue was purified with silica gel column chromatography (200 g, ethyl acetate→ethyl acetate/ethanol=10:1) to give 7-bromo-1-formyl-N-[4-[[N-methyl-N-(tetrahydro-2H-pyran-4-yl)amino]methyl]phenyl]-2,3-dihydro-1-benzazepine-4-carboxamide (2.13 g, 39%).

mp 173–175° C.; $^1$H NMR (200 MHz, CDCl$_3$) δ 1.66–1.77 (4H, m), 2.21 (3H, s), 2.58–2.73 (1H, m), 3.02 (2H, t, J=4.8 Hz), 3.37 (2H, td, J=10.3, 2.9 Hz), 3.58 (2H, s), 3.87 (2H, t, J=5.5 Hz), 4.02–4.08 (2H, m), 7.03 (1H, d, J=8.4 Hz), 7.32 (2H, d, J=8.4 Hz), 1H was concealed under 7.27–7.34, 7.50 (1H, s), 7.51 (1H, dd, J=8.5, 2.3 Hz), 7.52 (2H, d, J=8.4 Hz), 7.65 (1H, d, J=2.2 Hz), 8.49 (1H, s). IR (KBr) 2953, 2845, 1669, 1599, 1520, 1358, 1316, 1260, 1192, 733 cm$^{-1}$. Anal. Calcd. for C$_{25}$H$_{28}$N$_3$O$_3$Br: C, 60.24; H, 5.66; N, 8.43. Found: C, 60.15; H, 5.69; N, 8.49.

REFERENCE EXAMPLE 292

To t-butyl 7-bromo-1-methyl-2,3-dihydro-1-benzazepine-4-carboxylate (4.0 g), 4-ethoxyphenyl borate (2.35 g), 1M potassium carbonate solution (25 ml) and ethanol (25 ml) was added toluene (100 ml), and the mixture was stirred under argon atmosphere at room temperature for 30 minutes. To the mixture was added tetrakistriphenylphosphine palladium (0.55 g), and the mixture was ref luxed under argon atmosphere overnight. The organic layer was washed with water and saturated brine, and dried with anhydrous magnesium sulfate. Under reduced pressure, the solvent was evaporated, and the residue was purified with silica gel column (ethyl acetate/hexane) to give t-butyl 7-(4-ethoxyphenyl)-1-methyl-2,3-dihydro-1-benzazepine-4-carboxylate (4.0 g) as yellow crystals.

mp 140–142° C.; $^1$H-NMR($\delta$ ppm, CDCl$_3$) 1.43 (3H, t, J=7.0 Hz), 1.54 (9H, s), 2.82 (2H, t, J=4.8 Hz), 3.05 (3H, s), 3.27 (2H, t, J=4.8 Hz), 4.07 (2H,q,J=7.0 Hz), 6.83 (1H, d, J=8.4 Hz), 6.95 (2H, d, J=8.8 Hz), 7.38–7.49 (4H, m), 7.66 (1H, s). IR(KBr) n: 2978, 1694cm$^{-1}$. Anal. Calcd. for C$_{24}$H$_{29}$NO$_3$: C, 75.96; H, 7.70; N, 3.69. Found C, 75.91; H, 7.89; N, 3.49.

REFERENCE EXAMPLE 293

In dimethoxyethane (100 ml) was dissolved t-butyl 7-(4-ethoxyphenyl)-1-methyl-2,3-dihydro-1-benzazepine-4-carboxylate (4.0 g), and to the mixture was added 6N hydrochloric acid (25 ml). The mixture was refluxed for 3 hours, and the solvent was evaporated. Precipitated yellow powder was filtered and washed with ethyl acetate-hexane to give 7-(4-ethoxyphenyl)-1-methyl-2,3-dihydro-1-benzazepine-4-carboxylic acid hydrochloride (3.8 g).

mp 245–254° C.(dec.). $^1$H-NMR($\delta$ ppm, DMSO-d$_6$) 1.35 (3H, t, J=7.0 Hz), 2.77 (2H, br), 3.02 (3H, s), 3.25 (2H, br), 4.05 (2H,q,J=7.0 Hz), 6.94–6.98 (3H, m), 7.49–7.68 (5H, m). IR(KBr) v: 2976, 2880, 2475, 1701cm$^{-1}$.

REFERENCE EXAMPLE 294

In 1N hydrochloric acid (25 ml) and ethanol (20 ml) was dissolved ethyl 7-bromo-1-formyl-2,3-dihydro-1-benzazepine-4-carboxylate (1165 mg), and the mixture was refluxed for 2 hours. The mixture was neutralized with saturated sodium hydrogen carbonate solution, and the mixture was extracted with ethyl acetate (300 ml). The organic layer was washed with water (100 ml) and dried with anhydrous magnesium sulfate. The solvent was evaporated under reduced pressure, and the residue was purified with silica gel column chromatography (150 g, hexane/ethyl acetate=9:1) to give ethyl 7-bromo-2,3-dihydro-1-benzazepine-4-carboxylate (628 mg, 59%).

mp 120–121° C.; $^1$H NMR (200 MHz, CDCl$_3$) $\delta$ 1.34 (3H, t, J=7.1 Hz), 2.86 (2H, td, J=4.8, 1.2 Hz), 3.36 (2H, t, J=4.8 Hz), 4.25 (2H, q, J=7.1 Hz), 4.51–4.66 (1H, br), 6.49 (1H, d, J=8.8 Hz), 7.15 (1H, dd, J=8.7, 2.3 Hz), 7.39 (1H, d, J=2.2 Hz), 7.53 (1H, s). IR (KBr) 3377, 2978, 1694, 1493, 1248, 1209, 1173, 1090, 812 cm$^{-1}$. Anal. Calcd. for C$_{13}$H$_{14}$BrNO$_2$: C, 52.72; H, 4.76; N, 4.73. Found: C, 52.54; H, 4.88; N, 4.60.

REFERENCE EXAMPLE 295

In dichloromethane (30 ml) were dissolved 7-bromo-2,3-dihydro-1-benzazepine-4-carboxylic acid ethyl (457 mg) and triethylamine (1.29 ml), and to the mixture was added dropwise at 0° C. trifluoromethanesulfonic acid anhydride (1.56 ml). The mixture was stirred at 0° C. for 4 hours, and to the mixture was added water (50 ml) at 0° C. The mixture was extracted with dichloromethane (100 ml), and the organic layer was dried with anhydrous magnesium sulfate. The solvent was evaporated under reduced pressure, and the residue was purified with silica gel column chromatography (50 g, hexane/ethyl acetate=9:1) to give ethyl 7-bromo-1-[(trifluoromethyl)sulfonyl]-2,3-dihydro-1-benzazepine-4-carboxylate (516 mg, 78%).

$^1$H NMR (200 MHz, CDCl$_3$) $\delta$ 1.36 (3H, t, J=7.5 Hz), 3.00 (2H, t, J=6.0 Hz), 3.91–4.03 (2H, m), 4.30 (2H, q, J=7.2 Hz), 7.38 (1H, d, J=8.4 Hz), 7.45 (1H, dd, J=8.8, 2.2 Hz), 7.63 (1H+1H, s). IR (KBr) 2982, 1713, 1487, 1397, 1252, 1227, 1194, 1142, 1100, 1090, 700, 627 cm$^{-1}$.

REFERENCE EXAMPLE 296

In water/ethanol/toluene (1:1:10, 36.0 ml) 4-methylphenyl borate (194 mg) and ethyl 7-bromo-1-[(trifluoromethyl)sulfonyl]-2,3-dihydro-1-benzazepine-4-carboxylate (510 mg) were dissolved, and to the mixture was added potassium carbonate (395 mg). The mixture was stirred under argon atmosphere for 30 minutes, and to the mixture was added tetrakistriphenylphosphine palladium (138 mg). Under argon atmosphere, the mixture was refluxed for 17 hours, and the mixture was diluted with ethyl acetate (150 ml) and washed with water (50 ml) and saturated brine (50 ml). The organic layer was dried with anhydrous magnesium sulfate. The solvent was evaporated under reduced pressure, and the residue was purified with silica gel column chromatography (50 g, hexane/ethyl acetate=9:1) to give ethyl 7-(4-methylphenyl)-1-[(trifluoromethyl)sulfonyl]-2,3-dihydro-1-benzazepine-4-carboxylate (469 mg, 90%).

$^1$H NMR (200 MHz, CDCl$_3$) $\delta$ 1.37 (3H, t, J=7.2 Hz), 2.41 (3H, s), 3.02 (2H, t, J=6.0 Hz), 3.99–4.05 (2H, m), 4.31 (2H, q, J=7.1 Hz), 7.27 (2H, d, J=8.0 Hz), 7.43–7.56 (4H, m), 7.60–7.68 (1H, m), 7.77 (1H, s). IR (KBr) 2982, 1709, 1495, 1395, 1246, 1225, 1192, 1152, 1096, 812, 642, 588 cm$^{-1}$.

REFERENCE EXAMPLE 297

In 1N sodium hydroxide solution (3.0 ml) and THF/ethanol (1:1, 12.0 ml) was dissolved 7-(4-methylphenyl)-1-[(trifluoromethyl)sulfonyl]-2,3-dihydro-1-benzazepine-4-carboxylic acid ethyl (463 mg), and the mixture was stirred at room temperature for 14 hours. The mixture was neutralized with 1N hydrochloric acid (3.5 ml) and concentrated. To the residue was added water (40 ml), and the mixture was extracted with ethyl acetate (100 ml×3). The organic layer was dried with anhydrous magnesium sulfate, and the solvent was evaporated under reduced pressure to give 7-(4-methylphenyl)-1-[(trifluoromethyl)sulfonyl]-2,3-dihydro-1-benzazepine-4-carboxylic acid (393 mg, 91%).

$^1$H NMR (200 MHz, DMSO-d$_6$) $\delta$ 2.39 (3H, s), 2.94 (2H, t, J=6.2 Hz), 4.00–4.08 (2H, m), 7.28 (2H, d, J=8.6 Hz), 7.41–7.49 (1H, m), 7.56 (2H, d, J=8.4 Hz), 7.61–7.66 (1H, m), 7.73–7.77 (1H, m), 8.00 (1H, s).

REFERENCE EXAMPLE 298

To a solution of 4-nitrobenzaldehyde (3.02 g) and 2-aminopyridine (1.88 g) in 1,2-dichloroethane (70 ml) were added triacetoxy sodium boro hydride (5.93 g) and acetic acid (1.14 ml), and the mixture was stirred under nitrogen atmosphere at room temperature for 2 hours and concentrated. To the residue was added sodium bicarbonate solution, and the mixture was extracted with ethyl acetate, washed with brine, dried (anhydrous magnesium sulfate) and concentrated. The residue was purified with silica gel column chromatography (ethyl acetate/hexane=1/1), and to the purified materials were added ethyl acetate/diethylether and 1N hydrochloric acid. The aqueous layer was extracted and washed with diethylether, and to the mixture was added sodium carbonate. The mixture was extracted with ethyl acetate, and the extract was dried (anhydrous magnesium sulfate), concentrated and recrystallized from ethyl acetate/hexane to give 2-[(4-nitrophenyl)methylamino]pyridine (1.63 g) as pale yellow crystals.

m.p. 131–132° C.; $^1$H-NMR (200 MHz, CDCl$_3$) $\delta$: 4.67 (2H, d, J=6.0), 4.9–5.1 (1H, brm), 6.37 (1H, d, J=8.4), 6.63 (1H, dd, J=5.1, 6.9), 7.35–7.45 (1H, m), 7.52 (2H, d, J=8.8), 8.15–8.25 (1H, m), 8.18 (2H, d, J=8.8). IR (KBr) 1601, 1516, 1460, 1348, 1281, 1159, 999, 772cm$^{-1}$ Anal for C$_{12}$H$_{11}$N$_3$O$_2$ Calcd. C, 62.87; H, 4.84; N, 18.33: Found. C, 62.69; H, 4.69; N, 18.20.

REFERENCE EXAMPLE 299

To a solution of nicke l bromide (44 mg) in methanol (4 ml)/THF (4 ml) was added sodium boro hydride (40 mg), and the mixture was stirred. To the mixture was added 2-[(4-nitrophenyl)methylamino]pyridine (0.92 g) and then sodium boro hydride (414 mg), and the mixture was stirred at room temperature for 1 hour. To the mixture was added nickel bromide (44 mg)and sodium boro hydride (454 mg), and the mixture was stirred at room temperature for 2 hours. Insoluble materials were filtered off with sellaite, and to the filtrate was added sodium bicarbonate solution. The mixture was extracted with ethyl acetate and washed with brine. The extract was dried (anhydrous magnesium sulfate) and concentrated, and the residue was purified twice with silica gel column chromatography (ethyl acetate/hexane=1/1) to give 2-[(4-aminophenyl)methylamino]pyridine (369 mg) as pale red solid.

$^1$H-NMR (200 MHz, CDCl$_3$) δ: 3.4–3.8 (2H, br), 4.36 (2H, d, J=5.2), 4.7–4.85 (1H, br), 6.37 (1H, d, J=8.4), 6.58 (1H, dd, J=5.2, 8.0), 6.66 (2H, d, J=8.4), 7.15 (2H, d, J=8.4), 7.35–7.45 (1H, m), 8.05–8.15 (1H, m). IR (KBr) 1603, 1578, 1514, 1443, 1335, 1294, 1159, 818, 770cm$^{-1}$.

INDUSTRIAL APPLICABILITY

The compound of the formula (I) or a salt thereof of the present invention has potent antagonistic activity on MCP-1 receptor and can be advantageously used for the treatment or prophylaxis of various inflammatory diseases in human and animals, cardiac inf arction, myocarditis, etc.

What is claimed is:

1. A compound of the formula:

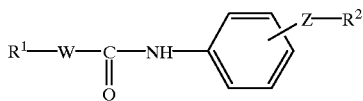

wherein $R^1$ is an optionally substituted 5- to 6-membered ring, W is a divalent group of the formula:

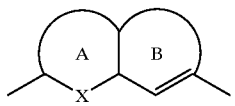

wherein the ring A is an optionally substituted 5- to 6-membered aromatic ring, X is an optionally substituted carbon atom, an optionally substituted nitrogen atom, sulfur atom or oxygen atom, the ring B is an optionally substituted 5- to 7-membered ring, Z is a chemical bond or a divalent group, $R^2$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group binding through a sulfur atom or (4) a group of the formula:

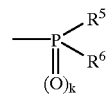

wherein k is 0 or 1, and when k is 0, a phosphorus atom may form a phosphonium; and $R^5$ and $R^6$ are independently an optionally substituted hydrocarbon group or an optionally substituted amino group, and $R^5$ and $R^6$ may bind to each other to form a cyclic group together with the adjacent phosphorus atom, or a salt thereof.

2. A compound according to claim 1, wherein $R^1$ is benzene, furan, thiophene, pyridine, cyclopentane, cyclohexane, pyrrolidine, piperidine, piperazine, morpholine, thiomorpholine or tetrahydropyran, each of which may be substituted.

3. A compound according to claim 1, wherein $R^1$ is an optionally substituted benzene.

4. A compound according to claim 1, wherein the ring A is furan, thiophene, pyrrole, pyridine or benzene, each of which may be substituted.

5. A compound according to claim 1, wherein the ring A is an optionally substituted benzene.

6. A compound according to claim 1, wherein the ring B is a 5- to 7-membered ring group of the formula:

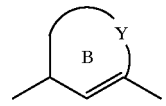

wherein Y is —Y'—(CH$_2$)$_m$— (wherein Y' is —S—, —O—, —NH— or —CH$_2$—, and m is an integer of 0–2), —CH=CH— or —N=CH—), which may have a substituent at any possible position.

7. A compound according to claim 6, wherein Y is —Y'—(CH$_2$)$_2$— (wherein Y' is —S—, —O—, —NH— or —CH$_2$—).

8. A compound according to claim 6, wherein Y is —(CH$_2$)$_2$—, —(CH$_2$)$_3$— or —O—(CH$_2$)$_2$—.

9. A compound according to claim 8, wherein the ring A is an optionally substituted benzene.

10. A compound according to claim 1, wherein Z is an optionally substituted C$_{1-3}$ alkylene.

11. A compound according to claim 1, wherein Z is a divalent group of the formula: —Z'—(CH$_2$)$_n$— (wherein Z' is —CH(OH)—, —C(O)— or —CH$_2$—, and n is an integer of 0–2) in which an optional methylene group may be substituted.

12. A compound according to claim 1, wherein Z is methylene.

13. A compound according to claim 1, wherein Z is substituted at para position of the benzene ring.

14. A compound according to claim 1, wherein $R^2$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, or (3) a group of the formula:

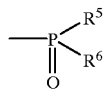

wherein R⁵ and R⁶ are independently an optionally substituted hydrocarbon group, and R⁵ and R⁶ may bind to each other to form a cyclic group together with the adjacent phosphorus atom.

15. A compound of the formula:

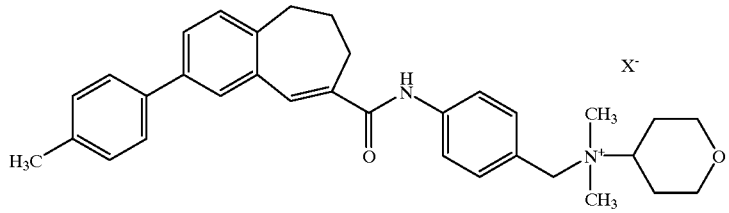

wherein X⁻ is an anion.

16. A compound according to claim 15, wherein X is a halogen atom.

17. A compound selected from the group consisting of

N-methyl-N-[4-[[[2-(4-methylphenyl)-6,7-dihydro-5H-benzocyclohepten-8-yl]carbonyl]amino]benzyl] piperidinium iodide, N-methyl-N-[4-[[[7-(4-methylphenyl)-2,3-dihydro-1-benzoxepin-4-yl]carbonyl]amino]benzyl]piperidinium iodide, N-[4-[N-methyl-N-(tetrahydropyran-4-yl)aminomethyl] phenyl]-7-(4-methylphenyl)-2,3-dihydro-1-benzoxepine-4-carboxmide, N-[4-[N-methyl-N-(tetrahydropyran-4-yl)aminomethyl] phenyl]-7-(4-morpholinophenyl)-2,3-dihydro-1-benzoxepine-4-carboxmide, 7-(4-ethoxyphenyl)-N-[4-[N-methyl-N-(tetrahydropyran-4-yl)aminomethyl]phenyl]-2,3-dihydro-1-benzoxepine-4-carboxmide, N,N-dimethyl-N-[4-[[[2-(4-methylphenyl)-6,7-dihydro-5H-benzocyclohepten-8-yl]carbonyl]amino]benzyl]-N-(tetrahydropyran-4-yl)ammonium iodide and N-methyl-N-[4-[[[7-(4-methylphenyl)-3,4-dihydronaphthalen-2-yl]carbonyl]amino]benzyl] piperidinium iodide, or a salt thereof.

18. A method for producing a compound of the formula:

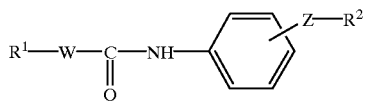

wherein each symbol is as defined in claim 1 or a salt thereof, which comprises subjecting a compound of the formula:

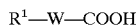

wherein each symbol is as defined in claim 1, a salt or a reactive derivative thereof to condensation reaction with a compound of the formula:

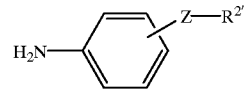

wherein Z is as defined in claim 1 and R²' is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group binding through a sulfur atom or (4) a group of the formula:

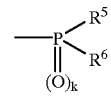

wherein k is 0 or 1, and when k is 0, a phosphorus atom may form a phosphonium; and R⁵ and R⁶ are independently an optionally substituted hydrocarbon group or an optionally substituted amino group, and R⁵ and R⁶ may bind to each other to form a cyclic group together with the adjacent phosphorus atom, the above groups (1)–(4) being optionally protected, or a salt thereof, and, if desired, subjecting the obtained product to deprotection, oxidation, reduction and/or ammoniumation.

19. A pharmaceutical composition comprising a compound according to claim 1 or a salt thereof.

20. A composition according to claim 19, which is for antagonizing MCP-1 receptor.

21. A composition according to claim 19, which is for the treatment or prophylaxis of cardiac infarction or myocarditis.

22. A pharmaceutical composition for antagonizing MCP-1 receptor, which comprises a compound of the formula:

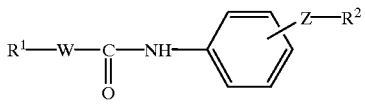

wherein R¹ is an optionally substituted 5- to 6-membered ring, W is a divalent group of the formula:

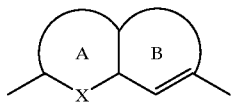

wherein the ring A is an optionally substituted 5- to 6-membered aromatic ring, X is an optionally substituted carbon atom, an optionally substituted nitrogen atom, sulfur atom or oxygen atom, the ring B is an optionally substituted 5- to 7-membered ring, Z is a chemical bond or a divalent group, $R^2$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group binding through a sulfur atom or (4) a group of the formula:

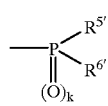

wherein k is 0 or 1, and when k is 0, a phosphorus atom may form a phosphonium; and $R^{5'}$ and $R^{6'}$ are independently an optionally substituted hydrocarbon group, an optionally substituted hydroxy group or an optionally substituted amino group, and $R^{5'}$ and $R^{6'}$ may bind to each other to form a cyclic group together with the adjacent phosphorus atom, or a salt thereof.

23. A method for antagonizing MCP-1 receptor which comprises administering to a mammal in need thereof an effective amount of a compound of the formula:

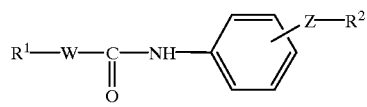

wherein $R^1$ is an optionally substituted 5- to 6-membered ring;

W is a divalent group of the formula:

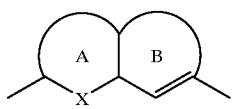

wherein the ring A is an optionally substituted 5- to 6-membered aromatic ring, X is an optionally substituted carbon atom, an optionally substituted nitrogen atom, sulfur atom or oxygen atom, and the ring B is an optionally substituted 5- to 7-membered ring; Z is a chemical bond or a divalent group; $R^2$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group binding through a sulfur atom or (4) a group of the formula:

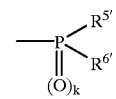

wherein k is 0 or 1, and when k is 0, a phosphorus atom may form a phosphonium; and $R^{5'}$ and $R^{6'}$ are independently an optionally substituted hydrocarbon group, an optionally substituted hydroxy group or an optionally substituted amino group, and $R^{5'}$ and $R^{6'}$ may bind to each other to form a cyclic group together with the adjacent phosphorus atom, or a salt thereof.

24. A method for antagonizing MCP-1 receptor which comprises administering to a mammal in need thereof an effective amount of a compound according to claim 1 or a salt thereof.

25. A method of making a medicament for antagonizing MCP-1 receptor comprising using a compound of the formula:

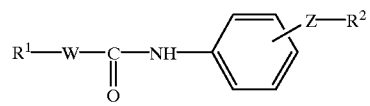

wherein $R^1$ is an optionally substituted 5- to 6-membered ring;

W is a divalent group of the formula:

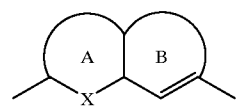

wherein the ring A is an optionally substituted 5- to 6-membered aromatic ring, X is an optionally substituted carbon atom, an optionally substituted nitrogen atom, sulfur atom or oxygen atom, and the ring B is an optionally substituted 5- to 7-membered ring; Z is a chemical bond or a divalent group; $R^2$ is (1) an optionally substituted amino group in which a nitrogen atom may form a quaternary ammonium, (2) an optionally substituted nitrogen-containing heterocyclic ring group which may contain a sulfur atom or an oxygen atom as ring constituting atoms and wherein a nitrogen atom may form a quaternary ammonium, (3) a group binding through a sulfur atom or (4) a group of the formula:

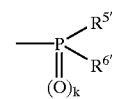

wherein k is 0 or 1, and when k is 0, a phosphorus atom may form a phosphonium; and $R^{5'}$ and $R^{6'}$ are independently an optionally substituted hydrocarbon group, an optionally substituted hydroxy group or an optionally substituted amino group, and $R^{5'}$ and $R^{6'}$ may bind to each other to form a cyclic group together with the adjacent phosphorus atom, or a salt thereof.

26. A method for making a medicament for antagonizing MCP-1 receptor comprising using the compound according to claim 1 or a salt thereof.

* * * * *